United States Patent
Masuda et al.

(10) Patent No.: US 8,754,113 B2
(45) Date of Patent: Jun. 17, 2014

(54) OXADIAZOLE DERIVATIVE HAVING ENDOTHELIAL LIPASE INHIBITORY ACTIVITY

(75) Inventors: Koji Masuda, Toyonaka (JP); Shiro Kida, Toyonaka (JP); Naoki Yoshikawa, Tokyo (JP); Manabu Katou, Toyonaka (JP); Terukazu Kato, Toyonaka (JP); Mado Nakajima, Toyonaka (JP); Eiichi Kojima, Toyonaka (JP); Mitsuhiro Yonehara, Toyonaka (JP)

(73) Assignee: Shionogi & Co., Ltd., Osaka-shi (JP)

( * ) Notice: Subject to any disclaimer, the term of this patent is extended or adjusted under 35 U.S.C. 154(b) by 0 days.

(21) Appl. No.: 13/516,441

(22) PCT Filed: Dec. 14, 2010

(86) PCT No.: PCT/JP2010/072440
§ 371 (c)(1),
(2), (4) Date: Jun. 15, 2012

(87) PCT Pub. No.: WO2011/074560
PCT Pub. Date: Jun. 23, 2011

(65) Prior Publication Data
US 2012/0253040 A1    Oct. 4, 2012

(30) Foreign Application Priority Data

Dec. 15, 2009 (JP) ................................. 2009-283965
Apr. 21, 2010 (JP) ................................. 2010-098009

(51) Int. Cl.
| A61K 31/428 | (2006.01) |
| A61K 31/423 | (2006.01) |
| A61K 31/4245 | (2006.01) |
| C07D 413/06 | (2006.01) |
| C07D 417/06 | (2006.01) |

(52) U.S. Cl.
CPC ............ *A61K 31/428* (2013.01); *A61K 31/423* (2013.01); *A61K 31/4245* (2013.01); *C07D 413/06* (2013.01); *C07D 417/06* (2013.01)
USPC ........... 514/367; 514/375; 548/143; 548/152; 548/217

(58) Field of Classification Search
None
See application file for complete search history.

(56) References Cited

U.S. PATENT DOCUMENTS

| 8,299,104 | B2 * | 10/2012 | Schwink et al. ............... 514/364 |
| 8,338,614 | B2 * | 12/2012 | McGaughey et al. ......... 548/131 |
| 2002/0133023 | A1 * | 9/2002 | Nagarajan et al. ............ 548/236 |
| 2006/0052423 | A1 | 3/2006 | Leber et al. |
| 2006/0252790 | A1 | 11/2006 | Allen et al. |
| 2007/0082890 | A1 | 4/2007 | Buettelmann et al. |
| 2008/0090867 | A1 | 4/2008 | Zoller et al. |
| 2008/0139538 | A1 * | 6/2008 | McGaughey et al. ......... 514/221 |
| 2008/0161370 | A1 | 7/2008 | Zoller et al. |
| 2008/0167339 | A1 | 7/2008 | Zoller et al. |
| 2008/0167355 | A1 | 7/2008 | Zoller et al. |
| 2008/0287448 | A1 | 11/2008 | Zoller et al. |
| 2008/0287503 | A1 | 11/2008 | Petry et al. |
| 2009/0030011 | A1 | 1/2009 | Petry et al. |
| 2009/0076068 | A1 | 3/2009 | Zoller et al. |
| 2009/0082367 | A1 | 3/2009 | Yoshimura et al. |
| 2010/0041663 | A1 | 2/2010 | He et al. |
| 2010/0152045 | A1 | 6/2010 | Lyga et al. |
| 2010/0173961 | A1 | 7/2010 | Zoller et al. |
| 2010/0190801 | A1 | 7/2010 | Petry et al. |
| 2010/0256097 | A1 | 10/2010 | Altman et al. |
| 2010/0286133 | A1 | 11/2010 | Zoller et al. |
| 2011/0039883 | A1 | 2/2011 | Zoller et al. |
| 2011/0071196 | A1 | 3/2011 | Bartolozzi et al. |
| 2011/0118321 | A1 | 5/2011 | Petry et al. |

(Continued)

FOREIGN PATENT DOCUMENTS

| WO | 00 71536 | 11/2000 |
| WO | 2004 056823 | 7/2004 |

(Continued)

OTHER PUBLICATIONS

Chemical Abstract Registry No. 400824-78-4, indexed in the Registry File on STN CAS Online Mar. 14, 2002.*
Ito et al., A medium-term rat liver bioassay for rapid in vivo detection of carcinogenic potental of chemicals. Cancer Science 2003, 94, 3-8.*
Lohani, S. (2006) Understanding nucleation process in the crystallization of polymorphs. (Doctoral dissertataion). Retrieved from ProQuest Dissertataions and Thesis. (Assession Order No. AAT3234930).*
Morissette, S. L., Almarsson, O., Peterson, M. L., Remenar, J. F., Read, M. J., Lemmo, A. V., Ellis, S., Cima, M. J., Gardner, C. R. High-throughput crystallization: polymorphs, salts, co-crystals, and solvates of pharmaceutical solids. Advanced Drug Delivery Reviews. Feb. 2004, 56, 275-300.*

(Continued)

*Primary Examiner* — Michael Barker
*Assistant Examiner* — Po-Chih Chen
(74) *Attorney, Agent, or Firm* — Oblon, Spivak, McClelland, Maier & Neustadt, L.L.P.

(57) ABSTRACT

A compound represented by the formula:

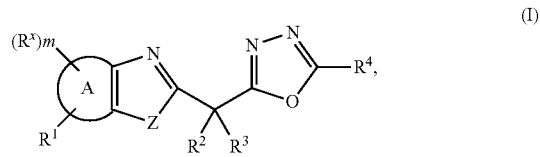

or its pharmaceutically acceptable salt. Ring A is aromatic carbocycle or aromatic heterocycle, Z is —O— or —S—, $R^1$ is hydrogen, halogen, hydroxy, cyano, nitro, carboxy, substituted or unsubstituted alkyl, substituted or unsubstituted alkenyl or the like, $R^2$ and $R^3$ are each independently hydrogen, halogen, hydroxy or the like, $R^4$ is a group represented by the formula: —$(CR^6R^7)_n$—$R^8$, $R^6$ and $R^7$ are each independently hydrogen, halogen, hydroxy or the like, n is an integer of 0 to 3, $R^8$ is carboxy, cyano, substituted or unsubstituted alkyl or the like, $R^x$ is halogen, hydroxy, cyano, nitro, carboxy, substituted or unsubstituted alkyl, substituted or unsubstituted alkenyl or the like, and m is an integer of 0 to 3.

17 Claims, No Drawings

(56) References Cited

U.S. PATENT DOCUMENTS

| | | | |
|---|---|---|---|
| 2011/0136869 A1 | 6/2011 | Bartolozzi et al. |
| 2011/0251386 A1 | 10/2011 | Masuda et al. |
| 2012/0289507 A1 | 11/2012 | He et al. |
| 2013/0030022 A1 | 1/2013 | Bartolozzi et al. |

FOREIGN PATENT DOCUMENTS

| | | |
|---|---|---|
| WO | 2004 093872 | 11/2004 |
| WO | 2004 094393 | 11/2004 |
| WO | 2004 094394 | 11/2004 |
| WO | 2005 032550 | 4/2005 |
| WO | 2006 053250 | 5/2006 |
| WO | 2006 078577 | 7/2006 |
| WO | 2006 111321 | 10/2006 |
| WO | 2006 110215 | 12/2006 |
| WO | 2006 131231 | 12/2006 |
| WO | 2006 131233 | 12/2006 |
| WO | WO 2006/130403 A1 | 12/2006 |
| WO | 2007 042178 | 4/2007 |
| WO | 2007 045392 | 4/2007 |
| WO | 2007 045393 | 4/2007 |
| WO | WO 2007/042421 A1 | 4/2007 |
| WO | 2007 105753 | 9/2007 |
| WO | 2007 110215 | 10/2007 |
| WO | 2007 110216 | 10/2007 |
| WO | 2007 131232 | 11/2007 |
| WO | 2008 084303 | 7/2008 |
| WO | 2008 156726 | 12/2008 |
| WO | 2009 123164 | 10/2009 |
| WO | 2009 133834 | 11/2009 |
| WO | WO 2010/007120 A1 | 1/2010 |
| WO | 2010 044441 | 4/2010 |
| WO | WO 2010/147792 A2 | 12/2010 |
| WO | WO 2011/037795 A1 | 3/2011 |
| WO | 2012 081563 | 6/2012 |

OTHER PUBLICATIONS

Yoshihisa Kurasawa, et al., "Tautomeric Behaviors of 3-(1,3,4-Oxadiazol-2-yl) Methylene-2-oxo-1,2,3,4-Tetrahydroquinoxalines", Heterocycles. International Journal for Reviews and Communications in Heterocyclic Chemistry, vol. 20, No. 10, Jan. 1, 1983, pp. 1917-1921.

Al-Soud,Y.A., et al., "Synthesis, antitumor and antiviral properties of some 1,2,4-triazole derivatives," II Farmaco, vol. 59, pp. 775-783, (Aug. 23, 2004).

Ram, V.J., et al., "Synthesis of Bis (1,2,4-triazoles, 1,3,4-oxadiazoles, 1,3,4-thiadiazoles) and Related Compounds," Agricultural and Biological Chemistry, vol. 41, No. 1, pp. 137-142, (1977).

Labouta, I.M., et al., "Synthesis of Some Substituted Benzimidazoles with Potential Antimicrobial Activity," Monatshefte fuer Chemie, vol. 120, No. 6-7, pp. 571-574, (1989).

Broedl, U.C., et al., "Endothelial Lipase: A Modulator of Lipoprotein Metabolism Upregulated by Inflammation," TCM, vol. 14, No. 5, pp. 202-206, (2004).

Ishida, T., et al., "Endothelial Lipase Modulated Susceptibility to Antherosclerosis in Apolipoprotein-E-deficient Mice," Journal of Biological Chemistry, vol. 279, No. 43, pp. 45085-45092, (Oct. 22, 2004).

International Search Report Issued Mar. 29, 2011 in PCT/JP10/72440 Filed Dec. 14, 2010.

Supplementary Search Report issued Feb. 27, 2013 in European Application No. 10 83 7586.6.

Database Registry Chemical Abstract, XP002692747, Database Accession No. 400824-78-4, Mar. 14, 2002, 5 pages.

Heinz Gehlen, et al., "Zur Kenntnis der 2-Amino-1.3.4-oxdiazole, XVII. Über die Acylierung der 2-Amino-5-(alkyl, aryl)-1.3.4-oxdiazole", Justus Liebigs Annalen der Chemie, vol. 703, No. 1, May 17, 1967, pp. 131-135.

Yoshihisa Kurasawa, et al. "Tautomeric Character of 3-Heteroarylmethylene-2-oxo-1,2,3,4-tetrahydroquinoxalines", Chemical and Pharmaceutical Bulletin, vol. 33, No. 3, Jan. 1, 1985, pp. 1249-1255.

Hasan Tashtoush, et al., "$^1$H and $^{13}$C NMR Spectroscopy of Substituted Bis-1,3,4-oxadiazoles", Magnetic Resonance in Chemistry, vol. 30, No. 9, Sep. 1, 1992, pp. 910-913.

T. V. Romanova, et al., "Esterification of 1,2,5-oxadiazolylacetic acids with polynitro alcohols", Russian Chemical Bulletin, International Edition, vol. 58, No. 10, Oct. 2009, pp. 2188-2190.

Gerd Blankenstein, et al., "Die Chemie der 2-Amino-1,3,4-oxdiazole", Zeitschrift Fuer Chemie, vol. 2, 1962, pp. 69-76.

V. V. Kiseleva, et al., "Synthesis of C-azolylacetic acids esters based on carbethoxyethylacetimidate", Bulletin of the Academy of Sciences of the USSR, Division of Chemical Science, vol. 39, No. 9, 1990, pp. 1888-1895.

M. K. Jani, et al., "Synthesis and Antimicrobial Activity of some Bis-1,3,4-oxadiazoles", Journal of the Indian Chemical Society, vol. 67, No. 19-4522, Jan. 1, 1990, pp. 607-609.

Yoshihisa Kurasawa, et al., "Tautomeric Behaviors of 3-(1,3,4-Oxadiazol-2-yl) Methylene-2-oxo-1,2,3,4-Tetrahydroquinoxalines", Heterocycles, International Journal for Reviews and Communications in Heterocyclic Chemistry, vol. 20, No. 10, Jan. 1, 1983, pp. 1917-1921.

\* cited by examiner

OXADIAZOLE DERIVATIVE HAVING ENDOTHELIAL LIPASE INHIBITORY ACTIVITY

FIELD OF THE INVENTION

The present invention relates to a pharmaceutically useful compound having inhibitory activity on endthelial lipase (hereinafter, referred to as EL).

BACKGROUND ART

Endothelial lipase (EL) is a Triglyceride Lipase family on a par with Lipoprotein Lipase (LPL) and Hepatic Lipase (HL). Studies in the knockout mouse and transgenic mouse have indicated that EL is associated with HDLc metabolism by the strong phospholipase activity, and EL is accepted as a factor which regulates plasma HDLc levels (Non-Patent Document 1).

Plasma HDLc levels have been accepted as an inverse correlate of coronary artery disease (CAD) risk. HDLc is supposed to have an anti-atherosclerotic effect through acceleration of reverse cholesterol transport accompanied with anti-oxidizing and anti-inflammatory effects. Low HDLc levels are accepted as one of the risk factors of CAD.

Therefore, an EL inhibitor serves as a therapeutic agent for CAD through its effect of increasing HDLc levels. Actually, an increase of HDLc levels and a decrease of atherosclerotic lesion area have been reported in EL-deficient atherogenic mice (Non-Patent Document 2).

These facts suggest the possibility of a selective inhibitor of EL as a therapeutic agent for dyslipideamia and atherosclerosis.

Patent Document 1, 2 and 3 disclose various compounds having an inhibitory activity on hepatic lipase and/or endothelial lipase, but oxadiazole derivative such as the present compound has not been disclosed.

Patent Document 4 discloses a compound having inhibitory activity on triglyceride lipase, lipoprotein lipase, hepatic lipase, pancreatic lipase or endothelial lipase, but oxadiazole derivative such as the present compound has not been disclosed.

Patent Document 5 to 15 disclose various compounds having inhibitory activity on EL, but oxadiazole derivative such as the present compound has not been disclosed.

Patent Document 16 discloses an oxadiazole derivative having inhibitory activity on PDF (peptide deformylase). For example, the following compound is disclosed.

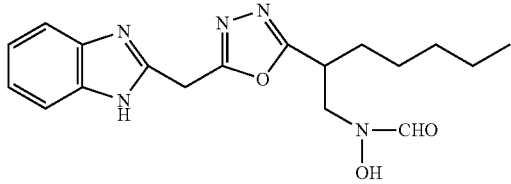

But patent document 16 does not describe any inhibitory activity on EL and the increasing activity of HDLc.

PRIOR ART DOCUMENT

Patent Document

[Patent Document 1] WO2004/093872
[Patent Document 2] WO2004/094393
[Patent Document 3] WO2004/094394
[Patent Document 4] WO2006/053250
[Patent Document 5] WO2007/042178
[Patent Document 6] WO2007/045392
[Patent Document 7] WO2007/045393
[Patent Document 8] WO2007/110216
[Patent Document 9] WO2007/110215
[Patent Document 10] WO2006/131231
[Patent Document 11] WO2006/131232
[Patent Document 12] WO2006/131233
[Patent Document 13] WO2006/111321
[Patent Document 14] WO2009/123164
[Patent Document 15] WO2009/133834
[Patent Document 16] JP2006-514693

Non-Patent Document

[Non-patent Document 1] TCM, Vol. 14, No. 5, 2004, p. 202-206
[Non-patent Document 2] The Journal of Biological Chemistry Vol. 279, No. 43, Issue of October 22, 45085-45092, 2004

DISCLOSURE OF INVENTION

Problems to be Solved by the Invention

The present invention provides a useful endothelial lipase inhibitor.

Means for Solving the Problem

The present inventors have intensively studied to synthesize the excellent compounds having inhibitory activity on endothelial lipase.

The present invention includes:
(1)
A compound represented by the formula (I):

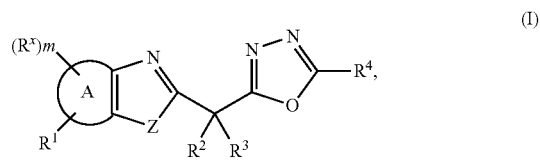

its pharmaceutically acceptable salt, or a solvate thereof, wherein
Ring A is aromatic carbocycle or aromatic heterocycle,
Z is —$NR^5$—, —O— or —S—,
$R^5$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxycarbonyl or substituted or unsubstituted acyl,
$R^1$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino, $R^2$ and $R^3$ are each independently hydrogen, halogen, hydroxy, cyano, nitro, carboxy, substituted or unsubstituted alkyl or substituted or unsubstituted alkyloxy, $R^2$ and $R^3$ taken together may form oxo, $R^4$ is a group represented by the formula: —$(CR^6R^7)n$-$R^8$, wherein $R^6$ and $R^7$ are each independently hydrogen, halogen, hydroxy, carboxy, substituted or unsubstituted alkyl or substituted or unsubstituted alkyloxy, $R^6$ and $R^7$ taken together with the adjacent carbon atom to which they are attached may form a substituted or unsubstituted ring, n is an integer of 0 to 3, $R^8$ is carboxy, cyano, substituted or unsubstituted alkyl, substituted or unsubstituted acyl, with the proviso that n is not 0 when $R^8$ is substituted or unsubstituted acyl, substituted or unsubstituted alkyloxycarbonyl, substituted or unsubstituted alkylsulfonyl, substituted or unsubstituted carbamoyl, substituted or unsubstituted amino, substituted or unsubstituted carbamoyloxy or substituted or unsubstituted alkyloxy, $R^x$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino, m is an integer of 0 to 3, with the proviso that the compounds wherein Z is —$NR^5$—, n is 0 and $R^8$ is substituted or unsubstituted amino and the compound shown as follows are excluded:

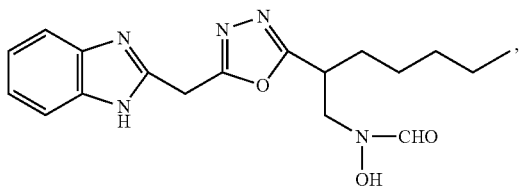 [SMILES: CCCCCC(CN(O)C=O)c1nnc(Cc2nc3ccccc3[nH]2)o1]

(2)

The compound according to the above (1), its pharmaceutically acceptable salt, or a solvate thereof, wherein Z is —O— or —S—, (3)

The compound according to the above (2), its pharmaceutically acceptable salt, or a solvate thereof, wherein Z is —S—, (4)

The compound according to any one of the above (1) to (3), its pharmaceutically acceptable salt, or a solvate thereof, wherein Ring A is aromatic carbocycle, (5)

The compound according to any one of the above (1) to (4), its pharmaceutically acceptable salt, or a solvate thereof, wherein Ring A is benzene ring, (6)

The compound according to the above (1), its pharmaceutically acceptable salt, or a solvate thereof, wherein the compound represented by the formula (I) is a compound represented by the formula (II):

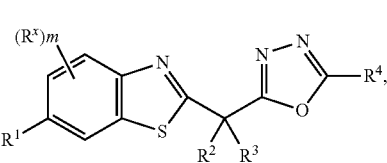

wherein $R^1$, $R^2$, $R^3$, $R^4$, $R^x$ and m are as defined in the above (1), (7)

The compound according to any one of the above (1) to (6), its pharmaceutically acceptable salt, or a solvate thereof, wherein $R^1$ is halogen, cyano, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl or substituted or unsubstituted amino, (8)

The compound according to any one of the above (1) to (7), its pharmaceutically acceptable salt, or a solvate thereof, wherein $R^1$ is halogen, cyano, substituted or unsubstituted alkyl, substituted or unsubstituted aryl, substituted or unsubstituted heteroaryl, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl or substituted or unsubstituted heterocyclylsulfonyl, (9)

The compound according to any one of the above (1) to (8), its pharmaceutically acceptable salt, or a solvate thereof, wherein $R^1$ is substituted or unsubstituted aryl, (10)

The compound according to any one of the above (1) to (9), its pharmaceutically acceptable salt, or a solvate thereof, wherein $R^8$ is carboxy, cyano, substituted or unsubstituted alkyloxycarbonyl, substituted or unsubstituted alkylsulfonyl, substituted or unsubstituted carbamoyl, substituted or unsubstituted amino or substituted or unsubstituted carbamoyloxy, (11)

The compound according to the above (10), its pharmaceutically acceptable salt, or a solvate thereof, wherein $R^8$ is carboxy, cyano, substituted or unsubstituted carbamoyl or substituted or unsubstituted amino, (12)

The compound according to the above (11), its pharmaceutically acceptable salt, or a solvate thereof, wherein $R^8$ is substituted or unsubstituted carbamoyl, (13)

The compound according to the above (12), its pharmaceutically acceptable salt, or a solvate thereof, wherein $R^8$ is a group represented by the formula: —(C=O)—$NR^9$—($CR^{10}R^{11}$)—$R^{12}$, wherein $R^9$ is hydrogen, substituted or unsubstituted alkyl, substituted or unsubstituted aryl, substituted or unsubstituted heteroaryl, substituted or unsubstituted cycloalkyl, substituted or unsubstituted cycloalkenyl or substituted or unsubstituted heterocyclyl, $R^{10}$ and $R^{11}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl or substituted or unsubstituted alkyloxy, $R^{10}$ and $R^{11}$ taken together with the adjacent carbon atom to which they are attached may form a substituted or unsubstituted ring, $R^{12}$ is cyano, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl or substituted or unsubstituted acyl, substituted or unsubstituted carbamoyl or substituted or unsubstituted alkyloxycarbonyl, (14)

The compound according to any one of the above (1) to (13), its pharmaceutically acceptable salt, or a solvate thereof, wherein n is 1, (15)

The compound according to any one of the above (1) to (14), its pharmaceutically acceptable salt, or a solvate thereof, wherein $R^2$ and $R^3$ are hydrogen, (15-1)

The compound according to any one of the above (1) to (15), its pharmaceutically acceptable salt, or a solvate thereof, wherein m is 0 and Ring A is benzene ring, (15-2)

The compound according to any one of the above (1) to (3), (7) to (15), its pharmaceutically acceptable salt, or a solvate thereof, wherein Ring A is aromatic heterocycle other than pyridine, (16)

A compound represented by the formula (III):

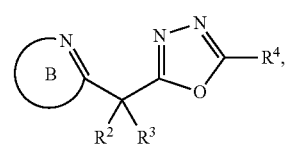

its pharmaceutically acceptable salt, or a solvate thereof, wherein

Ring B is substituted or unsubstituted nitrogen-containing hetero ring, $R^2$ and $R^3$ are each independently hydrogen, halogen, hydroxy, cyano, nitro, carboxy, substituted or unsubstituted alkyl or substituted or unsubstituted alkyloxy, $R^2$ and $R^3$ taken together may form oxo, $R^4$ is a group represented by the formula: —($CR^6R^7$)n-$R^8$, wherein $R^6$ and $R^7$ are each independently hydrogen, halogen, hydroxy, carboxy, substituted or unsubstituted alkyl or substituted or unsubstituted alkyloxy, $R^6$ and $R^7$ taken together with the adjacent carbon atom to which they are attached may form a substituted or unsubstituted ring, n is an integer of 0 to 3, $R^8$ is carboxy, cyano, substituted or unsubstituted alkyl, substituted or unsubstituted acyl, with the proviso that n is not 0 when $R^8$ is substituted or unsubstituted acyl, substituted or unsubstituted alkyloxycarbonyl, substituted or unsubstituted alkylsulfonyl, substituted or unsubstituted carbamoyl, substituted or unsubstituted amino, substituted or unsubstituted carbamoyloxy or substituted or unsubstituted alkyloxy, with the proviso that the compounds wherein Ring B is substituted or unsubstituted benzimidazole, n is 0 and $R^8$ is substituted or unsubstituted amino and the compound shown as follows are excluded:

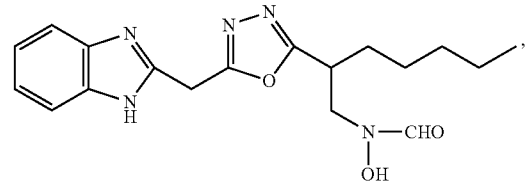 [SMILES: CCCCCC(CN(O)C=O)c1nnc(Cc2nc3ccccc3[nH]2)o1]

(17)

The compound according to the above (16), its pharmaceutically acceptable salt, or a solvate thereof, wherein Ring B is a group represented by the formula:

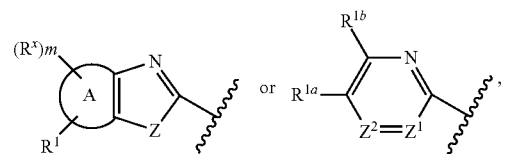

wherein

Ring A is aromatic carbocycle, non-aromatic carbocycle, aromatic heterocycle or non-aromatic heterocycle, Z is —$NR^5$—, —O— or —S—, $R^5$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxycarbonyl or substituted or unsubstituted acyl, $R^1$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino, $R^x$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino, m is an integer of 0 to 3, $R^{1a}$ and $R^{1b}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino, $R^{1a}$ and $R^{1b}$ taken together with the adjacent carbon atom to which they are attached may form a substituted or unsubstituted ring, $Z^1$ is $=CR^1-$ or $=N-$, $Z^2$ is $-CR^1=$ or $-N=$, (18)

The compound according to the above (17), its pharmaceutically acceptable salt, or a solvate thereof, wherein $R^{1a}$ and $R^{1b}$ taken together with the adjacent carbon atom to which they are attached form a substituted or unsubstituted ring, (19)

A pharmaceutical composition comprising the compound according to any one of the above (1) to (18), its pharmaceutically acceptable salt, or a solvate thereof, (20)

A pharmaceutical composition comprising the compound according to any one of the above (1) to (18), its pharmaceutically acceptable salt, or a solvate thereof, which has an inhibitory activity on endothelial lipase.

Further, the present invention includes:

(21)

The pharmaceutical composition according to the above (19) for treating and/or preventing lipid metabolism abnormality, (22)

The pharmaceutical composition according to the above (19) for treating and/or preventing hyperlipidemia, (23)

The pharmaceutical composition according to the above (19) for treating and/or preventing arteriosclerosis, (24)

A method for preventing or treating lipid metabolism abnormality, comprising administering the compound according to any one of the above (1) to (18), its pharmaceutically acceptable salt, or a solvate thereof, (25)

A method for preventing or treating hyperlipidemia, comprising administering the compound according to any one of the above (1) to (18), its pharmaceutically acceptable salt, or a solvate thereof, (26)

A method for preventing or treating arteriosclerosis, comprising administering the compound according to any one of the above (1) to (18), its pharmaceutically acceptable salt, or a solvate thereof, (27)

A use of the compound according to any one of the above (1) to (18), its pharmaceutically acceptable salt, or a solvate thereof for manufacturing a medicament of treatment and/or prevention of lipid metabolism abnormality, (28)

A use of the compound according to any one of the above (1) to (18), its pharmaceutically acceptable salt, or a solvate thereof for manufacturing a medicament of treatment and/or prevention of hyperlipidemia, (29)

A use of the compound according to any one of the above (1) to (18), its pharmaceutically acceptable salt, or a solvate thereof for manufacturing a medicament of treatment and/or prevention of arteriosclerosis,

(30)
The compound according to any one of the above (1) to (18), its pharmaceutically acceptable salt, or a solvate thereof for the treatment and/or prevention of lipid metabolism abnormality,

(31)
The compound according to any one of the above (1) to (18), its pharmaceutically acceptable salt, or a solvate thereof for the treatment and/or prevention of hyperlipidemia,

(32)
The compound according to any one of the above (1) to (18), its pharmaceutically acceptable salt, or a solvate thereof for the treatment and/or prevention of arteriosclerosis.

Further, the present invention includes:
(1A)
A compound represented by the formula (I):

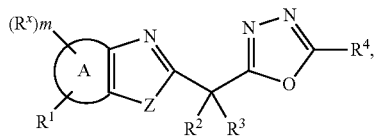

its pharmaceutically acceptable salt, or a solvate thereof, wherein
Ring A is aromatic carbocycle or aromatic heterocycle,
Z is —NR$^5$—, —O— or —S—,
R$^5$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxycarbonyl or substituted or unsubstituted acyl,
R$^1$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino,
R$^2$ and R$^3$ are each independently hydrogen, halogen, hydroxy, cyano, nitro, carboxy, substituted or unsubstituted alkyl or substituted or unsubstituted alkyloxy,
R$^2$ and R$^3$ taken together with the adjacent carbon atom to which they are attached may form oxo,
R$^4$ is a group represented by the formula: —(CR$^6$R$^7$)n-R$^8$, wherein R$^6$ and R$^7$ are each independently hydrogen, halogen, hydroxy, carboxy, substituted or unsubstituted alkyl or substituted or unsubstituted alkyloxy, R$^6$ and R$^7$ taken together with the adjacent carbon atom to which they are attached may form a substituted or unsubstituted ring, n is an integer of 0 to 3, R$^8$ is carboxy, cyano, substituted or unsubstituted alkyl, substituted or unsubstituted acyl, with the proviso that n is not 0 when R$^8$ is substituted or unsubstituted acyl, substituted or unsubstituted alkyloxycarbonyl, substituted or unsubstituted alkylsulfonyl, substituted or unsubstituted carbamoyl, substituted or unsubstituted amino, substituted or unsubstituted carbamoyloxy or substituted or unsubstituted alkyloxy,
R$^x$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino,
m is an integer of 0 to 3,
with the proviso that
the compounds wherein Z is —NR$^5$—, n is 0 and R$^8$ is substituted or unsubstituted amino,
the compounds wherein a group represented by the formula:

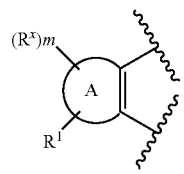

is a group represented by the formula:

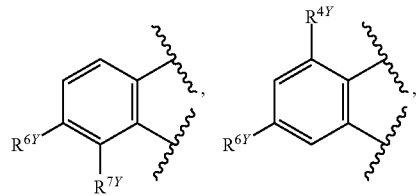

-continued

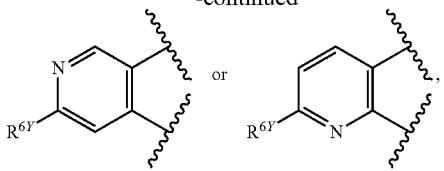

wherein $R^{4Y}$ is substituted or unsubstituted alkyloxy, $R^{6Y}$ is halogen, substituted or unsubstituted aryl or substituted or unsubstituted heteroaryl, $R^{7Y}$ is halogen, and the compound shown as follows are excluded:

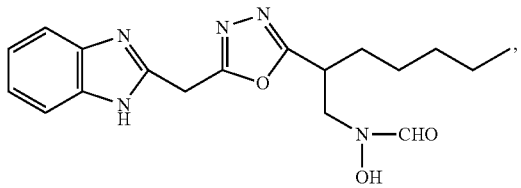 [SMILES: CCCCCC(CN(O)C=O)c1nnc(Cc2nc3ccccc3[nH]2)o1]

(2A)

The compound according to the above (1A), its pharmaceutically acceptable salt, or a solvate thereof, wherein Z is —O— or —S—, (3A)

The compound according to the above (2A), its pharmaceutically acceptable salt, or a solvate thereof, wherein Z is —S—, (4A)

The compound according to any one of the above (1A) to (3A), its pharmaceutically acceptable salt, or a solvate thereof, wherein Ring A is aromatic carbocycle, (5A)

The compound according to any one of the above (1A) to (4A), its pharmaceutically acceptable salt, or a solvate thereof, wherein Ring A is benzene ring, (6A)

The compound according to the above (1A), its pharmaceutically acceptable salt, or a solvate thereof, wherein the compound represented by the formula (I) is a compound represented by the formula (II):

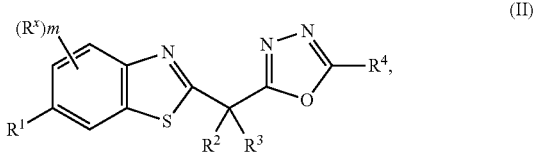

wherein $R^1$, $R^2$, $R^3$, $R^4$, $R^x$ and m are as defined in the above (1A), (7A)

The compound according to any one of the above (1A) to (6A), its pharmaceutically acceptable salt, or a solvate thereof, wherein $R^1$ is halogen, cyano, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl or substituted or unsubstituted amino, (8A)

The compound according to any one of the above (1A) to (7A), its pharmaceutically acceptable salt, or a solvate thereof, wherein $R^1$ is halogen, cyano, substituted or unsubstituted alkyl, substituted or unsubstituted aryl, substituted or unsubstituted heteroaryl, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl or substituted or unsubstituted heterocyclylsulfonyl, (9A)

The compound according to any one of the above (1A) to (8A), its pharmaceutically acceptable salt, or a solvate thereof, wherein $R^1$ is substituted or unsubstituted aryl, (10A)

The compound according to any one of the above (1A) to (9A), its pharmaceutically acceptable salt, or a solvate thereof, wherein $R^8$ is carboxy, cyano, substituted or unsubstituted alkyloxycarbonyl, substituted or unsubstituted alkylsulfonyl, substituted or unsubstituted carbamoyl, substituted or unsubstituted amino or substituted or unsubstituted carbamoyloxy, (11A)

The compound according to the above (10A), its pharmaceutically acceptable salt, or a solvate thereof, wherein $R^8$ is carboxy, cyano, substituted or unsubstituted carbamoyl or substituted or unsubstituted amino, (12A)

The compound according to the above (11A), its pharmaceutically acceptable salt, or a solvate thereof, wherein $R^8$ is substituted or unsubstituted carbamoyl, (13A)

The compound according to the above (12A), its pharmaceutically acceptable salt, or a solvate thereof, wherein $R^8$ is a group represented by the formula: —(C=O)—$NR^9$—($CR^{10}R^{11}$)—$R^{12}$, wherein $R^9$ is hydrogen, substituted or unsubstituted alkyl, substituted or unsubstituted aryl, substituted or unsubstituted heteroaryl, substituted or unsubstituted cycloalkyl, substituted or unsubstituted cycloalkenyl or substituted or unsubstituted heterocyclyl, $R^{10}$ and $R^{11}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl or substituted or unsubstituted alkyloxy, $R^{10}$ and $R^{11}$ taken together with the adjacent carbon atom to which they are attached may form a substituted or unsubstituted ring, $R^{12}$ is cyano, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl or substituted or unsubstituted alkyloxycarbonyl, (14A)

The compound according to any one of the above (1A) to (13A), its pharmaceutically acceptable salt, or a solvate thereof, wherein n is 1, (15A)

The compound according to any one of the above (1A) to (14A), its pharmaceutically acceptable salt, or a solvate thereof, wherein $R^2$ and $R^3$ are hydrogen, (16A)

A compound represented by the formula (III):

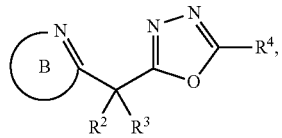

(III)

its pharmaceutically acceptable salt, or a solvate thereof, wherein

Ring B is substituted or unsubstituted nitrogen-containing hetero ring, $R^2$ and $R^3$ are each independently hydrogen, halogen, hydroxy, cyano, nitro, carboxy, substituted or unsubstituted alkyl or substituted or unsubstituted alkyloxy, $R^2$ and $R^3$ taken together with the adjacent carbon atom to which they are attached may form oxo, $R^4$ is a group represented by the formula: —$(CR^6R^7)$n-$R^8$, wherein $R^6$ and $R^7$ are each independently hydrogen, halogen, hydroxy, carboxy, substituted or unsubstituted alkyl or substituted or unsubstituted alkyloxy, $R^6$ and $R^7$ taken together with the adjacent carbon atom to which they are attached may form a substituted or unsubstituted ring, n is an integer of 0 to 3, $R^8$ is carboxy, cyano, substituted or unsubstituted alkyl, substituted or unsubstituted acyl, with the proviso that n is not 0 when $R^8$ is substituted or unsubstituted acyl, substituted or unsubstituted alkyloxycarbonyl, substituted or unsubstituted alkylsulfonyl, substituted or unsubstituted carbamoyl, substituted or unsubstituted amino, substituted or unsubstituted carbamoyloxy or substituted or unsubstituted alkyloxy, with the proviso that the compounds wherein Ring B is substituted or unsubstituted benzimidazole, n is 0 and $R^8$ is substituted or unsubstituted amino, the compounds wherein a group represented by the formula:

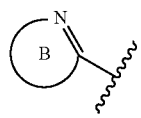

is a group represented by the formula:

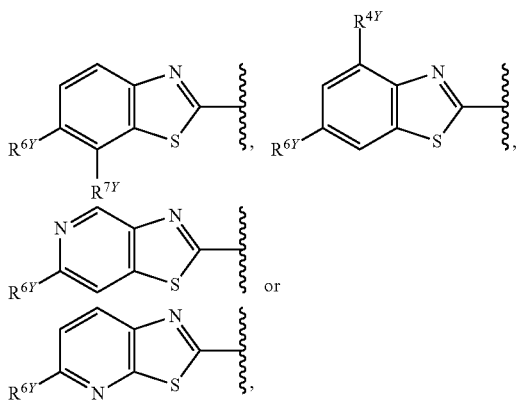

wherein $R^{4Y}$ is substituted or unsubstituted alkyloxy, $R^{6Y}Y$ is halogen, substituted or unsubstituted aryl or substituted or unsubstituted heteroaryl and $R^{7Y}$ is halogen, and the compound shown as follows are excluded:

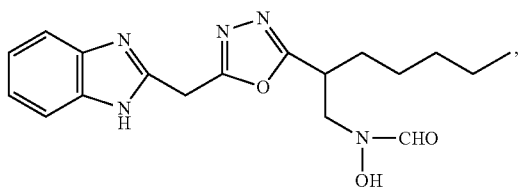 [SMILES: CCCCCC(CN(O)C=O)c1nnc(Cc2nc3ccccc3[nH]2)o1]

(17A)

The compound according to the above (16A), its pharmaceutically acceptable salt, or a solvate thereof, wherein Ring B is a group represented by the formula:

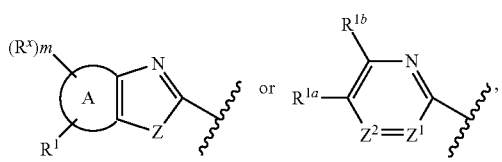

wherein

Ring A is aromatic carbocycle, non-aromatic carbocycle, aromatic heterocycle or non-aromatic heterocycle, Z is —$NR^5$—, —O— or —S—, $R^5$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxycarbonyl or substituted or unsubstituted acyl, $R^1$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino, $R^x$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino, m is an integer of 0 to 3, $R^{1a}$ and $R^{1b}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino, $R^{1a}$ and $R^{1b}$ taken together with the adjacent carbon atom to which they are attached may form a substituted or unsubstituted ring, $Z^1$ is $=CR^1-$ or $=N-$,
$Z^2$ is $-CR^1=$ or $-N=$, (18A)

The compound according to the above (17A), its pharmaceutically acceptable salt, or a solvate thereof, wherein $R^{1a}$ and $R^{1b}$ taken together with the adjacent carbon atom to which they are attached form a substituted or unsubstituted ring, (19A)

A pharmaceutical composition comprising the compound according to any one of the above (1A) to (18A), its pharmaceutically acceptable salt, or a solvate thereof, (20A)

A pharmaceutical composition comprising the compound according to any one of the above (1A) to (18A), its pharmaceutically acceptable salt, or a solvate thereof, which has an inhibitory activity on endothelial lipase.

Further, the present invention includes:

(21A)

The pharmaceutical composition according to the above (19A) for treating and/or preventing lipid metabolism abnormality, (22A)

The pharmaceutical composition according to the above (19A) for treating and/or preventing hyperlipidemia, (23A)

The pharmaceutical composition according to the above (19A) for treating and/or preventing arteriosclerosis, (24A)

A method for preventing or treating lipid metabolism abnormality, comprising administering the compound according to any one of the above (1A) to (18A), its pharmaceutically acceptable salt, or a solvate thereof, (25A)

A method for preventing or treating hyperlipidemia, comprising administering the compound according to any one of the above (1A) to (18A), its pharmaceutically acceptable salt, or a solvate thereof, (26A)

A method for preventing or treating arteriosclerosis, comprising administering the compound according to any one of the above (1A) to (18A), its pharmaceutically acceptable salt, or a solvate thereof, (27A)

A use of the compound according to any one of the above (1A) to (18A), its pharmaceutically acceptable salt, or a solvate thereof for manufacturing a medicament of treatment and/or prevention of lipid metabolism abnormality, (28A)

A use of the compound according to any one of the above (1A) to (18A), its pharmaceutically acceptable salt, or a solvate thereof for manufacturing a medicament of treatment and/or prevention of hyperlipidemia, (29A)

A use of the compound according to any one of the above (1A) to (18A), its pharmaceutically acceptable salt, or a solvate thereof for manufacturing a medicament of treatment and/or prevention of arteriosclerosis, (30A)

The compound according to any one of the above (1A) to (18A), its pharmaceutically acceptable salt, or a solvate thereof for the treatment and/or prevention of lipid metabolism abnormality, (31A)

The compound according to any one of the above (1A) to (18A), its pharmaceutically acceptable salt, or a solvate thereof for the treatment and/or prevention of hyperlipidemia, (32A)

The compound according to any one of the above (1A) to (18A), its pharmaceutically acceptable salt, or a solvate thereof for the treatment and/or prevention of arteriosclerosis.

Effect of the Invention

Since the present compound has an inhibitory activity on endothelial lipase, pharmaceutical compositions comprising the present compound are very useful as medicaments, especially, as medicaments for treatment and/or prevention of lipid metabolism abnormality, hyperlipidemia, arteriosclerosis, atherosclerosis, hypercholesterolemia, hypertriglyceridemia, diabetes, obesity and/or syndrome X.

Moreover, the present compound selectively inhibits endothelial lipase, and has high selectivity to Hepatic Lipase (HL) and Lipoprotein Lipase (LPL). Furthermore, the present compound has an efficiency as a medicament. Here, the efficiency as a medicament includes high metabolic stability, a weak drug-metabolizing enzyme induction, a weak inhibition of drug metabolizing enzyme that metabolizes other drug, a high oral absorption, a low clearance, a long half-life period enough to exhibit drug efficacy and so on.

Mode for Carrying Out the Invention

In the following, meanings of terms used in the present specification will be explained. Each term has the same meaning when used alone or in combination with other term in this description.

"Halogen" includes fluorine, chlorine, bromine or iodine.

"Alkyl" means a C1 to C10 straight or branched alkyl group, and example includes methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferable is C1 to C6 or C1 to C4 alkyl, and example includes methyl, ethyl, n-propyl, isopropyl, n-butyl, isobutyl, sec-butyl, tert-butyl, n-pentyl, isopentyl, neopentyl, n-hexyl or isohexyl.

"Alkenyl" means C2 to C8 straight or branched alkenyl having one or more double bond(s) in the above "alkyl", and example includes vinyl, 1-propenyl, 2-propenyl, 1-butenyl, 2-butenyl, 3-butenyl, 1,3-butadienyl, 3-methyl-2-butenyl or the like.

"Alkynyl" means C2 to C8 straight or branched alkynyl having one or more triple bond(s) in the above "alkyl", and example includes ethynyl, propinyl, butynyl or the like. Furthermore, "Alkynyl" may have a double bond.

"Cycloalkyl" means a C3 to C15 cyclic saturated hydrocarbon group, and example includes cyclopropyl, cyclobutyl, cyclopentyl, cyclohexyl, cycloheptyl, cyclooctyl, bridged cyclic hydrocarbon group, Spiro hydrocarbon group or the like. Preferable is cyclopropyl, cyclobutyl, cyclopentyl, cyclohexyl or bridged cyclic hydrocarbon group.

"Bridged cyclic hydrocarbon group" includes a group which is derived by excluding one hydrogen from a C5 to C8 aliphatic cycle which consists of two or more rings that share two or more atoms. Example includes bicyclo[2.1.0]pentyl, bicyclo[2.2.1]heptyl, bicyclo[2.2.2]octyl, bicyclo[3.2.1]octyl, tricyclo[2.2.1.0]heptyl or the like.

"Spiro hydrocarbon group" includes a group which is derived by excluding one hydrogen from a cycle which consists of two hydrocarbon rings that share one carbon atom. Example includes spiro[3.4]octyl or the like.

"Cycloalkenyl" means C3 to C10 cyclic unsaturated aliphatic hydrocarbon group, and example includes cyclopropenyl (e.g.: 1-cyclopropenyl), cyclobutenyl (e.g.: 1-cyclobutenyl), cyclopentenyl (e.g.: 1-cyclopenten-1-yl, 2-cyclopenten-1-yl), cyclohexenyl (e.g.: 1-cyclohexen-1-yl, 2-cyclohexen-1-yl or 3-cyclohexen-1-yl), cycloheptenyl (e.g.: 1-cycloheptenyl), cyclooctenyl (e.g.: 1-cyclooctenyl) or the like. Preferable is cyclopropenyl, cyclobutenyl, cyclopentenyl or cyclohexenyl. Cycloalkenyl also includes bridged cyclic hydrocarbon group and spiro hydrocarbon group which have an unsaturated bond in the ring.

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl). Preferable is phenyl or naphthyl (1-naphthyl or 2-naphthyl).

"Heteroaryl" means a monocyclic aromatic heterocyclic group or a fused aromatic heterocyclic group. The monocyclic aromatic heterocyclic group means a group derived from a 5- to 8-membered aromatic ring which may contain 1 to 4 oxygen, sulfur and/or nitrogen atom(s) in the ring, and may have a bond at a substitutable arbitrary position.

The fused aromatic heterocyclic group means a group in which a 5- to 8-membered aromatic ring optionally containing 1 to 4 oxygen, sulfur and/or nitrogen atom(s) in the ring is fused with 1 to 4 of 5- to 8-membered aromatic carbocycle(s) or other 5- to 8-membered aromatic heterocycle(s), and which may have a bond at a substitutable arbitrary position.

Example of the "heteroaryl" includes furyl (e.g.: 2-furyl or 3-furyl), thienyl (e.g.: 2-thienyl or 3-thienyl), pyrrolyl (e.g.: 1-pyrrolyl, 2-pyrrolyl or 3-pyrrolyl), imidazolyl (e.g.: 1-imidazolyl, 2-imidazolyl or 4-imidazolyl), pyrazolyl (e.g.: 1-pyrazolyl, 3-pyrazolyl or 4-pyrazolyl), triazolyl (e.g.: 1,2,4-triazole-1-yl, 1,2,4-triazole-3-yl or 1,2,4-triazole-4-yl), tetrazolyl (e.g.: 1-tetrazolyl, 2-tetrazolyl or 5-tetrazolyl), oxazolyl (e.g.: 2-oxazolyl, 4-oxazolyl or 5-oxazolyl), isoxazolyl (e.g.: 3-isoxazolyl, 4-isoxazolyl or 5-isoxazolyl), thiazolyl (e.g.: 2-thiazolyl, 4-thiazolyl or 5-thiazolyl), thiadiazolyl, isothiazolyl (e.g.: 3-isothiazolyl, 4-isothiazolyl or 5-isothiazolyl), pyridyl (e.g.: 2-pyridyl, 3-pyridyl or 4-pyridyl), pyridazinyl (e.g.: 3-pyridazinyl or 4-pyridazinyl), pyrimidinyl (e.g.: 2-pyrimidinyl, 4-pyrimidinyl or 5-pyrimidinyl), furazanyl (e.g.: 3-furazanyl), pyrazinyl (e.g.: 2-pyrazinyl), oxadiazolyl (e.g.: 1,3,4-oxadiazole-2-yl), benzofuryl (e.g.: 2-benzo[b]furyl, 3-benzo[b]furyl, 4-benzo[b]furyl, 5-benzo[b]furyl, 6-benzo[b]furyl or 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g.: 1-benzimidazolyl, 2-benzimidazolyl, 4-benzimidazolyl or 5-benzimidazolyl), dibenzofuryl, benzoxazolyl, benzothiazolyl, quinoxalinyl (e.g.: 2-quinoxalinyl, 5-quinoxalinyl or 6-quinoxalinyl), cinnolinyl (e.g.: 3-cinnolinyl, 4-cinnolinyl, 5-cinnolinyl, 6-cinnolinyl, 7-cinnolinyl or 8-cinnolinyl), quinazolinyl (e.g.: 2-quinazolinyl, 4-quinazolinyl, 5-quinazolinyl, 6-quinazolinyl, 7-quinazolinyl or 8-quinazolinyl), quinolyl (e.g.: 2-quinolyl, 3-quinolyl, 4-quinolyl, 5-quinolyl, 6-quinolyl, 7-quinolyl or 8-quinolyl), phthalazinyl (e.g.: 1-phthalazinyl, 5-phthalazinyl or 6-phthalazinyl), isoquinolyl (e.g.: 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g.: 2-pteridinyl, 4-pteridinyl, 6-pteridinyl or 7-pteridinyl), carbazolyl, phenanthridinyl, acridinyl (e.g.: 1-acridinyl, 2-acridinyl, 3-acridinyl, 4-acridinyl or 9-acridinyl), indolyl (e.g.: 1-indolyl, 2-indolyl, 3-indolyl, 4-indolyl, 5-indolyl, 6-indolyl or 7-indolyl), isoindolyl, phenadinyl (e.g.: 1-phenadinyl or 2-phenadinyl), phenothiadinyl (e.g.: 1-phenothiadinyl, 2-phenothiadinyl, 3-phenothiadinyl or 4-phenothiadinyl) or the like.

"Heterocyclyl" means a nonaromatic heterocyclic group which contains at least one nitrogen, oxygen or sulfur atom(s) in the ring, and may have a bond at a substitutable arbitrary position. Moreover, the nonaromatic heterocyclic group can be bridged with a C1 to C4 alkyl chain, or can be fused with cycloalkane (5- to 6-membered ring is preferable) or benzene ring. "Nonaromatic heterocyclic group" can be saturated or unsaturated as long as it is non-aromatic. Preferable is a 5- to 8-membered ring. Example includes 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperadinyl, 2-piperadinyl, 2-morpholinyl, 3-morpholinyl, morpholino, tetrahydropyranyl or the like.

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclylcarbonyl.

The alkyl part of "alkylcarbonyl", the alkenyl part of "alkenylcarbonyl", the cycloalkyl part of "cycloalkylcarbonyl", the cycloalkenyl part of "cycloalkenylcarbonyl", the aryl part of "arylcarbonyl", the heteroaryl part of "heteroarylcarbonyl" and the heterocyclyl part of "heterocyclylcarbonyl" respectively mean the above "alkyl", the above "alkenyl", the above "cycloalkyl", the above "cycloalkenyl", the above "aryl", the above "heteroaryl" and the above "heterocyclyl".

The alkyl part of "alkyloxycarbonyl", "alkyloxy", "alkylthio" and "alkylsulfonyl" means the above "alkyl".

The cycloalkyl part of "cycloalkyloxy", "cycloalkylthio" and "cycloalkylsulfonyl" means the above "cycloalkyl".

The cycloalkenyl part of "cycloalkenyloxy", "cycloalkenylthio" and "cycloalkenylsulfonyl" means the above "cycloalkenyl".

The aryl part of "aryloxy", "arylthio" and "arylsulfonyl" means the above "aryl".

The heteroaryl part of "heteroaryloxy", "heteroarylthio" and "heteroarylsulfonyl" means the above "heteroaryl".

The heterocyclyl part of "heterocyclyloxy", "heterocyclylthio" and "heterocyclylsulfonyl" means the above "heterocyclyl."

"Aromatic carbocycle" means a monocyclic aromatic carbocycle (e.g.: benzene ring) or a fused aromatic carbocycle. Herein, as the "fused aromatic carbocycle", example includes C10 to C14 fused aromatic carbocycle or the like. An example includes naphthalene, phenanthrene, anthracene or the like.

"Nonaromatic carbocycle" means a 5 to 10 membered nonaromatic carbocycle which may have a saturated or an unsaturated bond partially and may be fused with aryl or heteroaryl.

"Aromatic hetero ring" means a aromatic ring which contains one or more heteroatom(s) selected from the group consisting of nitrogen atom, sulfur atom and oxygen atom other than the carbon atom in the ring. The ring includes a monocycle or a fused ring.

As the "aromatic hetero ring", example includes a ring derived from the above "heteroaryl", and especially a 6-membered ring is preferable. An example includes pyridine, pyridazine, pyrimidine, pyrazine or the like.

"Nonaromatic hetero ring" means a nonaromatic ring which contains one or more heteroatom(s) selected from the group consisting of nitrogen atom, sulfur atom and oxygen atom other than the carbon atom in the ring. The ring means a 5 to 10 membered ring which may have a saturated or an unsaturated bond partially and may be fused with aryl or aromatic hetero ring.

"Nitrogen-containing hetero ring" means a ring which contains at least one nitrogen atom in the ring, and moreover may nitrogen, sulfur and/or oxygen atom(s). The ring includes a monocycle or a fused ring, and may include an aromatic hetero ring or a nonaromatic hetero ring.

"Substituted alkyl", "substituted alkenyl", "substituted alkynyl", "substituted aryl", "substituted heteroaryl", "substituted cycloalkyl", "substituted cycloalkenyl", "substituted heterocyclyl", "substituted alkyloxycarbonyl", "substituted acyl", "substituted alkyloxy", "substituted aryloxy", "substituted heteroaryloxy", "substituted cycloalkyloxy", "substituted cycloalkenyloxy", "substituted heterocyclyloxy", "substituted alkylthio", "substituted arylthio", "substituted heteroarylthio", "substituted cycloalkylthio", "substituted cycloalkenylthio", "substituted heterocyclylthio", "substituted alkylsulfonyl", "substituted arylsulfonyl", "substituted heteroarylsulfonyl", "substituted cycloalkylsulfonyl", "substituted cycloalkenylsulfonyl", "substituted heterocyclylsulfonyl", "substituted carbamoyl", "substituted carbamoyloxy", "substituted alkylcarbonyl", "substituted alkenylcarbonyl", "substituted cycloalkylcarbonyl", "substituted cycloalkenylcarbonyl", "substituted arylcarbonyl", "substituted heteroarylcarbonyl", "substituted heterocyclylcarbonyl", "a ring formed by taking together $R^6$ and $R^7$ with the adjacent carbon atom to which they are attached" or "a ring formed by taking together $R^{10}$ and $R^{11}$ with the adjacent carbon atom to which they are attached" may be substituted with 1 to 4 substituent(s) selected from a group consisting of, for example, halogen, hydroxy, carboxy, nitro, cyano, substituted or unsubstituted alkyl (an example of a substituent of substituted alkyl includes halogen, hydroxy, carboxy, nitro, cyano, alkyl, alkenyl, alkynyl, substituted or unsubstituted aryl (an example of a substituent of substituted aryl includes carboxy, cyano or alkyloxycarbonyl.), substituted or unsubstituted heteroaryl (an example of a substituent of substituted heteroaryl includes carboxy or alkyloxycarbonyl.), substituted or unsubstituted cycloalkyl (an example of a substituent of substituted cycloalkyl includes $CH_2OH$.), cycloalkenyl, heterocyclyl, alkyloxy, alkyloxycarbonyl, alkyloxycarbonylamino, substituted or unsubstituted carbamoyl (an example of a substituent of substituted carbamoyl includes alkyl, $CH_2CN$, $CH_2CH_2N(CH_3)_2$, $CH_2CH_2CH_2N(CH_3)_2$, $CH_2OH$, $CH_2CH_2OH$, $CH_2CH_2CH_2OH$), dimethylamino, substituted or unsubstituted acyl (an example of a substituent of substituted acyl includes alkyl.). e.g.: methyl, ethyl, isopropyl, tert-butyl, $CF_3$, $CH_2OH$, $CH_2CH_2OH$, $CH_2COOCH_3$, $CH_2NH_2$, $CH_2CN$ or benzyl), substituted or unsubstituted alkenyl (an example of a substituent of substituted alkenyl includes halogen, hydroxy, carboxy, nitro, cyano, alkyl, alkenyl, alkynyl, aryl, heteroaryl, cycloalkyl, cycloalkenyl or heterocyclyl. e.g.: vinyl), substituted or unsubstituted alkynyl (an example of a substituent of substituted alkynyl includes halogen, hydroxy, carboxy, nitro, cyano, alkyl, alkenyl, alkynyl, aryl, heteroaryl, cycloalkyl, cycloalkenyl or heterocyclyl. e.g.: ethynyl), substituted or unsubstituted aryl (an example of a substituent of substituted aryl includes halogen, hydroxy, carboxy, nitro, cyano, amino, substituted or unsubstituted alkyl (an example of a substituent of substituted alkyl includes halogen.), alkenyl, alkynyl, aryl, heteroaryl, cycloalkyl, cycloalkenyl, heterocyclyl, substituted or unsubstituted alkyloxy (an example of a substituent of substituted alkyloxy includes heterocyclyl, amino, dimethylamino or alkyloxycarbonylamino.), cycloalkyloxy, substituted or unsubstituted heterocyclyloxy (an example of a substituent of substituted heterocyclyloxy includes alkyl, alkyloxycarbonyl or acyl.), alkylheterocyclyloxy, alkyloxycarbonyl, carbamoyl, alkyloxycarbonylamino or substituted or unsubstituted heterocyclylamino (an example of a substituent of substituted heterocyclylamino includes alkyl.). e.g.: phenyl or naphthyl), substituted or unsubstituted cycloalkyl (an example of a substituent of substituted cycloalkyl includes halogen, hydroxy, carboxy, nitro, cyano, substituted or unsubstituted alkyl (an example of a substituent of substituted alkyl includes alkyloxy.), alkenyl, alkynyl, substituted or unsubstituted aryl (an example of a substituent of substituted aryl includes halogen.), cycloalkyl, cycloalkenyl, heteroaryl, heterocyclyl, alkyloxycarbonyl or CH$_2$OH. e.g.: cyclopropyl or cyclobutyl), substituted or unsubstituted cycloalkenyl (an example of a substituent of substituted cycloalkenyl includes halogen, hydroxy, carboxy, nitro, cyano, alkyl, alkenyl, alkynyl, aryl, heteroaryl, cycloalkyl, cycloalkenyl or heterocyclyl. e.g.: cyclopropenyl), substituted or unsubstituted heteroaryl (an example of a substituent of substituted heteroaryl includes halogen, hydroxy, carboxy, nitro, cyano, alkyl, alkenyl, alkynyl, aryl, heteroaryl, cycloalkyl, cycloalkenyl, heterocyclyl or substituted or unsubstituted alkyloxy (an example of a substituent of substituted alkyloxy includes dimethylamino.). e.g.: tetrazolyl, indolyl or pyrazolyl), substituted or unsubstituted heterocyclyl (an example of a substituent of substituted heterocyclyl includes halogen, hydroxy, carboxy, nitro, cyano, alkyl, alkenyl, alkynyl, aryl, heteroaryl, cycloalkyl, cycloalkenyl, heterocyclyl or alkylsulfonyl. e.g.: pyrrolidinyl, morpholinyl, piperazinyl or piperidyl), substituted or unsubstituted alkyloxy (an example of a substituent of substituted alkyloxy includes halogen, hydroxy, carboxy, nitro, cyano, alkyl, alkenyl, alkynyl, aryl, heteroaryl, cycloalkyl, cycloalkenyl or heterocyclyl. e.g.: methoxy, ethoxy, propoxy, OCF$_3$ or butoxy), substituted or unsubstituted aryloxy (an example of a substituent of substituted aryloxy includes halogen, hydroxy, carboxy, nitro, cyano, alkyl, alkenyl, alkynyl, aryl, heteroaryl, cycloalkyl, cycloalkenyl or heterocyclyl. e.g.: phenyloxy), substituted or unsubstituted silyloxy, substituted or unsubstituted amino (e.g.: alkylamino (e.g.: methylamino, ethylamino or dimethylamino), acylamino (e.g.: acetylamino or benzoylamino), arylalkylamino (e.g.: benzylamino or tritylamino), hydroxyamino, alkyloxycarbonylamino, alkylsulfonylamino, carbamoylamino, heterocyclylcarbonylamino, arylsulfonylamino, heteroarylsulfonylamino), substituted or unsubstituted carbamoyl (an example of a substituent of substituted carbamoyl includes hydroxy, cyano, alkyl, alkenyl, alkynyl, aryl, heteroaryl, cycloalkyl, cycloalkenyl, heterocyclyl, alkyloxy or alkylsulfonyl. e.g.: alkylcarbamoyl (e.g.: methylcarbamoyl, ethylcarbamoyl, dimethylcarbamoyl, phenylethylcarbamoyl, dimethylaminoethylcarbamoyl, isopropylcarbamoyl or hydroxyethylcarbamoyl), alkylsulfonylcarbamoyl, heteroarylalkylcarbamoyl or substituted or unsubstituted alkyloxycarbamoyl), substituted or unsubstituted carbamoyloxy (an example of a substituent of substituted carbamoyloxy includes halogen, alkyl, alkenyl, alkynyl, aryl, heteroaryl, cycloalkyl, cycloalkenyl or heterocyclyl.), substituted or unsubstituted acyl (an example of a substituent of substituted acyl includes halogen, hydroxy, carboxy, nitro, cyano, alkyl, alkenyl, alkynyl, aryl, heteroaryl, cycloalkyl, cycloalkenyl or heterocyclyl. e.g.: alkylcarbonyl, arylcarbonyl, heteroarylcarbonyl, heterocyclylcarbonyl, formyl or acetyl), substituted or unsubstituted alkylsulfonyl (an example of a substituent of substituted alkylsulfonyl includes halogen, hydroxy, carboxy, nitro, cyano, alkyl, alkenyl, alkynyl, aryl, heteroaryl, cycloalkyl, cycloalkenyl or heterocyclyl. e.g.: methanesulfonyl or ethanesulfonyl), substituted or unsubstituted arylsulfonyl (an example of a substituent of substituted arylsulfonyl includes halogen, hydroxy, carboxy, nitro, cyano, alkyl, alkenyl, alkynyl, aryl, heteroaryl, cycloalkyl, cycloalkenyl or heterocyclyl.), substituted or unsubstituted heteroarylsulfonyl (an example of a substituent of substituted heteroarylsulfonyl includes halogen, hydroxy, carboxy, nitro, cyano, alkyl, alkenyl, alkynyl, aryl, heteroaryl, cycloalkyl, cycloalkenyl or heterocyclyl.), substituted or unsubstituted cycloalkylsulfonyl (an example of a substituent of substituted cycloalkylsulfonyl includes halogen, hydroxy, carboxy, nitro, cyano, alkyl, alkenyl, alkynyl, aryl, heteroaryl, cycloalkyl, cycloalkenyl or heterocyclyl.), substituted or unsubstituted heterocyclylsulfonyl (an example of a substituent of substituted heterocyclylsulfonyl includes halogen, hydroxy, carboxy, nitro, cyano, alkyl, alkenyl, alkynyl, aryl, heteroaryl, cycloalkyl, cycloalkenyl or heterocyclyl.), substituted or unsubstituted sulfamoyl (an example of a substituent of substituted sulfamoyl includes alkyl, alkenyl, alkynyl, aryl, heteroaryl, cycloalkyl, cycloalkenyl or heterocyclyl.), substituted or unsubstituted alkyloxycarbonyl (an example of a substituent of substituted alkyloxycarbonyl includes halogen, hydroxy, carboxy, nitro, cyano, alkyl, alkenyl, alkynyl, aryl, heteroaryl, cycloalkyl, cycloalkenyl or heterocyclyl. e.g.: methoxycarbonyl, ethoxycarbonyl or tert-butoxycarbonyl), substituted or unsubstituted aryloxycarbonyl (an example of a substituent of substituted aryloxycarbonyl includes halogen, hydroxy, carboxy, nitro, cyano, alkyl, alkenyl, alkynyl, aryl, heteroaryl, cycloalkyl, cycloalkenyl or heterocyclyl.), substituted or unsubstituted heteroaryloxycarbonyl (an example of a substituent of substituted heteroaryloxycarbonyl includes halogen, hydroxy, carboxy, nitro, cyano, alkyl, alkenyl, alkynyl, aryl, heteroaryl, cycloalkyl, cycloalkenyl or heterocyclyl.), substituted or unsubstituted heterocyclyloxycarbonyl (an example of a substituent of substituted heterocyclyloxycarbonyl includes halogen, hydroxy, carboxy, nitro, cyano, alkyl, alkenyl, alkynyl, aryl, heteroaryl, cycloalkyl, cycloalkenyl or heterocyclyl.), alkylsulfinyl,
cycloalkylsulfinyl,
arylsulfinyl,
heteroarylsulfinyl,
heterocyclylsulfinyl,
nitroso,
alkenyloxy (e.g.: vinyloxy or allyloxy),
arylalkyloxy (e.g.: benzyloxy),
azide,
isocyano,
isocyanato,
thiocyanato,
isothiocyanato,
mercapto,
alkylthio (e.g.: methylthio),
formyloxy,
haloformyl,
oxalo,
thioformyl, thiocarboxy,
dithiocarboxy,
thiocarbamoyl,
sulfino,
sulfo,
sulfoamino,
hydrazino,
ureide,
amidino,
guanidino,
phthalimide,
oxo and the like.

Example of a substituent of "substituted carbamoyl", "substituted amino" or "substituted carbamoyloxy" includes hydroxy, substituted or unsubstituted alkyl (an example of a substituent of substituted alkyl includes halogen, hydroxy, carboxy, nitro, cyano, alkyl, substituted or unsubstituted aryl (an example of a substituent of substituted aryl includes carboxy, cyano or alkyloxycarbonyl.), substituted or unsubstituted heteroaryl (an example of a substituent of substituted heteroaryl includes carboxy or alkyloxycarbonyl.), substituted or unsubstituted cycloalkyl (an example of a substituent of substituted cycloalkyl includes $CH_2OH$.), dimethylamino, alkyloxy, alkyloxycarbonyl, substituted or unsubstituted carbamoyl (an example of a substituent of substituted carbamoyl includes alkyl, $CH_2CN$, $CH_2CH_2N(CH_3)_2$, $CH_2CH_2CH_2N(CH_3)_2$, $CH_2OH$, $CH_2CH_2OH$, $CH_2CH_2CH_2OH$), substituted or unsubstituted acyl (an example of a substituent of substituted acyl includes alkyl.).), substituted or unsubstituted alkenyl (an example of a substituent of substituted alkenyl includes halogen, hydroxy, carboxy, nitro, cyano, alkyl, alkenyl, alkynyl, aryl, heteroaryl, cycloalkyl, cycloalkenyl or heterocyclyl. e.g.: vinyl), substituted or unsubstituted alkynyl (an example of a substituent of substituted alkynyl includes halogen, hydroxy, carboxy, nitro, cyano, alkyl, alkenyl, alkynyl, aryl, heteroaryl, cycloalkyl, cycloalkenyl or heterocyclyl. e.g.: ethynyl), substituted or unsubstituted aryl (an example of a substituent of substituted aryl includes halogen, hydroxy, carboxy, nitro, cyano, substituted or unsubstituted alkyl (an example of a substituent of substituted alkyl includes heterocyclylalkyl.), alkenyl, alkynyl, aryl, heteroaryl, cycloalkyl, cycloalkenyl, heterocyclyl, substituted or unsubstituted alkyloxy (an example of a substituent of substituted alkyloxy includes heterocyclyl, amino, dimethylamino, alkyloxycarbonylamino, $N(CH_3)(COOC(CH_3)_3)$ or $NHCH_3$.), cycloalkyloxy, substituted or unsubstituted heterocyclyloxy (an example of a substituent of substituted heterocyclyloxy includes alkyl, alkyloxycarbonyl or acyl.), alkyloxycarbonyl, alkylheterocyclyloxy, carbamoyl, alkyloxycarbonylamino, amino or substituted or unsubstituted heterocyclylamino (an example of a substituent of substituted heterocyclylamino includes alkyl.).), substituted or unsubstituted heteroaryl (an example of a substituent of substituted heteroaryl includes halogen, hydroxy, carboxy, nitro, cyano, alkyl, alkenyl, alkynyl, aryl, heteroaryl, cycloalkyl, cycloalkenyl, heterocyclyl or substituted or unsubstituted alkyloxy (an example of a substituent of substituted alkyloxy includes dimethylamino.).), substituted or unsubstituted cycloalkyl (an example of a substituent of substituted cycloalkyl includes halogen, hydroxy, carboxy, nitro, cyano, substituted or unsubstituted alkyl (an example of a substituent of substituted alkyl includes alkyloxy.), alkenyl, alkynyl, substituted or unsubstituted aryl (an example of a substituent of substituted aryl includes halogen.), heteroaryl, cycloalkyl, cycloalkenyl, heterocyclyl, $CH_2OH$, alkyloxycarbonyl.), substituted or unsubstituted cycloalkenyl (an example of a substituent of substituted cycloalkenyl includes halogen, hydroxy, carboxy, nitro, cyano, alkyl, alkenyl, alkynyl, aryl, heteroaryl, cycloalkyl, cycloalkenyl or heterocyclyl. e.g.: cyclopropenyl), substituted or unsubstituted heterocyclyl (an example of a substituent of substituted heterocyclyl includes halogen, hydroxy, carboxy, nitro, cyano, alkyl, alkenyl, alkynyl, aryl, heteroaryl, cycloalkyl, cycloalkenyl, heterocyclyl or alkylsulfonyl.), alkyloxy,
aryloxy,
heteroaryloxy,
cycloalkyloxy,
heterocyclyloxy, substituted or unsubstituted acyl (an example of a substituent of substituted acyl includes hydroxy, cyano or alkyloxy.), substituted or unsubstituted alkyloxycarbonyl (an example of a substituent of substituted alkyloxycarbonyl includes alkyl.), aryloxycarbonyl,
heteroaryloxycarbonyl,
cycloalkyloxycarbonyl,
heterocyclyloxycarbonyl, substituted or unsubstituted sulfamoyl (an example of a substituent of substituted sulfamoyl includes substituted or unsubstituted alkyl (an example of a substituent of substituted alkyl includes carboxy or dimethylamino.) or alkyloxycarbonyl.), substituted or unsubstituted alkylsulfonyl (an example of a substituent of substituted alkylsulfonyl includes halogen or aryl.), substituted or unsubstituted arylsulfonyl (an example of a substituent of substituted arylsulfonyl includes halogen or alkyloxy.), heteroarylsulfonyl,
cycloalkylsulfonyl,
heterocyclylsulfonyl, substituted or unsubstituted carbamoyl (an example of a substituent of substituted carbamoyl includes alkyl.), alkylsulfinyl,
arylsulfinyl,
heteroarylsulfinyl,
cycloalkylsulfinyl,
heterocyclylsulfinyl,
amino or the like.

The alkyl part of "alkyloxycarbonyl", "alkyloxycarbonylamino", "alkylamino", "arylalkylamino", "alkylaminoalkyl", "alkyloxycarbonylamino", "alkylsulfonylamino", "alkyloxy", "alkylsulfonyl", "alkylcarbamoyl", "alkylsulfonylcarbamoyl", "heteroarylalkylcarbamoyl", "substituted or unsubstituted alkyloxycarbamoyl", "alkylcarbonyl", "alkylsulfinyl", "arylalkyloxy", "alkylheterocyclyloxy" and "alkylthio" means the above "alkyl".

The alkenyl part of "alkenyloxy" means the above "alkenyl".

The aryl part of "arylalkylamino", "arylsulfonylamino", "arylcarbonyl", "aryloxycarbonyl", "arylsulfinyl", "arylalkyloxy" and "arylsulfonyl" means the above "aryl".

The heteroaryl part of "heteroarylalkylcarbamoyl", "heteroarylsulfonylamino", "heteroarylcarbonyl", "heteroaryloxycarbonyl", "heteroarylsulfonyl" and "heteroarylsulfinyl" means the above "heteroaryl".

The heterocyclyl part of "heterocyclylcarbonyl", "heterocyclylcarbonylamino", "heterocyclyloxycarbonyl", "heterocyclylsulfonyl", "alkylheterocyclyloxy", "heterocyclylamino" and "heterocyclylsulfinyl" means the above "heterocyclyl."

The cycloalkyl part of "cycloalkylsulfonyl" and "cycloalkylsulfinyl" means the above "cycloalkyl".

Among the present compounds, the following embodiments are preferable.

Ring A means aromatic carbocycle, nonaromatic carbocycle, aromatic hetero ring or nonaromatic hetero ring which is fused with the adjacent 5 membered ring.

Ring A in the formula (I) means aromatic carbocycle or aromatic hetero ring which is fused with the adjacent 5 membered ring. Ring A includes not only a monocycle but also a fused ring (2 to 3 fused ring), and especially a monocycle is preferable. A substitutable arbitrary position in Ring A is substituted with $R^1$ (including hydrogen), and (a) substitutable arbitrary position(s) other than the position which is substituted with $R^1$ may be substituted with 0 to 3 of $R^X$.

As the Ring A, for example, the following rings are included. In the following rings, a substitutable arbitrary position other than the position which is substituted with $R^1$ (including hydrogen) may be substituted with 0 to 3 of $R^X$.

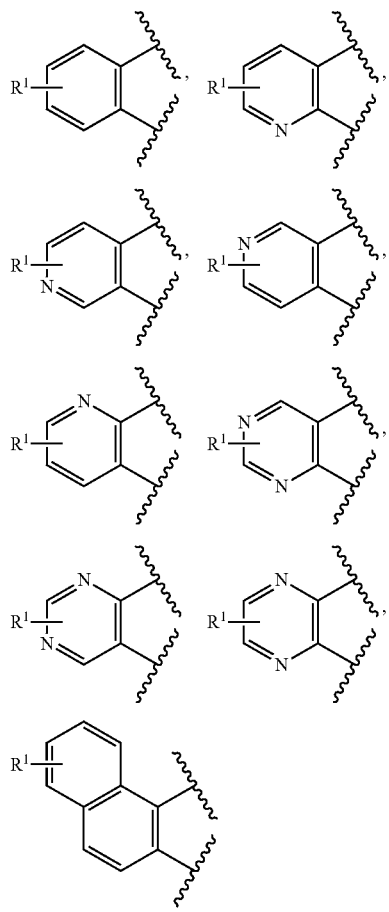

Herein, $R^1$ has the same meaning as the above. In the above formula, a substitutable arbitrary position in Ring A may be substituted with $R^1$.

Preferably, the following rings are included:

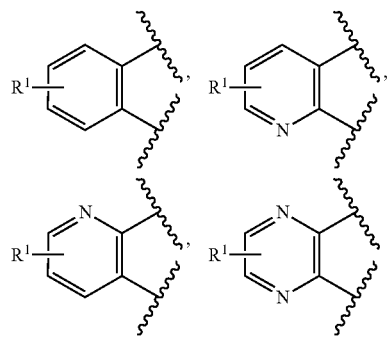

Z is —$NR^5$—, —O— or —S—. Preferable is —O— or —S— and more preferable is —S—.

$R^5$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxycarbonyl or substituted or unsubstituted acyl.

Preferable is hydrogen, substituted or unsubstituted alkyl, substituted or unsubstituted aryl or substituted or unsubstituted cycloalkyl.

$R^1$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino.

Preferable is hydrogen, halogen, cyano, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl or substituted or unsubstituted amino.

More preferable is hydrogen, halogen, cyano, substituted or unsubstituted alkyl, substituted or unsubstituted aryl, substituted or unsubstituted heteroaryl, substituted or unsubstituted aryloxy, substituted or unsubstituted heteroaryloxy, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl or substituted or unsubstituted amino.

$R^2$ and $R^3$ are each independently hydrogen, halogen, hydroxy, cyano, nitro, carboxy, substituted or unsubstituted alkyl or substituted or unsubstituted alkyloxy, $R^2$ and $R^3$ taken together with the adjacent carbon atom to which they are attached may form oxo.

Preferable is hydrogen.

$R^4$ is a group represented by the formula: —$(CR^6R^7)n$-$R^8$.

$R^6$ and $R^7$ are each independently hydrogen, halogen, hydroxy, carboxy, substituted or unsubstituted alkyl or substituted or unsubstituted alkyloxy, $R^6$ and $R^7$ taken together with the adjacent carbon atom to which they are attached may form a substituted or unsubstituted ring.

Preferable is hydrogen.

"A ring formed by taking together $R^6$ and $R^7$ with the adjacent carbon atom to which they are attached" means a 3- to 15-membered saturated or unsaturated hydrocarbon ring or a 3- to 15-membered saturated or unsaturated hetero ring containing 1 to 4 oxygen, sulfur, and/or nitrogen atom(s) in said hydrocarbon ring. Preferable is nonaromatic ring, and an example includes cyclopropane, cyclobutane, cyclopentane, cyclohexane, cycloheptane, cyclooctane, cyclopropene, cyclobutene, cyclopentene, cyclohexene, cycloheptene, a saturated or unsaturated hetero ring containing 1 to 4 oxygen, sulfur, and/or nitrogen atom(s) in the above hydrocarbon ring.

Preferably, the following rings are included:

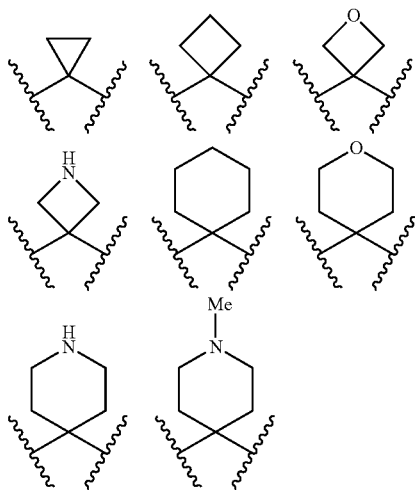

n is an integer of 0 to 3. Preferable is 1 or 2. More preferable is 1.

$R^8$ is carboxy, cyano, substituted or unsubstituted alkyl, substituted or unsubstituted acyl, with the proviso that n is not 0 when $R^8$ is substituted or unsubstituted acyl, substituted or unsubstituted alkyloxycarbonyl, substituted or unsubstituted alkylsulfonyl, substituted or unsubstituted carbamoyl, substituted or unsubstituted amino, substituted or unsubstituted carbamoyloxy or substituted or unsubstituted alkyloxy.

Preferable is carboxy, cyano, substituted or unsubstituted carbamoyl or substituted or unsubstituted amino.

More preferable is a group represented by the formula: —(C=O)—$NR^9$—$(CR^{10}R^{11})$—$R^{12}$.

$R^9$ is hydrogen, substituted or unsubstituted alkyl, substituted or unsubstituted aryl, substituted or unsubstituted heteroaryl, substituted or unsubstituted cycloalkyl, substituted or unsubstituted cycloalkenyl or substituted or unsubstituted heterocyclyl.

Preferable is hydrogen, substituted or unsubstituted alkyl, substituted or unsubstituted aryl, substituted or unsubstituted heteroaryl, substituted or unsubstituted cycloalkyl or substituted or unsubstituted heterocyclyl.

$R^{10}$ and $R^{11}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl or substituted or unsubstituted alkyloxy, $R^{10}$ and $R^{11}$ taken together with the adjacent carbon atom to which they are attached may form a substituted or unsubstituted ring.

Preferable is hydrogen or substituted or unsubstituted alkyl, or $R^{10}$ and $R^{11}$ taken together with the adjacent carbon atom to which they are attached may form a substituted or unsubstituted ring.

"A ring formed by taking together $R^{10}$ and $R^{11}$ with the adjacent carbon atom to which they are attached" means a 3- to 15-membered saturated or unsaturated hydrocarbon ring or a 3- to 15-membered saturated or unsaturated hetero ring containing 1 to 4 oxygen, sulfur, and/or nitrogen atom(s) in said hydrocarbon ring. Preferable is nonaromatic ring, and an example includes cyclopropane, cyclobutane, cyclopentane, cyclohexane, cycloheptane, cyclooctane, cyclopropene, cyclobutene, cyclopentene, cyclohexene, cycloheptene, a saturated or unsaturated hetero ring containing 1 to 4 oxygen, sulfur, and/or nitrogen atom(s) in the above hydrocarbon ring.

Preferable is cyclopropane.

$R^{12}$ is cyano, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl or substituted or unsubstituted alkyloxycarbonyl.

Preferable is cyano, carboxy, substituted or unsubstituted alkyl, substituted or unsubstituted aryl, substituted or unsubstituted heteroaryl, substituted or unsubstituted cycloalkyl or substituted or unsubstituted heterocyclyl.

$R^x$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino.

Preferable is halogen, cyano, substituted or unsubstituted alkynyl, substituted or unsubstituted aryl, substituted or unsubstituted heteroaryl, substituted or unsubstituted heterocyclyl, substituted or unsubstituted alkyloxy, substituted or unsubstituted aryloxy, substituted or unsubstituted alkylsulfonyl, substituted or unsubstituted arylsulfonyl, substituted or unsubstituted carbamoyl or substituted or unsubstituted amino.

More preferable is halogen, cyano, substituted or unsubstituted aryl, substituted or unsubstituted heteroaryl, substituted or unsubstituted alkyloxy, substituted or unsubstituted aryloxy or substituted or unsubstituted alkylsulfonyl.

m is an integer of 0 to 3. Preferable is an integer of 0 to 2.

Ring B in the formula (III) is nitrogen-containing hetero ring in which at least the one atom neighboring to the carbon atom binding to a group represented by the formula:

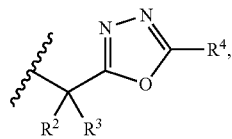

wherein $R^2$, $R^3$ and $R^4$ in the above formula have the same meaning as the above, is nitrogen atom.

Ring B includes not only a monocycle but also a fused ring (2 to 3 fused ring), and especially a monocycle or a bicycle is preferable. Ring B may include a heteroatom other than the nitrogen atom shown in the above formula (III) and the constituent atom of the Ring B includes carbon atom, oxygen atom, nitrogen atom or sulfur atom. The bond constructing the Ring B includes a single bond or a double bond.

Ring B may be substituted with a substituent other than a group represented by the formula:

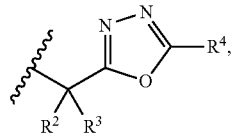

wherein $R^2$, $R^3$ and $R^4$ have the same meaning as the above.

As the Ring B, for example, the following rings are included.

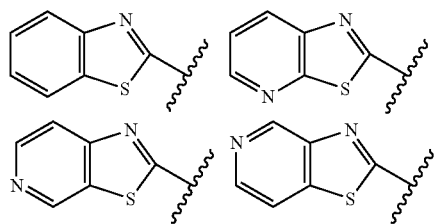

-continued

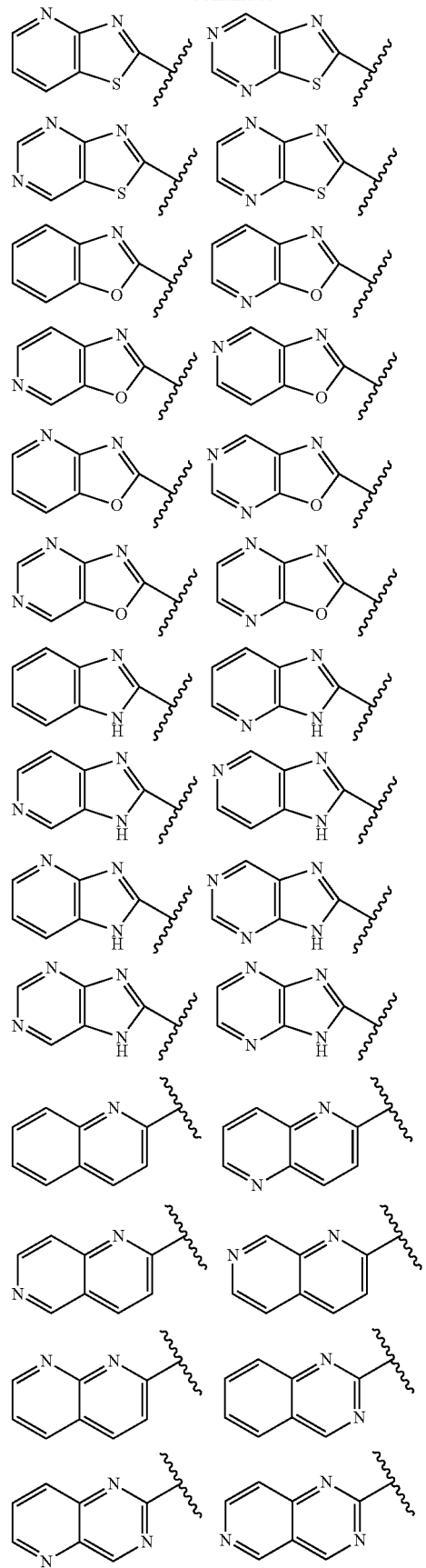

-continued

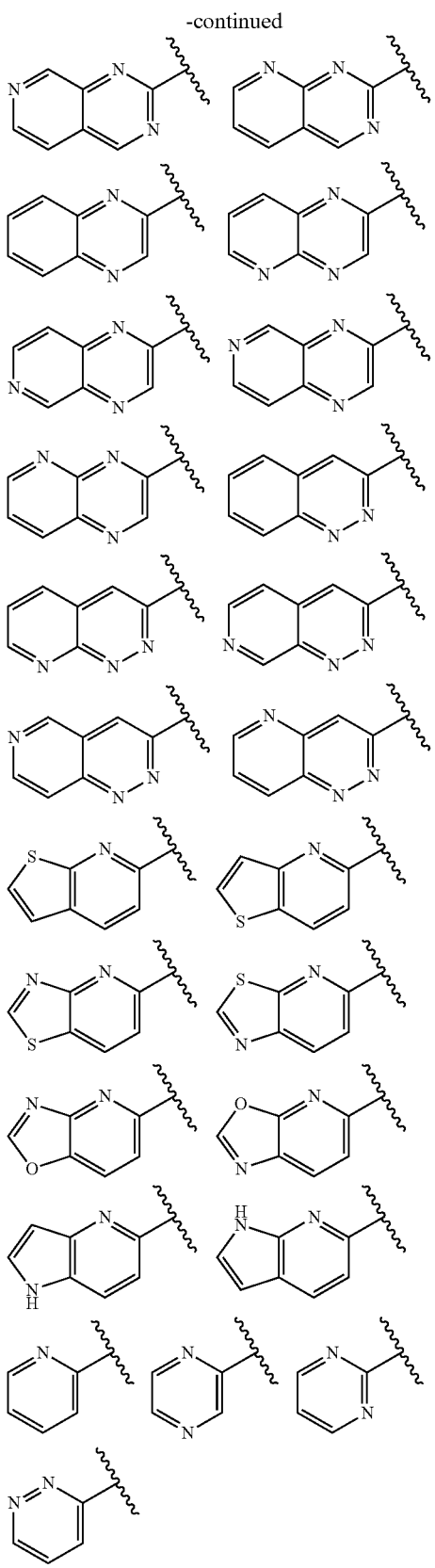

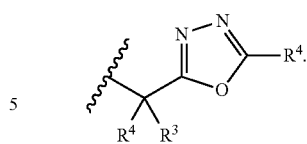

As Ring B, preferable is a group represented by the formula:

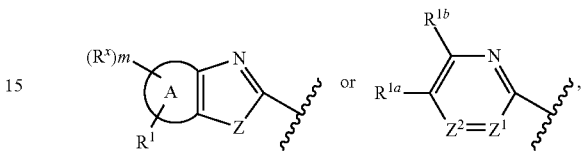

wherein Ring A, $R^x$, m, $R^1$, Z, $R^{1a}$, $R^{1b}$, $Z^1$ and $Z^2$ have the same meaning as the above.

An example of (a) substituent(s) on Ring B, other than the group represented by the formula:

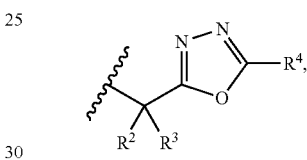

includes halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted amino or the like. Ring B may be substituted with 1 to 4 of the substituent(s).

$Z^1$ is =$CR^1$— or =N—.
$Z^2$ is —$CR^1$= or —N=.
$R^{1a}$ and $R^{1b}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycly- In the above Ring B, a substitutable arbitrary position may be substituted with a substituent other than a group represented by the formula:

loxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino, or $R^{1a}$ and $R^{1b}$ taken together with the adjacent carbon atom to which they are attached may form a substituted or unsubstituted ring.

"A ring formed by taking together $R^{10}$ and $R^{11}$ with the adjacent carbon atom to which they are attached" means a 3- to 15-membered saturated or unsaturated hydrocarbon ring or a 3- to 15-membered saturated or unsaturated hetero ring containing 1 to 4 oxygen, sulfur, and/or nitrogen atom(s) in said hydrocarbon ring. Preferable is aromatic ring.

For example, the following rings are exemplified.

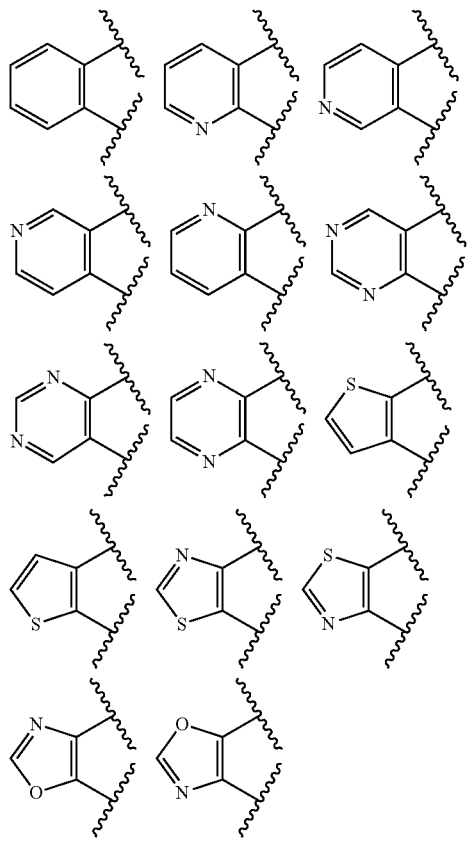

An example of (a) substituent(s) of "a ring formed by taking together $R^{1a}$ and $R^{1b}$ with the adjacent carbon atom to which they are attached" includes halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted amino or the like.

In the above Ring, a substitutable arbitrary position may be substituted with 1 to 4 of the above substituent(s).

One or more hydrogen, carbon or other atoms of the compound of formula (I), (II) and (III) of the present invention can be replaced by an isotope of the hydrogen, carbon or other atoms.

For example, compounds of formula (I) include all radiolabeled forms of compounds of formula (I). The "radiolabeled," "radiolabeled form" and the like of the compound of formula (I) are encompassed by the present invention and useful as a research and/or diagnostic tool in metabolism pharmacokinetic studies and in binding assays.

Examples of isotopes that can be incorporated into the compound of formula (I) of the present invention include isotopes of hydrogen, carbon, nitrogen, oxygen, phosphorous, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Radiolabeled compounds of the present invention can be prepared by methods known in the art. For example, tritiated compounds of formula (I) can be prepared by introducing tritium into the particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

As a pharmaceutically acceptable salt of the present compound, the following salts can be included.

As a basic salt, example includes alkali metal salt such as sodium salt or potassium salt; alkaline earth metal salt such as calcium salt or strontium salt; metal salt such as beryllium salt, magnesium salt, zinc salt or transition metal salt; ammonium salt; aliphatic amine salt such as trimethylamine salt, triethylamine salt, dicyclohexylamine salt, ethanolamine salt, diethanolamine salt, triethanolamine salt, procaine salt, meglumine salt, diethanolamine salt or ethylenediamine salt; aralkylamine salt such as N,N-dibenzylethylenediamine salt or benethamine salt; heterocyclic aromatic amine salt such as pyridine salt, picoline salt, quinoline salt, or isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt, or tetrabutylammonium salt; basic amino acid salt such as arginine salt or lysine salt or the like.

As an acidic salt, example includes inorganic acid salt such as hydrochloride, sulfate, nitrate, phosphate, carbonate, hydrogencarbonate, or perchlorate; organic acid salt such as acetate, propionate, lactate, maleate, fumarate, tartrate, malate, citrate or ascorbate; sulfonate such as methanesulfonate, isethionate, benzenesulfonate or p-toluenesulfonate; acidic amino acid salt such as aspartate or glutamate or the like.

The term "solvate" means a solvate of a compound of the present invention or a pharmaceutically acceptable salt thereof, and example includes alcohol (e.g., ethanol) solvate, hydrate or the like. Example of hydrate includes monohydrate, dihydrate or the like.

The term "inhibition", as used herein, means that the present compound inhibits work of EL.

The term "pharmaceutically acceptable", as used herein, means being not harmful for prevention or treatment.

A general method for producing the present compound is exemplified below. Also extraction, purification and the like may be conducted in a procedure performed in usual organic chemical experiment.

The compound represented by the Formula (I-1) can be synthesized by the following method.

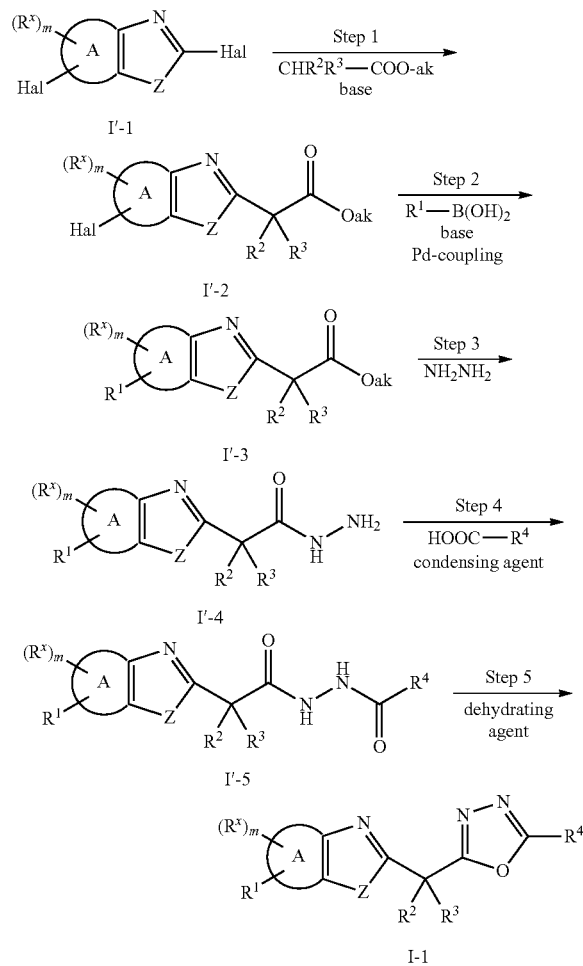

wherein each symbol in the above scheme has the same meaning as the above, and as to the compound represented by the Formula (I'-1), a known compound can be used, or a compound derived from a known compound by a usual method can be used. ak is C1 to C3 alkyl and Hal is halogen.

Step 1

Step 1 is a process for preparing the compound represented by the Formula (I'-2) which comprises reacting the compound represented by the Formula (I'-1) with the compound represented by the Formula: $CHR^2R^3$—COO-ak.

As a solvent, example includes N,N-dimethylformamide, dimethylsulfoxide, aromatic hydrocarbons (e.g., toluene, benzene, xylene or the like), saturated hydrocarbons (e.g., cyclohexane, hexane or the like), halogenated hydrocarbons (e.g., dichloromethane, chloroform, 1,2-dichloroethane or the like), ethers (e.g., tetrahydrofuran, diethylether, dioxane, 1,2-dimethoxyethane or the like), esters (e.g., methyl acetate, ethyl acetate or the like), ketones (e.g., acetone, methylethylketone or the like), nitriles (e.g., acetonitrile or the like), alcohols (e.g., methanol, ethanol, t-butanol or the like), water, a mixed solvent thereof or the like.

Preferably, aromatic hydrocarbons (e.g., toluene, benzene, xylene or the like) or ethers (e.g., tetrahydrofuran, diethylether, dioxane, 1,2-dimethoxyethane or the like) can be used.

As a base, example includes metal hydrides (e.g., sodium hydride or the like), metal hydroxides (e.g., sodium hydroxide, potassium hydroxide, lithium hydroxide, barium hydroxide or the like), metal carbonates (e.g., sodium carbonate, calcium carbonate, cesium carbonate or the like), metal alkoxides (e.g., sodium methoxide, sodium ethoxide, potassium t-butoxide or the like), sodium hydrogen carbonate, metal sodium, metal amide, organic amines (e.g., triethylamine, diisopropylethylamine, DBU, 2,6-lutidine or the like), pyridine, alkyl lithiums (n-BuLi, sec-BuLi, tert-BuLi or the like) or the like.

Preferably, metal sodium or metal amide can be used.

The reaction can be performed at −78 to 30° C. for 0.5 to 12 hours.

As a compound represented by the Formula: $CHR^2R^3$—COO-ak, example includes butyl acetate, ethyl acetate or methyl acetate.

Step 2

Step 2 is a process for preparing the compound represented by the Formula (I'-3) which comprises reacting the compound represented by the Formula (I'-2) with the compound represented by the Formula: $R^1$—$B(OH)_2$ in the presence of a palladium catalyst.

As a solvent, a solvent described in Step 1 can be used. Preferably, aromatic hydrocarbons (e.g., toluene, benzene, xylene or the like) or ethers (e.g., tetrahydrofuran, diethylether, dioxane, 1,2-dimethoxyethane or the like) can be used. The reaction can be performed under the conditions which do not use a solvent by using microwave.

As a base, a base described in Step 1 can be used. Preferably, metal carbonates (e.g., sodium carbonate, calcium carbonate, cesium carbonate or the like) or organic amines (e.g., triethylamine, diisopropylethylamine, DBU, 2,6-lutidine or the like) can be used.

The reaction can be performed in the presence of palladium catalyst (e.g., $Pd(PPh_3)_4$, $PdCl_2$, $Pd(OAc)_2$, $Pd(dba)_2$ or the like) and phosphine ligand (e.g., $PPh_3$, BINAP or the like) at a temperature at which a solvent being used is refluxed, for 0.5 to 12 hours. The reaction can be performed at 80 to 200° C. for 5 minutes to 1 hour by using microwave. This reaction can be performed in a solvent described above or without any solvent.

As a compound represented by the Formula: $R^1$—$B(OH)_2$, example includes phenyl boronic acid or the like.

Step 3

Step 3 is a process for preparing the compound represented by the Formula (I'-4) which comprises reacting the compound represented by the Formula (I'-3) with hydrazine.

As a solvent, a solvent described in Step 1 can be used. Preferably, N,N-dimethylformamide, alcohols (e.g., methanol, ethanol, t-butanol or the like) or N-methyl-2-pyrrolidone can be used.

The reaction can be performed at a temperature at which a solvent being used is refluxed, for 0.5 to 12 hours.

The reaction can be performed at 80 to 200° C. for 5 minutes to 1 hour by using microwave. This reaction can be performed in a solvent described in Step 1 or without any solvent.

Step 4

Step 4 is a process for preparing the compound represented by the Formula (I'-5) which comprises reacting the compound represented by the Formula (I'-4) with the compound represented by the Formula: HOOC—R⁴.

This reaction can be performed with the reaction condition known as the condition used for the condensation reaction of carboxylic acid and amine. For example, a condensing agent such as N,N'-dicyclohexylcarbodiimide (DCC), 1-ethyl-3-(3-dimethylaminopropyl)carbodiimide (WSCD) or the like can be used. 1-Hydroxybenzotriazole (HOBt), 3,4-dihydro-3-hydroxy-4-oxo-1,2,3-benzotriazine (HOOBt), N-hydroxysuccinimide (HOSu) or the like can be used as an additive.

As a solvent, a solvent described in Step 1 can be used. Preferably, anhydrous dimethylformamide, N,N-dimethylformamide, dimethylsulfoxide or N-methyl-2-pyrrolidone can be used.

The reaction can be performed at room temperature or a temperature at which a solvent being used is refluxed, for 0.5 to 24 hours.

The reaction can be performed at 80 to 200° C. for 5 minutes to 1 hour by using microwave. This reaction can be performed in a solvent described in Step 1 or without any solvent.

As a compound represented by the Formula: HOOC—R⁴, example includes 3-tert-butoxy-3-oxopropanoic acid, 4-tert-butoxy-4-oxobutanoic acid, 2-(tert-butoxycarbonylamino)acetic acid or the like.

Step 5

Step 5 is a process for preparing the compound represented by the Formula (I-1) which comprises dehydrating the compound represented by the Formula (I'-5).

As a solvent, a solvent described in Step 1 can be used. Preferably, halogenated hydrocarbons (e.g., dichloromethane, chloroform, 1,2-dichloroethane or the like) or ethers (e.g., tetrahydrofuran, diethylether, dioxane, 1,2-dimethoxyethane or the like) can be used.

As a dehydrating agent, burgess reagent, TsCl and organic amines, MsCl and organic amines, PPh₃ and CBr₄, PPh₃ and C₂Cl₆ or the like can be used.

The reaction can be performed at room temperature or a temperature at which a solvent being used is refluxed, for 0.5 to 24 hours.

The reaction can be performed at 80 to 200° C. for 5 minutes to 1 hour by using microwave. This reaction can be performed in a solvent described in Step 1 or without any solvent.

The compound represented by the Formula (II-1) can be synthesized by the same scheme as described above.

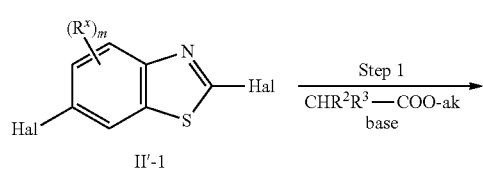

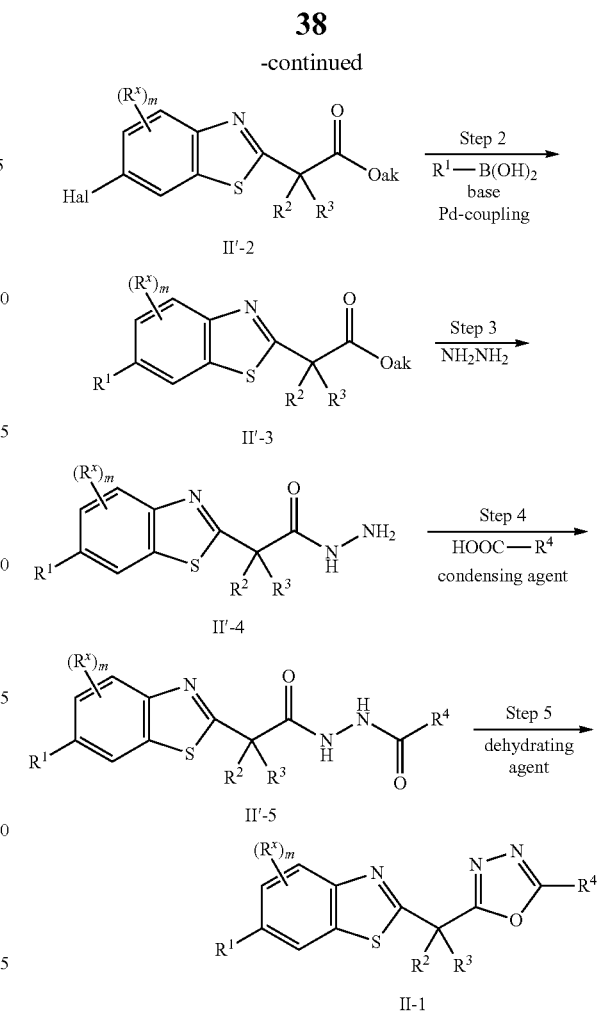

wherein each symbol in the above scheme has the same meaning as the above, and as to the compound represented by the Formula (II'-1), a known compound can be used, or a compound derived from a known compound by a usual method can be used. ak is C1 to C3 alkyl and Hal is halogen.

The compound represented by the Formula (III-1) can be synthesized by the same scheme as described above.

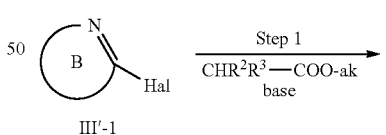

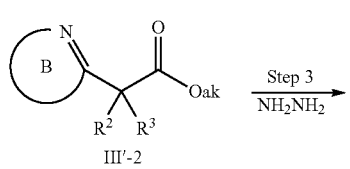

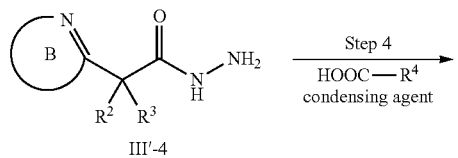

-continued

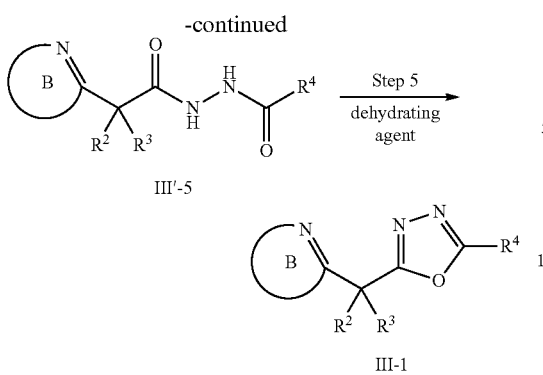

wherein each symbol in the above scheme has the same meaning as the above, and as to the compound represented by the Formula (III'-1), a known compound can be used, or a compound derived from a known compound by a usual method can be used. ak is C1 to C3 alkyl and Hal is halogen.

As to the compound represented by the Formula (III'-1), a commercially available compound can be used. The compound represented by the Formula can be synthesized by the organic synthesis reaction known well. For preparing a final compound which has a substituent on Ring B, the compound represented by the Formula (III'-1) which has such a substituent on Ring B can be used, instead such a substituent can be introduced to Ring B in the middle of Step 1 to 5, or such a substituent can be introduced after preparing the compound represented by the Formula (III-1).

The compound represented by the Formula (I'-2) can be synthesized by the following method.

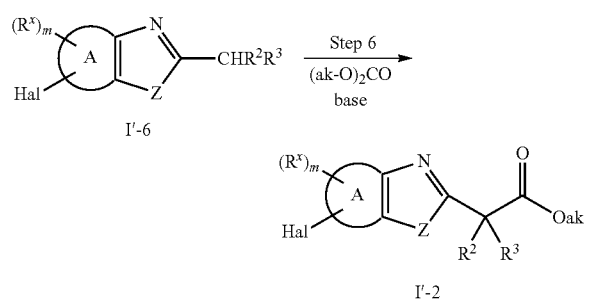

wherein each symbol in the above scheme has the same meaning as the above, and as to the compound represented by the Formula (I'-6), a known compound can be used, or a compound derived from a known compound by a usual method can be used. ak is C1 to C3 alkyl and Hal is halogen.

Step 6

Step 6 is a process for preparing the compound represented by the Formula (I'-2) which comprises reacting the compound represented by the Formula (I'-6) with the compound represented by the Formula: (ak-O)₂CO.

As a solvent, a solvent described in Step 1 can be used. Preferably, ethers (e.g., tetrahydrofuran, diethylether, dioxane or the like) can be used.

As a base, a base described in Step 1 can be used. Preferably, metal amide or alkyl lithiums (n-BuLi, sec-BuLi or tert-BuLi) can be used.

The reaction can be performed at −78 to 30° C. for 0.5 to 24 hours.

As a compound represented by the Formula: (ak-O)₂CO, example includes diethyl carbonate or the like.

The compound represented by the Formula (II'-2) can be synthesized by the same scheme as described above.

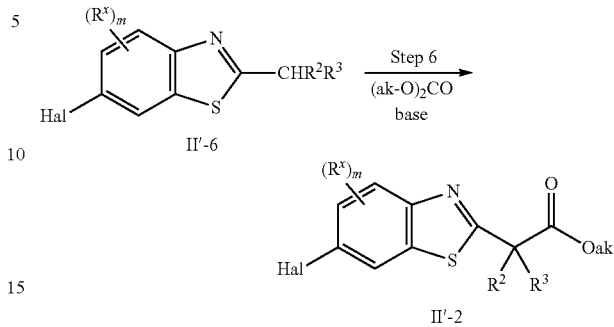

wherein each symbol in the above scheme has the same meaning as the above, and as to the compound represented by the Formula (II'-6), a known compound can be used, or a compound derived from a known compound by a usual method can be used. ak is C1 to C3 alkyl and Hal is halogen.

The compound represented by the Formula (III'-2) can be synthesized by the same scheme as described above.

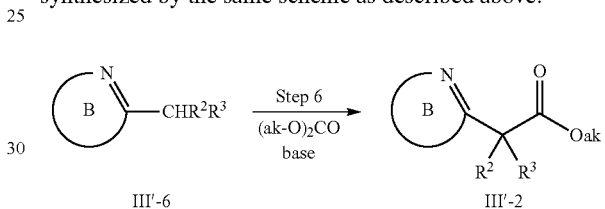

wherein each symbol in the above scheme has the same meaning as the above, and as to the compound represented by the Formula (III'-6), a known compound can be used, or a compound derived from a known compound by a usual method can be used. ak is C1 to C3 alkyl.

The compound represented by the Formula (I'-1), wherein Z is S can be synthesized by the following method.

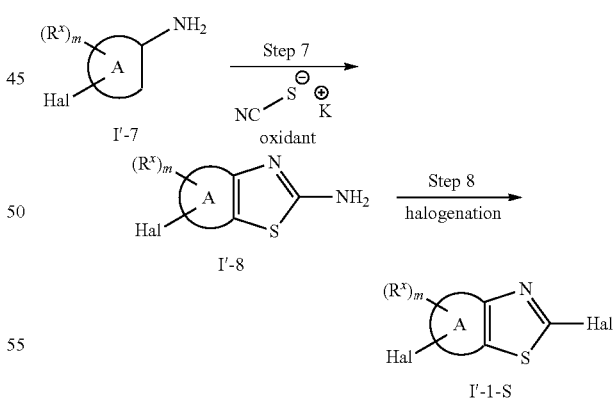

wherein each symbol in the above scheme has the same meaning as the above, and as to the compound represented by the Formula (I'-7), a known compound can be used, or a compound derived from a known compound by a usual method can be used. Hal is halogen.

Step 7

Step 7 is a process for preparing the compound represented by the Formula (I'-8) which comprises reacting the compound represented by the Formula (I'-7) with potassium thiocyanate.

As a solvent, a solvent described in Step 1 can be used. Preferably, halogenated hydrocarbons (e.g., dichloromethane, chloroform, 1,2-dichloroethane or the like), acetic acid or water can be used.

As an oxidant, bromine or iodine can be used.

The reaction can be performed at −20 to 50° C. for 0.5 to 48 hours.

Step 8

Step 8 is a process for preparing the compound represented by the Formula (I'-1-S) which comprises halogenating the compound represented by the Formula (I'-8).

As a solvent, a solvent described in Step 1 can be used. Preferably, nitriles (e.g., acetonitrile or the like) can be used.

As a halogenating agent, copper chloride (II) or copper bromide (II) can be used.

The reaction can be performed at −20 to 90° C. for 0.5 to 48 hours.

The compound represented by the Formula (II'-1) can be synthesized by the same scheme as described above.

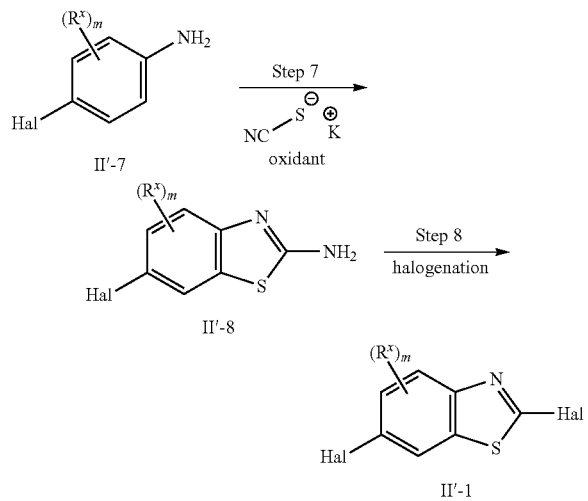

wherein each symbol in the above scheme has the same meaning as the above, and as to the compound represented by the Formula (II'-7), a known compound can be used, or a compound derived from a known compound by a usual method can be used. Hal is halogen.

The compound represented by the Formula (I'-1), wherein Z is S and Ring A is aromatic heterocycle can be synthesized by the following method.

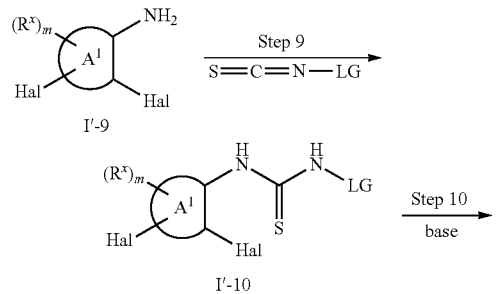

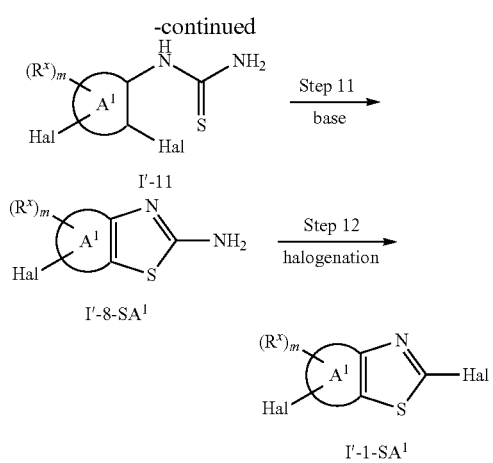

wherein Ring $A^1$ is aromatic heterocycle and the other symbols in the above scheme have the same meanings as the above, and as to the compound represented by the Formula (I'-9), a known compound can be used, or a compound derived from a known compound by a usual method can be used. Hal is halogen and LG is a leaving group. LG is, for example, an acetyl group, a benzoyl group or the like.

Step 9

Step 9 is a process for preparing the compound represented by the Formula (I'-10) which comprises reacting the compound represented by the Formula (I'-9) with the compound represented by the Formula: S=C=N-LG.

As a solvent, a solvent described in Step 1 can be used. Preferably, aromatic hydrocarbons (e.g., toluene, benzene, xylene or the like), ethers (e.g., tetrahydrofuran, diethylether, dioxane, 1,2-dimethoxyethane or the like), esters (e.g., methyl acetate, ethyl acetate or the like) or ketones (e.g., acetone, methylethylketone or the like) can be used.

The reaction can be performed at room temperature or a temperature at which a solvent being used is refluxed, for 0.5 to 24 hours.

As a compound represented by the Formula: S=C=N-LG, example includes benzoyl isothiocyanate or the like.

Step 10

Step 10 is a process for converting the compound represented by the Formula (I'-10) into the compound represented by the Formula (I'-11).

As a solvent, a solvent described in Step 1 can be used. Preferably, aromatic hydrocarbons (e.g., toluene, benzene, xylene or the like), ethers (e.g., tetrahydrofuran, diethylether, dioxane, 1,2-dimethoxyethane or the like) or alcohols (e.g., methanol, ethanol, t-butanol or the like) can be used.

As a base, a base described in Step 1 can be used. Preferably, metal hydroxides (e.g., sodium hydroxide, potassium hydroxide, lithium hydroxide, barium hydroxide or the like) or metal alkoxides (e.g., sodium methoxide, sodium ethoxide, potassium t-butoxide or the like) can be used.

The reaction can be performed at room temperature or a temperature at which a solvent being used is refluxed, for 0.5 to 24 hours.

Step 11

Step 11 is a process for converting the compound represented by the Formula (I'-11) into the compound represented by the Formula (I'-8-SA$^1$).

As a solvent, a solvent described in Step 1 can be used. Preferably, N,N-dimethylformamide, dimethylsulfoxide, aromatic hydrocarbons (e.g., toluene, benzene, xylene or the like) or ethers (e.g., tetrahydrofuran, diethylether, dioxane, 1,2-dimethoxyethane or the like) can be used.

As a base, a base described in Step 1 can be used. Preferably, metal hydrides (e.g., sodium hydride or the like), metal alkoxides (e.g., sodium methoxide, sodium ethoxide, potassium t-butoxide or the like), metal sodium or metal amide can be used.

The reaction can be performed at room temperature or a temperature at which a solvent being used is refluxed, for 0.5 to 24 hours.

Step 12

Step 12 is a process for preparing the compound represented by the Formula (I'-1-SA$^1$) which comprises halogenating the compound represented by the Formula (I'-8-SA$^1$). The reaction can be performed under the same conditions as the above Step 8.

The compound represented by the Formula (II'-1) can be synthesized by the following method.

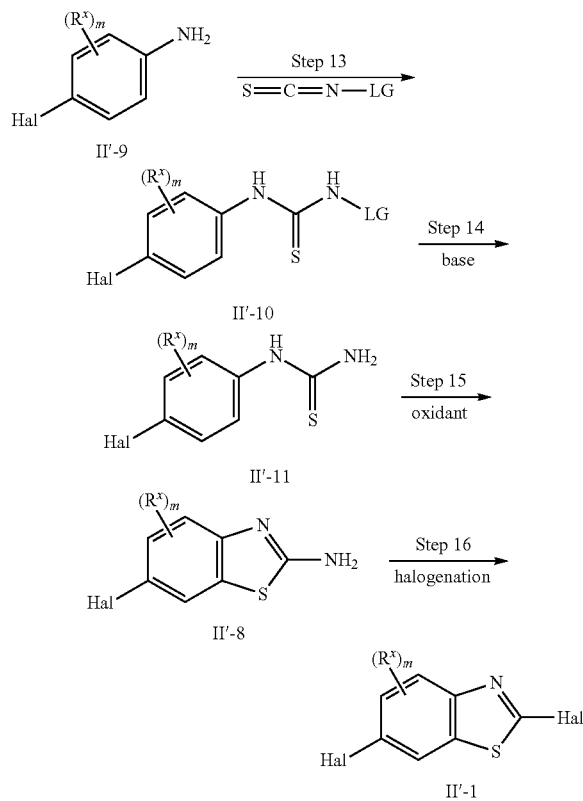

wherein each symbol in the above scheme has the same meaning as the above, and as to the compound represented by the Formula (II'-9), a known compound can be used, or a compound derived from a known compound by a usual method can be used. Hal is halogen and LG is a leaving group. LG is, for example, an acetyl group, a benzoyl group or the like.

Step 13

Step 13 is a process for preparing the compound represented by the Formula (II'-10) which comprises reacting the compound represented by the Formula (II'-9) with the compound represented by the Formula: S=C=N-LG.

The reaction can be performed under the same conditions as the above Step 9.

Step 14

Step 14 is a process for converting the compound represented by the Formula (II'-10) into the compound represented by the Formula (II'-11).

The reaction can be performed under the same conditions as the above Step 10.

Step 15

Step 15 is a process for converting the compound represented by the Formula (II'-11) into the compound represented by the Formula (II'-8).

As a solvent, a solvent described in Step 1 can be used. Preferably, halogenated hydrocarbons (e.g., dichloromethane, chloroform, 1,2-dichloroethane or the like), acetic acid or water can be used.

As an oxidant, bromine or iodine can be used.

The reaction can be performed at −20 to 50° C. for 0.5 to 48 hours.

Step 16

Step 16 is a process for preparing the compound represented by the Formula (II'-1) which comprises halogenating the compound represented by the Formula (II'-8).

The reaction can be performed under the same conditions as the above Step 8.

The compound represented by the Formula (I'-14) can be synthesized by the following method.

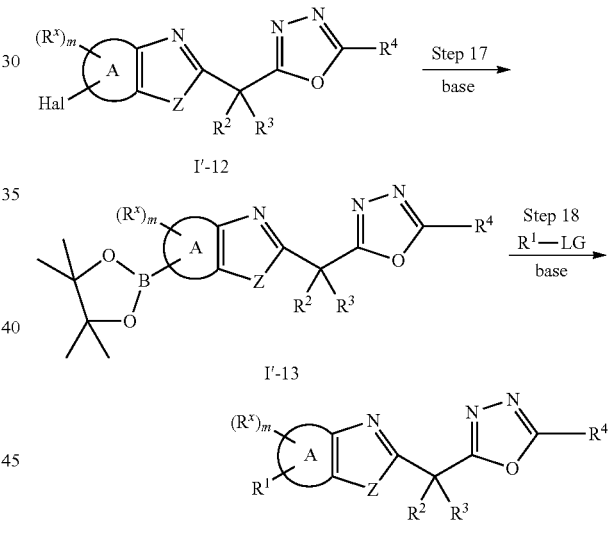

wherein each symbol in the above scheme has the same meaning as the above, and as to the compound represented by the Formula (I'-12), a known compound can be used, or a compound derived from a known compound by a usual method can be used. Hal is halogen and LG is a leaving group. LG is, for example, halogen, -OMs, -OTs, -OTf, -ONs or the like. Here, "Ms" represents methanesulfonyl group, "Ts" represents para-toluenesulfonyl group, "Tf" represents trifluoromethanesulfonyl group, and "Ns" represents ortho-nitrobenzenesulfonyl group.

Step 17

Step 17 is a process for preparing the compound represented by the Formula (I'-13) which comprises reacting the compound represented by the Formula (I'-12) with a boronic acid ester in the presence of a palladium catalyst.

As a solvent, a solvent described in Step 1 can be used. Preferably, N,N-dimethylformamide, dimethylacetoamide, aromatic hydrocarbons (e.g., toluene, benzene, xylene or the like) or ethers (e.g., tetrahydrofuran, diethylether, dioxane, 1,2-dimethoxyethane or the like) can be used.

As a base, a base described in Step 1 can be used. Preferably, metal acetate, such as potassium acetate can be used.

The reaction can be performed in the presence of palladium catalyst (e.g., Pd(PPh$_3$)$_4$, PdCl$_2$, Pd(OAc)$_2$, Pd(dba)$_2$, PdCl$_2$(dppf) CH$_2$Cl$_2$ or the like) and phosphine ligand (e.g., PPh$_3$, BINAP or the like) at 0 to 120° C. for 0.5 to 48 hours.

The reaction can be performed at 80 to 200° C. for 5 minutes to 1 hour by using microwave. This reaction can be performed in a solvent described above.

As a boronic acid ester, example includes Bis(pinacolato) diboron or the like.

Step 18

Step 18 is a process for preparing the compound represented by the Formula (I'-14) which comprises reacting the compound represented by the Formula (I'-13) with the compound represented by the Formula: R$^1$-LG in the presence of a palladium catalyst.

As a solvent, a solvent described in Step 1 can be used. Preferably, aromatic hydrocarbons (e.g., toluene, benzene, xylene or the like) or ethers (e.g., tetrahydrofuran, diethylether, dioxane, 1,2-dimethoxyethane or the like) can be used.

As a base, a base described in Step 1 can be used. Preferably, metal carbonates (e.g., sodium carbonate, calcium carbonate, cesium carbonate or the like) or organic amines (e.g., triethylamine, diisopropylethylamine, DBU, 2,6-lutidine or the like) can be used.

The reaction can be performed in the presence of palladium catalyst (e.g., Pd(PPh$_3$)$_4$, PdCl$_2$, Pd(OAc)$_2$, Pd(dba)$_2$, PdCl$_2$(dppf) CH$_2$Cl$_2$ or the like) and phosphine ligand (e.g., PPh$_3$, BINAP or the like) at 0 to 120° C. for 0.5 to 48 hours.

The reaction can be performed at 80 to 200° C. for 5 minutes to 1 hour by using microwave. This reaction can be performed in a solvent described above.

As a compound represented by the Formula: R$^1$-LG, example includes 2-bromopyridine or the like.

The compound represented by the Formula (II'-14) can be synthesized by the same scheme as described above.

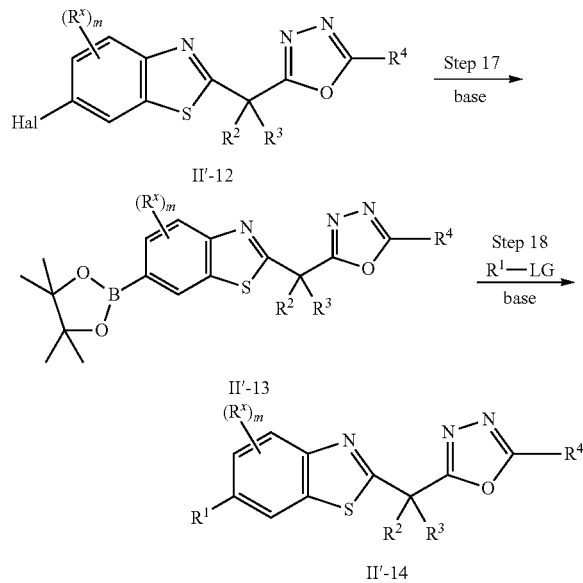

wherein each symbol in the above scheme has the same meaning as the above, and as to the compound represented by the Formula (II'-12), a known compound can be used, or a compound derived from a known compound by a usual method can be used. Hal is halogen and LG is a leaving group. LG is, for example, halogen, -OMs, -OTs, -OTf, -ONs or the like. Here, "Ms" represents methanesulfonyl group, "Ts" represents para-toluenesulfonyl group, "Tf" represents trifluoromethanesulfonyl group, and "Ns" represents ortho-nitrobenzenesulfonyl group.

Various substituents in the present compound can be introduced by referring to (1) Alan R. Katriszly et al., Comprehensive Heterocyclic Chemistry (2) Alan R. Katriszly et al., Comprehensive Heterocyclic Chemistry II (3) RODD'S CHEMISTRY OF CARBON COMPOUNDS VOLUME IV HETEROCYCLIC COMPOUNDS or the like.

The present compound has excellent inhibitory activity on endothelial lipase. Therefore, it can be used for treatment or prevention of a disease concerning endothelial lipase, especially, disease such as lipid metabolism abnormality, hyperlipidemia, diabetes, obesity, arteriosclerosis, atherosclerosis and/or syndrome X. It is particularly useful in treatment or prevention of hyperlipidemia, arteriosclerosis or lipid metabolism abnormality.

A compound used in the present invention can be orally or parenterally administered. When administered orally, the compound used in the present invention can be used in any dose form including normal formulations, for example, solid formulations such as a tablet, powder, granule, capsule or the like; aqueous formulations; oleaginous suspensions; or liquid formulations such as syrup or elixir. When administered parenterally, the compound used in the present invention can be used as an aqueous or oleaginous suspension for injection or nasal solution. In preparation of such formulations, a conventional excipient, binder, lubricant, aqueous solvent, oleaginous solvent, emulsifying agent, suspending agent, preservative, stabilizer and the like can be optionally used. Especially, using in a form of an oral formulation is preferred.

A formulation of the compound used in the present invention can be produced by combining (e.g., mixing) a therapeutically effective amount of the compound used in the present invention with a pharmaceutically acceptable carrier or diluent. Formulation of the compound used in the present invention can be produced by a known method using a well-known easily available ingredient.

A dose of the compound used in the present invention is different depending on an administration method, an age, a weight and the condition of a patient, and a kind of a disease and, in the case of oral administration, usually about 0.05 mg to 3000 mg, preferably about 0.1 mg to 1000 mg per a day for adult person may be administered, if necessary, in divided doses. In addition, in the case of parenteral administration, about 0.01 mg to 1000 mg, preferably about 0.05 mg to 500 mg per a day for adult person may be administered. In administration, it can be used together with other therapeutic agents.

The present invention is further explained by the following Examples, which are not intended to limit the scope of the present invention.

The NMR spectrum or LC/MS data of the present compound and its intermediate was described below.

NMR analysis was measured by 300 MHz or 400 MHz using CDCl$_3$ or dimethylsulfoxide (DMSO).

LC/MS was measured under the following condition.

Method C:

Shim-pack XR-ODS 50Lx3.0 (made by Shimazu) was used for measurement. A three minute linear gradient was run from 10:90-100:0 of acetonitrile/water (0.1% formic acid) with 1.6 ml/min of flow rate, and acetonitrile was passed for 30 seconds.

The terms used in the Examples are as follows.
NaHMDS: sodium bis(trimethylsilyl)amide
THF: tetrahydrofuran
WSCD: 1-ethyl-3-(3-dimethylamino propyl)carbodiimide
HOBt: 1-hydroxybenzotriazole
Boc: t-butoxycarbonyl group
HATU: O-(7-azabenzotriazole-1-yl)-N,N,N',N'-tetramethyluronium hexafluoro phosphate
Et$_3$N: triethylamine
DIBAL: diisobutyl aluminium hydride
DMAP: 4-dimethylaminopyridine
NBS: N-bromosuccinimide
LHMDS: lithium bis(trimethylsilyl)amide
TBAB: tetrabutylammonium bromide
PdCl$_2$(dppf)CH$_2$Cl$_2$:

EXAMPLE 1

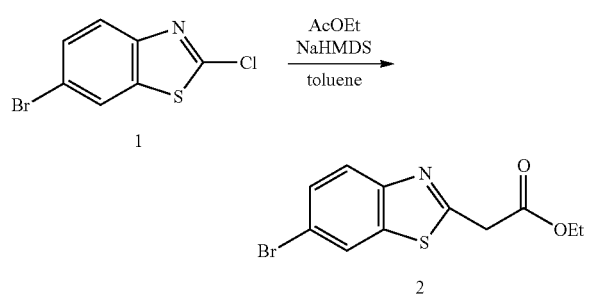

To a solution of 2M NaHMDS THF solution (111 mL, 211 mmol) in anhydrous toluene (375 mL) was added dropwise ethyl acetate (11.30 mL, 116 mmol) under nitrogen atmosphere at −60° C. for 10 minutes. The resulting solution was stirred at −60° C. for 1 hour. To the reaction solution was added dropwise a solution of 6-bromo-2-chloro benzothiazole 1 (25 g, 101 mmol) in anhydrous toluene (125 ml). After dropping, the reaction solution was stirred at 0° C. for 2 hours.

To the reaction solution were added 1M hydrochloric acid and ethyl acetate, then the mixture was extracted with ethyl acetate. The organic layer was washed with brine, dried over magnesium sulfate. The solvent was removed under reduced pressure. The residue was washed with a mixed solvent of hexane and diisopropyl ether to give Compound 2 (27.1 g, 90%) as a yellow solid.

Compound 2; 1H-NMR (CDCl3) δ: 1.31 (t, J=7.2, 3.0 Hz, 3H), 4.15 (s, 2H), 4.26 (q, J=7.2 Hz, 2H), 7.57 (dd, J=8.7, 1.8 Hz, 1H), 7.86 (d, J=9.0 Hz, 1H), 8.01 (d, J=1.8 Hz, 1H)

EXAMPLE 2

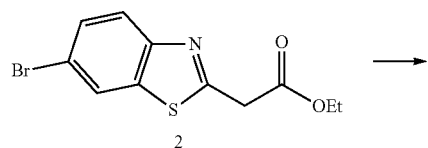

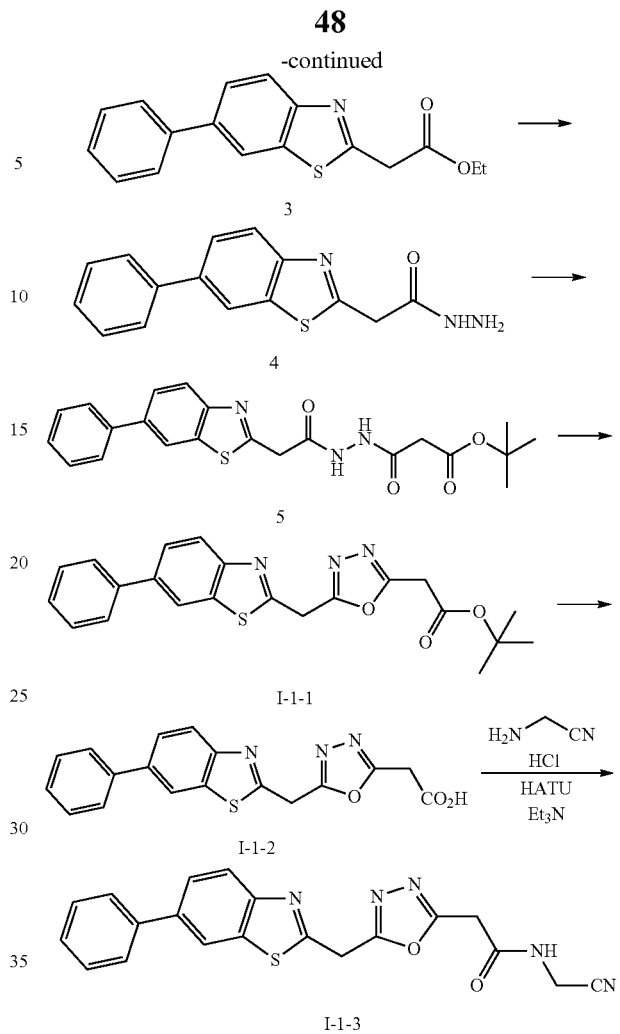

To a solution of Compound 2 (20 g, 67 mmol) in anhydrous 1,4-dioxane (200 mL) were added TETRAKIS(TRIPHENYLPHOSPHINE) PALLADIUM (0) (5.39 g, 4.66 mmol), PHENYLBORONIC ACID (9.75 g, 80 mmol) and K$_3$PO$_4$ (35.4 g, 167 mmol) at room temperature, then the reaction mixture was refluxed for 6 hours. The reaction mixture was cooled to room temperature. To the reaction mixture were added 1M hydrochloric acid and ethyl acetate, then the reaction mixture was extracted with ethyl acetate. The organic layer was washed with brine and dried over sodium sulfate. The solvent was removed under reduced pressure. The obtained residue was purified by column chromatography to give Compound 3 (16.1 g, 81%) as a yellow solid.

Compound 3; $^1$H-NMR (CDCl3) δ: 1.31 (t, J=6.9 Hz, 3H), 4.19 (s, 2H), 4.27 (q, J=7.2 Hz, 2H), 7.38 (t, J=7.5 Hz, 1H), 7.48 (t, J=7.2 Hz, 2H), 7.63-7.73 (m, 3H), 8.06 (m, 2H)

To a solution of Compound 3 (9.8 g, 33 mmol) in anhydrous N-methylpyrrolidone (100 mL) was added hydrazine hydrate (7.99 mL, 165 mmol), then the reaction mixture was stirred at 95° C. for 7 hours. The reaction mixture was cooled to room temperature. To the reaction mixture was added water, then the insoluble residue was collected by filtration and washed with ethyl acetate/hexane.

The obtained product was dried under reduced pressure to give Compound 4 (4.0 g, 33%) as a yellows solid.

Compound 4; 1H-NMR (DMSO-d6) δ: 4.00 (s, 2H), 4.37 (s, 2H), 7.39 (t, J=7.6 Hz, 1H), 7.50 (t, J=7.6 Hz, 2H), 7.74-7.80 (m, 3H), 8.00 (d, J=8.4 Hz, 1H), 8.38 (s, 1H)

To a solution of Compound 4 (4.5 g, 16 mmol) in anhydrous dimethylformamide (45 ml) were successively added 3-tert-butoxy-3-oxopropanoic acid (3.34 g, 20.83 mmol), WSCD-HCl (6.14 g, 32.0 mmol) and HOBt (2.81 g, 20.83 mmol) under nitrogen atmosphere at room temperature, then the reaction mixture was stirred for 14 hours. To the reaction solution were added 0.1M hydrochloric acid and ethyl acetate, then the reaction solution was extracted with ethyl acetate. The organic layer was washed with brine and dried over sodium sulfate. To the residue was added ethyl acetate/hexane, then the insoluble residue was collected by filtration to give Compound 5 (3.2 g, 47%).

Compound 5; 1H-NMR (DMSO-d6) δ: 1.41 (s, 9H), 3.21 (s, 2H), 4.15 (s, 2H), 7.39 (t, J=6.9 Hz, 1H), 7.50 (t, J=7.5 Hz, 2H), 7.74-7.82 (m, 3H), 8.02 (d, J=8.4 Hz, 1H), 8.39 (s, 1H), 10.41 (br s, 1H).

To a solution of Compound 5 (3.2 mg, 7.4 mmol) in anhydrous dimethoxyethane (150 ml) was added Burgess reagent (2.65 g, 11.10 mmol), then the reaction mixture was stirred at 90° C. for 1 hour. The solvent was removed under reduced pressure. To the residue were added water and ethyl acetate, then the mixture was extracted with ethyl acetate. The organic layer was washed with brine and dried over sodium sulfate. The solvent was removed under reduced pressure, then the obtained residue was purified by column chromatography to give Compound (I-1-1) (1.77 g, 59%). Compound (I-1-1); 1H-NMR (CDCl3) δ: 1.42 (s, 9H), 3.88 (s, 2H), 4.76 (s, 2H), 7.38 (t, J=7.2 Hz, 1H), 7.45 (t, J=7.8 Hz, 2H), 7.61-7.64 (m, 2H), 7.72 (d, J=8.4 Hz, 1H), 8.04-8.08 (m, 2H)

To a solution of Compound (I-1-1) (1.76 g, 4.32 mmol) in dichloromethane (20 mL) was added trifluoroacetic acid (10 mL), then the reaction mixture was stirred at room temperature for 3 hours. The solvent was removed under reduced pressure. To the obtained residue was added ethyl acetate, then the insoluble residue was collected by filtration. The insoluble residue was washed with n-hexane, then dried under reduced pressure to give Compound (I-1-2) (1.38 g, 91%).

Compound (I-1-2); 1H-NMR (DMSO-d6) δ: 4.08 (s, 2H), 4.97 (s, 2H), 7.40 (t, J=7.5 Hz, 1H), 7.50 (t, J=7.2 Hz, 2H), 7.76 (d, J=7.2 Hz, 2H), 7.83 (d, J=9.3 Hz, 1H), 8.38 (s, 1H), 8.05 (d, J=8.4 Hz, 1H), 8.43 (s, 1H)

To a solution of Compound (I-1-2) (1.33 g, 3.79 mmol) in dimethylformamide were successively added 2-aminoacetonitrile hydrochloride (0.525 g, 5.68 mmol), HATU (2.159 g, 5.68 mmol) and Et3N (1.049 mL, 7.57 mmol) with ice-cooling, then the reaction mixture was stirred at room temperature for 3 hours. To the reaction solution were added 0.1M hydrochloric acid and ethyl acetate, then the reaction solution was extracted with ethyl acetate. The organic layer was washed with brine and dried over sodium sulfate. The solvent was removed under reduced pressure. The obtained residue was purified by column chromatography to give Compound (I-1-3) (1.23 g, 83%) as a yellow solid.

Compound (I-1-3); 1H-NMR (CDCl3) δ: 3.97 (s, 2H), 4.24 (d, J=5.6 Hz, 2H), 4.76 (s, 2H), 7.39 (t, J=7.4 Hz, 1H), 7.48 (t, J=7.4 Hz, 2H), 7.63 (d, J=7.1 Hz, 2H), 7.74 (dd, J=8.6, 1.5 Hz, 1H), 8.02-8.07 (m, 3H).

EXAMPLE 3

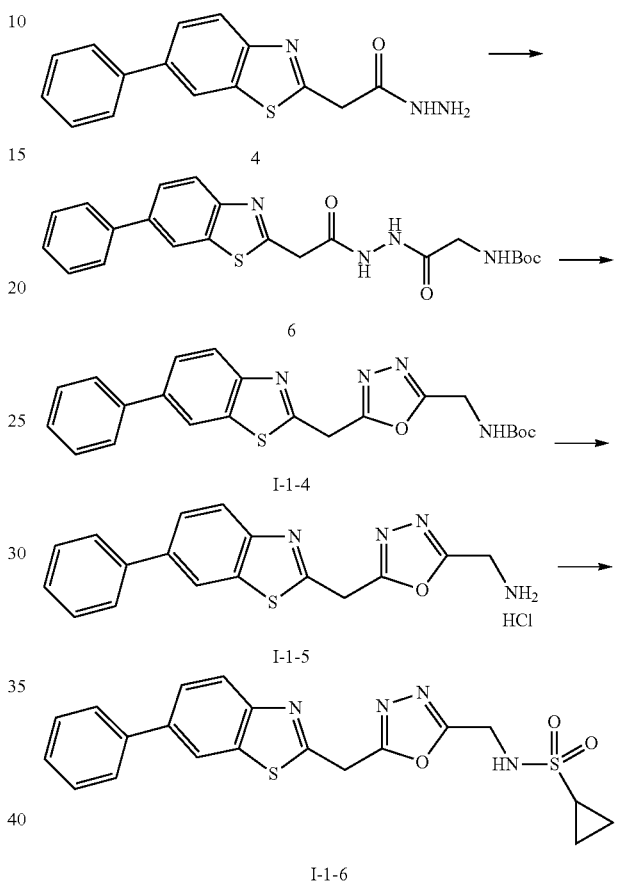

To a solution of Compound 4 (600 mg, 2.2 mmol) in anhydrous dimethylformamide (45 ml) were successively added 2-(tert-butoxycarbonylamino) acetic acid (464 mg, 2.65 mmol), WSCD HCl (609 mg, 3.18 mmol) and HOBt (86 mg, 0.635 mmol) under nitrogen atmosphere at room temperature, then the reaction mixture was stirred for 4 hours. To the reaction solution were added 1M hydrochloric acid and ethyl acetate, then the reaction solution was extracted with ethyl acetate. The organic layer was washed with brine and dried over sodium sulfate. To the residue was added ethyl acetate/hexane, then the insoluble residue was collected by filtration to give Compound 6 (640 mg, 69%).

Compound 6; 1H-NMR (DMSO-d6) δ: 1.42 (s, 9H), 3.59 (d, J=6.4 Hz, 2H), 4.11 (s, 2H), 7.01 (br-s, 1H), 7.39 (t, J=7.6 Hz, 1H), 7.50 (t, J=7.6 Hz, 2H), 7.73-7.81 (m, 3H), 8.01 (d, J=8.8 Hz, 1H), 8.38 (s, 1H), 10.19 (br s, 1H).

To a solution of Compound 6 (540 mg, 1.23 mmol) in anhydrous dimethoxyethane (15 ml) was added Burgess reagent (730 mg, 3.1 mmol), then the reaction mixture was stirred at 110° C. for 30 minutes under microwave irradiation. The solvent was removed under reduced pressure. To the residue were added water and ethyl acetate, then the mixture was extracted with ethyl acetate. The organic layer was washed with brine and dried over sodium sulfate. The solvent was removed under reduced pressure, then the obtained residue was purified by column chromatography to give Compound (I-1-4) (241 mg, 47%).

Compound (I-1-4); 1H-NMR (CDCl3) δ: 1.44 (s, 9H), 4.56 (d, J=5.1 Hz, 2H), 4.74 (s, 2H), 5.10 (br s, 1H), 7.39 (t, J=7.1 Hz, 1H), 7.47 (t, J=7.6 Hz, 2H), 7.63 (d, J=7.6 Hz, 2H), 7.72 (d, J=9.1 Hz, 1H), 8.05-8.07 (m, 2H).

To a solution of Compound (I-1-4) (220 mg, 0.521 mmol) in dichloromethane (2 mL) was added trifluoroacetic acid (1 mL), then the reaction mixture was stirred at room temperature for 4 hours. The solvent was removed under reduced pressure. To the obtained residue was added ethyl acetate, then the insoluble residue was collected by filtration. The insoluble residue was washed with ethyl acetate/n-hexane, then dried under reduced pressure to give Compound (I-1-5) (185 mg, 99%). Compound (I-1-5); 1H-NMR (DMSO-d6) δ: 4.44 (s, 2H), 5.02 (s, 2H), 7.41 (t, J=7.4 Hz, 1H), 7.51 (t, J=7.6 Hz, 2H), 7.75 (d, J=7.1 Hz, 2H), 7.83 (dd, J=8.4, 1.8 Hz, 1H), 8.04 (d, J=8.6 Hz, 1H), 8.45 (d, J=1.5 Hz, 1H), 8.79 (br s, 3H).

To a solution of Compound (I-1-5) (50 mg, 0.139 mmol) in dichloromethane (2 mL) were successively added cyclopropanesulfonyl chloride (0.017 mL, 0.167 mmol) and Et₃N (0.058 mL, 0.418 mmol) with ice-cooling, then the reaction mixture was stirred at room temperature for 24 hours. To the reaction solution were added 0.1M hydrochloric acid and ethyl acetate, then the reaction solution was extracted with ethyl acetate. The organic layer was washed with brine and dried over sodium sulfate. The solvent was removed under reduced pressure. The obtained residue was purified by column chromatography to give Compound (I-1-6) (16 mg, 27%) as a yellow solid.

Compound (I-1-6); 1H-NMR (DMSO-d6) δ: 0.83-0.87 (m, 4H), 4.47 (s, 2H), 4.98 (s, 2H), 7.40 (t, J=7.4 Hz, 1H), 7.49-7.52 (m, 2H), 7.76 (d, J=7.6 Hz, 2H), 7.83 (dd, J=8.6, 2.0 Hz, 1H), 8.01-8.04 (m, 2H), 8.44 (d, J=2.0 Hz, 1H)

EXAMPLE 4

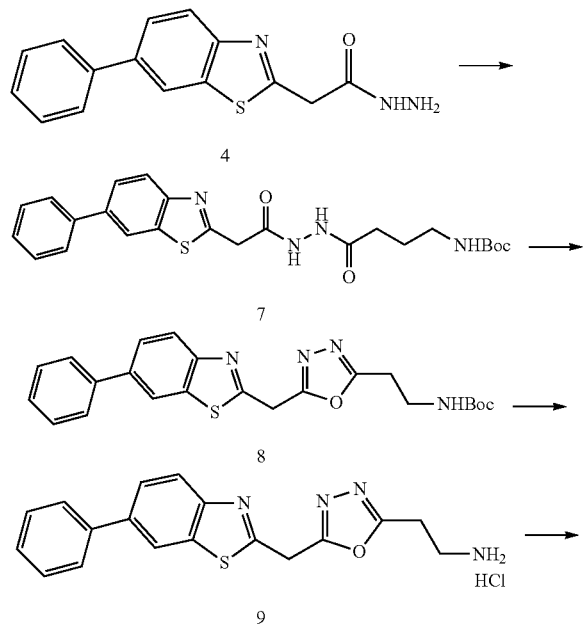

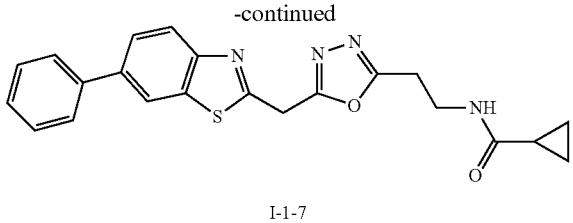

I-1-7

To a solution of Compound 4 (600 mg, 2.2 mmol) in anhydrous dimethylformamide (45 ml) were successively added 3-(tert-butoxycarbonylamino) propanoic acid (593 mg, 3.13 mmol), WSCD HCl (721 mg, 3.76 mmol) and HOBt (102 mg, 0.752 mmol) under nitrogen atmosphere at room temperature, then the reaction mixture was stirred for 4 hours. To the reaction solution were added 0.1M hydrochloric acid and ethyl acetate, then the reaction solution was extracted with ethyl acetate. The organic layer was washed with brine and dried over sodium sulfate. The insoluble residue was collected by filtration, then was washed with diethylether to give Compound 7 (809 mg, 71%).

Compound 7; 1H-NMR (CDCl3) δ: 1.42 (s, 9H), 2.53 (t, J=4.8 Hz, 2H), 3.46 (q, J=5.6 Hz, 2H), 4.13 (s, 2H), 5.32 (br-s, 1H), 7.37 (m, 1H), 7.46 (t, J=8.4 Hz, 2H), 7.59-7.70 (m, 3H), 8.01-8.06 (m, 2H), 8.81 (br-s, 1H)

To a solution of Compound 7 (758 mg, 1.67 mmol) in anhydrous dimethoxyethane (15 ml) was added Burgess reagent (795 mg, 3.3 mmol), then the reaction mixture was stirred at 110° C. for 10 minutes under microwave irradiation. The solvent was removed under reduced pressure. To the residue were added water and ethyl acetate, then the mixture was extracted with ethyl acetate. The organic layer was washed with brine and dried over sodium sulfate. The solvent was removed under reduced pressure, then the obtained residue was purified by column chromatography to give Compound 8 (417 mg, 57%).

Compound 8; $^1$H-NMR (DMSO-$d_6$) δ: 1.34 (s, 9H), 2.96 (t, J=6.59 Hz, 2H), 3.30 (dt, J=6.59, 5.58 Hz, 2H), 4.90 (s, 2H), 6.97 (d, J=5.58 Hz, 1H), 7.37-7.53 (m, 3H), 7.75 (d, J=7.60 Hz, 2H), 7.82 (dd, J=8.36, 1.77 Hz, 1H), 8.05 (d, J=8.36 Hz, 1H), 8.43 (d, J=1.77 Hz, 1H).

To a solution of Compound 8 (380 mg, 0.871 mmol) in dichloromethane (4 mL) was added trifluoroacetic acid (2 mL), then the reaction mixture was stirred at room temperature for 4 hours. The solvent was removed under reduced pressure. To the obtained residue were added ethyl acetate and 2N hydrochloric acid/ethyl acetate solution, then the insoluble residue was collected by filtration. The insoluble residue was washed with ethyl acetate/n-hexane to give Compound 9 (185 mg, 57%). Compound 9; 1H-NMR (DMSO-d6) δ: 3.22 (s, 4H), 4.94 (s, 2H), 7.41 (t, J=7.4 Hz, 3H), 7.51 (t, J=7.9 Hz, 3H), 7.76 (d, J=7.6 Hz, 2H), 7.83 (dd, J=8.6, 2.0 Hz, 1H), 7.99 (br s, 3H), 8.05 (d, J=8.6 Hz, 1H), 8.45 (d, J=2.0 Hz, 1H).

To a solution of Compound 9 (120 mg, 0.32 mmol) in anhydrous dimethylformamide (2 ml) were successively added cyclopropanecarboxylic acid (42 mg, 0.48 mmol), WSCD HCl (93 mg, 0.48 mmol), HOBt (65 mg, 0.48 mmol) and Et₃N (0.134 mL, 0.965 mmol) at room temperature, then the reaction mixture was stirred for 2 hours. To the reaction solution were added 10% aqueous citric acid and ethyl acetate, then the reaction solution was extracted with ethyl acetate. The organic layer was washed with brine and dried over sodium sulfate. The solvent was removed under reduced pressure. The obtained residue was purified by column chromatography to give Compound (I-1-7) (50 mg, 38%) as a yellow solid.

Compound (I-1-7); $^1$H-NMR (DMSO-$d_6$) δ: 0.58-0.66 (m, 4H), 1.47-1.50 (m, 1H), 2.99 (t, J=6.59 Hz, 2H), 3.44 (dt, J=6.59, 5.58 Hz, 2H), 4.91 (s, 2H), 7.37-7.54 (m, 3H), 7.75 (d, J=7.10 Hz, 2H), 7.83 (dd, J=8.62, 1.52 Hz, 1H), 8.05 (d, J=8.62 Hz, 2H), 8.25 (t, J=5.58 Hz, 1H), 8.43 (d, J=1.52 Hz, 1H).

EXAMPLE 5

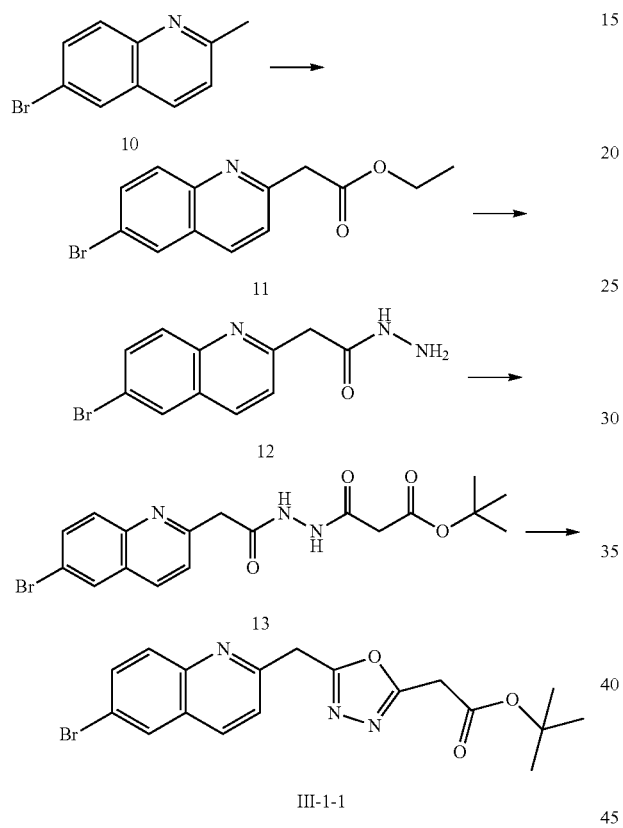

To a solution of 6-bromo-2-methylquinoline 10 (1.5 g, 6.75 mmol) in anhydrous THF (40 mL) was added dropwise lithium hexamethyldisilazide (1M, tetrahydrofuran solution) (27 mL, 27 mmol) under nitrogen atmosphere at −60° C. The resulting solution was stirred below −60° C. for 30 minutes. To the reaction solution was added diethyl carbonate (1.76 mL, 14.9 mmol), then the reaction solution was stirred at room temperature for 3 hours. After the completion of the reaction, to the reaction solution was added 1N HCl. The reaction solution was extracted with ethyl acetate. The organic layer was washed with saturated sodium bicarbonate solution and brine, then dried over sodium sulfate. The solvent was removed under reduced pressure. The obtained residue was purified by column chromatography to give Compound 11 (1.51 g, 76%).

Compound 11; $^1$H-NMR (CDCl3) δ: 1.27 (t, J=7.5 Hz, 3H), 4.02 (s, 2H), 4.21 (q, J=6.9 Hz, 2H), 7.46 (d, J=8.7 Hz, 1H), 7.77 (d, J=7.5 Hz, 1H), 7.91-7.97 (m, 2H), 8.05 (d, J=8.7 Hz, 1H)

To a solution of Compound 11 (1.41 g, 4.79 mmol) in ethanol (20 mL) was added hydrazine hydrate (0.84 g, 16.8 mmol), then the reaction mixture was refluxed for 5 hours. The reaction mixture was cooled to room temperature, then the obtained crystal was collected by filtration to give Compound 12 (1.2 g, 89%).

Compound 12; $^1$H-NMR (DMSO-d6) δ: 3.76 (s, 2H), 4.28 (s, 2H), 7.57 (d, J=8.4 Hz, 1H), 7.85-7.91 (m, 2H), 8.25-8.31 (m, 2H), 9.36 (br-s, 1H)

To a solution of Compound 12 (1.1 g, 3.93 mmol) in anhydrous dimethylformamide (12 ml) were successively added 3-tert-butoxy-3-oxopropanoic acid (0.76 g, 4.71 mmol), WSCD HCl (0.90 g, 4.71 mmol), HOBt (0.11 g, 0.79 mmol) and triethylamine (1.36 ml, 9.82 mmol) under nitrogen atmosphere at room temperature, then the reaction mixture was stirred for 14 hours. To the reaction solution was added 1N hydrochloric acid, then the reaction solution was extracted with ethyl acetate. The extraction was washed with brine and dried over sodium sulfate. The solvent was removed under reduced pressure. The residue was crystallized with diethylether, then the obtained crystal was collected by filtration to give Compound 13 (1.2 g, 72%).

Compound 13; $^1$H-NMR (DMSO-d6) δ: 1.40 (s, 9H), 3.17 (s, 2H), 3.88 (s, 2H), 7.60 (d, J=8.4 Hz, 1H), 7.85-7.90 (m, 2H), 8.26 (s, 1H), 8.31 (d, J=8.4 Hz, 1H), 10.26 (br-s, 1H)

To a solution of Compound 13 (1 g, 2.37 mmol) in anhydrous dichloromethane (40 mL) were successively added carbon tetrabromide (864 mg, 2.6 mmol), triphenylphosphine (1.37 g, 5.2 mmol) and triethylamine (0.36 ml, 2.6 mmol) with ice-cooling, then the reaction mixture was stirred at 3° C. for 1 hour. To the reaction solution was added aqueous sodium bicarbonate, then the reaction solution was extracted with ethyl acetate. The extraction was washed with brine and dried over sodium sulfate. The solvent was removed under reduced pressure. The obtained residue was purified by column chromatography to give Compound (III-1-1) (623 mg, 65%).

Compound (III-1-1); LC/MS Rt=2.16 min, MS: 405.75 (ES+), method: C

EXAMPLE 6

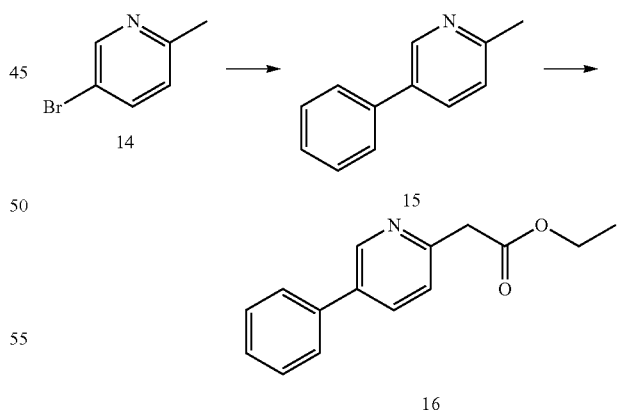

To a solution of 5-bromo-2-methylpyridine 14 (1.1 g, 6.39 mmol) in anhydrous dimethoxyethane (10 ml) were added TETRAKIS(TRIPHENYLPHOSPHINE) PALLADIUM (0) (0.37 g, 0.32 mmol), PHENYLBORONIC ACID (940 mg, 7.7 mmol) and 2M aqueous potassium carbonate solution (4.8 ml, 9.6 mmol) under nitrogen atmosphere at room temperature, then the reaction mixture was stirred at 140° C. for 15 minutes under microwave irradiation. To the reaction solution was added 1N hydrochloric acid, then the reaction solution was extracted with ethyl acetate. The extraction was washed with brine and dried over sodium sulfate. The solvent was removed under reduced pressure. The obtained residue was purified by column chromatography to give Compound 15 (988 mg, 92%).

Compound 15; LC/MS Rt=0.82 min, MS:170.10 (ES+), method:C

To a solution of Compound 15 (970 mg, 5.79 mmol) in anhydrous THF (20 mL) was added dropwise lithium hexamethyldisilazide (1M, tetrahydrofuran solution) (13 mL, 13 mmol) under nitrogen atmosphere at −60° C. The resulting solution was stirred below −60° C. for 30 minutes. To the reaction solution was added diethyl carbonate (787 mg, 6.66 mmol), then the reaction solution was stirred at room temperature overnight. To the reaction solution were added water and ethyl acetate, then the reaction solution was extracted with ethyl acetate. The organic layer was washed with brine and dried over sodium sulfate. The solvent was removed under reduced pressure, then the obtained residue was purified by column chromatography to give Compound 16 (681 mg, 49%).

Compound 16; $^1$H-NMR (CDCl3) δ: 1.29 (t, J=6.9 Hz, 3H), 3.89 (s, 2H), 4.21 (q, J=7.2 Hz, 2H), 7.35-7.60 (m, 6H), 7.86 (d, J=9.0 Hz, 1H), 8.79 (br-s, 1H)

The present compounds can be synthesized from Compound 16 according to Examples 1-5.

EXAMPLE 7

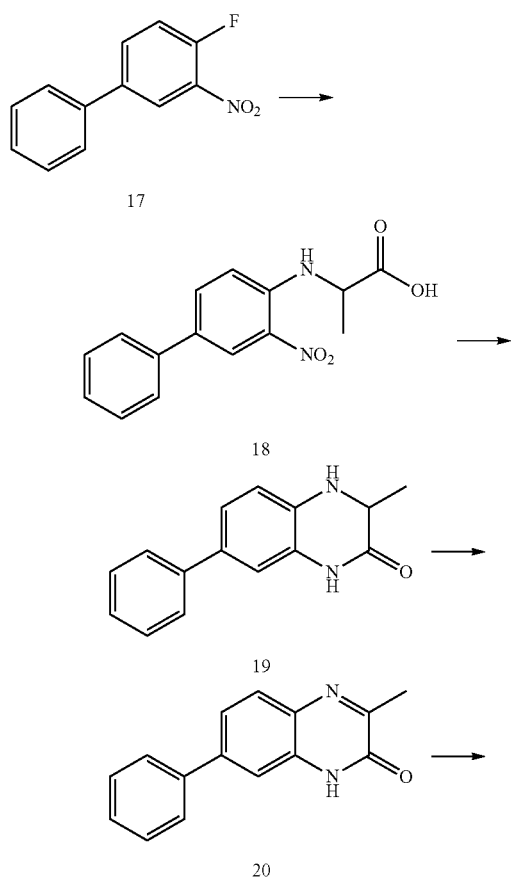

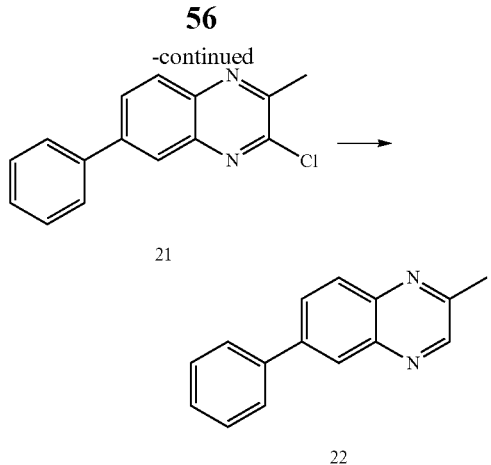

To a solution of Compound 17 (7.65 g, 35.2 mmol) in anhydrous dimethylformamide (60 mL) were added L-alanine (3.14 g, 35.2 mmol) and sodium hydroxide (17.61 ml, 35.2 mmol), then the reaction mixture was stirred at 70° C. for 24 hours. To the reaction solution was added 1N hydrochloric acid, then the reaction solution was extracted with ethyl acetate. The extraction was washed with brine and dried over sodium sulfate. The solvent was removed under reduced pressure to give Compound 18 (4.35 g, 43%).

Compound 18; $^1$H-NMR (DMSO-d$_6$) δ: 1.51 (d, J=7.1 Hz, 3H), 4.55 (dq, J=7.0, 7.0 Hz, 1H), 7.12 (d, J=9.1 Hz, 1H), 7.35 (t, J=7.4 Hz, 1H), 7.46 (t, J=7.9 Hz, 2H), 7.67 (t, J=4.3 Hz, 2H), 7.93 (dd, J=8.9, 2.3 Hz, 1H), 8.34 (d, J=2.0 Hz, 1H), 8.39 (d, J=7.1 Hz, 1H).

To a solution of Compound 18 (4.35 g, 15.19 mmol) in ethanol (64 mL) was added SnCl$_2$ dihydrate (10.29 g, 45.6 mmol), then the reaction mixture was stirred at 90° C. for 5 hours. To the reaction solution was added 1N hydrochloric acid, then the reaction solution was extracted with ethyl acetate. The extraction was washed with brine and dried over sodium sulfate. The solvent was removed under reduced pressure. The obtained residue was purified by column chromatography to give Compound 19 (3.62 g, 38%).

Compound 19; LC/MS Rt=1.69 min, MS:238.70 (MS+), method:C

To a aqueous solution of 2N sodium hydroxide (13.13 ml, 26.3 mmol) were added Compound 19 (1.39 g, 5.83 mmol) and 3% hydrogen peroxide solution (13.23 ml, 11.67 mmol), then the reaction mixture was stirred at 100° C. for 20 minutes. To the reaction solution was added acetic acid (1.668 ml, 29.2 mmol), then the obtained crystal was collected by filtration to give Compound 20 (1.31 g, 95%).

Compound 20; $^1$H-NMR (DMSO-d$_6$) δ: 2.42 (s, 3H), 7.43 (t, J=7.4 Hz, 1H), 7.49-7.54 (m, 3H), 7.57 (dd, J=8.6, 2.0 Hz, 1H), 7.68 (d, J=7.6 Hz, 2H), 7.77 (d, J=8.1 Hz, 1H).

To a Compound 20 (1.31 g, 5.54 mmol) was added phosphorous oxychloride (3.50 ml, 37.7 mmol), then the reaction mixture was stirred at 95° C. for 1 hour. The solvent was removed under reduced pressure. To the residue was added 2N aqueous sodium hydroxide solution (40 ml), then the resulting mixture was extracted with chloroform. The extraction was washed with brine and dried over sodium sulfate. The solvent was removed under reduced pressure to give Compound 21 (1.48 g, quant).

Compound 21; $^1$H-NMR (CDCl$_3$) δ: 2.86 (s, 3H), 7.43 (t, J=7.4 Hz, 1H), 7.52 (t, J=7.4 Hz, 2H), 7.73 (d, J=7.1 Hz, 2H), 8.02 (dd, J=8.6, 2.0 Hz, 1H), 8.08 (d, J=8.6 Hz, 1H), 8.19 (d, J=2.0 Hz, 1H).

To a solution of Compound 21 (1.48 g, 5.81 mmol) in ethanol (30 ml) were added triethylamine (0.805 ml, 5.81 mmol) and palladium carbon (309 mg, 2.91 mmol), then the reaction mixture was stirred under $H_2$ atmosphere for 4 hours. After the completion of the reaction, palladium carbon was removed, then the solvent was removed under reduced pressure. The obtained residue was purified by column chromatography to give Compound 22 (805 mg, 63%).

Compound 22; $^1$H-NMR (CDCl$_3$) δ: 2.80 (s, 3H), 7.43 (t, J=7.4 Hz, 1H), 7.52 (t, J=7.4 Hz, 2H), 7.76 (d, J=7.1 Hz, 2H), 8.02 (dd, J=8.6, 2.0 Hz, 1H), 8.08 (d, J=8.6 Hz, 1H), 8.28 (d, J=1.5 Hz, 1H), 8.77 (s, 1H).

The present compounds can be synthesized from Compound 22 according to Examples 1-6.

EXAMPLE 8

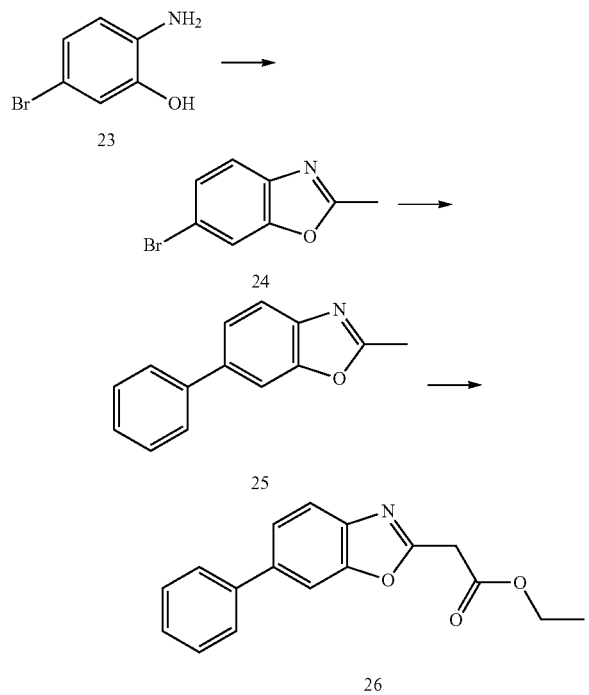

To an AcOH (1.521 μl, 0.027 mmol) were added 2-amino-5-bromophenol 23 (500 mg, 2.66 mmol) and 1,1,1-trimethoxyethane (600 μl, 4.79 mmol), then the reaction mixture was refluxed for 30 minutes. To the reaction solution was added water, then the reaction solution was extracted with ethyl acetate. The extraction was washed with brine and dried over magnesium sulfate. The solvent was removed under reduced pressure. The obtained residue was purified by column chromatography to give Compound 24 (481 mg, 85%).

Compound 24; $^1$H-NMR (CDCl$_3$) δ: 2.63 (s, 3H), 7.42 (dd, J=8.62, 2.03 Hz, 1H), 7.51 (d, J=8.62 Hz, 1H), 7.64 (d, J=2.03 Hz, 1H).

To a solution of Compound 24 (480 mg, 2.264 mmol) in 1,4-dioxane (7 mL) were added TETRAKIS(TRIPHENYLPHOSPHINE) PALLADIUM (0) (183 mg, 0.158 mmol), PHENYLBORONIC ACID (414 mg, 3.40 mmol) and 2M aqueous potassium phosphate solution (3.4 ml, 6.8 mmol) under nitrogen atmosphere at room temperature, then the reaction mixture was stirred at 150° C. for 40 minutes under microwave irradiation. To the reaction solution was added 1N hydrochloric acid, then the reaction solution was extracted with ethyl acetate. The extraction was washed with brine and dried over sodium sulfate. The solvent was removed under reduced pressure. The obtained residue was purified by column chromatography to give Compound 25 (385 mg, 81%).

Compound 25; $^1$H-NMR (DMSO-d6) δ: 2.64 (s, 3H), 7.38 (dd, J=8.4, 2.0 Hz, 1H), 7.47-7.51 (m, 2H), 7.64 (d, J=2.0 Hz, 1H), 7.77-7.75 (m, 3H), 7.96 (s, 1H)

To a solution of Compound 25 (380 mg, 1.82 mmol) in anhydrous THF (4 mL) was added dropwise lithium hexamethyldisilazide (1M, tetrahydrofuran solution) (3.81 ml, 3.81 mmol) under nitrogen atmosphere at −60° C. The resulting solution was stirred below −60° C. for 30 minutes. To the reaction solution was added diethyl carbonate (0.24 mL, 1.99 mmol), then the reaction solution was stirred for 30 minutes with ice-cooling. To the reaction solution was added water, then the reaction solution was extracted with ethyl acetate. The extraction was washed with brine and dried over sodium sulfate. The solvent was removed under reduced pressure. The obtained residue was purified by column chromatography to give Compound 26 (316 mg, 62%).

Compound 26; $^1$H-NMR (DMSO-d6) δ: 1.22 (t, J=8.0 Hz, 3H), 4.18 (q, J=4.4 Hz, 2H), 4.24 (s, 2H), 7.39 (dd, J=8.4, 2.0 Hz, 1H), 7.49 (t, J=8.4 Hz, 2H), 7.66-7.82 (m, 4H), 8.03 (s, 1H)

The present compounds can be synthesized from Compound 26 according to Examples 1-7.

EXAMPLE 9

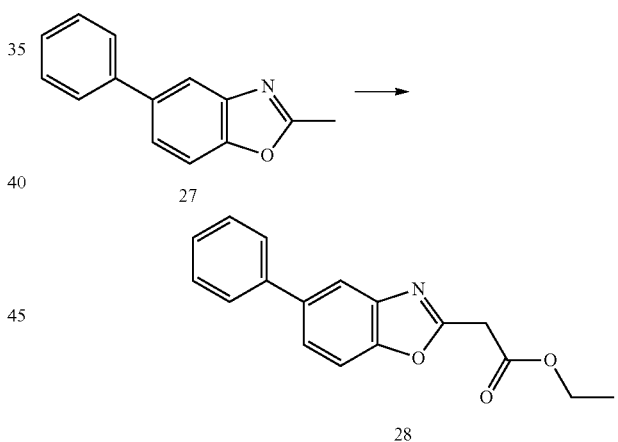

To a solution of 2-methyl-5-phenylbenzo[d]oxazole 27 (3 g, 14.34 mmol) in anhydrous THF (120 mL) was added dropwise lithium hexamethyldisilazide (1M, tetrahydrofuran solution) (32 ml, 32 mmol) under nitrogen atmosphere at −60° C. To the reaction solution was added diethyl carbonate (2.1 mL, 17.20 mmol) at −60° C., then the reaction solution was stirred for 30 minutes with ice-cooling. To the reaction solution was added saturated aqueous ammonium, then the reaction solution was extracted with ethyl acetate. The extraction was washed with brine and dried over sodium sulfate. The solvent was removed under reduced pressure. The obtained residue was purified by column chromatography to give Compound 28 (3.58 g, 89%).

Compound 28; $^1$H-NMR (CDCl3) δ: 1.31 (t, J=7.1 Hz, 3H), 4.05 (s, 2H), 4.27 (q, J=7.2 Hz, 2H), 7.38 (t, J=7.6 Hz, 1H), 7.48 (t, J=8.4 Hz, 2H), 7.58-7.63 (m, 3H), 7.92 (s, 1H)

The present compounds can be synthesized from Compound 28 according to Examples 1-8.

EXAMPLE 10

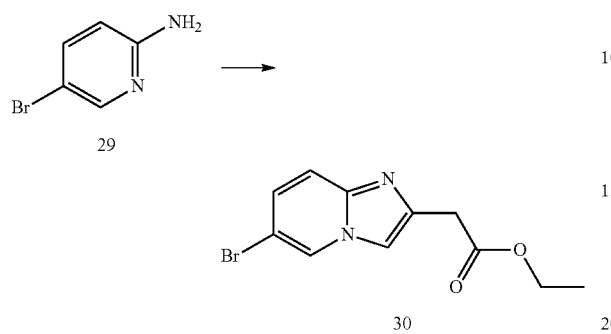

To a solution of ethyl 4-chloro-3-oxobutanoate (4.94 g, 30.0 mmol) in toluene (100 mL) was added 5-bromopyridin-2-amine 29 (5.19 g, 30.0 mmol) at room temperature, then the reaction mixture was refluxed. To the reaction solution were added 10% aqueous sodium bicarbonate solution and ethyl acetate, then the reaction solution was extracted with ethyl acetate. The organic layer was washed with brine and dried over sodium sulfate. The solvent was removed under reduced pressure. The obtained residue was purified by column chromatography to give Compound 30 (2.0 g, 24%) as a solid.

Compound 30; $^1$H-NMR (CDCl3) δ: 1.29 (t, J=7.1 Hz, 3H), 3.86 (s, 2H), 4.21 (q, J=7.2 Hz, 2H), 7.21 (d, J=12 Hz, 1H), 7.45 (d, J=9.6 Hz, 1H), 7.58 (s, 1H), 8.22 (s, 1H)

The present compounds can be synthesized from Compound 30 according to Examples 1-9.

EXAMPLE 11

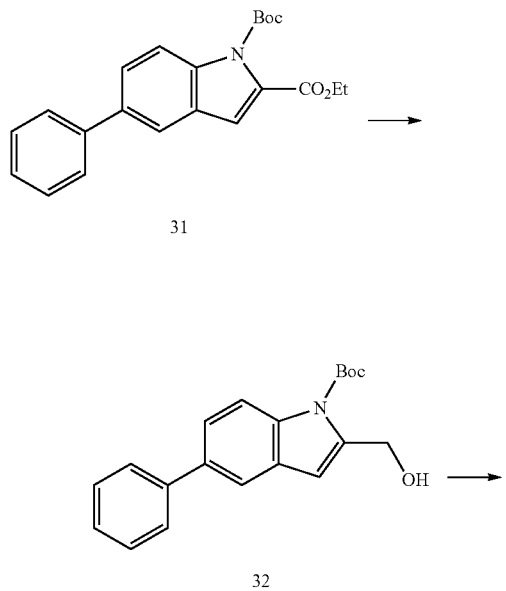

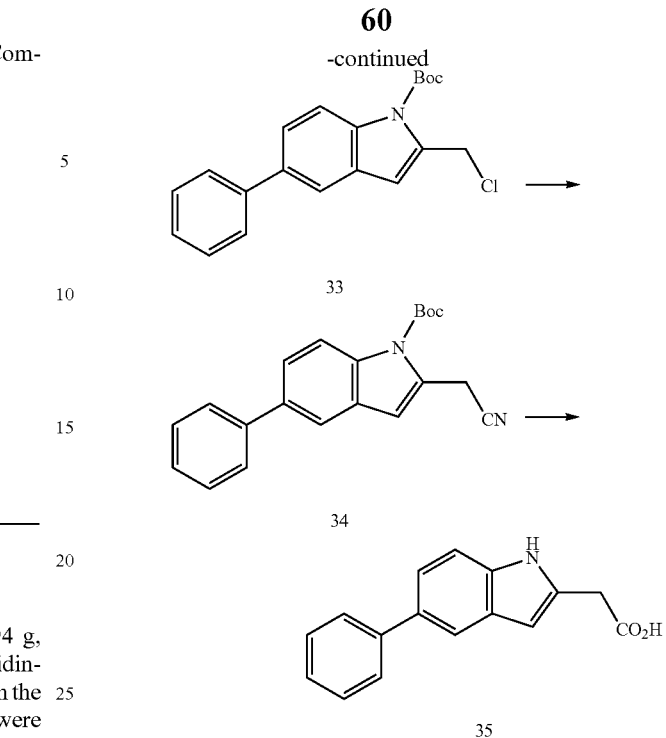

To a solution of 1-tert-butyl 2-ethyl 5-phenyl-1H-indole-1,2-dicarboxylate 31 (3.08 g, 8.43 mmol) in anhydrous dichloromethane (30 mL) was added dropwise DIBAL (1.02 M, hexane solution) (20.26 ml, 21.07 mmol) under nitrogen atmosphere at −78° C. The reaction mixture was stirred at −78° C. for 2 hours. To the reaction solution was added aqueous POTASSIUM SODIUM TARTRATE solution, then the reaction solution was stirred at room temperature overnight. The aqueous layer was extracted with ethyl acetate. The extraction was washed with brine and dried over magnesium sulfate. The solvent was removed under reduced pressure. The obtained residue was purified by column chromatography to give Compound 32 (1.86 g, 68%).

Compound 32; $^1$H-NMR (CDCl$_3$) δ: 1.74 (s, 9H), 4.84 (d, J=7.2 Hz, 2H), 6.64 (s, 1H), 7.35 (t, J=7.5 Hz, 1H), 7.46 (t, J=7.5 Hz, 2H), 7.53-7.67 (m, 3H), 7.73 (s, 1H), 8.04 (d, J=8.7 Hz, 1H)

To a solution of Compound 32 (3.08 g, 8.43 mmol) in anhydrous dichloromethane (38 ml) were successively added mesyl chloride (20.26 ml, 21.07 mmol), triethylamine (1.28 ml, 9.20 mmol) and DMAP (140 mg, 1.15 mmol) under nitrogen atmosphere at room temperature, then the reaction mixture was stirred for 3 hours. To the reaction solution was added 1N hydrochloric acid, then the reaction solution was extracted with chloroform. The extraction was washed with brine and dried over sodium sulfate. The solvent was removed under reduced pressure to give Compound 33 (2.0 g, quant).

To a solution of Compound 33 (2.0 g, 5.85 mmol) in anhydrous dichloromethane (40 mL) was added tetraethylammonium cyanide (2.29 g, 14.63 mmol) under nitrogen atmosphere, then the reaction mixture was refluxed for 2 hours. To the reaction solution was added water, then the reaction solution was extracted with chloroform. The extraction was washed with brine and dried over sodium sulfate. The solvent was removed under reduced pressure to give Compound 34 (940 mg, 48%).

Compound 34; $^1$H-NMR (DMSO-d6) δ: 1.67 (s, 9H), 4.39 (s, 2H), 6.87 (s, 1H), 7.36 (t, J=7.5 Hz, 1H), 7.48 (t, J=8.1 Hz, 2H), 7.63-7.72 (m, 3H), 7.91 (s, 1H), 8.15 (d, J=8.7 Hz, 1H)

In a mixed solvent of methanol (8 mL) and 1,4-dioxane (8 mL) was dissolved Compound 34 (800 mg, 2.407 mmol). To the obtained mixture was added 5N aqueous sodium hydroxide solution (9.5 ml, 48.2 mmol), then the reaction mixture was refluxed for 4 hours. To the reaction solution was added 1N hydrochloric acid, then the reaction solution was extracted with ethyl acetate. The extraction was washed with brine and dried over magnesium sulfate. The solvent was removed under reduced pressure to give Compound 35 (580 mg, 96%).

Compound 35; $^1$H-NMR (CDCl$_3$) δ: 3.76 (s, 2H), 6.33 (s, 1H), 7.25-7.47 (m, 5H), 7.65 (d, J=7.75 Hz, 2H), 7.72 (s, 1H), 12.52 (s, 1H)

The present compounds can be synthesized from Compound 35 according to Examples 1-10.

EXAMPLE 12

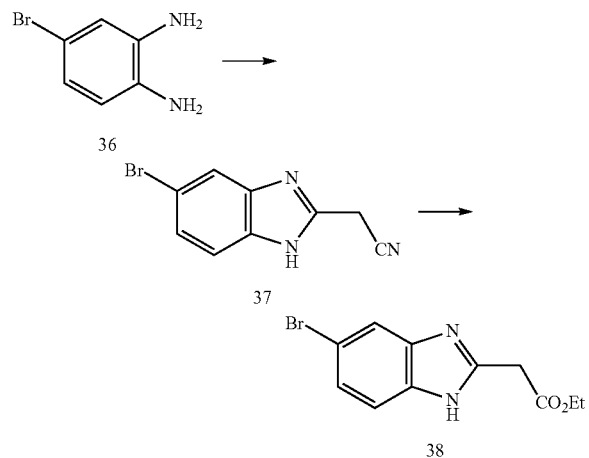

To a 4-bromobenzene-1,2-diamine 36 (3.35 g, 17.91 mmol) was added 2-cyanoacetamide (3.31 g, 39.4 mmol), then the reaction mixture was stirred at 210° C. for 25 minutes under microwave irradiation. To the reaction solution was added water, then the reaction solution was extracted with ethyl acetate. The extraction was washed respectively with water and brine, then dried over magnesium sulfate. The solvent was removed under reduced pressure, then the obtained residue was purified by column chromatography to give Compound 37 (3.02 g, 71%).

Compound 37; $^1$H-NMR (DMSO-d6) δ: 4.42 (s, 2H), 7.34 (dd, J=9.0, 2.1 Hz, 1H), 7.52 (d, J=8.7 Hz, 1H), 7.78 (s, 1H), 12.79 (s, 1H)

To a solution of Compound 37 (1.62 g, 6.86 mmol) in ethanol (40 mL) was added 4N hydrochloric acid (ethyl acetate solution) (17.16 ml, 68.6 mmol), then the reaction mixture was refluxed for 2 hours. The part of the solvent was removed under reduced pressure. To the reaction solution was added 10% aqueous sodium bicarbonate solution, then the reaction solution was extracted with ethyl acetate. The extraction was washed respectively with water and brine, then dried over magnesium sulfate. The solvent was removed under reduced pressure, then the obtained residue was purified by column chromatography to give Compound 38 (1.92 g, 99%).

Compound 38; $^1$H-NMR (CDCl$_3$) δ: 1.33 (t, J=7.2 Hz, 3H), 4.06 (s, 2H), 4.27 (q, J=7.2 Hz, 2H), 7.35 (d, J=6.3 Hz, 2H), 10.42 (brs, 1H)

The present compounds can be synthesized from Compound 38 according to Examples 1-11.

EXAMPLE 13

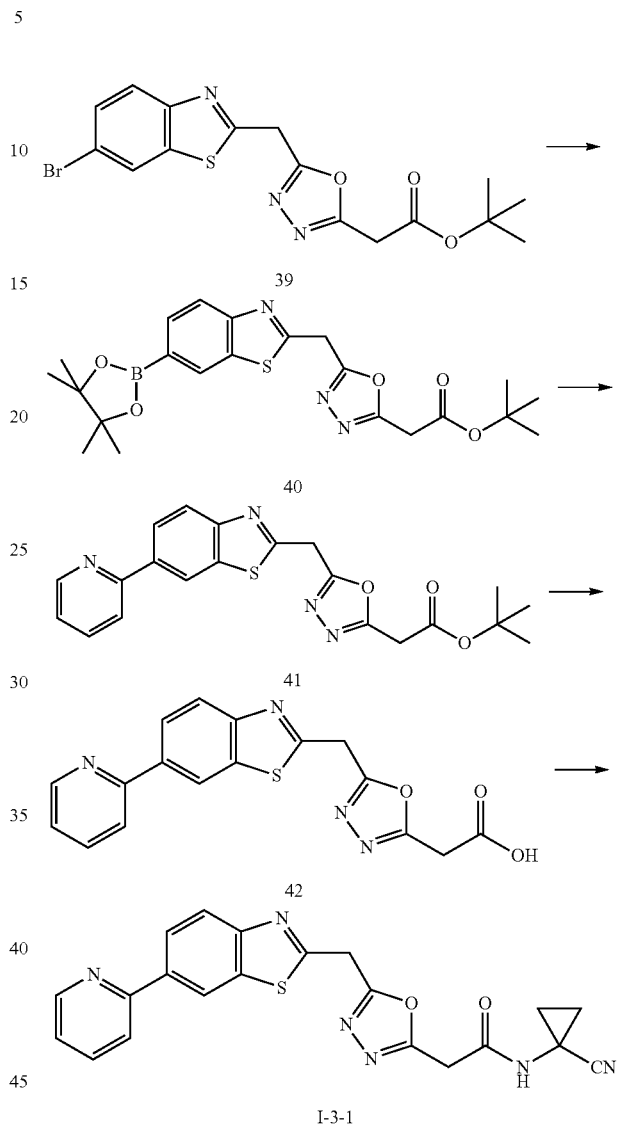

To a solution of Compound 39 (10 g, 24.4 mmol) in anhydrous 1,4-dioxane (150 mL) were added PdCl$_2$(dppf) CH$_2$Cl$_2$ (1 g, 1.22 mmol), 4,4,4',4',5,5,5',5'-octamethyl-2,2'-bi(1,3,2-dioxaborolane) (9.28 g, 36.6 mmol), potassium acetate (7.18 g, 73.1 mmol) under nitrogen atmosphere at room temperature, then the reaction mixture was stirred at 90° C. for 3 hours. To the reaction solution were added 10% aqueous sodium bicarbonate solution and ethyl acetate, then the reaction solution was extracted with ethyl acetate. The extraction was washed with brine, then dried over sodium sulfate. The solvent was removed under reduced pressure to give Compound 40 (13 g, quant.) as a crude product.

Compound 40; $^1$H-NMR (CDCl$_3$) δ: 1.37 (s, 12H), 1.41 (s, 9H), 3.88 (s, 2H), 4.75 (s, 2H), 7.90 (dd, J=8.11, 1.01 Hz, 1H), 7.99 (d, J=8.11 Hz, 1H), 8.34 (s, 1H).

To a solution of Compound 40 (1.26 g, 2.75 mmol) in anhydrous tetrahydrofuran (12 ml) were added PdCl$_2$(dppf) CH$_2$Cl$_2$ (41.4 mg, 0.057 mmol), 2-bromopyridine (0.54 ml, 5.51 mmol), cesium carbonate (2.7 g, 8.26 mmol) and water (4 ml) under nitrogen atmosphere at room temperature, then the reaction mixture was stirred at 120° C. for 20 minutes under microwave irradiation. To the reaction solution were added 10% aqueous sodium bicarbonate solution and ethyl acetate, then the reaction solution was extracted with ethyl acetate. The extraction was washed with brine, then dried over sodium sulfate. The solvent was removed under reduced pressure. The obtained residue was purified by column chromatography to give Compound 41 (349 mg, 31%).

Compound 41; $^{1}$H-NMR (CDCl$_{3}$) δ: 1.42 (s, 9H), 3.89 (s, 2H), 4.76 (s, 2H), 7.26-7.30 (m, 1H), 7.77-7.82 (m, 2H), 8.06-8.13 (m, 2H), 8.57 (d, J=1.01 Hz, 1H), 8.70-8.74 (m, 1H).

To a solution of Compound 41 (349 mg, 0.854 mmol) in dichloromethane (4 mL) was added trifluoroacetic acid (2 mL), then the reaction mixture was stirred at room temperature for 2 hours. The solvent was removed under reduced pressure to give Compound 42 (301 mg, quant.) as a crude product.

Compound 42; $^{1}$H-NMR (DMSO-d$_{6}$) δ: 4.09 (s, 2H), 4.99 (s, 2H), 7.48-7.51 (m, 1H), 8.04 (td, J=7.73, 1.86 Hz, 1H), 8.10 (d, J=8.62 Hz, 1H), 8.14 (d, J=8.11 Hz, 1H), 8.25 (dd, J=8.62, 1.52 Hz, 1H), 8.75 (d, J=5.07 Hz, 1H), 8.85 (d, J=1.52 Hz, 1H).

To a solution of Compound 42 (301 mg, 0.854 mmol) in dimethylformamide (4 ml) were successively added 1-aminocyclopropanecarbonitrile hydrochloride (304 mg, 2.56 mmol), triethylamine (0.8 mL, 6.7 mmol) and HATU (812 mg, 2.14 mmol) under nitrogen atmosphere, then the reaction mixture was stirred at room temperature for 2 hours. To the reaction solution was added 10% aqueous sodium bicarbonate solution, then the reaction solution was extracted with ethyl acetate. The extraction was washed with brine, then dried over sodium sulfate. The solvent was removed under reduced pressure. The obtained residue was purified by column chromatography to give Compound (I-3-1) (220 mg, 62%) as a white solid.

Compound (I-3-1); $^{1}$H-NMR (DMSO-d$_{6}$) δ: 1.14 (dd, J=8.36, 5.32 Hz, 2H), 1.49 (dd, J=8.11, 5.58 Hz, 2H), 3.91 (s, 2H), 4.97 (s, 2H), 7.37-7.40 (m, 1H), 7.93 (td, J=7.73, 1.69 Hz, 1H), 8.07 (dd, J=8.62, 2.03 Hz, 2H), 8.27 (dd, J=8.62, 2.03 Hz, 1H), 8.70 (d, J=4.56 Hz, 1H), 8.85 (d, J=1.52 Hz, 1H), 9.23 (s, 1H).

EXAMPLE 14

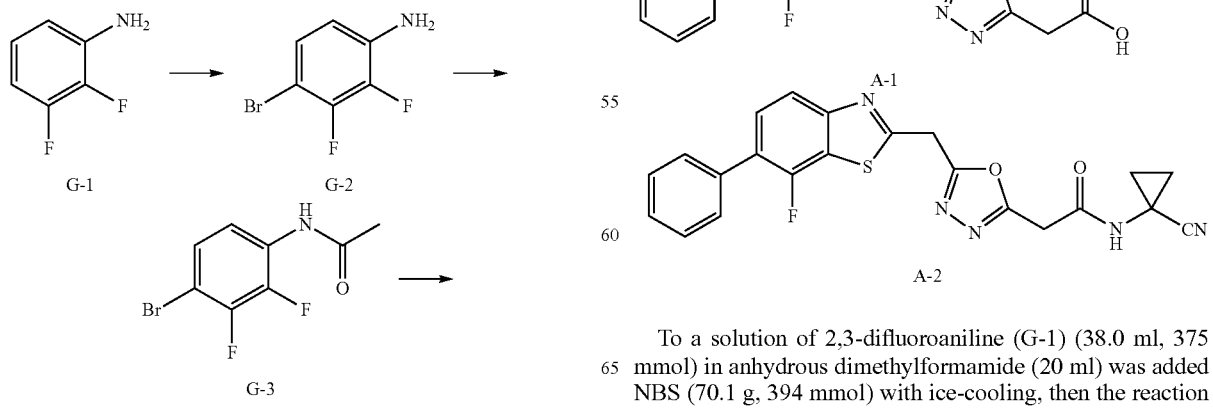

To a solution of 2,3-difluoroaniline (G-1) (38.0 ml, 375 mmol) in anhydrous dimethylformamide (20 ml) was added NBS (70.1 g, 394 mmol) with ice-cooling, then the reaction mixture was stirred for 1 hour. To the reaction solution was added water, then the reaction solution was extracted with ethyl acetate. The extraction was washed with brine and dried over sodium sulfate. The solvent was removed under reduced pressure to give Compound (G-2) (81.9 g, quant.) as an oil.

Compound (G-2);

Method C: Rt=1.81 min, 207.65 (ES+)

To a solution of Compound (G-2) (78 g, 375 mmol) in anhydrous dichloromethane (250 mL) was added acetic anhydride (53.2 ml, 563 mmol) at room temperature, then the reaction mixture was stirred for 1 hour. After the completion of the reaction, the insoluble residue was collected by filtration to give Compound (G-3) (85.3 g, 91%).

Compound (G-3);

$^1$H-NMR (DMSO-d6) δ: 2.10 (s, 3H), 7.48 (t, J=7.2 Hz, 1H), 7.72 (t, J=7.2 Hz, 1H), 10.32 (s, 1H).

To a solution of Compound (G-3) (80.32 g, 321 mmol) in anhydrous toluene (400 mL) was added Lawesson's reagent (78 g, 193 mmol) at room temperature, then the reaction mixture was refluxed for 1 hour. After confirming the disappearance of the starting material, to the reaction mixture was added cesium carbonate (314 g, 964 mmol), then the reaction mixture was refluxed for 1 hour. To the reaction solution was added water, then the reaction solution was extracted with ethyl acetate. The extraction was washed with brine and dried over sodium sulfate. The solvent was removed under reduced pressure. The obtained residue was purified by column chromatography to give Compound (G-4) (69.7 g, 88%) as an oil.

Compound (G-4);

$^1$H-NMR (DMSO-d6) δ: 2.85 (s, 3H), 7.73-7.81 (m, 2H).

To a solution of Compound (G-4) (60.9 g, 247 mmol) in anhydrous THF (600 mL) was added dropwise lithium hexamethyldisilazide (1M, tetrahydrofuran solution) (544 ml, 544 mmol) under nitrogen atmosphere at −60° C. The resulting solution was stirred below −60° C. for 30 minutes. To the reaction solution was added diethyl carbonate (36 ml, 297 mmol), then the reaction solution was stirred at room temperature for 3 hours. After the completion of the reaction, to the reaction solution was added 1N hydrochloric acid. The reaction solution was extracted with ethyl acetate. The organic layer was washed respectively with saturated sodium bicarbonate solution and brine, then dried over sodium sulfate. The solvent was removed under reduced pressure. The obtained residue was purified by column chromatography to give Compound (G-5) (71.4 g, 91%).

Compound (G-5);

$^1$H-NMR (DMSO-d6) δ: 1.23 (t, J=7.2 Hz, 3H), 4.19 (q, J=7.2 Hz, 2H), 4.41 (s, 2H), 7.81 (d, J=1.5 Hz, 1H), 7.83 (s, 1H).

To a solution of Compound (G-5) (68.34 g, 215 mmol) in ethanol (700 mL) was added hydrazine hydrate (31.3 ml, 644 mmol), then the reaction mixture was refluxed for 4 hours. The reaction mixture was cooled to room temperature. The obtained crystal was collected by filtration to give Compound (G-6) (60.6 g, 93%).

Compound (G-6);

$^1$H-NMR (DMSO-d6) δ: 4.06 (s, 2H), 4.40 (br-s, 2H), 7.78 (d, J=0.9 Hz, 1H), 7.79 (d, J=0.9 Hz, 1H), 9.51 (br-s, 1H).

To a solution of Compound (G-6) (60.6 g, 199 mmol) in anhydrous dimethylformamide (500 ml) were successively added 3-tert-butoxy-3-oxopropanoic acid (46.1 ml, 299 mmol), WSCD HCl (57.3 g, 299 mmol), HOBt (13.5 g, 100 mmol) and triethylamine (55.3 ml, 399 mmol) under nitrogen atmosphere at room temperature, then the reaction mixture was stirred for 3 hours. To the reaction solution was added water, then the reaction solution was extracted with ethyl acetate. The extraction was washed with brine and dried over sodium sulfate. The solvent was removed under reduced pressure. The obtained residue was crystallized with diisopropyl ether, then the obtained crystal was collected by filtration to give Compound (G-7) (80.6 g, 91%).

Compound (G-7);

$^1$H-NMR (DMSO-d6) δ: 1.40 (s, 9H), 3.21 (s, 2H), 4.22 (s, 2H), 7.80-7.82 (m, 2H), 10.42 (br-s, 2H).

To a solution of Compound (G-7) (6.72 g, 15.1 mmol) in anhydrous 1,4-dioxane (60 ml) was added Burgess reagent (7.2 g, 30.2 mmol), then the reaction mixture was stirred at 90° C. for 2 hours. The solvent was removed under reduced pressure. To the residue was added water, then the reaction solution was extracted with ethyl acetate. The extraction was washed with brine and dried over sodium sulfate. The solvent was removed under reduced pressure. The obtained residue was purified by column chromatography to give Compound (G-8) (3.62 g, 56%).

Compound (G-8);

$^1$H-NMR (DMSO-d6) δ: 1.35 (s, 9H), 4.09 (s, 2H), 5.04 (s, 2H), 7.80-7.87 (m, 2H).

To a solution of Compound (G-8) (450 mg, 1.051 mmol) in anhydrous 1,4-dioxane (4 mL) were added TETRAKIS (TRIPHENYLPHOSPHINE) PALLADIUM (0) (72.9 mg, 0.063 mmol), PHENYLBORONIC ACID (192 mg, 1.58 mmol) and 2M aqueous sodium carbonate solution (790 μl, 1.58 mmol) under nitrogen atmosphere at room temperature, then the reaction mixture was stirred at 120° C. for 30 minutes under microwave irradiation. To the reaction mixture were added 1M hydrochloric acid and ethyl acetate, then the reaction mixture was extracted with ethyl acetate. The extraction was washed with brine and dried over sodium sulfate. The solvent was removed under reduced pressure. The obtained residue was purified by column chromatography to give Compound (G-9) (471 mg, quant.) as an oil.

Compound (G-9);

$^1$H-NMR (DMSO-d6) δ: 1.36 (s, 9H), 4.10 (s, 2H), 5.05 (s, 2H), 7.30-7.56 (m, 3H), 7.63-7.93 (m, 4H).

To a solution of Compound (G-9) (455 mg, 1.07 mmol) in dichloromethane (5 mL) was added trifluoroacetic acid (2 mL), then the reaction mixture was stirred at room temperature for 2 hours. The solvent was removed under reduced pressure. The obtained crystal was washed with hexan to give Compound (A-1) (230 mg, 58%).

Compound (A-1);

$^1$H-NMR (DMSO-d6) δ: 4.09 (s, 2H), 5.04 (s, 2H), 7.42-7.55 (m, 3H), 7.63-7.73 (m, 3H), 7.96 (d, J=7.8 Hz, 1H).

To a solution of Compound (A-1) (90 mg, 0.24 mmol) in dimethylformamide (3 ml) were successively added 1-aminocyclopropanecarbonitrile hydrochloride (38 mg, 0.32 mmol), WSCD HCl (70 mg, 0.37 mmol), HOBt (9.9 mg, 0.07 mmol) and Et$_3$N (0.084 mL, 0.61 mmol) under nitrogen atmosphere, then the reaction mixture was stirred at room temperature for 16 hours. To the reaction solution was added 10% aqueous sodium bicarbonate solution, then the reaction solution was extracted with ethyl acetate. The extraction was washed with brine and dried over sodium sulfate. The solvent was removed under reduced pressure. The obtained residue was purified by column chromatography to give Compound (A-2) (73 mg, 69%).

Compound (A-2);

¹H-NMR (DMSO-d6) δ: 1.14 (dd, J=8.4, 5.3 Hz, 2H), 1.49 (dd, J=8.4, 5.3 Hz, 2H), 3.92 (s, 2H), 5.04 (s, 2H), 7.42-7.56 (m, 3H), 7.62-7.73 (m, 2H), 7.96 (d, J=8.4 Hz, 1H), 9.24 (s, 1H).

EXAMPLE 15

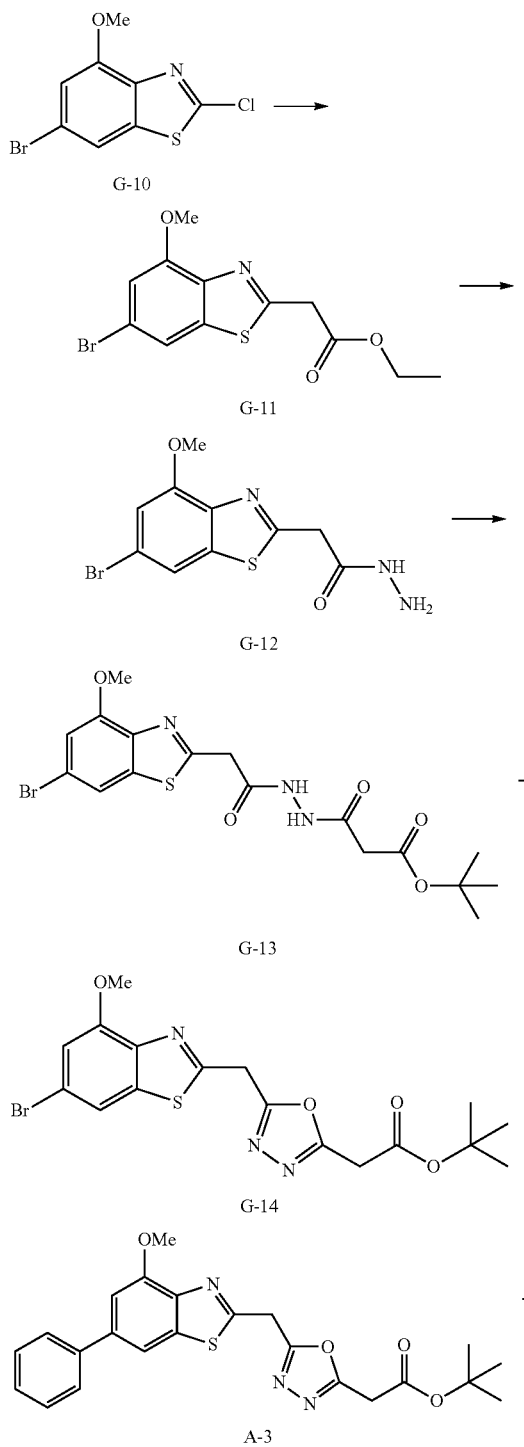

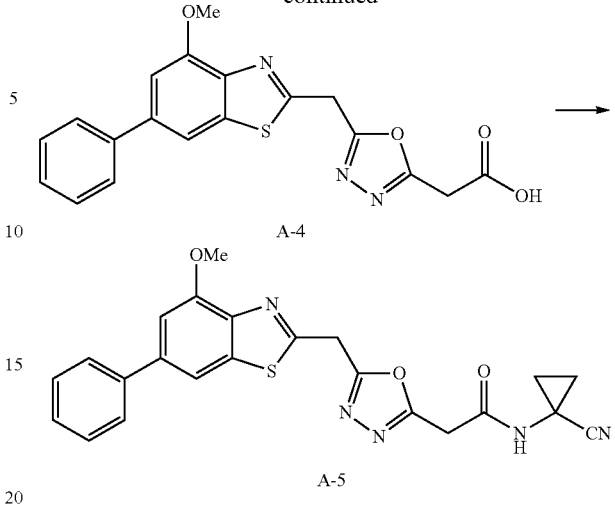

To a solution of Compound (G-10) (370 mg, 1.33 mmol) in anhydrous toluene (6 mL) was added dropwise sodium hexamethyldisilazide (1.9M, tetrahydrofuran solution) (1.61 mL, 3.1 mmol) under nitrogen atmosphere at −60° C. The resulting solution was stirred below −60° C. for 15 minutes. To the reaction solution was added diethyl carbonate (140 mg, 1.59 mmol) below −60° C. The reaction solution was warmed to room temperature, then the reaction solution was stirred for 3 hours. After the completion of the reaction, to the reaction solution was added 1N hydrochloric acid. The reaction solution was extracted with ethyl acetate. The organic layer was washed respectively with saturated sodium bicarbonate solution and brine, then dried over sodium sulfate. The solvent was removed under reduced pressure. The obtained residue was purified by column chromatography to give Compound (G-11) (345 mg, 79%).

Compound (G-11);

¹H-NMR (CDCl3) δ: 1.32 (t, J=7.2 Hz, 3H), 4.06 (s, 3H), 4.22 (s, 2H), 4.25 (q, J=7.2 Hz, 2H), 7.04 (s, 1H), 7.63 (s, 1H)

To a solution of Compound (G-11) (5.0 g, 15.1 mmol) in ethanol (20 mL) was added hydrazine hydrate (2.27 g, 45.4 mmol), then the reaction mixture was refluxed for 4 hours. The reaction solution was cooled to room temperature. The obtained crystal was collected by filtration to give Compound (G-12) (4.5 g, 93%).

Compound (G-12);

¹H-NMR (DMSO-d6) δ: 3.95 (s, 5H), 4.36 (s, 2H), 7.18 (s, 1H), 7.88 (s, 1H), 9.46 (br-s, 1H)

To a solution of Compound (G-12) (4.5 g, 14.2 mmol) in anhydrous dimethylformamide (10 ml) were successively added 3-tert-butoxy-3-oxopropanoic acid (2.96 g, 18.5 mmol), WSCD-HCl (3.55 g, 18.5 mmol), HOBt (580 mg, 4.27 mmol) and triethylamine (2.96 ml, 21.4 mmol) under nitrogen atmosphere at room temperature, then the reaction mixture was stirred for 3 hours. To the reaction solution was added water, then the reaction solution was extracted with ethyl acetate. The extraction was washed with brine and dried over sodium sulfate. The solvent was removed under reduced pressure. The obtained crystal was collected by filtration to give Compound (G-13) (6.0 g, 92%).

Compound (G-13);

Method C: Rt=1.81 min, 459.85 (ES+)

To a solution of Compound (G-13) (1.1 g, 2.4 mmol) in anhydrous dichloromethane (20 mL) were successively added carbon tetrabromide (880 mg, 2.64 mmol), triphenylphosphine (1.37 g, 5.28 mmol) and triethylamine (0.37 ml, 2.64 mmol) with ice-cooling, then the reaction mixture was stirred at 3° C. for 1 hour. To the reaction solution was added aqueous sodium bicarbonate solution, then the reaction solution was extracted with ethyl acetate. The extraction was washed with brine and dried over sodium sulfate. The solvent was removed under reduced pressure. The obtained residue was purified by column chromatography to give Compound (G-14) (360 mg, 34%).
Compound (G-14);
$^1$H-NMR (CDCl3) δ: 1.42 (s, 9H), 3.87 (s, 2H), 4.04 (s, 3H), 4.75 (s, 2H), 7.04 (s, 1H), 7.59 (s, 1H)

To a solution of Compound (G-14) (180 mg, 0.41 mmol) in anhydrous tetrahydrofuran (4 mL) were added TETRAKIS (TRIPHENYLPHOSPHINE) PALLADIUM (0) (47 mg, 0.041 mmol), PHENYLBORONIC ACID (65 mg, 0.53 mmol) and 2M aqueous sodium carbonate solution (510 μl, 1.02 mmol) under nitrogen atmosphere at room temperature, then the reaction mixture was stirred at 120° C. for 30 minutes under microwave irradiation. To the reaction solution were added 1M hydrochloric acid and ethyl acetate, then the reaction solution was extracted with ethyl acetate. The extraction was washed with brine and dried over sodium sulfate. The solvent was removed under reduced pressure. The obtained residue was purified by column chromatography to give Compound (A-3) (152 mg, 85%) as an oil. Compound (A-3);
$^1$H-NMR (CDCl3) δ: 1.42 (s, 9H), 3.87 (s, 2H), 4.11 (s, 3H), 4.79 (s, 2H), 7.13 (s, 1H), 7.37-7.52 (m, 3H), 7.60-7.65 (m, 3H)

To a solution of Compound (A-3) (150 mg, 0.34 mmol) in dichloromethane (2 mL) was added trifluoroacetic acid (1 mL), then the reaction mixture was stirred at room temperature for 2 hours. The solvent was removed under reduced pressure. The obtained crystal was washed with hexane to give Compound (A-4) (106 mg, 81%).
Compound (A-4);
$^1$H-NMR (DMSO-d6) δ: 4.03 (s, 3H), 4.08 (s, 2H), 4.92 (s, 2H), 7.30 (s, 1H), 7.41 (d, J=7.2 Hz, 1H), 7.50 (t, J=7.5 Hz, 2H), 7.78 (d, J=7.2 Hz, 2H), 7.95 (s, 1H)

To a solution of Compound (A-4) (95 mg, 0.25 mmol) in dimethylformamide (3 ml) were successively added 1-aminocyclopropanecarbonitrile hydrochloride (38 mg, 0.32 mmol), HATU (123 mg, 0.37 mmol) and Et$_3$N (0.084 mL, 0.62 mmol) under nitrogen atmosphere, then the reaction mixture was stirred at room temperature for 4 hours. To the reaction solution was added 10% aqueous sodium bicarbonate solution, the reaction mixture was extracted with ethyl acetate. The extraction was washed with brine and dried over sodium sulfate. The solvent was removed under reduced pressure. The obtained residue was purified by column chromatography to give Compound (A-5) (63 mg, 57%).
Compound (A-5);
$^1$H-NMR (DMSO-d6) δ: 1.14 (dd, J=8.4, 5.3 Hz, 2H), 1.48 (dd, J=8.4, 5.3 Hz, 2H), 3.91 (s, 2H), 4.04 (s, 3H), 4.92 (s, 2H), 7.30 (s, 1H), 7.40 (t, J=7.2 Hz, 1H), 7.50 (t, J=8.1 Hz, 2H), 7.78 (d, J=7.2 Hz, 2H), 7.95 (s, 1H), 9.23 (s, 1H).

The compounds shown below were prepared in accordance with the above examples. The data of NMR or LC/MS were shown for each compounds.

TABLE 1

| No. | Structure | NMR(δ) |
| --- | --- | --- |
| I-1-8 | [structure] | (CDCl3) δ : 2.55 (s, 3H), 4.72 (s, 2H), 7.39 (t, J = 7.4 Hz, 1H), 7.47 (t, J = 7.6 Hz, 2H), 7.63 (d, J = 7.1 Hz, 2H), 7.73 (dd, J = 8.6, 1.5 Hz, 1H), 8.06-8.09 (m, 2H). |
| I-1-9 | [structure] | (DMSO-d6) δ: 2.73 (t, J = 7.1 Hz, 2H), 3.06 (t, J = 7.1 Hz, 2H), 4.92 (s, 2H), 7.40 (t, J = 7.4 Hz, 1H), 7.50 (t, J = 7.6 Hz, 2H), 7.75 (d, J = 7.1 Hz, 2H), 7.82 (dd, J = 8.4, 1.8 Hz, 1H), 8.05 (d, J = 8.6 Hz, 1H), 8.43 (d, J = 2.0 Hz, 1 H), 12.39 (br s, 1H). |
| I-1-10 | [structure] | (DMSO-d6) δ: 1.33 (t, J = 7.1 Hz, 3H), 4.42 (q, J = 7.1 Hz, 2H), 5.10 (s, 2H), 7.40 (t, J = 7.4 Hz, 1H), 7.50 (t, J = 7.6 Hz, 2H), 7.76 (d, J = 7.6 Hz, 2H), 7.83 (dd, J = 8.4, 1.8 Hz, 1H), 8.05 (d, J = 8.6 Hz, 1H), 8.45 (d, J = 1.5 Hz, 1H). |

TABLE 1-continued

| No. | Structure | NMR(δ) |
|---|---|---|
| I-1-11 | 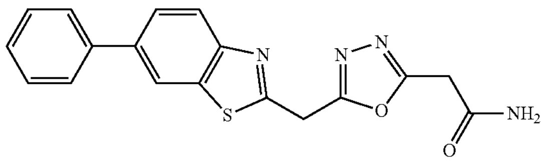 [SMILES: NC(=O)Cc1nnc(Cc2nc3ccc(-c4ccccc4)cc3s2)o1] | (DMSO-d6) δ: 3.83 (s, 2H), 4.94 (s, 2H), 7.26 (br s, 1H), 7.40 (t, J = 7.4 Hz, 1H), 7.50 (t, J = 7.9 Hz, 2H), 7.71-7.77 (m, 3H), 7.83 (t, J = 5.1 Hz, 1H), 8.05 (d, J = 8.1 Hz, 1H), 8.44 (s, 1H). |
| I-1-12 | 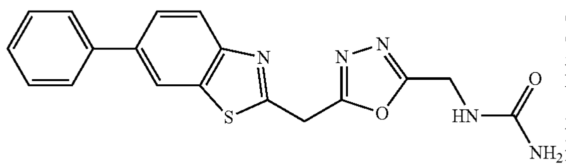 [SMILES: NC(=O)NCc1nnc(Cc2nc3ccc(-c4ccccc4)cc3s2)o1] | (DMSO-d6) δ: 4.42 (d, J = 6.1 Hz, 2H), 4.93 (s, 2H), 5.73 (s, 2H), 6.60 (t, J = 6.1 Hz, 1H), 7.40 (t, J = 7.4 Hz, 1H), 7.50 (t, J = 7.6 Hz, 2H), 7.75 (d, J = 7.6 Hz, 2H), 7.82 (dd, J = 8.6, 1.5 Hz, 1H), 8.05 (d, J = 8.6 Hz, 1H), 8.43 (d, J = 1.5 Hz, 1H). |

TABLE 2

| No. | Structure | NMR(δ) |
|---|---|---|
| I-1-13 | 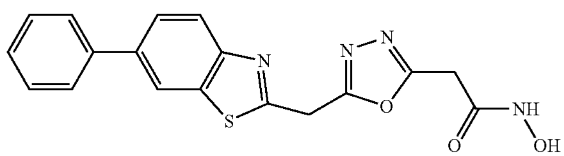 [SMILES: O=C(Cc1nnc(Cc2nc3ccc(-c4ccccc4)cc3s2)o1)NO] | (DMSO-d6) δ: 3.74 (s, 2H), 4.94 (s, 2H), 7.40 (t, J = 7.4 Hz, 1H), 7.50 (t, J = 7.6 Hz, 2H), 7.76 (d, J = 7.1 Hz, 2H), 7.83 (dd, J = 8.6, 1.5 Hz, 1H), 8.05 (d, J = 8.1 Hz, 1H), 8.43 (d, J =1.5 Hz, 1H), 9.08 (s, 1H), 10.83 (s, 1H). |
| I-1-14 | 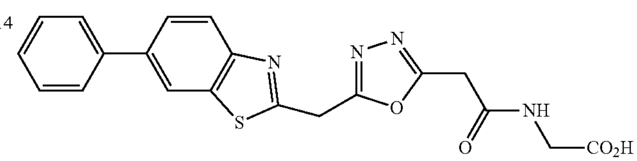 | (DMSO-d6) δ: 3.76 (br s, 2H), 3.95 (s, 2H), 4.94 (s, 2H), 7.40 (t, J = 7.4 Hz, 1H), 7.50 (t, J = 7.9 Hz, 2H), 7.76 (t, J = 4.3 Hz, 2H), 7.82 (dd, J = 8.6, 1.5 Hz, 1H), 8.05 (d, J = 8.1 Hz, 1H), 8.43 (d, J = 1.0 Hz, 1H), 8.55 (br s, 1H). |
| I-1-15 | 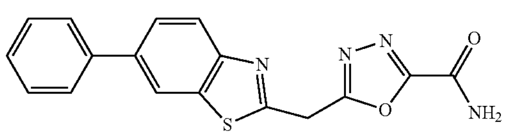 [SMILES: NC(=O)c1nnc(Cc2nc3ccc(-c4ccccc4)cc3s2)o1] | (DMSO-d6) δ: 5.06 (s, 2H), 7.40-7.51 (m, 3H), 7.75-7.84 (m, 3H), 8.04-8.07 (m, 1H), 8.26 (br s, 1H), 8.45 (br s, 1H), 8.67 (br s, 1H). |
| I-1-16 | 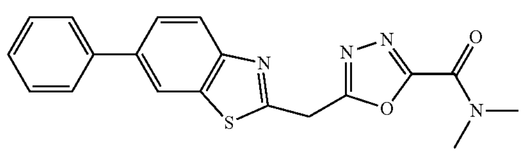 [SMILES: CN(C)C(=O)c1nnc(Cc2nc3ccc(-c4ccccc4)cc3s2)o1] | (CDCl3) δ: 3.17 (s, 3H), 3.49 (s, 3H), 4.81 (s, 2H), 7.38 (t, J = 7.4 Hz, 1H), 7.47 (t, J = 7.6 Hz, 2H), 7.63 (d, J = 7.1 Hz, 2H), 7.72 (dd, J = 8.6, 1.5 Hz, 1H), 8.04-8.07 (m, 2H). |
| I-1-17 | 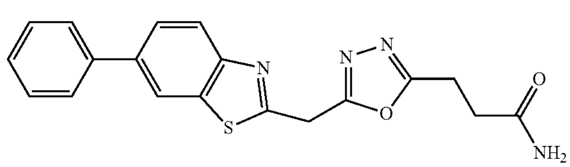 [SMILES: NC(=O)CCc1nnc(Cc2nc3ccc(-c4ccccc4)cc3s2)o1] | (CDCl3) δ: 2.79 (t, J = 7.4 Hz, 2H), 3.20 (t, J = 7.1 Hz, 2H), 4.72 (s, 2H), 5.34 (br s, 1H), 5.71 (br s, 1H), 7.39 (t, J = 7.4 Hz, 1H), 7.47 (t, J = 7.6 Hz, 2H), 7.63 (d, J = 7.1 Hz, 2H), 7.73 (dd, J = 8.4, 1.8 Hz, 1H), 8.05-8.07 (m, 2H). |

TABLE 3

| No. | Structure | NMR(δ) |
|---|---|---|
| I-1-18 | 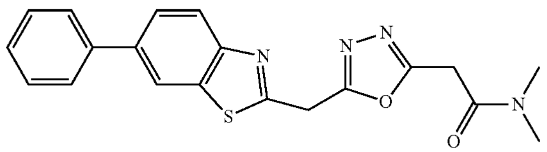 [SMILES: CN(C)C(=O)Cc1nnc(Cc2nc3ccc(-c4ccccc4)cc3s2)o1] | (CDCl3) δ: 2.99 (s, 3H), 3.11 (s, 3H), 4.00 (s, 2H), 4.75 (s, 2H), 7.38 (t, J = 7.4 Hz, 1H), 7.47 (t, J = 7.6 Hz, 2H), 7.63 (d, J = 8.1 Hz, 2H), 7.72 (dd, J = 8.6, 2.0 Hz, 1H), 8.04-8.07 (m, 2H). |
| I-1-19 | 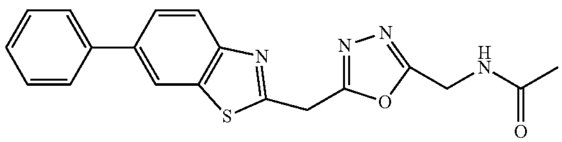 [SMILES: CC(=O)NCc1nnc(Cc2nc3ccc(-c4ccccc4)cc3s2)o1] | (DMSO-d6) δ: 1.87 (s, 3H), 4.49 (d, J = 5.6 Hz, 2H), 4.94 (s, 2H), 7.40 (t, J = 7.4 Hz, 1H), 7.50 (t, J = 7.6 Hz, 2H), 7.75 (d, J = 7.1 Hz, 2H), 7.83 (dd, J = 8.6, 1.5 Hz, 1H), 8.05 (d, J = 8.6 Hz, 1H), 8.43 (d, J = 2.0 Hz, 1H), 8.61 (t, J = 5.8 Hz, 1H). |
| I-1-20 | 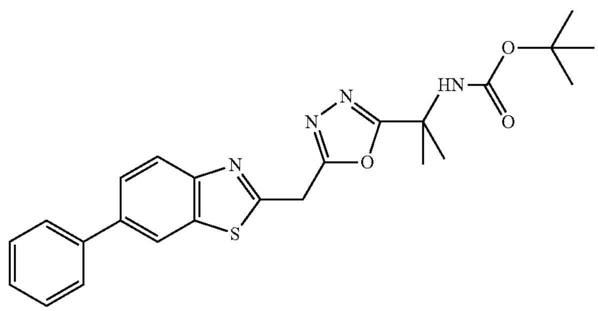 [SMILES: CC(C)(C)OC(=O)NC(C)(C)c1nnc(Cc2nc3ccc(-c4ccccc4)cc3s2)o1] | (CDCl3) δ: 1.31 (s, 9H), 1.72 (s, 6H), 4.74 (s, 2H), 5.00 (br s, 1H), 7.38 (t, J = 7.4 Hz, 1H), 7.47 (t, J = 7.6 Hz, 2H), 7.63 (d, J = 7.1 Hz, 2H), 7.72 (d, J = 8.1 Hz, 1H), 8.04-8.06 (m, 2H). |
| I-1-21 | 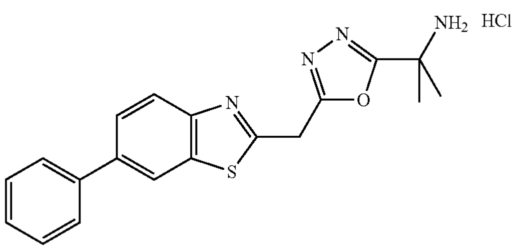 [SMILES: Cl ; CC(C)(N)c1nnc(Cc2nc3ccc(-c4ccccc4)cc3s2)o1] | (DMSO-d6) δ: 1.70 (s, 6H), 5.02 (s, 2H), 7.41 (t, J = 7.4 Hz, 1H), 7.51 (t, J = 7.9 Hz, 2H), 7.75 (d, J = 7.1 Hz, 2H), 7.83 (dd, J = 8.6, 1.5 Hz, 1H), 8.04 (d, J = 8.6 Hz, 1H), 8.45 (d, J = 1.5 Hz, 1H), 9.05 (br s, 3H). |
| I-1-22 | 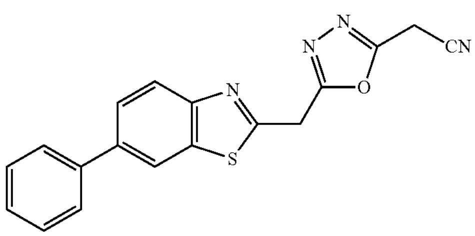 [SMILES: N#CCc1nnc(Cc2nc3ccc(-c4ccccc4)cc3s2)o1] | (CDCl3) δ: 4.07 (s, 2H), 4.78 (s, 2H), 7.39 (t, J = 7.4 Hz, 1H), 7.48 (t, J = 7.4 Hz, 2H), 7.63 (d, J = 7.6 Hz, 2H), 7.74 (dd, J = 8.6, 1.5 Hz, 1H), 8.06-8.08 (m, 2H). |

TABLE 4

| No. | Structure | NMR(δ) |
|---|---|---|
| I-1-23 | 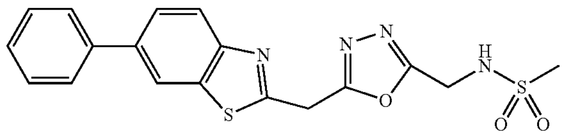 [SMILES: CS(=O)(=O)NCc1nnc(Cc2nc3ccc(-c4ccccc4)cc3s2)o1] | (CDCl3) δ: 3.06 (s, 3H), 4.63 (d, J = 6.1 Hz, 2H), 4.76 (s, 2H), 5.07 (t, J = 5.8 Hz, 1H), 7.39 (t, J = 6.8 Hz, 1H), 7.48 (t, J = 7.9 Hz, 2H), 7.63 (dd, J = 7.1, 1.0 Hz, 2H), 7.73 (dd, J = 8.6, 2.0 Hz, 1H), 8.03-8.07 (m, 2H). |

TABLE 4-continued

| No. | Structure | NMR(δ) |
| --- | --- | --- |
| I-1-24 | 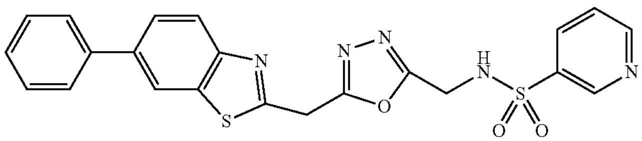 [SMILES: O=S(=O)(NCc1nnc(Cc2nc3ccc(-c4ccccc4)cc3s2)o1)c1cccnc1] | (DMSO-d6) δ: 4.43 (s, 2H), 4.84 (s, 2H), 7.40 (t, J = 7.4 Hz, 1H), 7.51 (t, J = 7.9 Hz, 2H), 7.57 (dd, J = 8.1, 4.6 Hz, 1H), 7.76 (d, J = 8.1 Hz, 2H), 7.84 (d, J = 8.6 Hz, 1H), 8.05 (d, J = 8.6 Hz, 1H), 8.13 (d, J = 8.1 Hz, 1H), 8.45 (s, 1H), 8.77 (d, J = 4.6 Hz, 1H), 8.92-8.92 (m, 2H). |
| I-1-25 | 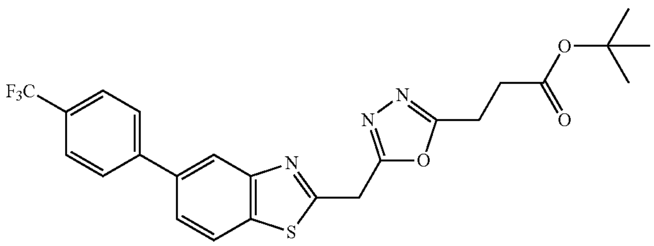 [SMILES: CC(C)(C)OC(=O)CCc1nnc(Cc2nc3cc(-c4ccc(C(F)(F)F)cc4)ccc3s2)o1] | (CDCl3) δ: 1.42 (s, 9H), 2.77 (t, J = 7.4 Hz, 2H), 3.13 (t, J = 7.4 Hz, 2H), 4.73 (s, 2H), 7.66 (d, J = 8.1 Hz, 1H), 7.72-7.78 (m, 4H), 7.96 (d, J = 8.6 Hz, 1H), 8.24 (s, 1H). |
| I-1-26 | 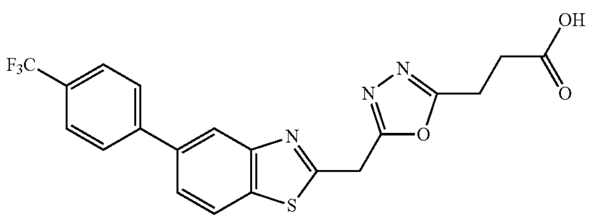 [SMILES: O=C(O)CCc1nnc(Cc2nc3cc(-c4ccc(C(F)(F)F)cc4)ccc3s2)o1] | (DMSO-d6) δ: 2.72 (t, J = 6.8 Hz, 2H), 3.05 (t, J = 7.1 Hz, 2H), 4.94 (s, 2H), 7.85 (d, J = 8.1 Hz, 3H), 8.02 (d, J = 8.1 Hz, 2H), 8.25 (d, J = 8.6 Hz, 1H), 8.36 (s, 1H). |
| I-1-27 | 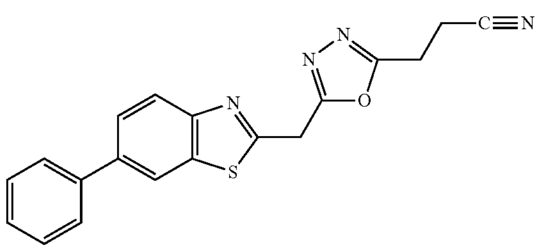 [SMILES: N#CCCc1nnc(Cc2nc3ccc(-c4ccccc4)cc3s2)o1] | (CDCl3) δ: 2.93 (t, J = 7.6 Hz, 2H), 3.25 (t, J = 7.6 Hz, 2H), 4.75 (s, 2H), 7.39 (t, J = 7.1 Hz, 1H), 7.48 (t, J = 7.4 Hz, 2H), 7.63 (d, J = 8.1 Hz, 2H), 7.73 (dd, J = 8.6, 1.5 Hz, 1H), 8.05-8.08 (m, 2H). |

TABLE 5

| No. | Structure | NMR(δ) |
| --- | --- | --- |
| I-1-28 | 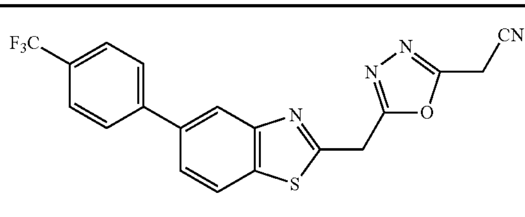 | (CDCl3) δ: 4.08 (s, 2H), 4.80 (s, 2H), 7.67 (dd, J = 8.4, 1.8 Hz, 1H), 7.74-7.77 (m, 4H), 7.98 (d, J = 8.6 Hz, 1H), 8.25 (d, J = 1.5 Hz, 1H). |

TABLE 5-continued

| No. | Structure | NMR(δ) |
|---|---|---|
| I-1-29 | 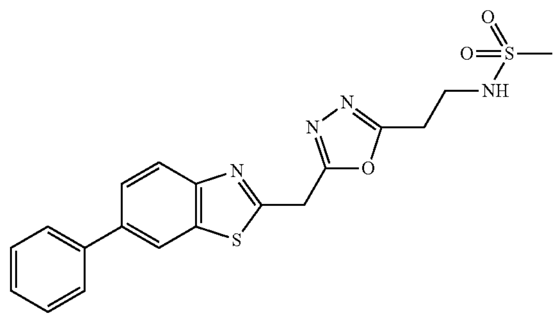 [SMILES: CS(=O)(=O)NCCc1nnc(Cc2nc3ccc(-c4ccccc4)cc3s2)o1] | (CDCl3) δ: 2.98 (s, 3H), 3.15 (t, J = 6.1 Hz, 2H), 3.66 (q, J = 6.3 Hz, 2H), 4.74 (s, 2H), 5.20 (t, J = 6.1 Hz, 1H), 7.39 (t, J = 7.4 Hz, 1H), 7.48 (t, J = 7.9 Hz, 2H), 7.63 (d, J = 7.1 Hz, 2H), 7.73 (dd, J = 8.6, 1.5 Hz, 1H), 8.06-8.08 (m, 2H). |
| I-1-30 | 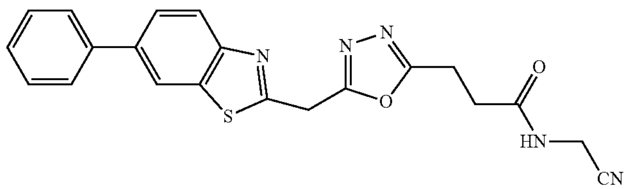 [SMILES: N#CCNC(=O)CCc1nnc(Cc2nc3ccc(-c4ccccc4)cc3s2)o1] | (DMSO-d6) δ: 2.67 (t, J = 7.1 Hz, 2H), 3.09 (t, J = 7.1 Hz, 2H), 4.13 (d, J = 5.6 Hz, 2H), 4.91 (s, 2H), 7.40 (t, J = 7.4 Hz, 1H), 7.50 (t, J = 7.6 Hz, 2H), 7.76 (d, J = 8.1 Hz, 2H), 7.83 (d, J = 8.6 Hz, 1H), 8.05 (d, J = 8.6 Hz, 1H), 8.43 (s, 1H), 8.73 (t, J = 5.3 Hz, 1H). |
| I-1-31 | 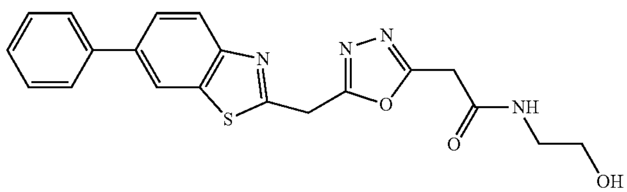 [SMILES: O=C(Cc1nnc(Cc2nc3ccc(-c4ccccc4)cc3s2)o1)NCCO] | (CDCl3) δ: 2.55 (br s, 1H), 3.51 (q, J = 4.8 Hz, 2H), 3.77 (t, J = 4.8 Hz, 2H), 3.93 (s, 2H), 4.77 (s, 2H), 7.41 (t, J = 6.8 Hz, 1H), 7.50 (t, J = 7.9 Hz, 2H), 7.65 (d, J = 8.1 Hz, 2H), 7.75 (dd, J = 8.6, 1.5 Hz, 1H), 8.07-8.09 (m, 2H). |
| I-1-32 | 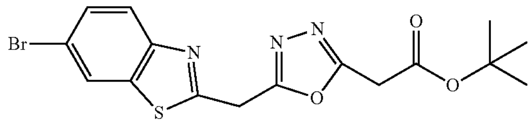 [SMILES: CC(C)(C)OC(=O)Cc1nnc(Cc2nc3ccc(Br)cc3s2)o1] | (CDCl3) δ: 1.42 (s, 9H), 3.88 (s, 2H), 4.72 (s, 2H), 7.60 (dd, J = 8.6, 2.0 Hz, 1H), 7.86 (d, J = 8.6 Hz, 1H), 8.01 (d, J = 1.5 Hz, 1H). |

TABLE 6

| No. | Structure | NMR(δ) |
|---|---|---|
| I-1-33 | 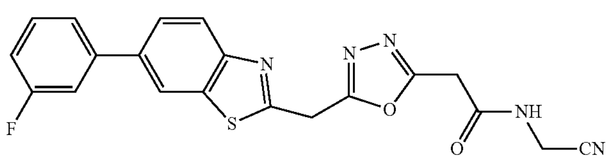 [SMILES: N#CCNC(=O)Cc1nnc(Cc2nc3ccc(-c4cccc(F)c4)cc3s2)o1] | (DMSO-d6) δ: 3.99 (s, 2H), 4.19 (d, J = 5.6 Hz, 2H), 4.97 (s, 2H), 7.21-7.26 (m, 1H), 7.51-7.63 (m, 3H), 7.87 (dd, J = 8.6, 1.5 Hz, 1H), 8.06 (d, J = 8.6 Hz, 1H), 8.50 (d, J = 2.0 Hz, 1H), 9.03 (t, J = 5.3 Hz, 1H). |
| I-1-34 | 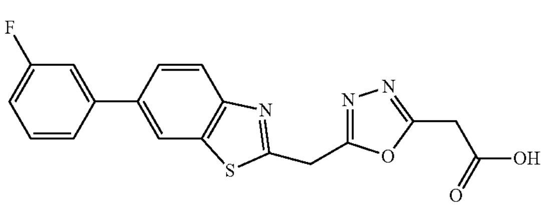 [SMILES: O=C(O)Cc1nnc(Cc2nc3ccc(-c4cccc(F)c4)cc3s2)o1] | (DMSO-d6) δ: 4.08 (s, 2H), 4.98 (s, 2H), 7.23 (t, J = 7.9 Hz, 1H), 7.52-7.63 (m, 3H), 7.87 (dd, J = 8.6, 2.0 Hz, 1H), 8.05 (d, J = 8.6 Hz, 1H), 8.50 (d, J = 1.5 Hz, 1H), 13.10 (br s, 1H). |

TABLE 6-continued

| No. | Structure | NMR(δ) |
|---|---|---|
| I-1-35 | (structure) | (CDCl3) δ: 1.42 (s, 9H), 3.89 (s, 2H), 4.75 (s, 2H), 7.16 (t, J = 8.6 Hz, 2H), 7.57-7.60 (m, 2H), 7.66 (dd, J = 8.6, 1.5 Hz, 1H), 8.01 (d, J = 1.0 Hz, 1H), 8.05 (d, J = 8.6 Hz, 1H). |
| I-1-36 | (structure) | (CDCl3) δ: 1.43 (s, 9H), 3.89 (s, 2H), 4.77 (s, 2H), 7.71-7.74 (m, 5H), 8.07-8.11 (m, 2H). |
| I-1-37 | (structure) | (DMSO-d6) δ: 3.99 (s, 2H), 4.19 (d, J = 5.6 Hz, 2H), 4.96 (s, 2H), 7.33 (t, J = 8.9 Hz, 2H), 7.78-7.82 (m, 3H), 8.04 (d, J = 8.6 Hz, 1H), 8.42 (d, J = 1.5 Hz, 1H), 9.03 (t, J = 5.3 Hz, 1H). |

TABLE 7

| No. | Structure | NMR(δ) |
|---|---|---|
| I-1-38 | (structure) | (DMSO-d6) δ: 3.99 (s, 2H), 4.20 (d, J = 5.6 Hz, 2H), 4.98 (s, 2H), 7.86 (d, J = 8.6 Hz, 2H), 7.90 (dd, J = 8.4, 1.8 Hz, 1H), 7.99 (d, J = 8.1 Hz, 2H), 8.10 (d, J = 8.1 Hz, 1H), 8.54 (d, J = 2.0 Hz, 1H), 9.03 (t, J = 5.3 Hz, 1H). |
| I-1-39 | (structure) | (DMSO-d6) δ: 4.08 (s, 2H), 4.99 (s, 2H), 7.84-7.89 (m, 3H), 7.99 (d, J = 8.1 Hz, 2H), 8.10 (d, J = 8.6 Hz, 1H), 8.55 (d, J = 1.5 Hz, 1H), 13.11 (br s, 1H). |
| I-1-40 | (structure) | (CDCl3) δ: 1.45 (s, 9H), 3.14 (s, 3H), 3.92 (s, 2H), 4.79 (s, 2H), 7.69-7.78 (m, 2H), 7.93-7.99 (m, 2H), 8.11-8.15 (m, 2H), 8.23 (t, J = 1.8 Hz, 1H). |
| I-1-41 | (structure) | (CDCl3) δ: 3.12 (s, 3H), 3.97 (s, 2H), 4.25 (d, J = 5.6 Hz, 2H), 4.78 (s, 2H), 7.67-7.76 (m, 2H), 7.91-7.97 (m, 3H), 8.09-8.13 (m, 2H), 8.21 (s, 1H). |

TABLE 7-continued

| No. | Structure | NMR(δ) |
|---|---|---|
| I-1-42 | 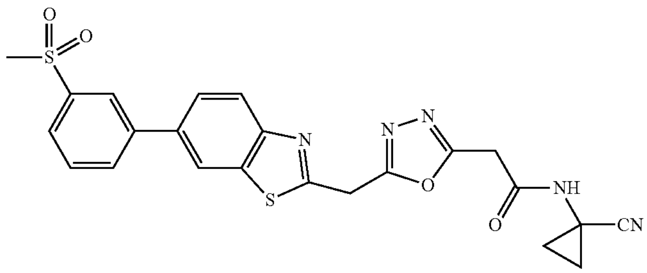 [SMILES: CS(=O)(=O)c1cccc(-c2ccc3nc(Cc4nnc(CC(=O)NC5(C#N)CC5)o4)sc3c2)c1] | (CDCl3) δ: 1.30 (dd, J = 8.4, 5.8 Hz, 2H), 1.60 (dd, J = 8.6, 6.1 Hz, 2H), 3.12 (s, 3H), 3.92 (s, 2H), 4.77 (s, 2H), 7.67-7.77 (m, 2H), 7.91-7.98 (m, 3H), 8.09-8.13 (m, 2H), 8.21 (s, 1H). |

TABLE 8

| No. | Structure | NMR(δ) |
|---|---|---|
| I-1-43 | 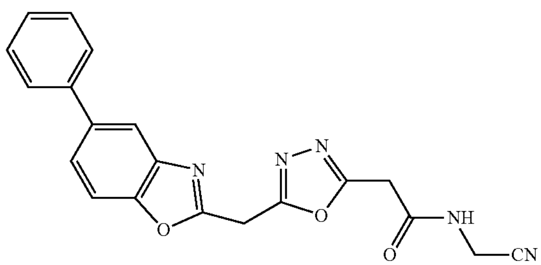 [SMILES: N#CCNC(=O)Cc1nnc(Cc2nc3cc(-c4ccccc4)ccc3o2)o1] | (DMSO-d6) δ: 4.00 (s, 2H), 4.20 (d, J = 5.1 Hz, 2H), 4.88 (s, 2H), 7.38 (t, J = 7.4 Hz, 1H), 7.48 (t, J = 7.6 Hz, 2H), 7.70-7.73 (m, 3H), 7.82 (d, J = 8.6 Hz, 1H), 8.01 (d, J = 1.5 Hz, 1H), 9.03 (t, J = 5.3 Hz, 1H). |
| I-1-44 | 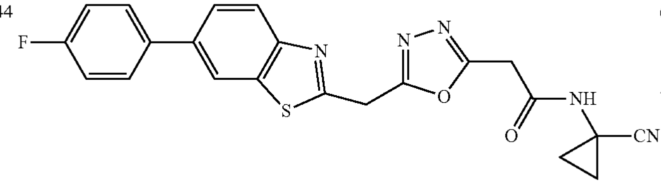 | (DMSO-d6) δ: 1.14 (dd, J = 8.4, 5.8 Hz, 2H), 1.49 (dd, J = 8.4, 5.3 Hz, 2H), 3.91 (s, 2H), 4.96 (s, 2H), 7.31-7.35 (m, 2H), 7.78-7.82 (m, 3H), 8.04 (d, J = 8.6 Hz, 1H), 8.42 (d, J = 2.0 Hz, 1H), 9.23 (s, 1H). |
| I-1-45 | 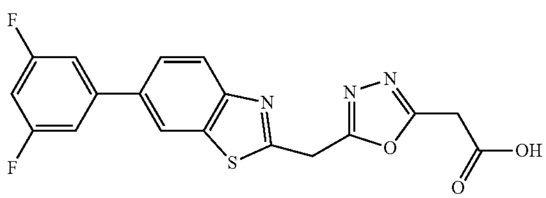 [SMILES: O=C(O)Cc1nnc(Cc2nc3ccc(-c4cc(F)cc(F)c4)cc3s2)o1] | (DMSO-d6) δ: 4.08 (s, 2H), 4.98 (s, 2H), 7.27 (tt, J = 9.1, 2.2 Hz, 1H), 7.53-7.57 (m, 2H), 7.91 (dd, J = 8.6, 2.0 Hz, 1H), 8.06 (d, J = 8.6 Hz, 1H), 8.55 (d, J = 1.5 Hz, 1H). |
| I-1-46 | 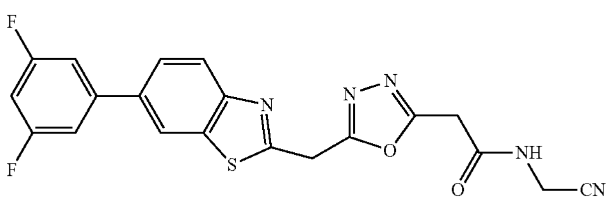 [SMILES: N#CCNC(=O)Cc1nnc(Cc2nc3ccc(-c4cc(F)cc(F)c4)cc3s2)o1] | (DMSO-d6) δ: 3.99 (s, 2H), 4.19 (d, J = 5.6 Hz, 2H), 4.97 (s, 2H), 7.27 (tt, J = 9.1, 2.1 Hz, 1H), 7.55 (d, J = 7.1 Hz, 2H), 7.91 (dd, J = 8.6, 2.0 Hz, 1H), 8.06 (d, J = 8.6 Hz, 1H), 8.54 (d, J = 1.5 Hz, 1H), 9.02 (t, J = 5.3 Hz, 1H). |
| I-1-47 | 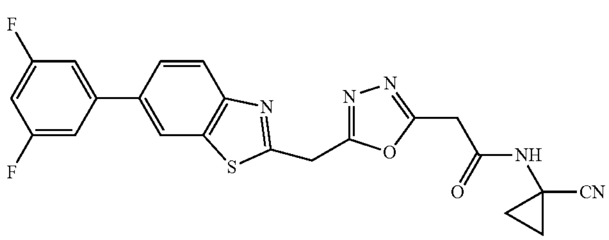 [SMILES: N#CC1(NC(=O)Cc2nnc(Cc3nc4ccc(-c5cc(F)cc(F)c5)cc4s3)o2)CC1] | (DMSO-d6) δ: 1.14 (dd, J = 8.4, 5.8 Hz, 2H), 1.49 (dd, J = 8.4, 5.3 Hz, 2H), 3.91 (s, 2H), 4.98 (s, 2H), 7.24-7.30 (m, 1H), 7.53-7.57 (m, 2H), 7.91 (dd, J = 8.6, 2.0 Hz, 1H), 8.06 (d, J = 8.6 Hz, 1H), 8.55 (d, J = 1.5 Hz, 1H), 9.23 (s, 1H). |

TABLE 9

| No. | Structure | NMR(δ) |
|---|---|---|
| I-1-48 | 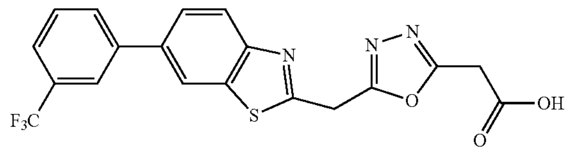 [SMILES: O=C(O)Cc1nnc(Cc2nc3ccc(-c4cccc(C(F)(F)F)c4)cc3s2)o1] | (DMSO-d6) δ: 4.08 (s, 2H), 4.98 (s, 2H), 7.73-7.78 (m, 2H), 7.92 (dd, J = 8.6, 1.5 Hz, 1H), 8.07-8.10 (m, 3H), 8.57 (d, J = 1.0 Hz, 1H), 13.12 (br s, 1H). |
| I-1-49 | 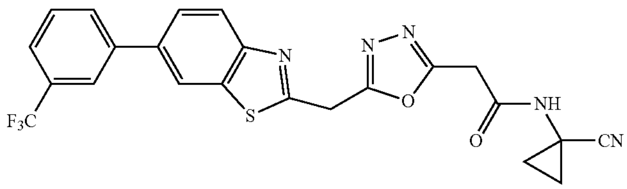 [SMILES: N#CC1(NC(=O)Cc2nnc(Cc3nc4ccc(-c5cccc(C(F)(F)F)c5)cc4s3)o2)CC1] | (DMSO-d6) δ: 1.14 (dd, J = 8.1, 5.6 Hz, 2H), 1.49 (dd, J = 8.4, 5.3 Hz, 2H), 3.91 (s, 2H), 4.98 (s, 2H), 7.72-7.78 (m, 2H), 7.92 (dd, J = 8.6, 2.0 Hz, 1H), 8.07-8.10 (m, 3H), 8.57 (d, J = 2.0 Hz, 1H), 9.23 (s, 1H). |
| I-1-50 | 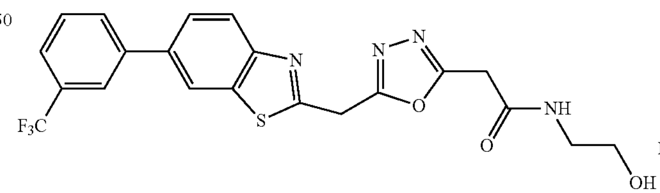 | (DMSO-d6) δ: 3.14 (q, J = 5.9 Hz, 2H), 3.41 (q, J = 5.7 Hz, 2H), 3.87 (s, 2H), 4.70 (t, J = 5.6 Hz, 1H), 4.96 (s, 2H), 7.72-7.78 (m, 2H), 7.92 (dd, J = 8.6, 2.0 Hz, 1H), 8.07-8.10 (m, 3H), 8.30 (t, J = 5.6 Hz, 1H), 8.57 (d, J = 1.5 Hz, 1H). |
| I-1-51 | 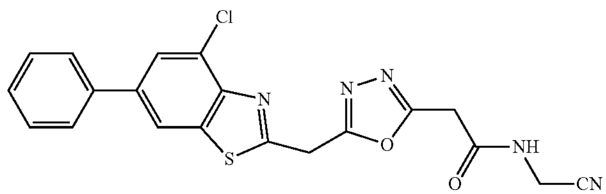 [SMILES: N#CCNC(=O)Cc1nnc(Cc2nc3c(Cl)cc(-c4ccccc4)cc3s2)o1] | (DMSO-d6) δ: 4.02 (,s, 2H), 4.20 (d, J = 5.7 Hz, 2H), 5.00 (s, 2H), 7.41-7.45 (m, 1H), 7.48-7.53 (m, 2H), 7.75-7.80 (m, 2H), 7.94 (s, 1H), 8.44 (s, 1H), 9.03 (t, J = 5.4Hz, 1H). |
| I-1-52 | 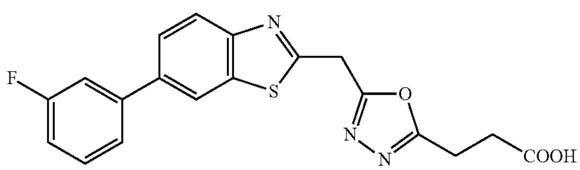 [SMILES: O=C(O)CCc1nnc(Cc2nc3ccc(-c4cccc(F)c4)cc3s2)o1] | (DMSO-d6) δ: 2.73 (t, J = 7.0 Hz, 2H), 3.06 (t, J = 7.0 Hz, 2H), 4.93 (s, 2H), 7.23 (m, 1H), 7.54 (dd, J = 14.3, 7.6 Hz, 1H), 7.62 (d, J = 8.1 Hz, 2H), 7.87 (dd, J = 8.6, 2.0 Hz, 1H), 8.06 (d, J = 8.6 Hz, 1H), 8.49 (d, J = 2.0 Hz, 1H). |

TABLE 10

| No. | Structure | NMR(δ) |
|---|---|---|
| I-1-53 | 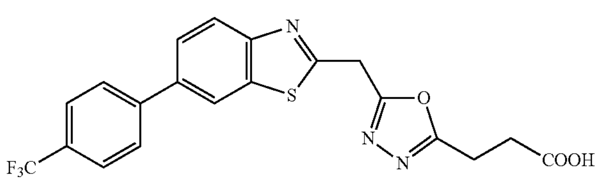 [SMILES: O=C(O)CCc1nnc(Cc2nc3ccc(-c4ccc(C(F)(F)F)cc4)cc3s2)o1] | (DMSO-d6) δ: 2.74 (t, J = 7.1 Hz, 2H), 3.06 (t, J = 7.1 Hz, 2H), 4.94 (s, 2H), 7.83-7.93 (m, 3H), 7.99 (d, J = 8.2 Hz, 2H), 8.10 (d, J = 8.6 Hz, 1H), 8.54 (d, J = 1.7 Hz, 1H). |
| I-1-54 | 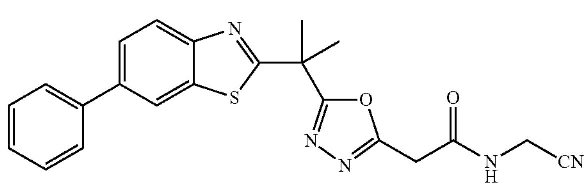 [SMILES: CC(C)(c1nnc(CC(=O)NCC#N)o1)c1nc2ccc(-c3ccccc3)cc2s1] | (DMSO-d6) δ: 1.96 (s, 6H), 3.97 (s, 2H), 4.18 (d, J = 4.7 Hz, 2H), 7.40 (t, J = 7.2 Hz, 1H), 7.50 (t, J = 7.6 Hz, 2H), 7.75 (d, J = 7.1 Hz, 2H), 7.83 (dd, J = 8.5, 1.8 Hz, 1H), 8.07 (d, J = 8.5 Hz, 1H), 8.43 (d, J = 1.8 Hz, 1H), 9.00 (m, 1H). |

TABLE 10-continued

| No. | Structure | NMR(δ) |
|---|---|---|
| I-1-55 | [structure] | (CDCl3) δ: 1.74 (s, 6H), 3.92 (s, 2H), 4.76 (s, 2H), 7.39 (t, J = 7.4 Hz, 1H), 7.48 (t, J = 7.6 Hz, 2H), 7.62-7.64 (m, 2H), 7.73 (dd, J = 8.6, 1.5 Hz, 1H), 7.79 (s, 1H), 8.05-8.07 (m, 2H). |
| I-1-56 | [structure] | (DMSO-d6) δ: 3.99 (s, 2H), 4.19 (d, J = 5.6 Hz, 2H), 4.97 (s, 2H), 7.73-7.78 (m, 2H), 7.92 (dd, J = 8.4, 1.8 Hz, 1H), 8.08 (t, J = 4.1 Hz, 3H), 8.57 (d, J = 1.5 Hz, 1H), 9.03 (t, J = 5.3 Hz, 1H). |
| I-1-57 | [structure] | (CDCl3) δ: 1.42 (s, 9H), 3.89 (s, 2H), 4.76 (s, 2H), 7.16-7.25 (m, 2H), 7.33-7.39 (m, 1H), 7.48 (td, J = 7.7, 1.7 Hz, 1H), 7.67 (dt, J = 8.4, 1.6 Hz, 1H), 8.04-8.08 (m, 2H). |

TABLE 11

| No. | Structure | NMR(δ) |
|---|---|---|
| I-1-58 | [structure] | (DMSO-d6) δ: 3.99 (s, 2H), 4.19 (d, J = 5.6 Hz, 2H), 4.97 (s, 2H), 7.33-7.38 (m, 2H), 7.44-7.49 (m, 1H), 7.61 (td, J = 8.0, 1.7 Hz, 1H), 7.69 (d, J = 8.6 Hz, 1H), 8.07 (d, J = 8.6 Hz, 1H), 8.32 (s, 1H), 9.02 (t, J = 5.3 Hz, 1H). |
| I-1-59 | [structure] | (CDCl3) δ: 2.06-2.25 (m, 2H), 2.36-2.44 (m, 2H), 2.77-2.86 (m, 2H), 3.93 (s, 2H), 4.76 (s, 2H), 7.39 (t, J = 7.4 Hz, 1H), 7.48 (t, J = 7.4 Hz, 2H), 7.63 (d, J = 7.6 Hz, 2H), 7.74 (dd, J = 8.6, 2.0 Hz, 1H), 8.02-8.07 (m, 3H). |
| I-1-60 | [structure] | (DMSO-d6) δ: 3.84 (s, 3H), 3.99 (s, 2H), 4.20 (d, J = 5.58 Hz, 2H), 4.92 (s, 2H), 7.35 (m, 1H), 7.43 (m, 2H), 7.51 (m, 2H), 7.67 (s, 1H), 7.99 (s, 1H), 9.02 (t, J = 5.32 Hz, 1H). |
| I-1-61 | [structure] | (DMSO-d6) δ: 1.14 (dd, J = 8.6, 5.6 Hz, 2H), 1.49 (dd, J = 8.4, 5.3 Hz, 2H), 3.91 (s, 2H), 4.97 (s, 2H), 7.32-7.38 (m, 2H), 7.44-7.49 (m, 1H), 7.61 (td, J = 8.0, 1.9 Hz, 1H), 7.70 (dd, J = 8.6, 1.5 Hz, 1H), 8.07 (d, J = 8.6 Hz, 1H), 8.32 (s, 1H), 9.23 (s, 1H). |

TABLE 11-continued

| No. | Structure | NMR(δ) |
|---|---|---|
| I-1-62 | 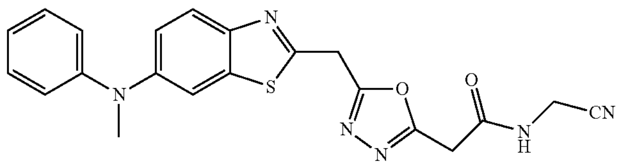 [SMILES: CN(c1ccccc1)c1ccc2nc(Cc3nnc(CC(=O)NCC#N)o3)sc2c1] | (DMSO-d6) δ: 3.32 (s, 3H), 3.98 (s, 1H), 4.19 (d, J = 5.6 Hz, 2H), 4.85 (s, 2H), 7.00 (t, J = 7.4 Hz, 1H), 7.04-7.13 (m, 3H), 7.31 (t, J = 7.9 Hz, 2H), 7.66 (d, J = 2.5 Hz, 1H), 7.81 (d, J = 9.1 Hz, 1H), 9.01 (t, J = 5.6 Hz, 1H) |

TABLE 12

| No. | Structure | NMR(δ) |
|---|---|---|
| I-1-63 | 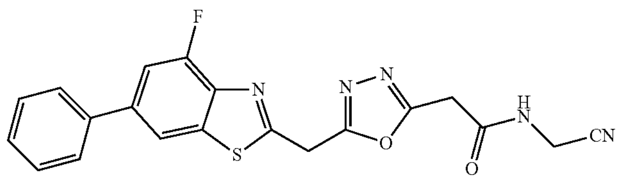 [SMILES: N#CCNC(=O)Cc1nnc(Cc2nc3c(F)cc(-c4ccccc4)cc3s2)o1] | (DMSO-d6) δ: 4.00(s, 2H), 4.20 (d, J = 5.4 Hz, 2H), 5.00 (s, 2H), 7.38-7.44 (m, 1H), 7.48-7.53 (m, 2H), 7.71-7.80 (m, 3H), 8.30 (d, J = 1.5Hz, 1H), 9.03 (t, J = 5.4Hz, 1H). |
| I-1-64 | 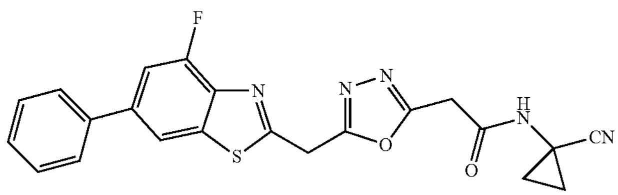 [SMILES: N#CC1(NC(=O)Cc2nnc(Cc3nc4c(F)cc(-c5ccccc5)cc4s3)o2)CC1] | (DMSO-d6) δ: 1.14 (dd, J = 8.40, 5.70 Hz, 2H), 1.49 (dd, J = 8.40, 5.54 Hz, 2H), 3.91 (s, 2H), 5.00 (s, 2H), 7.39-7.54 (m, 3H), 7.72-7.81 (m, 3H), 8.23 (d, J = 1.5 Hz, 1H), 9.23 (s, 1H). |
| I-1-65 | 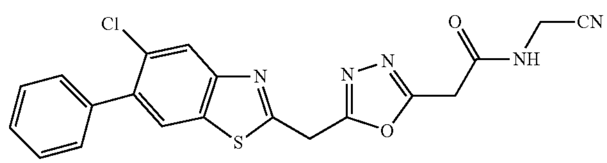 [SMILES: N#CCNC(=O)Cc1nnc(Cc2nc3cc(Cl)c(-c4ccccc4)cc3s2)o1] | (DMSO-d6) δ: 3.99 (s, 2H), 4.20 (d, J = 5.58 Hz, 2H), 4.99 (s, 2H), 7.55-7.43 (m, 5H), 8.19 (s, 1H), 8.21 (s, 1H), 9.03 (t, J = 5.58 Hz, 1H). |
| I-1-66 | 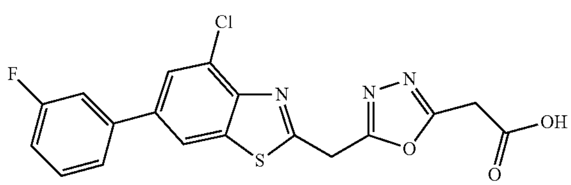 [SMILES: O=C(O)Cc1nnc(Cc2nc3c(Cl)cc(-c4cccc(F)c4)cc3s2)o1] | (DMSO-d6) δ: 4.09 (s, 1H), 5.03 (s, 2H), 7.23-7.29 (m, 1H), 7.51-7.59 (m, 1H), 7.64-7.69 (m, 2H), 8.06 (s, 1H), 8.50 (s, 1H), 13.16 (s, 1H). |
| I-1-67 | 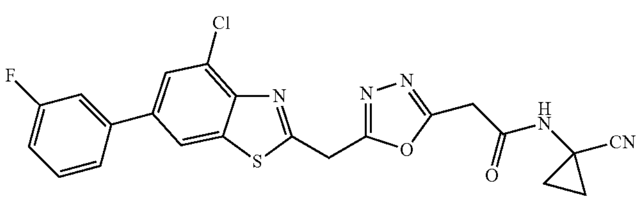 [SMILES: N#CC1(NC(=O)Cc2nnc(Cc3nc4c(Cl)cc(-c5cccc(F)c5)cc4s3)o2)CC1] | (DMSO-d6) δ: 1.14 (dd, J = 8.70, 5.70 Hz, 2H), 1.49 (dd, J = 8.70, 5.70 Hz, 2H), 3.92 (s, 2H), 5.00 (s, 2H), 7.23-7.29 (m, 1H), 7.51-7.58 (m, 1H), 7.64-7.69 (m, 2H), 8.01 (s, 1H), 8.50 (s, 1H), 9.23 (s, 1H) |

TABLE 13

| No. | Structure | NMR(δ) |
|---|---|---|
| I-1-68 | 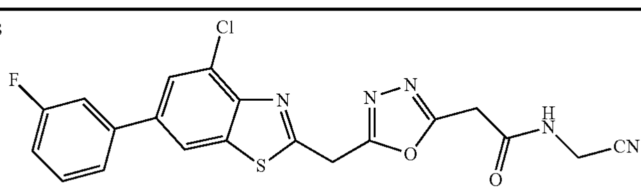 | (DMSO-d6) δ: 4.03 (s, 2H), 4.20 (d, J = 5.4 Hz, 2H), 5.02 (s, 2H), 7.24-7.29 (m, 1H), 7.51-7.59 (m, 1H), 7.64-7.69 (m, 2H), 8.01 (t, J = 1.2Hz, 1H), 8.45 (t, J = 1.2Hz, 1H), 9.02 (t, J = 1.2 Hz, 1H). |

TABLE 13-continued

| No. | Structure | NMR(δ) |
|---|---|---|
| I-1-69 | 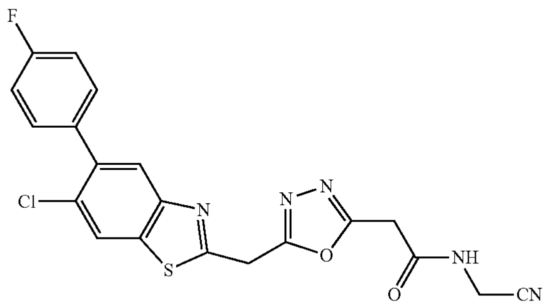 [SMILES: N#CCNC(=O)Cc1nnc(Cc2nc3cc(-c4ccc(F)cc4)c(Cl)cc3s2)o1] | (DMSO-d6) δ: 3.98 (s, 2H), 4.19 (d, J = 5.6 Hz, 2H), 4.97 (s, 2H), 7.32 (t, J = 8.9 Hz, 2H), 7.52-7.55 (m, 2H), 7.98 (s, 1H), 8.42 (s, 1H), 9.02 (t, J = 5.3 Hz, 1H). |
| I-1-70 | 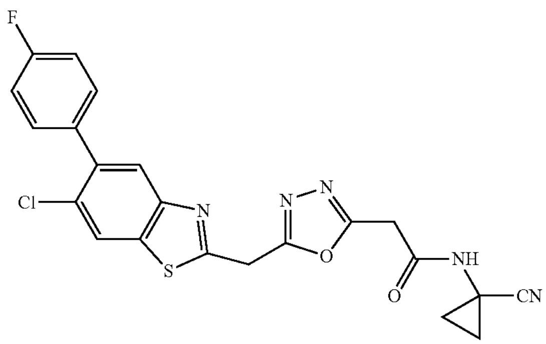 [SMILES: N#CC1(NC(=O)Cc2nnc(Cc3nc4cc(-c5ccc(F)cc5)c(Cl)cc4s3)o2)CC1] | (DMSO-d6) δ: 1.13 (dd, J = 8.1, 5.6 Hz, 2H), 1.49 (dd, J = 8.4, 5.3 Hz, 2H), 3.90 (s, 2H), 4.98 (s, 2H), 7.32 (t, J = 8.9 Hz, 2H), 7.52-7.56 (m, 2H), 7.98 (s, 1H), 8.42 (s, 1H), 9.23 (s, 1H). |
| I-1-71 | 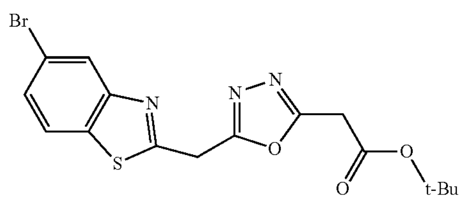 [SMILES: CC(C)(C)OC(=O)Cc1nnc(Cc2nc3cc(Br)ccc3s2)o1] | (DMSO-d6) δ: 1.34 (s, 9H), 4.07 (s, 2H), 4.98 (s, 2H), 7.64 (dd, J = 8.6, 2.0 Hz, 1H), 8.11 (d, J = 8.6 Hz, 1H), 8.20 (d, J = 2.0 Hz, 1H). |
| I-1-72 | 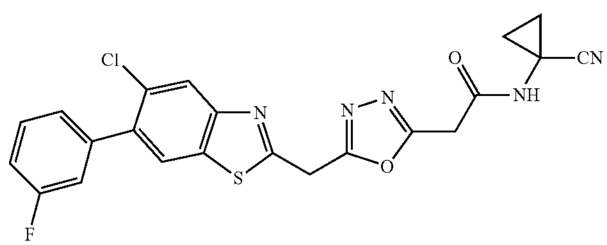 [SMILES: N#CC1(NC(=O)Cc2nnc(Cc3nc4cc(Cl)c(-c5cccc(F)c5)cc4s3)o2)CC1] | (DMSO-d6) δ: 1.14 (dd, J = 8.11, 5.58 Hz, 2H), 1.49 (dd, J = 8.11, 5.58 Hz, 2H), 3.91 (s, 2H), 5.00 (s, 2H), 7.36-7.27 (m, 3H), 7.54 (m, 1H), 8.23 (s, 1H), 8.24 (s, 1H), 9.24 (s, 1H). |

TABLE 14

| No. | Structure | NMR(δ) |
|---|---|---|
| I-1-73 | 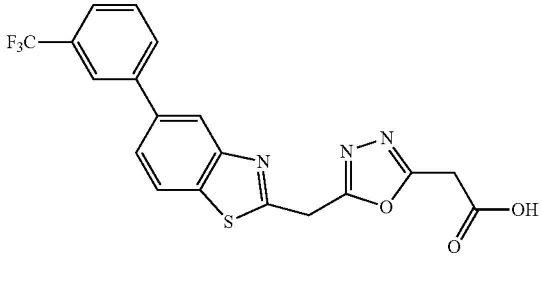 [SMILES: O=C(O)Cc1nnc(Cc2nc3cc(-c4cccc(C(F)(F)F)c4)ccc3s2)o1] | (DMSO-d6) δ: 4.08 (s, 2H), 4.99 (s, 2H), 7.72-7.78 (m, 2H), 7.87 (dd, J = 8.4, 1.8 Hz, 1H), 8.09-8.12 (m, 2H), 8.24 (d, J = 8.6 Hz, 1H), 8.37 (d, J= 1.5 Hz, 1H). |

TABLE 14-continued

| No. | Structure | NMR(δ) |
|---|---|---|
| I-1-74 | 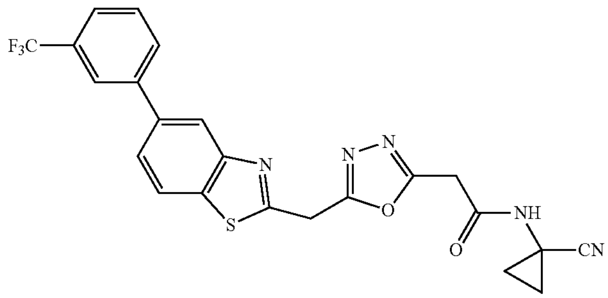 [SMILES: N#CC1(NC(=O)Cc2nnc(Cc3nc4cc(-c5cccc(C(F)(F)F)c5)ccc4s3)o2)CC1] | (DMSO-d6) δ: 1.14 (dd, J = 8.4, 5.3 Hz, 2H), 1.49 (dd, J = 8.1, 5.6 Hz, 2H), 3.91 (s, 2H), 4.98 (s, 2H), 7.72-7.78 (m, 2H), 7.87 (dd, J = 8.6, 1.5 Hz, 1H), 8.09-8.12 (m, 2H), 8.24 (d, J = 8.6 Hz, 1H), 8.37 (d, J = 1.5 Hz, 1H), 9.24 (s, 1H). |
| I-1-75 | 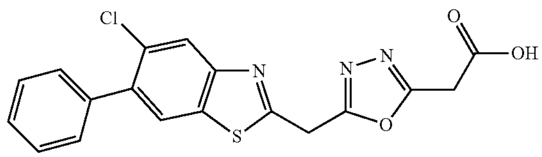 [SMILES: O=C(O)Cc1nnc(Cc2nc3cc(Cl)c(-c4ccccc4)cc3s2)o1] | (DMSO-d6) δ: 4.08 (s, 2H), 4.99 (s, 2H), 7.51-7.43 (m, 5H), 8.20 (s, 1H), 8.21 (s, 1H), 13.11 (s, 1H). |
| I-1-76 | 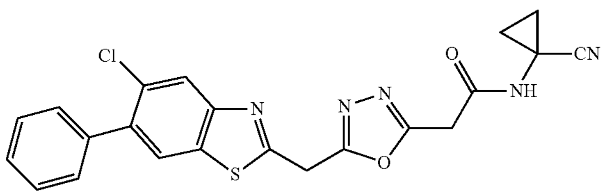 [SMILES: N#CC1(NC(=O)Cc2nnc(Cc3nc4cc(Cl)c(-c5ccccc5)cc4s3)o2)CC1] | (DMSO-d6) δ: 1.14 (2.0H, dd, J = 8.11, 5.58 Hz), 1.49 (2.0H, dd, J = 8.11, 5.58 Hz), 3.91 (2.0H, s), 4.99 (2.0H, s), 7.52-7.43 (5.0H, m), 8.20 (1.0H, s), 8.21 (1.0H, s), 9.23 (1.0H, s). |
| I-1-77 | 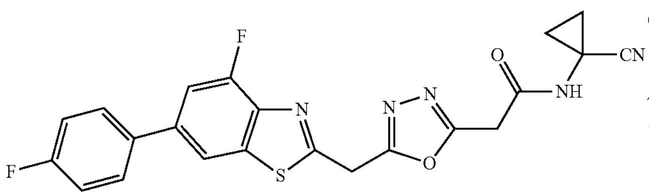 | (DMSO-d6) δ: 1.14 (dd, J = 8.70, 5.70 Hz, 2H), 1.49 (dd, J = 8.70, 5.70 Hz, 2H), 3.92 (s, 2H), 5.00 (2H, s), 7.34 (2H, t, J = 9.0Hz), 7.73 (1H, d, J = 10.80 Hz), 7.81-7.86 (2H, m), 8.29 (1H, s), 9.23 (1H, s). |

TABLE 15

| No. | Structure | NMR(δ) | retention time | Mass | method |
|---|---|---|---|---|---|
| I-1-78 | 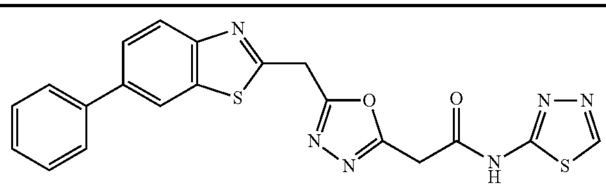 | | 1.85 | 435.05 (ES+) | C |
| I-1-79 | 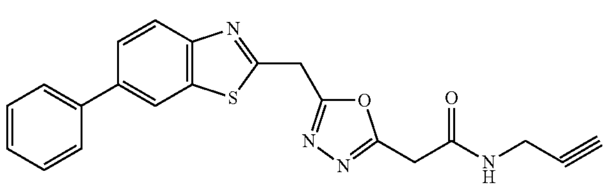 [SMILES: C#CCNC(=O)Cc1nnc(Cc2nc3ccc(-c4ccccc4)cc3s2)o1] | (DMSO-d6) δ: 4.18 (s, 2H), 4.76 (s, 2H), 6.54 (s, 1H), 7.37-7.49 (m, 3H), 7.61 (d, J = 7.8 Hz, 2H), 7.70 (d, J = 9.0Hz, 1H), 8.03-8.06 (m, 2H) | | | |
| I-1-80 | 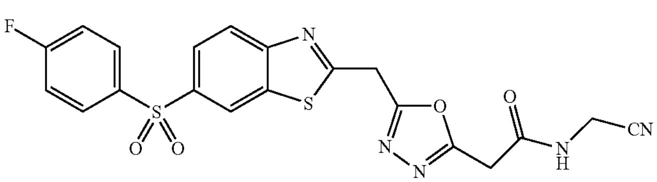 [SMILES: N#CCNC(=O)Cc1nnc(Cc2nc3ccc(S(=O)(=O)c4ccc(F)cc4)cc3s2)o1] | (DMSO-d6) δ: 3.97 (s, 2H), 4.18 (d, J = 5.6 Hz, 2H), 5.02 (s, 2H), 7.47 (t, J = 8.6 Hz, 2H), 8.01-8.10 (m, 3H), 8.17 (d, J = 9.1 Hz, 1H), 8.92 (d, J = 2.0 Hz, 1H), 9.01 (t, J = 5.6 Hz, 1H). | | | |

TABLE 15-continued

| No. | Structure | NMR(δ) | retention time | Mass | method |
|---|---|---|---|---|---|
| I-1-81 | 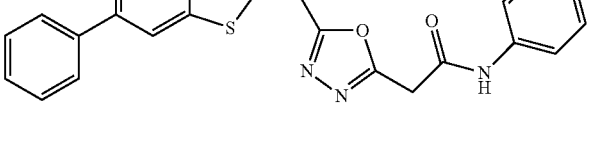 | (DMSO-d6) δ: 1.14 (dd, J = 8.40, 5.70 Hz, 2H), 1.49 (dd, J = 8.40, 5.54 Hz, 2H), 3.92 (s, 2H), 5.01 (s, 2H), 7.49-7.56 (m, 3H), 8.16-8.19 (m, 3H), 8.45 (d, J = 8.7 Hz, 1H), 9.24 (brs, 1H). | | | |
| I-1-82 | 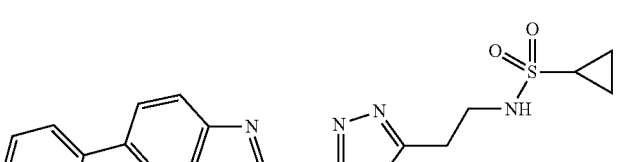 | (CDCl3) δ: 3.55 (t, J = 4.8 Hz, 2H), 3.63-3.71 (m, 6H), 4.01 (s, 2H), 4.75 (s, 2H), 7.37-7.41 (m, 1H), 7.47 (t, J = 7.6 Hz, 2H), 7.63 (t, J = 4.1 Hz, 2H), 7.72 (dd, J = 8.6, 2.0 Hz, 1H), 8.04-8.07 (m, 2H). | | | |

TABLE 16

| No. | Structure | NMR(δ) |
|---|---|---|
| I-1-83 | 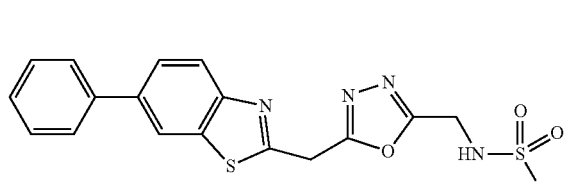 | 1H-NMR (DMSO-d6) δ: 4.13 (s, 2H), 4.97 (s, 2H), 7.08 (t, J = 7.4 Hz, 1H), 7.32 (t, J = 8.1 Hz, 2H), 7.40 (t, J = 7.4 Hz, 1H), 7.50 (t, J = 7.9 Hz, 2H), 7.56 (d, J = 7.6 Hz, 2H). 7.76 (d, J = 7.1 Hz, 2H), 7.83 (dd, J = 8.6, 2.0 Hz. 1H), 8.05 (d, J = 8.6 Hz, 1H), 8.43 (d, J = 1.5 Hz, 1H), 10.39 (s, 1H). |
| I-1-84 | 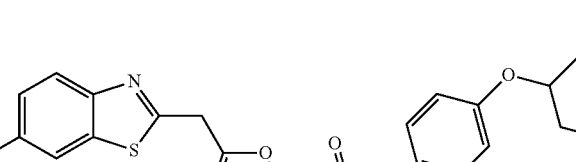 | 1H-NMR (CDCl3) δ: 0.96-1.02 (m, 2H), 1.13-1.21 (m, 2H), 2.43 (tt, J = 8.11, 3.63 Hz, 1H), 3.15 (t, J = 6.08 Hz, 2H), 3.68 (dt, J = 6.08, 6.34 Hz, 2H), 4.73 (s, 2H), 5.22 (t, J = 6.34 Hz, 1H), 7.33-7.52 (m, 3H), 7.63 (d, J = 7.10 Hz, 2H), 7.73 (dd, J = 8.62, 1.52 Hz, 1H), 8.05-8.09 (m, 2H). |
| I-1-85 | 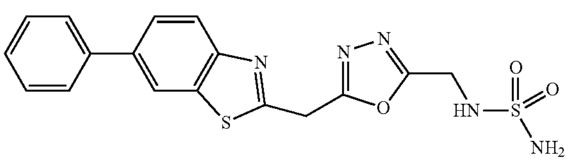 [SMILES: NS(=O)(=O)NCc1nnc(Cc2nc3ccc(-c4ccccc4)cc3s2)o1] | (DMSO-d6) δ: 4.32 (d, J = 6.1 Hz, 2H), 4.95 (s, 2H), 6.77 (br s, 2H), 7.38-7.44 (m, 2H), 7.48-7.52 (m, 2H), 7.76 (d, J = 7.1 Hz, 2H), 7.83 (dd, J = 8.6, 2.0 Hz, 1H), 8.05 (d, J = 8.6 Hz, 1H), 8.44 (d, J = 1.5 Hz, 1H). |
| I-1-86 | 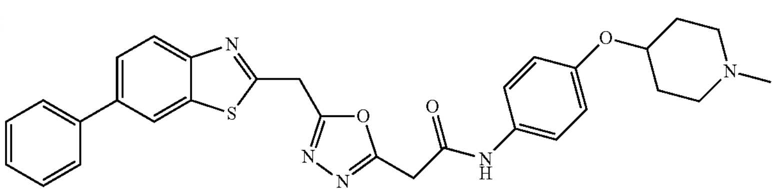 [SMILES: CN1CCC(Oc2ccc(NC(=O)Cc3nnc(Cc4nc5ccc(-c6ccccc6)cc5s4)o3)cc2)CC1] | 1H-NMR (DMSO-d6) δ: 1.53-1.64 (m, 2H), 1.84-1.92 (m, 3H), 2.09-2.18 (m, 3H), 2.16 (s, 3H), 2.55-2.63 (m, 3H), 4.08 (s, 2H), 4.22-4.31 (m, 1H), 4.97 (s, 2H), 6.89 (d, J = 9.1 Hz, 2H), 7.37-7.46 (m, 3H), 7.50 (t, J = 7.6 Hz, 2H), 7.76 (d, J = 7.1 Hz, 2H), 7.82 (dd, J = 8.6, 1.5 Hz, 1H), 8.04 (d, J = 8.6 Hz, 1H), 8.43 (d, J = 1.5 Hz, 1H), 10.24 (s, 1H). |

TABLE 16-continued
| No. | Structure | NMR(δ) |
|---|---|---|
| I-1-87 | 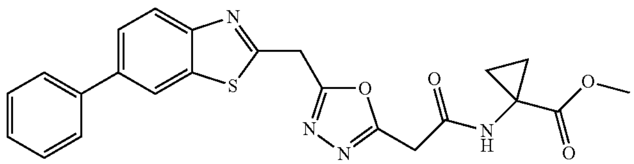 [SMILES: COC(=O)C1(NC(=O)Cc2nnc(Cc3nc4ccc(-c5ccccc5)cc4s3)o2)CC1] | 1H-NMR (DMSO-d6) δ: 1.01-1.05 (m, 2H), 1.32-1.39 (m, 2H), 3.56 (s, 3H), 3.86 (s, 2H), 4.95 (s, 2H), 7.40 (t, J = 7.4 Hz, 1H), 7.50 (t, J = 7.6 Hz, 2H), 7.76 (d, J = 7.1 Hz, 2H), 7.83 (dd, J = 8.6, 2.0 Hz, 1H), 8.05 (d, J = 8.6 Hz, 1H), 8.44 (d, J = 1.5 Hz, 1H), 8.94 (s, 1H). |
TABLE 17
| No. | Structure | NMR(δ) |
|---|---|---|
| I-1-88 | 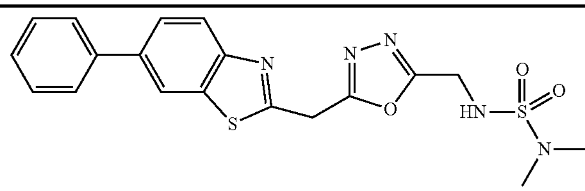 | (CDCl3) δ: 2.79 (s, 6H), 4.52 (d, J = 3.5 Hz, 2H), 4.78 (s, 2H), 4.92 (br s, 1H), 7.41 (t, J = 7.4 Hz, 1H), 7.48-7.52 (m, 2H), 7.64-7.67 (m, 2H), 7.76 (dd, J = 8.4, 1.8 Hz, 1H), 8.06-8.10 (m, 2H). |
| I-1-89 | 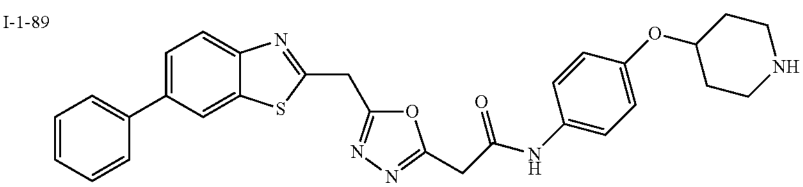 | 1H-NMR (DMSO-d6) δ: 1.37-1.48 (m, 2H), 1.85-1.92 (m, 2H), 2.52-2.62 (m, 2H), 2.91-2.98 (m, 2H), 3.35-3.42 (m, 1H), 4.08 (s, 2H), 4.27-4.36 (m, 1H), 4.97 (s, 2H), 6.89 (d, J = 9.1 Hz, 2H), 7.37-7.46 (m, 3H), 7.50 (t, J = 7.6 Hz, 2H), 7.76 (d, J = 7.1 Hz, 2H), 7.83 (dd, J = 8.6, 1.5 Hz, 1H), 8.05 (d, J = 8.6 Hz, 1H), 8.44 (d, J = 1.5 Hz, 1H), 10.25 (s, 1H). |
TABLE 18
| No. | Structure | NMR (δ) |
|---|---|---|
| I-2-1 | 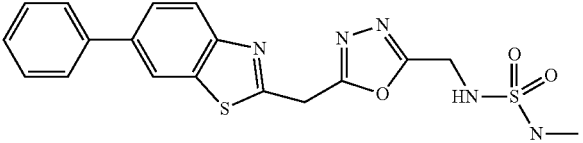 | (DMSO-d6) δ: 1.34 (s, 9H), 4.07 (s, 2H), 4.98 (s, 2H), 7.64 (dd, J = 8.6, 2.0 Hz, 1H), 8.11 (d, J = 8.6 Hz, 1H), 8.20 (d, J = 2.0 Hz, 1H). |
| I-2-2 | 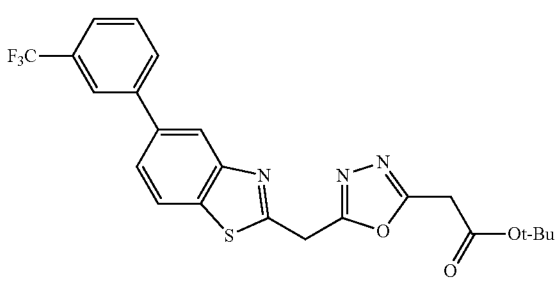 [SMILES: CC(C)(C)OC(=O)Cc1nnc(Cc2nc3cc(-c4cccc(C(F)(F)F)c4)ccc3s2)o1] | (CDCl3) δ: 1.43 (s, 9H), 3.89 (s, 2H), 4.77 (s, 2H), 7.59-7.66 (m, 3H), 7.82-7.97 (m, 3H), 8.24 (d, J = 1.5 Hz, 1H). |

TABLE 18-continued

| No. | Structure | NMR (δ) |
|---|---|---|
| I-2-3 | 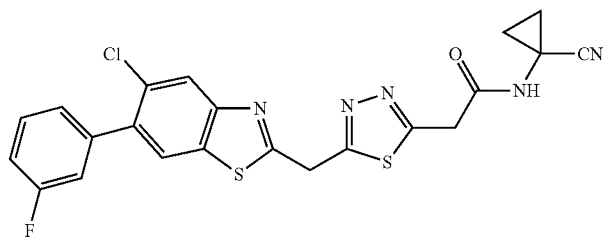 | (DMSO-d$_6$) δ: 1.14 (dd, J = 8.11, 5.58 Hz, 2H), 1.49 (dd, J = 8.11, 5.58 Hz, 2H), 3.91 (s, 2H), 5.00 (s, 2H), 7.27-7.36 (m, 3H), 7.54 (brs, 1H), 8.23 (s, 1H), 8.24 (s, 1H), 9.24 (s, 1H). |
| I-2-4 | 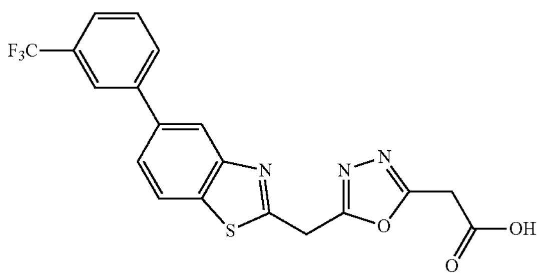 [SMILES: O=C(O)Cc1nnc(Cc2nc3cc(-c4cccc(C(F)(F)F)c4)ccc3s2)o1] | (DMSO-d6) δ: 4.08 (s, 2H), 4.99 (s, 2H), 7.72-7.78 (m, 2H), 7.87 (dd, J = 8.4, 1.8 Hz, 1H), 8.09-8.12 (m, 2H), 8.24 (d, J = 8.6 Hz, 1H), 8.37 (d, J = 1.5 Hz, 1H). |
| I-2-5 | 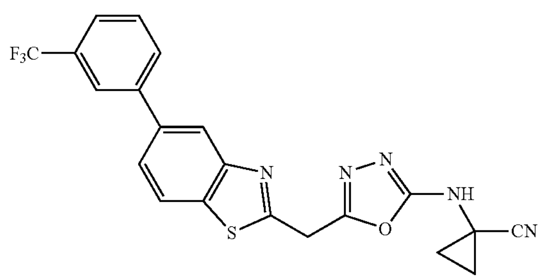 [SMILES: N#CC1(Nc2nnc(Cc3nc4cc(-c5cccc(C(F)(F)F)c5)ccc4s3)o2)CC1] | (DMSO-d6) δ: 1.14 (dd, J = 8.4, 5.3 Hz, 2H), 1.49 (dd, J = 8.1, 5.6 Hz, 2H), 3.91 (s, 2H), 4.98 (s, 2H), 7.72-7.78 (m, 2H), 7.87 (dd, J = 8.6, 1.5 Hz, 1H), 8.09-8.12 (m, 2H), 8.24 (d, J = 8.6 Hz, 1H), 8.37 (d, J = 1.5 Hz, 1H), 9.24 (s, 1H). |

TABLE 19

| No. | Structure | NMR (δ) |
|---|---|---|
| I-2-6 | 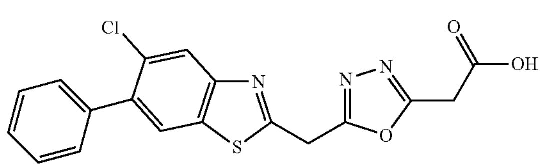 [SMILES: O=C(O)Cc1nnc(Cc2nc3cc(Cl)c(-c4ccccc4)cc3s2)o1] | (DMSO-d$_6$) δ: 4.08 (s, 2H), 4.99 (s, 2H), 7.41-7.53 (m, 5H), 8.20 (s, 1H), 8.21 (s, 1H), 13.11 (br s, 1H). |
| I-2-7 | 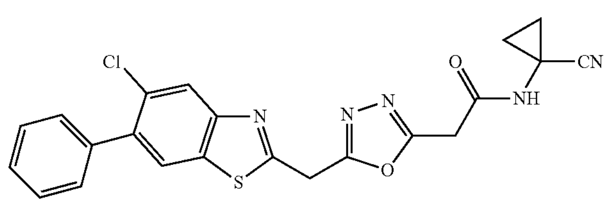 [SMILES: N#CC1(NC(=O)Cc2nnc(Cc3nc4cc(Cl)c(-c5ccccc5)cc4s3)o2)CC1] | (DMSO-d$_6$) δ: 1.14 (dd, J = 8.11, 5.58 Hz, 2H), 1.49 (dd, J = 8.11, 5.58 Hz, 2H), 3.91 (s, 2H), 4.99 (s, 2H), 7.43-7.52 (m, 5H), 8.20 (s, 1H), 8.21 (s, 1H), 9.23 (s, 1H). |
| I-2-8 | 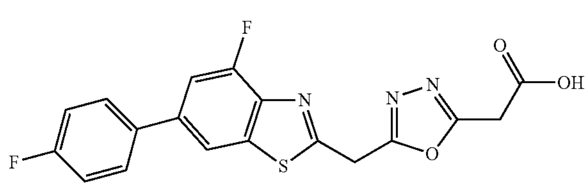 [SMILES: O=C(O)Cc1nnc(Cc2nc3c(F)cc(-c4ccc(F)cc4)cc3s2)o1] | |

TABLE 19-continued

| No. | Structure | NMR (δ) |
|---|---|---|
| I-2-9 | 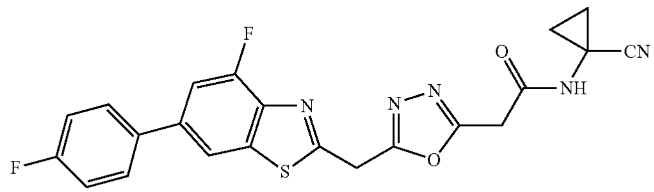 [SMILES: N#CC1(NC(=O)Cc2nnc(Cc3nc4c(F)cc(-c5ccc(F)cc5)cc4s3)o2)CC1] | (DMSO-d6) δ: 1.14 (dd, J = 8.70, 5.70 Hz, 2H), 1.49 (dd, J = 8.70, 5.70 Hz, 2H), 3.92 (s, 2H), 5.00 (s, 2H), 7.34 (t, J = 9.0 Hz, 2H), 7.72-7.86 (m, 3H), 8.29 (s, 1H), 8.29 (s, 1H), 9.23 (s, 1H). |
| I-2-10 | 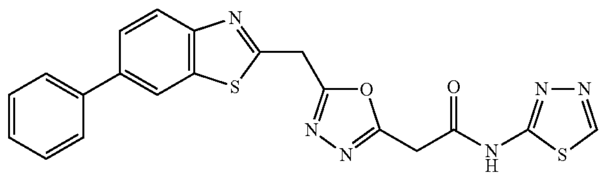 [SMILES: O=C(Cc1nnc(Cc2nc3ccc(-c4ccccc4)cc3s2)o1)Nc1nncs1] | |

TABLE 20

| No. | Structure | NMR (δ) |
|---|---|---|
| I-2-11 | 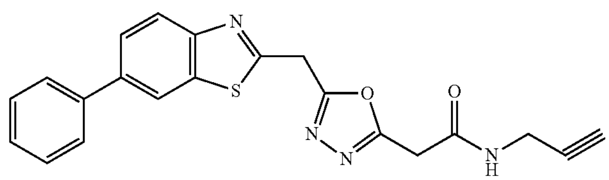 [SMILES: C#CCNC(=O)Cc1nnc(Cc2nc3ccc(-c4ccccc4)cc3s2)o1] | (DMSO-d$_6$) δ: 3.14 (s, 1H), 3.90 (s, 2H), 4.95 (s, 2H), 7.40 (t, J = 7.5 Hz, 1H), 7.46-7.53 (m, 2H), 7.74-7.84 (m, 3H), 8.05 (d, J = 8.4 Hz, 2H), 8.43 (s, 1H), 8.75 (br-s, 1H) |
| I-2-12 | 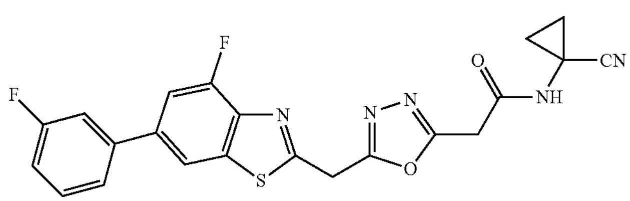 [SMILES: N#CC1(NC(=O)Cc2nnc(Cc3nc4c(F)cc(-c5cccc(F)c5)cc4s3)o2)CC1] | (DMSO-d6) δ: 1.14 (dd, J = 8.70, 5.70 Hz, 2H), 1.49 (dd, J = 8.70, 5.70 Hz, 2H), 3.92 (s, 2H), 5.02 (s, 2H), 7.26 (t, J = 8.70 Hz, 1H), 7.51-7.72 (m, 3H), 7.81 (d, J = 14.1 Hz, 1H), 8.38 (s, 1H), 9.23 (s, 1H). |
| I-2-13 | 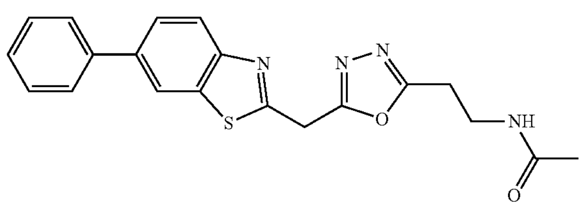 [SMILES: CC(=O)NCCc1nnc(Cc2nc3ccc(-c4ccccc4)cc3s2)o1] | (CDCl3) δ: 1.96 (s, 3H), 3.05 (t, J = 6.1 Hz, 2H), 3.74 (q, J = 6.1 Hz, 2H), 4.73 (s, 2H), 6.22 (s, 1H), 7.39 (t, J = 7.4 Hz, 1H), 7.46-7.49 (m, 2H), 7.62-7.64 (m, 2H), 7.73 (dd, J = 8.6, 1.5 Hz, 1H), 8.05-8.08 (m, 2H). |
| I-2-14 | 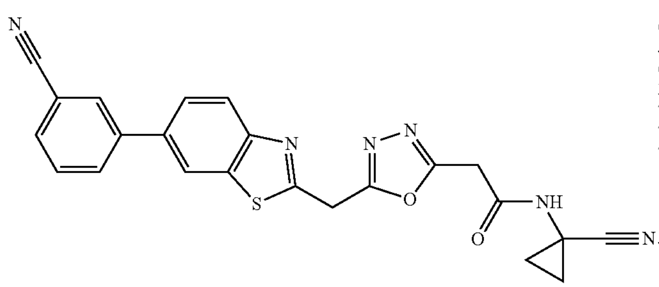 [SMILES: N#Cc1cccc(-c2ccc3nc(Cc4nnc(CC(=O)NC5(C#N)CC5)o4)sc3c2)c1] | (DMSO-d6) δ: 1.14 (dd, J = 8.1, 5.6 Hz, 2H), 1.49 (dd, J = 8.4, 5.3 Hz, 2H), 3.91 (s, 2H), 4.98 (s, 2H), 7.71 (t, J = 7.9 Hz, 1H), 7.86 (d, J = 8.1 Hz, 1H), 7.92 (dd, J = 8.6, 2.0 Hz, 1H), 8.08 (d, J = 8.6 Hz, 1H), 8.12 (d, J = 8.1 Hz, 1H), 8.26 (s, 1H), 8.55 (d, J = 1.5 Hz, 1H), 9.23 (s, 1H). |

TABLE 20-continued

| No. | Structure | NMR (δ) |
|---|---|---|
| I-2-15 | 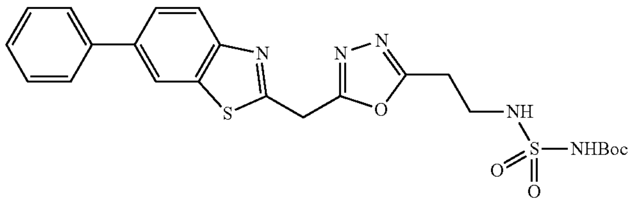 [SMILES: CC(C)(C)OC(=O)NS(=O)(=O)NCCc1nnc(Cc2nc3ccc(-c4ccccc4)cc3s2)o1] | (CDCl3) δ: 1.47 (s, 9H), 3.16 (t, J = 6.3 Hz, 2H), 3.67 (q, J = 6.4 Hz, 2H), 4.74 (s, 2H), 5.80 (t, J = 6.3 Hz, 1H), 7.37-7.49 (m, 3H), 7.62-7.67 (m, 3H), 7.73 (dd, J = 8.4, 1.8 Hz, 1H), 8.06-8.09 (m, 2H). |

TABLE 21

| No. | Structure | NMR (δ) |
|---|---|---|
| I-2-16 | 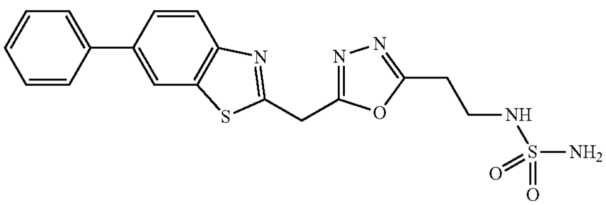 [SMILES: NS(=O)(=O)NCCc1nnc(Cc2nc3ccc(-c4ccccc4)cc3s2)o1] | (DMSO-d6) δ: 3.08 (t, J = 6.8 Hz, 2H), 3.29 (q, J = 6.8 Hz, 2H), 4.91 (s, 2H), 6.63 (s, 2H), 6.75 (t, J = 6.0 Hz, 1H), 7.40 (t, J = 7.6 Hz, 1H), 7.48-7.54 (m, 2H), 7.75 (d, J = 8.0 Hz, 2H), 7.83 (d, J = 8.0 Hz, 1H), 8.05 (d, J = 8.0 Hz, 1H), 8.43 (s, 1H) |
| I-2-17 | 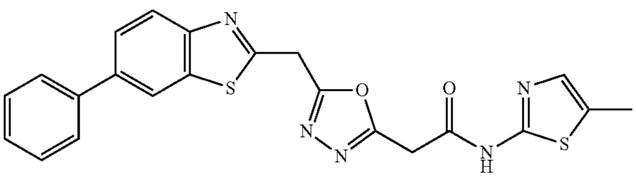 [SMILES: Cc1cnc(NC(=O)Cc2nnc(Cc3nc4ccc(-c5ccccc5)cc4s3)o2)s1] | (DMSO-d$_6$): 4.18 (s, 2H), 4.76 (s, 3H), 6.54 (s, 1H), 7.38 (t, J = 6.9 Hz, 1H), 7.42-7.50 (m, 2H), 7.60-7.72 (m, 3H), 8.03-8.06 (m, 2H) |
| I-2-18 | 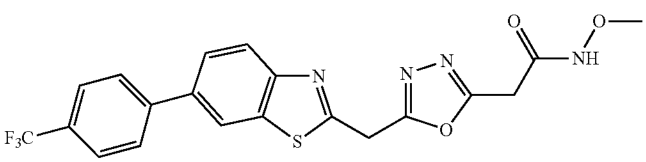 [SMILES: CONC(=O)Cc1nnc(Cc2nc3ccc(-c4ccc(C(F)(F)F)cc4)cc3s2)o1] | (DMSO-d$_6$) δ: 3.60 (s, 3H), 3.77 (s, 2H), 4.98 (s, 2H), 7.82-7.93 (m, 3H), 7.99 (d, J = 8.11 Hz, 2H), 8.09 (d, J = 8.62 Hz, 1H), 8.55 (d, J = 1.52 Hz, 1H), 11.48 (s, 1H). |
| I-2-19 | 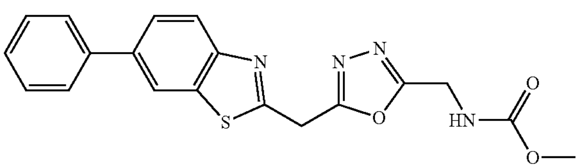 [SMILES: COC(=O)NCc1nnc(Cc2nc3ccc(-c4ccccc4)cc3s2)o1] | (CDCl3) δ: 3.73 (s, 3H), 4.63 (d, J = 6.1 Hz, 2H), 4.74 (s, 2H), 5.31 (br s, 1H), 7.39 (t, J = 7.4 Hz, 1H), 7.46-7.49 (m, 2H), 7.63 (d, J = 7.1 Hz, 2H), 7.73 (dd, J = 8.6, 1.5 Hz, 1H), 8.05-8.08 (m, 2H). |
| I-2-20 | 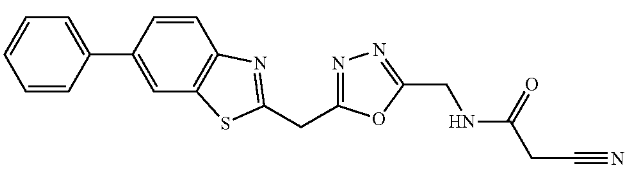 [SMILES: N#CCC(=O)NCc1nnc(Cc2nc3ccc(-c4ccccc4)cc3s2)o1] | (DMSO-d6) δ: 3.75 (s, 2H), 4.57 (d, J = 5.6 Hz, 2H), 4.95 (s, 2H), 7.40 (t, J = 7.4 Hz, 1H), 7.48-7.52 (m, 2H), 7.74-7.77 (m, 2H), 7.83 (dd, J = 8.6, 1.5 Hz, 1H), 8.05 (d, J = 8.6 Hz, 1H), 8.43 (d, J = 2.0 Hz, 1H), 9.03 (t, J = 5.6 Hz, 1H). |

TABLE 22

| No. | Structure | NMR (δ) |
|---|---|---|
| I-2-21 | 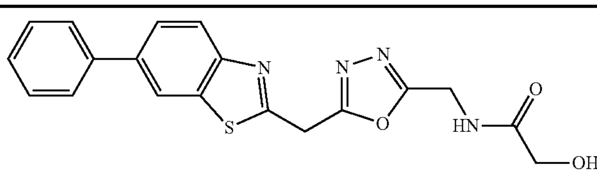 | (CDCl3) δ: 4.21 (s, 2H), 4.73 (s, 2H), 4.76 (d, J = 6.1 Hz, 2H), 7.29 (br s, 1H), 7.37-7.41 (m, 1H), 7.45-7.50 (m, 2H), 7.61-7.64 (m, 2H), 7.72 (dd, J = 8.6, 1.5 Hz, 1H), 8.04-8.07 (m, 2H). |

TABLE 22-continued

| No. | Structure | NMR (δ) |
|---|---|---|
| I-2-22 | 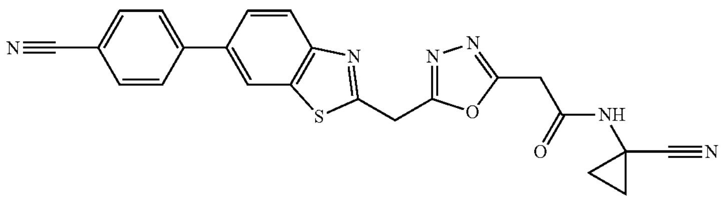 [SMILES: N#Cc1ccc(-c2ccc3nc(Cc4nnc(CC(=O)NC5(C#N)CC5)o4)sc3c2)cc1] | (DMSO-d6) δ: 1.14 (dd, J = 8.4, 5.3 Hz, 2H), 1.49 (dd, J = 8.4, 5.3 Hz, 2H), 3.91 (s, 2H), 4.98 (s, 2H), 7.90-7.98 (m, 5H), 8.10 (d, J = 8.6 Hz, 1H), 8.57 (d, J = 1.5 Hz, 1H), 9.24 (s, 1H). |
| I-2-23 | 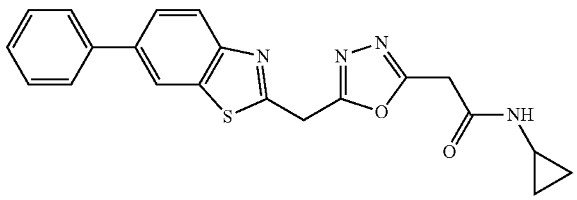 [SMILES: O=C(Cc1nnc(Cc2nc3ccc(-c4ccccc4)cc3s2)o1)NC1CC1] | (CDCl3) δ: 0.53-0.57 (m, 2H), 0.77-0.82 (m, 2H), 2.72-2.79 (m, 1H), 3.84 (s, 2H), 4.74 (s, 2H), 7.03 (br s, 1H), 7.39 (t, J = 7.4 Hz, 1H), 7.46-7.50 (m, 2H), 7.62-7.65 (m, 2H), 7.73 (dd, J = 8.6, 2.0 Hz, 1H), 8.05-8.08 (m, 2H). |
| I-2-24 | 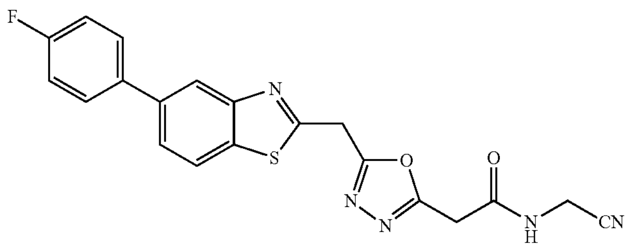 [SMILES: N#CCNC(=O)Cc1nnc(Cc2nc3cc(-c4ccc(F)cc4)ccc3s2)o1] | (DMSO-d6) δ: 3.99 (s, 2H), 4.19 (d, J = 5.6 Hz, 2H), 4.96 (s, 2H), 7.32 (t, J = 8.9 Hz, 2H), 7.76 (d, J = 8.6 Hz, 1H), 7.81-7.84 (m, 2H), 8.19 (d, J = 8.1 Hz, 1H), 8.24-8.26 (m, 1H), 9.03 (t, J = 5.3 Hz, 1H). |
| I-2-25 | 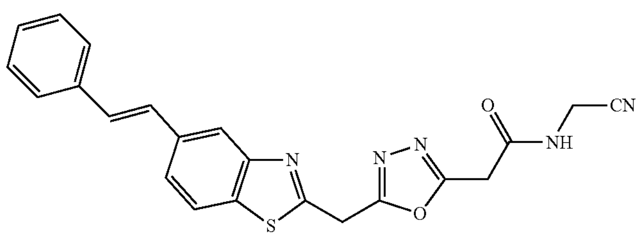 [SMILES: N#CCNC(=O)Cc1nnc(Cc2nc3cc(/C=C/c4ccccc4)ccc3s2)o1] | (DMSO-d$_6$) δ: 3.99 (s, 2H), 4.20 (d, J = 5.58 Hz, 2H), 4.95 (s, 2H), 7.29 (m, 1H), 7.37-7.43 (m, 4H), 7.64 (d, J = 7.10 Hz, 2H), 7.76 (dd, J = 8.62, 1.52 Hz, 1H), 8.10 (d, J = 8.62 Hz, 1H), 8.19 (d, J = 1.52 Hz, 1H), 9.03 (t, J = 5.32 Hz, 1H). |

TABLE 23

| No. | Structure | NMR (δ) |
|---|---|---|
| I-2-26 | 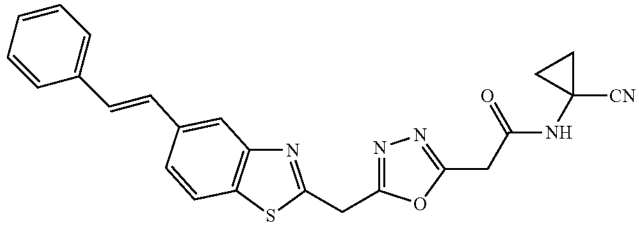 [SMILES: N#CC1(NC(=O)Cc2nnc(Cc3nc4cc(/C=C/c5ccccc5)ccc4s3)o2)CC1] | (DMSO-d$_6$) δ: 1.14 (dd, J = 8.36, 5.32 Hz, 2H), 1.49 (dd, J = 8.11, 5.58 Hz, 2H), 3.91 (s, 2H), 4.95 (s, 2H), 7.29 (m, 1H), 7.36-7.43 (m, 4H), 7.64 (d, J = 7.60 Hz, 2H), 7.76 (dd, J = 8.36, 1.27 Hz, 1H), 8.10 (d, J = 8.11 Hz, 1H), 8.19 (d, J = 1.01 Hz, 1H), 9.24 (s, 1H). |
| I-2-27 | 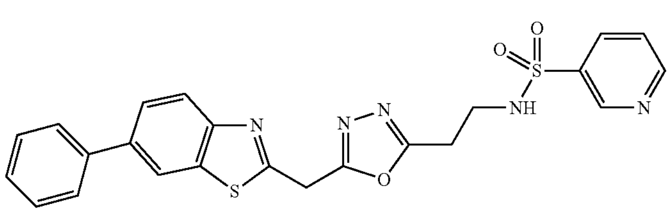 [SMILES: O=S(=O)(NCCc1nnc(Cc2nc3ccc(-c4ccccc4)cc3s2)o1)c1cccnc1] | (CDCl$_3$) δ: 3.09 (t, J = 5.83 Hz, 2H), 3.54 (dt, J = 5.83, 6.08 Hz, 2H), 4.72 (s, 2H), 5.77 (t, J = 6.08 Hz, 1H), 7.39 (m, 1H), 7.43-7.51 (m, 3H), 7.61-7.66 (m, 2H), 7.73 (m, 1H), 8.05-8.10 (m, 2H), 8.15 (m, 1H), 8.80 (d, J = 4.56 Hz, 1H), 9.09 (s, 1H). |

TABLE 23-continued

| No. | Structure | NMR (δ) |
|---|---|---|
| I-2-28 | 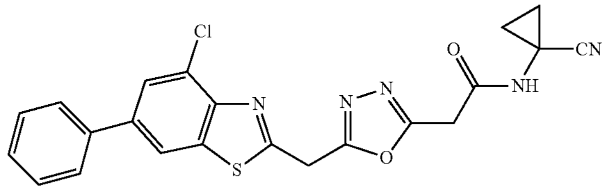 [SMILES: N#CC1(NC(=O)Cc2nnc(Cc3nc4c(Cl)cc(-c5ccccc5)cc4s3)o2)CC1] | (DMSO-d6) δ: 1.14 (dd, J = 8.70, 5.70 Hz, 2H), 1.49 (dd, J = 8.70, 5.70 Hz, 2H), 3.92 (s, 2H), 5.02 (s, 2H) 7.40-7.52 (m, 3H), 7.78 (d, J = 6.60 Hz, 1H), 8.45 (d, J = 1.50 Hz, 1H), 9.24 (s, 1H). |
| I-2-29 | 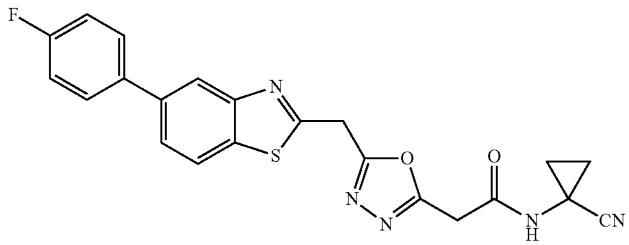 [SMILES: N#CC1(NC(=O)Cc2nnc(Cc3nc4cc(-c5ccc(F)cc5)ccc4s3)o2)CC1] | (DMSO-d6) δ: 1.14 (dd, J = 8.4, 5.3 Hz, 2H), 1.49 (dd, J = 8.4, 5.3 Hz, 2H), 3.91 (s, 2H), 4.97 (s, 2H), 7.32 (t, J = 8.9 Hz, 2H), 7.76 (dd, J = 8.4, 1.8 Hz, 1H), 7.79-7.78 (m, 2H), 8.19 (d, J = 8.1 Hz, 1H), 8.25 (d, J = 1.5 Hz, 1H), 9.24 (s, 1H). |
| I-2-30 | 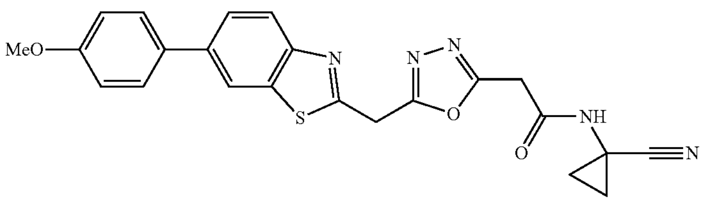 [SMILES: COc1ccc(-c2ccc3nc(Cc4nnc(CC(=O)NC5(C#N)CC5)o4)sc3c2)cc1] | (DMSO-d6) δ: 1.14 (dd, J = 8.4, 5.3 Hz, 2H), 1.49 (dd, J = 8.4, 5.3 Hz, 2H), 3.81 (s, 3H), 3.91 (s, 2H), 4.94 (s, 2H), 7.05-7.07 (m, 2H), 7.69-7.71 (m, 2H), 7.78 (dd, J = 8.6, 2.0 Hz, 1H), 8.01 (d, J = 8.1 Hz, 1H), 8.37 (d, J = 1.5 Hz, 1H), 9.23 (s, 1H). |

TABLE 24

| No. | Structure | NMR (δ) |
|---|---|---|
| I-2-31 | 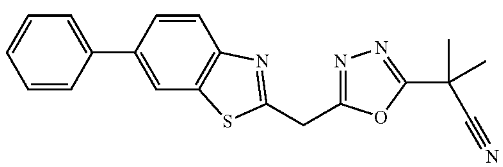 [SMILES: CC(C)(C#N)c1nnc(Cc2nc3ccc(-c4ccccc4)cc3s2)o1] | (DMSO-d6) δ: 1.82 (s, 6H), 5.01 (s, 2H), 7.40 (t, J = 7.4 Hz, 1H), 7.48-7.52 (m, 2H), 7.75-7.77 (m, 2H), 7.83 (dd, J = 8.4, 1.8 Hz, 1H), 8.05 (d, J = 8.1 Hz, 1H), 8.45 (d, J = 2.0 Hz, 1H). |
| I-2-32 | 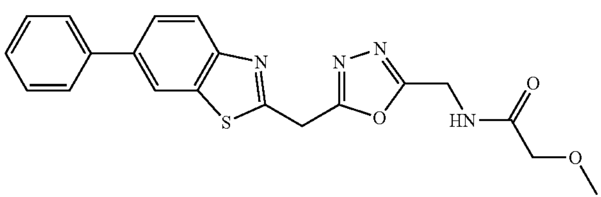 [SMILES: COCC(=O)NCc1nnc(Cc2nc3ccc(-c4ccccc4)cc3s2)o1] | (DMSO-d6) δ: 3.28 (s, 3H), 3.86 (s, 2H), 4.53 (d, J = 6.1 Hz, 2H), 4.94 (s, 2H), 7.40 (t, J = 7.4 Hz, 1H), 7.50 (t, J = 7.6 Hz, 2H), 7.76 (d, J = 7.1 Hz, 2H), 7.82 (dd, J = 8.4, 1.8 Hz, 1H), 8.04 (d, J = 8.6 Hz, 1H), 8.43 (d, J = 1.5 Hz, 1H), 8.57 (t, J = 5.8 Hz, 1H). |
| I-2-33 | 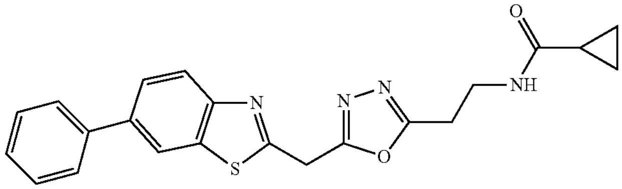 [SMILES: O=C(NCCc1nnc(Cc2nc3ccc(-c4ccccc4)cc3s2)o1)C1CC1] | (DMSO-d$_6$) δ: 0.58-0.66 (m, 4H), 1.48 (m, 1H), 2.99 (t, J = 6.59, 5.58 Hz, 2H), 4.91 (s, 2H), 7.40 (t, J = 7.35 Hz, 1H), 7.50 (dd, J = 7.35, 7.10 Hz, 2H), 7.75 (d, J = 7.10 Hz, 2H), 7.83 (dd, J = 8.36, 1.77 Hz, 1H), 8.05 (d, J = 8.36 Hz, 1H), 8.25 (t, J = 5.58 Hz, 1H), 8.43 (d, J = 1.77 Hz, 1H). |

TABLE 24-continued

| No. | Structure | NMR (δ) |
|---|---|---|
| I-2-34 | 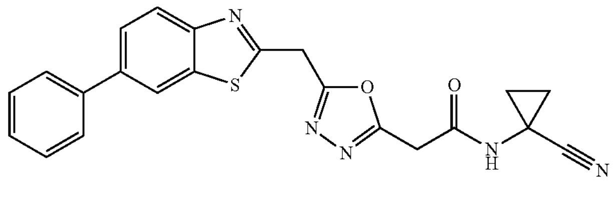 [SMILES: N#CC1(NC(=O)Cc2nnc(Cc3nc4ccc(-c5ccccc5)cc4s3)o2)CC1] | (DMSO-d6) δ: 1.14 (dd, J = 8.4, 5.3 Hz, 2H), 1.49 (dd, J = 8.1, 5.6 Hz, 2H), 3.91 (s, 2H), 4.96 (s, 2H), 7.38-7.43 (m, 1H), 7.50 (t, J = 7.6 Hz, 2H), 7.76 (d, J = 7.1 Hz, 2H), 7.83 (dd, J = 8.6, 2.0 Hz, 1H), 8.05 (d, J = 8.6 Hz, 1H), 8.44 (d, J = 1.5 Hz, 1H), 9.24 (s, 1H). |
| I-2-35 | 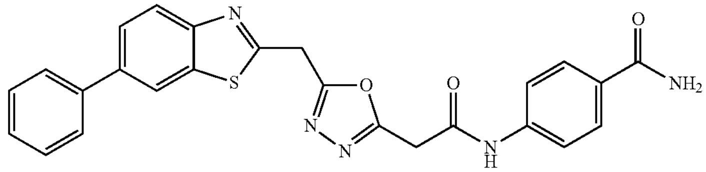 [SMILES: NC(=O)c1ccc(NC(=O)Cc2nnc(Cc3nc4ccc(-c5ccccc5)cc4s3)o2)cc1] | (DMSO-d6) δ: 4.17 (s, 2H), 4.98 (s, 2H), 7.25 (s, 1H), 7.38-7.43 (m, 1H), 7.50 (t, J = 7.6 Hz, 2H), 7.62 (d, J = 8.6 Hz, 2H), 7.76 (d, J = 7.1 Hz, 2H), 7.81-7.88 (m, 4H), 8.05 (d, J = 8.1 Hz, 1H), 8.44 (d, J = 2.0 Hz, 1H), 10.61 (s, 1H). |

TABLE 25

| No. | Structure | NMR (δ) |
|---|---|---|
| I-2-36 | 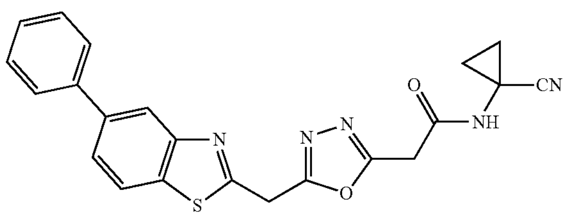 [SMILES: N#CC1(NC(=O)Cc2nnc(Cc3nc4cc(-c5ccccc5)ccc4s3)o2)CC1] | (DMSO-d$_6$) δ: 1.14 (dd, J = 8.36, 5.32 Hz, 2H), 1.49 (dd, J = 8.36, 5.32 Hz, 2H), 3.91 (s, 2H), 4.97 (s, 2H), 7.40 (t, J = 7.35 Hz, 1H), 7.50 (dd, J = 7.35, 6.59 Hz, 2H), 7.75-7.81 (m, 3H), 8.19 (d, J = 8.62 Hz, 1H), 8.25 (d, J = 1.52 Hz, 1H), 9.24 (s, 1H). |
| I-2-37 | 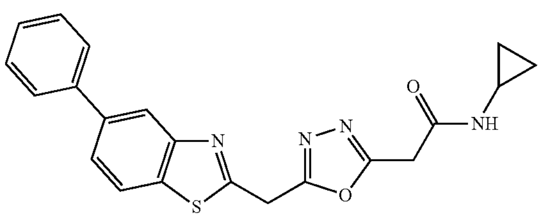 [SMILES: O=C(Cc1nnc(Cc2nc3cc(-c4ccccc4)ccc3s2)o1)NC1CC1] | |
| I-2-38 | 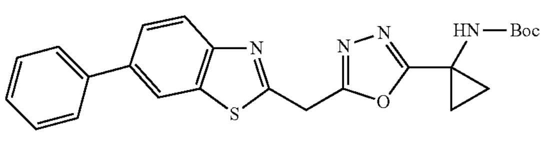 [SMILES: CC(C)(C)OC(=O)NC1(c2nnc(Cc3nc4ccc(-c5ccccc5)cc4s3)o2)CC1] | (DMSO-d$_6$) δ: 1.22-1.43 (m, 13H), 4.89 (s, 2H), 7.40 (t, J = 7.35 Hz, 1H), 7.50 (dd, J = 7.60, 7.35 Hz, 2H), 7.75 (d, J = 7.60 Hz, 2H), 7.82 (dd, J = 8.62, 2.03 Hz, 1H), 7.96 (s, 1H), 8.04 (d, J = 8.62 Hz, 1H), 8.42 (d, J = 2.03 Hz, 1H). |
| I-2-39 | 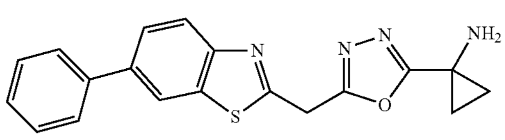 [SMILES: NC1(c2nnc(Cc3nc4ccc(-c5ccccc5)cc4s3)o2)CC1] | (DMSO-d$_6$) δ: 1.04-1.18 (m, 4H), 2.72 (s, 2H), 4.88 (s, 2H), 7.40 (t, J = 7.35 Hz, 1H), 7.50 (dd, J = 7.35, 7.10 Hz, 2H), 7.75 (d, J = 7.10 Hz, 2H), 7.82 (dd, J = 8.62, 1.52 Hz, 1H), 8.05 (d, J = 8.62 Hz, 1H), 8.43 (d, J = 1.52 Hz, 1H). |

TABLE 25-continued

| No. | Structure | NMR (δ) |
|---|---|---|
| I-2-40 | 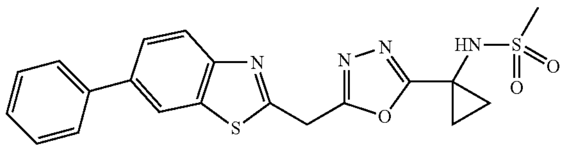 [SMILES: CS(=O)(=O)NC1(c2nnc(Cc3nc4ccc(-c5ccccc5)cc4s3)o2)CC1] | (DMSO-d$_6$) δ: 1.43-1.54 (m, 4H), 2.97 (s, 3H), 4.93 (s, 2H), 7.40 (t, J = 7.35 Hz, 1H), 7.50 (dd, J = 7.35, 7.60 Hz, 2H), 7.76 (d, J = 7.60 Hz, 2H), 7.82 (dd, J = 8.62, 1.52 Hz, 1H), 8.04 (d, J = 8.62 Hz, 1H), 8.44 (d, J = 1.52 Hz, 1H), 8.61 (s, 1H). |

TABLE 26

| No. | Structure | NMR (δ) |
|---|---|---|
| I-2-41 | 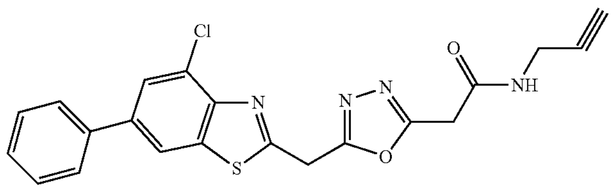 [SMILES: C#CCNC(=O)Cc1nnc(Cc2nc3c(Cl)cc(-c4ccccc4)cc3s2)o1] | (DMSO-d6) δ: 3.15 (s, 1H), 3.91 (s, 4H), 5.00 (s, 2H), 7.40-7.54 (m, 3H), 7.78 (d, J = 8.40 Hz, 1H), 7.94 (s, 1H), 8.44 (s, 1H), 8.76 (brs, 1H). |
| I-2-42 | 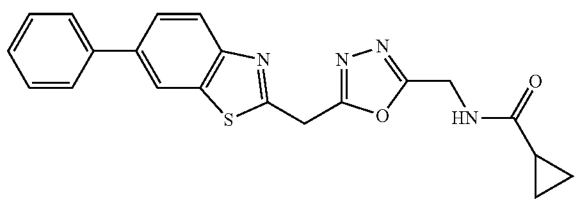 [SMILES: O=C(NCc1nnc(Cc2nc3ccc(-c4ccccc4)cc3s2)o1)C1CC1] | (DMSO-d6) δ: 0.67-0.69 (m, 4H), 1.56-1.62 (m, 1H), 4.53 (d, J = 5.6 Hz, 2H), 4.95 (s, 2H), 7.40 (t, J = 7.4 Hz, 1H), 7.48-7.52 (m, 2H), 7.75-7.77 (m, 2H), 7.83 (dd, J = 8.6, 1.5 Hz, 1H), 8.05 (d, J = 8.6 Hz, 1H), 8.44 (d, J = 2.0 Hz, 1H), 8.82 (t, J = 5.8 Hz, 1H). |
| I-2-43 | 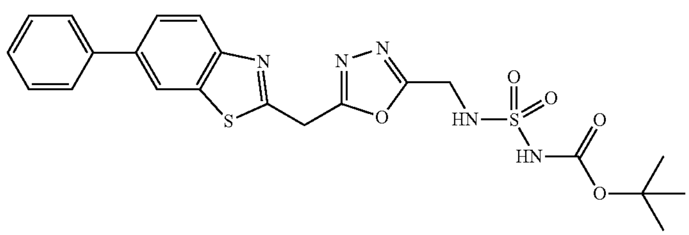 [SMILES: CC(C)(C)OC(=O)NS(=O)(=O)NCc1nnc(Cc2nc3ccc(-c4ccccc4)cc3s2)o1] | (DMSO-d6) δ: 1.40 (s, 9H), 4.41 (d, J = 5.6 Hz, 2H), 4.95 (s, 2H), 7.38-7.42 (m, 1H), 7.48-7.52 (m, 2H), 7.74-7.77 (m, 2H), 7.83 (dd, J = 8.6, 1.5 Hz, 1H), 8.05 (d, J = 8.6 Hz, 1H), 8.44-8.48 (m, 2H), 11.05 (s, 1H). |
| I-2-44 | 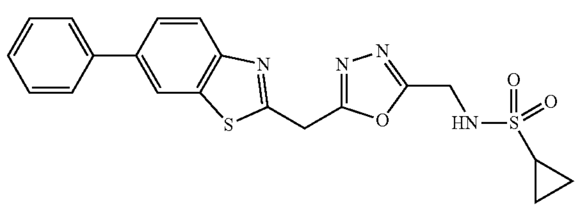 [SMILES: O=S(=O)(NCc1nnc(Cc2nc3ccc(-c4ccccc4)cc3s2)o1)C1CC1] | (DMSO-d6) δ: 0.83-0.87 (m, 4H), 4.47 (s, 2H), 4.98 (s, 2H), 7.40 (t, J = 7.4 Hz, 1H), 7.49-7.52 (m, 2H), 7.76 (d, J = 7.6 Hz, 2H), 7.83 (dd, J = 8.6, 2.0 Hz, 1H), 8.01-8.04 (m, 2H), 8.44 (d, J = 2.0 Hz, 1H). |
| I-2-45 | 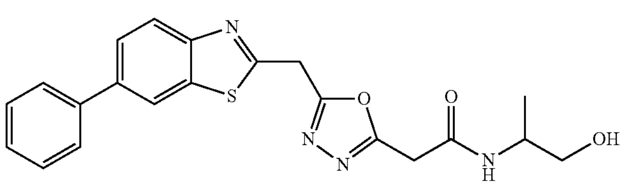 [SMILES: CC(CO)NC(=O)Cc1nnc(Cc2nc3ccc(-c4ccccc4)cc3s2)o1] | (DMSO-d6) δ: 1.03 (d, J = 6.6 Hz, 3H), 3.21-3.29 (m, 1H), 3.33-3.38 (m, 1H), 3.69-3.79 (m, 1H), 3.85 (s, 2H), 4.72 (t, J = 5.6 Hz, 1H), 4.94 (s, 2H), 7.38-7.43 (m, 1H), 7.50 (t, J = 7.6 Hz, 2H), 7.73-7.78 (m, 2H), 7.83 (dd, J = 8.6, 2.0 Hz, 1H), 8.05 (d, J = 8.6 Hz, 1H), 8.11 (d, J = 7.6 Hz, 1H), 8.44 (d, J = 2.0 Hz, 1H). |

TABLE 27

| No. | Structure | NMR (δ) |
|---|---|---|
| I-2-46 | 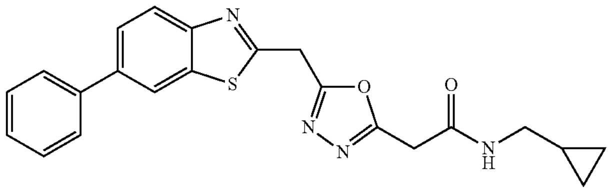 [SMILES: O=C(Cc1nnc(Cc2nc3ccc(-c4ccccc4)cc3s2)o1)NCC1CC1] | (DMSO-d6) δ: 0.12-0.17 (m, 2H), 0.36-0.42 (m, 2H), 0.82-0.93 (m, 1H), 2.95 (t, J = 6.3 Hz, 2H), 3.86 (s, 2H), 4.94 (s, 2H), 7.38-7.43 (m, 1H), 7.50 (t, J = 7.6 Hz, 2H), 7.74-7.77 (m, 2H), 7.83 (dd, J = 8.4, 1.8 Hz, 1H), 8.05 (d, J = 8.6 Hz, 1H), 8.37 (t, J = 5.1 Hz, 1H), 8.43 (d, J = 1.5 Hz, 1H). |
| I-2-47 | 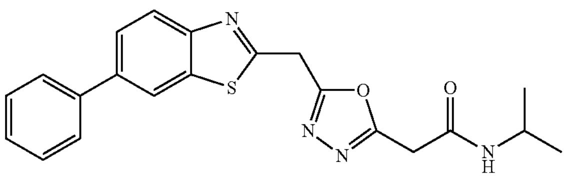 [SMILES: CC(C)NC(=O)Cc1nnc(Cc2nc3ccc(-c4ccccc4)cc3s2)o1] | (DMSO-d6) δ: 1.05 (d, J = 6.6 Hz, 6H), 3.76-3.85 (m, 1H), 3.81 (s, 2H), 4.94 (s, 2H), 7.38-7.43 (m, 1H), 7.50 (t, J = 7.6 Hz, 2H), 7.76 (d, J = 7.6 Hz, 2H), 7.83 (d, J = 8.6 Hz, 1H), 8.04 (d, J = 8.1 Hz, 1H), 8.18 (d, J = 7.1 Hz, 1H), 8.44 (s, 1H). |
| I-2-48 | 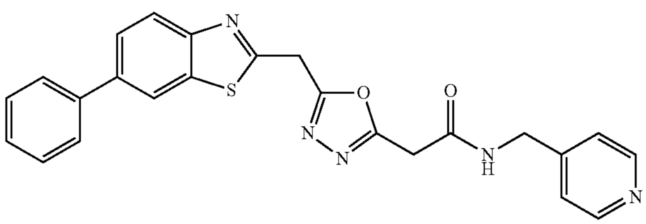 [SMILES: O=C(Cc1nnc(Cc2nc3ccc(-c4ccccc4)cc3s2)o1)NCc1ccncc1] | (DMSO-d6) δ: 4.00 (s, 2H), 4.33 (d, J = 5.6 Hz, 2H), 4.96 (s, 2H), 7.26 (d, J = 5.6 Hz, 2H), 7.38-7.43 (m, 1H), 7.50 (t, J = 7.6 Hz, 2H), 7.74-7.78 (m, 2H), 7.83 (dd, J = 8.6, 2.0 Hz, 1H), 8.05 (d, J = 8.1 Hz, 1H), 8.44 (d, J = 1.5 Hz, 1H), 8.46-8.49 (m, 2H), 8.90 (t, J = 5.8 Hz, 1H). |
| I-2-49 | 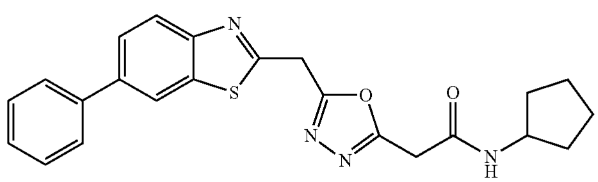 [SMILES: O=C(Cc1nnc(Cc2nc3ccc(-c4ccccc4)cc3s2)o1)NC1CCCC1] | (DMSO-d6) δ: 1.31-1.40 (m, 2H), 1.42-1.54 (m, 2H), 1.55-1.66 (m, 2H), 1.73-1.83 (m, 2H), 3.81 (s, 2H), 3.91-4.01 (m, 1H), 4.94 (s, 2H), 7.38-7.43 (m, 1H), 7.50 (t, J = 7.6 Hz, 2H), 7.73-7.78 (m, 2H), 7.83 (dd, J = 8.6, 2.0 Hz, 1H), 8.05 (d, J = 8.6 Hz, 1H), 8.26 (d, J = 7.1 Hz, 1H), 8.44 (d, J = 1.5 Hz, 1H). |
| I-2-50 | 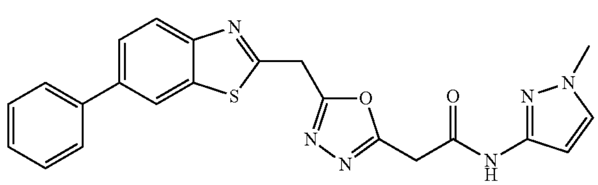 [SMILES: Cn1ccc(NC(=O)Cc2nnc(Cc3nc4ccc(-c5ccccc5)cc4s3)o2)n1] | (DMSO-d6) δ: 3.73 (s, 3H), 4.08 (s, 2H), 4.96 (s, 2H), 6.39 (d, J = 2.0 Hz, 1H), 7.38-7.42 (m, 1H), 7.50 (t, J = 7.6 Hz, 2H), 7.55 (d, J = 2.0 Hz, 1H), 7.76 (d, J = 7.1 Hz, 2H), 7.82 (dd, J = 8.4, 1.8 Hz, 1H), 8.05 (d, J = 8.6 Hz, 1H), 8.43 (d, J = 1.5 Hz, 1H), 10.82 (s, 1H). |

TABLE 28

| No. | Structure | NMR (δ) |
|---|---|---|
| I-2-51 | 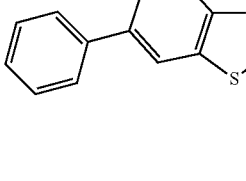 | (DMSO-d$_6$) δ: 3.13 (t, J = 6.08 Hz, 2H), 3.74 (t, J = 6.08 Hz, 2H), 3.93 (d, J = 5.58 Hz, 2H), 4.93 (s, 2H), 5.06 (dd, J = 10.39, 1.52 Hz, 1H), 5.17 (dd, J = 17.24, 1.52 Hz, 1H), 5.78 (m, 1H), 7.40 (t, J = 7.10 Hz, 1H), 7.50 (dd, J = 7.10, 7.10 Hz, 2H), 7.75 (d, J = 7.10 Hz, 2H), 7.83 (dd, J = 8.62, 1.52 Hz, 1H), 8.04 (d, J = 8.62 Hz, 1H), 8.43 (d, J = 1.52 Hz, 1H). |
| I-2-52 | 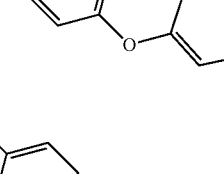 | (DMSO-d$_6$) δ: 4.06 (s, 2H), 4.91 (s, 2H), 7.10-7.15 (m, 2H), 7.18-7.28 (m, 3H), 7.73 (d, J = 2.53 Hz, 1H), 7.97 (d, J = 8.62 Hz, 1H). |
| I-2-53 | 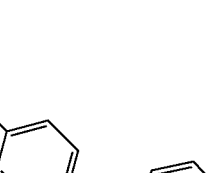 | (DMSO-d$_6$) δ: 1.13 (dd, J = 8.36, 5.32 Hz, 2H), 1.49 (dd, J = 8.11, 5.58 Hz, 2H), 3.90 (s, 2H), 4.90 (s, 2H), 7.09-7.16 (m, 2H), 7.19-7.29 (m, 3H), 7.73 (d, J = 2.53 Hz, 1H), 7.97 (d, J = 8.62 Hz, 1H), 9.23 (s, 1H). |
| I-2-54 | 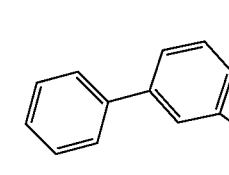 | (DMSO-d$_6$) δ: 3.98 (s, 2H), 4.19 (d, J = 5.58 Hz, 2H), 4.90 (s, 2H), 7.09-7.15 (m, 2H), 7.19-7.29 (m, 3H), 7.73 (d, J = 2.53 Hz, 1H), 7.97 (d, J = 9.12 Hz, 1H), 9.02 (t, J = 5.32 Hz, 1H). |
| I-2-55 | 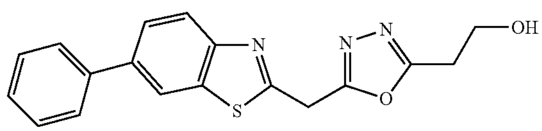 [SMILES: OCCc1nnc(Cc2nc3ccc(-c4ccccc4)cc3s2)o1] | (DMSO-d$_6$) δ: 2.99 (t, J = 6.08 Hz, 2H), 3.76 (dt, J = 6.08, 5.58 Hz, 2H), 4.90-4.95 (m, 3H), 7.40 (t, J = 7.35 Hz, 1H), 7.50 (dd, J = 7.35, 7.60 Hz, 2H), 7.76 (d, J = 7.60 Hz, 2H), 7.83 (dd, J = 8.36, 1.77 Hz, 1H), 8.05 (d, J = 8.36 Hz, 1H), 8.43 (d, J = 1.77 Hz, 1H). |

TABLE 29

| No. | Structure | NMR (δ) |
|---|---|---|
| I-2-56 | 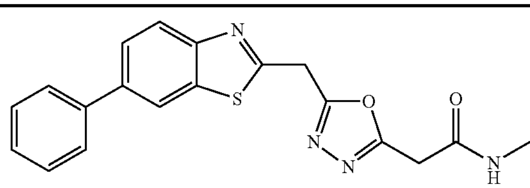 | (DMSO-d6) δ: 2.61 (d, J = 4.6 Hz, 3H), 3.84 (s, 2H), 4.94 (s, 2H), 7.38-7.42 (m, 1H), 7.50 (t, J = 7.6 Hz, 2H), 7.73-7.78 (m, 2H), 7.83 (dd, J = 8.6, 1.5 Hz, 1H), 8.05 (d, J = 8.1 Hz, 1H), 8.18-8.24 (m, 1H), 8.44 (d, J = 2.0 Hz, 1H). |

TABLE 29-continued

| No. | Structure | NMR (δ) |
|---|---|---|
| I-2-57 | 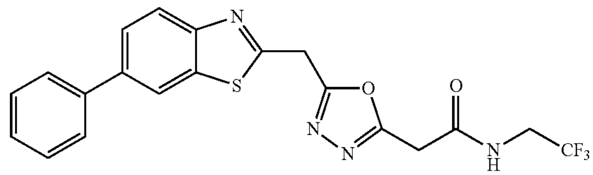 [SMILES: O=C(Cc1nnc(Cc2nc3ccc(-c4ccccc4)cc3s2)o1)NCC(F)(F)F] | (DMSO-d6) δ: 3.90-4.00 (m, 2H), 4.00 (s, 2H), 4.95 (s, 2H), 7.38-7.42 (m, 1H), 7.50 (t, J = 7.6 Hz, 2H), 7.76 (d, J = 7.1 Hz, 2H), 7.83 (dd, J = 8.4, 1.8 Hz, 1H), 8.05 (d, J = 8.6 Hz, 1H), 8.44 (d, J = 2.0 Hz, 1H), 8.99 (t, J = 6.1 Hz, 1H). |
| I-2-58 | 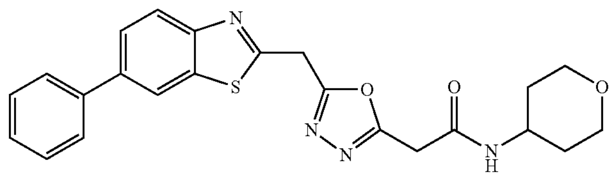 [SMILES: O=C(Cc1nnc(Cc2nc3ccc(-c4ccccc4)cc3s2)o1)NC1CCOCC1] | (DMSO-d6) δ: 1.31-1.41 (m, 2H), 1.65-1.71 (m, 2H), 3.68-3.81 (m, 3H), 3.84 (s, 2H), 4.94 (s, 2H), 7.38-7.42 (m, 1H), 7.50 (t, J = 7.6 Hz, 2H), 7.73-7.78 (m, 2H), 7.83 (dd, J = 8.6, 2.0 Hz, 1H), 8.04 (d, J = 8.6 Hz, 1H), 8.31 (d, J = 7.6 Hz, 1H), 8.44 (d, J = 2.0 Hz, 1H). |
| I-2-59 | 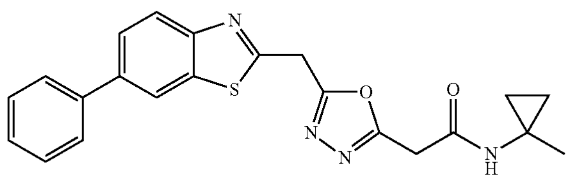 [SMILES: CC1(NC(=O)Cc2nnc(Cc3nc4ccc(-c5ccccc5)cc4s3)o2)CC1] | (DMSO-d6) δ: 0.49-0.53 (m, 2H), 0.58-0.61 (m, 2H), 1.25 (s, 3H), 3.75 (s, 2H), 4.94 (s, 2H), 7.38-7.42 (m, 1H), 7.50 (t, J = 7.6 Hz, 2H), 7.73-7.78 (m, 2H), 7.83 (dd, J = 8.6, 2.0 Hz, 1H), 8.04 (d, J = 8.6 Hz, 1H), 8.44 (d, J = 1.5 Hz, 1H), 8.49 (s, 1H). |
| I-2-60 | 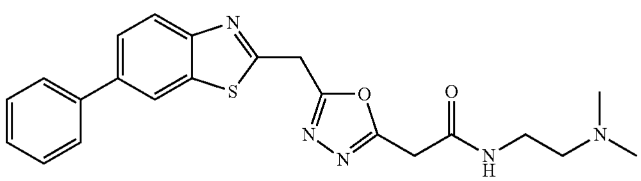 [SMILES: CN(C)CCNC(=O)Cc1nnc(Cc2nc3ccc(-c4ccccc4)cc3s2)o1] | (DMSO-d6) δ: 2.12 (s, 6H), 2.27 (t, J = 6.6 Hz, 2H), 3.15 (q, J = 6.3 Hz, 2H), 3.87 (s, 2H), 4.94 (s, 2H), 7.39-7.41 (m, 1H), 7.50 (t, J = 7.6 Hz, 2H), 7.75 (d, J = 7.6 Hz, 2H), 7.83 (dd, J = 8.6, 1.5 Hz, 1H), 8.05 (d, J = 8.1 Hz, 1H), 8.22 (t, J = 5.3 Hz, 1H), 8.44 (d, J = 1.5 Hz, 1H). |

TABLE 30

| No. | Structure | NMR (δ) |
|---|---|---|
| I-2-61 | 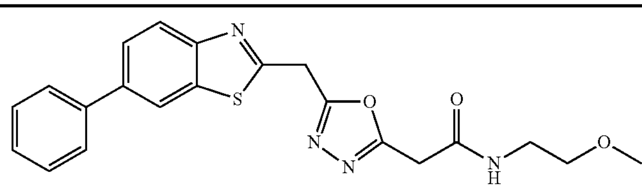 | (DMSO-d6) δ: 3.21-3.26 (m, 2H), 3.23 (s, 3H), 3.32-3.37 (m, 2H), 3.88 (s, 2H), 4.94 (s, 2H), 7.38-7.42 (m, 1H), 7.50 (t, J = 7.6 Hz, 2H), 7.76 (d, J = 7.6 Hz, 2H), 7.83 (dd, J = 8.6, 2.0 Hz, 1H), 8.05 (d, J = 8.6 Hz, 1H), 8.39 (t, J = 5.3 Hz, 1H), 8.44 (d, J = 1.5 Hz, 1H). |
| I-2-62 | 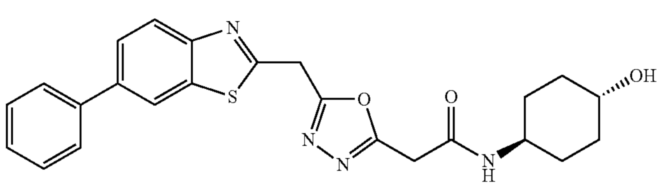 [SMILES: O=C(Cc1nnc(Cc2nc3ccc(-c4ccccc4)cc3s2)o1)N[C@H]1CC[C@H](O)CC1] | (DMSO-d6) δ: 1.10-1.23 (m, 5H), 1.70-1.83 (m, 5H), 3.32-3.39 (m, 1H), 3.40-3.47 (m, 1H), 3.81 (s, 2H), 4.51 (d, J = 4.1 Hz, 1H), 4.94 (s, 2H), 7.39-7.41 (m, 1H), 7.50 (t, J = 7.6 Hz, 2H), 7.73-7.78 (m, 2H), 7.83 (dd, J = 8.4, 1.8 Hz, 1H), 8.04 (d, J = 8.6 Hz, 1H), 8.15 (d, J = 7.6 Hz, 1H), 8.43 (d, J = 2.0 Hz, 1H). |

TABLE 30-continued

| No. | Structure | NMR (δ) |
|---|---|---|
| I-2-63 | 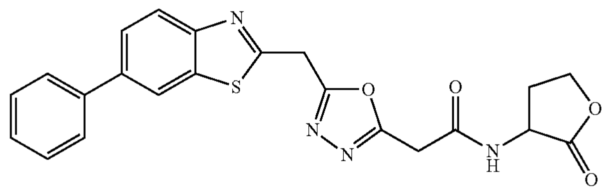 [SMILES: O=C(Cc1nnc(Cc2nc3ccc(-c4ccccc4)cc3s2)o1)NC1CCOC1=O] | (DMSO-d6) δ: 2.07-2.19 (m, 1H), 2.38-2.46 (m, 1H), 3.96 (d, J = 2.0 Hz, 2H), 4.16-4.24 (m, 1H), 4.30-4.37 (m, 1H), 4.56-4.64 (m, 1H), 4.96 (s, 2H), 7.38-7.42 (m, 1H), 7.50 (t, J = 7.6 Hz, 2H), 7.76 (d, J = 7.1 Hz, 2H), 7.83 (dd, J = 8.4, 1.8 Hz, 1H), 8.05 (d, J = 8.6 Hz, 1H), 8.44 (d, J = 1.5 Hz, 1H), 8.84 (d, J = 8.1 Hz, 1H). |
| I-2-64 | 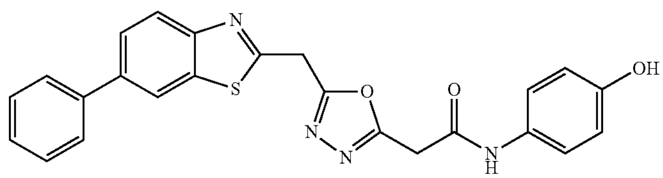 [SMILES: O=C(Cc1nnc(Cc2nc3ccc(-c4ccccc4)cc3s2)o1)Nc1ccc(O)cc1] | (DMSO-d6) δ: 4.05 (s, 2H), 4.97 (s, 2H), 6.67-6.72 (m, 2H), 7.31-7.35 (m, 2H), 7.37-7.43 (m, 1H), 7.50 (t, J = 7.6 Hz, 2H), 7.73-7.78 (m, 2H), 7.83 (dd, J = 8.6, 2.0 Hz, 1H), 8.05 (d, J = 8.1 Hz, 1H), 8.43 (d, J = 1.5 Hz, 1H), 9.24 (s, 1H), 10.13 (s, 1H). |
| I-2-65 | 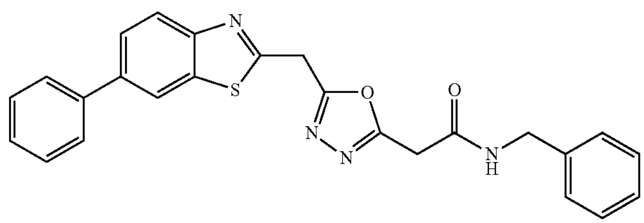 [SMILES: O=C(Cc1nnc(Cc2nc3ccc(-c4ccccc4)cc3s2)o1)NCc1ccccc1] | (DMSO-d6) δ: 3.94 (s, 2H), 4.29 (d, J = 6.1 Hz, 2H), 4.95 (s, 2H), 7.20-7.32 (m, 5H), 7.38-7.42 (m, 1H), 7.50 (t, J = 7.6 Hz, 2H), 7.76 (d, J = 7.1 Hz, 2H), 7.83 (dd, J = 8.6, 2.0 Hz, 1H), 8.05 (d, J = 8.6 Hz, 1H), 8.44 (d, J = 2.0 Hz, 1H), 8.79 (t, J = 5.8 Hz, 1H). |

TABLE 31

| No. | Structure | NMR (δ) |
|---|---|---|
| I-2-66 | 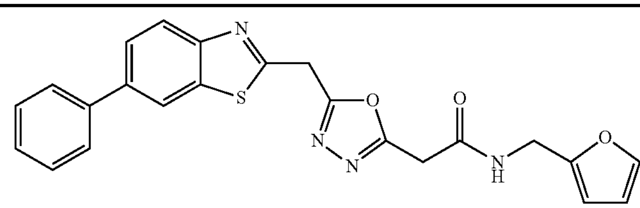 | (DMSO-d6) δ: 3.91 (s, 2H), 4.28 (d, J = 5.6 Hz, 2H), 4.95 (s, 2H), 6.26 (d, J = 2.5 Hz, 1H), 6.37 (dd, J = 3.3, 1.8 Hz, 1H), 7.38-7.42 (m, 1H), 7.50 (t, J = 7.6 Hz, 2H), 7.57 (d, J = 1.0 Hz, 1H), 7.76 (d, J = 7.1 Hz, 2H), 7.83 (dd, J = 8.4, 1.8 Hz, 1H), 8.05 (d, J = 8.6 Hz, 1H), 8.44 (d, J = 1.5 Hz, 1H), 8.77 (t, J = 5.3 Hz, 1H). |
| I-2-67 | 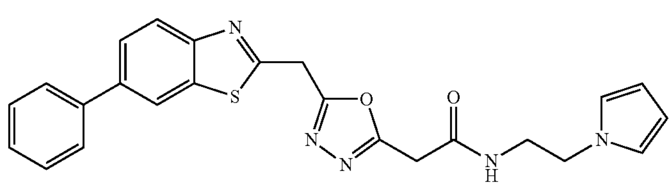 [SMILES: O=C(Cc1nnc(Cc2nc3ccc(-c4ccccc4)cc3s2)o1)NCCn1cccc1] | (DMSO-d6) δ: 3.35 (q, J = 5.6 Hz, 2H), 3.86 (s, 2H), 3.93 (t, J = 6.1 Hz, 2H), 4.94 (s, 2H), 5.96 (t, J = 2.3 Hz, 2H), 6.71 (t, J = 2.3 Hz, 2H), 7.38-7.42 (m, 1H), 7.50 (t, J = 7.6 Hz, 2H), 7.73-7.78 (m, 2H), 7.82 (dd, J = 8.6, 2.0 Hz, 1H), 8.05 (d, J = 8.6 Hz, 1H), 8.44 (d, J = 1.5 Hz, 2H). |

TABLE 31-continued

| No. | Structure | NMR (δ) |
|---|---|---|
| I-2-68 | 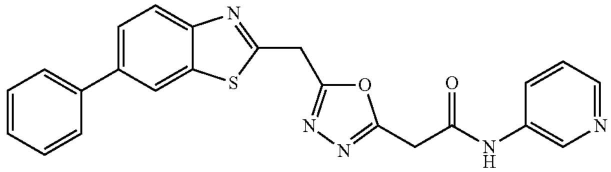 [SMILES: O=C(Cc1nnc(Cc2nc3ccc(-c4ccccc4)cc3s2)o1)Nc1cccnc1] | (DMSO-d6) δ: 4.18 (s, 2H), 4.98 (s, 2H), 7.36 (dd, J = 8.6, 4.6 Hz, 1H), 7.38-7.42 (m, 1H), 7.50 (t, J = 7.6 Hz, 2H), 7.76 (d, J = 7.6 Hz, 2H), 7.83 (dd, J = 8.4, 1.8 Hz, 1H), 7.98-8.02 (m, 1H), 8.05 (d, J = 8.1 Hz, 1H), 8.29 (dd, J = 4.6, 1.5 Hz, 1H), 8.44 (d, J = 1.5 Hz, 1H), 8.71 (d, J = 2.5 Hz, 1H), 10.63 (s, 1H). |
| I-2-69 | 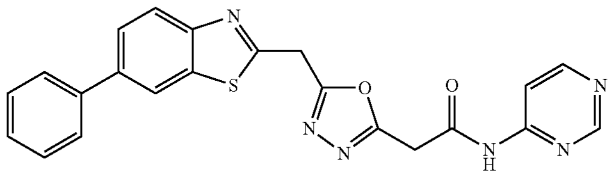 [SMILES: O=C(Cc1nnc(Cc2nc3ccc(-c4ccccc4)cc3s2)o1)Nc1ccncn1] | (DMSO-d6) δ: 4.29 (s, 2H), 4.98 (s, 2H), 7.38-7.42 (m, 1H), 7.50 (t, J = 7.6 Hz, 2H), 7.73-7.78 (m, 2H), 7.83 (dd, J = 8.6, 1.5 Hz, 1H), 7.97-8.02 (m, 1H), 8.05 (d, J = 8.6 Hz, 1H), 8.44 (d, J = 1.5 Hz, 1H), 8.68 (d, J = 6.1 Hz, 1H), 8.91 (s, 1H), 11.34 (s, 1H). |
| I-2-70 | 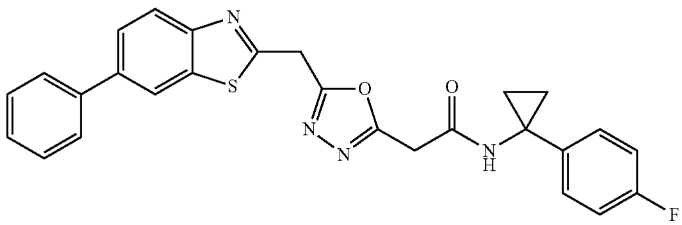 [SMILES: O=C(Cc1nnc(Cc2nc3ccc(-c4ccccc4)cc3s2)o1)NC1(c2ccc(F)cc2)CC1] | (DMSO-d6) δ: 1.10-1.17 (m, 4H), 3.89 (s, 2H), 4.95 (s, 2H), 7.00-7.07 (m, 2H), 7.15-7.02 (m, 2H), 7.38-7.42 (m, 1H), 7.50 (t, J = 7.6 Hz, 2H), 7.73-7.78 (m, 2H), 7.83 (dd, J = 8.6, 2.0 Hz, 1H), 8.04 (d, J = 8.6 Hz, 1H), 8.43 (d, J = 2.0 Hz, 1H), 9.03 (s, 1H). |

TABLE 32

| No. | Structure | NMR (δ) |
|---|---|---|
| I-2-71 | 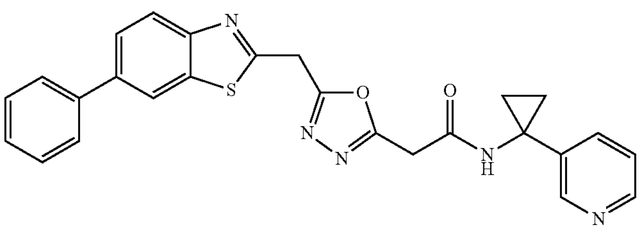 [SMILES: O=C(Cc1nnc(Cc2nc3ccc(-c4ccccc4)cc3s2)o1)NC1(c2cccnc2)CC1] | (DMSO-d6) δ: 1.15-1.27 (m, 4H), 3.94 (s, 2H), 4.95 (s, 2H), 7.25 (dd, J = 7.9, 4.8 Hz, 1H), 7.38-7.42 (m, 1H), 7.50 (t, J = 7.9 Hz, 3H), 7.76 (d, J = 7.6 Hz, 2H), 7.83 (dd, J = 8.6, 2.0 Hz, 1H), 8.05 (d, J = 8.6 Hz, 1H), 8.35 (dd, J = 4.8, 1.3 Hz, 1H), 8.42 (dd, J = 9.9, 1.8 Hz, 2H), 9.10 (s, 1H). |
| I-2-72 | 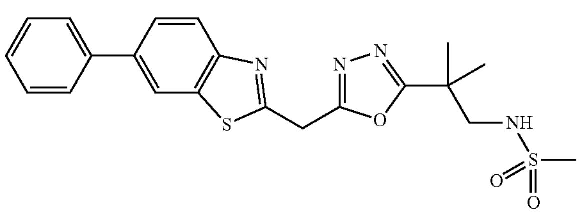 [SMILES: CC(C)(CNS(C)(=O)=O)c1nnc(Cc2nc3ccc(-c4ccccc4)cc3s2)o1] | (CDCl3) δ: 1.44 (s, 6H), 2.97 (s, 3H), 3.44 (d, J = 7.1 Hz, 2H), 4.74 (s, 2H), 5.32 (t, J = 6.8 Hz, 1H), 7.26 (s, 3H), 7.37-7.41 (m, 1H), 7.46-7.50 (m, 2H), 7.64 (d, J = 8.1 Hz, 2H), 7.73 (d, J = 8.6 Hz, 1H), 8.06-8.09 (m, 2H). |
| I-2-73 | 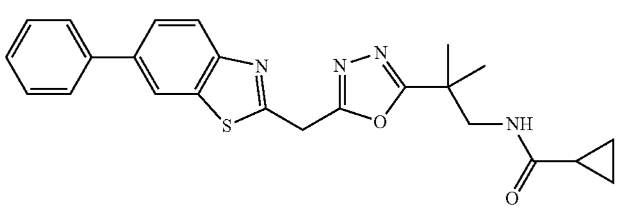 [SMILES: CC(C)(CNC(=O)C1CC1)c1nnc(Cc2nc3ccc(-c4ccccc4)cc3s2)o1] | (DMSO-d6) δ: 0.59-0.61 (m, 4H), 1.30 (s, 6H), 1.52-1.59 (m, 1H), 4.88 (s, 2H), 7.40 (t, J = 7.4 Hz, 1H), 7.48-7.52 (m, 2H), 7.74-7.77 (m, 2H), 7.83 (dd, J = 8.6, 2.0 Hz, 1H), 8.05 (d, J = 8.6 Hz, 1H), 8.11 (t, J = 6.1 Hz, 1H), 8.43 (d, J = 2.0 Hz, 1H). |

TABLE 32-continued

| No. | Structure | NMR (δ) |
|---|---|---|
| I-2-74 | 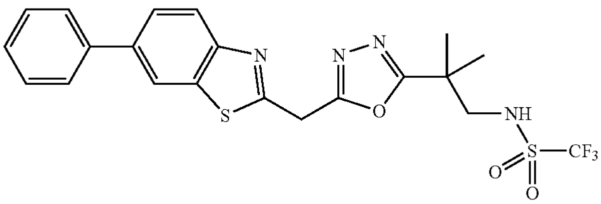 [SMILES: CC(C)(CNS(=O)(=O)C(F)(F)F)c1nnc(Cc2nc3ccc(-c4ccccc4)cc3s2)o1] | (CDCl3) δ: 1.45 (s, 6H), 3.56 (s, 2H), 4.75 (s, 2H), 6.43 (br s, 1H), 7.39 (t, J = 7.4 Hz, 1H), 7.46-7.50 (m, 2H), 7.62-7.64 (m, 2H), 7.74 (dd, J = 8.4, 1.8 Hz, 1H), 8.05-8.07 (m, 2H). |
| I-2-75 | 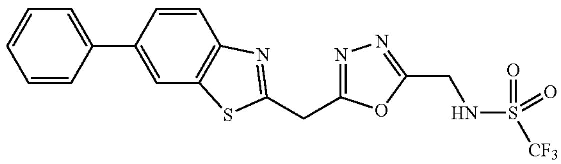 [SMILES: O=S(=O)(NCc1nnc(Cc2nc3ccc(-c4ccccc4)cc3s2)o1)C(F)(F)F] | (CDCl3) δ: 4.72 (s, 2H), 4.77 (s, 2H), 7.37-7.41 (m, 1H), 7.45-7.49 (m, 2H), 7.61-7.63 (m, 2H), 7.73 (dd, J = 8.4, 1.8 Hz, 1H), 8.02-8.06 (m, 2H). |

TABLE 33

| No. | Structure | NMR(δ) |
|---|---|---|
| I-2-76 | 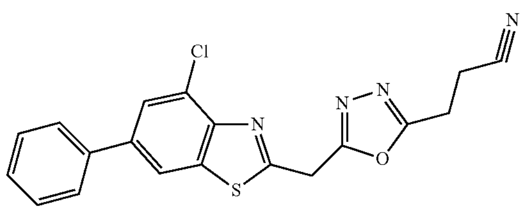 [SMILES: N#CCCc1nnc(Cc2nc3c(Cl)cc(-c4ccccc4)cc3s2)o1] | (DMSO-d6) δ: 2.98 (t, J = 6.60 Hz, 2H), 3.27 (t, J = 6.60 Hz, 2H), 5.01 (s, 2H), 7.40-7.54 (m, 3H), 7.78 (d, J = 6.60 Hz, 2H), 7.94 (d, J = 1.80 Hz, 1H), 8.44 (d, J = 1.80 Hz, 1H). |
| I-2-77 | 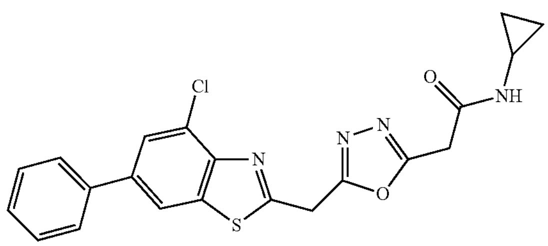 [SMILES: O=C(Cc1nnc(Cc2nc3c(Cl)cc(-c4ccccc4)cc3s2)o1)NC1CC1] | 1H-NMR (DMSO-d6) δ: 0.38-0.43 (m, 2H), 0.59-2.65 (m, 2H), 2.55-2.67 (m, 1H), 3.80 (s, 2H), 5.0 (s, 2H), 7.40-7.54 (m, 3H), 7.78 (d, J = 6.90 Hz, 2H), 7.94 (d, J = 1.50 Hz, 1H), 8.36 (brs, 1H), 8.45 (d, J = 1.50 Hz, 1H). |
| I-2-78 | 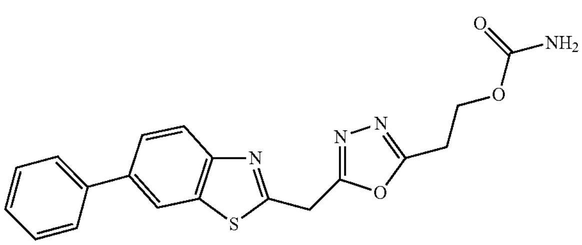 [SMILES: NC(=O)OCCc1nnc(Cc2nc3ccc(-c4ccccc4)cc3s2)o1] | (DMSO-$d_6$) δ: 3.18 (t, J = 6.08 Hz, 2H), 4.26 (t, J = 6.08 Hz, 2H), 4.93 (s, 2H), 6.56 (br s, 2H), 7.40 (t, J = 7.35 Hz, 1H), 7.50 (dd, J = 7.35, 7.60 Hz, 2H), 7.76 (d, J = 7.60 Hz, 2H), 7.82 (dd, J = 8.62, 1.52 Hz, 1H), 8.05 (d, J = 8.62 Hz, 1H), 8.43 (d, J = 1.52 Hz, 1H). |
| I-2-79 | 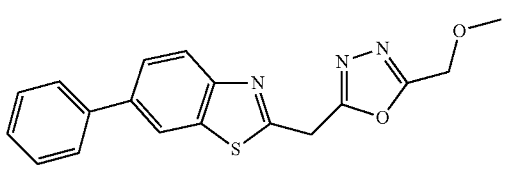 [SMILES: COCc1nnc(Cc2nc3ccc(-c4ccccc4)cc3s2)o1] | (CDCl$_3$) δ: 3.46 (s, 3H), 4.66 (s, 2H), 4.77 (s, 2H), 7.39 (t, J = 7.35 Hz, 1H), 7.47 (dd, J = 7.60, 7.35 Hz, 2H), 7.63 (d, J = 7.60 Hz, 2H), 7.73 (dd, J = 8.62, 1.52 Hz, 1H), 8.04-8.09 (m, 2H). |

TABLE 33-continued

| No. | Structure | NMR(δ) |
| --- | --- | --- |
| I-2-80 | MeO-C6H4-benzothiazole-CH2-oxadiazole-CH2-C(O)-NH-CH2-CN | 2009-7312-028-01 1H-NMR (DMSO-d6) δ: 3.81 (s, 3H), 3.99 (s, 2H), 4.20 (d, J = 5.6 Hz, 2H), 4.94 (s, 2H), 7.05-7.07 (m, 2H), 7.68-7.71 (m, 2H), 7.78 (dd, J = 8.6, 2.0 Hz, 1H), 8.01 (d, J = 8.6 Hz, 1H), 8.37 (d, J = 2.0 Hz, 1H), 9.03 (t, J = 5.3 Hz, 1H). |

TABLE 34

| No. | Structure | NMR(δ) |
| --- | --- | --- |
| I-2-81 | phenyl-benzothiazole-CH2-(5-methyloxazole) | (CDCl3) δ: 2.31 (s, 3H), 4.60 (s, 2H), 6.73 (d, J = 1.0 Hz, 1H), 7.38 (t, J = 7.4 Hz, 1H), 7.44-7.49 (m, 2H), 7.61-7.64 (m, 2H), 7.70 (dd, J = 8.6, 2.0 Hz, 1H), 8.04-8.08 (m, 2H). |
| I-2-82 | 4-Cl,6-phenyl-benzothiazole-CH2-oxadiazole-CH2-C(O)-NH-CH2-(1-hydroxymethylcyclopropyl) | (DMSO-d6) δ: 0.33 (d, J = 6.30 Hz, 4H), 3.11 (d, J = 5.40 Hz, 2H), 3.24 (d, J = 5.70 Hz, 2H), 3.89 (s, 2H), 5.00 (s, 2H), 7.40-7.54 (m, 3H), 7.78 (d, J = 7.50 Hz, 1H), 7.94 (d, J = 1.20 Hz, 1H), 8.26 (brs, 1H), 8.44 (d, J = 1.20 Hz, 1H). |
| I-2-83 | phenyl-benzothiazole-CH2-oxadiazole-CH2OH | (DMSO-d6) δ: 4.64 (d, J = 6.08 Hz, 2H), 4.97 (s, 2H), 5.91 (t, J = 6.08 Hz, 1H), 7.40 (t, J = 7.35 Hz, 1H), 7.50 (dd, J = 7.60, 7.35 Hz, 2H), 7.76 (d, J = 7.60 Hz, 2H), 7.83 (dd, J = 8.62, 1.52 Hz, 1H), 8.05 (d, J = 8.62 Hz, 1H), 8.44 (d, J = 1.52 Hz, 1H). |
| I-2-84 | phenyl-benzothiazole-CH2-oxadiazole-CH2-C(O)-NH-(indanyl) | (DMSO-d6) δ: 1.72-1.82 (m, 1H), 2.34-2.43 (m, 1H), 2.75-2.83 (m, 1H), 2.87-2.96 (m, 1H), 3.91 (d, J = 2.5 Hz, 2H), 4.97 (s, 2H), 5.25 (q, J = 7.8 Hz, 1H), 7.10-7.15 (m, 1H), 7.17-7.26 (m, 3H), 7.38-7.42 (m, 1H), 7.50 (t, J = 7.6 Hz, 2H), 7.73-7.78 (m, 2H), 7.83 (dd, J = 8.4, 1.8 Hz, 1H), 8.05 (d, J = 8.6 Hz, 1H), 8.45 (d, J = 1.5 Hz, 1H), 8.69 (d, J = 8.1 Hz, 1H). |

TABLE 35

| No. | Structure | NMR(δ) |
|---|---|---|
| I-2-85 | 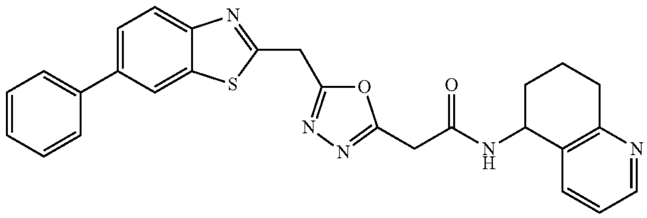 [SMILES: O=C(Cc1nnc(Cc2nc3ccc(-c4ccccc4)cc3s2)o1)NC1CCCc2ncccc21] | (DMSO-d6) δ: 1.63-1.74 (m, 1H), 1.74-1.85 (m, 1H), 1.85-1.95 (m, 2H), 2.81 (q, J = 6.3 Hz, 2H), 3.92 (d, J = 3.5 Hz, 2H), 4.96 (s, 3H), 7.13 (dd, J = 7.6, 4.6 Hz, 1H), 7.38-7.43 (m, 1H), 7.48-7.55 (m, 3H), 7.76 (d, J = 7.1 Hz, 2H), 7.83 (dd, J = 8.4, 1.8 Hz, 1H), 8.05 (d, J = 8.1 Hz, 1H), 8.35 (dd, J = 3.5, 1.8 Hz, 1H), 8.45 (d, J = 1.5 Hz, 1H), 8.74 (d, J = 8.6 Hz, 1H). |
| I-2-86 | 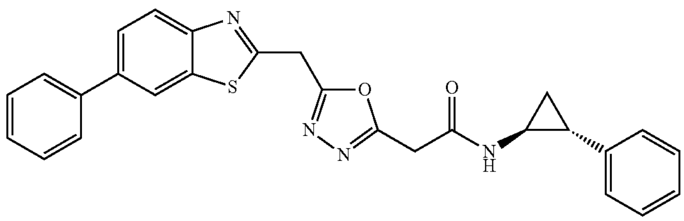 [SMILES: O=C(Cc1nnc(Cc2nc3ccc(-c4ccccc4)cc3s2)o1)N[C@H]1C[C@@H]1c1ccccc1] | (DMSO-d6) δ: 1.15 (t, J = 7.1 Hz, 2H), 1.91-1.98 (m, 1H), 2.78-2.85 (m, 1H), 3.85 (s, 2H), 4.95 (s, 2H), 7.08 (d, J = 7.1 Hz, 2H), 7.11-7.17 (m, 1H), 7.21-7.26 (m, 2H), 7.38-7.42 (m, 1H), 7.50 (t, J = 7.6 Hz, 2H), 7.75 (d, J = 7.6 Hz, 2H), 7.82 (dd, J = 8.6, 1.5 Hz, 1H), 8.05 (d, J = 8.6 Hz, 1H), 8.43 (d, J = 2.0 Hz, 1H), 8.63 (d, J = 4.1 Hz, 1H). |
| I-2-87 | 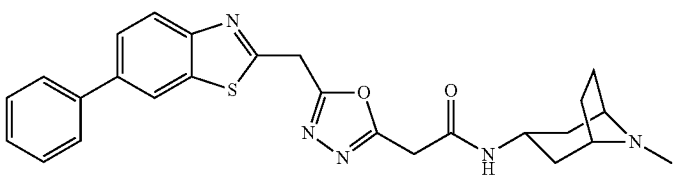 [SMILES: CN1C2CCC1CC(NC(=O)Cc1nnc(Cc3nc4ccc(-c5ccccc5)cc4s3)o1)C2] | (DMSO-d6) δ: 1.40-1.55 (m, 6H), 1.86-1.92 (m, 2H), 2.14 (s, 3H), 3.01 (s, 2H), 3.78-3.88 (m, 1H), 3.79 (s, 2H), 4.93 (s, 2H), 7.38-7.43 (m, 1H), 7.50 (t, J = 7.6 Hz, 2H), 7.76 (d, J = 7.1 Hz, 2H), 7.83 (dd, J = 8.6, 2.0 Hz, 1H), 8.05 (d, J = 8.6 Hz, 1H), 8.13 (d, J = 8.1 Hz, 1H), 8.44 (d, J = 2.0 Hz, 1H). |
| I-2-88 | 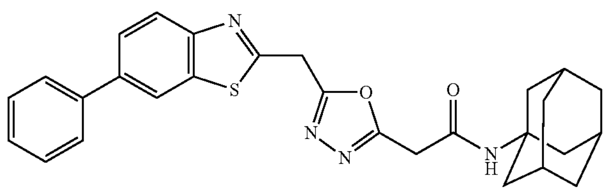 [SMILES: O=C(Cc1nnc(Cc2nc3ccc(-c4ccccc4)cc3s2)o1)NC12CC3CC(CC(C3)C1)C2] | (DMSO-d6) δ: 1.57 (s, 6H), 1.87 (d, J = 2.5 Hz, 6H), 1.96 (s, 3H), 3.57-3.63 (m, 1H), 3.79 (s, 2H), 4.94 (s, 2H), 7.38-7.42 (m, 1H), 7.50 (t, J = 7.9 Hz, 2H), 7.73-7.85 (m, 4H), 8.04 (d, J = 8.6 Hz, 1H), 8.43 (d, J = 1.5 Hz, 1H). |

TABLE 36

| No. | Structure | NMR(δ) |
|---|---|---|
| I-2-89 | 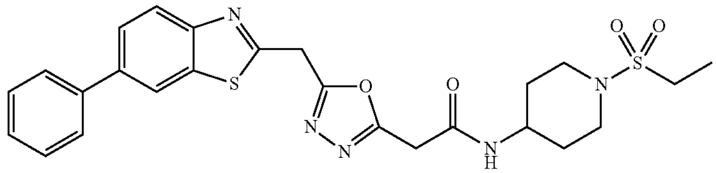 [SMILES: CCS(=O)(=O)N1CCC(NC(=O)Cc2nnc(Cc3nc4ccc(-c5ccccc5)cc4s3)o2)CC1] | (DMSO-d6) δ: 1.19 (t, J = 7.4 Hz, 3H), 1.32-1.43 (m, 2H), 1.75-1.83 (m, 2H), 2.87-2.95 (m, 2H), 3.01 (q, J = 7.3 Hz, 2H), 3.46-3.54 (m, 2H), 3.65-3.74 (m, 1H), 3.85 (s, 2H), 4.94 (s, 2H), 7.38-7.43 (m, 1H), 7.50 (t, J = 7.6 Hz, 2H), 7.76 (d, J = 7.1 Hz, 2H), 7.83 (dd, J = 8.6, 2.0 Hz, 1H), 8.05 (d, J = 8.6 Hz, 1H), 8.35 (d, J = 7.6 Hz, 1H), 8.44 (d, J = 1.5 Hz, 1H). |

TABLE 36-continued

| No. | Structure | NMR(δ) |
|---|---|---|
| I-2-90 | 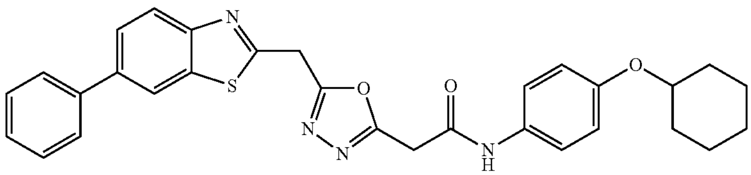 [SMILES: O=C(Cc1nnc(Cc2nc3ccc(-c4ccccc4)cc3s2)o1)Nc1ccc(OC2CCCCC2)cc1] | (DMSO-d6) δ: 1.20-1.44 (m, 5H), 1.47-1.55 (m, 1H), 1.65-1.72 (m, 2H), 1.85-1.92 (m, 2H), 4.08 (s, 2H), 4.21-4.28 (m, 1H), 4.97 (s, 2H), 6.87 (d, J = 9.1 Hz, 2H), 7.38-7.45 (m, 3H), 7.50 (t, J = 7.6 Hz, 2H), 7.76 (d, J = 7.6 Hz, 2H), 7.83 (dd, J = 8.6, 2.0 Hz, 1H), 8.05 (d, J = 8.6 Hz, 1H), 8.43 (d, J = 1.5 Hz, 1H), 10.23 (s, 1H). |
| I-2-91 | 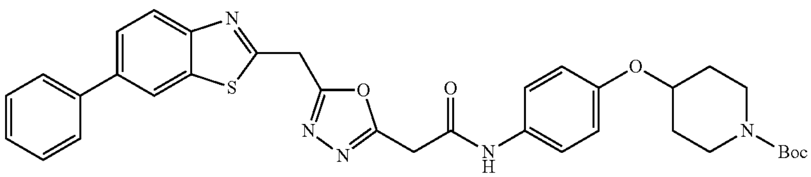 [SMILES: CC(C)(C)OC(=O)N1CCC(Oc2ccc(NC(=O)Cc3nnc(Cc4nc5ccc(-c6ccccc6)cc5s4)o3)cc2)CC1] | (DMSO-d6) δ: 1.40 (s, 9H), 1.42-1.53 (m, 2H), 1.82-1.91 (m, 2H), 3.10-3.19 (m, 2H), 3.60-3.67 (m, 2H), 4.08 (s, 2H), 4.43-4.50 (m, 1H), 4.97 (s, 2H), 6.92 (d, J = 9.1 Hz, 2H), 7.38-7.53 (m, 5H), 7.76 (d, J = 7.1 Hz, 2H), 7.83 (dd, J = 8.6, 1.5 Hz, 1H), 8.05 (d, J = 8.6 Hz, 1H), 8.43 (d, J = 2.0 Hz, 1H), 10.26 (s, 1H). |
| I-2-92 | 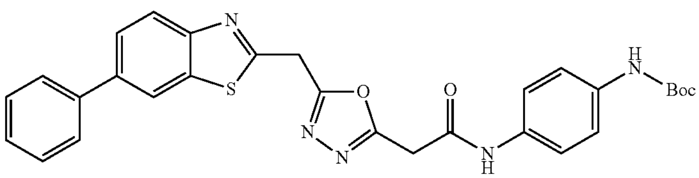 [SMILES: CC(C)(C)OC(=O)Nc1ccc(NC(=O)Cc2nnc(Cc3nc4ccc(-c5ccccc5)cc4s3)o2)cc1] | (DMSO-d6) δ: 1.46 (s, 9H), 4.09 (s, 2H), 4.97 (s, 2H), 7.35-7.45 (m, 5H), 7.50 (t, J = 7.6 Hz, 2H), 7.76 (d, J = 7.1 Hz, 2H), 7.82 (dd, J = 8.6, 1.5 Hz, 1H), 8.04 (d, J = 8.6 Hz, 1H), 8.43 (d, J = 1.5 Hz, 1H), 9.28 (s, 1H), 10.28 (s, 1H). |
| I-2-93 | 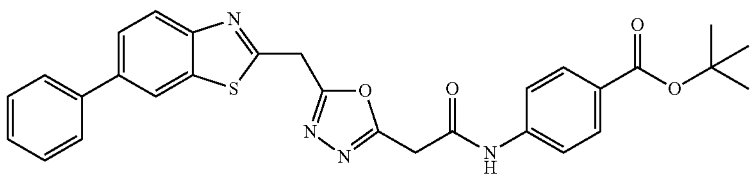 [SMILES: CC(C)(C)OC(=O)c1ccc(NC(=O)Cc2nnc(Cc3nc4ccc(-c5ccccc5)cc4s3)o2)cc1] | (DMSO-d6) δ: 1.53 (s, 9H), 4.18 (s, 2H), 4.98 (s, 2H), 7.38-7.43 (m, 1H), 7.50 (t, J = 7.6 Hz, 2H), 7.67 (d, J = 8.6 Hz, 2H), 7.76 (d, J = 7.1 Hz, 2H), 7.81-7.88 (m, 3H), 8.04 (d, J = 8.6 Hz, 1H), 8.44 (d, J = 1.5 Hz, 1H), 10.72 (s, 1H). |

TABLE 37

| No. | Structure | NMR(δ) |
|---|---|---|
| I-2-94 | 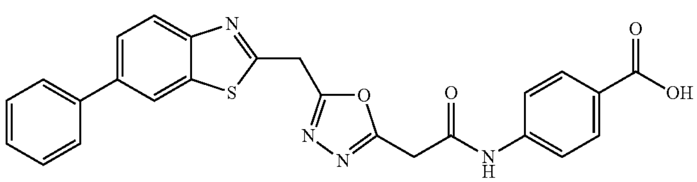 [SMILES: O=C(Cc1nnc(Cc2nc3ccc(-c4ccccc4)cc3s2)o1)Nc1ccc(C(=O)O)cc1] | (DMSO-d6) δ: 4.19 (s, 2H), 4.98 (s, 2H), 7.38-7.43 (m, 1H), 7.50 (t, J = 7.6 Hz, 2H), 7.68 (d, J = 9.1 Hz, 2H), 7.76 (d, J = 7.6 Hz, 2H), 7.83 (dd, J = 8.6, 2.0 Hz, 1H), 7.91 (d, J = 8.6 Hz, 2H), 8.05 (d, J = 8.6 Hz, 1H), 8.44 (d, J = 1.5 Hz, 1H), 10.71 (s, 1H), 12.77 (s, 1H). |

TABLE 37-continued

| No. | Structure | NMR(δ) |
|---|---|---|
| I-2-95 | 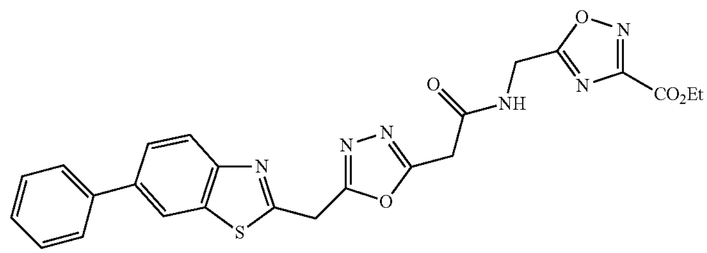 [SMILES: CCOC(=O)c1noc(CNC(=O)Cc2nnc(Cc3nc4ccc(-c5ccccc5)cc4s3)o2)n1] | (DMSO-d$_6$) δ: 1.31 (t, J = 7.10 Hz, 3H), 4.03 (s, 2H), 4.39 (q, J = 7.10 Hz, 2H), 4.70 (d, J = 6.08 Hz, 2H), 4.95 (s, 2H), 7.40 (t, J = 7.35 Hz, 1H), 7.50 (dd, J = 7.35, 7.10 Hz, 2H), 7.76 (d, J = 7.10 Hz, 2H), 7.82 (dd, J = 8.36, 2.03 Hz, 1H), 8.05 (d, J = 8.36 Hz, 1H), 8.43 (d, J = 2.03 Hz, 1H), 9.23 (t, J = 6.08 Hz, 1H). |
| I-2-96 | 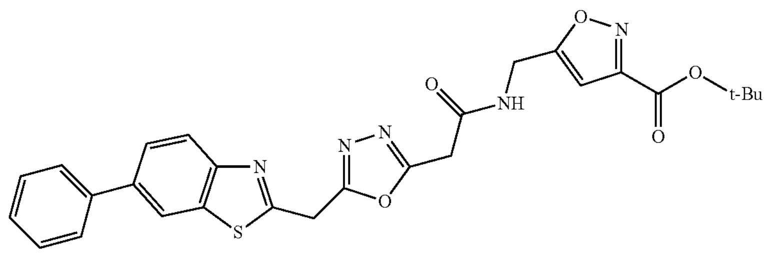 [SMILES: CC(C)(C)OC(=O)c1cc(CNC(=O)Cc2nnc(Cc3nc4ccc(-c5ccccc5)cc4s3)o2)on1] | (DMSO-d$_6$) δ: 1.53 (s, 9H), 3.99 (s, 2H), 4.50 (d, J = 5.58 Hz, 2H), 4.95 (s, 2H), 6.68 (s, 1H), 7.40 (t, J = 7.35 Hz, 1H), 7.50 (dd, J = 7.10, 7.35 Hz, 2H), 7.75 (d, J = 7.10 Hz, 2H), 7.82 (dd, J = 8.62, 1.52 Hz, 1H), 8.04 (d, J = 8.62 Hz, 1H), 8.43 (d, J = 1.52 Hz, 1H), 9.01 (t, J = 5.58 Hz, 1H). |
| I-2-97 | 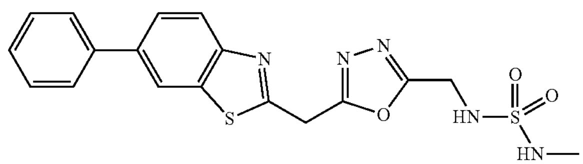 [SMILES: CNS(=O)(=O)NCc1nnc(Cc2nc3ccc(-c4ccccc4)cc3s2)o1] | (CDCl3) δ: 2.66 (d, J = 5.6 Hz, 3H), 4.54 (d, J = 6.6 Hz, 2H), 4.78 (s, 2H), 4.85 (q, J = 5.6 Hz, 1H), 5.06 (t, J = 6.3 Hz, 1H), 7.42 (t, J = 7.4 Hz, 1H), 7.48-7.52 (m, 2H), 7.64-7.66 (m, 2H), 7.75 (dd, J = 8.6, 2.0 Hz, 1H), 8.05-8.09 (m, 2H). |
| I-2-98 | 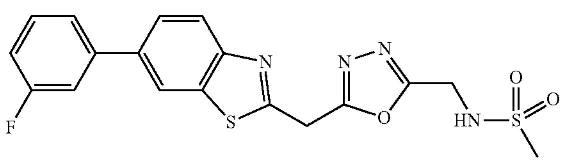 [SMILES: CS(=O)(=O)NCc1nnc(Cc2nc3ccc(-c4cccc(F)c4)cc3s2)o1] | (CDCl3) δ: 3.09 (s, 3H), 4.66 (d, J = 6.6 Hz, 2H), 4.78 (s, 2H), 5.16 (t, J = 6.1 Hz, 1H), 7.09-7.13 (m, 1H), 7.34-7.37 (m, 1H), 7.41-7.49 (m, 2H), 7.73 (dd, J = 8.6, 1.5 Hz, 1H). 8.06-8.09 (m, 2H). |

TABLE 38

| No. | Structure | NMR(δ) | retention time | Mass | method |
|---|---|---|---|---|---|
| I-2-99 | 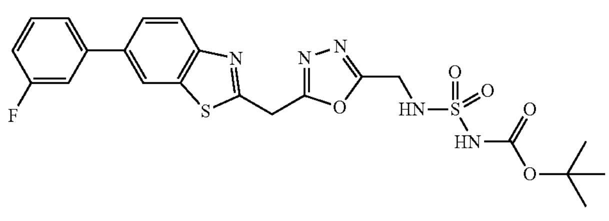 [SMILES: CC(C)(C)OC(=O)NS(=O)(=O)NCc1nnc(Cc2nc3ccc(-c4cccc(F)c4)cc3s2)o1] | (DMSO-d6) δ: 1.40 (s, 9H), 4.41 (d, J = 5.6 Hz, 2H), 4.96 (s, 2H), 7.21-7.26 (m, 1H), 7.51-7.57 (m, 1H), 7.61-7.64 (m, 2H), 7.87 (dd, J = 8.6, 2.0 Hz, 1H), 8.05 (d, J = 8.6 Hz, 1H), 8.50 (d, J = 1.5 Hz, 2H), 11.05 (s, 1H). | | | |
| I-2-100 | 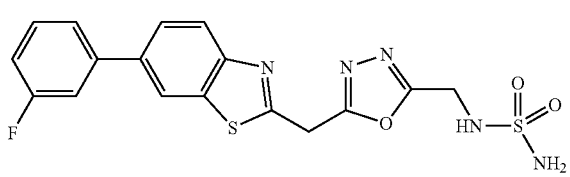 | (DMSO-d6) δ: 4.32 (d, J = 5.6 Hz, 2H), 4.96 (s, 2H), 6.77 (s, 2H), 7.21-7.26 (m, 1H), 7.43 (t, J = 6.1 Hz, 1H), 7.54 (dd, J = 14.4, 7.9 Hz, 1H), 7.61-7.64 (m, 2H), 7.87 (dd, J = 8.4, 1.8 Hz, 1H), 8.06 (d, J = 8.6 Hz, 1H), 8.50 (d, J = 2.0 Hz, 1H). | | | |

TABLE 38-continued

| No. | Structure | NMR(δ) | retention time | Mass | method |
|---|---|---|---|---|---|
| I-2-101 | 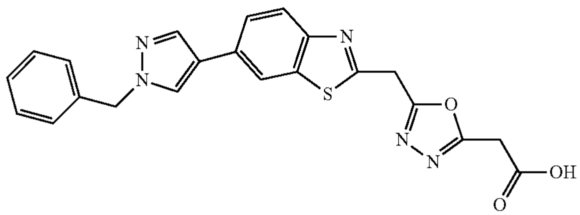 [SMILES: O=C(O)Cc1nnc(Cc2nc3ccc(-c4cnn(Cc5ccccc5)c4)cc3s2)o1] | | 1.68 | 432.15 | C |
| I-2-102 | 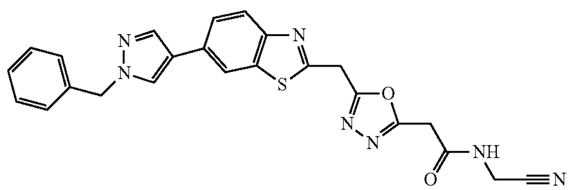 [SMILES: N#CCNC(=O)Cc1nnc(Cc2nc3ccc(-c4cnn(Cc5ccccc5)c4)cc3s2)o1] | (DMSO-d$_6$) δ 3.99 (s, 2H), 4.20 (s, 2H), 4.92 (s, 2H), 5.37 (s, 2H), 7.30-7.38 (m, 5H), 7.74 (d, J = 9.0 Hz, 1H), 7.94 (d, J = 9.0 Hz, 1H), 8.01 (s, 1H), 8.32 (s, 1H), 8.37 (s, 1H), 9.03 (s, 1H) | | | |
| I-2-103 | 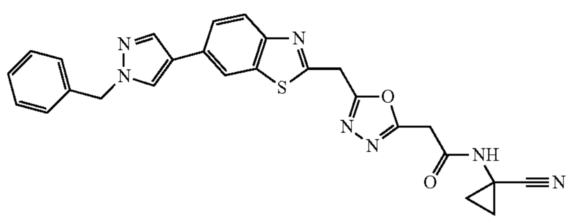 [SMILES: N#CC1(NC(=O)Cc2nnc(Cc3nc4ccc(-c5cnn(Cc6ccccc6)c5)cc4s3)o2)CC1] | (DMSO-d$_6$) δ 1.12-1.24 (m, 2H), 1.47-1.50 (m, 2H), 3.90 (s, 2H),, 4.91 (s, 2H), 5.37 (s, 2H), 7.28-7.38 (m, 5H), 7.74 (d, J = 9.0 Hz, 1H), 7.94 (d, J = 9.0 Hz, 1H), 8.01 (s, 1H), 8.32 (s, 1H), 8.37 (s, 1H), 9.23 (s, 1H) | | | |

TABLE 39

| No. | Structure | NMR(δ) |
|---|---|---|
| I-2-104 | 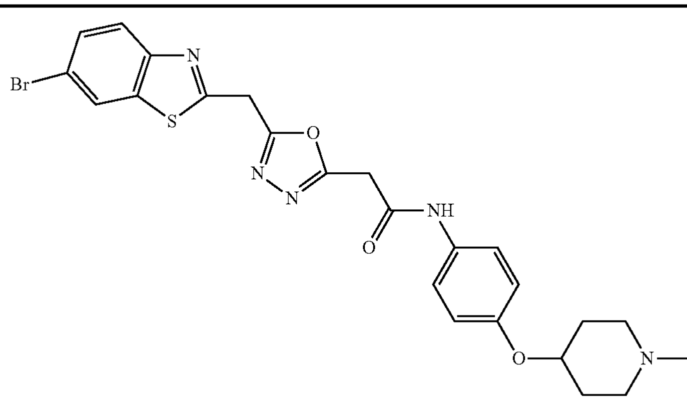 | (DMSO-d$_6$) δ 1.76-2.18 (m, 4H) 2.78 (s, 3H),, 3.16-3.38 (m, 4H), 4.08 (s, 2H), 4.54 (bs, 1H), 4.95 (s, 2H) 6.97 (d, J = 9.0 Hz, 2H), 7.49 (d, J = 9.0 Hz, 2H), 7.68 (d, J = 6.0 Hz, 1H), 7.92 (d, J = 6.0 Hz, 1H), 8.42 (s, 1H), 10.27 (s, 1H). |
| I-2-105 | 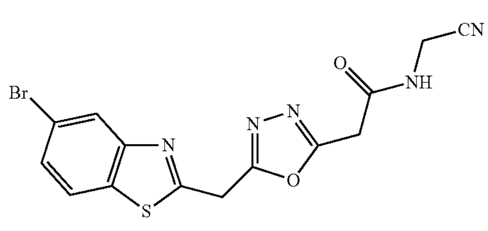 [SMILES: N#CCNC(=O)Cc1nnc(Cc2nc3cc(Br)ccc3s2)o1] | (DMSO-d$_6$) δ: 3.98 (s, 2H), 4.19 (d, J = 5.58 Hz, 2H), 4.96 (s, 2H), 7.63 (dd, J = 8.62, 1.77 Hz, 1H), 8.10 (d, J = 8.62 Hz, 1H), 8.22 (d, J = 1.77 Hz, 1H), 9.01 (t, J = 5.58 Hz, 1H). |

TABLE 39-continued

| No. | Structure | NMR(δ) |
|---|---|---|
| I-2-106 | 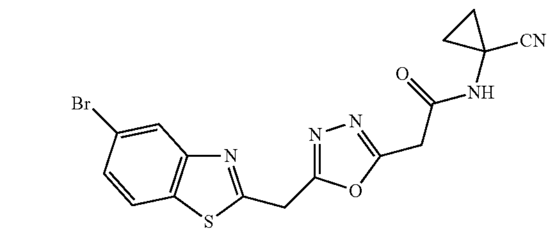 [SMILES: N#CC1(NC(=O)Cc2nnc(Cc3nc4cc(Br)ccc4s3)o2)CC1] | (DMSO-d$_6$) δ: 1.13 (dd, J = 8.36, 5.83 Hz, 2H), 1.48 (dd, J = 8.36, 5.83 Hz, 2H), 3.90 (s, 2H), 4.96 (s, 2H), 7.64 (dd, J = 8.62, 1.52 Hz, 1H), 8.10 (d, J = 8.62 Hz, 1H), 8.22 (d, J = 1.52 Hz, 1H), 9.22 (s, 1H). |
| I-2-107 | 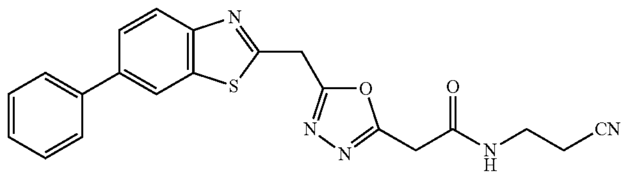 [SMILES: N#CCCNC(=O)Cc1nnc(Cc2nc3ccc(-c4ccccc4)cc3s2)o1] | (DMSO-d$_6$) δ: 2.65 (t, J = 6.6 Hz, 2H), 3.33 (t, J = 6.6 Hz, 2H), 3.91 (s, 2H), 4.94 (s, 2H), 7.40 (t, J = 6.9 Hz, 1H), 7.46-7.53 (m, 2H), 7.73-7.85 (m, 3H), 8.05 (d, J = 8.7 Hz, 1H), 8.43 (s, 1H), 8.68 (br-s, 1H) |
| I-2-108 | 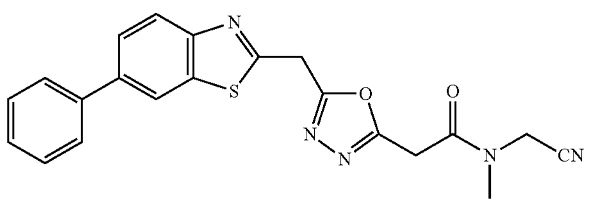 [SMILES: CN(CC#N)C(=O)Cc1nnc(Cc2nc3ccc(-c4ccccc4)cc3s2)o1] | (DMSO-d$_6$) δ: 3.13 (s, 3H), 4.34 (s, 2H), 4.41 (s, 2H), 4.97 (s, 2H), 7.40 (t, J = 6.9 Hz, 1H), 7.46-7.53 (m, 2H), 7.73-7.85 (m, 3H), 8.05 (d, J = 8.4 Hz, 1H), 8.43 (s, 1H) |

TABLE 40

| No. | Structure | NMR(δ) |
|---|---|---|
| I-2-109 | 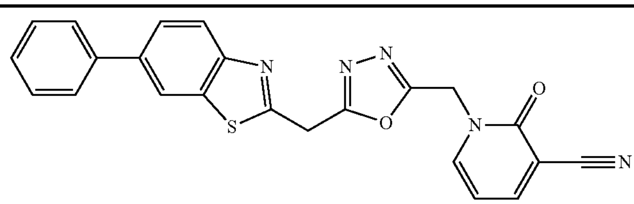 | (DMSO-d6) δ: 4.98 (s, 2H), 5.49 (s, 2H), 6.54 (t, J = 6.8 Hz, 1H), 7.40 (t, J = 7.4 Hz, 1H), 7.48-7.52 (m, 2H), 7.74-7.77 (m, 2H), 7.83 (dd, J = 8.6, 2.0 Hz, 1H), 8.04 (d, J = 8.6 Hz, 1H), 8.23-8.28 (m, 2H), 8.43 (d, J = 1.5 Hz, 1H). |
| I-2-110 | 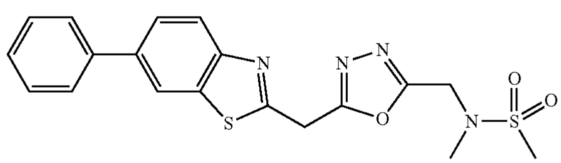 [SMILES: CN(Cc1nnc(Cc2nc3ccc(-c4ccccc4)cc3s2)o1)S(C)(=O)=O] | (CDCl3) δ: 2.97 (s, 3H), 3.01 (s, 3H), 4.70 (s, 2H), 4.76 (s, 2H), 7.37-7.41 (m, 1H), 7.46-7.50 (m, 2H), 7.62-7.64 (m, 2H), 7.73 (dd, J = 8.6, 2.0 Hz, 1H), 8.04 (d, J = 8.1 Hz, 1H), 8.07 (d, J = 1.5 Hz, 1H). |
| I-2-111 | 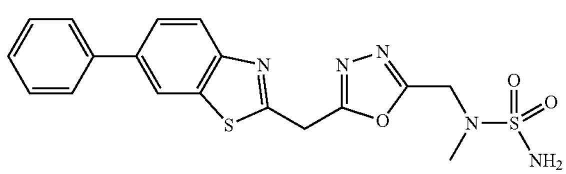 | (CDCl3) δ: 2.97 (s, 3H), 4.68 (s, 2H), 4.76 (s, 2H), 5.25 (s, 2H), 7.39 (t, J = 7.4 Hz, 1H), 7.46-7.50 (m, 2H), 7.62-7.64 (m, 2H), 7.73 (dd, J = 8.6, 1.5 Hz, 1H), 8.03 (d, J = 8.6 Hz, 1H), 8.07 (d, J = 1.5 Hz, 1H). |
| I-2-112 | 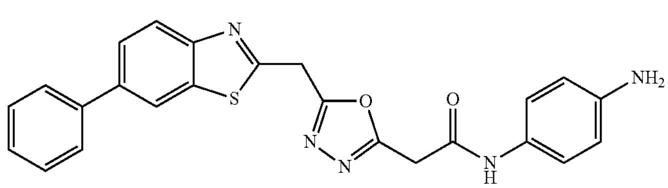 [SMILES: Nc1ccc(NC(=O)Cc2nnc(Cc3nc4ccc(-c5ccccc5)cc4s3)o2)cc1] | (DMSO-d6) δ: 4.02 (s, 2H), 4.91 (s, 2H), 4.96 (s, 2H), 6.50 (d, J = 8.1 Hz, 2H), 7.18 (d, J = 8.6 Hz, 2H), 7.38-7.43 (m, 1H), 7.50 (t, J = 7.6 Hz, 2H), 7.76 (d, J = 8.1 Hz, 2H), 7.83 (d, J = 8.1 Hz, 1H), 8.05 (d, J = 8.6 Hz, 1H), 8.43 (s, 1H), 9.96 (s, 1H). |

TABLE 40-continued

| No. | Structure | NMR(δ) |
|---|---|---|
| I-2-113 | 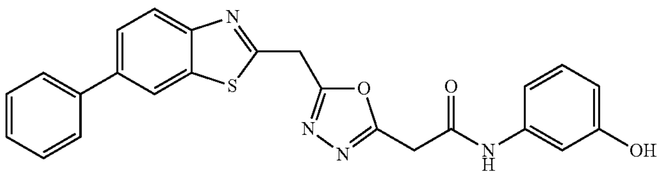 [SMILES: O=C(Cc1nnc(Cc2nc3ccc(-c4ccccc4)cc3s2)o1)Nc1cccc(O)c1] | (DMSO-d6) δ: 4.10 (s, 2H), 4.97 (s, 2H), 6.47 (dd, J = 7.9, 2.3 Hz, 1H), 6.93 (d, J = 7.6 Hz, 1H), 7.08 (t, J = 8.1 Hz, 1H), 7.13 (s, 1H), 7.37-7.43 (m, 1H), 7.50 (t, J = 7.6 Hz, 2H), 7.76 (d, J = 7.6 Hz, 2H), 7.82 (dd, J = 8.4, 1.8 Hz, 1H), 8.05 (d, J = 8.1 Hz, 1H), 8.43 (d, J = 1.5 Hz, 1H), 9.40 (s, 1H), 10.25 (s, 1H). |

TABLE 41

| No. | Structure | NMR(δ) |
|---|---|---|
| I-2-114 | 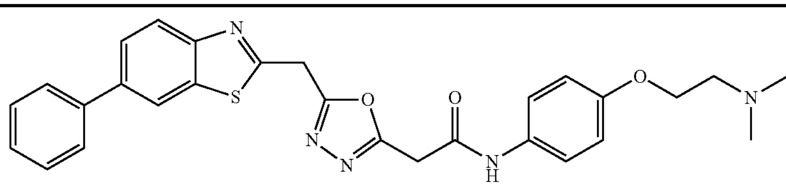 | (DMSO-d6) δ: 2.20 (s, 6H), 2.59 (t, J = 5.8 Hz, 2H), 3.99 (t, J = 5.8 Hz, 2H), 4.08 (s, 2H), 4.97 (s, 2H), 6.86-6.91 (m, 2H), 7.37-7.47 (m, 3H), 7.50 (t, J = 7.6 Hz, 2H), 7.73-7.78 (m, 2H), 7.82 (dd, J = 8.6, 2.0 Hz, 1H), 8.04 (d, J = 8.6 Hz, 1H), 8.43 (d, J = 1.5 Hz, 1H), 10.23 (s, 1H). |
| I-2-115 | 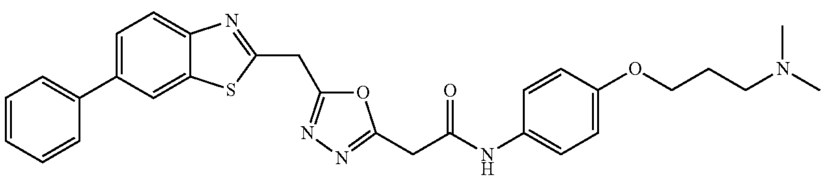 [SMILES: CN(C)CCCOc1ccc(NC(=O)Cc2nnc(Cc3nc4ccc(-c5ccccc5)cc4s3)o2)cc1] | (DMSO-d6) δ: 1.76-1.85 (m, 2H), 2.13 (s, 6H), 2.33 (t, J = 7.4 Hz, 2H), 3.94 (t, J = 6.3 Hz, 2H), 4.08 (s, 2H), 4.97 (s, 2H), 6.87 (d, J = 9.1 Hz, 2H), 7.37-7.46 (m, 3H), 7.50 (t, J = 7.6 Hz, 2H), 7.73-7.78 (m, 2H), 7.82 (dd, J = 8.4, 1.8 Hz, 1H), 8.04 (d, J = 8.6 Hz, 1H), 8.43 (d, J = 1.5 Hz, 1H), 10.23 (s, 1H). |
| I-2-116 | 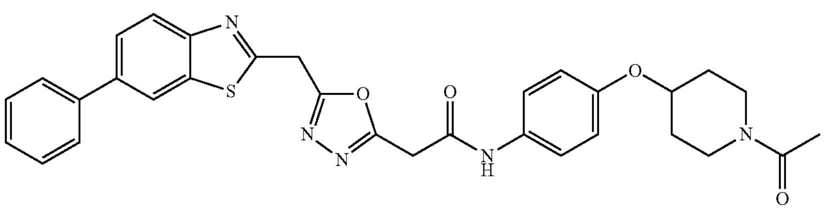 [SMILES: CC(=O)N1CCC(Oc2ccc(NC(=O)Cc3nnc(Cc4nc5ccc(-c6ccccc6)cc5s4)o3)cc2)CC1] | (DMSO-d6) δ: 1.40-1.51 (m, 1H), 1.52-1.62 (m, 1H), 1.80-1.97 (m, 2H), 2.00 (s, 3H), 3.15-3.24 (m, 1H), 3.38 (q, J = 7.1 Hz, 1H), 3.61-3.69 (m, 1H), 3.78-3.86 (m, 1H), 4.08 (s, 2H), 4.48-4.56 (m, 1H), 4.96 (s, 2H), 6.93 (d, J = 9.1 Hz, 2H), 7.37-7.53 (m, 5H), 7.76 (d, J = 7.1 Hz, 2H), 7.83 (dd, J = 8.6, 2.0 Hz, 1H), 8.04 (d, J = 8.6 Hz, 1H), 8.43 (d, J = 1.5 Hz, 1H), 10.25 (s, 1H). |
| I-2-117 | 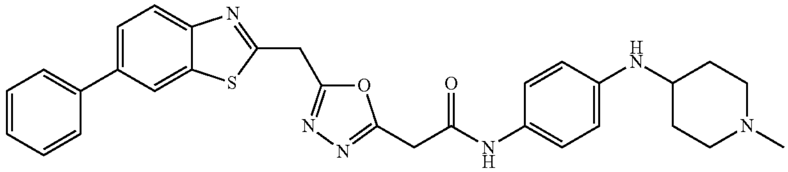 [SMILES: CN1CCC(Nc2ccc(NC(=O)Cc3nnc(Cc4nc5ccc(-c6ccccc6)cc5s4)o3)cc2)CC1] | (DMSO-d6) δ: 1.29-1.40 (m, 2H), 1.80-1.88 (m, 2H), 1.98 (t, J = 10.9 Hz, 2H), 2.15 (s, 3H), 2.66-2.74 (m, 2H), 3.05-3.15 (m, 1H), 4.02 (s, 2H). 4.96 (s, 2H), 5.26 (d, J = 8.1 Hz, 1H), 6.51 (d, J = 9.1 Hz, 2H), 7.22 (d, J = 8.6 Hz, 2H), 7.38-7.43 (m, 1H), 7.50 (t, J = 7.6 Hz, 2H), 7.75 (d, J = 7.1 Hz, 2H), 7.82 (dd, J = 8.6, 2.0 Hz, 1H), 8.04 (d, J = 8.6 Hz, 1H), 8.43 (d, J = 2.0 Hz, 1H), 9.96 (s, 1H). |

TABLE 42

| No. | Structure | NMR(δ) |
|---|---|---|
| I-2-118 | 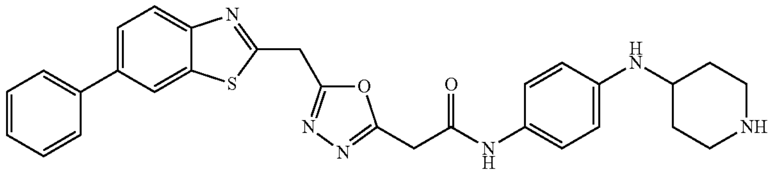 [SMILES: O=C(Cc1nnc(Cc2nc3ccc(-c4ccccc4)cc3s2)o1)Nc1ccc(NC2CCNCC2)cc1] | (DMSO-d6) δ: 1.15-1.26 (m, 3H), 1.81-1.88 (m, 2H), 2.52-2.59 (m, 2H), 2.93-2.99 (m, 2H), 3.15-3.27 (m, 1H), 4.02 (s, 2H), 4.96 (s, 2H), 5.29 (d, J = 8.1 Hz, 1H), 6.51 (d, J = 8.6 Hz, 2H), 7.22 (d, J = 9.1 Hz, 2H), 7.38-7.42 (m, 1H), 7.50 (t, J = 7.6 Hz, 2H), 7.73-7.78 (m, 2H), 7.82 (dd, J = 8.6, 1.5 Hz, 1H), 8.04 (d, J = 8.6 Hz, 1H), 8.43 (d, J = 1.5 Hz, 1H), 9.96 (s, 1H). |
| I-2-119 | 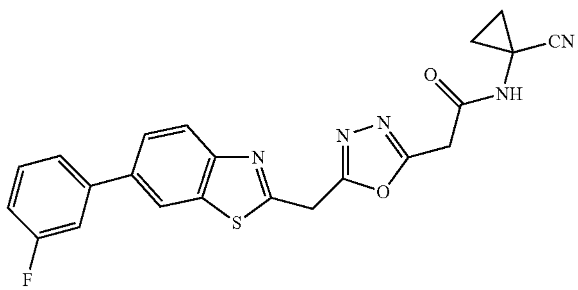 [SMILES: N#CC1(NC(=O)Cc2nnc(Cc3nc4ccc(-c5cccc(F)c5)cc4s3)o2)CC1] | (DMSO-d$_6$) δ: 1.14 (dd, J = 8.36, 5.32 Hz, 2H), 1.49 (dd, J = 8.36, 5.32 Hz, 2H), 3.91 (s, 2H), 4.97 (s, 2H), 7.20-7.26 (m, 1H), 7.50-7.65 (m, 3H), 7.87 (dd, J = 8.62, 1.52 Hz, 1H), 8.06 (d, J = 8.62 Hz, 1H), 8.49 (d, J = 1.52 Hz, 1H), 9.23 (s, 1H). |
| I-2-120 | 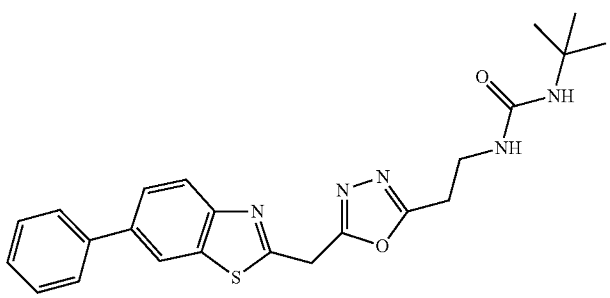 [SMILES: CC(C)(C)NC(=O)NCCc1nnc(Cc2nc3ccc(-c4ccccc4)cc3s2)o1] | (DMSO-d$_6$) δ: 1.18 (s, 9H), 2.93 (t, J = 6.59 Hz, 2H), 3.35 (dt, J = 6.59, 6.08 Hz, 2H), 4.91 (s, 2H), 5.75 (s, 1H), 5.82 (t, J = 6.08 Hz, 1H), 7.40 (t, J = 7.35 Hz, 1H), 7.50 (dd, J = 7.10, 7.35 Hz, 2H), 7.75 (d, J = 7.10 Hz, 2H), 7.82 (dd, J = 8.62, 1.52 Hz, 1H), 8.05 (d, J = 8.62 Hz, 1H), 8.42 (d, J = 1.52 Hz, 1H). |
| I-2-121 | 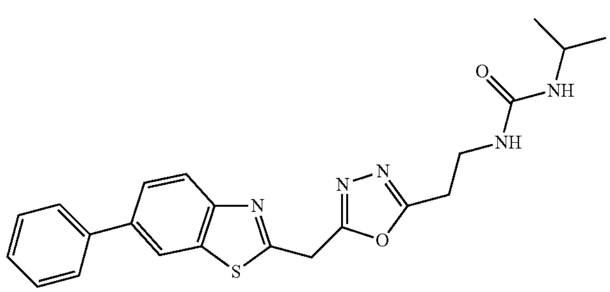 [SMILES: CC(C)NC(=O)NCCc1nnc(Cc2nc3ccc(-c4ccccc4)cc3s2)o1] | (DMSO-d$_6$) δ: 0.99 (d, J = 6.59 Hz, 6H), 2.95 (t, J = 6.59 Hz, 2H), 3.37 (dt, J = 6.59, 5.83 Hz, 2H), 3.62 (m, 1H), 4.91 (s, 2H), 5.80 (d, J = 7.60 Hz, 1H), 5.88 (t, J = 5.83 Hz, 1H), 7.40 (t, J = 7.35 Hz, 1H), 7.50 (dd, J = 7.60, 7.35 Hz, 2H), 7.75 (d, J = 7.60 Hz, 2H), 7.82 (dd, J = 8.62, 1.52 Hz, 1H), 8.05 (d, J = 8.62 Hz, 1H), 8.42 (d, J = 1.52 Hz, 1H). |

TABLE 43

| No. | Structure | NMR(δ) |
|---|---|---|
| I-2-122 | 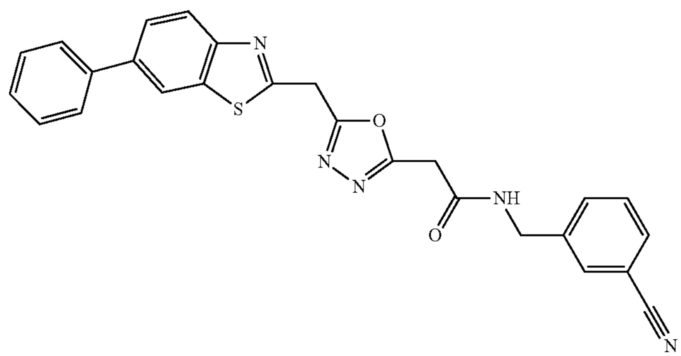 [SMILES: N#Cc1cccc(CNC(=O)Cc2nnc(Cc3nc4ccc(-c5ccccc5)cc4s3)o2)c1] | (DMSO-d$_6$) δ 4.00 (s, 2H), 4.37 (s, 2H), 4.96 (s, 2H),, 7.37-7.80 (m, 9H), 7.83 (d, J = 6.0 Hz, 1H), 8.05 (d, J = 6.0 Hz, 1H), 8.44 (s, 1H), 8.89 (s, 1H) |
| I-2-123 | 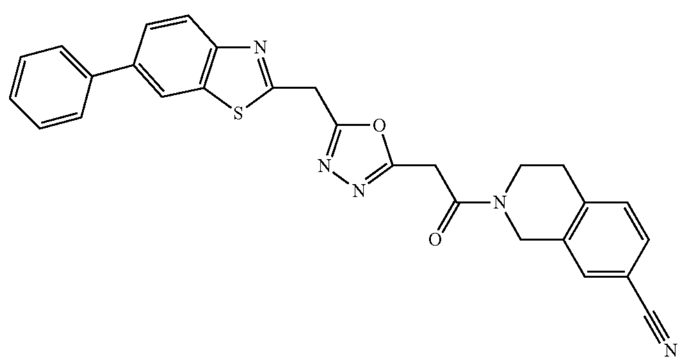 [SMILES: N#Cc1ccc2c(c1)CN(C(=O)Cc1nnc(Cc3nc4ccc(-c5ccccc5)cc4s3)o1)CC2] | (DMSO-d$_6$) δ 2.84-3.01 (m, 2H), 3.58-3.77 (m, 2H), 4.35 (s, 2H), 4.65-4.78 (m, 2H), 4.96 (s, 2H), 7.37-7.78 (m 8H), 7.83 (d, J = 6.0 Hz, 1H), 8.02 (d, J = 6.0 Hz, 1H), 8.43 (s, 1H) |
| I-2-124 | 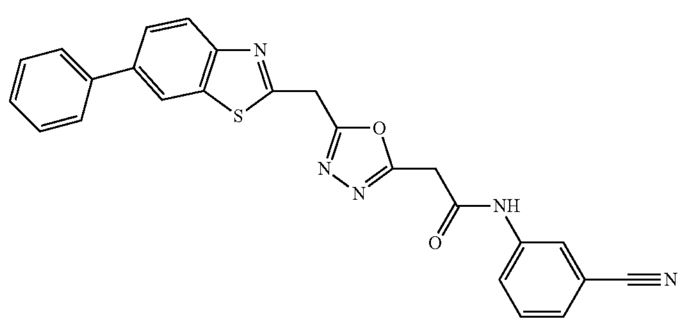 [SMILES: N#Cc1cccc(NC(=O)Cc2nnc(Cc3nc4ccc(-c5ccccc5)cc4s3)o2)c1] | (DMSO-d$_6$) δ 4.19 (s, 2H), 4.98 (s, 2H),, 7.37-7.86 (m, 10H), 8.04 (m, 1H), 8.44 (s, 1H), 10.78 (s, 1H) |
| I-2-125 | 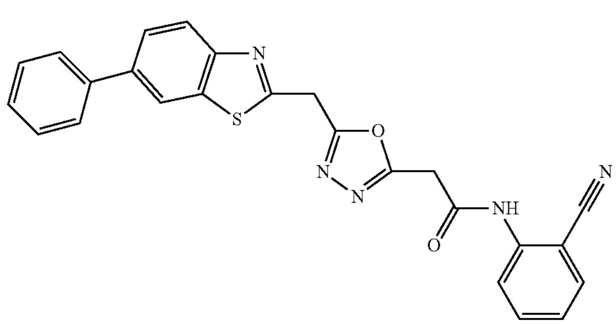 [SMILES: N#Cc1ccccc1NC(=O)Cc1nnc(Cc2nc3ccc(-c4ccccc4)cc3s2)o1] | (DMSO-d$_6$) δ 4.25 (s, 2H), 4.98 (s, 2H),, 7.34-7.78 (m, 10H), 8.05 (d, J = 6.0 Hz, 1H), 8.43 (s, 1H), 10.65 (s, 1H) |

TABLE 43-continued

| No. | Structure | NMR(δ) |
|---|---|---|
| I-2-126 | 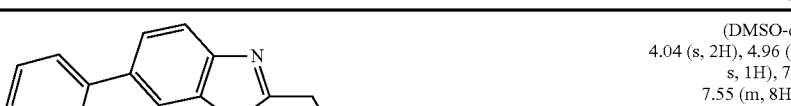 | (DMSO-d$_6$) δ 4.04 (s, 2H), 4.96 (s, 2H), 6.16 (b s, 1H), 7.36-7.55 (m, 8H), 7.73-7.84 (m, 3H), 8.04-8.07 (m, 1H), 8.43 (s, 1H), 9.63 (s, 1H) |

TABLE 44

| No. | Structure | NMR(δ) |
|---|---|---|
| I-2-127 | 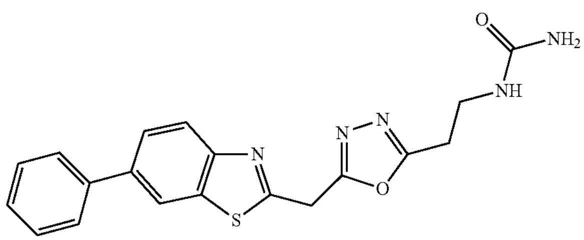 [SMILES: NC(=O)NCCc1nnc(Cc2nc3ccc(-c4ccccc4)cc3s2)o1] | (DMSO-d$_6$) δ: 2.95 (t, J = 6.59 Hz, 2H), 3.36 (dt, J = 6.59, 5.58 Hz, 2H), 4.91 (s, 2H), 5.51 (s, 2H), 6.12 (t, J = 5.58 Hz, 1H), 7.40 (t, J = 7.35 Hz, 1H), 7.50 (dd, J = 7.60, 7.35 Hz, 2H), 7.75 (d, J = 7.60 Hz, 2H), 7.82 (dd, J = 8.62, 1.52 Hz, 1H), 8.05 (d, J = 8.62 Hz, 1H), 8.43 (d, J = 1.52 Hz, 1H). |
| I-2-128 | 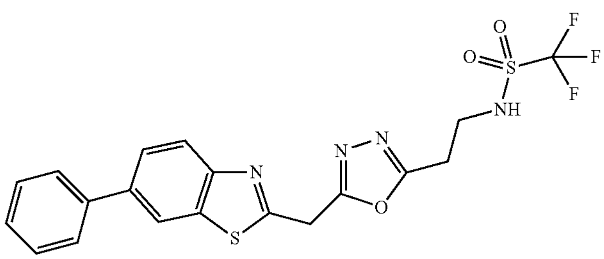 [SMILES: O=S(=O)(NCCc1nnc(Cc2nc3ccc(-c4ccccc4)cc3s2)o1)C(F)(F)F] | (CDCl$_3$) δ: 3.16 (t, J = 5.58 Hz, 2H), 3.81 (t, J = 5.58 Hz, 2H), 4.74 (s, 2H), 6.43 (brs, 1H), 7.39 (t, J = 7.35 Hz, 1H), 7.48 (dd, J = 7.60, 7.35 Hz, 2H), 7.63 (d, J = 7.60 Hz, 2H), 7.73 (dd, J = 8.62, 2.03 Hz, 1H), 8.04-8.09 (m, 2H). |
| I-2-129 | 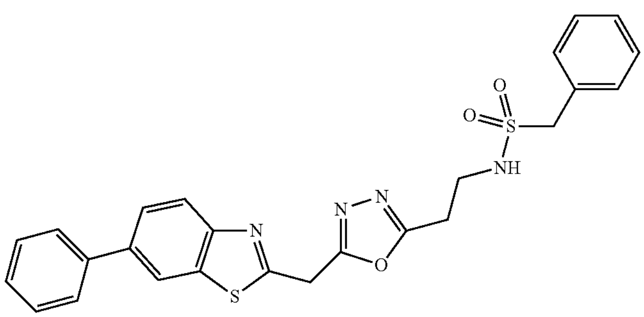 [SMILES: O=S(=O)(Cc1ccccc1)NCCc1nnc(Cc2nc3ccc(-c4ccccc4)cc3s2)o1] | (DMSO-d$_6$) δ: 3.01 (t, J = 6.84 Hz, 2H), 3.24-3.32 (m, 2H), 4.34 (s, 2H), 4.91 (s, 2H), 7.31-7.43 (m, 7H), 7.50 (dd, J = 7.10, 7.35 Hz, 2H), 7.75 (d, J = 7.10 Hz, 2H), 7.82 (dd, J = 8.36, 1.52 Hz, 1H), 8.05 (d, J = 8.62 Hz, 1H), 8.43 (d, J = 1.52 Hz, 1H). |
| I-2-130 | 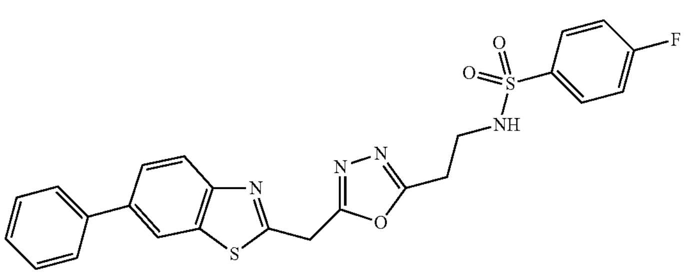 [SMILES: O=S(=O)(NCCc1nnc(Cc2nc3ccc(-c4ccccc4)cc3s2)o1)c1ccc(F)cc1] | (CDCl$_3$) δ: 3.05 (t, J = 6.08 Hz, 2H), 3.48 (dt, J = 6.08, 6.84 Hz, 2H), 4.71 (s, 2H), 5.51 (t, J = 6.84 Hz, 1H), 7.15-7.21 (m, 2H), 7.39 (t, J = 7.35 Hz, 1H), 7.47 (dd, J = 7.60, 7.35 Hz, 2H), 7.63 (d, J = 7.60 Hz, 2H), 7.73 (dd, J = 8.62, 2.03 Hz, 1H), 7.85-7.91 (m, 2H), 8.05-8.09 (m, 2H). |

TABLE 44-continued

| No. | Structure | NMR(δ) |
|---|---|---|
| I-2-131 | 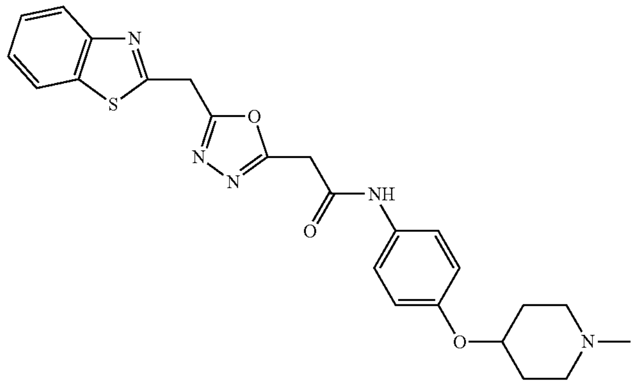 [SMILES: CN1CCC(Oc2ccc(NC(=O)Cc3nnc(Cc4nc5ccccc5s4)o3)cc2)CC1] | (DMSO-d$_6$) δ 1.72-2.23 (m, 4H) 2.82 (s, 3H),, 3.00-3.38 (m, 4H), 4.08 (s, 2H), 4.54 (s, 1H), 4.95 (s, 2H) 6.90-7.03 (m,, 2H), 7.45-7.55 (m, 4H), 7.98 (d, J = 6.0 Hz, 1H), 8.12 (d, J = 6.0 Hz, 1H), 10.28 (s, 1H) |

TABLE 45

| No. | Structure | NMR(δ) |
|---|---|---|
| I-2-132 | 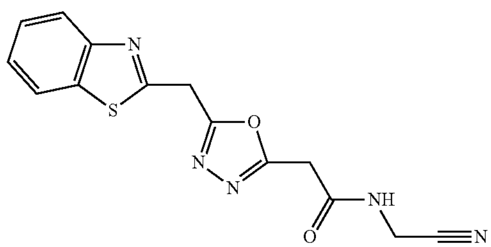 [SMILES: N#CCNC(=O)Cc1nnc(Cc2nc3ccccc3s2)o1] | (DMSO-d$_6$) δ 3.99 (s, 2H), 4.18-4.22 (m, 2H), 4.94 (s, 2H) 7.46-7.57 (m, 2H), 7.98 (d, J = 6.0 Hz, 1H), 8.14 (d, J = 6.0 Hz, 1H), 9.03 (s, 1H) |
| I-2-133 | 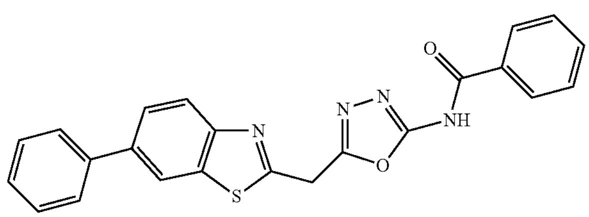 [SMILES: O=C(Nc1nnc(Cc2nc3ccc(-c4ccccc4)cc3s2)o1)c1ccccc1] | (DMSO-d$_6$) δ: 4.97 (s, 2H), 7.40 (t, J = 7.35 Hz, 1H), 7.47-7.57 (m, 4H), 7.65 (t, J = 7.10 Hz, 1H), 7.76 (d, J = 7.10 Hz, 2H), 7.83 (dd, J = 8.62, 2.03 Hz, 1H), 7.99 (d, J = 7.60 Hz, 2H), 8.06 (d, J = 8.62 Hz, 1H), 8.45 (d, J = 1.52 Hz, 1H), 12.01 (s, 1H). |
| I-2-134 | 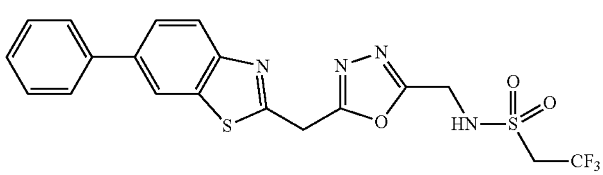 [SMILES: O=S(=O)(CC(F)(F)F)NCc1nnc(Cc2nc3ccc(-c4ccccc4)cc3s2)o1] | (CDCl3) δ: 4.06 (q, J = 9.0 Hz, 2H), 4.68 (d, J = 5.1 Hz, 2H), 4.75 (s, 2H), 5.52 (br s, 1H), 7.39 (t, J = 7.4 Hz, 1H), 7.46-7.49 (m, 2H), 7.62-7.64 (m, 2H), 7.73 (dd, J = 8.6, 1.5 Hz, 1H), 8.04-8.07 (m, 2H). |
| I-2-135 | 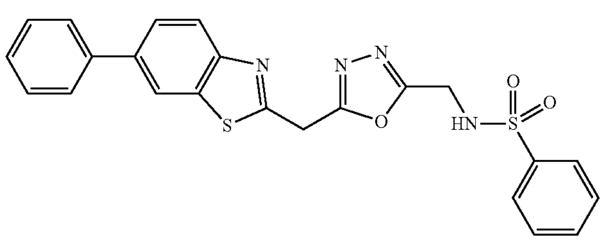 [SMILES: O=S(=O)(NCc1nnc(Cc2nc3ccc(-c4ccccc4)cc3s2)o1)c1ccccc1] | (DMSO-d6) δ: 4.32 (s, 2H), 4.82 (s, 2H), 7.40 (t, J = 7.4 Hz, 1H), 7.49-7.62 (m, 5H), 7.74-7.77 (m, 4H), 7.83 (dd, J = 8.6, 2.0 Hz, 1H), 8.05 (d, J = 8.6 Hz, 1H), 8.45 (d, J = 2.0 Hz, 1H), 8.60 (br s, 1H). |

TABLE 45-continued

| No. | Structure | NMR(δ) |
| --- | --- | --- |
| I-2-136 | 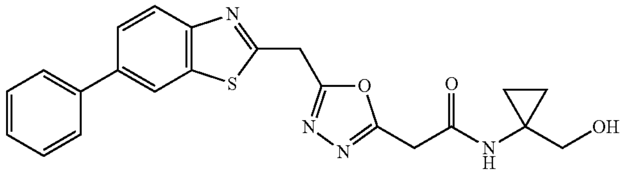 [SMILES: O=C(Cc1nnc(Cc2nc3ccc(-c4ccccc4)cc3s2)o1)NC1(CO)CC1] | (DMSO-d6) δ: 0.55-0.57 (m, 2H), 0.63-0.67 (m, 2H), 3.39 (d, J = 5.7 Hz, 2H), 3.80 (s, 2H), 4.71 (br-s, 1H), 4.94 (s, 2H), 7.39 (m, 1H), 7.47-7.53 (m, 3H), 7.73-7.84 (m, 3H), 8.05 (d, J = 8.7 Hz, 1H), 8.43 (s, 1H), 8.55 (s, 1H) |

TABLE 46

| No. | Structure | NMR(δ) |
| --- | --- | --- |
| I-2-137 | 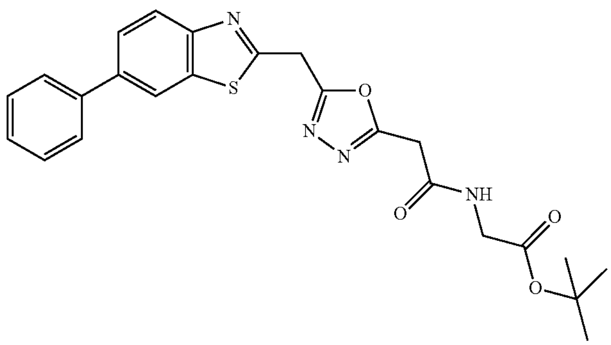 [SMILES: CC(C)(C)OC(=O)CNC(=O)Cc1nnc(Cc2nc3ccc(-c4ccccc4)cc3s2)o1] | (DMSO-d$_6$) δ 1.38 (s, 9H), 3.76 (d, J = 6.0 Hz, 2H), 3.94 (s, 2H), 4.94 (s, 2H), 7.38-7.42 (m, 1H), 7.50 (t, J = 6.0 Hz, 2H), 7.75 (d, J = 6.0 Hz, 2H), 7.83 (d, J = 6.0 Hz, 1H), 8.05 (d, J = 6.0 Hz, 1H), 8.43 (s, 1H), 8.64 (t, J = 6.0 Hz, 1H) |
| I-2-138 | 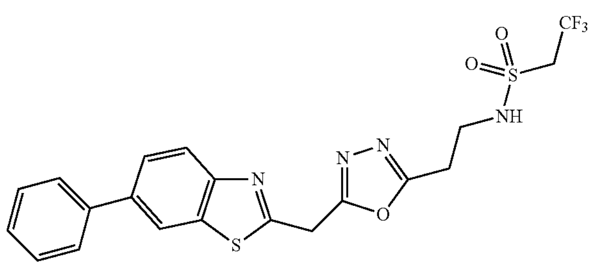 [SMILES: O=S(=O)(CC(F)(F)F)NCCc1nnc(Cc2nc3ccc(-c4ccccc4)cc3s2)o1] | (CDCl$_3$) δ: 3.14 (t, J = 6.08 Hz, 2H), 3.71 (dt, J = 6.08, 5.07 Hz, 2H), 3.85 (q, J = 9.12 Hz, 2H), 4.73 (s, 2H), 5.80 (t, J = 5.07 Hz, 1H), 7.39 (t, J = 7.35 Hz, 1H), 7.47 (dd, J = 7.35, 7.60 Hz, 2H), 7.63 (d, J = 7.60 Hz, 2H), 7.73 (dd, J = 8.62, 2.03 Hz, 1H), 8.04-8.09 (m, 2H). |
| I-2-139 | 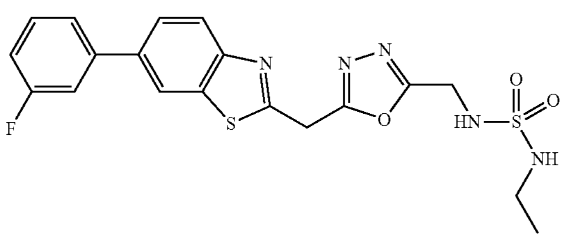 [SMILES: CCNS(=O)(=O)NCc1nnc(Cc2nc3ccc(-c4cccc(F)c4)cc3s2)o1] | (CDCl3) δ: 1.10 (t, J = 7.4 Hz, 3H), 3.01-3.08 (m, 2H), 4.51 (d, J = 6.6 Hz, 2H), 4.64 (t, J = 5.6 Hz, 1H), 4.76 (s, 2H), 4.92 (t, J = 5.6 Hz, 1H), 7.07-7.10 (m, 1H), 7.32-7.34 (m, 1H), 7.39-7.47 (m, 2H), 7.71 (dd, J = 8.4, 1.8 Hz, 1H), 8.06-8.08 (m, 2H). |
| I-2-140 | 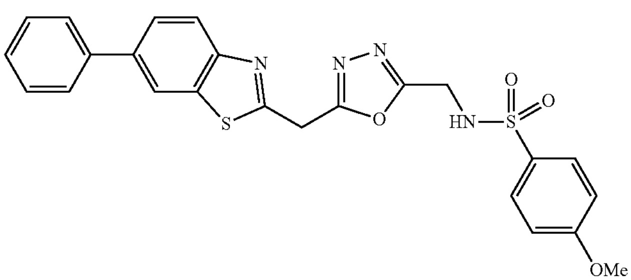 [SMILES: COc1ccc(S(=O)(=O)NCc2nnc(Cc3nc4ccc(-c5ccccc5)cc4s3)o2)cc1] | (CDCl3) δ: 3.83 (s, 3H), 4.44 (d, J = 6.1 Hz, 2H), 4.62 (s, 2H), 5.14 (t, J = 6.3 Hz, 1H), 6.88-6.91 (m, 2H), 7.39 (t, J = 7.1 Hz, 1H), 7.46-7.50 (m, 2H), 7.63 (d, J = 7.6 Hz, 2H), 7.72-7.78 (m, 3H), 8.04-8.07 (m, 2H). |

TABLE 46-continued

| No. | Structure | NMR(δ) |
|---|---|---|
| I-2-141 | 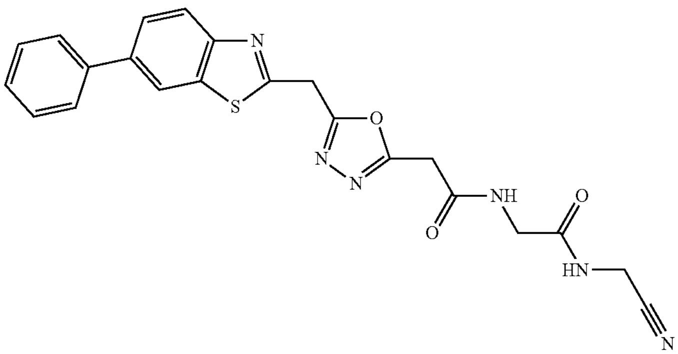 [SMILES: N#CCNC(=O)CNC(=O)Cc1nnc(Cc2nc3ccc(-c4ccccc4)cc3s2)o1] | (DMSO-d$_6$) δ 3.79 (d, J = 6.0 Hz, 2H), 3.97 (s, 2H), 4.14 (d, J = 6.0 Hz, 2H), 4.95 (s, 2H), 7.35-7.44 (m, 1H), 7.50 (t, J = 6.0 Hz, 2H), 7.76 (d, J = 6.0 Hz, 2H), 7.83 (d, J = 6.0 Hz, 1H), 8.05 (d, J = 6.0 Hz, 1H), 8.44 (s, 1H), 8.66 (t, J = 6.0 Hz, 1H) |

TABLE 47

| No. | Structure | NMR(δ) |
|---|---|---|
| I-2-142 | 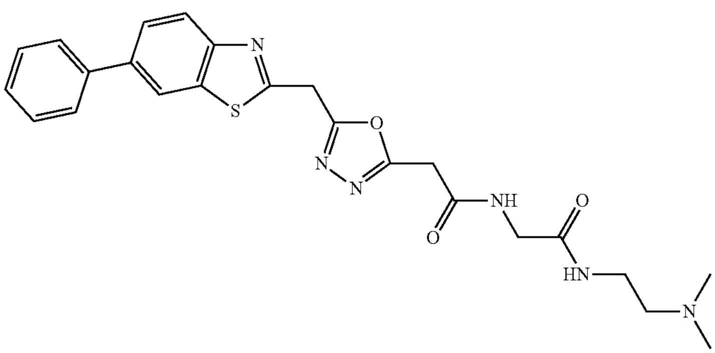 [SMILES: CN(C)CCNC(=O)CNC(=O)Cc1nnc(Cc2nc3ccc(-c4ccccc4)cc3s2)o1] | (DMSO-d$_6$) δ 2.78 (s, 6H), 3.11 (t, J = 3.0 Hz, 2H), 3.2-3.36 (m, 2H), 3.76 (d, J = 3.0 Hz, 2H), 3.98 (s, 2H), 4.95 (s, 2H), 7.35-7.44 (m, 1H), 7.51 (t, J = 6.0 Hz, 2H), 7.76 (d, J = 6.0 Hz, 2H), 7.83 (d, J = 6.0 Hz, 1H), 8.05 (d, J = 6.0 Hz, 1H) 8.16 (t, J = 3.0 Hz, 1H), 8.44 (s, 1H), 8.60 (t, J = 6.0 Hz, 1H) |
| I-2-143 | 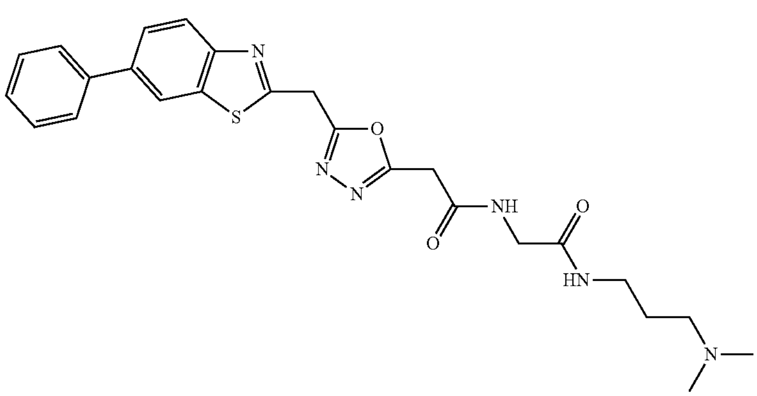 [SMILES: CN(C)CCCNC(=O)CNC(=O)Cc1nnc(Cc2nc3ccc(-c4ccccc4)cc3s2)o1] | (DMSO-d$_6$) δ 1.68-1.80 (m, 2H), 2.70 (s, 6H), 2.89-2.95 (m, 2H), 3.10-3.26 (m, 2H), 3.71 (d, J = 3.0 Hz, 2H), 3.97 (s, 2H), 4.95 (s, 2H), 7.33-7.42 (m, 1H), 7.51 (t, J = 6.0 Hz, 2H), 7.76 (d, J = 6.0 Hz, 2H), 7.83 (d, J = 6.0 Hz, 1H), 8.05 (d, J = 6.0 Hz, 1H) 8.06 (t, J = 3.0 Hz, 1H), 8.44 (s, 1H), 8.62 (t, J = 6.0 Hz, 1H) |

TABLE 47-continued
| No. | Structure | NMR(δ) |
|---|---|---|
| I-2-144 | 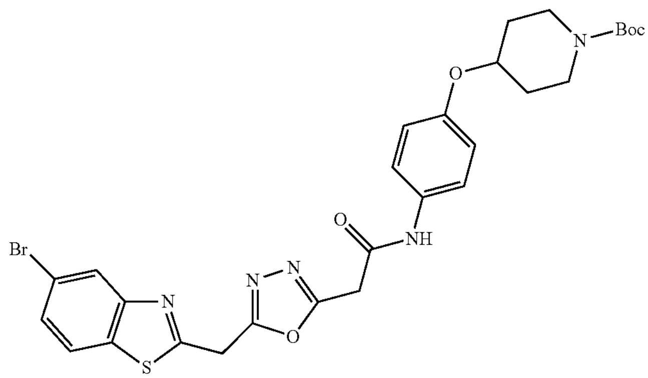 [SMILES: CC(C)(C)OC(=O)N1CCC(Oc2ccc(NC(=O)Cc3nnc(Cc4nc5cc(Br)ccc5s4)o3)cc2)CC1] | (DMSO-d$_6$) δ: 1.40 (s, 9H), 1.44-1.53 (m, 2H), 1.84-1.91 (m, 2H), 3.12-3.19 (m, 2H), 3.60-3.69 (m, 2H), 4.07 (s, 2H), 4.47 (m, 1H), 4.97 (s, 2H), 6.93 (d, J = 8.62 Hz, 2H), 7.44 (d, J = 8.62 Hz, 2H), 7.64 (d, J = 8.62 Hz, 1H), 8.10 (d, J = 8.62 Hz, 1H), 8.22 (s, 1H), 10.24 (s, 1H). |
| I-2-145 | 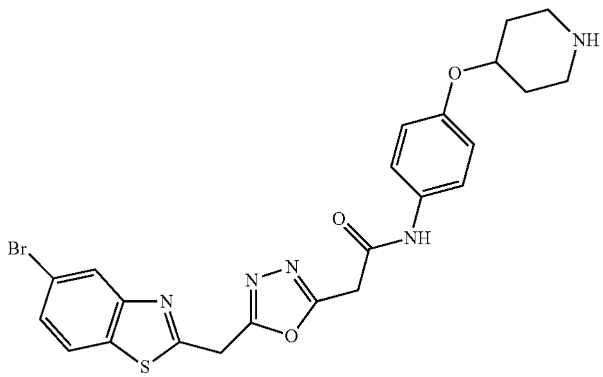 [SMILES: O=C(Cc1nnc(Cc2nc3cc(Br)ccc3s2)o1)Nc1ccc(OC2CCNCC2)cc1] | (DMSO-d$_6$) δ: 1.37-1.47 (m, 2H), 1.84-1.92 (m, 2H), 2.51-2.60 (m, 2H), 2.90-2.98 (m, 2H), 4.06 (s, 2H), 4.28-4.35 (m, 1H), 4.97 (s, 2H), 6.89 (d, J = 8.62 Hz, 2H), 7.43 (d, J = 9.12 Hz, 2H), 7.63 (d, J = 9.12 Hz, 1H), 8.10 (d, J = 8.62 Hz, 1H), 8.22 (s, 1H), 10.22 (s, 1H). |
| I-2-146 | 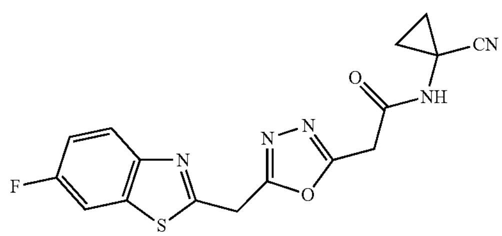 [SMILES: N#CC1(NC(=O)Cc2nnc(Cc3nc4ccc(F)cc4s3)o2)CC1] | (DMSO-d$_6$) δ: 1.13 (dd, J = 8.11, 5.58 Hz, 2H), 1.48 (dd, J = 8.11, 5.58 Hz, 2H), 3.90 (s, 2H), 4.93 (s, 2H), 7.39 (m, 1H), 7.99-8.07 (m, 2H), 9.22 (s, 1H). |
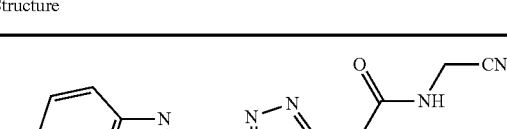
TABLE 48
| No. | Structure | NMR(δ) |
|---|---|---|
| I-2-147 | 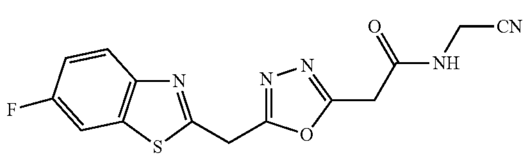 [SMILES: N#CCNC(=O)Cc1nnc(Cc2nc3ccc(F)cc3s2)o1] | (DMSO-d$_6$) δ: 3.98 (s, 2H), 4.19 (d, J = 5.58 Hz, 2H), 4.93 (s, 2H), 7.39 (ddd, J = 9.12, 3.04, 9.12 Hz, 1H), 7.98-8.06 (m, 2H), 9.02 (t, J = 5.32 Hz, 1H). |
| I-2-148 | 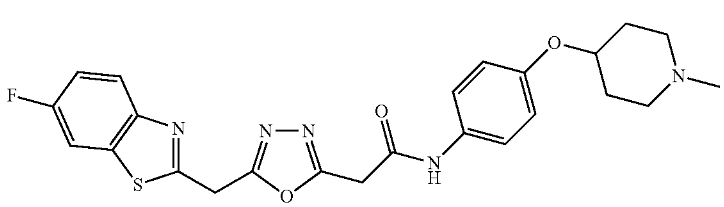 [SMILES: CN1CCC(Oc2ccc(NC(=O)Cc3nnc(Cc4nc5ccc(F)cc5s4)o3)cc2)CC1] | (DMSO-d$_6$) δ: 1.57-1.67 (m, 2H), 1.86-1.95 (m, 2H), 2.16-2.29 (m, 5H), 2.60-2.72 (m, 2H), 4.07 (s, 2H), 4.30 (m, 1H), 4.94 (s, 2H), 6.90 (d, J = 9.12 Hz, 2H), 7.36-7.47 (m, 3H), 7.97-8.06 (m, 2H), 10.23 (s, 1H). |
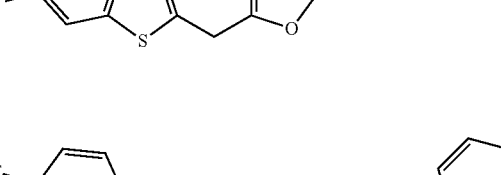

TABLE 48-continued

| No. | Structure | NMR(δ) |
|---|---|---|
| I-2-149 | 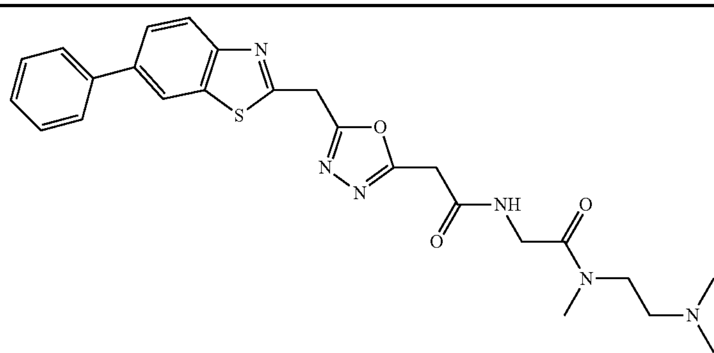 | (DMSO-d$_6$) δ 2.82(s, 6H), 2.94(s, 3H), 3.23-3.38(m, 2H), 3.60-3.70(m, 2H), 4.01(s, 4H), 4.94(s, 2H), 7.37-7.44(m, 1H), 7.51(t, J = 6.0 Hz, 2H), 7.76(d, J = 6.0 Hz, 2H), 7.83(d, J = 6.0 Hz, 1H), 8.05(d, J = 6.0 Hz, 1H), 8.44(s, 1H), 9.06(bs, 1H) |
| I-2-150 | 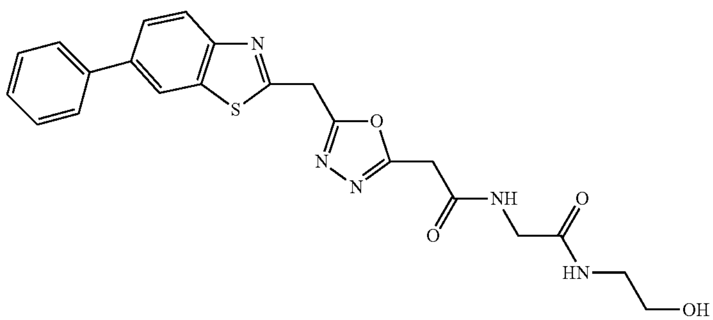 [SMILES: O=C(CNC(=O)Cc1nnc(Cc2nc3ccc(-c4ccccc4)cc3s2)o1)NCCO] | (DMSO-d$_6$) δ 3.14(q, J = 3.0 Hz, 2H), 3.30-3.40(m, 2H), 3.72(d, J = 3.0 Hz, 2H), 3.96(s, 2H), 4.94(s, 2H), 7.37-7.44(m, 1H), 7.50(t, J = 6.0 Hz, 2H), 7.76(d, J = 6.0 Hz, 2H), 7.83(d, J = 6.0 Hz, 1H), 7.94(bs, 1H), 8.05(d, J = 6.0 Hz, 1H), 8.43(s, 1H), 8.54(bs, 1H) |
| I-2-151 | 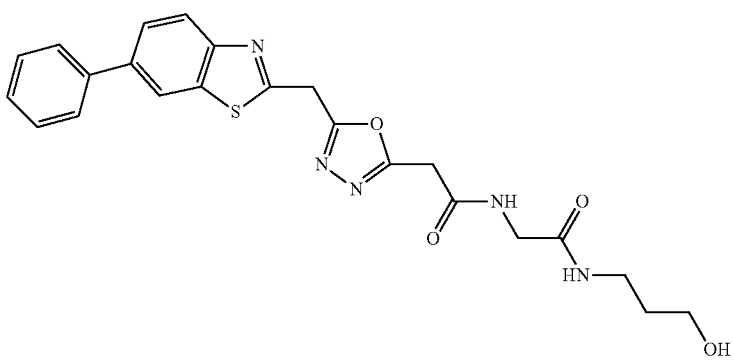 [SMILES: O=C(CNC(=O)Cc1nnc(Cc2nc3ccc(-c4ccccc4)cc3s2)o1)NCCCO] | (DMSO-d$_6$) δ 1.55(dd, J = 6.0, 6.0 Hz, 2H), 3.12(q, J = 6.0 Hz, 2H), 3.30-3.40(m, 2H), 3.70(d, J = 3.0 Hz, 2H), 3.96(s, 2H), 4.95(s, 2H), 7.35-7.44(m, 1H), 7.50(t, J = 6.0 Hz, 2H), 7.75(d, J = 6.0 Hz, 2H), 7.82(d, J = 6.0 Hz, 1H), 7.91(bs, 1H), 8.05(d, J = 6.0 Hz, 1H), 8.43(s, 1H), 8.56(bs, 1H) |

TABLE 49

| No. | Structure | NMR(δ) |
|---|---|---|
| I-2-152 | 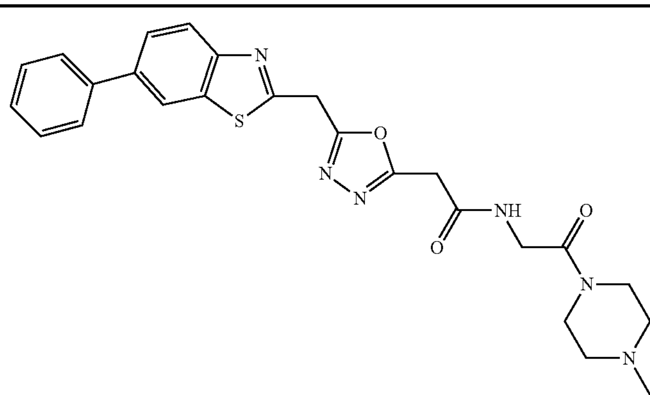 | (DMSO-d$_6$) δ 2.81(s, 3H)2.81-3.04(m, 4H), 3.70-4.25(m, 4H), 4.00(s, 4H), 4.94(s, 2H), 7.35-7.45(m, 1H), 7.51(t, J = 6.0 Hz, 2H), 7.76(d, J = 6.0 Hz, 2H), 7.83(d, J = 6.0 Hz, 1H), 8.05(d, J = 6.0 Hz, 1H), 8.43(s, 1H), 8.51(bs, 1H), 9.62(bs, 1H) |

TABLE 49-continued

| No. | Structure | NMR(δ) |
|---|---|---|
| I-2-153 | 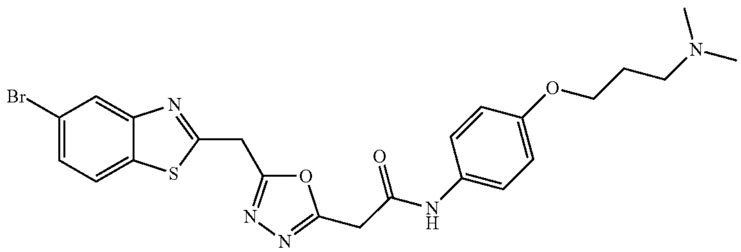 [SMILES: CN(C)CCCOc1ccc(NC(=O)Cc2nnc(Cc3nc4cc(Br)ccc4s3)o2)cc1] | (DMSO-d6) δ: 1.77-1.85 (m, 2H), 2.13 (s, 6H), 2.33 (t, J = 7.1 Hz, 2H), 3.94 (t, J = 6.3 Hz, 2H), 4.07 (s, 2H), 4.97 (s, 2H), 6.85-6.89 (m, 2H), 7.41-7.47 (m, 2H), 7.64 (dd, J = 8.6, 2.0 Hz, 1H), 8.10 (d, J = 8.6 Hz, 1H), 8.21 (d, J = 2.0 Hz, 1H), 10.22 (s, 1H). |
| I-2-154 | 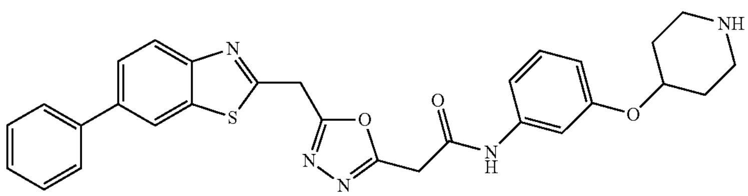 [SMILES: O=C(Cc1nnc(Cc2nc3ccc(-c4ccccc4)cc3s2)o1)Nc1cccc(OC2CCNCC2)c1] | (DMSO-d6) δ: 1.53-1.63 (m, 2H), 1.92-1.99 (m, 2H), 2.72-2.80 (m, 2H), 3.01-3.08 (m, 2H), 4.12 (s, 2H), 4.38-4.45 (m, 1H), 4.97 (s, 2H), 6.69 (dd, J = 8.1, 2.0 Hz, 1H), 7.02-7.06 (m, 1H), 7.21 (t, J = 8.1 Hz, 1H), 7.31 (s, 1H), 7.38-7.43 (m, 1H), 7.50 (t, J = 7.6 Hz, 2H), 7.75 (d, J = 7.1 Hz, 2H), 7.83 (dd, J = 8.6, 2.0 Hz, 1H), 8.04 (d, J = 8.6 Hz, 1H), 8.43 (d, J = 1.5 Hz, 1H), 10.39 (s, 1H). |
| I-2-155 | 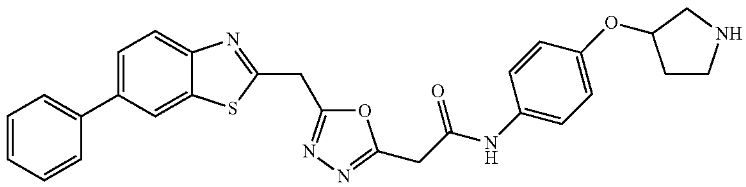 [SMILES: O=C(Cc1nnc(Cc2nc3ccc(-c4ccccc4)cc3s2)o1)Nc1ccc(OC2CCNC2)cc1] | (DMSO-d6) δ: 1.66-1.75 (m, 1H), 1.92-2.01 (m, 1H), 2.70-2.90 (m, 2H), 3.01 (dd, J = 12.2, 5.6 Hz, 1H), 3.17 (d, J = 3.5 Hz, 1H), 4.10 (s, 2H), 4.74-4.80 (m, 1H), 4.96 (s, 2H), 6.84 (d, J = 9.1 Hz, 2H), 7.37-7.53 (m, 6H), 7.76 (d, J = 7.1 Hz, 2H), 7.78-7.84 (m, 1H), 8.05 (d, J = 8.6 Hz, 1H), 8.43 (s, 1H), 10.40 (s, 1H). |

TABLE 50

| No. | Structure | NMR(δ) |
|---|---|---|
| I-2-156 | 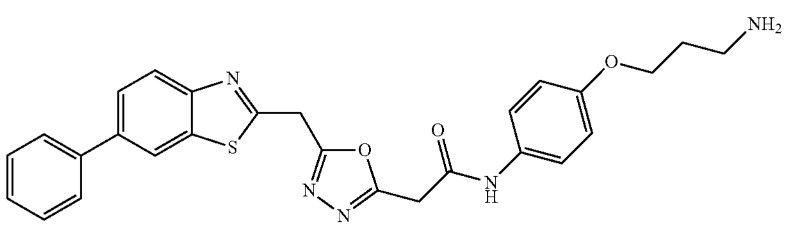 [SMILES: NCCCOc1ccc(NC(=O)Cc2nnc(Cc3nc4ccc(-c5ccccc5)cc4s3)o2)cc1] | (DMSO-d6) δ: 1.74-1.82 (m, 2H), 2.70 (t, J = 6.8 Hz, 2H), 3.17 (s, 2H), 3.98 (t, J = 6.3 Hz, 2H), 4.11 (s, 2H), 4.96 (s, 2H), 6.87 (d, J = 8.6 Hz, 2H), 7.37-7.43 (m, 1H), 7.45-7.53 (m, 4H), 7.76 (d, J = 8.1 Hz, 2H), 7.83 (d, J = 8.6 Hz, 1H), 8.05 (d, J = 8.6 Hz, 1H), 8.44 (s, 1H), 10.45 (s, 1H). |
| I-2-157 | 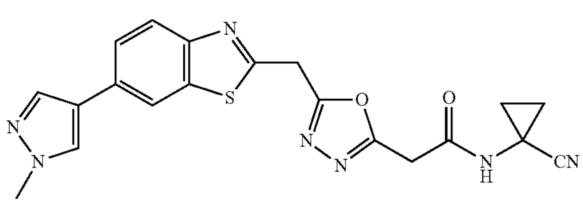 [SMILES: Cn1cc(-c2ccc3nc(Cc4nnc(CC(=O)NC5(C#N)CC5)o4)sc3c2)cn1] | (DMSO-d6) δ: 1.14 (dd, J = 8.1, 5.6 Hz, 2H), 1.49 (dd, J = 8.1, 5.6 Hz, 2H), 3.88 (s, 3H), 3.91 (s, 2H), 4.92 (s, 2H), 7.73 (dd, J = 8.4, 1.8 Hz, 1H), 7.92-7.96 (m, 2H), 8.21 (s, 1H), 8.3 (s, 1H), 9.24 (s, 1H). |

TABLE 50-continued

| No. | Structure | NMR(δ) |
|---|---|---|
| I-2-158 | 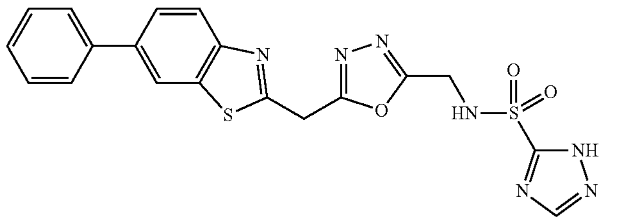 [SMILES: O=S(=O)(NCc1nnc(Cc2nc3ccc(-c4ccccc4)cc3s2)o1)c1ncn[nH]1] | (DMSO-d6) δ: 4.48 (s, 2H), 4.93 (s, 2H), 7.40 (t, J = 7.4 Hz, 1H), 7.50 (t, J = 7.6 Hz, 2H), 7.76 (d, J = 7.6 Hz, 2H), 7.83 (dd, J = 8.4, 1.8 Hz, 1H), 8.06 (d, J = 8.1 Hz, 1H), 8.44 (d, J = 1.5 Hz, 1H), 8.75 (s, 1H), 9.02 (s, 1H). |
| I-2-159 | 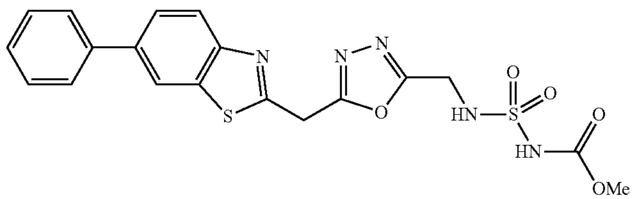 [SMILES: COC(=O)NS(=O)(=O)NCc1nnc(Cc2nc3ccc(-c4ccccc4)cc3s2)o1] | (DMSO-d6) δ: 3.62 (s, 3H), 4.42 (d, J = 5.6 Hz, 2H), 4.94 (s, 2H), 7.40 (t, J = 7.4 Hz, 1H), 7.48-7.52 (m, 2H), 7.74-7.77 (m, 2H), 7.83 (dd, J = 8.6, 2.0 Hz, 1H), 8.05 (d, J = 8.6 Hz, 1H), 8.44 (d, J = 1.5 Hz, 1H), 8.64 (s, 1H), 11.40 (s, 1H). |
| I-2-160 | 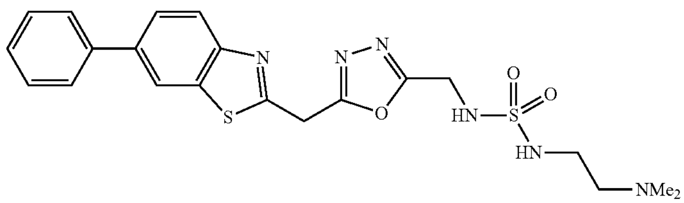 [SMILES: CN(C)CCNS(=O)(=O)NCc1nnc(Cc2nc3ccc(-c4ccccc4)cc3s2)o1] | (CDCl3) δ: 2.27 (s, 6H), 2.40 (t, J = 5.1 Hz, 2H), 3.24 (t, J = 5.3 Hz, 2H), 4.52 (s, 2H), 4.76 (s, 2H), 7.37-7.41 (m, 1H), 7.46-7.50 (m, 2H), 7.62-7.64 (m, 2H), 7.73 (dd, J = 8.4, 1.8 Hz, 1H), 8.03-8.07 (m, 2H). |

TABLE 51

| No. | Structure | NMR(δ) |
|---|---|---|
| I-2-161 | 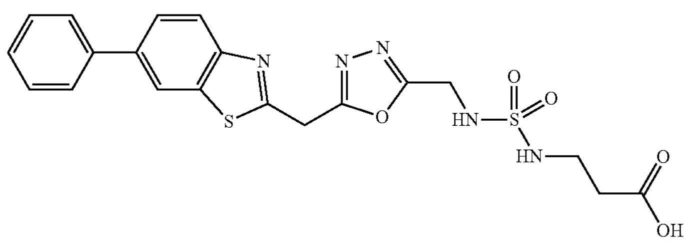 [SMILES: O=C(O)CCNS(=O)(=O)NCc1nnc(Cc2nc3ccc(-c4ccccc4)cc3s2)o1] | (DMSO-d6) δ: 2.40 (t, J = 7.4 Hz, 2H), 3.01-3.03 (br m, 2H), 4.28 (d, J = 6.1 Hz, 2H), 4.96 (s, 2H), 7.09 (s, 1H), 7.40 (t, J = 7.4 Hz, 1H), 7.48-7.52 (m, 2H), 7.75-7.83 (m, 4H), 8.05 (d, J = 8.6 Hz, 1H), 8.43 (d, J = 1.5 Hz, 1H). |
| I-2-162 | 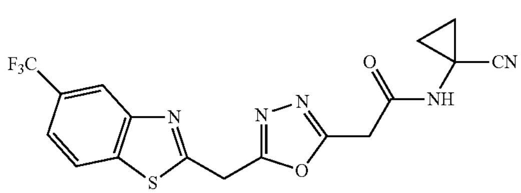 [SMILES: N#CC1(NC(=O)Cc2nnc(Cc3nc4cc(C(F)(F)F)ccc4s3)o2)CC1] | (DMSO-d$_6$) δ: 1.13 (dd, J = 8.11, 5.58 Hz, 2H), 1.48 (dd, J = 8.11, 5.58 Hz, 2H), 3.90 (s, 2H), 5.02 (s, 2H), 7.80 (d, J = 8.62 Hz, 1H), 8.34-8.42 (m, 2H), 9.23 (s, 1H). |
| I-2-163 | 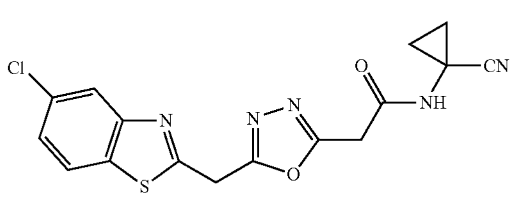 [SMILES: N#CC1(NC(=O)Cc2nnc(Cc3nc4cc(Cl)ccc4s3)o2)CC1] | (DMSO-d$_6$) δ: 1.13 (dd, J = 8.11, 5.58 Hz, 2H), 1.49 (dd, J = 8.11, 5.58 Hz, 2H), 3.90 (s, 2H), 4.97 (s, 2H), 7.53 (dd, J = 8.62, 1.52 Hz, 1H), 8.09 (d, J = 1.52 Hz, 1H), 8.16 (d, J = 8.62 Hz, 1H), 9.23 (s, 1H). |

TABLE 51-continued

| No. | Structure | NMR(δ) |
|---|---|---|
| I-2-164 | 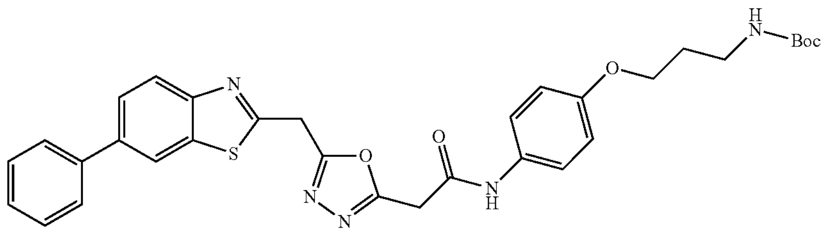 [SMILES: CC(C)(C)OC(=O)NCCCOc1ccc(NC(=O)Cc2nnc(Cc3nc4ccc(-c5ccccc5)cc4s3)o2)cc1] | (DMSO-d6) δ: 1.37 (s, 9H), 1.76-1.83 (m, 2H), 3.06 (q, J = 6.4 Hz, 2H), 3.92 (t, J = 6.3 Hz, 2H), 4.08 (s, 2H), 4.97 (s, 2H), 6.86 (d, J = 8.6 Hz, 3H), 7.37-7.53 (m, 5H), 7.76 (d, J = 7.1 Hz, 2H), 7.83 (dd, J = 8.6, 2.0 Hz, 1H), 8.05 (d, J = 8.6 Hz, 1H), 8.43 (d, J = 1.5 Hz, 1H), 10.23 (s, 1H). |
| I-2-165 | 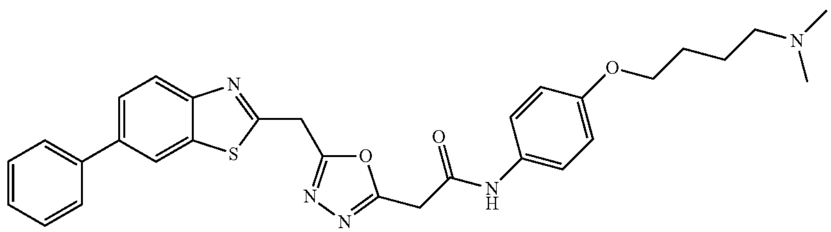 [SMILES: CN(C)CCCCOc1ccc(NC(=O)Cc2nnc(Cc3nc4ccc(-c5ccccc5)cc4s3)o2)cc1] | (DMSO-d6) δ: 1.47-1.55 (m, 2H), 1.64-1.72 (m, 2H), 2.10 (s, 6H), 2.22 (t, J = 7.4 Hz, 2H), 3.92 (t, J = 6.6 Hz, 2H), 4.08 (s, 2H), 4.97 (s, 2H), 6.87 (d, J = 9.1 Hz, 2H), 7.38-7.46 (m, 3H), 7.50 (t, J = 7.6 Hz, 2H), 7.76 (d, J = 7.6 Hz, 2H), 7.83 (d, J = 8.6 Hz, 1H), 8.04 (d, J = 8.6 Hz, 1H), 8.43 (s, 1H), 10.23 (s, 1H). |

TABLE 52

| No. | Structure | NMR(δ) |
|---|---|---|
| I-2-166 | 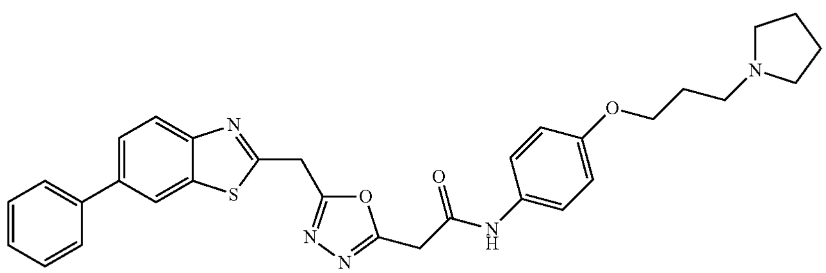 [SMILES: O=C(Cc1nnc(Cc2nc3ccc(-c4ccccc4)cc3s2)o1)Nc1ccc(OCCCN2CCCC2)cc1] | δ: 1.64-1.69 (m, 4H), 1.81-1.88 (m, 2H), 2.39-2.43 (m, 4H), 2.47-2.52 (m, 2H), 3.95 (t, J = 6.3 Hz, 2H), 4.08 (s, 2H), 4.97 (s, 2H), 6.87 (d, J = 8.6 Hz, 2H), 7.37-7.47 (m, 3H), 7.50 (t, J = 7.6 Hz, 2H), 7.76 (d, J = 7.6 Hz, 2H), 7.83 (d, J = 8.6 Hz, 1H), 8.04 (d, J = 8.6 Hz, 1H), 8.43 (s, 1H), 10.23 (s, 1H). |
| I-2-167 | 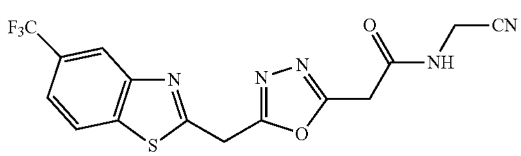 [SMILES: N#CCNC(=O)Cc1nnc(Cc2nc3cc(C(F)(F)F)ccc3s2)o1] | (DMSO-d$_6$) δ: 3.99 (s, 2H), 4.19 (d, J = 5.58 Hz, 2H), 5.02 (s, 2H), 7.80 (d, J = 8.11 Hz, 1H), 8.34-8.42 (m, 2H), 9.02 (t, J = 5.58 Hz, 1H). |
| I-2-168 | 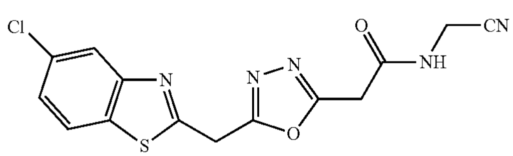 [SMILES: N#CCNC(=O)Cc1nnc(Cc2nc3cc(Cl)ccc3s2)o1] | (DMSO-d$_6$) δ: 3.98 (s, 2H), 4.19 (d, J = 5.58 Hz, 2H), 4.96 (s, 2H), 7.52 (dd, J = 8.62, 1.52 Hz, 1H), 8.09 (d, J = 1.52 Hz, 1H), 8.16 (d, J = 8.62 Hz, 1H), 9.02 (t, J = 5.58 Hz, 1H). |
| I-2-169 | 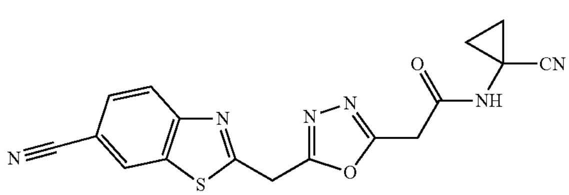 [SMILES: N#Cc1ccc2nc(Cc3nnc(CC(=O)NC4(C#N)CC4)o3)sc2c1] | (DMSO-d6) δ: 1.14 (dd, J = 8.70, 5.70 Hz, 2H), 1.49 (dd, J = 8.70, 5.70 Hz, 2H), 3.92 (s, 2H), 5.02 (s, 2H), 7.40-7.52 (m, 3H), 7.78 (d, J = 6.60 Hz, 1H), 8.45 (d, J = 1.50 Hz, 1H), 9.24 (s, 1H). |

TABLE 52-continued

| No. | Structure | NMR(δ) |
|---|---|---|
| I-2-170 | 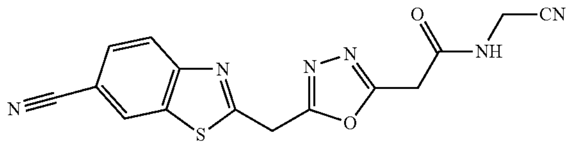 [SMILES: N#CCNC(=O)Cc1nnc(Cc2nc3ccc(C#N)cc3s2)o1] | (DMSO-d6) δ: 1.14 (dd, J = 8.70, 5.70 Hz, 2H), 1.49 (dd, J = 8.70, 5.70 Hz, 2H), 3.92 (s, 2H), 5.05 (s, 2H), 7.94 (d, J = 8.40 Hz, 1H), 8.17 (d, J = 8.40 Hz, 1H), 8.76 (d, J = 1.80 Hz, 1H), 9.24 (s, 1H). |

TABLE 53

| No. | Structure | NMR(δ) |
|---|---|---|
| I-2-171 | 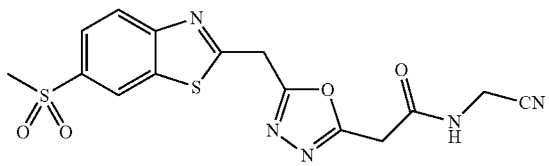 [SMILES: CS(=O)(=O)c1ccc2nc(Cc3nnc(CC(=O)NCC#N)o3)sc2c1] | 1H-NMR (DMSO-d6) δ: 3.28 (s, 3H), 3.99 (s, 2H), 4.19 (d, J = 5.6 Hz, 2H), 5.04 (s, 2H), 8.03 (dd, J = 8.6, 1.5 Hz, 1H), 8.21 (d, J = 8.6 Hz, 1H), 8.81 (d, J = 2.0 Hz, 1H), 9.02 (t, J = 5.6 Hz, 1H). |
| I-2-172 | 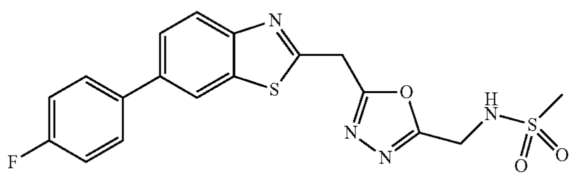 [SMILES: CS(=O)(=O)NCc1nnc(Cc2nc3ccc(-c4ccc(F)cc4)cc3s2)o1] | 1H-NMR (DMSO-d6) δ: 2.96 (s, 3H), 4.47 (d, J = 6.1 Hz, 2H), 4.98 (s, 2H), 7.33 (t, J = 8.9 Hz, 2H), 7.76-7.83 (m, 3H), 7.95 (t, J = 5.8 Hz, 1H), 8.03 (d, J = 8.6 Hz, 1H), 8.40-8.44 (m, 1H). |
| I-2-173 | 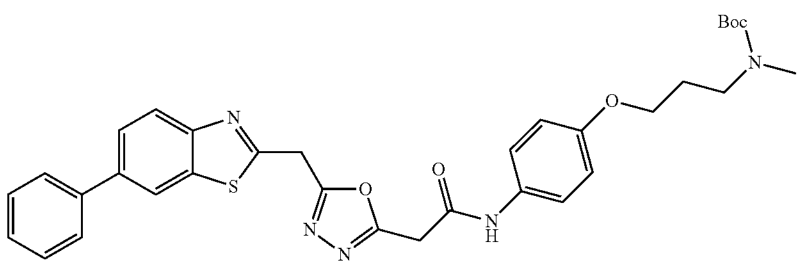 [SMILES: CN(CCCOc1ccc(NC(=O)Cc2nnc(Cc3nc4ccc(-c5ccccc5)cc4s3)o2)cc1)C(=O)OC(C)(C)C] | (CDCl3) δ: 1.43 (s, 9H), 1.94-2.02 (m, 2H), 2.87 (s, 3H), 3.39 (t, J = 6.8 Hz, 2H), 3.94 (t, J = 5.8 Hz, 2H), 4.02 (s, 2H), 4.77 (s, 2H), 6.84 (d, J = 8.6 Hz, 2H), 7.37-7.50 (m, 5H), 7.63 (d, J = 7.6 Hz, 2H), 7.73 (d, J = 8.6 Hz, 1H), 8.04-8.07 (m, 2H), 8.81 (s, 1H). |
| I-2-174 | 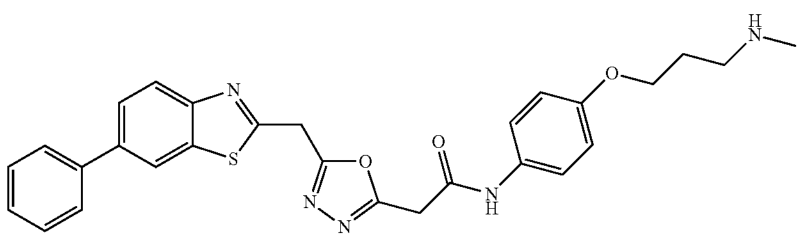 [SMILES: CNCCCOc1ccc(NC(=O)Cc2nnc(Cc3nc4ccc(-c5ccccc5)cc4s3)o2)cc1] | (DMSO-d6) δ: 1.78-1.85 (m, 2H), 2.29 (s, 3H), 2.60 (t, J = 6.8 Hz, 2H), 3.96 (t, J = 6.6 Hz, 2H), 4.08 (s, 2H), 4.97 (s, 2H), 6.87 (d, J = 9.1 Hz, 2H), 7.37-7.47 (m, 3H), 7.50 (t, J = 7.6 Hz, 2H), 7.76 (d, J = 7.6 Hz, 2H), 7.83 (dd, J = 8.4, 1.8 Hz, 1H), 8.04 (d, J = 8.1 Hz, 1H), 8.43 (d, J = 1.5 Hz, 1H), 10.24 (s, 1H). |
| I-2-175 | 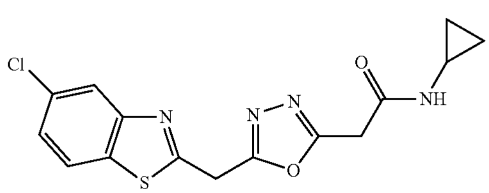 [SMILES: O=C(Cc1nnc(Cc2nc3cc(Cl)ccc3s2)o1)NC1CC1] | (DMSO-d6) δ: 0.37-0.43 (m, 2H), 0.58-0.66 (m, 2H), 2.62 (m, 1H), 3.78 (s, 2H), 4.95 (s, 2H), 7.53 (dd, J = 8.62, 2.03 Hz, 1H), 8.09 (d, J = 2.03 Hz, 1H), 8.17 (d, J = 8.62 Hz, 1H), 8.35 (d, J = 3.55 Hz, 1H). |

TABLE 54

| No. | Structure | NMR(δ) |
|---|---|---|
| I-2-176 | 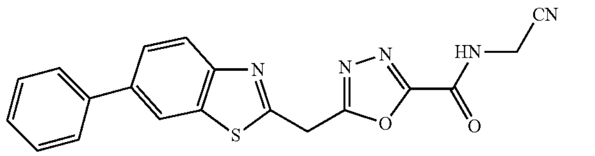 [SMILES: N#CCNC(=O)c1nnc(Cc2nc3ccc(-c4ccccc4)cc3s2)o1] | (DMSO-d$_6$) δ: 4.35 (d, J = 4.06 Hz, 2H), 5.08 (s, 2H), 7.40 (t, J = 7.35 Hz, 1H), 7.51 (dd, J = 7.60, 7.35 Hz, 2H), 7.76 (d, J = 7.60 Hz, 2H), 7.83 (dd, J = 8.11, 1.52 Hz, 1H), 8.06 (d, J = 8.11 Hz, 1H), 8.45 (d, J = 1.52 Hz, 1H), 10.04 (t, J = 4.06 Hz, 1H). |
| I-2-177 | 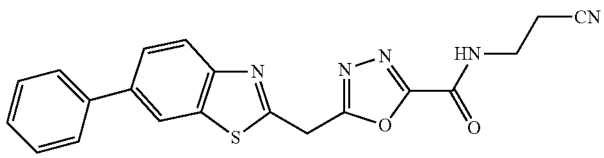 [SMILES: N#CCCNC(=O)c1nnc(Cc2nc3ccc(-c4ccccc4)cc3s2)o1] | (DMSO-d$_6$) δ: 2.80 (t, J = 6.34 Hz, 2H), 3.52 (dt, J = 6.34, 5.83 Hz, 2H), 5.07 (s, 2H), 7.40 (t, J = 7.35 Hz, 1H), 7.50 (dd, J = 7.60, 7.35 Hz, 2H), 7.76 (d, J = 7.60 Hz, 2H), 7.83 (dd, J = 8.11, 1.52 Hz, 1H), 8.06 (d, J = 8.11 Hz, 1H), 8.45 (d, J = 1.52 Hz, 1H), 9.63 (t, J = 5.83 Hz, 1H). |
| I-2-178 | 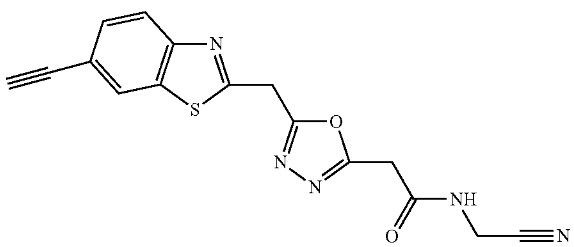 [SMILES: C#Cc1ccc2nc(Cc3nnc(CC(=O)NCC#N)o3)sc2c1] | (DMSO-d$_6$) δ; 3.99 (s, 2H), 4.19 (d, J = 6.0 Hz, 2H), 4.30 (s, 1H), 4.96 (s, 2H), 7.59 (d, J = 6.0 Hz, 1H), 7.97(d, J = 6.0 Hz, 1H), 8.31(s, 1H) 9.04(t, J = 6.0 Hz, 1H) |
| I-2-179 | 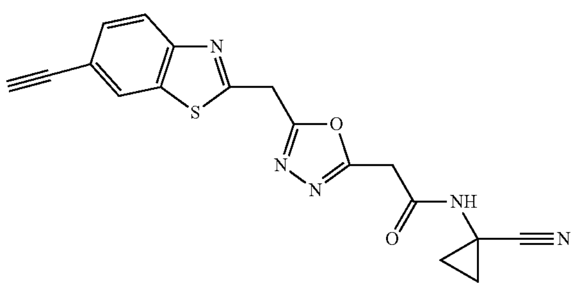 [SMILES: C#Cc1ccc2nc(Cc3nnc(CC(=O)NC4(C#N)CC4)o3)sc2c1] | (DMSO-d$_6$) δ; 1.05-1.16 (m, 2H), 1.40-1.55 (m, 2H), 3.91(s, 2H), 4.30 (s, 1H), 4.96 (s, 2H), 7.59 (d, J = 6.0 Hz, 1H), 7.97 (d, J = 6.0 Hz, 1H), 8.31(s, 1H), 9.25 (s, 1H) |
| I-2-180 | 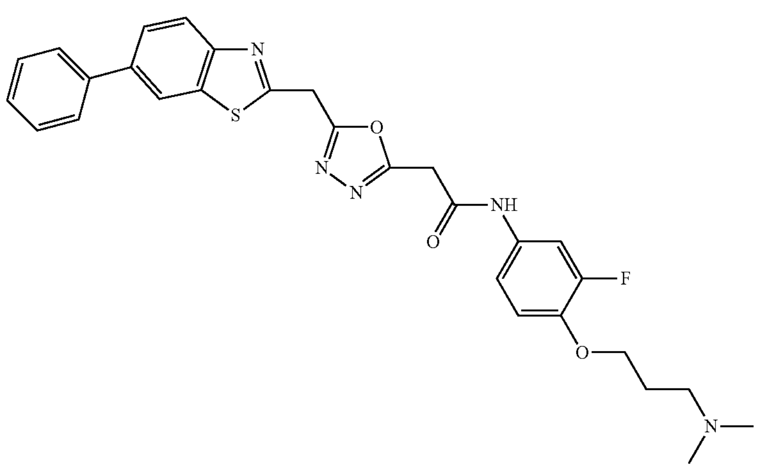 [SMILES: CN(C)CCCOc1ccc(NC(=O)Cc2nnc(Cc3nc4ccc(-c5ccccc5)cc4s3)o2)cc1F] | (DMSO-d$_6$) δ 2.05-2.09(m, 2H), 2.76(s, 6H), 3.10-3.18(m, 2H), 4.07(t, J = 3.0 Hz, 2H), 4.11(s, 2H), 4.97(s, 2H), 7.14 (t, J = 6.0 Hz, 1H), 7.22-7.24(m, 1H), 7.39-7.56(m, 4H), 7.76(d, J = 6.0 Hz, 2H), 7.83(d, J = 6.0 Hz, 1H), 8.05(d, J = 9.0 Hz, 1H), 8.44(s, 1H), 10.44(s, 1H) |

TABLE 55

| No. | Structure | NMR(δ) |
|---|---|---|
| I-2-181 | 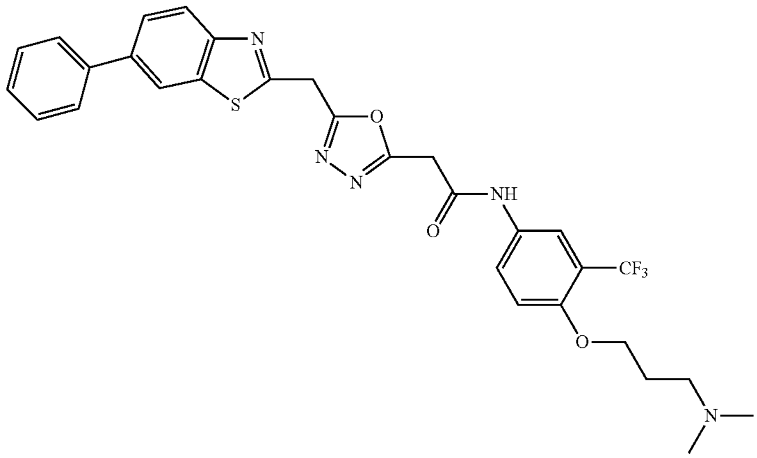 [SMILES: CN(C)CCCOc1ccc(NC(=O)Cc2nnc(Cc3nc4ccc(-c5ccccc5)cc4s3)o2)cc1C(F)(F)F] | (DMSO-d$_6$) δ 2.00-2.10(m, 2H), 2.74(s, 6H), 3.10-3.15(m, 2H), 4.12(s, 2H)4.14(t, J = 3.0 Hz, 2H), 4.97(s, 2H), 7.24 (t, J = 9.0 Hz, 1H), 7.39-7.52(m, 3H), 7.72-7.77(m, 3H,), 7.83(dd, J = 3.0, 6.0 Hz, 1H)7.90(d, J = 3.0 Hz, 1H), 8.04(d, J = 9.0 Hz, 1H), 8.44(d, J = 3.0 Hz, 1H), 10.54(s, 1H) |
| I-2-182 | 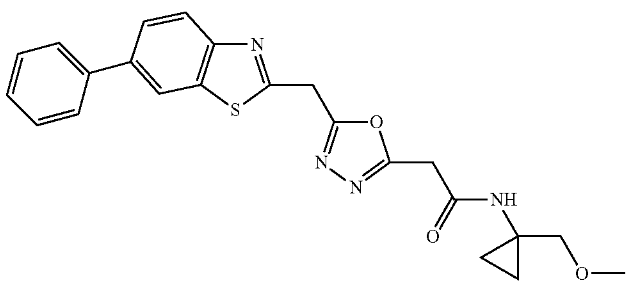 [SMILES: COCC1(NC(=O)Cc2nnc(Cc3nc4ccc(-c5ccccc5)cc4s3)o2)CC1] | (DMSO-d$_6$) δ: 0.60-0.63(m, 2H), 0.66-0.69(m, 2H), 3.21(s, 3H), 3.79 (s, 2H), 4.94(s, 2H), 7.38-7.42(m, 1H), 7.52(t, J = 6.0 Hz, 2H), 7.76(d, J = 6.0 Hz, 2H), 7.83 (dd, J = 3.0, 6.0 Hz, 1H), 8.05(d, J = 6.0 Hz, 1H), 8.44(d, J = 3.0 Hz, 1H), 8.59(s, 1H) |
| I-2-183 | 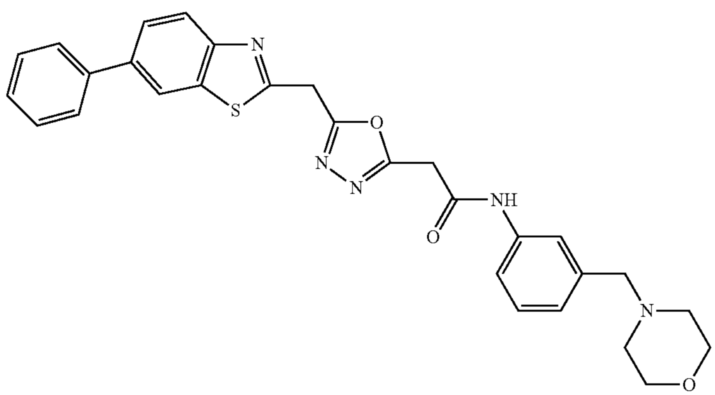 [SMILES: O=C(Cc1nnc(Cc2nc3ccc(-c4ccccc4)cc3s2)o1)Nc1cccc(CN2CCOCC2)c1] | (DMSO-d$_6$) δ: 0.3.00-3.12(m, 2H), 3.23-3.43(m, 2H)3.56-3.66(m, 2H), 3.93-3.96(m, 2H), 4.16(s, 2H), 4.32 (s, 2H), 4.97(s, 2H), 7.17-7.25(m, 1H), 7.39-7.53(m, 4H), 7.76(d, 6 Hz, 2H), 7.82(dd, J = 3.0, 6.0 Hz, 1H), 7.90 (bs, 1H), 8.05(d, J = 6.0 Hz, 1H), 8.44(d, J = 3.0 Hz, 1H), 9.75(bs, 1H), 10.57(s, 1H) |
| I-2-184 | 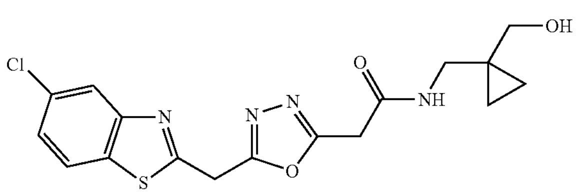 [SMILES: O=C(Cc1nnc(Cc2nc3cc(Cl)ccc3s2)o1)NCC1(CO)CC1] | (DMSO-d$_6$) δ: 0.28-0.38 (m, 4H), 3.11 (d, J = 5.58 Hz, 2H), 3.24 (d, J = 5.58 Hz, 2H), 3.87 (s, 2H), 4.46 (t, J = 5.58 Hz, 1H), 4.95 (s, 2H), 7.52 (dd, J = 8.62, 2.03 Hz, 1H), 8.09 (d, J = 2.03 Hz, 1H), 8.16 (d, J = 8.62 Hz, 1H), 8.24 (t, J = 5.58 Hz, 1H). |
| I-2-185 | 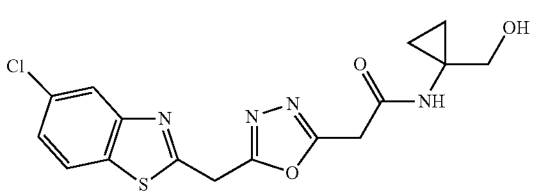 [SMILES: O=C(Cc1nnc(Cc2nc3cc(Cl)ccc3s2)o1)NC1(CO)CC1] | (DMSO-d$_6$) δ: 0.55 (dd, J = 6.59, 4.56 Hz, 2H), 0.66 (dd, J = 6.59, 4.56 Hz, 2H), 3.39 (d, J = 5.83 Hz, 2H), 3.79 (s, 2H), 4.69 (t, J = 5.83 Hz, 1H), 4.94 (s, 2H), 7.53 (dd, J = 8.62, 2.03 Hz, 1H), 8.09 (d, J = 2.03 Hz, 1H), 8.16 (d, J = 8.62 Hz, 1H), 8.53 (s, 1H). |

TABLE 56

| No. | Structure | NMR(δ) |
|---|---|---|
| I-2-186 | 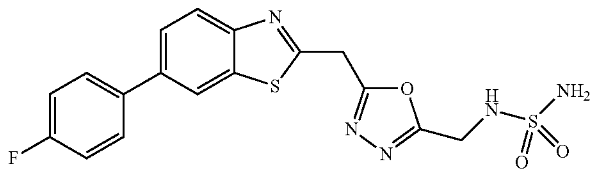 [SMILES: NS(=O)(=O)NCc1nnc(Cc2nc3ccc(-c4ccc(F)cc4)cc3s2)o1] | 1H-NMR (CDCl3) δ: 4.61 (d, J = 6.6 Hz, 2H), 4.75 (s, 2H), 5.17 (s, 2H), 5.26 (t, J = 6.3 Hz, 1H), 7.16 (t, J = 8.9 Hz, 2H), 7.54-7.61 (m, 2H), 7.67 (dd, J = 8.6, 2.0 Hz, 1H), 7.99-8.05 (m, 2H). |
| I-2-187 | 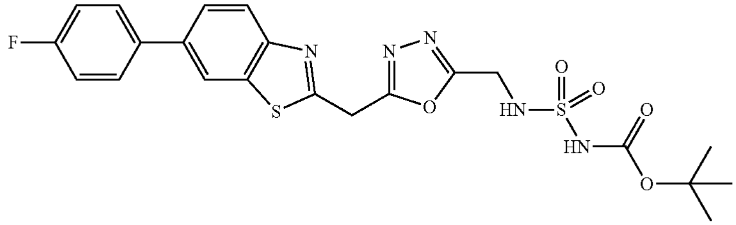 [SMILES: CC(C)(C)OC(=O)NS(=O)(=O)NCc1nnc(Cc2nc3ccc(-c4ccc(F)cc4)cc3s2)o1] | 1H-NMR (DMSO-d6) δ: 1.40 (s, 9H), 4.41 (d, J = 5.6 Hz, 2H), 4.95 (s, 2H), 7.33 (t, J = 8.6 Hz, 2H), 7.78-7.83 (m, 3H), 8.04 (d, J = 8.6 Hz, 1H), 8.42 (s, 1H), 8.48 (s, 1H), 11.04 (s, 1H). |
| I-2-188 | 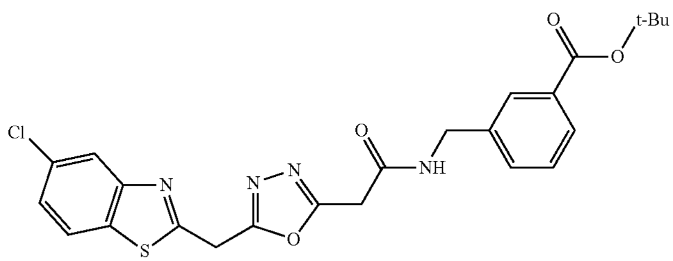 [SMILES: CC(C)(C)OC(=O)c1cccc(CNC(=O)Cc2nnc(Cc3nc4cc(Cl)ccc4s3)o2)c1] | (DMSO-d$_6$) δ: 1.54 (s, 9H), 3.95 (s, 2H), 4.35 (d, J = 6.08 Hz, 2H), 4.96 (s, 2H), 7.39-7.55 (m, 3H), 7.75-7.82 (m, 2H), 8.08 (d, J = 2.03 Hz, 1H), 8.16 (d, J = 8.62 Hz, 1H), 8.86 (t, J = 6.08 Hz, 1H). |
| I-2-189 | 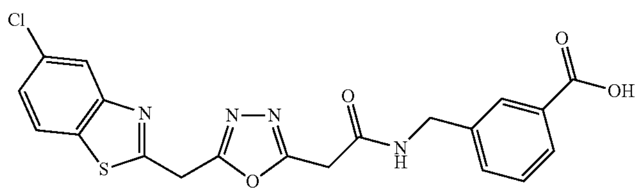 [SMILES: O=C(Cc1nnc(Cc2nc3cc(Cl)ccc3s2)o1)NCc1cccc(C(=O)O)c1] | (DMSO-d$_6$) δ: 3.95 (s, 2.0H), 4.36 (d, J = 5.58 Hz, 2.0H), 4.95 (s, 2.0H), 7.43 (t, J = 7.60 Hz, 1.0H), 7.47-7.55 (m, 2.0H), 7.80-7.88 (m, 2.0H), 8.08 (d, J = 2.03 Hz, 1.0H), 8.16 (d, J = 8.62 Hz, 1.0H), 8.86 (t, J = 5.83 Hz, 1.0H), 12.96 (s, 1.0H). |
| I-2-190 | 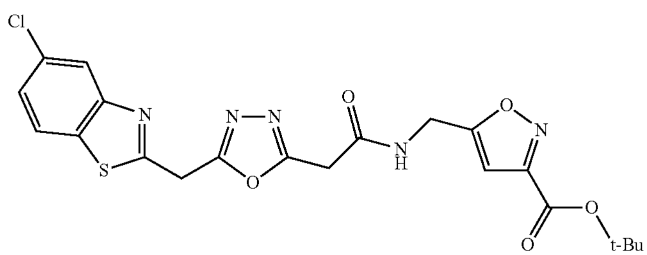 [SMILES: CC(C)(C)OC(=O)c1cc(CNC(=O)Cc2nnc(Cc3nc4cc(Cl)ccc4s3)o2)on1] | (DMSO-d$_6$) δ: 1.53 (s, 9H), 3.98 (s, 2H), 4.50 (d, J = 6.08 Hz, 2H), 4.95 (s, 2H), 6.67 (s, 1H), 7.52 (dd, J = 8.62, 2.03 Hz, 1H), 8.08 (d, J = 2.03 Hz, 1H), 8.16 (d, J = 8.62 Hz, 1H), 9.00 (t, J = 6.08 Hz, 1H). |

TABLE 57

| No. | Structure | NMR(δ) |
|---|---|---|
| I-2-191 | 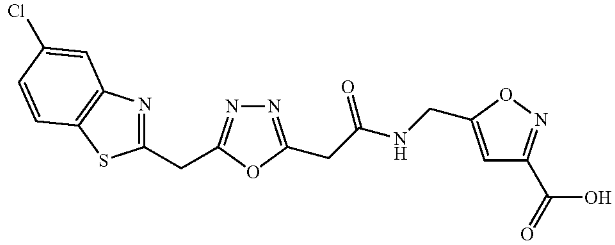 [SMILES: O=C(Cc1nnc(Cc2nc3cc(Cl)ccc3s2)o1)NCc1cc(C(=O)O)no1] | (DMSO-d$_6$) δ: 3.98 (s, 2H), 4.50 (d, J = 5.58 Hz, 2H), 4.95 (s, 2H), 6.69 (s, 1H), 7.52 (dd, J = 8.62, 2.03 Hz, 1H), 8.09 (d, J = 2.03 Hz, 1H), 8.16 (d, J = 8.62 Hz, 1H), 9.00 (t, J = 5.58 Hz, 1H). |

TABLE 57-continued

| No. | Structure | NMR(δ) |
|---|---|---|
| I-2-192 | 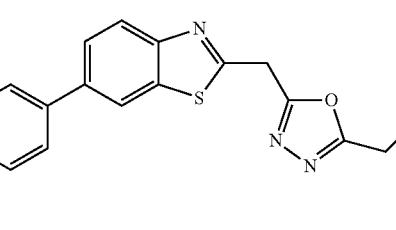 | (DMSO-d6) δ: 1.78-1.84 (m, 2H), 2.13 (s, 6H), 2.32 (t, J = 7.1 Hz, 2H), 4.12 (s, 2H), 4.21 (t, J = 6.6 Hz, 2H), 4.97 (s, 2H), 6.78 (d, J = 9.1 Hz, 1H), 7.37-7.43 (m, 1H), 7.50 (t, J = 7.6 Hz, 2H), 7.76 (d, J = 7.1 Hz, 2H), 7.84 (td, J = 8.7, 2.2 Hz, 2H), 8.04 (d, J = 8.1 Hz, 1H), 8.30 (d, J = 2.5 Hz, 1H), 8.43 (d, J = 1.5 Hz, 1H), 10.41 (s, 1H). |
| I-2-193 | 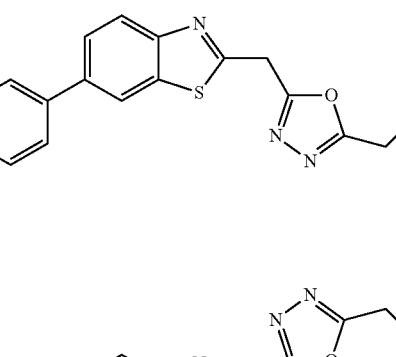 | (DMSO-d6) δ: 2.81-2.85 (m, 10H), 3.52 (br s, 4H), 3.96 (s, 3H), 4.16 (s, 2H), 4.95 (s, 2H), 7.38-7.43 (m, 1H), 7.51 (t, J = 7.6 Hz, 2H), 7.74-7.78 (m, 2H), 7.83 (dd, J = 8.4, 1.8 Hz, 1H), 8.05 (d, J = 8.6 Hz, 1H), 8.44 (d, J = 2.0 Hz, 1H), 8.98 (t, J = 5.3 Hz, 1H). |
| I-2-194 | 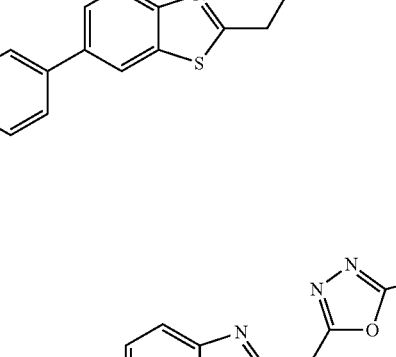 | 1H-NMR (DMSO-d6) δ: 3.06 (s, 3H), 3.35 (t, J = 7.9 Hz, 2H), 3.61 (t, J = 7.6 Hz, 2H), 4.94 (s, 2H), 7.40 (t, J = 7.4 Hz, 1H), 7.50 (t, J = 7.6 Hz, 2H), 7.75 (d, J = 7.6 Hz, 2H), 7.83 (dd, J = 8.6, 2.0 Hz, 1H), 8.05 (d, J = 8.6 Hz, 1H), 8.43 (d, J = 1.5 Hz, 1H). |
| I-2-195 | 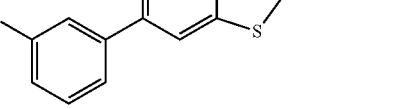 | (DMSO-d6) δ: 3.99 (s, 2H), 4.19 (d, J = 5.40 Hz, 2H), 5.02 (s, 2H), 7.93 (dd, J = 6.90, 1.80 Hz, 1H,), 7.16 (d, J = 8.40 Hz, 1H), 8.74 (s, 1H), 9.02 (brs, 1H). |

TABLE 58

| No. | Structure | NMR(δ) | retention time | Mass | method |
|---|---|---|---|---|---|
| I-2-196 | Br-benzothiazole-oxadiazole-CH2-C(O)NH-CH2-CN structure | ¹H-NMR (DMSO-d₆) δ: 3.99 (s, 2H), 4.19 (d, J = 5.6 Hz, 2H), 4.98 (s, 2H), 7.39 (t, J = 7.9 Hz, 1H), 7.78 (d, J = 7.1 Hz, 1H), 8.14 (d, J = 8.1 Hz, 1H), 9.03 (t, J = 5.6 Hz, 1H). | | | |

TABLE 58-continued

| No. | Structure | NMR(δ) | retention time | Mass | method |
|---|---|---|---|---|---|
| I-2-197 | 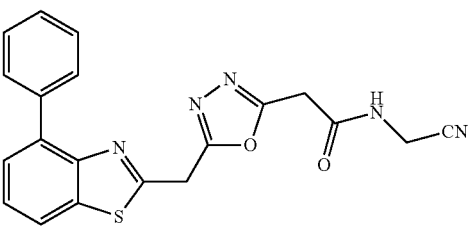 [SMILES: N#CCNC(=O)Cc1nnc(Cc2nc3c(-c4ccccc4)cccc3s2)o1] | ¹H-NMR (DMSO-d₆) δ: 3.98 (s, 2H), 4.19 (d, J = 5.6 Hz, 2H), 4.94 (s, 2H), 7.40 (t, J = 7.4 Hz, 1H), 7.49 (t, J = 7.6 Hz, 2H), 7.55 (t, J = 7.9 Hz, 1H), 7.62 (d, J = 7.1 Hz, 1H), 7.80 (d, J = 7.6 Hz, 2H), 8.11 (d, J = 7.1 Hz, 1H), 9.01 (t, J = 5.1 Hz, 1H). | | | |
| I-2-198 | 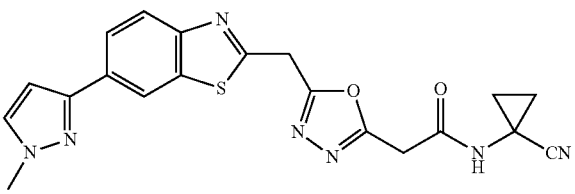 [SMILES: Cn1ccc(-c2ccc3nc(Cc4nnc(CC(=O)NC5(C#N)CC5)o4)sc3c2)n1] | (DMSO-d6) δ: 1.14 (dd, J = 8.70, 5.70 Hz, 2H), 1.49 (dd, J = 8.70, 5.70 Hz, 2H), 3.32 (s, 3H), 4.98 (s, 2H), 6.49 (d, J = 1.8 Hz, 1H), 7.50 (d, J = 1.8 Hz, 1H), 7.67 (d, J = 7.2 Hz, 1H), 8.08 (d, J = 8.7 Hz, 1H), 8.33 (s, 1H), 9.24 (s, 1H). | | | |
| I-2-199 | 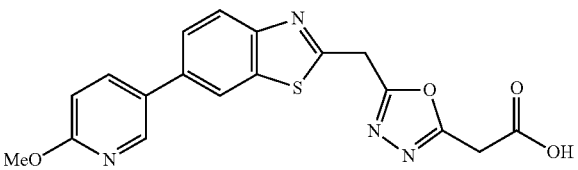 [SMILES: COc1ccc(-c2ccc3nc(Cc4nnc(CC(=O)O)o4)sc3c2)cn1] | | 1.54 | 382.95 (MS+) | C |
| I-2-200 | 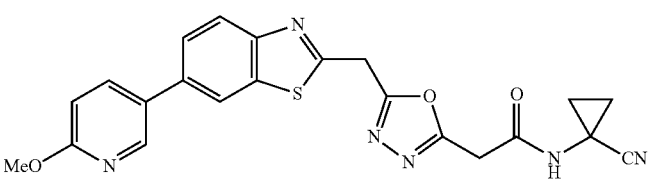 [SMILES: COc1ccc(-c2ccc3nc(Cc4nnc(CC(=O)NC5(C#N)CC5)o4)sc3c2)cn1] | (DMSO-d6) δ: 1.14 (dd, J = 8.70, 5.70 Hz, 2H), 1.49 (dd, J = 8.70, 5.70 Hz, 2H), 3.32 (s, 3H), 4.96 (s, 2H), 6.49 (d, J = 1.8 Hz, 1H), 7.50 (d, J = 1.8 Hz, 1H), 7.67 (d, J = 7.2 Hz, 1H), 8.08 (d, J = 8.7 Hz, 1H), 8.33 (s, 1H), 9.24 (s, 1H). | | | |

TABLE 59

| No. | Structure | NMR(δ) |
|---|---|---|
| I-2-201 | 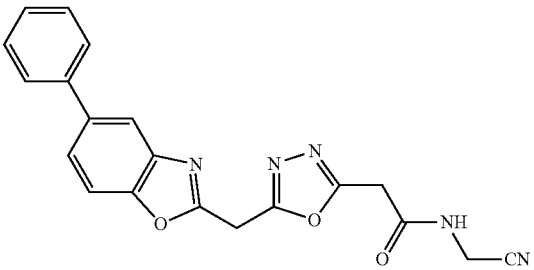 [SMILES: N#CCNC(=O)Cc1nnc(Cc2nc3cc(-c4ccccc4)ccc3o2)o1] | 1H-NMR (DMSO-d6) δ: 4.00 (s, 2H), 4.20 (d, J = 5.1 Hz, 2H), 4.88 (s, 2H). 7.38 (t, J = 7.4 Hz, 1H), 7.48 (t, J = 7.6 Hz, 2H), 7.70-7.73 (m, 3H), 7.82 (d, J = 8.6 Hz, 1H), 8.01 (d, J = 1.5 Hz, 1H), 9.03 (t, J = 5.3 Hz, 1H). |
| I-2-202 | 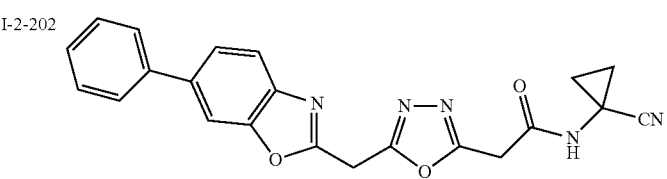 | ¹H-NMR (DMSO-d₆) δ: 1.14 (dd, J = 8.11, 5.58 Hz, 2H), 1.49 (dd, J = 8.11, 5.58 Hz, 2H), 3.92 (s, 2H), 4.88 (s, 2H), 7.39 (t, J = 7.10 Hz, 1H), 7.46-7.52 (m, 2H), 7.69-7.77 (m, 3H), 7.81 (d, J = 8.62 Hz, 1H), 8.05 (d, J = 1.01 Hz, 1H), 9.24 (s, 1H). |

TABLE 59-continued

| No. | Structure | NMR(δ) |
|---|---|---|
| I-2-203 | 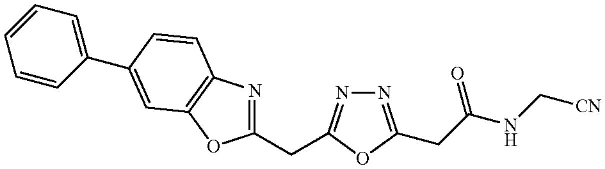 [SMILES: N#CCNC(=O)Cc1nnc(Cc2nc3ccc(-c4ccccc4)cc3o2)o1] | ¹H-NMR (DMSO-d₆) δ: 4.00 (s, 2H), 4.20 (d, J = 5.58 Hz, 2H), 4.88 (s, 2H), 7.39 (m, 1H), 7.46-7.52 (m, 2H), 7.68-7.76 (m, 3H), 7.81 (d, J = 8.62 Hz, 1H), 8.04 (d, J = 1.01 Hz, 1H), 9.03 (t, J = 5.58 Hz, 1H). |
| I-2-204 | 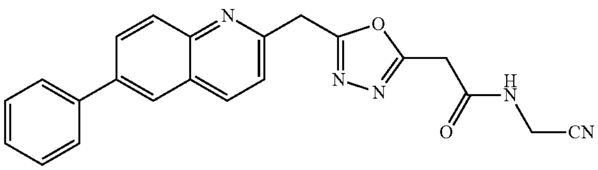 [SMILES: N#CCNC(=O)Cc1nnc(Cc2ccc3cc(-c4ccccc4)ccc3n2)o1] | ¹H-NMR (DMSO-d₆) δ: 3.95 (s, 2H), 4.19 (d, J = 5.4 Hz, 2H), 4.66 (s, 2H), 7.43(m, 1H), 7.50-7.60 (m, 3H), 7.84 (d, J = 7.2 Hz, 2H), 8.00-8.12 (m, 2H), 8.29(s, 1H), 8.45(d, J = 8.4 Hz, 1H), 9.00(br-s, 1H) |
| I-2-205 | 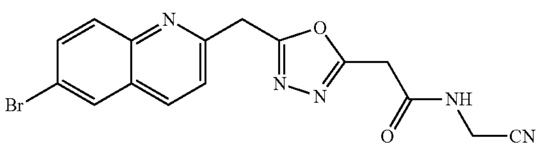 [SMILES: N#CCNC(=O)Cc1nnc(Cc2ccc3cc(Br)ccc3n2)o1] | ¹H-NMR (DMSO-d₆) δ: 3.95 (s, 2H), 4.18 (d, J = 5.7 Hz, 2H), 4.63 (s, 2H), 7.61(d, J = 8.4 Hz, 1H), 7.88 (s, 2H), 8.29 (s, 1H), 8.37 (d, J = 8.7 Hz, 1H), 8.99 (br-s, 1H) |

TABLE 60

| No. | Structure | NMR(δ) |
|---|---|---|
| I-2-206 | 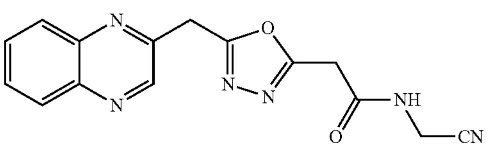 [SMILES: N#CCNC(=O)Cc1nnc(Cc2cnc3ccccc3n2)o1] | ¹H-NMR (DMSO-d₆) δ: 3.96 (s, 2H), 4.18 (d, J = 5.6 Hz, 2H), 4.77 (s, 2H), 7.84-7.89 (m, 2H), 8.01-8.06 (m, 1H), 8.09-8.15 (m, 1H), 8.96-9.03 (m, 2H). |
| I-2-207 | 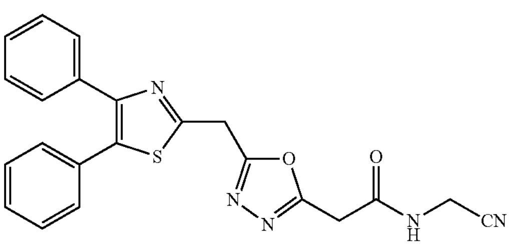 [SMILES: N#CCNC(=O)Cc1nnc(Cc2nc(-c3ccccc3)c(-c3ccccc3)s2)o1] | ¹H-NMR (DMSO-d₆) δ: 3.99(s, 2H), 4.19(d, J = 5.7 Hz, 1H), 4.84(s, 2H), 7.29-7.42(m, 10H), 9.03(br-s, 1H). |
| I-2-208 | 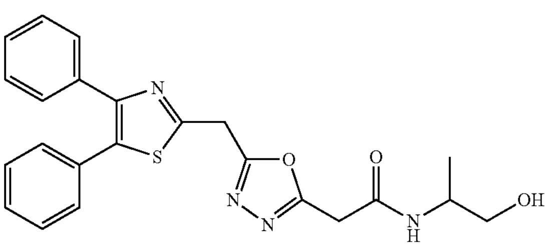 [SMILES: CC(CO)NC(=O)Cc1nnc(Cc2nc(-c3ccccc3)c(-c3ccccc3)s2)o1] | ¹H-NMR (DMSO-d₆) δ: 1.16(d, J = 6.9 Hz, 3H), 2.72(m, 1H), 3.49(m, 1H), 3.62(br-s, 1H), 3.87(s, 2H), 4.09(m, 1H), 4.65(s, 2H), 6.98(br-s, 1H), 7.25-7.33(m, 8H), 7.46-7.49(m, 2H). |
| I-2-209 | 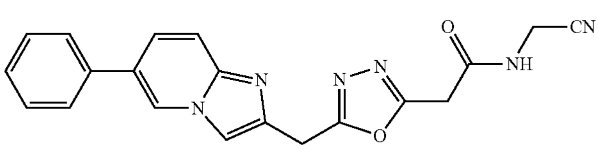 [SMILES: N#CCNC(=O)Cc1nnc(Cc2cn3cc(-c4ccccc4)ccc3n2)o1] | ¹H-NMR (DMSO-d₆) δ: 3.94 (s, 2H), 4.19 (d, J = 5.58 Hz, 2H), 4.40 (s, 2H), 7.40 (t, J = 7.35 Hz, 1H), 7.47-7.53 (m, 2H), 7.56-7.61 (m, 2H), 7.68-7.72 (m, 2H), 7.92 (s, 1H), 8.89 (s, 1H), 8.99 (t, J = 5.58 Hz, 1H). |

TABLE 60-continued

| No. | Structure | NMR(δ) |
|---|---|---|
| I-2-210 | 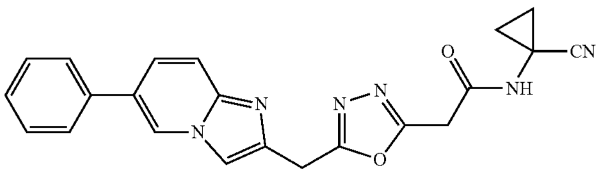 [SMILES: N#CC1(NC(=O)Cc2nnc(Cc3cn4cc(-c5ccccc5)ccc4n3)o2)CC1] | ¹H-NMR (DMSO-d₆) δ: 1.13 (dd, J = 8.11, 5.58 Hz, 2H), 1.48 (dd, J = 8.11, 5.58 Hz, 2H), 3.86 (s, 2H), 4.40 (s, 2H), 7.40 (t, J = 7.35 Hz, 1H), 7.47-7.53 (m, 2H), 7.56-7.61 (m, 2H), 7.67-7.72 (m, 2H), 7.92 (s, 1H), 8.89 (m, 1H), 9.20 (s, 1H). |

TABLE 61

| No. | Structure | NMR(δ) |
|---|---|---|
| I-2-211 | 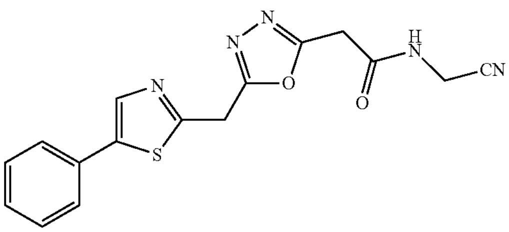 [SMILES: N#CCNC(=O)Cc1nnc(Cc2ncc(-c3ccccc3)s2)o1] | ¹H-NMR (DMSO-d₆) δ: 3.98 (s, 2H), 4.19 (d, J = 5.6 Hz, 2H), 4.79 (s, 2H), 7.37 (t, J = 7.4 Hz, 1H), 7.45 (t, J = 7.6 Hz, 2H), 7.65 (d, J = 7.1 Hz, 2H), 8.14 (s, 1H), 9.01 (t, J = 5.3 Hz, 1H). |
| I-2-212 | 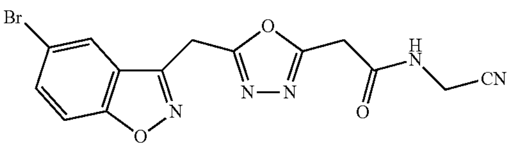 [SMILES: N#CCNC(=O)Cc1nnc(Cc2noc3ccc(Br)cc23)o1] | ¹H-NMR (DMSO-d₆) δ: 3.97 (s, 2H), 4.19 (d, J = 5.58 Hz, 2H), 4.83 (s, 2H), 7.77-7.86 (m, 2H), 8.14 (d, J = 1.52 Hz, 1H), 9.01 (t, J = 5.58 Hz, 1H). |
| I-2-213 | 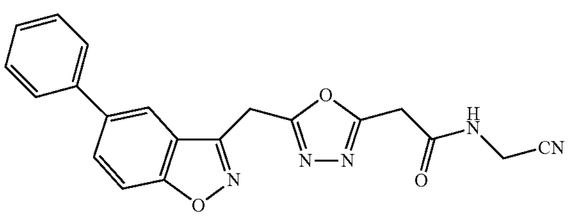 [SMILES: N#CCNC(=O)Cc1nnc(Cc2noc3ccc(-c4ccccc4)cc23)o1] | ¹H-NMR (DMSO-d₆) δ: 3.97 (s, 2H), 4.17 (d, J = 5.58 Hz, 2H), 4.88 (s, 2H), 7.41 (t, J = 7.35 Hz, 1H), 7.48-7.54 (m, 2H), 7.69-7.74 (m, 2H), 7.86 (d, J = 8.62 Hz, 1H), 7.99 (dd, J = 8.62, 2.03 Hz, 1H), 8.13 (d, J = 1.52 Hz, 1H), 9.00 (t, J = 5.58 Hz, 1H). |
| I-2-214 | 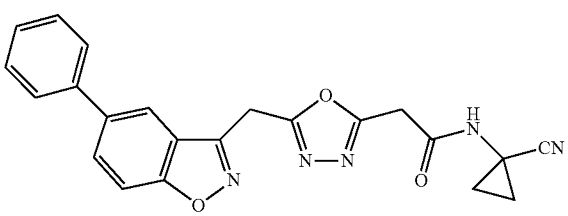 [SMILES: N#CC1(NC(=O)Cc2nnc(Cc3noc4ccc(-c5ccccc5)cc34)o2)CC1] | ¹H-NMR (DMSO-d₆) δ: 1.10 (dd, J = 8.62, 5.58 Hz, 2H), 1.46 (dd, J = 8.62, 5.58 Hz, 2H), 3.89 (s, 2H), 4.89 (s, 2H), 7.41 (t, J = 7.35 Hz, 1H), 7.48-7.54 (m, 2H), 7.69-7.75 (m, 2H), 7.86 (d, J = 8.62 Hz, 1H), 8.00 (dd, J = 8.87, 1.77 Hz, 1H), 8.13 (d, J = 1.77 Hz, 1H), 9.20 (s, 1H). |
| I-2-215 | 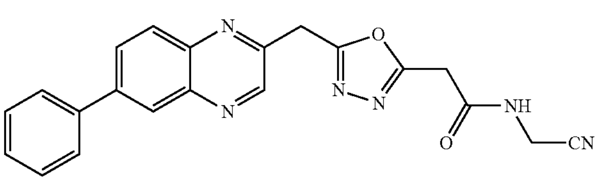 [SMILES: N#CCNC(=O)Cc1nnc(Cc2cnc3cc(-c4ccccc4)ccc3n2)o1] | ¹H-NMR (DMSO-d₆) δ: 3.97 (s, 2H), 4.19 (d, J = 5.6 Hz, 2H), 4.78 (s, 2H), 7.47 (t, J = 7.4 Hz, 1H), 7.56 (t, J = 7.6 Hz, 2H), 7.91 (d, J = 7.1 Hz, 2H), 8.11 (d, J = 9.1 Hz, 1H), 8.22 (dd, J = 9.1, 2.0 Hz, 1H), 8.37 (d, J = 2.0 Hz, 1H), 9.00 (t, J = 5.1 Hz, 1H), 9.04 (s, 1H). |

TABLE 62

| No. | Structure | NMR(δ) |
|---|---|---|
| I-2-216 | 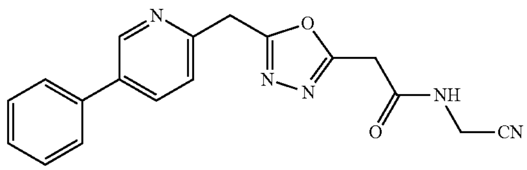 [SMILES: N#CCNC(=O)Cc1nnc(Cc2ccc(-c3ccccc3)cn2)o1] | ¹H-NMR (DMSO-d₆) δ: 3.95 (s, 2H), 4.19 (d, J = 5.4 Hz, 2H), 4.49 (s, 2H), 7.41-7.53 (m, 4H), 7.72 (d, J = 7.2 Hz, 2H), 8.10 (d, J = 8.7 Hz, 1H), 8.81(s, 1H), 9.00 (br-s, 1H). |
| I-2-217 | 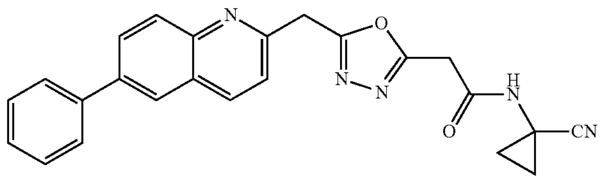 [SMILES: N#CC1(NC(=O)Cc2nnc(Cc3ccc4cc(-c5ccccc5)ccc4n3)o2)CC1] | (DMSO-d6) δ: 1.12 (dd, J = 8.70, 5.70 Hz, 2H), 1.48 (dd, J = 8.70, 5.70 Hz, 2H), 3.87 (s, 2H), 4.66 (s, 2H), 7.43 (t, J = 6.9 Hz, 1H), 7.50-7.60 (m, 3H), 7.84 (d, J = 4.2 Hz, 2H), 8.02 (d, J = 8.4 Hz, 1H), 8.09 (d, J = 2.4 Hz, 1H), 8.29 (s, 1H), 8.45 (d, J = 8.4 Hz, 1H), 9.21 (s, 1H). |
| I-2-218 | 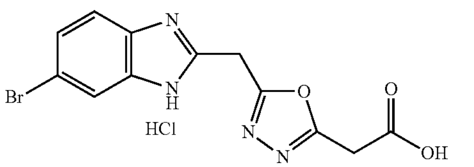 [SMILES: O=C(O)Cc1nnc(Cc2nc3ccc(Br)cc3[nH]2)o1 ; Cl] | (DMSO-d6) δ: 4.09 (s, 2H), 4.89 (s, 2H), 7.57 (dd, J = 8.4, 1.8 Hz, 1H), 7.69 (d, J = 8.7 Hz, 1H) |
| I-2-219 | 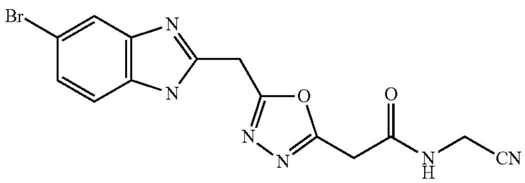 [SMILES: N#CCNC(=O)Cc1nnc(Cc2nc3cc(Br)ccc3[nH]2)o1] | (DMSO-d6) δ: 3.96 (s, 2H), 4.19 (d, J = 5.4 Hz, 2H), 4.59 (s, 2H), 7.31 (t, J = 9.3 Hz, 1H) 7.49 (dd, J = 19.2, 9.0 Hz, 1H), 7.73 (d, J = 22.2 Hz, 1H), 9.01 (t, J = 5.5 Hz, 1H), 12.73 (d, J = 17.7 Hz, 1H). |

TABLE 63

| No. | Structure | NMR(δ) | retention time | Mass | method |
|---|---|---|---|---|---|
| I-3-2 | 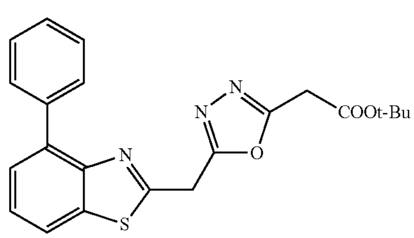 | | 2.47 | 408.00 (MS+) | C |
| I-3-3 | 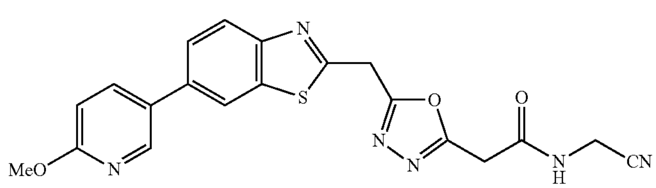 [SMILES: COc1ccc(-c2ccc3nc(Cc4nnc(CC(=O)NCC#N)o4)sc3c2)cn1] | | 1.56 | 421.30 (M+) | C |

TABLE 63-continued

| No. | Structure | NMR(δ) | retention time | Mass | method |
|---|---|---|---|---|---|
| I-3-4 | 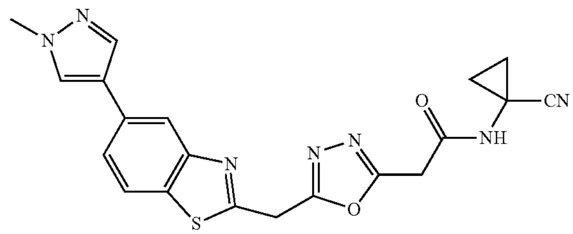 [SMILES: Cn1cc(-c2ccc3sc(Cc4nnc(CC(=O)NC5(C#N)CC5)o4)nc3c2)cn1] | (DMSO-d6) δ: 1.14 (dd, J = 8.36, 5.32 Hz, 2H), 1.49 (dd, J = 8.36, 5.32 Hz, 2H), 3.88 (s, 3H), 3.90 (s, 2H), 4.93 (s, 2H), 7.68 (dd, J = 8.36, 1.52 Hz, 1H), 7.98 (s, 1H), 8.06 (d, J = 8.36 Hz, 1H), 8.18 (d, J = 1.52 Hz, 1H), 8.24 (s, 1H), 9.22 (s, 1H). | | | |
| I-3-5 | 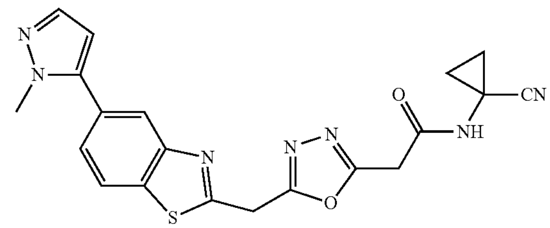 [SMILES: Cn1nccc1-c1ccc2sc(Cc3nnc(CC(=O)NC4(C#N)CC4)o3)nc2c1] | (DMSO-d6) δ: 1.14 (dd, J = 8.36, 5.58 Hz, 2H), 1.48 (dd, J = 8.36, 5.58 Hz, 2H), 3.90 (m, 5H), 4.98 (s, 2H), 6.50 (d, J = 2.03 Hz, 1H), 7.50 (d, J = 2.03 Hz, 1H), 7.62 (dd, J = 8.36, 1.52 Hz, 1H), 8.14 (d, J = 1.52 Hz, 1H), 8.23 (d, J = 8.36 Hz, 1H), 9.22 (s, 1H). | | | |
| I-3-6 | 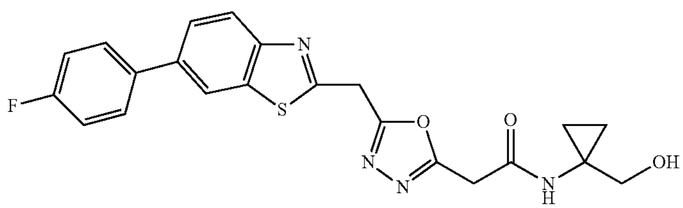 [SMILES: O=C(Cc1nnc(Cc2nc3ccc(-c4ccc(F)cc4)cc3s2)o1)NC1(CO)CC1] | (DMSO-d6) δ: 0.55 (dd, J = 6.6, 4.6 Hz, 2H), 0.66 (dd, J = 6.6, 4.6 Hz, 2H), 3.39 (d, J = 5.6 Hz, 2H), 3.79 (s, 2H), 4.69 (t, J = 5.8 Hz, 1H), 4.93 (s, 2H), 7.33 (t, J = 8.9 Hz, 2H), 7.77-7.83 (m, 3H), 8.04 (d, J = 8.6 Hz, 1H), 8.42 (d, J = 1.5 Hz, 1H), 8.53 (s, 1H). | 1.76 | 439.05 (MS+) | C |

TABLE 64

| No. | Structure | NMR(δ) | retention time | Mass | method |
|---|---|---|---|---|---|
| I-3-7 | 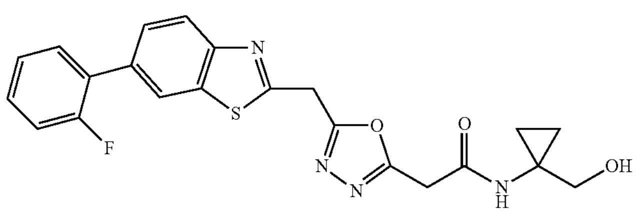 [SMILES: O=C(Cc1nnc(Cc2nc3ccc(-c4ccccc4F)cc3s2)o1)NC1(CO)CC1] | (DMSO-d6) δ: 0.56 (dd, J = 6.8, 4.9 Hz, 2H), 0.67 (dd, J = 6.8, 4.9 Hz, 2H), 3.39 (d, J = 6.1 Hz, 2H), 3.79 (s, 2H), 4.69 (t, J = 5.8 Hz, 1H), 4.95 (s, 2H), 7.31-7.39 (m, 2H), 7.44-7.49 (m, 1H), 7.61 (td, J = 7.9, 1.8 Hz, 1H), 7.69 (dt, J = 8.6, 1.8 Hz, 1H), 8.07 (d, J = 8.6 Hz, 1H), 8.32 (s, 1H), 8.53 (s, 1H). | 1.72 | 439.05 (MS+) | C |
| I-3-8 | 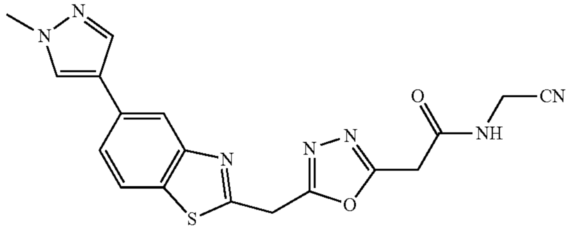 [SMILES: Cn1cc(-c2ccc3sc(Cc4nnc(CC(=O)NCC#N)o4)nc3c2)cn1] | (DMSO-d6) δ: 3.88 (s, 3H), 3.98 (s, 2H), 4.19 (d, J = 5.58 Hz, 2H), 4.92 (s, 2H), 7.68 (dd, J = 8.11, 1.52 Hz, 1H), 7.98 (s, 1H), 8.06 (d, J = 8.11 Hz, 1H), 8.18 (d, J = 1.52 Hz, 1H), 8.24 (s, 1H), 9.01 (t, J = 5.58 Hz, 1H). | | | |

TABLE 64-continued

| No. | Structure | NMR(δ) | retention time | Mass | method |
|---|---|---|---|---|---|
| I-3-9 | 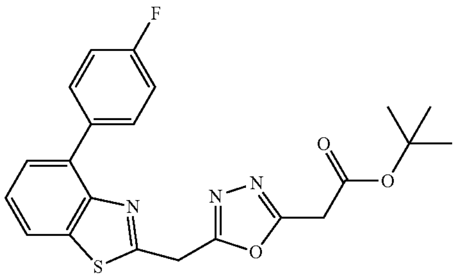 [SMILES: CC(C)(C)OC(=O)Cc1nnc(Cc2nc3c(-c4ccc(F)cc4)cccc3s2)o1] | (DMSO-d6) δ: 1.31 (s, 9H), 4.07 (s, 2H), 4.96 (s, 2H), 7.21-7.27 (m, 1H), 750-7.59 (m, 2H), 7.60-7.70 (m, 3H), 8.15 (d, J = 8.1 Hz, 1H). | | | |
| I-3-10 | 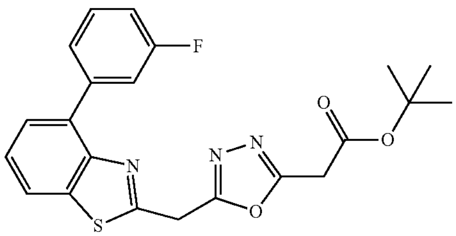 [SMILES: CC(C)(C)OC(=O)Cc1nnc(Cc2nc3c(-c4cccc(F)c4)cccc3s2)o1] | (DMSO-d6) δ: 1.14 (dd, J = 8.4, 5.3 Hz, 2H), 1.49 (dd, J = 8.4. 5.3 Hz. 2H), 3.91 (s, 2H), 4.94 (s, 2H), 7.41-7.64 (m, 5H), 7.80 (d, J = 6.9 Hz, 2H), 8.12 (d, J = 8.1 Hz, 1H), 9.23 (s, 1H). | | | |
| I-3-11 | 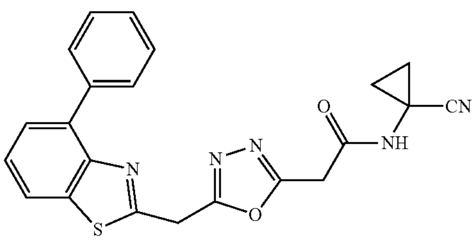 [SMILES: N#CC1(NC(=O)Cc2nnc(Cc3nc4c(-c5ccccc5)cccc4s3)o2)CC1] | DMSO-d6) δ: 0.54 (dd, J = 8.4, 5.3 Hz, 2H), 0.66 (dd, J = 8.4, 5.3 Hz. 2H), 3.38 (d, J = 6.0 Hz, 2H), 3.79 (s, 2H), 4.92 (s, 2H), 7.37-7.64 (m, 5H), 7.79 (s, 1H), 7.81 (d, J = 1.5 Hz, 1H), 8.12 (dd, J = 8.1, 1.5 Hz, 1H), 8.54 (s, 1H). | | | |

TABLE 65

| No. | Structure | NMR(δ) | retention time | Mass | method |
|---|---|---|---|---|---|
| I-3-12 | 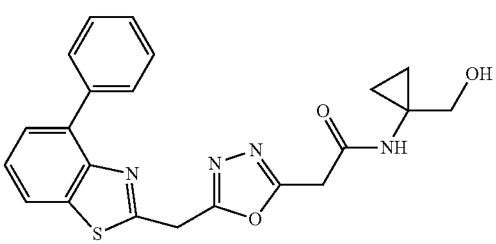 [SMILES: O=C(Cc1nnc(Cc2nc3c(-c4ccccc4)cccc3s2)o1)NC1(CO)CC1] | (DMSO-d6) δ: 4.081 (s, 2H), 4.95 (s, 2H), 7.41-7.64 (m, 5H), 7.79 (s, 1H), 7.81 (d, J = 1.5 Hz, 1H), 8.12 (dd, J = 8.1, 1.5 Hz, 1H).. | | | |
| I-3-13 | 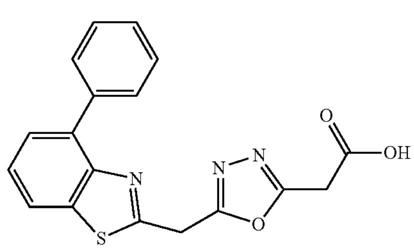 [SMILES: O=C(O)Cc1nnc(Cc2nc3c(-c4ccccc4)cccc3s2)o1] | (DMSO-d6) δ: 4.081 (s, 2H), 4.95 (s, 2H), 7.41-7.64 (m, 5H), 7.79 (s, 1H), 7.81 (d, J = 1.5 Hz, 1H), 8.12 (dd, J = 8.1, 1.5 Hz, 1H). | | | |

TABLE 65-continued

| No. | Structure | NMR(δ) | retention time | Mass | method |
|---|---|---|---|---|---|
| I-3-14 | 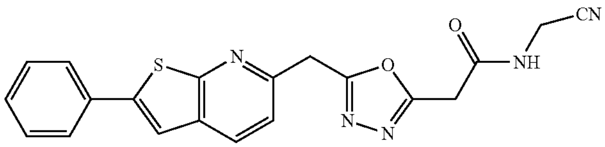 [SMILES: N#CCNC(=O)Cc1nnc(Cc2ccc3cc(-c4ccccc4)sc3n2)o1] | (DMSO-d6) δ: 3.95 (s, 2H), 4.18 (d, J = 5.6 Hz, 2H), 4.57 (s, 2H), 7.40-7.54 (m, 4H), 7.81 (d, J = 7.1 Hz, 2H), 7.87 (s, 1H), 8.24 (d, J = 8.1 Hz, 1H), 9.00 (t, J = 5.6 Hz, 1H). | 1.77 | 389.90 (MS+) | C |
| I-3-15 | 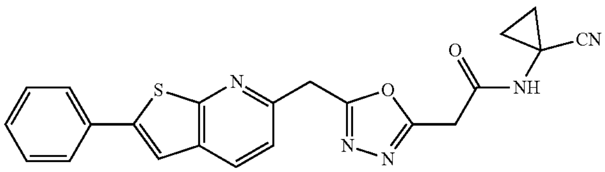 [SMILES: N#CC1(NC(=O)Cc2nnc(Cc3ccc4cc(-c5ccccc5)sc4n3)o2)CC1] | (DMSO-d6) δ: 1.13 (dd, J = 8.1, 5.6 Hz, 2H), 1.48 (dd, J = 8.4, 5.3 Hz, 2H), 3.87 (s, 2H), 4.57 (s, 2H), 7.40-7.54 (m, 4H), 7.81 (d, J = 7.1 Hz, 2H), 7.87 (s, 1H), 8.24 (d, J = 8.1 Hz, 1H), 9.21 (s, 1H). | 1.84 | 416.10 (MS+) | C |
| I-3-16 | 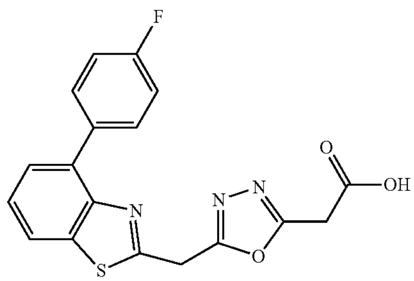 [SMILES: O=C(O)Cc1nnc(Cc2nc3c(-c4ccc(F)cc4)cccc3s2)o1] | (DMSO-d6) δ: 4.09 (s, 2H), 4.96 (s, 2H), 7.31 (t, J = 9.0 Hz, 2H), 755 (t, J = 7.8 Hz, 1H), 7.63 (d, J = 6.3 Hz, 1H), 7.83-7.89 (m, 2H), 8.11 (t, J = 7.8 Hz, 1H). | | | |

TABLE 66

| No. | Structure | NMR(δ) | retention time | Mass | method |
|---|---|---|---|---|---|
| I-3-17 | 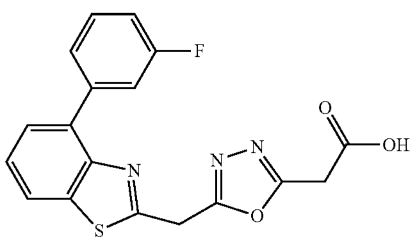 [SMILES: O=C(O)Cc1nnc(Cc2nc3c(-c4cccc(F)c4)cccc3s2)o1] | (DMSO-d6) δ: 4.07 (s, 2H), 4.96 (s, 2H), 7.21-7.27 (m, 1H), 750-7.59 (m, 2H), 7.60-7.70 (m, 3H), 8.15 (d, J = 8.1 Hz, 1H). | | | |
| I-3-18 | 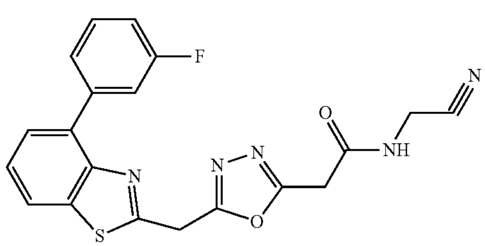 [SMILES: N#CCNC(=O)Cc1nnc(Cc2nc3c(-c4cccc(F)c4)cccc3s2)o1] | (DMSO-d6) δ: 3.99 (s, 2H), 4.19 (d, J = 5.7 Hz, 2H), 4.94 (s, 2H), 7.32 (t, J = 8.7 Hz, 2H), 7.52-7.64 (m, 2H), 7.86 (dd, J = 8.7, 5.7 Hz, 2H), 8.12 (d, J = 7.8 Hz, 1H), 9.02 (t, J = 5.3 Hz, 1H). | | | |

TABLE 66-continued

| No. | Structure | NMR(δ) | retention time | Mass | method |
|---|---|---|---|---|---|
| I-3-19 | 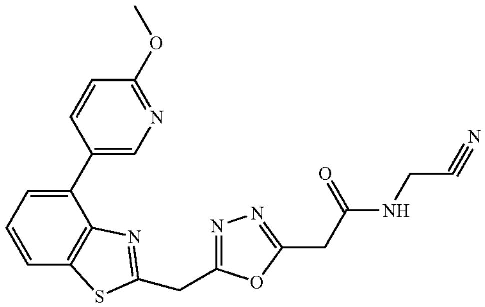 [SMILES: COc1ccc(-c2cccc3sc(Cc4nnc(CC(=O)NCC#N)o4)nc23)cn1] | (DMSO-d6) δ: 3.92 (s, 3H), 3.99 (s, 2H), 4.19 (d, J = 5.7 Hz, 2H), 4.95 (s, 2H), 6.94 (d, J = 8.7 Hz, 1H), 7.55 (t, J = 7.8 Hz, 1H), 7.66 (d, J = 6.3 Hz, 1H), 8..11 (d, J = 6.6 Hz, 1H), 8.14 (dd, J = 8.7, 2.4 Hz, 1H), 8.63 (d, J = 2.1 Hz, 1H), 9.03 (t, J = 5.3 Hz, 1H). | | | |
| I-3-20 | 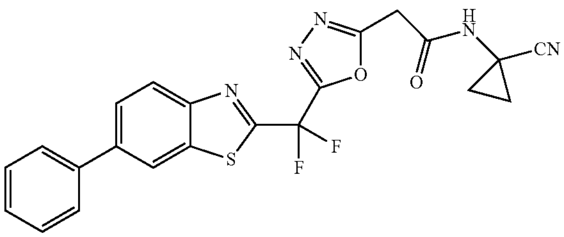 [SMILES: N#CC1(NC(=O)Cc2nnc(C(F)(F)c3nc4ccc(-c5ccccc5)cc4s3)o2)CC1] | (DMSO-d6) δ: 1.16 (dd, J = 8.1, 5.6 Hz, 2H), 1.50 (dd, J = 8.1, 5.6 Hz, 2H), 4.10 (s, 2H), 7.45 (t, J = 7.4 Hz, 1H), 7.54 (t, J = 7.6 Hz, 2H), 7.80 (d, J = 7.1 Hz, 2H), 8.01 (dd, J = 8.6. 2.0 Hz, 1H), 8.28 (d, J = 8.6 Hz, 1H), 8.68 (d, J = 1.5 Hz, 1H), 9.30 (s, 1H). | 2.27 | 451.90 (MS+) | C |
| I-3-21 | 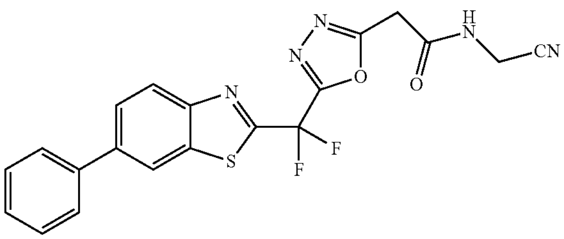 [SMILES: N#CCNC(=O)Cc1nnc(C(F)(F)c2nc3ccc(-c4ccccc4)cc3s2)o1] | (DMSO-d6) δ: 4.18 (s, 2H), 4.22 (d, J = 5.6 Hz, 2H), 7.45 (t, J = 7.1 Hz, 1H), 7.54 (dd, J = 10.4, 4.8 Hz, 2H), 7.80 (d, J = 7.1 Hz, 2H), 8.00 (dd, J = 8.9, 1.8 Hz, 1H), 8.28 (d, J = 8.6 Hz, 1H), 8.68 (d, J = 1.5 Hz, 1H), 9.10 (t, J = 5.6 Hz, 1H). | 2.19 | 425.90 (MS+) | C |

TABLE 67

| No. | Structure | NMR(δ) | retention time | Mass | method |
|---|---|---|---|---|---|
| I-3-22 | 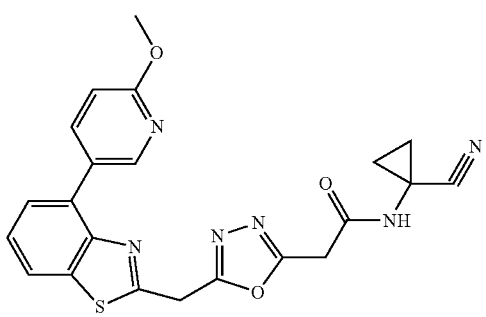 [SMILES: COc1ccc(-c2cccc3sc(Cc4nnc(CC(=O)NC5(C#N)CC5)o4)nc23)cn1] | (DMSO-d6) δ: 1.14 (dd, J = 8.4, 5.3 Hz, 2H), 1.49 (dd, J = 8.4, 5.3 Hz, 2H), 3.91 (s, 2H), 3.92 (s, 3H), 4.96 (s, 2H), 6.95 (d, J = 8.7 Hz, 1H), 7.55 (t, J = 7.2 Hz, 1H), 7.66 (d, J = 7.5 Hz, 1H), 8.11-8.19 (m, 2H), 8.63 (s, 1H), 9.22 (s, 1H). | | | |
| I-3-23 | 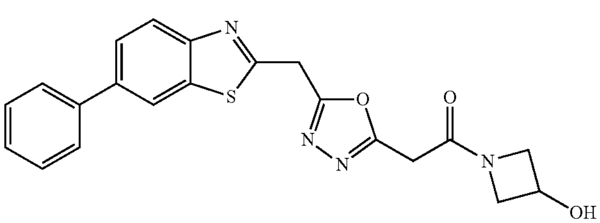 [SMILES: O=C(Cc1nnc(Cc2nc3ccc(-c4ccccc4)cc3s2)o1)N1CC(O)C1] | | 1.65 | 406.95 (M+) | C |

TABLE 67-continued

| No. | Structure | NMR(δ) | retention time | Mass | method |
|---|---|---|---|---|---|
| I-3-24 | 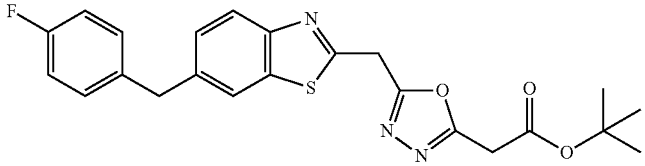 [SMILES: CC(C)(C)OC(=O)Cc1nnc(Cc2nc3ccc(Cc4ccc(F)cc4)cc3s2)o1] | (CDCl3) δ: 3.87 (s, 9H), 4.72 (s, 2H), 7.39 (t, J = 7.4 Hz, 1H), 7.47 (t, J = 7.6 Hz, 2H), 7.63 (d, J = 7.1 Hz, 2H), 7.73 (dd, J = 8.6, 1.5 Hz, 1H), 8.06-8.09 (m, 2H). | | | |
| I-3-25 | 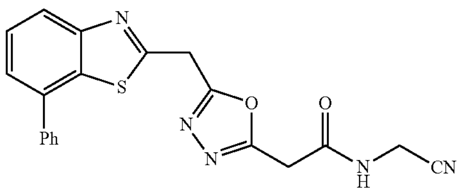 [SMILES: N#CCNC(=O)Cc1nnc(Cc2nc3cccc(-c4ccccc4)c3s2)o1] | (DMSO-d6) δ: 3.98 (s, 2H), 4.18 (d, J = 5.6 Hz, 2H), 4.95 (s, 2H), 7.48 (t, J = 9.9 Hz, 1H), 7.54-7.59 (m, 3H), 7.66 (t, J = 7.9 Hz, 1H), 7.71 (m, 2H), 8.01 (d, J = 7.1 Hz, 1H), 9.02 (t, J = 5.6 Hz, 1H). | 1.76 | 390.1 (MS+) | C |
| I-3-26 | 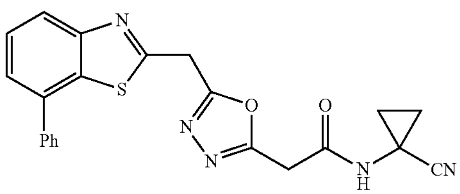 [SMILES: N#CC1(NC(=O)Cc2nnc(Cc3nc4cccc(-c5ccccc5)c4s3)o2)CC1] | (DMSO-d6) δ: 1.12 (dd, J = 8.1, 5.6 Hz, 2H), 1.47 (dd, J = 8.4, 5.3 Hz, 2H), 3.90 (s, 2H), 4.95 (s, 2H), 7.48 (t, J = 7.4 Hz, 1H), 7.54-7.59 (m, 3H), 7.66 (t, J = 7.9 Hz, 1H), 7.69-7.73 (m, 2H), 8.01 (dd, J = 8.1, 1.0 Hz, 1H), 9.22 (s, 1H). | 1.83 | 415.90 (MS+) | C |

TABLE 68

| No. | Structure | NMR(δ) | retention time | Mass | method |
|---|---|---|---|---|---|
| I-3-27 | 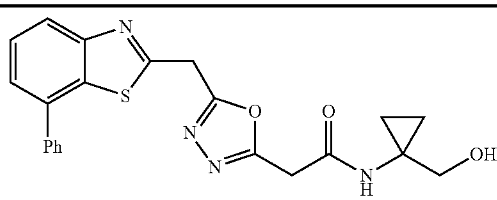 | (DMSO-d6) δ: 0.53 (dd, J = 6.8, 4.8 Hz, 2H), 0.65 (dd, J = 6.8, 4.8 Hz, 2H), 3.38 (d, J = 6.1 Hz, 2H), 3.78 (s, 2H), 4.69 (t, J = 5.8 Hz, 1H), 4.93 (s, 2H), 7.48 (t, J = 7.1 Hz, 1H), 7.53-7.59 (m, 3H), 7.66 (t, J = 7.9 Hz. 1H), 7.68-7.73 (m, 2H), 8.01 (dd, J = 8.1, 1.0 Hz, 1H), 8.53 (s, 1H). | 1.7 | 420.95 (MS+) | C |
| I-3-28 | 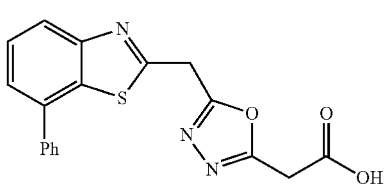 [SMILES: O=C(O)Cc1nnc(Cc2nc3cccc(-c4ccccc4)c3s2)o1] | | 1.76 | 351.80 (MS+) | C |

TABLE 68-continued

| No. | Structure | NMR(δ) | retention time | Mass | method |
|---|---|---|---|---|---|
| I-3-29 | 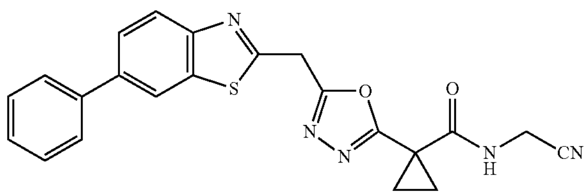 [SMILES: N#CCNC(=O)C1(c2nnc(Cc3nc4ccc(-c5ccccc5)cc4s3)o2)CC1] | | 2.06 | 416.00 (M+) | C |
| I-3-30 | 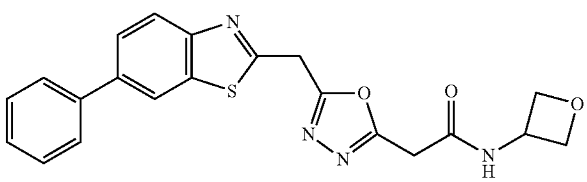 [SMILES: O=C(Cc1nnc(Cc2nc3ccc(-c4ccccc4)cc3s2)o1)NC1COC1] | (CDCl3) δ: 3.89 (br-s, 2H), 4.56 (br-s, 2H), 4.75 (m, 2H), 4.91 (br-s, 2H), 5.05 (m, 1H), 7.38-7.74 (m, 7H), 8.06 (br-s 2H). | | | |
| I-3-31 | 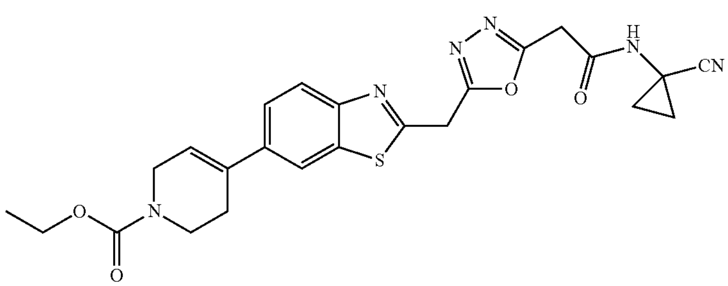 [SMILES: CCOC(=O)N1CC=C(c2ccc3nc(Cc4nnc(CC(=O)NC5(C#N)CC5)o4)sc3c2)CC1] | (DMSO-d6) δ: 1.13 (dd, J = 8.4, 5.8 Hz, 2H), 1.21 (t, J = 7.1 Hz, 3H), 1.48 (dd, J = 8.4, 5.3 Hz, 2H), 2.53-2.60 (m, 2H), 3.62 (t, J = 5.3 Hz, 2H), 3.90 (s, 2H), 4.02-4.14 (m, 4H), 4.92 (s, 2H), 6.28-6.30 (m, 1H), 7.63 (dd, J = 8.6, 1.5 Hz, 1H), 7.93 (d, J = 8.6 Hz, 1H), 8.17 (d, J = 1.5 Hz, 1H), 9.23 (s, 1H). | 1.73 | 493.00 (MS+) | C |

TABLE 69

| No. | Structure | NMR(δ) | retention time | Mass | method |
|---|---|---|---|---|---|
| I-3-32 | 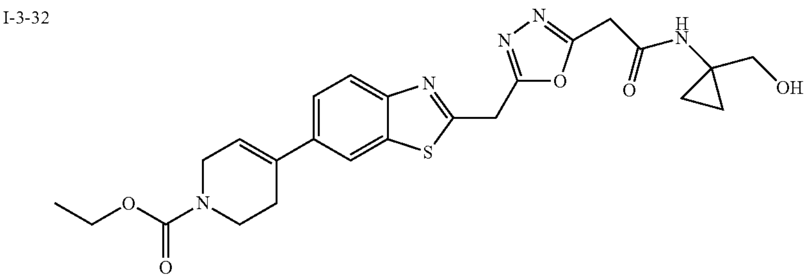 | (DMSO-d₆) δ: 0.55 (dd, J = 6.6, 5.1 Hz, 2H), 0.66 (dd, J = 6.6, 4.6 Hz, 2H), 1.21 (t, J = 7.1 Hz, 3H), 2.53-2.59 (m, 2H), 3.39 (d, J = 6.1 Hz, 2H), 3.61 (t, J = 5.3 Hz, 2H), 3.78 (s, 2H), 4.04-4.13 (m, 4H), 4.70 (t, J = 5.8 Hz, 1H), 4.90 (s, 2H), 6.27-6.30 (m, 1H), 7.63 (dd, J = 8.6, 1.5 Hz, 1H), 7.93 (d, J = 8.6 Hz, 1H), 8.16 (d, J = 1.5 Hz, 1H), 8.53 (s, 1H). | 1.53 | 498.05 (MS+) | C |
| I-3-33 | 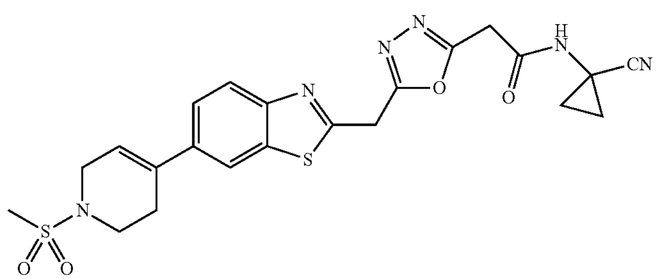 [SMILES: CS(=O)(=O)N1CC=C(c2ccc3nc(Cc4nnc(CC(=O)NC5(C#N)CC5)o4)sc3c2)CC1] | (DMSO-d₆) δ: 1.13 (dd, J = 8.1, 5.6 Hz, 2H), 1.48 (dd, J = 8.1, 5.6 Hz, 2H), 2.64-2.72 (m, 2H), 2.95 (s, 3H), 3.41 (t, J = 5.8 Hz, 2H), 3.87-3.93 (m, 4H), 4.93 (s, 2H), 6.31-6.34 (m, 1H), 7.66 (dd, J = 8.6, 2.0 Hz, 1H), 7.94 (d, J = 8.6 Hz, 1H), 8.19 (d, J = 1.5 Hz, 1H), 9.23 (s, 1H). | 1.41 | 499.00 (MS+) | C |
| I-3-34 | 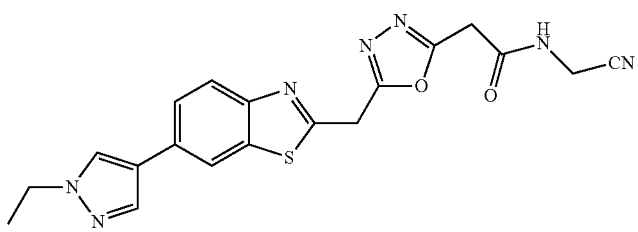 [SMILES: CCn1cc(-c2ccc3nc(Cc4nnc(CC(=O)NCC#N)o4)sc3c2)cn1] | (DMSO-d6) δ: 1.47 (t, J = 6.3 Hz, 3H), 3.99 (s, 2H), 4.13-4.21 (m, 4H), 4.92 (s, 2H), 7.74 (d, J = 6.6 Hz, 1H), 7.91-7.96 (m, 2H), 729 (d, J = 8.1 Hz, 2H), 9.02 (t, J = 5.3 Hz, 1H). | | | |

TABLE 69-continued

| No. | Structure | NMR(δ) | retention time | Mass | method |
|---|---|---|---|---|---|
| I-3-35 | 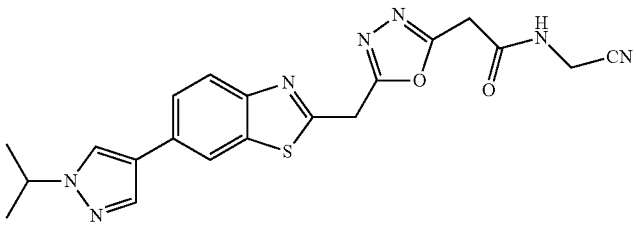 | (DMSO-d6) δ: 1.45 (s, 3H), 1.47 (s, 3H), 3.99 (s, 2H), 4.19 (d, J = 5.4 Hz, 2H), 4.51 (m, 1H), 4.91 (s, 2H), 7.74 (d, J = 6.6 Hz, 1H), 7.93 (d, J = 8.1 Hz, 2H), 8.32 (s, 2H), 9.02 (t, J = 5.3 Hz, 1H). | | | |

TABLE 70

| No. | Structure | NMR(δ) | retention time | Mass | method |
|---|---|---|---|---|---|
| I-3-36 | 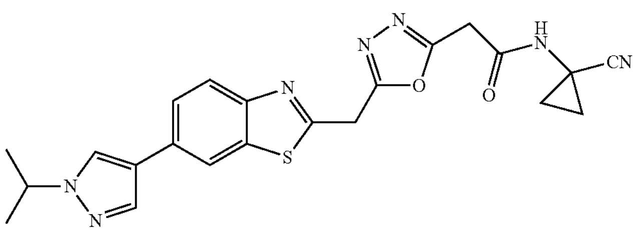 [SMILES: CC(C)n1cc(-c2ccc3nc(Cc4nnc(CC(=O)NC5(C#N)CC5)o4)sc3c2)cn1] | (DMSO-d6) δ: 1.14 (dd, J = 8.4, 5.3 Hz, 2H), 1.44 (s, 3H), 1.47 (s, 3H), 1.49 (dd, J = 8.4, 5.3 Hz, 2H), 3.91 (s, 2H), 4.51 (m, 1H), 4.92 (s, 2H), 7.75 (d J = 8.4 Hz, 1H), 7.94 (d, J = 8.7 Hz, 2H), 8.32 (s, 2H), 9.23 (s, 1H). | | | |
| I-3-37 | 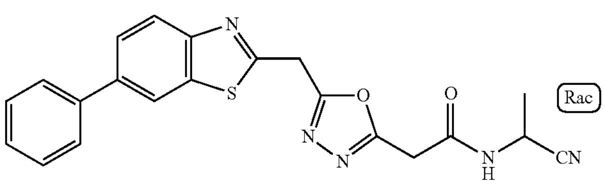 [SMILES: CC(C#N)NC(=O)Cc1nnc(Cc2nc3ccc(-c4ccccc4)cc3s2)o1] | | 1.86 | 403.95 (M+) | C |
| I-3-38 | 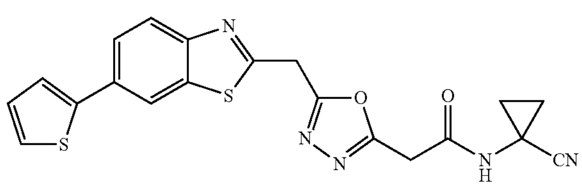 [SMILES: N#CC1(NC(=O)Cc2nnc(Cc3nc4ccc(-c5cccs5)cc4s3)o2)CC1] | (DMS0-d6) δ: 1.14 (dd, J = 8.3, 5.5 Hz, 2H), 1.49 (dd, J = 8.3, 5.5 Hz, 2H), 3.91 (s, 2H), 4.95 (s, 2H), 7.18 (dd, J = 5.0, 3.5 Hz, 1H), 7.58-7.63 (m, 2H), 7.82 (dd, J = 8.5, 1.9 Hz, 1H), 8.00 (d, J = 8.2 Hz, 1H), 8.45 (d, J = 1.5 Hz, 1H), 9.24 (s, 1H). | 1.78 | 421.90 (MS+) | C |
| I-3-39 | 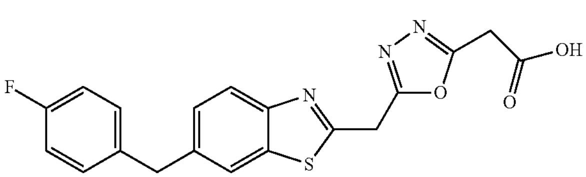 [SMILES: O=C(O)Cc1nnc(Cc2nc3ccc(Cc4ccc(F)cc4)cc3s2)o1] | | 1.89 | 383.80 (MS+) | C |

TABLE 70-continued

| No. | Structure | NMR(δ) | retention time | Mass | method |
|---|---|---|---|---|---|
| I-3-40 | 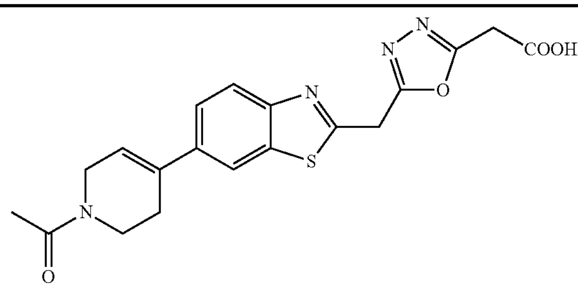 | | 1.18 | 398.90 (MS+) | C |

TABLE 71

| No. | Structure | NMR(δ) | retention time | Mass | method |
|---|---|---|---|---|---|
| I-3-41 | 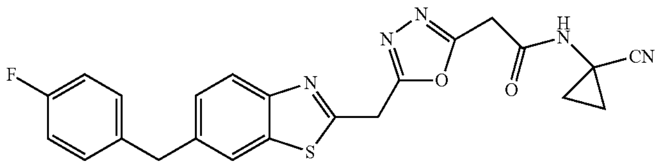 [SMILES: N#CC1(NC(=O)Cc2nnc(Cc3nc4ccc(Cc5ccc(F)cc5)cc4s3)o2)CC1] | (DMSO-d6) δ: 1.13 (dd, J = 8.1, 5.6 Hz, 2H), 1.48 (dd, J = 8.1, 5.6 Hz, 2H), 3.89 (s, 2H), 4.08 (s, 2H), 4.90 (s, 2H), 7.09-7.13 (m, 2H), 7.26-7.32 (m, 2H), 7.38 (dd, J = 8.6, 1.5 Hz, 1H), 7.89 (d, J = 8.6 Hz. 1H), 7.96 (d, J = 1.0 Hz, 1H), 9.22 (s, 1H). | 1.98 | 447.95 (MS+) | C |
| I-3-42 | 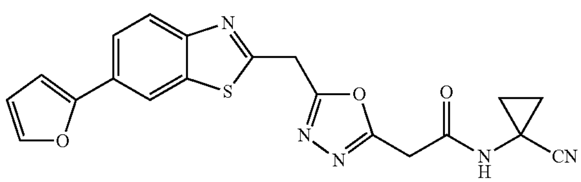 | (DMSO-d6) δ: 1.14 (dd, J = 8.3, 5.5 Hz, 2H), 1.49 (dd, J = 8.3, 5.5 Hz, 2H), 3.91 (s, 2H), 4.95 (s, 2H), 6.65 (dd, J = 3.3, 1.9 Hz, 1H), 7.06 (d, J = 3.4 Hz, 1H), 7.81 (d, J =1.5 Hz, 1H), 7.87 (dd, J = 8.6, 1.4 Hz, 1H), 8.01 (d, J = 8.9 Hz, 1H), 8.45 (d, J = 1.3 Hz, 1H), 9.24 (s, 1H). | 1.71 | 405.90 (MS+) | C |
| I-3-43 | 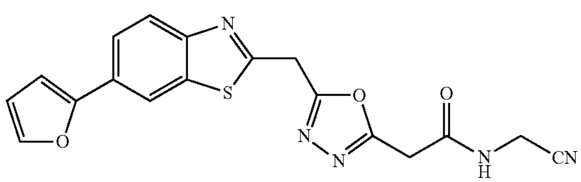 | (DMSO-d6) δ: 3.99 (s, 2H), 4.19 (d, J = 5.6 Hz, 2H), 4.94 (s, 2H), 6.64 (dd, J = 3.3, 1.8 Hz, 1H)), 7.06 (d, J = 3.0 Hz, 1H), 7.81 (d, J = 1.0 Hz, 1H), 7.87 (dd, J = 8.6, 2.0 Hz, 1H), 8.00 (d, J = 8.6 Hz, 1H), 8.44 (d, J = 1.5 Hz, 1H), 9.03 (t, J = 5.3 Hz, 1H). | 1.63 | 380.00 (MS+) | C |
| I-3-44 | 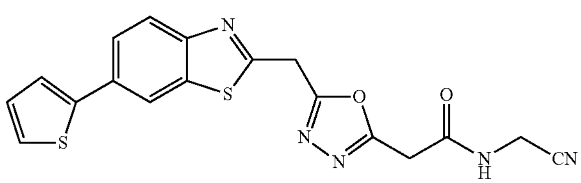 [SMILES: N#CCNC(=O)Cc1nnc(Cc2nc3ccc(-c4ccco4)cc3s2)o1] | (DMSO-d6) δ: 3.99 (s, 2H), 4.19 (d, J = 5.6 Hz, 2H), 4.94 (s, 2H), 7.18 (dd, J = 5.1, 4.1 Hz, 1H)), 7.59-7.63 (m, 2H), 7.82 (dd, J = 8.4, 1.8 Hz, 1H), 7.99 (d, J = 8.6 Hz, 1H), 8.44 (d, J = 2.0 Hz, 1H), 9.03 (t, J = 5.3 Hz, 1H). | 1.74 | 395.80 (MS+) | C |
| I-3-45 | 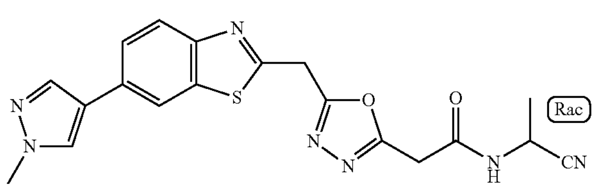 [SMILES: CC(C#N)NC(=O)Cc1nnc(Cc2nc3ccc(-c4cnn(C)c4)cc3s2)o1] | (DMSO-d6) δ: 1.59 (d, J = 7.2 Hz, 3H), 3.94-3.97 (m, 5H), 4.73 (s, 2H), 4.92 (m, 1H), 7.59 (d, J = 6.9 Hz, 1H), 7.67 (s, 1H), 7.805 (s, 1H), 7.94-7.99 (m, 3H) | | | |

TABLE 72

| No. | Structure | NMR(δ) | retention time | Mass | method |
|---|---|---|---|---|---|
| I-3-46 | 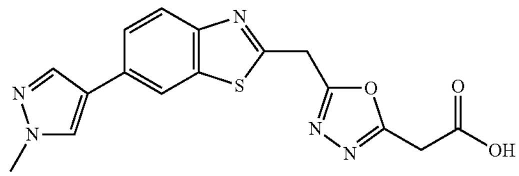 [SMILES: Cn1cc(-c2ccc3nc(Cc4nnc(CC(=O)O)o4)sc3c2)cn1] | (DMSO-d6) δ: 3.88 (s, 3H), 4.07 (s, 2H), 4.92 (s, 2H), 7.72 (d, J = 8.4Hz, 2H), 7.92-7.96 (m, 2H), 8.21 (s, 1H), 8.29(s, 2H) | | | |
| I-3-47 | 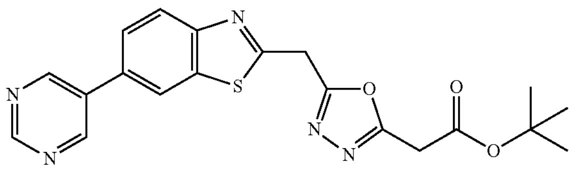 [SMILES: CC(C)(C)OC(=O)Cc1nnc(Cc2nc3ccc(-c4cncnc4)cc3s2)o1] | (CDCl3) δ: 1.44 (s, 9H), 3.90 (s, 2H), 4.78 (s, 2H), 7.71 (d, J = 9.0 Hz, 1H), 8.09 (s, 1H), 8.16 (d, J = 8.7 Hz, 1H), 9.02 (s, 2H), 9.25 (s, 1H) | | | |
| I-3-48 | 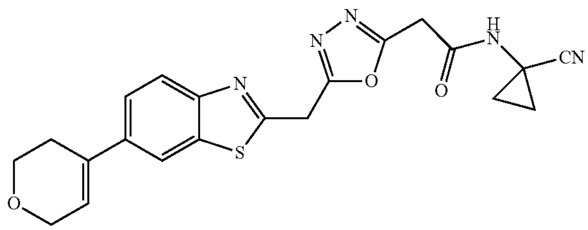 [SMILES: N#CC1(NC(=O)Cc2nnc(Cc3nc4ccc(C5=CCOCC5)cc4s3)o2)CC1] | (DMSO-d6) δ: 1.13 (dd, J = 8.36, 5.32 Hz, 2H), 1.48 (dd, J = 8.36, 5.32 Hz, 2H), 3.85 (t, J = 5.58 Hz, 2H), 3.90 (s, 2H), 4.26 (q, J = 2.70 Hz, 2H), 4.92 (s, 2H), 6.37-6.40 (m, 1H), 7.65 (dd, J = 8.62, 1.52 Hz, 1H), 7.93 (d, J = 8.62 Hz, 1H), 8.17 (d, J = 2.03 Hz, 1H), 9.23 (s, 1H). | 1.49 | 422.00 (MS+) | C |
| I-3-49 | 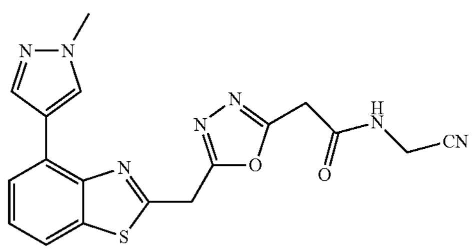 [SMILES: Cn1cc(-c2cccc3sc(Cc4nnc(CC(=O)NCC#N)o4)nc23)cn1] | (DMSO-d6) δ: 3.91 (s, 3H), 4.02 (s, 2H), 4.18 (d, J = 5.4 Hz, 2H), 4.99 (s, 2H), 7.44 (t, J = 9.6 Hz, 1H), 7.78 (d, J = 2.3 Hz, 1H), 7.92 (d, J = 7.5Hz, 1H), 8.17 (s, 1H), 8.44 (s, 1H), 9.02 (t, J = 5.3 Hz, 1H). | | | |
| I-3-50 | 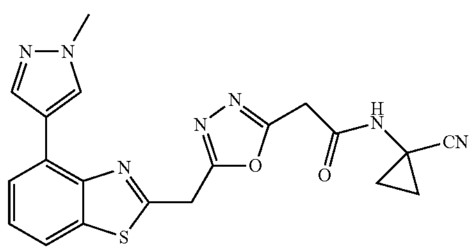 [SMILES: Cn1cc(-c2cccc3sc(Cc4nnc(CC(=O)NC5(C#N)CC5)o4)nc23)cn1] | (DMSO-d6) δ: 1.14 (dd, J = 8.4, 5.3 Hz, 2H), 1.49 (dd, J = 8.4, 5.3 Hz, 2H), 3.92 (s, 3H), 3.93 (s, 2H), 5.00 (s, 2H), 7.44 (t J = 8.1 Hz, 1H), 7.78 (d, J = 8.1 Hz, 1H), 8.16 (s, 1H), 8.44 (s, 1H), 9.24 (s, 1H). | | | |

TABLE 73

| No. | Structure | NMR(δ) | retention time | Mass | method |
|---|---|---|---|---|---|
| I-3-51 | 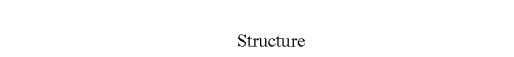 | (DMSO-d6) δ: 1.42 (t, J = 7.2 Hz, 3H), 4.08 (s, 2H), 4.15 (q, J = 7.2 Hz, 2H), 4.94 (s, 2H), 7.73 (dd, J = 8.1, 1.5 Hz, 1H), 7.93 (s, 1H), 7.95 (d, J = 6.9 Hz, 1H), 8.28 (s, 1H), 8.31 (d, J = 1.5Hz, 1H). | | | |

TABLE 73-continued

| No. | Structure | NMR(δ) | retention time | Mass | method |
|---|---|---|---|---|---|
| I-3-52 | (1-ethylpyrazol-4-yl)-benzothiazole-CH2-oxadiazole-CH2-C(O)NH-C(CN)(cyclopropyl) | (DMSO-d6) δ: 1.14 (dd, J = 8.4, 5.3 Hz, 2H), 1.42 (t, J = 7.2 Hz, 3H), 1.49 (dd, J = 8.4, 5.3 Hz, 2H), 3.91 (s, 2H), 8.17 (q J = 7.2 Hz, 1H), 4.91 (s, 2H), 7.73 (dd, J = 8.1, 1.5 Hz, 1H), 7.93 (s, 1H), 7.95 (d, J = 6.9 Hz, 1H), 8.28 (s, 1H), 8.31 (d, J = 1.5Hz, 1H).. | | | |
| I-3-53 | (2-chlorophenyl)-benzothiazole-CH2-oxadiazole-CH2-C(O)NH-C(CN)(cyclopropyl) | | 2.43 | 449.07 (MS+) | C |
| I-3-54 | (3-chlorophenyl)-benzothiazole-CH2-oxadiazole-CH2-C(O)NH-C(CN)(cyclopropyl) | | 2.56 | 449.07 (MS+) | C |
| I-3-55 | (4-chlorophenyl)-benzothiazole-CH2-oxadiazole-CH2-C(O)NH-C(CN)(cyclopropyl) | | 2.43 | 449.07 (MS+) | C |

TABLE 74

| No. | Structure | retention time | Mass | method |
|---|---|---|---|---|
| I-3-56 | (5-chlorothiophen-2-yl)-benzothiazole-CH2-oxadiazole-CH2-C(O)NH-C(CN)(cyclopropyl) | 2.58 | 455.03 (MS+) | C |
| I-3-57 | (4-(hydroxymethyl)phenyl)-benzothiazole-CH2-oxadiazole-CH2-C(O)NH-C(CN)(cyclopropyl) | 1.92 | 445.12 (MS+) | C |
| I-3-58 | (2-methylphenyl)-benzothiazole-CH2-oxadiazole-CH2-C(O)NH-C(CN)(cyclopropyl) | 2.34 | 429.13 (MS+) | C |

TABLE 74-continued

| No. | Structure | retention time | Mass | method |
|---|---|---|---|---|
| I-3-59 | 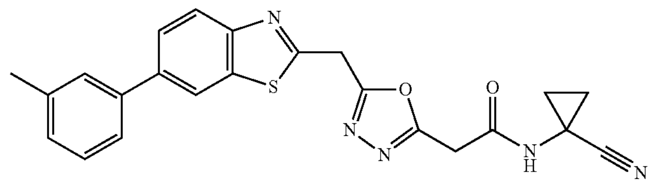 [SMILES: Cc1cccc(-c2ccc3nc(Cc4nnc(CC(=O)NC5(C#N)CC5)o4)sc3c2)c1] | 2.4 | 429.13 (MS+) | C |
| I-3-60 | 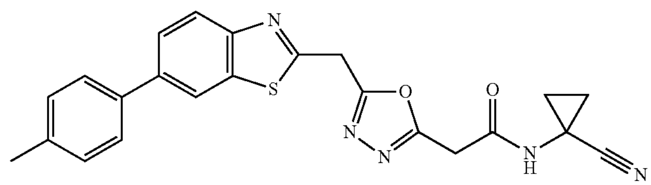 [SMILES: Cc1ccc(-c2ccc3nc(Cc4nnc(CC(=O)NC5(C#N)CC5)o4)sc3c2)cc1] | 2.37 | 429.13 (MS+) | C |

TABLE 75

| No. | Structure | retention time | Mass | method |
|---|---|---|---|---|
| I-3-61 | 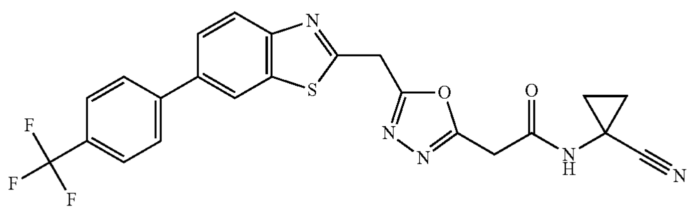 [SMILES: N#CC1(NC(=O)Cc2nnc(Cc3nc4ccc(-c5ccc(C(F)(F)F)cc5)cc4s3)o2)CC1] | 2.62 | 483.10 (MS+) | C |
| I-3-62 | 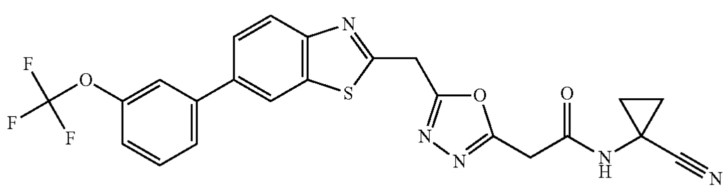 [SMILES: N#CC1(NC(=O)Cc2nnc(Cc3nc4ccc(-c5cccc(OC(F)(F)F)c5)cc4s3)o2)CC1] | 2.64 | 499.09 (MS+) | C |
| I-3-63 | 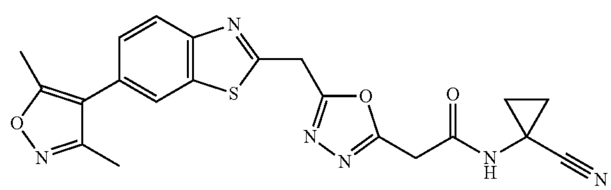 [SMILES: Cc1noc(C)c1-c1ccc2nc(Cc3nnc(CC(=O)NC4(C#N)CC4)o3)sc2c1] | 2.07 | 434.12 (MS+) | C |
| I-3-64 | 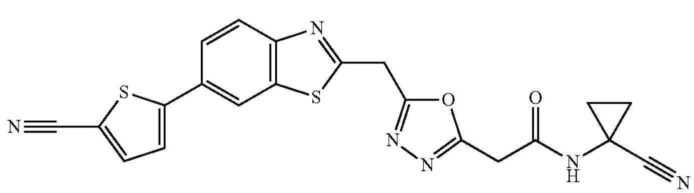 [SMILES: N#Cc1ccc(-c2ccc3nc(Cc4nnc(CC(=O)NC5(C#N)CC5)o4)sc3c2)s1] | 2.27 | 446.06 (MS+) | C |
| I-3-65 | 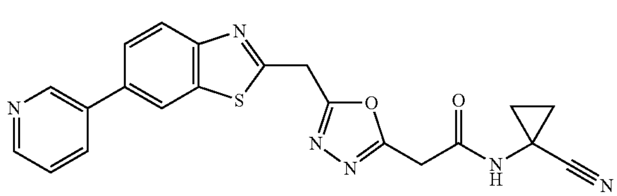 | 1.38 | 416.11 (MS+) | C |

TABLE 76

| No. | Structure | retention time | Mass | method |
|---|---|---|---|---|
| I-3-66 | 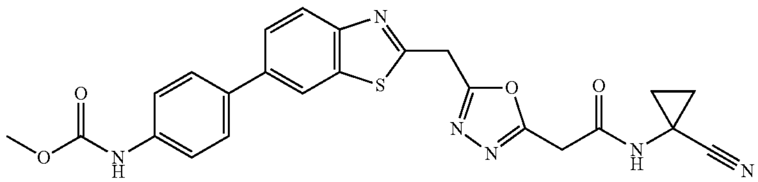 [SMILES: COC(=O)Nc1ccc(-c2ccc3nc(Cc4nnc(CC(=O)NC5(C#N)CC5)o4)sc3c2)cc1] | 2.14 | 488.13 (MS+) | C |
| I-3-67 | 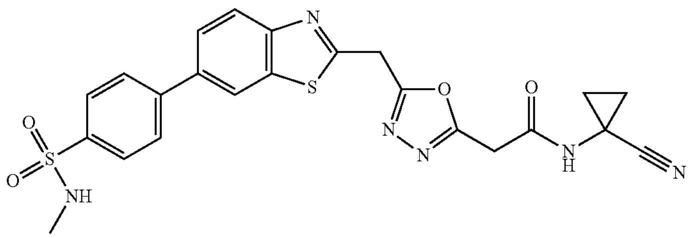 [SMILES: CNS(=O)(=O)c1ccc(-c2ccc3nc(Cc4nnc(CC(=O)NC5(C#N)CC5)o4)sc3c2)cc1] | 2.03 | 508.10 (MS+) | C |
| I-3-68 | 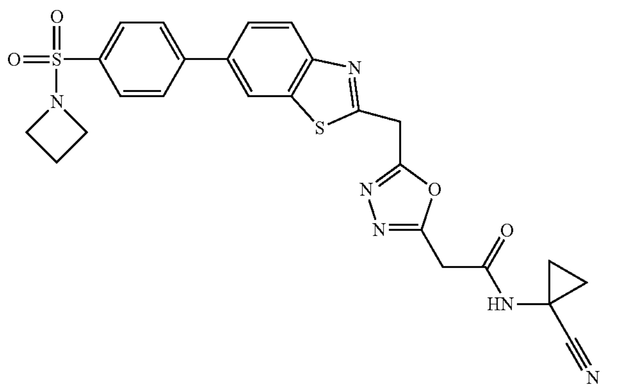 [SMILES: N#CC1(NC(=O)Cc2nnc(Cc3nc4ccc(-c5ccc(S(=O)(=O)N6CCC6)cc5)cc4s3)o2)CC1] | 2.21 | 534.11 (MS+) | C |
| I-3-69 | 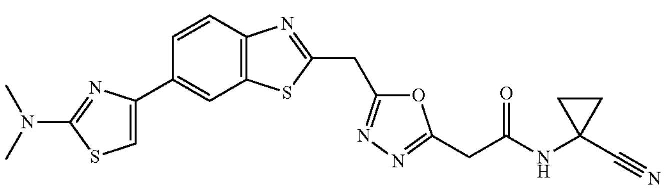 [SMILES: CN(C)c1nc(-c2ccc3nc(Cc4nnc(CC(=O)NC5(C#N)CC5)o4)sc3c2)cs1] | 2.16 | 465.10 (MS+) | C |
| I-3-70 | 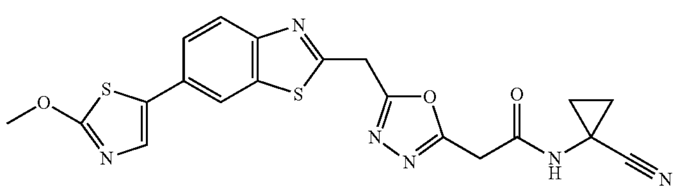 [SMILES: COc1ncc(-c2ccc3nc(Cc4nnc(CC(=O)NC5(C#N)CC5)o4)sc3c2)s1] | 2.16 | 452.07 (MS+) | C |

TABLE 77

| No. | Structure | NMR(δ) | retention time | Mass | method |
|---|---|---|---|---|---|
| I-3-71 | 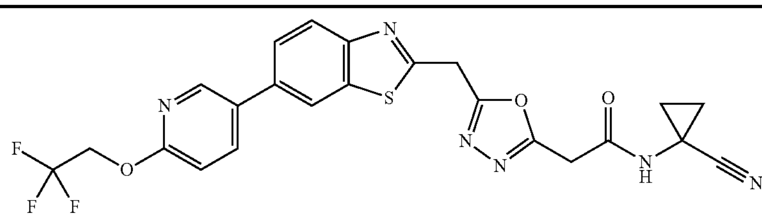 | | 2.53 | 514.10 (MS+) | C |

TABLE 77-continued

| No. | Structure | NMR(δ) | retention time | Mass | method |
|---|---|---|---|---|---|
| I-3-72 | 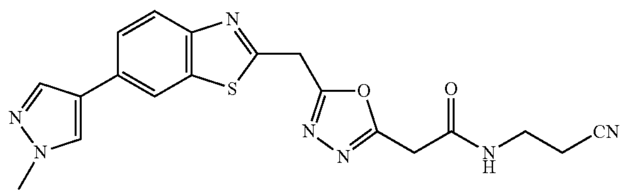 [SMILES: Cn1cc(-c2ccc3nc(Cc4nnc(CC(=O)NCCC#N)o4)sc3c2)cn1] | | 1.14 | 408.25 (MS+) | C |
| I-3-73 | 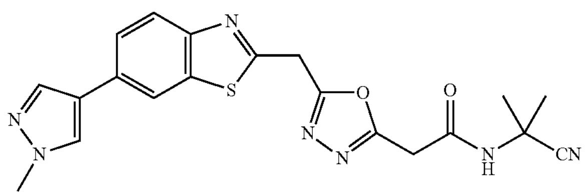 [SMILES: Cn1cc(-c2ccc3nc(Cc4nnc(CC(=O)NC(C)(C)C#N)o4)sc3c2)cn1] | (CDCl3) δ: 1.74 (s, 6H), 3.91 (s, 2H), 3.97 (s, 3H), 4.73 (s, 2H), 7.61 (d, J = 8.62 Hz, 1H), 7.67 (s, 1H), 7.81 (s, 2H), 7.94-7.99 (m, 1H) | | | |
| I-3-74 | 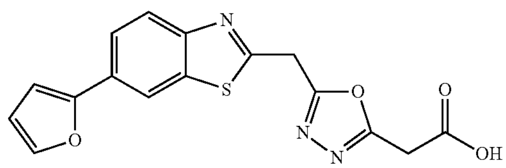 [SMILES: O=C(O)Cc1nnc(Cc2nc3ccc(-c4ccco4)cc3s2)o1] | | 1.59 | 341.75 (MS+) | C |
| I-3-75 | 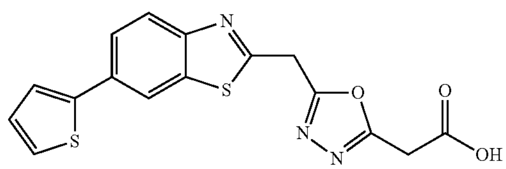 | | 1.7 | 357.80 (MS+) | C |

TABLE 78

| No. | Structure | NMR(δ) | retention time | Mass | method |
|---|---|---|---|---|---|
| I-3-76 | 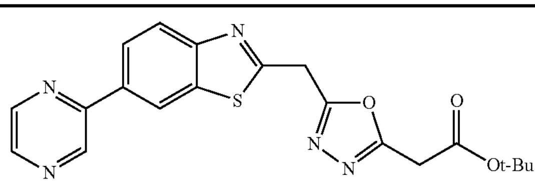 | | 1.87 | 409.90 (MS+) | C |
| I-3-77 | 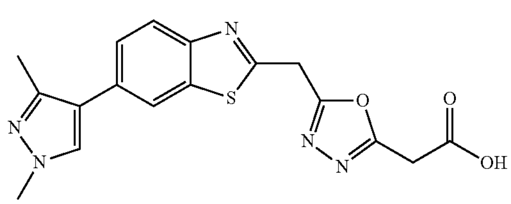 [SMILES: Cc1nn(C)cc1-c1ccc2nc(Cc3nnc(CC(=O)O)o3)sc2c1] | | 1.19 | 369.85 (MS+) | C |

TABLE 78-continued

| No. | Structure | NMR(δ) | retention time | Mass | method |
|---|---|---|---|---|---|
| I-3-78 | 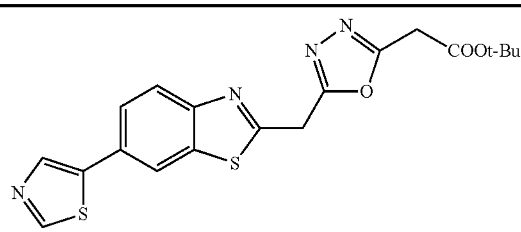 | | 1.92 | 414.90 (MS+) | C |
| I-3-79 | 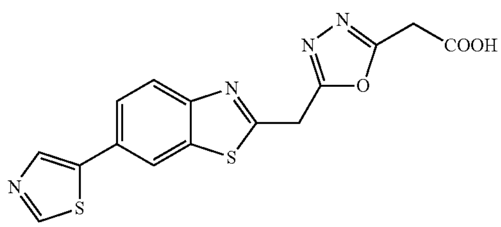 [SMILES: O=C(O)Cc1nnc(Cc2nc3ccc(-c4cncs4)cc3s2)o1] | | 1.24 | 358.80 (MS+) | C |
| I-3-80 | 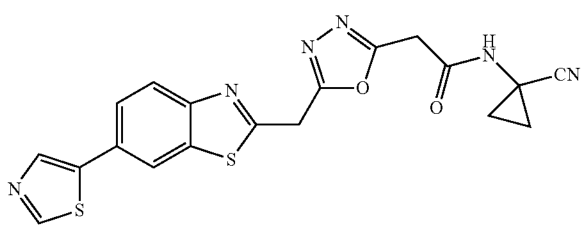 [SMILES: N#CC1(NC(=O)Cc2nnc(Cc3nc4ccc(-c5cncs5)cc4s3)o2)CC1] | (DMSO-d6) δ: 1.14 (dd, J = 8.36, 5.32 Hz, 2H), 1.49 (dd, J = 8.36, 5.32 Hz, 2H), 3.91 (s, 2H), 4.96 (s, 2H), 7.86 (dd, J = 8.62, 1.52 Hz, 1H), 8.03 (d, J = 8.62 Hz, 1H), 8.40 (s, 1H), 8.50 (d, J = 1.52 Hz, 1H), 9.13 (s, 1H), 9.23 (s, 1H). | 1.36 | 422.85 (MS+) | C |

TABLE 79

| No. | Structure | NMR(δ) | retention time | Mass | method |
|---|---|---|---|---|---|
| I-3-81 | 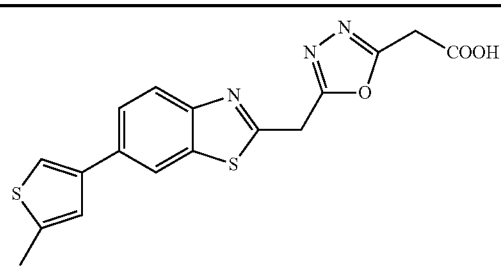 | | 1.91 | 371.95 (MS+) | C |
| I-3-82 | 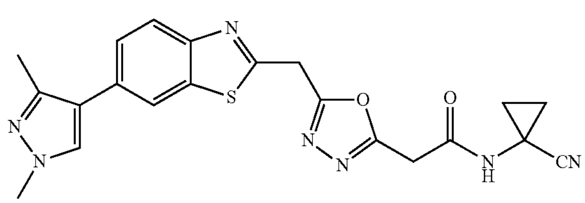 [SMILES: Cc1nn(C)cc1-c1ccc2nc(Cc3nnc(CC(=O)NC4(C#N)CC4)o3)sc2c1] | (DMSO-d6) δ: 1.14 (dd, J = 8.1, 5.6 Hz, 2H), 1.48 (dd, J = 8.1, 5.6 Hz, 2H), 2.34 (s, 3H), 3.80 (s, 3H), 3.90 (s, 2H), 4.92 (s, 2H), 7.57 (dd, J = 8.4, 1.8 Hz, 1H), 7.96 (d, J = 8.1 Hz, 2H), 7.97 (s, 1H), 8.13 (d, J = 1.5 Hz, 1H), 9.23 (s, 1H). | 1.29 | 433.90 (MS+) | C |
| I-3-83 | 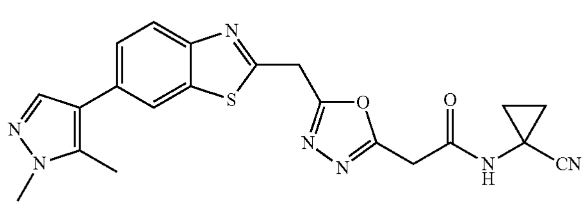 [SMILES: Cc1c(-c2ccc3nc(Cc4nnc(CC(=O)NC5(C#N)CC5)o4)sc3c2)cnn1C] | (DMSO-d6) δ: 1.14 (dd, J = 8.1, 5.6 Hz, 2H), 1.48 (dd, J = 8.1, 5.6 Hz, 2H), 2.41 (s, 3H), 3.80 (s, 3H), 3.90 (s, 2H), 4.93 (s, 2H), 7.55 (dd, J = 8.6, 1.5 Hz, 1H), 7.65 (s, 1H), 7.98 (d, J = 8.6 Hz, 1H), 8.12 (d, J = 1.5 Hz, 1H), 9.23 (s, 1H). | 1.34 | 433.95 (MS+) | C |

TABLE 79-continued

| No. | Structure | NMR(δ) | retention time | Mass | method |
|---|---|---|---|---|---|
| I-3-84 | 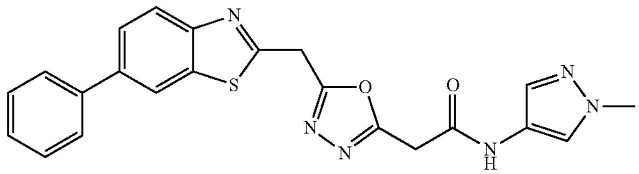 [SMILES: Cn1cc(NC(=O)Cc2nnc(Cc3nc4ccc(-c5ccccc5)cc4s3)o2)cn1] | DMSO-d6 δ: 3.78 (s, 3H), 4.04 (s, 2H), 4.96 (s, 2H), 7.37-7.42 (m, 1H), 7.50 (t, J = 6.9 Hz, 1H), 7.75-7.84 (m, 2H), 8.03 (d, J = 8.4 Hz, 1H), 8.29 (d, J = 1.5 Hz, 1H), 10.40 (s, 1H). | | | |
| I-3-85 | 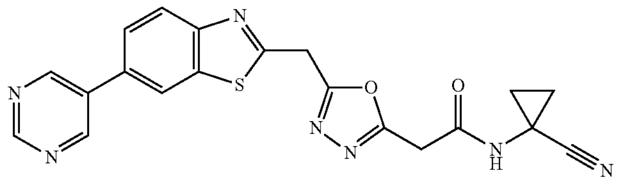 [SMILES: N#CC1(NC(=O)Cc2nnc(Cc3nc4ccc(-c5cncnc5)cc4s3)o2)CC1] | (DMSO-d6) δ: 1.13-1.15 (m, 2H), 1.47-1.50 (m, 2H), 3.91 (s, 2H), 4.99 (s, 2H), 7.98 (d, J = 8.7 Hz, 1H), 8.14 (d, J = 8.7 Hz, 1H), 8.62 (s, 1H), 9.19-9.25 (m, 4H) | | | |

TABLE 80

| No. | Structure | NMR(δ) | retention time | Mass | method |
|---|---|---|---|---|---|
| I-3-86 | 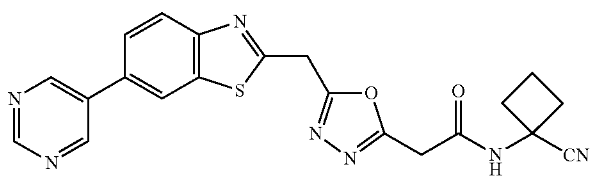 [SMILES: N#CC1(NC(=O)Cc2nnc(Cc3nc4ccc(-c5cncnc5)cc4s3)o2)CCC1] | (DMSO-d6) δ: 2.01-2.29 (m, 2H), 2.41(m, 2H), 2.81 (m, 2H), 3.94 (s, 2H), 4.79 (s, 2H), 7.72 (d, J = 8.36 Hz, 1H), 8.00 (br-s, 1H), 8.09 (s, 2H), 8.16 (d, J = 8.1 Hz, 1H), 9.02 (s, 2H), 9.25 (s, 1H) | | | |
| I-3-87 | 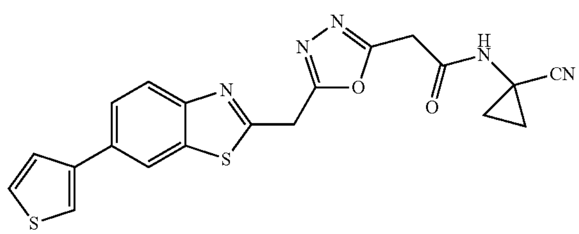 [SMILES: N#CC1(NC(=O)Cc2nnc(Cc3nc4ccc(-c5ccsc5)cc4s3)o2)CC1] | (DMSO-d6) δ: 1.14 (dd, J = 8.36, 5.32 Hz, 2H), 1.49 (dd, J = 8.36, 5.32 Hz, 2H), 3.91 (s, 2H), 4.94 (s, 2H), 7.65 (dd, J = 5.07, 1.52 Hz, 1H), 7.69 (dd, J = 5.07, 3.04 Hz, 1H), 7.90 (dd, J = 8.62, 1.52 Hz, 1H), 7.97-8.01 (m, 2H), 8.48 (d, J = 1.52 Hz, 1H), 9.23 (s, 1H). | 1.82 | 421.85 (MS+) | C |
| I-3-88 | 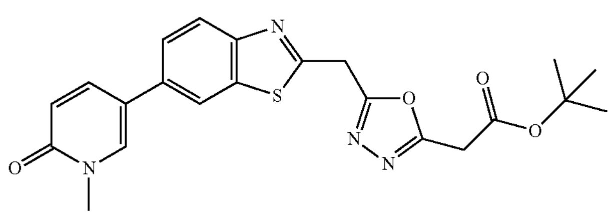 [SMILES: Cn1cc(-c2ccc3nc(Cc4nnc(CC(=O)OC(C)(C)C)o4)sc3c2)ccc1=O] | (DMSO-d6) δ: 1.43 (s, 9H), 3.65 (s, 3H), 3.89 (s, 2H), 4.74 (s, 2H), 7.51-7.65 (m, 2H), 7.65 (d, J = 7.5 Hz, 1H), 7.88 (s, 1H), 8.04 (d, J = 8.4 Hz, 1H) | | | |
| I-3-89 | 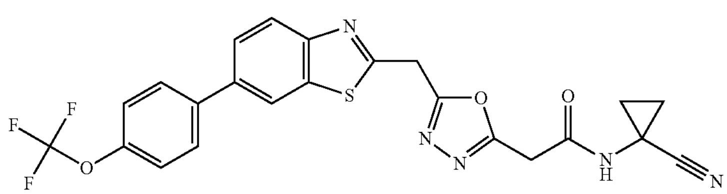 [SMILES: N#CC1(NC(=O)Cc2nnc(Cc3nc4ccc(-c5ccc(OC(F)(F)F)cc5)cc4s3)o2)CC1] | | 2.52 | 499.09 (M+) | C |

TABLE 80-continued

| No. | Structure | NMR(δ) | retention time | Mass | method |
|---|---|---|---|---|---|
| I-3-90 | 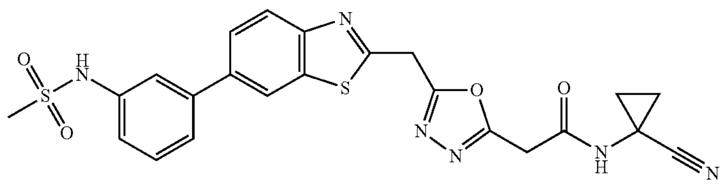 [SMILES: CS(=O)(=O)Nc1cccc(-c2ccc3nc(Cc4nnc(CC(=O)NC5(C#N)CC5)o4)sc3c2)c1] | | 1.92 | 508.10 (M+) | C |

TABLE 81

| No. | Structure | NMR(δ) | retention time | Mass | method |
|---|---|---|---|---|---|
| I-3-91 | 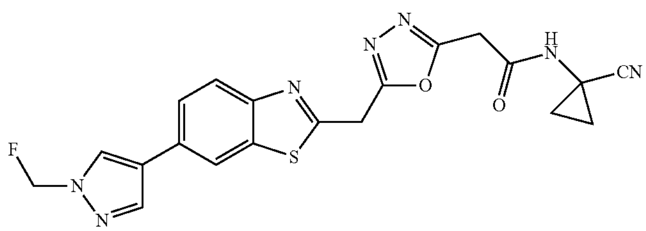 [SMILES: N#CC1(NC(=O)Cc2nnc(Cc3nc4ccc(-c5cnn(CF)c5)cc4s3)o2)CC1] | (DMSO-d6) δ: 1.14 (dd, J = 8.36, 5.83 Hz, 2H), 1.49 (dd, J = 8.36, 5.32 Hz, 2H), 3.91 (s, 2H), 4.94 (s, 2H), 6.19 (d, J = 53.23 Hz, 2H), 7.80 (dd, J = 8.36, 1.77 Hz, 1H), 7.99 (d, J = 8.11 Hz, 1H), 8.23 (s, 1H), 8.40 (d, J = 1.52 Hz, 1H), 8.58 (s, 1H), 9.23 (s, 1H). | 1.32 | 438.15 (MS+) | C |
| I-3-92 | 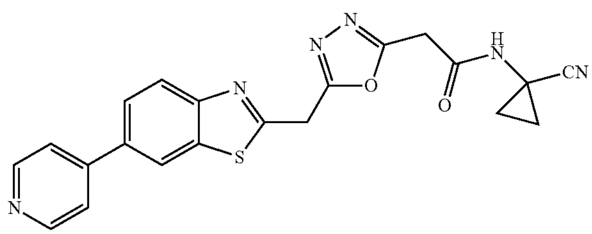 [SMILES: N#CC1(NC(=O)Cc2nnc(Cc3nc4ccc(-c5ccncc5)cc4s3)o2)CC1] | 1H-NMR (DMSO-d6) δ: 1.14 (dd, J = 8.36, 5.32 Hz, 2H), 1.49 (dd, J = 8.36, 5.32 Hz, 2H), 3.91 (s, 2H), 4.99 (s, 2H), 7.79-7.82 (m, 2H), 7.97 (dd, J = 8.62, 2.03 Hz, 1H), 8.11 (d, J = 8.62 Hz, 1H), 8.63 (d, J = 1.52 Hz, 1H), 8.66-8.69 (m, 2H), 9.24 (s, 1H). | 0.76 | 416.90 (MS+) | C |
| I-3-93 | 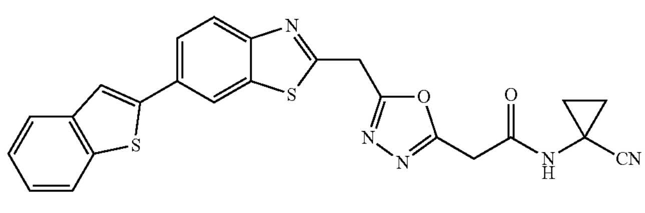 [SMILES: N#CC1(NC(=O)Cc2nnc(Cc3nc4ccc(-c5cc6ccccc6s5)cc4s3)o2)CC1] | (DMSO-d6) δ: 1.14 (dd, J = 8.1, 5.6 Hz, 2H), 1.49 (dd, J = 8.1, 5.6 Hz, 2H), 3.92 × 27 (s, 2H), 4.98 (s, 2H), 7.36-7.44 (m, 2H), 7.88 (d, J = 7.1 Hz, 1H), 7.93-7.98 (m, 2H), 8.01 (d, J = 7.6 Hz, 1H), 8.06 (d, J = 8.6 Hz, 1H), 8.58 (d, J = 2.0 Hz, 1H), 9.24 (s, 1H). | 2.19 | 471.90 (MS+) | C |
| I-3-94 | 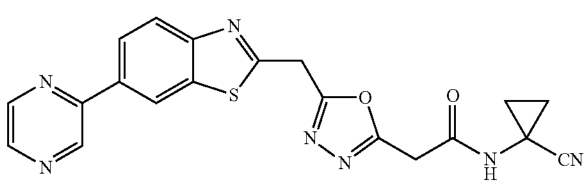 [SMILES: N#CC1(NC(=O)Cc2nnc(Cc3nc4ccc(-c5cnccn5)cc4s3)o2)CC1] | (DMSO-d6) δ: 1.14 (dd, J = 8.1, 5.6 Hz, 2H), 1.49 (dd, J = 8.1, 5.6 Hz, 2H), 3.92 (s, 2H), 5.00 (s, 2H), 8.12 (d, J = 8.6 Hz, 1H), 8.31 (dd, J = 8.6, 2.0 Hz, 1H), 8.65 (d, J = 2.5 Hz, 1H), 8.76 (dd, J = 2.5, 1.5 Hz, 1H), 8.94 (d, J = 1.5 Hz, 1H), 9.24 (s, 1H), 9.36 (d, J = 1.0 Hz, 1H). | 1.28 | 417.90 (MS+) | C |

TABLE 82

| No. | Structure | NMR(δ) | retention time | Mass | method |
|---|---|---|---|---|---|
| I-3-95 | 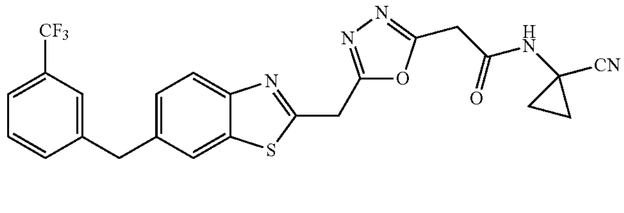 [SMILES: N#CC1(NC(=O)Cc2nnc(Cc3nc4ccc(Cc5cccc(C(F)(F)F)c5)cc4s3)o2)CC1] | (DMSO-d6) δ: 1.12 (dd, J = 8.36, 5.32 Hz, 2H), 1.47 (dd, J = 8.11, 5.58 Hz, 2H), 3.89 (s, 2H), 4.20 (s, 2H), 4.90 (s, 2H), 7.43 (dd, J = 8.36, 1.77 Hz, 1H), 7.50-7.61 (m, 3H), 7.65 (s, 1H), 7.91 (d, J = 8.11 Hz, 1H), 8.02 (d, J = 1.01 Hz, 1H), 9.23 (s, 1H). | 2.16 | 498.00 (MS+) | C |
| I-3-96 | 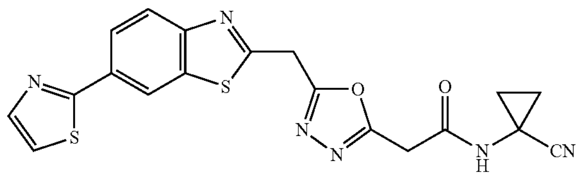 [SMILES: N#CC1(NC(=O)Cc2nnc(Cc3nc4ccc(-c5nccs5)cc4s3)o2)CC1] | (DMSO-d6) δ: 1.14 (m, 2H), 1.49 (m, 2H), 3.91 (s, 2H), 4.98 (s, 2H), 7.84 (d, J = 3.3 Hz, 1H), 7.97 (d, J = 3.3 Hz, 1H), 8.08-8.11 (m, 2H), 8.77 (s, 1H), 9.23 (s, 1H). | | | |
| I-3-97 | 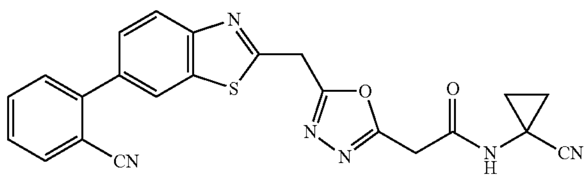 [SMILES: N#Cc1ccccc1-c1ccc2nc(Cc3nnc(CC(=O)NC4(C#N)CC4)o3)sc2c1] | (DMSO-d6) δ: 1.14 (m, 2H), 1.49 (m, 2H), 3.91 (s, 2H), 4.99 (s, 2H), 7.63 (t, J = 7.8 Hz, 1H), 7.70-7.72 (m, 3H), 7.84 (t, J = 7.8 Hz, 1H), 7.99 (d, J = 7.5 Hz, 1H), 8.13 (d, J = 7.8 Hz, 1H), 8.37 (s, 1H), 9.23 (s, 1H). | | | |
| I-3-98 | 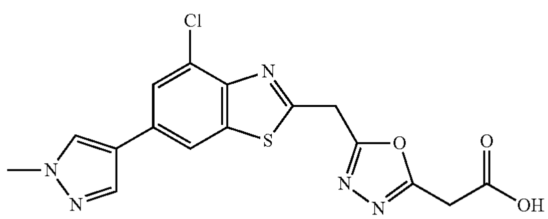 [SMILES: Cn1cc(-c2cc(Cl)c3nc(Cc4nnc(CC(=O)O)o4)sc3c2)cn1] | (DMSO-d6) δ: 3.88 (s, 3H), 4.08 (s, 2H), 4.98 (s, 2H), 7.88 (d, J = 1.5 Hz, 1H), 7.99 (s, 1H), 8.28-8.30 (m, 2H). | | | |
| I-3-99 | 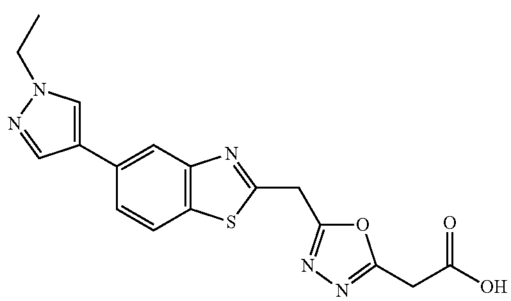 [SMILES: CCn1cc(-c2ccc3sc(Cc4nnc(CC(=O)O)o4)nc3c2)cn1] | (DMSO-d6) δ: 1.42 (t, J = 7.2 Hz, 3H), 4.08 (s, 2H), 4.15 (q, J = 7.2 Hz, 2H), 4.94 (s, 2H), 7.69 (dd, J = 8.1, 1.5 Hz, 1H), 7.99 (s, 1H), 8.05 (d, J = 6.9 Hz, 1H), 8.19 (d, J = 4.0 Hz, 1H), 8.31 (s, 1H) | | | |

TABLE 83

| No. | Structure | NMR(δ) | retention time | Mass | method |
|---|---|---|---|---|---|
| I-3-100 | 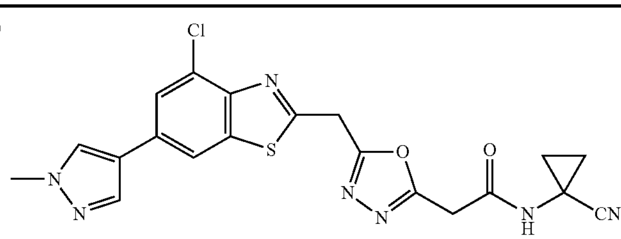 | (DMSO-d6) δ: 1.14 (dd, J = 8.4, 5.3 Hz, 2H), 1.49 (dd, J = 8.4, 5.3 Hz, 2H), 3.88 (s, 3H), 3.91 (s, 2H), 4.97 (s, 2H), 7.78 (d, J = 1.5 Hz, 1H), 7.99 (s, 1H), 8.28-8.30 (m, 2H), 9.23 (s, 1H). | | | |

TABLE 83-continued

| No. | Structure | NMR(δ) | retention time | Mass | method |
|---|---|---|---|---|---|
| I-3-101 | 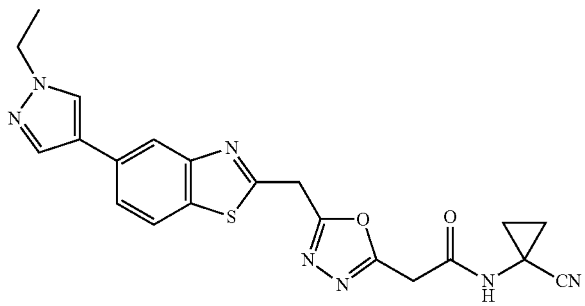 [SMILES: CCn1cc(-c2ccc3sc(Cc4nnc(CC(=O)NC5(C#N)CC5)o4)nc3c2)cn1] | (DMSO-d6) δ: 1.14 (dd, J = 8.4, 5.3 Hz, 2H), 1.42 (t, J = 7.2 Hz, 3H), 1.49 (dd, J = 8.4, 5.3 Hz, 2H), 3.91 (s, 2H), 7.69 (dd, J = 8.1, 1.50 Hz, 1H), 7.99 (s, 1H), 8.05 (d, J = 6.9 Hz, 1H), 8.19 (d, J = 4.0 Hz, 1H), 8.31 (s, 1H), 9.23 (s, 1H). | | | |
| I-3-102 | 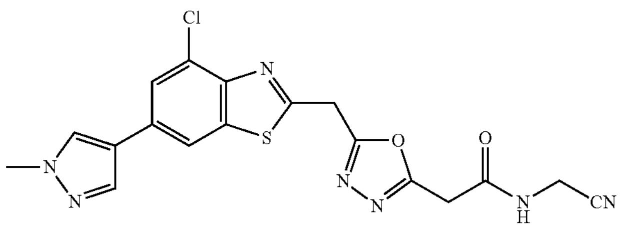 [SMILES: Cn1cc(-c2cc(Cl)c3nc(Cc4nnc(CC(=O)NCC#N)o4)sc3c2)cn1] | (DMSO-d6) δ: 3.87 (s, 3H), 3.99 (s, 2H), 4.19 (d, J = 5.4 Hz, 2H), 4.97 (s, 2H), 7.88 (d, J = 1.5 Hz, 1H), 7.99 (d, J = 1.5 Hz, 1H), 8.27-8.30 (m, 2H), 9.02 (t, J = 5.3 Hz, 1H). | | | |
| I-3-103 | 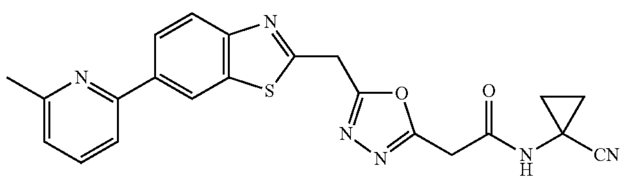 [SMILES: Cc1cccc(-c2ccc3nc(Cc4nnc(CC(=O)NC5(C#N)CC5)o4)sc3c2)n1] | (DMSO-d6) δ: 1.15 (m, 2H), 1.49 (m, 2H), 3.91 (s, 2H), 4.97 (s, 2H), 7.25 (s, J = 7.5 Hz, 1H), 7.80-7.85 (m, 2H), 8.05 (d, J = 9.3 Hz, 1H), 8.25 (d, J = 10.2 Hz, 1H), 8.83 (s, 1H), 9.24 (s, 1H) | | | |
| I-3-104 | 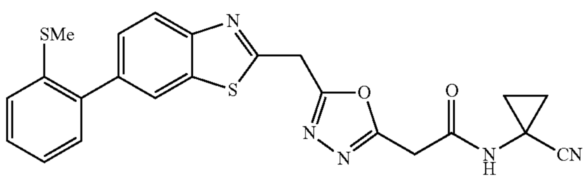 [SMILES: CSc1ccccc1-c1ccc2nc(Cc3nnc(CC(=O)NC4(C#N)CC4)o3)sc2c1] | (DMSO-d6) δ: 1.14 (dd, J = 8.1, 5.6 Hz, 2H), 1.49 (dd, J = 8.1, 5.6 Hz, 2H), 2.38 (s, 3 H), 3.91 (s, 2H), 4.96 (s, 2H), 7.23-7.28 (m, 2H), 7.35-7.45 (m, 2H), 7.50 (dd, J = 8.4, 1.8 Hz, 1H), 8.02 (d, J = 8.1 Hz, 1H), 8.10 (d, J = 1.5 Hz, 1H), 9.23 (s, 1H). | 1.96 | 461.95 (MS+) | C |

TABLE 84

| No. | Structure | NMR(δ) | retention time | Mass | method |
|---|---|---|---|---|---|
| I-3-105 | 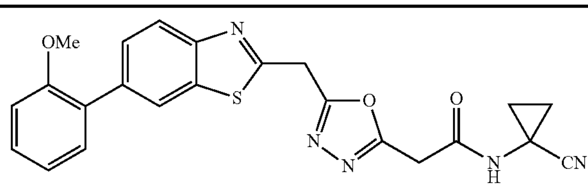 | (DMSO-d6) δ: 1.14 (dd, J = 8.1, 5.6 Hz, 2H), 1.49 (dd, J = 8.1, 5.6 Hz, 2H), 3.78 (s, 3H), 3.91 (s, 2H), 4.95 (s, 2H), 7.06 (t, J = 7.4 Hz, 1H), 7.15 (d, J = 8.1 Hz, 1H), 7.34-7.41 (m, 2H), 7.61 (dd, J = 8.4, 1.8 Hz, 1H), 7.99 (d, J = 8.6 Hz, 1H), 8.18 (d, J = 1.5 Hz, 1H), 9.23 (s, 1H). | 1.87 | 446.20 (MS+) | C |

TABLE 84-continued

| No. | Structure | NMR(δ) | retention time | Mass | method |
|---|---|---|---|---|---|
| I-3-106 | 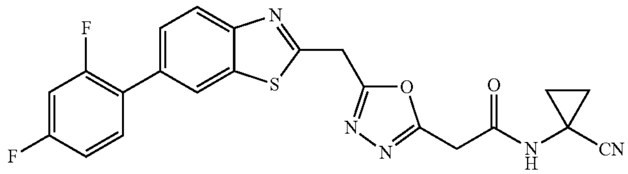 [SMILES: N#CC1(NC(=O)Cc2nnc(Cc3nc4ccc(-c5ccc(F)cc5F)cc4s3)o2)CC1] | (DMSO-d6) δ: 1.14 (dd, J = 8.1, 5.6 Hz, 2H), 1.49 (dd, J = 8.1, 5.6 Hz, 2H), 3.91 (s, 2H), 4.97 (s, 2H), 7.24 (td, J = 8.4, 2.0 Hz, 1H), 7.37-7.46 (m, 1H), 7.64-7.70 (m, 2H), 8.07 (d, J = 8.1 Hz, 1H), 8.30 (s, 1H), 9.23 (s, 1H). | 1.93 | 452.15 (MS+) | C |
| I-3-107 | 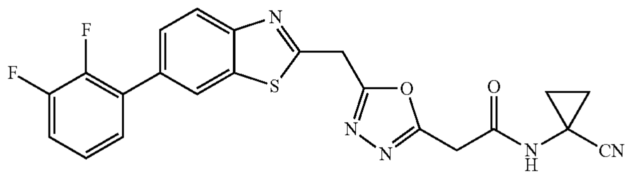 [SMILES: N#CC1(NC(=O)Cc2nnc(Cc3nc4ccc(-c5cccc(F)c5F)cc4s3)o2)CC1] | (DMSO-d6) δ: 1.14 (dd, J = 8.1, 5.6 Hz, 2H), 1.49 (dd, J = 8.1, 5.6 Hz, 2H), 3.91 (s, 2H), 4.99 (s, 2H), 7.32-7.37 (m, 1H), 7.42-7.53 (m, 2H), 7.72 (dt, J = 8.6, 1.8 Hz, 1H), 8.09 (d, J = 8.1 Hz, 1H), 8.36 (s, 1H), 9.24 (s, 1H). | 1.91 | 451.95 (MS+) | C |
| I-3-108 | 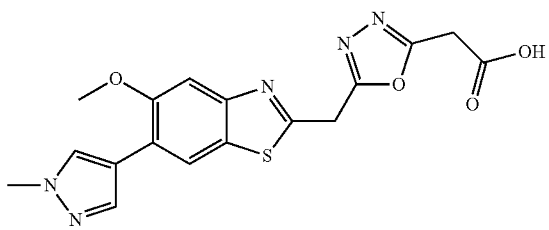 [SMILES: COc1cc2nc(Cc3nnc(CC(=O)O)o3)sc2cc1-c1cnn(C)c1] | | 1.25 | 386 | C |
| I-3-109 | 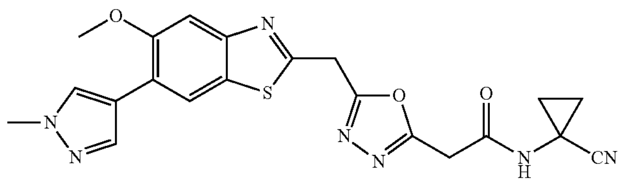 [SMILES: COc1cc2nc(Cc3nnc(CC(=O)NC4(C#N)CC4)o3)sc2cc1-c1cnn(C)c1] | (DMSO-d6) δ: 1.14 (dd, J = 8.4, 5.2 Hz, 2H), 1.49 (dd, J = 8.4, 5.3 Hz, 2H), 2.50 (s, 3H), 3.88 (s, 3H), 3.91 (s, 2H), 4.90 (s, 2H), 7.61 (s, 1H), 7.95 (s, 1H), 8.17 (s, 1H), 8.29 (s, 1H), 9.23 (s, 1H). | | | |

TABLE 85

| No. | Structure | NMR(δ) | retention time | Mass | method |
|---|---|---|---|---|---|
| I-3-110 | 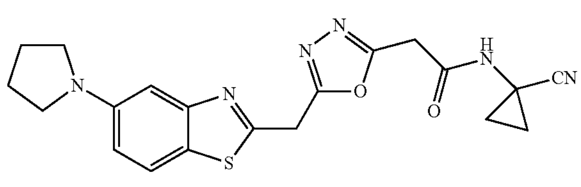 [SMILES: N#CC1(NC(=O)Cc2nnc(Cc3nc4cc(N5CCCC5)ccc4s3)o2)CC1] | (DMSO-d6) δ: 1.14 (dd, J = 8.36, 5.83 Hz, 2H), 1.48 (dd, J = 8.36, 5.32 Hz, 2H), 1.95-2.01 (m, 4H), 3.23-3.30 (m, 4H), 3.89 (s, 2H), 4.83 (s, 2H), 6.78 (dd, J = 8.87, 2.28 Hz, 1H), 7.01 (d, J = 2.03 Hz, 1H), 7.80 (d, J = 8.62 Hz, 1H), 9.22 (s, 1H). | 1.74 | 409.00 (MS+) | C |
| I-3-111 | 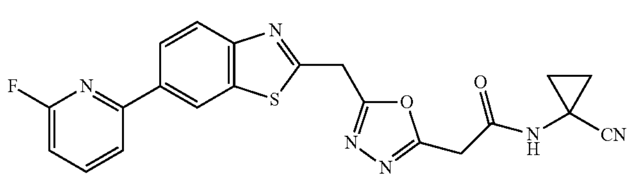 [SMILES: N#CC1(NC(=O)Cc2nnc(Cc3nc4ccc(-c5cccc(F)n5)cc4s3)o2)CC1] | (DMSO-d6) δ: 1.14 (dd, J = 8.4, 5.8 Hz, 2H), 1.48 (dd, J = 8.4, 5.3 Hz, 2H), 3.91 (s, 2H), 4.98 (s, 2H), 6.72 (dd, J = 7.8 Hz, 1H), 8.01-8.14 (m, 3H), 8.22 (d, J = 8.4 Hz, 1H), 8.85 (s, 1H), 9.23 (s, 1H) | | | |

TABLE 85-continued

| No. | Structure | NMR(δ) | retention time | Mass | method |
|---|---|---|---|---|---|
| I-3-112 | 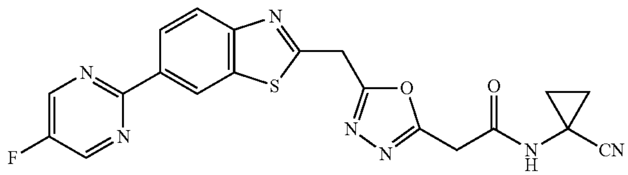 [SMILES: N#CC1(NC(=O)Cc2nnc(Cc3nc4ccc(-c5ncc(F)cn5)cc4s3)o2)CC1] | (DMSO-d6) δ: 1.14 (dd, J = 8.4, 5.8 Hz, 2H), 1.48 (dd, J = 8.4, 5.3 Hz, 2H), 3.91 (s, 2H), 4.98 (s, 2H), 8.11 (d, J = 9.0 Hz, 1H), 8.49 (d, J = 8.7 Hz, 1H), 9.03 (s, 3H), 9.08 (s, 1H), 9.23 (s, 1H) | | | |
| I-3-113 | 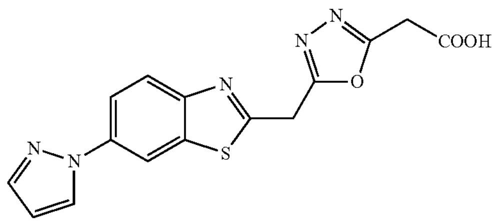 [SMILES: O=C(O)Cc1nnc(Cc2nc3ccc(-n4cccn4)cc3s2)o1] | | 1.28 | 341.80 (MS+) | C |
| I-3-114 | 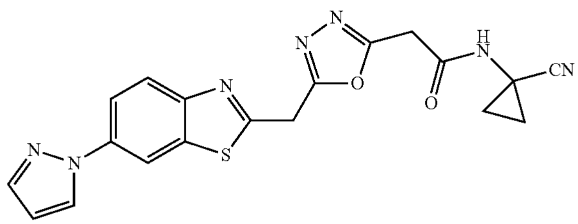 [SMILES: N#CC1(NC(=O)Cc2nnc(Cc3nc4ccc(-n5cccn5)cc4s3)o2)CC1] | (DMSO-d6) δ: 1.14 (dd, J = 8.36, 5.83 Hz, 2H), 1.49 (dd, J = 8.36, 5.32 Hz, 2H), 3.91 (s, 2H), 4.96 (s, 2H), 6.59 (dd, J = 2.53, 2.03 Hz, 1H), 7.80 (d, J = 1.52 Hz, 1H), 8.03 (dd, J = 8.87, 2.28 Hz, 1H), 8.08 (d, J = 8.62 Hz, 1H), 8.57 (d, J = 2.53 Hz, 1H), 8.60 (d, J = 2.03 Hz, 1H), 9.23 (s, 1H). | 1.4 | 405.95 (MS+) | C |

TABLE 86

| No. | Structure | NMR(δ) | retention time | Mass | method |
|---|---|---|---|---|---|
| I-3-115 | 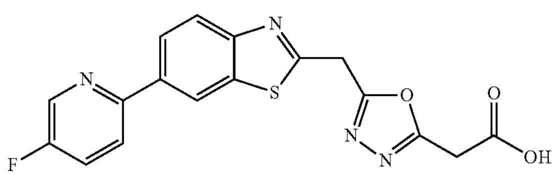 [SMILES: O=C(O)Cc1nnc(Cc2nc3ccc(-c4ccc(F)cn4)cc3s2)o1] | | 1.55 | 370.90 (MS+) | C |
| I-3-116 | 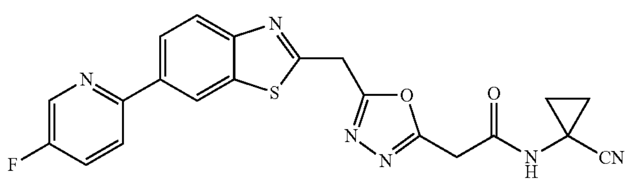 [SMILES: N#CC1(NC(=O)Cc2nnc(Cc3nc4ccc(-c5ccc(F)cn5)cc4s3)o2)CC1] | (DMSO-d6) δ: 1.14 (dd, J = 8.4, 5.6 Hz, 2H), 1.49 (dd, J = 8.4, 5.6 Hz, 2H), 3.91 (s, 2H), 4.97 (s, 2H), 7.88 (td, J = 8.7, 2.9 Hz, 1H), 8.07 (d, J = 8.6 Hz, 1H), 8.15 (dd, J = 8.9, 4.3 Hz, 1H), 8.23 (dd, J = 8.6, 1.5 Hz, 1H), 8.69 (d, J = 3.0 Hz, 1H), 8.81 (d, J = 1.5 Hz, 1H), 9.23 (s, 1H). | 1.61 | 434.95 (MS+) | C |
| I-3-117 | 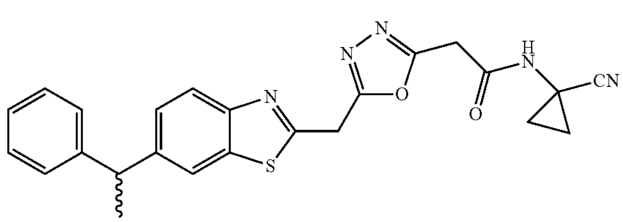 [SMILES: CC(c1ccccc1)c1ccc2nc(Cc3nnc(CC(=O)NC4(C#N)CC4)o3)sc2c1] | (DMSO-d6) δ: 1.12 (dd, J = 8.62, 5.58 Hz, 2H), 1.47 (dd, J = 8.11, 5.58 Hz, 2H), 1.64 (d, J = 7.60 Hz, 3H), 3.88 (s, 2H), 4.32 (q, J = 7.44 Hz, 1H), 4.89 (s, 2H), 7.14-7.20 (m, 1H), 7.25-7.31 (m, 4H), 7.39 (dd, J = 8.36, 1.77 Hz, 1H), 7.87 (d, J = 8.62 Hz, 1H), 8.03 (d, J = 2.03 Hz, 1H), 9.23 (s, 1H). | 2.06 | 443.95 (MS+) | C |

TABLE 86-continued

| No. | Structure | NMR(δ) | retention time | Mass | method |
|---|---|---|---|---|---|
| I-3-118 | 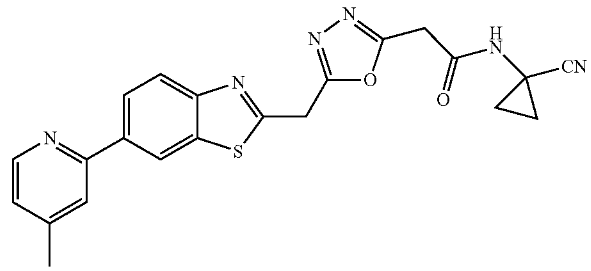 [SMILES: Cc1ccnc(-c2ccc3nc(Cc4nnc(CC(=O)NC5(C#N)CC5)o4)sc3c2)c1] | (DMSO-d6) δ: 1.14 (dd, J = 8.11, 5.58 Hz, 2H), 1.49 (dd, J = 8.11, 5.58 Hz, 2H), 2.41 (s, 3H), 3.91 (s, 2H), 4.97 (s, 2H), 7.22 (d, J = 5.07 Hz, 1H), 7.93 (s, 1H), 8.06 (d, J = 8.11 Hz, 1H), 8.26 (dd, J = 8.62, 2.03 Hz, 1H), 8.55 (d, J = 5.07 Hz, 1H), 8.84 (d, J = 1.52 Hz, 1H), 9.24 (s, 1H). | 1.05 | 430.95 (MS+) | C |
| I-3-119 | 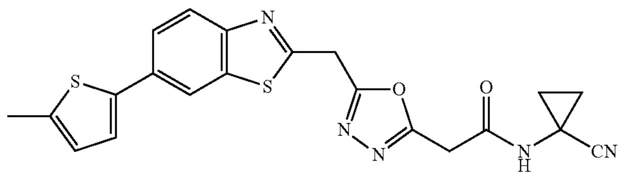 [SMILES: Cc1ccc(-c2ccc3nc(Cc4nnc(CC(=O)NC5(C#N)CC5)o4)sc3c2)s1] | (DMSO-d6) δ: 1.14 (dd, J = 8.4, 5.8 Hz, 2H), 1.48 (dd, J = 8.4, 5.3 Hz, 2H), 3.91 (s, 2H), 4.93 (s, 2H), 6.86 (s, 1H), 7.40 (s, 1H), 7.74 (d, J = 7.5 Hz, 2H), 7.96 (d, J = 7.5 Hz, 2H), 8.34 (s, 1H), 9.23 (s, 1H) | | | |

TABLE 87

| No. | Structure | NMR(δ) | retention time | Mass | method |
|---|---|---|---|---|---|
| I-3-120 | 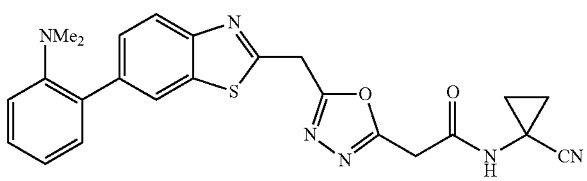 [SMILES: CN(C)c1ccccc1-c1ccc2nc(Cc3nnc(CC(=O)NC4(C#N)CC4)o3)sc2c1] | (DMSO-d6) δ: 1.14 (dd, J = 8.1, 5.6 Hz, 2H), 1.49 (dd, J = 8.1, 5.6 Hz, 2H), 2.47 (s, 6H), 3.91 (s, 2H), 4.94 (s, 2H), 7.04 (t, J = 7.6 Hz, 1H), 7.10 (d, J = 8.1 Hz, 1H), 7.23 (dd, J = 7.6, 1.5 Hz, 1H), 7.30 (td, J = 8.1, 2.0 Hz, 1H), 7.71 (dd, J = 8.4, 1.8 Hz, 1H), 8.00 (d, J = 8.6 Hz, 1H), 8.21 (d, J = 1.5 Hz, 1H), 9.23 (s, 1H). | 1.46 | 459.00 (MS+) | C |
| I-3-121 | 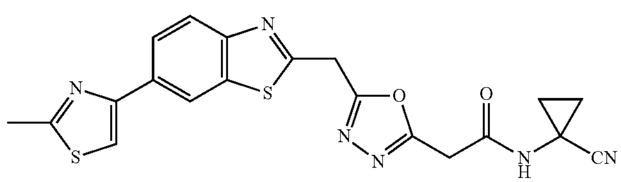 [SMILES: Cc1nc(-c2ccc3nc(Cc4nnc(CC(=O)NC5(C#N)CC5)o4)sc3c2)cs1] | (DMSO-d6) δ: 2.79 (s, 3H), 3.91 (s, 2H), 4.74 (s, 2H), 7.40 (s, 1H), 7.96-8.04 (m, 3H), 8.48 (s, 1H). | | | |
| I-3-122 | 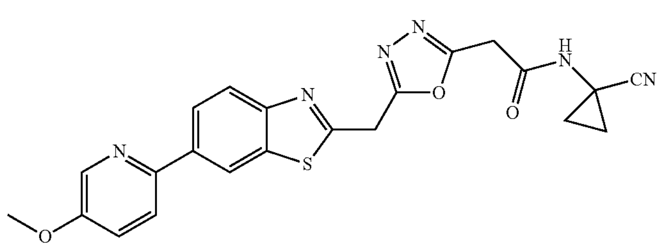 [SMILES: COc1ccc(-c2ccc3nc(Cc4nnc(CC(=O)NC5(C#N)CC5)o4)sc3c2)nc1] | (DMSO-d6) δ: 1.14 (dd, J = 8.11, 5.58 Hz, 2H), 1.49 (dd, J = 8.11, 5.58 Hz, 2H), 3.89 (s, 3H), 3.91 (s, 2H), 4.96 (s, 2H), 7.52 (dd, J = 8.62, 3.04 Hz, 1H), 8.03 (d, J = 8.62 Hz, 2H), 8.20 (dd, J = 8.62, 2.03 Hz, 1H), 8.41 (d, J = 3.04 Hz, 1H), 8.76 (d, J = 1.52 Hz, 1H), 9.23 (s, 1H). | 1.44 | 447.00 (MS+) | C |

TABLE 87-continued

| No. | Structure | NMR(δ) | retention time | Mass | method |
|---|---|---|---|---|---|
| I-3-123 | 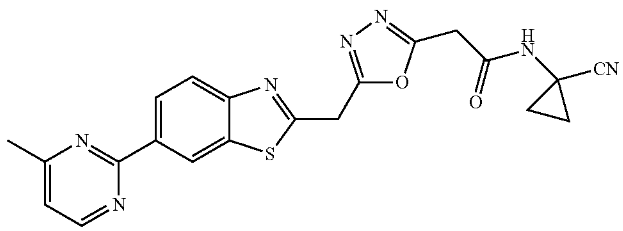 [SMILES: Cc1ccnc(-c2ccc3nc(Cc4nnc(CC(=O)NC5(C#N)CC5)o4)sc3c2)n1] | (DMSO-d6) δ: 1.14 (dd, J = 8.36, 5.32 Hz, 2H), 1.49 (dd, J = 8.11, 5.58 Hz, 2H), 2.57 (s, 3H), 3.91 (s, 2H), 4.98 (s, 2H), 7.36 (d, J = 5.07 Hz, 1H), 8.08 (d, J = 8.62 Hz, 1H), 8.55 (dd, J = 8.87, 1.77 Hz, 1H), 8.78 (d, J = 5.07 Hz, 1H), 9.12 (d, J = 1.52 Hz, 1H), 9.23 (s, 1H). | 1.54 | 431.95 (MS+) | C |

TABLE 88

| No. | Structure | NMR(δ) | retention time | Mass | method |
|---|---|---|---|---|---|
| I-3-124 | 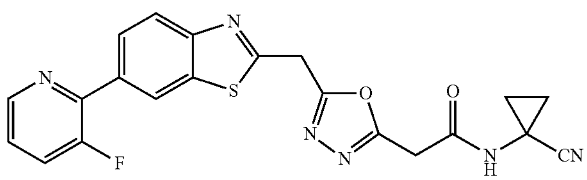 [SMILES: N#CC1(NC(=O)Cc2nnc(Cc3nc4ccc(-c5ncccc5F)cc4s3)o2)CC1] | (DMSO-d6) δ: 1.14 (dd, J = 8.1, 5.6 Hz, 2H), 1.49 (dd, J = 8.1, 5.6 Hz, 2H), 3.91 (s, 2H), 4.99 (s, 2H), 7.50-7.55 (m, 1H), 7.89 (ddd, J = 11.7, 8.4, 1.3 Hz, 1H), 8.06-8.13 (m, 2H), 8.58-8.60 (m, 1H), 8.68 (s, 1H), 9.23 (s, 1H). | 1.51 | 434.95 (MS+) | C |
| I-3-125 | 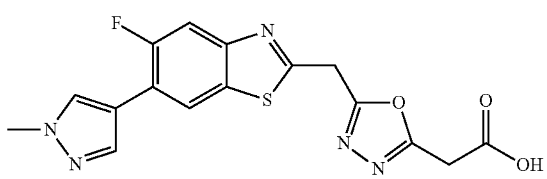 [SMILES: Cn1cc(-c2cc3sc(Cc4nnc(CC(=O)O)o4)nc3cc2F)cn1] | (DMSO-d6) δ: 3.91 (s, 3H), 4.08 (s, 2H), 4.95 (s, 2H), 7.89 (d, J = 12.0 Hz, 1H), 7.95 (s, 1H), 8.18 (d, J = 2.7 Hz, 1H), 8.45 (d, J = 7.0 Hz, 1H). | | | |
| I-3-126 | 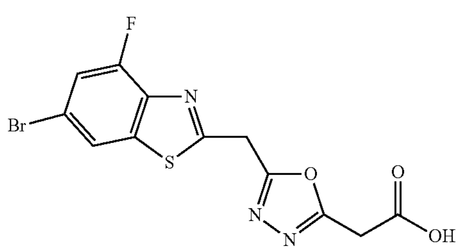 [SMILES: O=C(O)Cc1nnc(Cc2nc3c(F)cc(Br)cc3s2)o1] | (DMSO-d6) δ: 4.08 (s, 2H), 5.00 (s, 2H), 7.13 (dd, J = 9.6, 1.50 Hz, 1H), 8.29 (d, J = 2.5 Hz, 1H). | | | |
| I-3-127 | 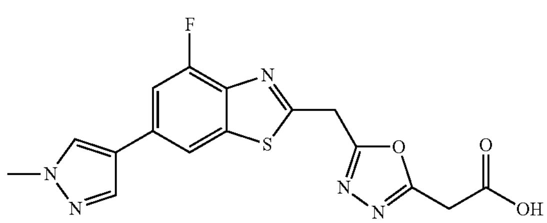 [SMILES: Cn1cc(-c2cc(F)c3nc(Cc4nnc(CC(=O)O)o4)sc3c2)cn1] | (DMSO-d6) δ: 3.91 (s, 2H), 4.95 (s, 2H), 7.89 (d, J = 12.0 Hz, 1H), 7.95 (s, 1H), 8.18 (d, J = 2.7 Hz, 1H), 8.45 (d, J = 7.0 Hz, 1H). | | | |
| I-3-128 | 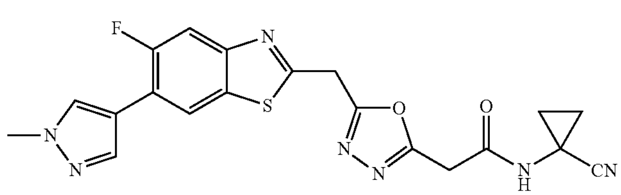 [SMILES: Cn1cc(-c2cc3sc(Cc4nnc(CC(=O)NC5(C#N)CC5)o4)nc3cc2F)cn1] | (DMSO-d6) δ: 1.14 (dd, J = 8.4, 5.3 Hz, 2H), 1.49 (dd, J = 8.4, 5.3 Hz, 2H), 3.91 (s, 2H), 4.95 (s, 2H), 7.89 (d, J = 12.0 Hz, 1H), 7.95 (s, 1H), 8.18 (d, J = 2.7 Hz, 1H), 8.45 (d, J = 7.0 Hz, 1H), 9.24 (s, 1H). | | | |

TABLE 89

| No. | Structure | NMR(δ) | retention time | Mass | method |
|---|---|---|---|---|---|
| I-3-129 | 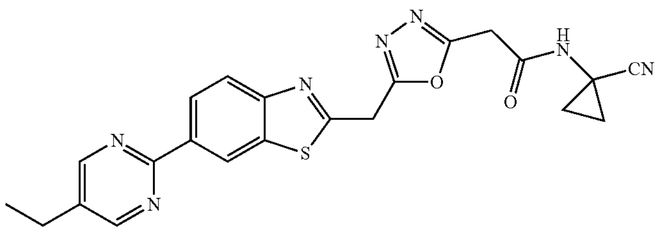 [SMILES: CCc1cnc(-c2ccc3nc(Cc4nnc(CC(=O)NC5(C#N)CC5)o4)sc3c2)nc1] | (DMSO-d6) δ: 1.14 (dd, J = 8.36, 5.83 Hz, 2H), 1.26 (t, J = 7.60 Hz, 3H), 1.48 (dd, J = 8.11, 5.58 Hz, 2H), 2.69 (q, J = 7.60 Hz, 2H), 3.91 (s, 2H), 4.98 (s, 2H), 8.08 (d, J = 8.62 Hz, 1H), 8.53 (dd, J = 8.62, 2.03 Hz, 1H), 8.83 (s, 2H), 9.10 (d, J = 2.03 Hz, 1H), 9.23 (s, 1H). | 1.73 | 446.00 (MS+) | C |
| I-3-130 | 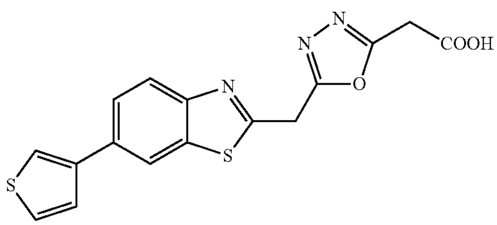 [SMILES: O=C(O)Cc1nnc(Cc2nc3ccc(-c4ccsc4)cc3s2)o1] | | 1.74 | 357.85 (MS+) | C |
| I-3-131 | 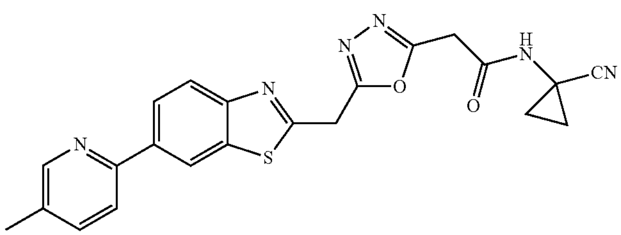 [SMILES: Cc1ccc(-c2ccc3nc(Cc4nnc(CC(=O)NC5(C#N)CC5)o4)sc3c2)nc1] | (DMSO-d6) δ: 1.14 (dd, J = 8.36, 5.83 Hz, 2H), 1.49 (dd, J = 8.11, 5.58 Hz, 2H), 2.35 (s, 3H), 3.91 (s, 2H), 4.96 (s, 2H), 7.74 (dd, J = 8.62, 2.53 Hz, 1H), 7.97 (d, J = 8.11 Hz, 1H), 8.05 (d, J = 8.62 Hz, 1H), 8.24 (dd, J = 8.62, 2.03 Hz, 1H), 8.54 (d, J = 2.03 Hz, 1H), 8.82 (d, J = 1.52 Hz, 1H), 9.23 (s, 1H). | 1.23 | 430.95 (MS+) | C |
| I-3-132 | 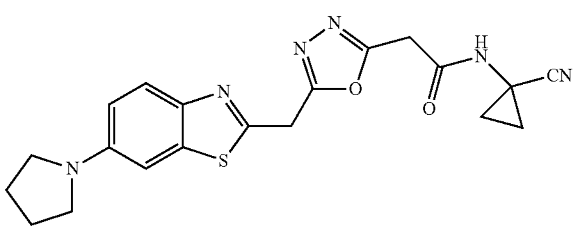 [SMILES: N#CC1(NC(=O)Cc2nnc(Cc3nc4ccc(N5CCCC5)cc4s3)o2)CC1] | (DMSO-d6) δ: 1.14 (dd, J = 8.36, 5.83 Hz, 2H), 1.48 (dd, J = 8.36, 5.32 Hz, 2H), 1.95-2.01 (m, 4H), 3.24-3.30 (m, 4H), 3.89 (s, 2H), 4.77 (s, 2H), 6.77 (dd, J = 8.87, 2.28 Hz, 1H), 7.08 (d, J = 2.53 Hz, 1H), 7.73 (d, J = 9.12 Hz, 1H), 9.22 (s, 1H). | 1.77 | 409.00 (MS+) | C |
| I-3-133 | 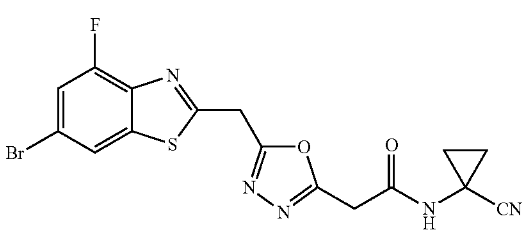 [SMILES: N#CC1(NC(=O)Cc2nnc(Cc3nc4c(F)cc(Br)cc4s3)o2)CC1] | (DMSO-d6) δ: 1.14 (dd, J = 8.4, 5.3 Hz, 2H), 1.49 (dd, J = 8.4, 5.3 Hz, 2H), 3.92 (s, 2H), 5.00 (s, 2H), 7.14 (dd, J = 10.2, 1.80 Hz, 1H), 8.29 (dd, J = 1.8, 0.60 Hz, 1H), 9.24 (s, 1H). | | | |

TABLE 90

| No. | Structure | NMR(δ) | retention time | Mass | method |
|---|---|---|---|---|---|
| I-3-134 | 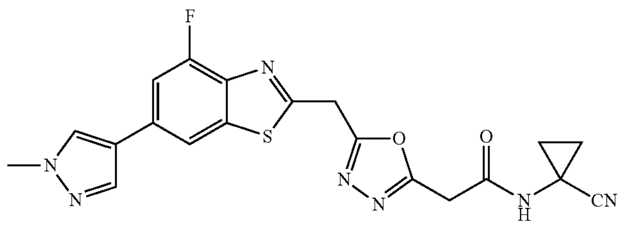 [SMILES: Cn1cc(-c2cc(F)c3nc(Cc4nnc(CC(=O)NC5(C#N)CC5)o4)sc3c2)cn1] | (DMSO-d6) δ: 1.14 (dd, J = 8.4, 5.3 Hz, 2H), 1.49 (dd, J = 8.4, 5.3 Hz, 2H), 3.88 (s, 3H), 3.91 (s, 2H), 5.00 (s, 2H), 7.65 (dd, J = 12.0, 1.5 Hz, 1H), 7.99 (s, 1H), 8.15 (d, J = 1.2 Hz, 1H), 8.25 (s, 1H), 9.24 (s, 1H). | | | |
| I-3-135 | 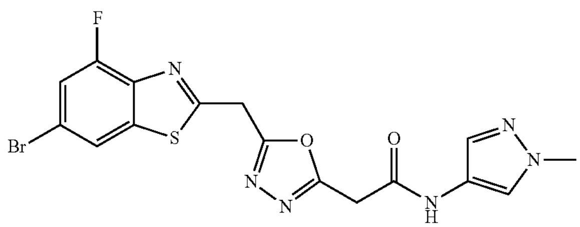 [SMILES: Cn1cc(NC(=O)Cc2nnc(Cc3nc4c(F)cc(Br)cc4s3)o2)cn1] | (DMSO-d6) δ: 3.78 (s, 2H), 5.00 (s, 2H), 7.40 (d, J = 0.9 Hz, 1H), 7.72 (dd, J = 10.2, 1.4 Hz, 1H), 7.84 (s, 1H), 8.29 (dd, J = 1.8, 0.9 Hz, 1H), 10.34 (brs, 1H). | | | |
| I-3-136 | 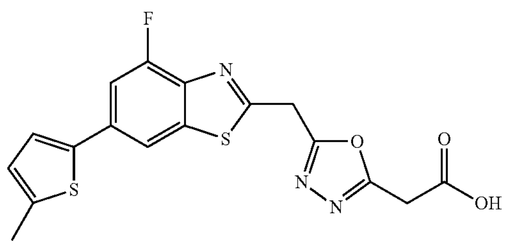 [SMILES: Cc1ccc(-c2cc(F)c3nc(Cc4nnc(CC(=O)O)o4)sc3c2)s1] | (DMSO-d6) δ: 2.50 (s, 3H), 4.08 (s, 2H), 4.98 (s, 2H), 6.87 (d, J = 2.4 Hz, 1H), 7.46 (d, J = 3.6 Hz, 1H), 7.65 (dd, J = 12.0, 1.8 Hz, 1H), 8.17 (d, J = 1.5 Hz, 1H). | | | |
| I-3-137 | 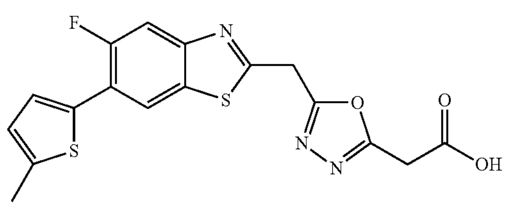 [SMILES: Cc1ccc(-c2cc3sc(Cc4nnc(CC(=O)O)o4)nc3cc2F)s1] | (DMSO-d6) δ: 2.50 (s, 3H), 4.08 (s, 2H), 4.98 (s, 2H), 6.92 (d, J = 2.4 Hz, 1H), 7.43 (d, J = 3.6 Hz, 1H), 7.94 (d, J = 12.0 Hz, 1H), 8.50 (d, J = 7.5 Hz, 1H). | | | |
| I-3-138 | 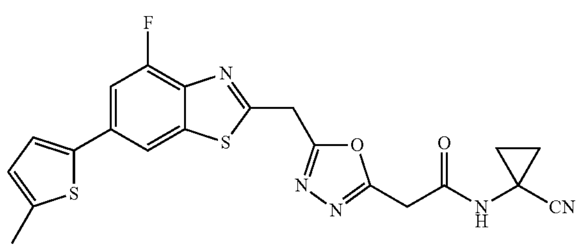 [SMILES: Cc1ccc(-c2cc(F)c3nc(Cc4nnc(CC(=O)NC5(C#N)CC5)o4)sc3c2)s1] | (DMSO-d6) δ: 1.14 (dd, J = 8.4, 5.3 Hz, 2H), 1.49 (dd, J = 8.4, 5.3 Hz, 2H), 2.50 (s, 3H), 3.91 (s, 2H), 4.97 (s, 2H), 6.87 (d, J = 2.4 Hz, 1H), 7.46 (d, J = 3.6 Hz, 1H), 7.65 (dd, J = 12.0, 1.80 Hz, 1H), 8.17 (d, J = 1.5 Hz, 1H), 9.24 (s, 1H). | | | |

TABLE 91

| No. | Structure | NMR(δ) | retention time | Mass | method |
|---|---|---|---|---|---|
| I-3-139 | 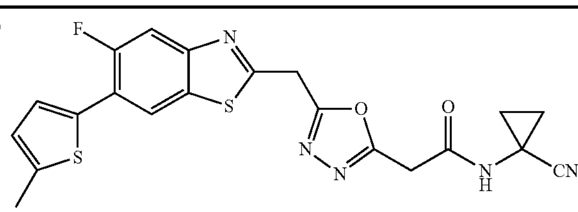 | (DMSO-d6) δ: 1.14 (dd, J = 8.4, 5.3 Hz, 2H), 1.49 (dd, J = 8.4, 5.3 Hz, 2H), 2.50 (s, 3H), 3.91 (s, 2H), 4.97 (s, 2H), 6.92 (d, J = 2.4 Hz, 1H), 7.43 (d, J = 3.6 Hz, 1H), 7.94 (d, J = 12.0 Hz, 1H), 8.50 (d, J = 7.5 Hz, 1H), 9.24 (s, 1H). | | | |

TABLE 91-continued

| No. | Structure | NMR(δ) | retention time | Mass | method |
|---|---|---|---|---|---|
| I-3-140 | 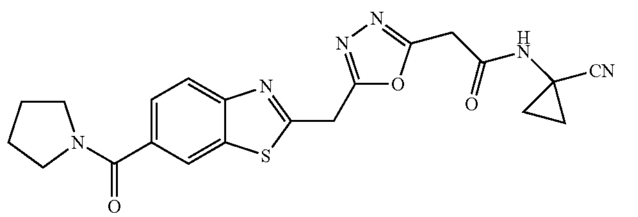 [SMILES: N#CC1(NC(=O)Cc2nnc(Cc3nc4ccc(C(=O)N5CCCC5)cc4s3)o2)CC1] | (DMSO-d₆) δ: 1.13 (dd, J = 8.36, 5.32 Hz, 2H), 1.48 (dd, J = 8.30, 5.32 Hz, 2H), 1.77-1.93 (m, 4H), 3.42 (t, J = 6.34 Hz, 2H), 3.50 (t, J = 6.84 Hz, 2H), 3.90 (s, 2H), 4.97 (s, 2H), 7.65 (dd, J = 8.36, 1.77 Hz, 1H), 8.01 (d, J = 8.11 Hz, 1H), 8.31 (d, J = 1.52 Hz, 1H), 9.23 (s, 1H). | 1.17 | 437.00 (MS+) | C |
| I-3-141 | 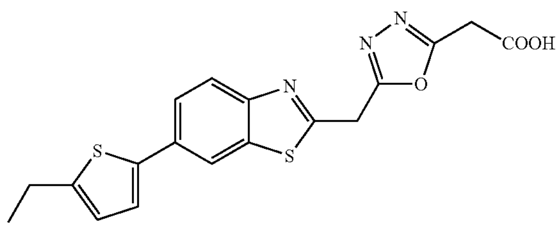 [SMILES: CCc1ccc(-c2ccc3nc(Cc4nnc(CC(=O)O)o4)sc3c2)s1] | | 2.13 | 385.85 (MS+) | C |
| I-3-142 | 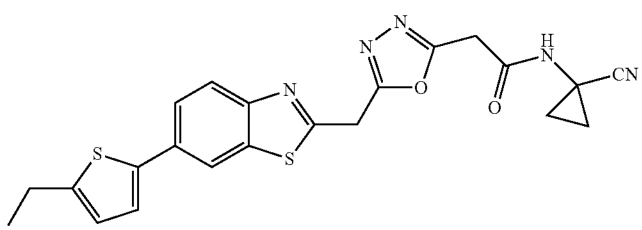 [SMILES: CCc1ccc(-c2ccc3nc(Cc4nnc(CC(=O)NC5(C#N)CC5)o4)sc3c2)s1] | (DMSO-d₆) δ: 1.14 (dd, J = 8.11, 5.58 Hz, 2H), 1.28 (t, J = 7.60 Hz, 3H), 1.48 (dd, J = 8.11, 5.58 Hz, 2H), 2.85 (q, J = 7.44 Hz, 2H), 3.90 (s, 2H), 4.93 (s, 2H), 6.89 (d, J = 3.55 Hz, 1H), 7.41 (d, J = 3.55 Hz, 1H), 7.75 (dd, J = 8.62, 2.03 Hz, 1H), 7.96 (d, J = 8.62 Hz, 1H), 8.35 (d, J = 2.03 Hz, 1H), 9.23 (s, 1H). | 2.19 | 449.95 (MS+) | C |
| I-3-143 | 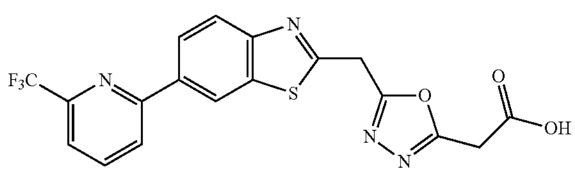 [SMILES: O=C(O)Cc1nnc(Cc2nc3ccc(-c4cccc(C(F)(F)F)n4)cc3s2)o1] | (DMSO-d6) δ: 4.09 (s, 2H), 5.00 (s, 2H), 7.91 (m, 1H), 8.13 (d, J = 8.7 Hz, 1H), 8.24-8.42 (m, 3H), 8.92 (s, 1H) | | | |

TABLE 92

| No. | Structure | NMR(δ) | retention time | Mass | method |
|---|---|---|---|---|---|
| I-3-144 | 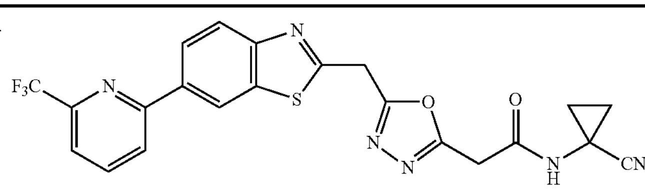 | (DMSO-d6) δ: 1.14 (dd, J = 8.36, 5.32 Hz, 2H), 1.49 (dd, J = 8.11, 5.58 Hz, 2H), 3.91 (s, 2H), 4.99 (s, 2H), 7.89 (d, J = 7.8 Hz, 1H), 8.13 (d, J = 8.7 Hz, 1H), 8.21-8.39 (m, 3H), 8.91 (s, 1H), 9.23 (s, 1H). | | | |
| I-3-145 | 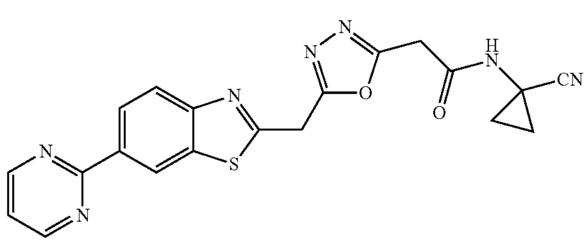 [SMILES: N#CC1(NC(=O)Cc2nnc(Cc3nc4ccc(-c5ncccn5)cc4s3)o2)CC1] | (DMSO-d₆) δ: 1.14 (dd, J = 8.36, 5.32 Hz, 2H), 1.49 (dd, J = 8.11, 5.58 Hz, 2H), 3.91 (s, 2H), 4.99 (s, 2H), 7.49 (t, J = 4.82 Hz, 1H), 8.10 (d, J = 8.62 Hz, 1H), 8.56 (dd, J = 8.62, 1.52 Hz, 1H), 8.95 (d, J = 5.07 Hz, 2H), 9.14 (d, J = 1.52 Hz, 1H), 9.23 (s, 1H). | 1.38 | 417.90 (MS+) | C |

TABLE 92-continued

| No. | Structure | NMR(δ) | retention time | Mass | method |
|---|---|---|---|---|---|
| I-3-146 | 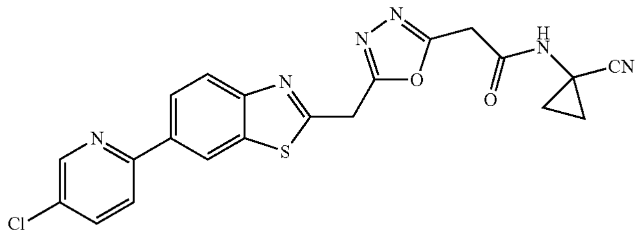 [SMILES: N#CC1(NC(=O)Cc2nnc(Cc3nc4ccc(-c5ccc(Cl)cn5)cc4s3)o2)CC1] | (DMSO-d$_6$) δ: 1.14 (dd, J = 8.36, 5.32 Hz, 2H), 1.49 (dd, J = 8.36, 5.32 Hz, 2H), 3.91 (s, 2H), 4.98 (s, 2H), 8.04-8.09 (m, 2H), 8.13 (d, J = 8.62 Hz, 1H), 8.25 (dd, J = 8.62, 1.52 Hz, 1H), 8.74 (d, J = 2.53 Hz, 1H), 8.86 (d, J = 2.03 Hz, 1H), 9.23 (s, 1H). | 1.84 | 450.90 (MS+) | C |
| I-3-147 | 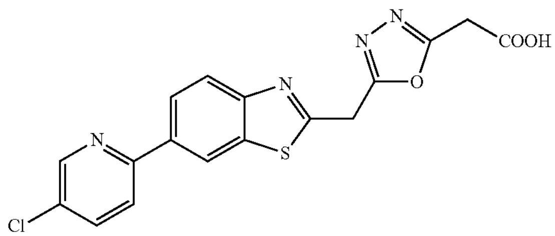 [SMILES: O=C(O)Cc1nnc(Cc2nc3ccc(-c4ccc(Cl)cn4)cc3s2)o1] | | 1.77 | 386.85 (MS+) | C |

TABLE 93

| No. | Structure | NMR(δ) | retention time | Mass | method |
|---|---|---|---|---|---|
| I-3-148 | 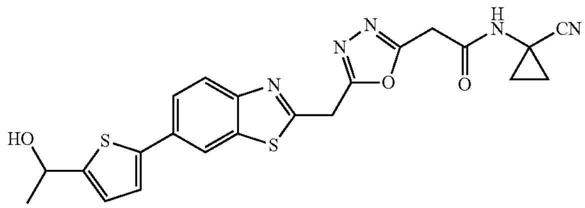 [SMILES: CC(O)c1ccc(-c2ccc3nc(Cc4nnc(CC(=O)NC5(C#N)CC5)o4)sc3c2)s1] | (DMSO-d$_6$) δ: 1.14 (dd, J = 8.11, 5.58 Hz, 2H), 1.45 (d, J = 6.08 Hz, 3H), 1.48 (dd, J = 8.36, 5.32 Hz, 2H), 3.91 (s, 2H), 4.91-4.99 (m, 3H), 5.63 (d, J = 3.55 Hz, 1H), 6.95 (d, J = 3.55 Hz, 1H), 7.42 (d, J = 3.55 Hz, 1H), 7.77 (dd, J = 8.62, 2.03 Hz, 1H), 7.97 (d, J = 8.62 Hz, 1H), 8.38 (d, J = 1.52 Hz, 1H), 9.30 (s, 1H). | 1.53 | 465.95 (MS+) | C |
| I-3-149 | 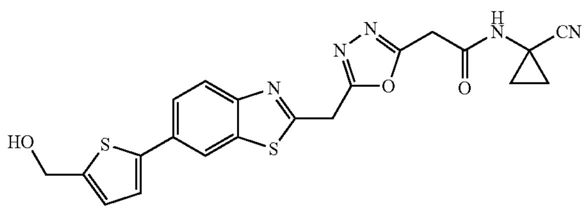 [SMILES: N#CC1(NC(=O)Cc2nnc(Cc3nc4ccc(-c5ccc(CO)s5)cc4s3)o2)CC1] | (DMSO-d$_6$) δ: 1.14 (dd, J = 8.36, 5.32 Hz, 2H), 1.48 (dd, J = 8.11, 5.58 Hz, 2H), 3.91 (s, 2H), 4.65 (d, J = 5.58 Hz, 2H), 4.94 (s, 2H), 5.54 (t, J = 5.83 Hz, 1H), 6.99 (d, J = 3.55 Hz, 1H), 7.44 (d, J = 3.55 Hz, 1H), 7.78 (dd, J = 8.62, 2.03 Hz, 1H), 7.97 (d, J = 8.62 Hz, 1H), 8.39 (d, J = 1.52 Hz, 1H), 9.26 (s, 1H). | 1.39 | 451.90 (MS+) | C |
| I-3-150 | 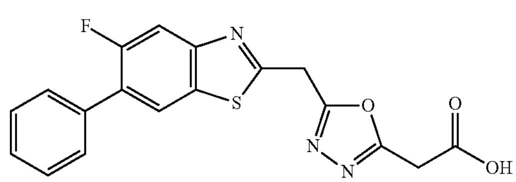 [SMILES: O=C(O)Cc1nnc(Cc2nc3cc(F)c(-c4ccccc4)cc3s2)o1] | (DMSO-d6) δ: 4.08 (s, 2H), 4.98 (s, 2H), 7.44-7.62 (m, 5H), 7.96 (d, J = 11.7 Hz, 1H), 8.31 (d, J = 7.5 Hz, 1H). | | | |
| I-3-151 | 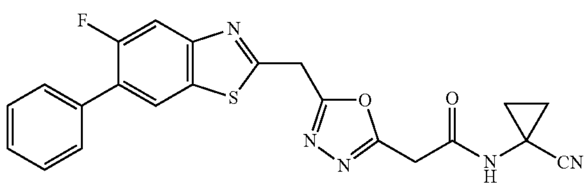 [SMILES: N#CC1(NC(=O)Cc2nnc(Cc3nc4cc(F)c(-c5ccccc5)cc4s3)o2)CC1] | (DMSO-d6) δ: 1.14 (dd, J = 8.4, 5.3 Hz, 2H), 1.49 (dd, J = 8.4, 5.3 Hz, 2H), 3.91 (s, 2H), 4.97 (s, 2H), 7.44-7.62 (m, 5H), 7.96 (d, J = 11.7 Hz, 1H), 8.31 (d, J = 7.2 Hz, 1H), 9.24 (s, 1H). | | | |

TABLE 93-continued

| No. | Structure | NMR(δ) | retention time | Mass | method |
|---|---|---|---|---|---|
| I-3-152 | 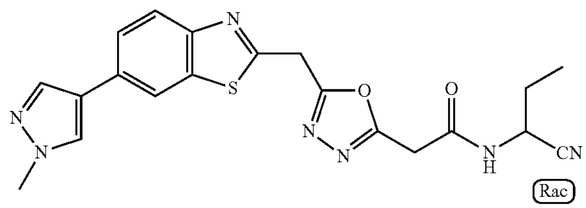 [SMILES: CCC(C#N)NC(=O)Cc1nnc(Cc2nc3ccc(-c4cnn(C)c4)cc3s2)o1] | (DMSO-d6) δ: 0.94 (t, J = 7.2H), 1.71-1.76 (m, 2H), 3.88 (s, 3H), 3.97 (s, 2H), 4.92 (s, 2H), 7.72 (d, J = 8.7 Hz, 1H), 7.91-7.95 (m, 2H), 8.21 (s, 3H), 8.29 (s, 1H), 9.09 (br-s, 1H). | | | |

TABLE 94

| No. | Structure | NMR(δ) | retention time | Mass | method |
|---|---|---|---|---|---|
| I-3-153 | 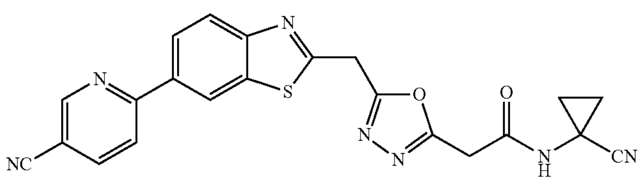 [SMILES: N#Cc1ccc(-c2ccc3nc(Cc4nnc(CC(=O)NC5(C#N)CC5)o4)sc3c2)nc1] | (DMSO-d6) δ: 1.14 (dd, J = 8.6, 5.6 Hz, 2H), 1.49 (dd, J = 8.4, 5.3 Hz, 2H), 3.91 (s, 2H), 5.00 (s, 2H), 8.12 (d, J = 8.6 Hz, 1H), 8.30 (d, J = 8.6 Hz, 1H), 8.34 (dd, J = 8.6, 2.0 Hz, 1H), 8.44 (dd, J = 8.6, 2.0 Hz, 1H), 8.98 (d, J = 1.5 Hz, 1H), 9.13 (d, J = 1.5 Hz, 1H), 9.23 (s, 1H). | 1.51 | 441.95 (MS+) | C |
| I-3-154 | 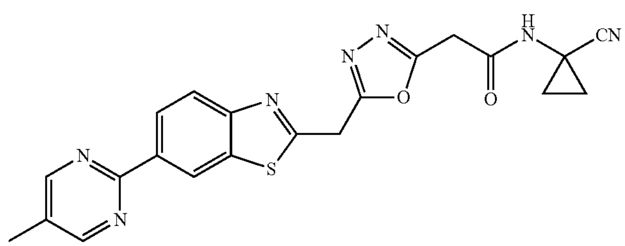 [SMILES: Cc1cnc(-c2ccc3nc(Cc4nnc(CC(=O)NC5(C#N)CC5)o4)sc3c2)nc1] | (DMSO-d$_6$) δ: 1.14 (dd, J = 8.11, 5.58 Hz, 2H), 1.49 (dd, J = 8.11, 5.58 Hz, 2H), 2.34 (s, 3H), 3.91 (s, 2H), 4.98 (s, 2H), 8.08 (d, J = 9.12 Hz, 1H), 8.53 (d, J = 8.62 Hz, 1H), 8.79 (s, 2H), 9.10 (s, 1H), 9.24 (s, 1H). | 1.53 | 431.95 (MS+) | C |
| I-3-155 | 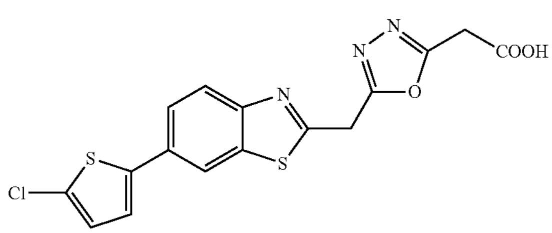 [SMILES: O=C(O)Cc1nnc(Cc2nc3ccc(-c4ccc(Cl)s4)cc3s2)o1] | | 2.08 | 391.85 (MS+) | C |
| I-3-156 | 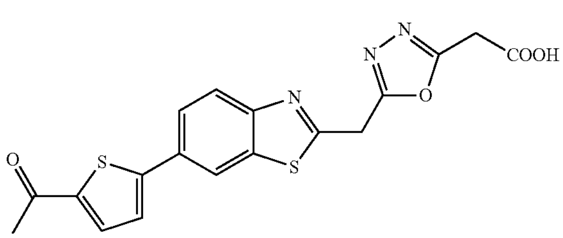 [SMILES: CC(=O)c1ccc(-c2ccc3nc(Cc4nnc(CC(=O)O)o4)sc3c2)s1] | | 1.57 | 399.85 (MS+) | C |

TABLE 94-continued

| No. | Structure | NMR(δ) | retention time | Mass | method |
|---|---|---|---|---|---|
| I-3-157 | 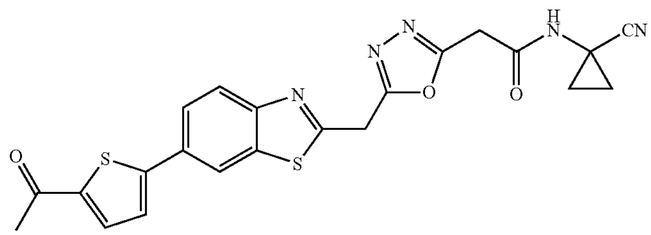 [SMILES: CC(=O)c1ccc(-c2ccc3nc(Cc4nnc(CC(=O)NC5(C#N)CC5)o4)sc3c2)s1] | (DMSO-d$_6$) δ: 1.14 (dd, J = 8.36, 5.32 Hz, 2H), 1.49 (dd, J = 8.36, 5.32 Hz, 2H), 2.56 (s, 3H), 3.91 (s, 2H), 4.97 (s, 2H), 7.74 (d, J = 4.06 Hz, 1H), 7.92 (dd, J = 8.36, 1.77 Hz, 1H), 7.99 (d, J = 4.06 Hz, 1H), 8.04 (d, J = 8.62 Hz, 1H), 8.60 (d, J = 2.03 Hz, 1H), 9.24 (s, 1H). | 1.65 | 463.95 (MS+) | C |

TABLE 95

| No. | Structure | NMR(δ) | retention time | Mass | method |
|---|---|---|---|---|---|
| I-3-158 | 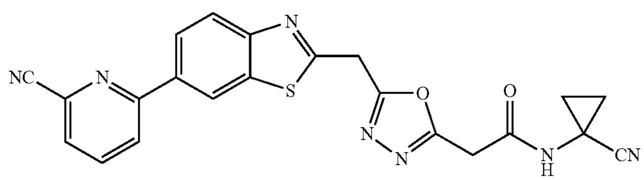 [SMILES: N#Cc1cccc(-c2ccc3nc(Cc4nnc(CC(=O)NC5(C#N)CC5)o4)sc3c2)n1] | (DMSO-d6) δ: 1.14 (dd, J = 8.1, 5.6 Hz, 2H), 1.49 (dd, J = 8.1, 5.6 Hz, 2H), 3.92 (s, 2H), 4.99 (s, 2H), 8.03 (dd, J = 7.6, 1.0 Hz, 1H), 8.12 (d, J = 8.6 Hz, 1H), 8.19 (t, J = 7.9 Hz, 1H), 8.27 (dd, J = 8.6, 1.5 Hz, 1H), 8.42 (d, J = 8.1 Hz, 1H), 8.92 (d, J = 2.0 Hz, 1H), 9.24 (s, 1H). | 1.57 | 442.20 (MS+) | C |
| I-3-159 | 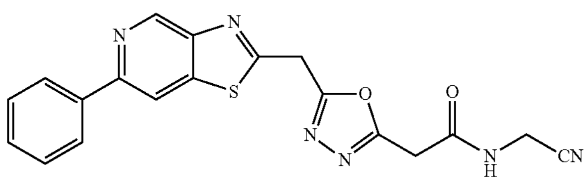 [SMILES: N#CCNC(=O)Cc1nnc(Cc2nc3cnc(-c4ccccc4)cc3s2)o1] | (DMSO-d6) δ: 4.00 (s, 2H), 4.20 (d, J = 5.6 Hz, 2H), 5.04 (s, 2H), 7.45 (t, J = 7.4 Hz, 1H), 7.53 (t, J = 7.4 Hz, 2H), 8.16 (d, J = 7.6 Hz, 2H), 8.79 (s, 1H), 9.03 (t, J = 5.6 Hz, 1H), 9.31 (d, J = 1.0 Hz, 1H). | 1.44 | 391.15 (MS+) | C |
| I-3-160 | 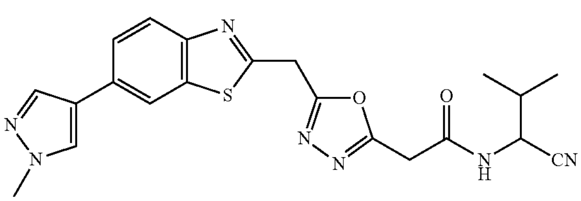 [SMILES: CC(C)C(C#N)NC(=O)Cc1nnc(Cc2nc3ccc(-c4cnn(C)c4)cc3s2)o1] | (CDCl3) δ: 1.07-1.14 (m, 6H), 2.11 (m, 1H), 3.95 (s, 2H), 3.97 (s, 3H), 4.73 (s, 2H), 4.78 (m, 1H), 7.60 (d, J = 7.8 Hz, 1H), 7.67 (s, 1H), 7.81(s, 1H), 7.93-7.99 (m, 3H). | | | |
| I-3-161 | 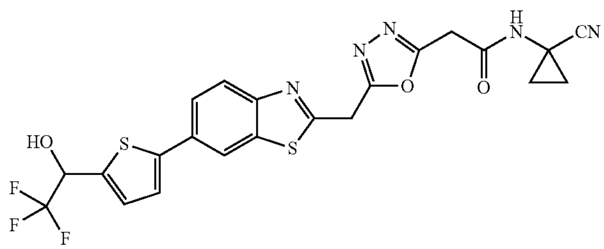 [SMILES: N#CC1(NC(=O)Cc2nnc(Cc3nc4ccc(-c5ccc(C(O)C(F)(F)F)s5)cc4s3)o2)CC1] | (DMSO-d$_6$) δ: 1.14 (dd, J = 8.36, 5.32 Hz, 2H), 1.48 (dd, J = 8.11, 5.58 Hz, 2H), 3.91 (s, 2H), 4.95 (s, 2H), 5.47-5.57 (m, 1H), 7.23 (d, J = 4.06 Hz, 1H), 7.38 (br s, 1H), 7.52 (d, J = 4.06 Hz, 1H), 7.81 (dd, J = 8.62, 1.52 Hz, 1H), 7.99 (d, J = 8.62 Hz, 1H), 8.45 (d, J = 1.52 Hz, 1H), 9.29 (s, 1H). | 1.71 | 520.25 (MS+) | C |

TABLE 96

| No. | Structure | NMR(δ) | retention time | Mass | method |
|---|---|---|---|---|---|
| I-3-162 | 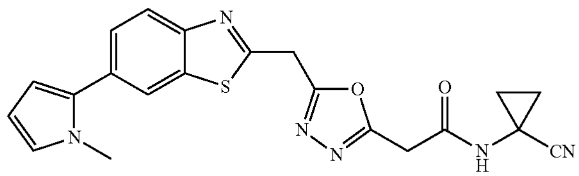 [SMILES: Cn1cccc1-c1ccc2nc(Cc3nnc(CC(=O)NC4(C#N)CC4)o3)sc2c1] | (DMSO-d6) δ: 1.14 (dd, J = 8.1, 5.6 Hz, 2H), 1.49 (dd, J = 8.1, 5.6 Hz, 2H), 3.69 (s, 3H), 3.91 (s, 2H), 4.94 (s, 2H), 6.09 (dd, J = 3.6, 2.5 Hz, 1H), 6.26 (dd, J = 3.6, 2.0 Hz, 1H), 6.88 (dd, J = 2.5, 2.0 Hz, 1H), 7.59 (dd, J = 8.6, 2.0 Hz, 1H), 7.98 (d, J = 8.6 Hz, 1H), 8.18 (d, J = 1.5 Hz, 1H), 9.23 (s, 1H). | 1.71 | 419.10 (MS+) | C |
| I-3-163 | 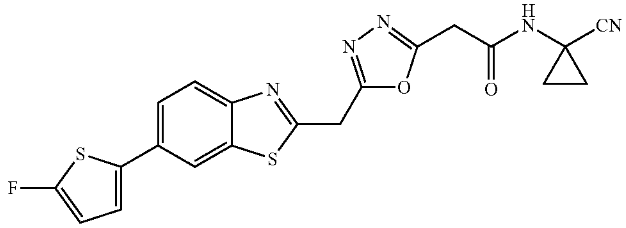 [SMILES: N#CC1(NC(=O)Cc2nnc(Cc3nc4ccc(-c5ccc(F)s5)cc4s3)o2)CC1] | (DMSO-d$_6$) δ: 1.14 (dd, J = 8.36, 5.32 Hz, 2H), 1.49 (dd, J = 8.11, 5.58 Hz, 2H), 3.91 (s, 2H), 4.94 (s, 2H), 6.82 (dd, J = 4.06, 2.03 Hz, 1H), 7.33 (t, J = 4.06 Hz, 1H), 7.75 (dd, J = 8.62, 2.03 Hz, 1H), 7.99 (d, J = 8.62 Hz, 1H), 8.37 (d, J = 2.03 Hz, 1H), 9.23 (s, 1H). | 1.97 | 439.90 (MS+) | C |
| I-3-164 | 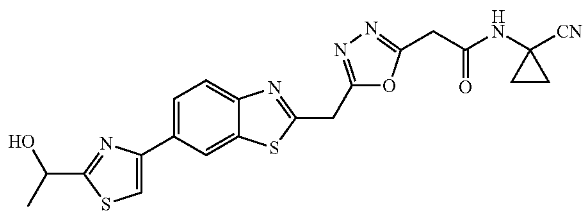 [SMILES: CC(O)c1nc(-c2ccc3nc(Cc4nnc(CC(=O)NC5(C#N)CC5)o4)sc3c2)cs1] | (DMSO-d$_6$) δ: 1.14 (dd, J = 8.62, 5.58 Hz, 2H), 1.49 (dd, J = 8.36, 5.32 Hz, 2H), 1.52 (d, J = 6.59 Hz, 3H), 3.91 (s, 2H), 4.95 (s, 2H), 5.02 (dq, J = 6.59, 5.07 Hz, 1H), 6.19 (d, J = 5.07 Hz, 1H), 8.01 (d, J = 8.62 Hz, 1H), 8.10 (s, 1H), 8.10 (dd, J = 8.62, 1.52 Hz, 1H), 8.67 (d, J = 1.52 Hz, 1H), 9.24 (s, 1H). | 1.37 | 466.95 (MS+) | C |
| I-3-165 | 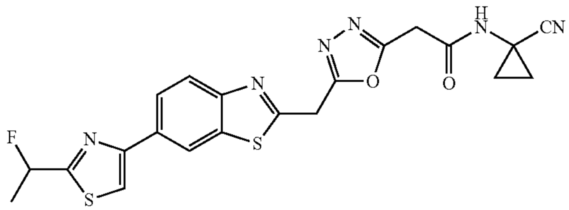 [SMILES: CC(F)c1nc(-c2ccc3nc(Cc4nnc(CC(=O)NC5(C#N)CC5)o4)sc3c2)cs1] | (DMSO-d$_6$) δ: 1.14 (dd, J = 8.36, 5.83 Hz, 2H), 1.49 (dd, J = 8.11, 5.58 Hz, 2H), 1.79 (dd, J = 24.33, 6.08 Hz, 3H), 3.91 (s, 2H), 4.96 (s, 2H), 6.10 (dq, J = 47.53, 6.42 Hz, 1H), 8.04 (d, J = 8.62 Hz, 1H), 8.13 (dd, J = 8.36, 1.77 Hz, 1H), 8.31 (s, 1H), 8.72 (d, J = 1.52 Hz, 1H), 9.24 (s, 1H). | 1.83 | 468.95 (MS+) | C |

TABLE 97

| No. | Structure | NMR(δ) | retention time | Mass | method |
|---|---|---|---|---|---|
| I-3-166 | 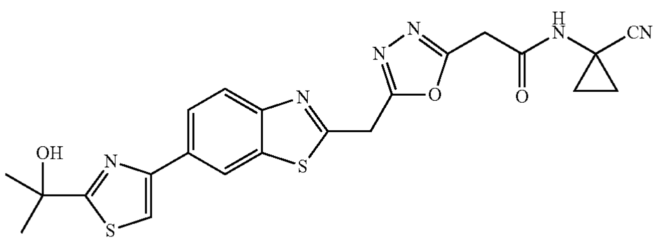 [SMILES: CC(C)(O)c1nc(-c2ccc3nc(Cc4nnc(CC(=O)NC5(C#N)CC5)o4)sc3c2)cs1] | (DMSO-d$_6$) δ: 1.14 (dd, J = 8.36, 5.83 Hz, 2H), 1.49 (dd, J = 8.36, 5.83 Hz, 2H), 1.59 (s, 6H), 3.91 (s, 2H), 4.95 (s, 2H), 6.05 (s, 1H), 8.01 (d, J = 8.62 Hz, 1H), 8.05 (s, 1H), 8.10 (dd, J = 8.62, 1.52 Hz, 1H), 8.68 (d, J = 1.52 Hz, 1H), 9.24 (s, 1H). | 1.5 | 480.95 (MS+) | C |

TABLE 97-continued

| No. | Structure | NMR(δ) | retention time | Mass | method |
|---|---|---|---|---|---|
| I-3-167 | 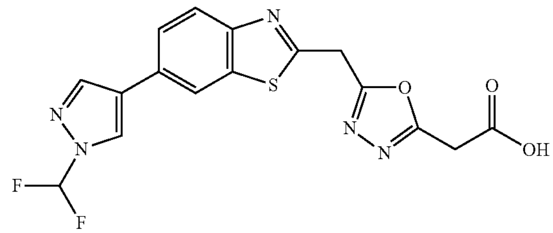 [SMILES: O=C(O)Cc1nnc(Cc2nc3ccc(-c4cnn(C(F)F)c4)cc3s2)o1] | | 1.43 | 391.85 (MS+) | C |
| I-3-168 | 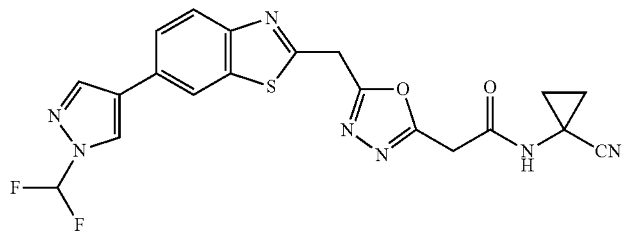 [SMILES: N#CC1(NC(=O)Cc2nnc(Cc3nc4ccc(-c5cnn(C(F)F)c5)cc4s3)o2)CC1] | (DMSO-d6) δ: 1.14 (dd, J = 8.4, 5.3 Hz, 2H), 1.48 (dd, J = 8.4, 5.3 Hz, 2H), 3.91 (s, 2H), 4.95 (s, 2H), 7.67-8.06 (m, 3H), 8.36 (s, 1H), 8.47 (s, 1H), 8.81 (s, 1H), 9.24 (s, 1H). | | | |
| I-3-169 | 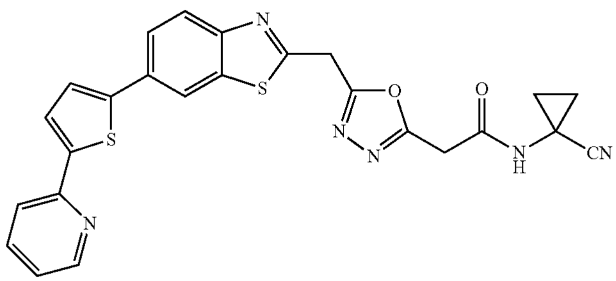 [SMILES: N#CC1(NC(=O)Cc2nnc(Cc3nc4ccc(-c5ccc(-c6ccccn6)s5)cc4s3)o2)CC1] | (DMSO-d6) δ: 1.14 (dd, J = 8.1, 5.6 Hz, 2H), 1.49 (dd, J = 8.1, 5.6 Hz, 2H), 3.91 (s, 2H), 4.96 (s, 2H), 7.30 (dd, J = 6.8, 5.3 Hz, 1H), 7.66 (d, J = 4.1 Hz, 1H), 7.83-7.92 (m, 3H), 7.97 (d, J = 8.1 Hz, 1H), 8.02 (d, J = 8.1 Hz, 1H), 8.52 (d, J = 2.0 Hz, 1H), 8.55 (d, J = 4.6 Hz, 1H), 9.23 (s, 1H). | 1.84 | 499.05 (MS+) | C |

TABLE 98

| No. | Structure | NMR(δ) | retention time | Mass | method |
|---|---|---|---|---|---|
| I-3-170 | 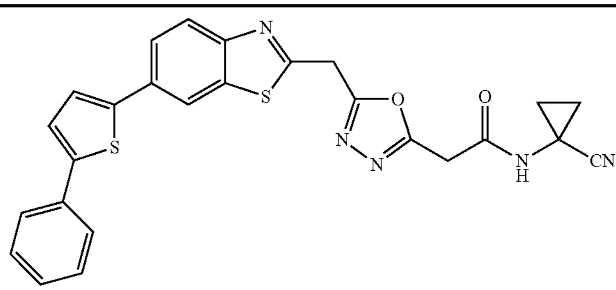 | (DMSO-d6) δ: 1.14 (dd, J = 8.1, 5.6 Hz, 2H), 1.49 (dd, J = 8.1, 5.6 Hz, 2H), 3.91 (s, 2H), 4.95 (s, 2H), 7.34 (t, J = 7.4 Hz, 1H), 7.45 (t, J = 7.6 Hz, 2H), 7.59 (d, J = 3.6 Hz, 1H), 7.65 (d, J = 3.6 Hz, 1H), 7.71 (d, J = 7.1 Hz, 2H), 7.86 (dd, J = 8.6, 1.5 Hz, 1H), 8.01 (d, J = 8.6 Hz, 1H), 8.49 (d, J = 1.5 Hz, 1H), 9.23 (s, 1H). | 2.3 | 498.05 (MS+) | C |

TABLE 99

| No. | Structure | NMR(δ) | retention time | Mass | method |
|---|---|---|---|---|---|
| A-6 | 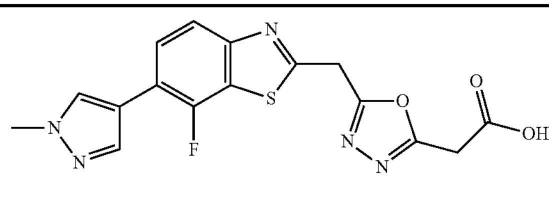 | (DMSO-d6) δ: 3.92 (s, 3H), 4.09 (s, 2H), 5.00 (s, 2H), 7.84-7.91 (m, 2H), 7.98 (s, 1H), 8.25 (d, J = 2.1 Hz, 1H). | | | |

TABLE 99-continued

| No. | Structure | NMR(δ) | retention time | Mass | method |
|---|---|---|---|---|---|
| A-7 | 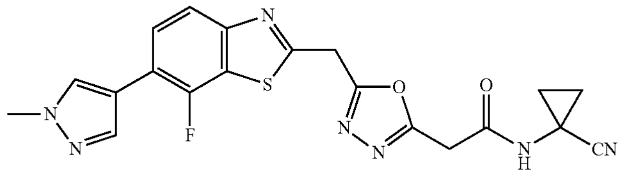 [SMILES: Cn1cc(-c2ccc3nc(Cc4nnc(CC(=O)NC5(C#N)CC5)o4)sc3c2F)cn1] | (DMSO-d6) δ: 1.14 (dd, J = 8.4, 5.3 Hz, 2H), 149 (dd, J = 8.4, 5.3 Hz, 2H), 2.51 (s, 3H), 3.92 (s, 4H), 5.00 (s, 2H), 7.84-7.91 (m, 2H), 7.98 (s, 1H), 8.25 (d, J = 2.1 Hz, 1H), 9.24 (s, 1H). | | | |
| A-8 | 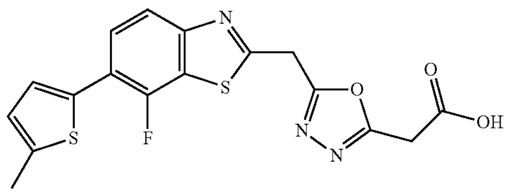 [SMILES: Cc1ccc(-c2ccc3nc(Cc4nnc(CC(=O)O)o4)sc3c2F)s1] | (DMSO-d6) δ: 2.50 (s, 3H), 4.09 (s, 2H), 5.02 (s, 2H), 6.92-6.94 (m, 1H), 7.48 (d, J = 3.3 Hz, 1H), 7.85-7.89 (m, 2H).. | | | |
| A-9 | 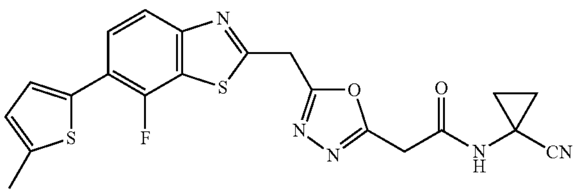 [SMILES: Cc1ccc(-c2ccc3nc(Cc4nnc(CC(=O)NC5(C#N)CC5)o4)sc3c2F)s1] | (DMSO-d6) δ: 1.14 (dd, J = 8.4, 5.3 Hz, 2H), 1.49 (dd, J = 8.4, 5.3 Hz, 2H), 2.50 (s, 3H), 3.92 (s, 2H), 5.00 (s, 2H), 6.91-6.93 (m, 1H), 7.48 (d, J = 3.6 Hz, 1H), 7.85-7.89 (m, 2H), 9.24 (s, 1H). | | | |
| A-10 | 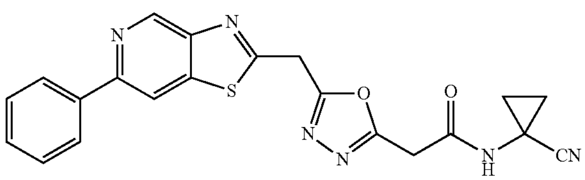 [SMILES: N#CC1(NC(=O)Cc2nnc(Cc3nc4cnc(-c5ccccc5)cc4s3)o2)CC1] | (DMSO-d6) δ: 1.14 (dd, J = 8.1, 5.6 Hz, 2H), 1.49 (dd, J = 8.1, 5.6 Hz, 2H), 3.92 (s, 2H), 5.04 (s, 2H), 7.45 (t, J = 7.4 Hz, 1H), 7.53 (t, J = 7.4 Hz, 2H), 8.16 (d, J = 7.1 Hz, 2H), 8.79 (s, 1H), 9.24 (s, 1H), 9.31 (s, 1H). | 1.54 | 417.20 (MS+) | C |

TABLE 100

| No. | Structure | NMR(δ) | retention time | Mass | method |
|---|---|---|---|---|---|
| A-11 | 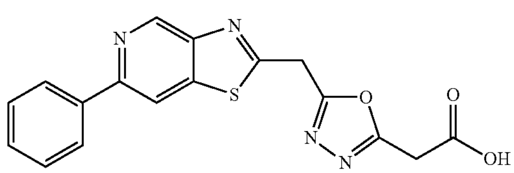 [SMILES: O=C(O)Cc1nnc(Cc2nc3cnc(-c4ccccc4)cc3s2)o1] | | 1.43 | 352.85 (MS+) | C |
| A-12 | 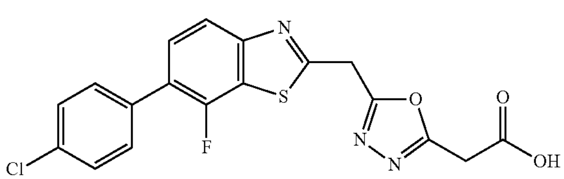 [SMILES: O=C(O)Cc1nnc(Cc2nc3ccc(-c4ccc(Cl)cc4)c(F)c3s2)o1] | (DMSO-d6) δ: 4.09 (s, 2H), 5.03 (s, 2H), 7.57-7.61 (m, 2H), 7.66-7.73 (m, 3H), 7.60 (d, J = 8.4 Hz, 1H). | | | |
| A-13 | 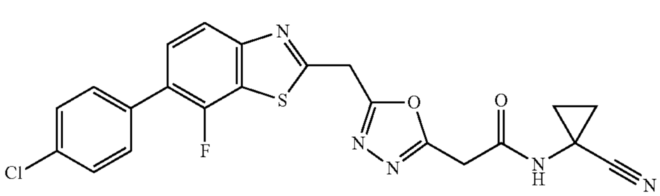 [SMILES: N#CC1(NC(=O)Cc2nnc(Cc3nc4ccc(-c5ccc(Cl)cc5)c(F)c4s3)o2)CC1] | (DMSO-d6) δ: 1.14 (dd, J = 8.4, 5.3 Hz, 2H), 1.49 (dd, J = 8.4, 5.3 Hz, 2H), 3.92 (s, 2H), 5.04 (s, 2H), 7.57-7.61 (m, 2H), 7.66-7.73 (m, 3H), 7.95 (d, J = 8.4 Hz, 1H), 9.24 (s, 1H). | | | |

TABLE 100-continued

| No. | Structure | NMR(δ) | retention time | Mass | method |
|---|---|---|---|---|---|
| A-14 | 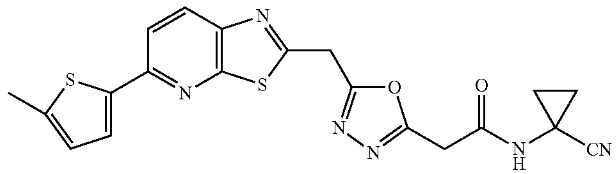 [SMILES: Cc1ccc(-c2ccc3nc(Cc4nnc(CC(=O)NC5(C#N)CC5)o4)sc3n2)s1] | (DMSO-d6) δ: 1.15 (dd, J = 8.2, 5.6 Hz, 2H), 1.49 (dd, J = 8.2, 5.6 Hz, 2H), 3.91 (s, 2H), 4.97 (s, 2H), 6.90 (s, 1H), 7.73 (s, 1H), 8.03 (d, J = 9.0 Hz, 1H), 8.35 (d, J = 8.7 Hz, 1H), 9.24 (s, 1H). | | | |
| A-15 | 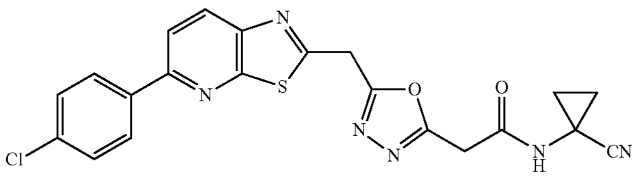 [SMILES: N#CC1(NC(=O)Cc2nnc(Cc3nc4ccc(-c5ccc(Cl)cc5)nc4s3)o2)CC1] | (DMSO-d6) δ: 1.14 (dd, J = 8.2, 5.6 Hz, 2H), 1.49 (dd, J = 8.2, 5.6 Hz, 2H), 3.92 (s, 2H), 5.02 (s, 2H), 7.59 (d, J = 8.7 Hz, 1H), 8.18-8.23 (s, 3H), 8.47 (d, J = 8.4 Hz, 1H), 9.24 (s, 1H). | | | |

TABLE 101

| No. | Structure | NMR(δ) | retention time | Mass | method |
|---|---|---|---|---|---|
| A-16 | 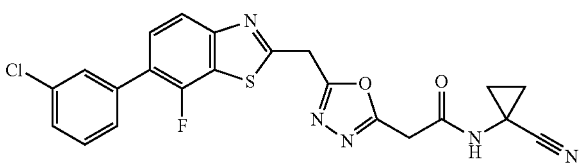 [SMILES: N#CC1(NC(=O)Cc2nnc(Cc3nc4ccc(-c5cccc(Cl)c5)c(F)c4s3)o2)CC1] | (DMSO-d6) δ: 1.14 (dd, J = 8.36, 5.32 Hz, 2H), 1.49 (dd, J = 8.36, 5.32 Hz, 2H), 3.92 (s, 2H), 5.03 (s, 2H), 7.53-7.65 (m, 3H), 7.71-7.76 (m, 2H), 7.97 (d, J = 8.40 Hz, 1H), 9.24 (s, 1H). | | | |
| A-17 | 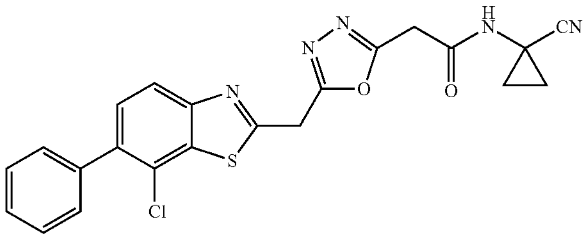 [SMILES: N#CC1(NC(=O)Cc2nnc(Cc3nc4ccc(-c5ccccc5)c(Cl)c4s3)o2)CC1] | (DMSO-d6) δ: 1.14 (dd, J = 8.11, 5.58 Hz, 2H), 1.49 (dd, J = 8.11, 5.58 Hz, 2H), 3.92 (s, 2H), 5.02 (s, 2H), 7.44-7.54 (m, 5H), 7.60 (d, J = 8.11 Hz, 1H), 8.05 (d, J = 8.11 Hz, 1H), 9.24 (s, 1H). | 2.06 | 449.9 (MS+) | C |
| A-18 | 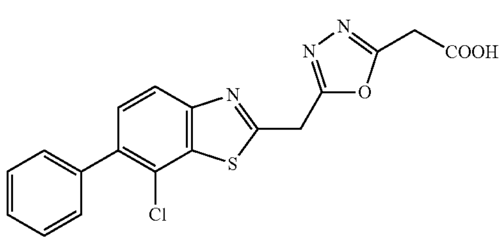 [SMILES: O=C(O)Cc1nnc(Cc2nc3ccc(-c4ccccc4)c(Cl)c3s2)o1] | | 2.01 | 385.90 (MS+) | C |
| A-19 | 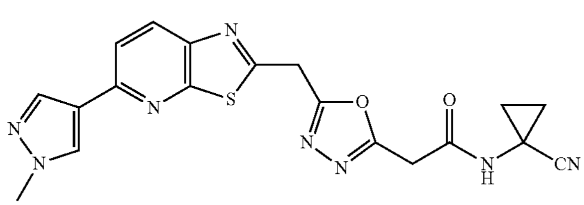 [SMILES: Cn1cc(-c2ccc3nc(Cc4nnc(CC(=O)NC5(C#N)CC5)o4)sc3n2)cn1] | (DMSO-d6) δ: 1.15 (dd, J = 8.2, 5.6 Hz, 2H), 1.49 (dd, J = 8.2, 5.8 Hz, 2H), 3.91 (s, 2H), 3.92 (s, 3H), 4.96 (s, 2H), 7.85 (d, J = 8.7 Hz, 1H), 8.01 (s, 1H), 8.33 (d, J = 9.0 Hz, 1H), 8.42 (s, 1H), 9.24 (s, 1H). | | | |

TABLE 101-continued

| No. | Structure | NMR(δ) | retention time | Mass | method |
|---|---|---|---|---|---|
| A-20 | 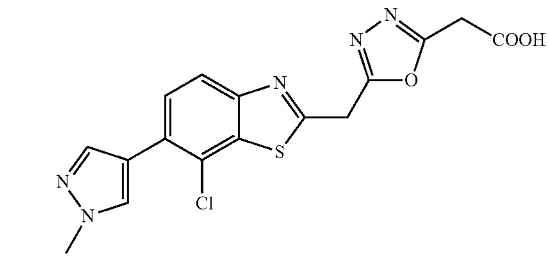 [SMILES: Cn1cc(-c2ccc3nc(Cc4nnc(CC(=O)O)o4)sc3c2Cl)cn1] | (DMSO-d6) δ: 3.92 (s, 3H), 4.09 (s, 2H), 4.99 (s, 2H), 7.78 (d, J = 8.62 Hz, 1H), 7.93-7.99 (m, 2H), 8.28 (s, 1H). | 1.37 | 389.90 (MS+) | C |

TABLE 102

| No. | Structure | NMR(δ) | retention time | Mass | method |
|---|---|---|---|---|---|
| A-21 | 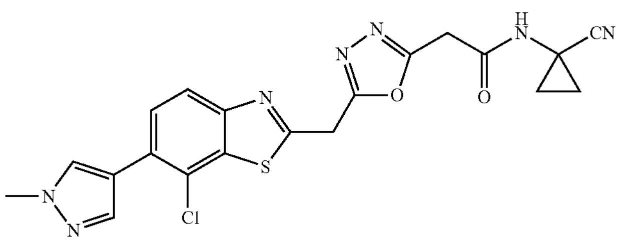 [SMILES: Cn1cc(-c2ccc3nc(Cc4nnc(CC(=O)NC5(C#N)CC5)o4)sc3c2Cl)cn1] | (DMSO-d6) δ: 1.14 (dd, J = 8.11, 5.58 Hz, 2H), 1.49 (dd, J = 8.36, 5.32 Hz, 2H), 3.91 (s, 2H), 3.92 (s, 3H), 4.99 (s, 2H), 7.78 (d, J = 8.11 Hz, 1H), 7.94 (s, 1H), 7.97 (d, J = 8.62 Hz, 1H), 8.28 (s, 1H), 9.24 (s, 1H). | 1.46 | 453.90 (MS+) | C |
| A-22 | 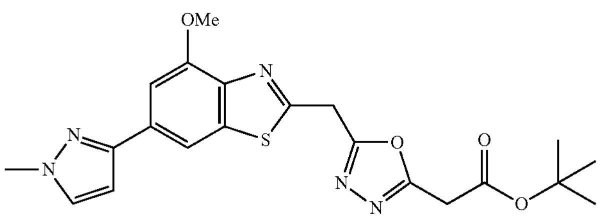 [SMILES: COc1cc(-c2ccn(C)n2)cc2sc(Cc3nnc(CC(=O)OC(C)(C)C)o3)nc12] | (CDCl3) δ: 1.39 (s, 9H), 3.86 (s, 2H), 3.97 (s, 3H), 4.09 (s, 3H), 4.76 (s, 2H), 6.99 (s, 1H), 7.51 (s, 1H), 7.67 (s, 1H), 7.80 (s, 1H). | | | |
| A-23 | 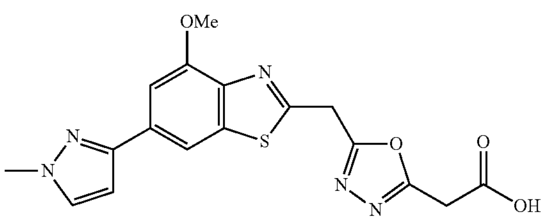 [SMILES: COc1cc(-c2ccn(C)n2)cc2sc(Cc3nnc(CC(=O)O)o3)nc12] | (DMSO-d6) δ: 3.89 (s, 3H), 3.99 (s, 3H), 4.07 (s, 2H), 4.88 (s, 2H), 7.24 (s, 1H), 7.83 (s, 1H), 7.97 (s, 1H), 8.25 (s, 1H) | | | |
| A-24 | 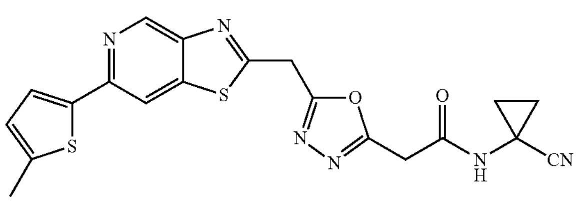 [SMILES: Cc1ccc(-c2cc3sc(Cc4nnc(CC(=O)NC5(C#N)CC5)o4)nc3cn2)s1] | (CDCl3) δ: 1.29 (dd, J = 8.4, 5.8 Hz, 2H), 1.59 (dd, J = 8.4, 5.8 Hz, 2H), 2.54 (s, 3H), 3.92 (s, 2H), 4.74 (s, 2H), 6.79 (dd, J = 3.6, 1.0 Hz, 1H), 7.42 (d, J = 3.6 Hz, 1H), 7.96 (s, 1H), 8.06 (s, 1H), 9.19 (s, 1H). | 1.72 | 437.00 (MS+) | C |
| A-25 | 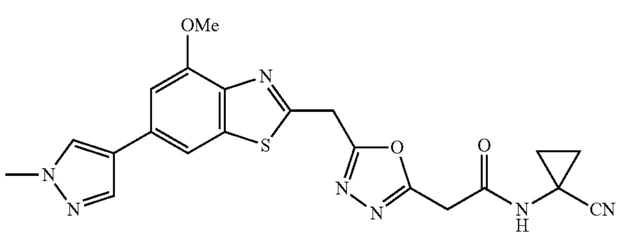 [SMILES: COc1cc(-c2cnn(C)c2)cc2sc(Cc3nnc(CC(=O)NC4(C#N)CC4)o3)nc12] | (DMSO-d6) δ: 1.14 (dd, J = 8.4, 5.3 Hz, 2H), 1.48 (dd, J = 8.4, 5.3 Hz, 2H), 3.88 (s, 3H), 3.91 (s, 2H), 3.99 (s, 3H), 4.88 (s, 2H), 7.24 (s, 1H), 7.83 (s, 1H), 7.97 (s, 1H), 8.25 (s, 1H), 9.23 (s, 1H). | | | |

TABLE 103

| No. | Structure | NMR(δ) | retention time | Mass | method |
|---|---|---|---|---|---|
| A-26 | 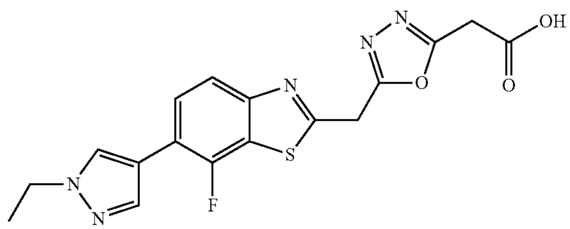 [SMILES: CCn1cc(-c2ccc3nc(Cc4nnc(CC(=O)O)o4)sc3c2F)cn1] | (DMSO-d6) δ: 1.42 (t, J = 7.2 Hz, 3H), 4.09 (s, 2H), 4.20 (s, 2H), 4.21 (q, J = 7.2 Hz, 2H), 5.00 (s, 2H), 7.84-7.92 (m, 2H), 7.99 (d, J = 2.1 Hz, 1H), 8.28 (d, J = 1.8 Hz, 1H). | | | |
| A-27 | 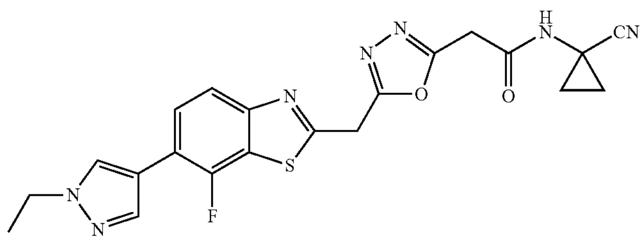 [SMILES: CCn1cc(-c2ccc3nc(Cc4nnc(CC(=O)NC5(C#N)CC5)o4)sc3c2F)cn1] | (DMSO-d6) δ: 1.14 (dd, J = 8.4, 5.3 Hz, 2H), 1.42 (t, J = 7.2 Hz, 3H), 1.49 (dd, J = 8.4, 5.3 Hz, 2H), 3.92 (s, 2H), 4.21 (q, J = 7.2 Hz, 2H), 5.00 (s, 2H), 7.84-7.92 (m, 2H), 7.99 (d, J = 1.50 Hz, 1H), 8.30 (d, J = 1.5 Hz, 1H), 9.24 (s, 1H). | | | |
| A-28 | 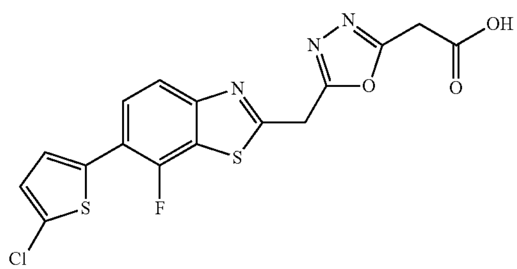 [SMILES: O=C(O)Cc1nnc(Cc2nc3ccc(-c4ccc(Cl)s4)c(F)c3s2)o1] | (DMSO-d6) δ: 4.09 (s, 2H), 5.03 (s, 2H), 7.27 (dd, J = 3.9, 0.9 Hz, 1H), 7.60 (d, J = 4.2 Hz, 1H), 7.92-7.97 (m, 2H). | | | |
| A-29 | 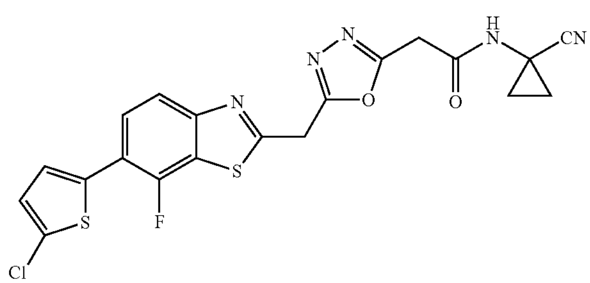 [SMILES: N#CC1(NC(=O)Cc2nnc(Cc3nc4ccc(-c5ccc(Cl)s5)c(F)c4s3)o2)CC1] | (DMSO-d6) δ: 1.14 (dd, J = 8.4, 5.3 Hz, 2H), 1.49 (dd, J = 8.4, 5.3 Hz, 2H), 3.92 (s, 2H), 5.03 (s, 2H), 727 (dd, J = 3.9, 1.2 Hz, 1H), 7.60 (d, J = 3.9 Hz, 1H), 7.90-7.98 (m, 2H), 9.24 (s, 1H). | | | |
| A-30 | 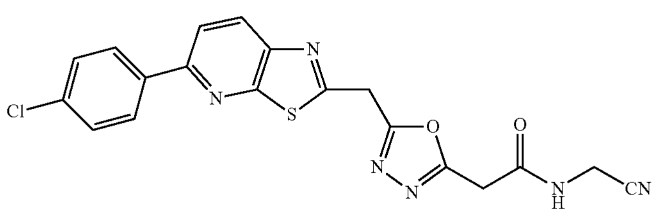 [SMILES: N#CCNC(=O)Cc1nnc(Cc2nc3ccc(-c4ccc(Cl)cc4)nc3s2)o1] | | 1.88 | 424.90 (M+) | C |

TABLE 104

| No. | Structure | NMR(δ) | retention time | Mass | method |
|---|---|---|---|---|---|
| A-31 | 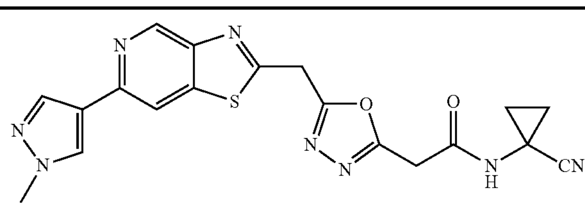 | (CDCl3) δ: 1.29 (dd, J = 8.1, 6.1 Hz, 2H), 1.59 (dd, J = 8.1, 6.1 Hz, 2H), 3.92 (s, 2H), 3.98 (s, 3H), 4.75 (s, 2H), 7.95 (s, 1H), 7.98 (s, 1H), 7.98-8.00 (m, 2H), 9.21 (d, J = 1.0 Hz, 1H). | 0.97 | 420.95 (MS+) | C |

TABLE 104-continued

| No. | Structure | NMR(δ) | retention time | Mass | method |
|---|---|---|---|---|---|
| A-32 | 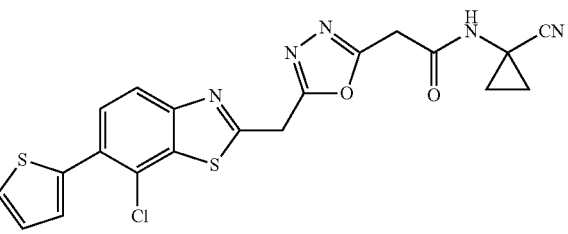 | (DMSO-d6) δ: 1.14 (dd, J = 8.11, 5.58 Hz, 2H), 1.49 (dd, J = 8.11, 5.58 Hz, 2H), 3.92 (s, 2H), 5.02 (s, 2H), 7.27 (d, J = 4.06 Hz, 1H), 7.45 (d, J = 4.06 Hz, 1H), 7.83 (d, J = 8.11 Hz, 1H), 8.04 (d, J = 8.62 Hz, 1H), 9.24 (s, 1H). | 2.32 | 489.85 & 491.80 (MS+) | C |
| A-33 | 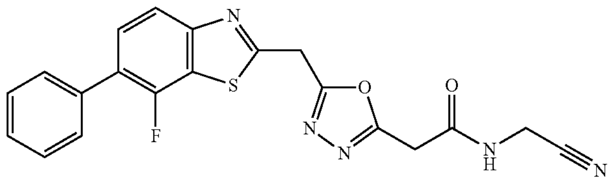 [SMILES: N#CCNC(=O)Cc1nnc(Cc2nc3ccc(-c4ccccc4)c(F)c3s2)o1] | (DMSO-d6) δ: 4.00 (s, 2H), 4.20 (d, J = 5.4 Hz, 2H), 5.02 (s, 2H), 7.43-7.55 (m, 3H), 7.63-7.70 (m, 3H), 7.96 (d, J = 7.4 Hz, 1H), 9.04 (t, J = 2.1 Hz, 1H). | | | |
| A-34 | 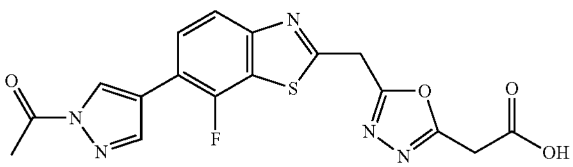 [SMILES: CC(=O)n1cc(-c2ccc3nc(Cc4nnc(CC(=O)O)o4)sc3c2F)cn1] | (DMSO-d6) δ: 2.50 (s, 3H), 4.09 (s, 2H), 5.00 (s, 2H), 7.84-7.96 (m, 2H), 8.17 (d, J = 1.8 Hz, 2H). | | | |
| A-35 | 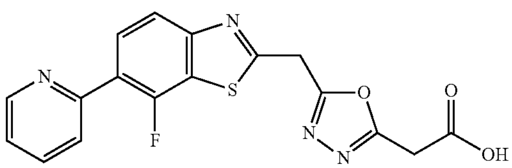 [SMILES: O=C(O)Cc1nnc(Cc2nc3ccc(-c4ccccn4)c(F)c3s2)o1] | (DMSO-d6) δ: 4.10 (s, 2H), 5.07 (s, 2H), 7.41-7.51 (m, 1H), 7.91-7.99 (m, 3H), 811 (t, J = 8.4 Hz, 1H), 8.77 (d, J = 4.0 Hz, 1H). | | | |

TABLE 105

| No. | Structure | NMR(δ) | retention time | Mass | method |
|---|---|---|---|---|---|
| A-36 | 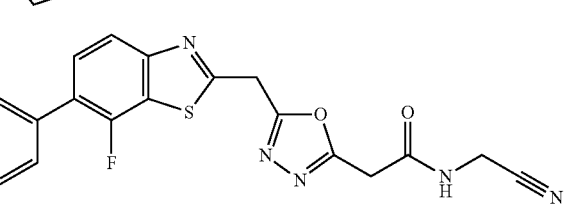 | (DMSO-d6) δ: 1.14 (dd, J = 8.1, 5.6 Hz, 2H), 1.49 (dd, J = 8.1, 5.6 Hz, 2H), 2.50 (s, 3H), 3.92 (s, 2H), 5.00 (s, 2H), 7.85-7.96 (m, 2H), 8.04 (s, 1H), 8.30 (s, 1H), 9.24 (s, 1H). | | | |
| A-37 | 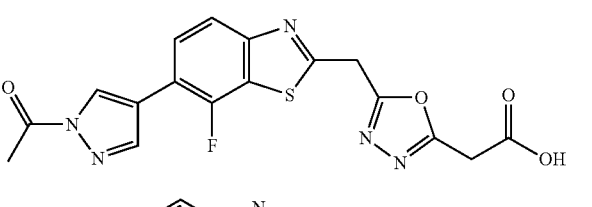 | (DMSO-d6) δ: 1.14 (dd, J = 8.1, 5.6 Hz, 2H), 1.49 (dd, J = 8.1, 5.6 Hz, 2H), 3.92 (s, 2H), 5.06 (s, 2H), 7.43-7.48 (m, 1H), 7.89-7.99 (m, 3H), 8.11 (t, J = 7.8 Hz, 1H), 8.75-8.78 (m, 1H), 9.24 (s, 1H). | | | |
| A-38 | 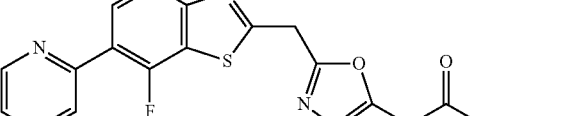 | (DMSO-d6) δ: 4.09 (s, 2H), 5.04 (s, 2H), 7.83 (s, 1H), 7.84 (d, J = 0.9 Hz, 1H). | | | |

TABLE 105-continued

| No. | Structure | NMR(δ) | retention time | Mass | method |
|---|---|---|---|---|---|
| A-39 | 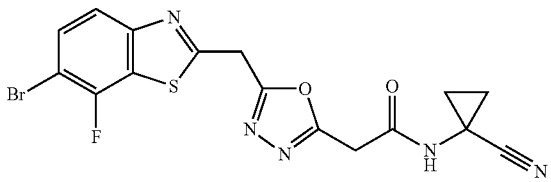 [SMILES: N#CC1(NC(=O)Cc2nnc(Cc3nc4ccc(Br)c(F)c4s3)o2)CC1] | (DMSO-d6) δ: 1.14 (dd, J = 8.4, 5.3 Hz, 2H), 1.49 (dd, J = 8.1, 5.6 Hz, 2H), 3.92 (s, 2H), 5.03 (s, 2H), 7.84 (s, 1H), 7.85 (d, J = 1.2 Hz, 1H), 9.24 (s, 1H). | | | |
| A-40 | 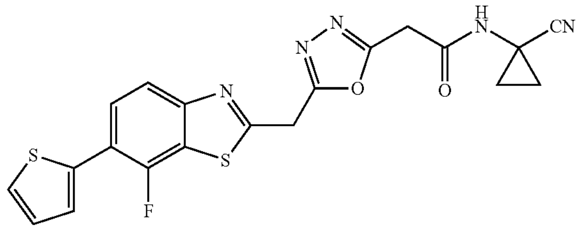 [SMILES: N#CC1(NC(=O)Cc2nnc(Cc3nc4ccc(-c5cccs5)c(F)c4s3)o2)CC1] | (DMSO-d6) δ: 1.14 (dd, J = 8.36, 5.32 Hz, 2H), 1.49 (dd, J = 8.11, 5.58 Hz, 2H), 3.92 (s, 2H), 5.03 (s, 2H), 7.24 (t, J = 4.06 Hz, 1H), 7.70 (d, J = 4.06 Hz, 1H), 7.75 (d, J = 5.07 Hz, 1H), 7.89-7.99 (m, 0H), 9.24 (s, 1H). | 1.91 | 438.10 (MS+) | C |

TABLE 106

| No. | Structure | NMR(δ) | retention time | Mass | method |
|---|---|---|---|---|---|
| A-41 | 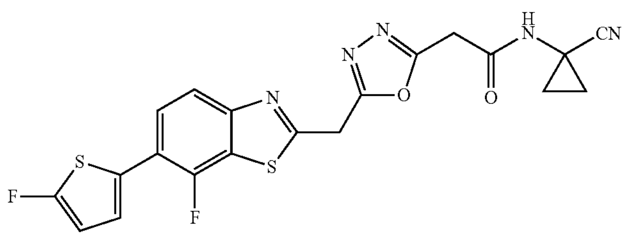 [SMILES: N#CC1(NC(=O)Cc2nnc(Cc3nc4ccc(-c5ccc(F)s5)c(F)c4s3)o2)CC1] | (DMSO-d6) δ: 1.14 (dd, J = 8.36, 5.32 Hz, 2H), 1.49 (dd, J = 8.36, 5.32 Hz, 2H), 3.92 (s, 2H), 5.03 (s, 2H), 6.89-6.92 (m, 1H), 7.43 (t, J = 3.80 Hz, 1H), 7.89-7.94 (m, 2H), 9.24 (s, 1H). | 2.05 | 457.9 | C |
| A-42 | 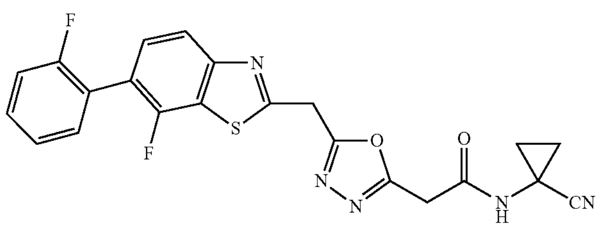 [SMILES: N#CC1(NC(=O)Cc2nnc(Cc3nc4ccc(-c5ccccc5F)c(F)c4s3)o2)CC1] | (DMSO-d6) δ: 1.14 (dd, J = 8.4, 5.3 Hz, 2H), 1.49 (dd, J = 8.4, 5.3 Hz, 2H), 3.92 (s, 2H), 5.05 (s, 2H), 7.36-7.45 (m, 2H), 7.52-7.68 (m, 3H), 7.98 (d, J = 8.4 Hz, 1H), 9.24 (s, 1H). | | | |
| A-43 | 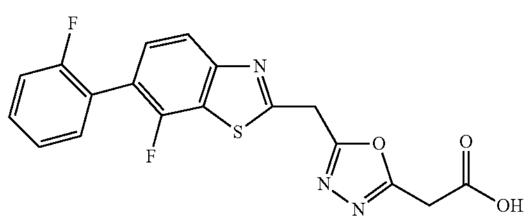 [SMILES: O=C(O)Cc1nnc(Cc2nc3ccc(-c4ccccc4F)c(F)c3s2)o1] | | 1.85 | 387.95 (MS+) | C |
| A-44 | 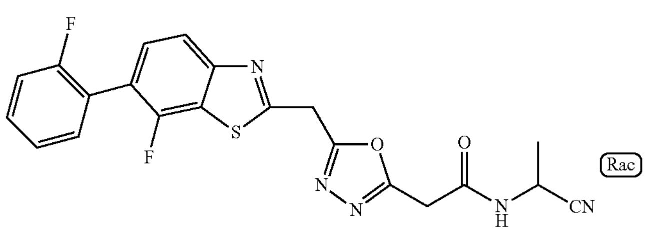 [SMILES: CC(C#N)NC(=O)Cc1nnc(Cc2nc3ccc(-c4ccccc4F)c(F)c3s2)o1] | | 1.92 | 440.25 (MS+) | C |

TABLE 106-continued

| No. | Structure | NMR(δ) | retention time | Mass | method |
|---|---|---|---|---|---|
| A-45 | 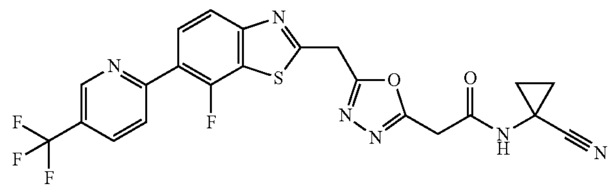 [SMILES: N#CC1(NC(=O)Cc2nnc(Cc3nc4ccc(-c5ccc(C(F)(F)F)cn5)c(F)c4s3)o2)CC1] | (DMSO-d6) δ: 1.14 (dd, J = 8.4, 5.3 Hz, 2H), 1.49 (dd, J = 8.4, 5.3 Hz, 2H), 3.92 (s, 2H), 5.07 (s, 2H), 8.03 (d, J = 8.7 Hz, 1H), 8.13-8.19 (m, 2H), 8.38-8.41 (m, 1H), 9.16 (s, 1H), 9.24 (s, 1H). | | | |

TABLE 107

| No. | Structure | NMR(δ) | retention time | Mass | method |
|---|---|---|---|---|---|
| A-46 | 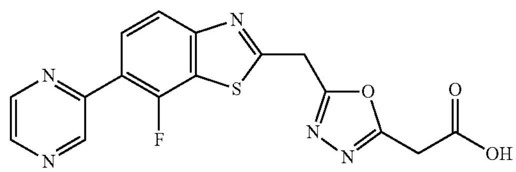 [SMILES: O=C(O)Cc1nnc(Cc2nc3ccc(-c4cnccn4)c(F)c3s2)o1] | (DMSO-d6) δ: 4.10 (s, 2H), 5.09 (s, 2H), 8.02-8.14 (m, 2H), , 8.71 (s, 1H), 8.85 (s, 1H), 9.15 (s, 1H). | | | |
| A-47 | 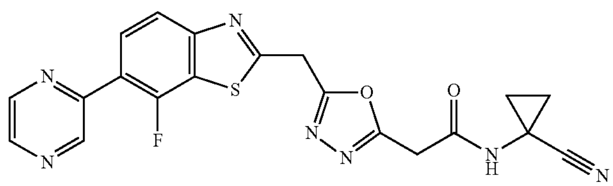 [SMILES: N#CC1(NC(=O)Cc2nnc(Cc3nc4ccc(-c5cnccn5)c(F)c4s3)o2)CC1] | (DMSO-d6) δ: 1.14 (dd, J = 8.4, 5.3 Hz, 2H), 1.49 (dd, J = 8.4, 5.3 Hz, 2H), 3.93 (s, 2H), 5.08 (s, 2H), 8.03 (d, J = 8.4 Hz, 1H), 8.12 (t, J = 8.1 Hz, 2H), 8.71 (d, J = 2.7 Hz, 1H), 8.85 (t, J = 2.4 Hz, 1H), 9.15 (dd, J = 2.7, 1.5 Hz, 1H), 9.24 (s, 1H). | | | |
| A-48 | 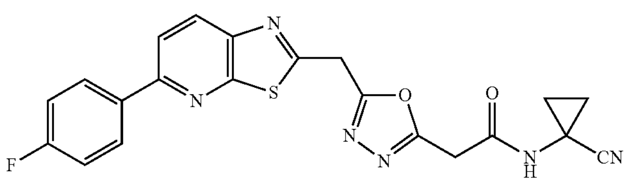 [SMILES: N#CC1(NC(=O)Cc2nnc(Cc3nc4ccc(-c5ccc(F)cc5)nc4s3)o2)CC1] | (DMSO-d6) δ: 1.15 (dd, J = 8.4, 5.3 Hz, 2H), 1.49 (dd, J = 8.4, 5.3 Hz, 2H), 3.92 (s, 2H), 5.01 (s, 2H), 7.36 (t, J = 9.0 Hz, 2H), 8.14-8.27 (m, 3H), 8.46 (d, J = 9.0 Hz, 1H), 9.26 (s, 1H). | | | |
| A-49 | 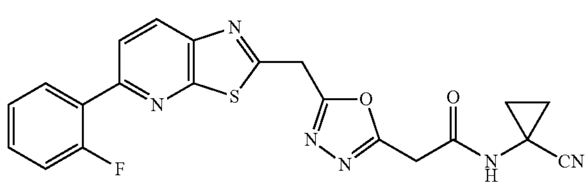 [SMILES: N#CC1(NC(=O)Cc2nnc(Cc3nc4ccc(-c5ccccc5F)nc4s3)o2)CC1] | | 1.71 | 435.25 (MS+) | C |
| A-50 | 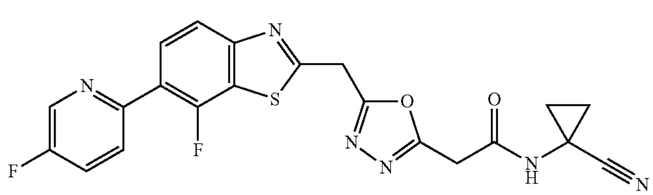 [SMILES: N#CC1(NC(=O)Cc2nnc(Cc3nc4ccc(-c5ccc(F)cn5)c(F)c4s3)o2)CC1] | (DMSO-d6) δ: 1.14 (dd, J = 8.4, 5.3 Hz, 2H), 1.49 (dd, J = 8.4, 5.3 Hz, 2H), 3.93 (s, 2H), 5.06 (s, 2H), 7.87-7.99 (m, 3H), 8.06 (t, J = 7.5 Hz, 1H), 8.77 (d, J = 2.7 Hz, 1H), 9.24 (s, 1H). | | | |

TABLE 108

| No. | Structure | NMR(δ) | retention time | Mass | method |
|---|---|---|---|---|---|
| A-51 | 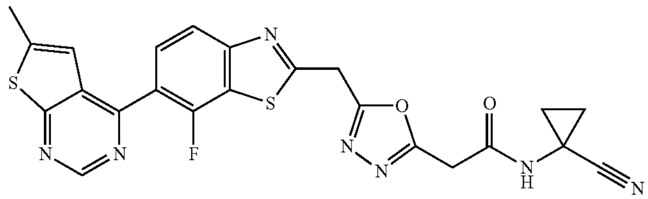 [SMILES: Cc1cc2c(-c3ccc4nc(Cc5nnc(CC(=O)NC6(C#N)CC6)o5)sc4c3F)ncnc2s1] | (DMSO-d6) δ: 1.14 (dd, J = 8.4, 5.3 Hz, 2H), 1.49 (dd, J = 8.4, 5.3 Hz, 2H), 2.63 (s, 3H), 3.93 (s, 2H), 5.10 (s, 2H), 7.21-7.28 (m, 1H), 7.90 (t, J = 7.8 Hz, 1H), 8.07 (d, J = 8.4 Hz, 1H), 9.15 (s, 1H), 9.24 (s, 1H). | | | |
| A-52 | 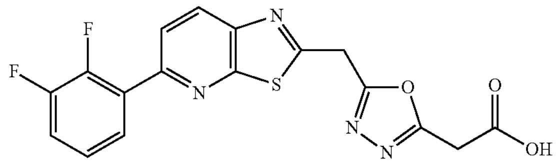 [SMILES: O=C(O)Cc1nnc(Cc2nc3ccc(-c4cccc(F)c4F)nc3s2)o1] | | 1.74 | 388.85 (MS+) | C |
| A-53 | 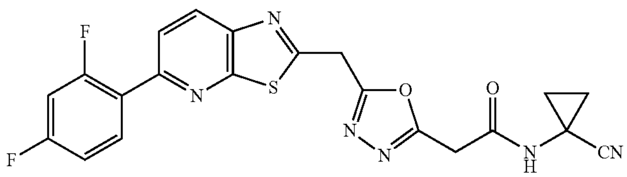 [SMILES: N#CC1(NC(=O)Cc2nnc(Cc3nc4ccc(-c5ccc(F)cc5F)nc4s3)o2)CC1] | (DMSO-d6) δ: 1.15 (dd, J = 8.4, 5.3 Hz, 2H), 1.49 (dd, J = 8.4, 5.3 Hz, 2H), 3.92 (s, 2H), 5.03 (s, 2H), 7.27 (m, 1H), 7.46 (m, 1H), 7.96 (d, J = 7.2 Hz, 1H), 8.06 (m, 1H), 8.49 (d, J = 8.7 Hz, 1H), 9.24 (s, 1H) | | | |
| A-54 | 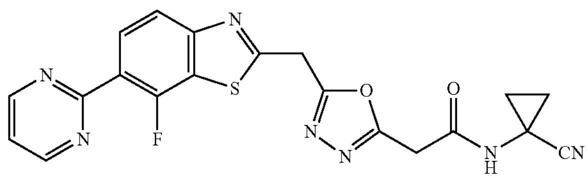 [SMILES: N#CC1(NC(=O)Cc2nnc(Cc3nc4ccc(-c5ncccn5)c(F)c4s3)o2)CC1] | (DMSO-d6) δ: 1.14 (dd, J = 8.4, 5.3 Hz, 2H), 1.49 (dd, J = 8.4, 5.3 Hz, 2H), 3.92 (s, 2H), 5.07 (s, 2H), 7.54 (t, J = 5.1 Hz, 1H), 8.00 (d, J = 9.0 Hz, 1H), 8.24 (t, J = 8.1 Hz, 1H), 8.99 (d, J = 4.5 Hz, 2H), 9.24 (s, 1H). | | | |
| A-55 | 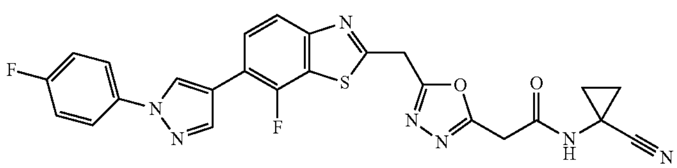 [SMILES: N#CC1(NC(=O)Cc2nnc(Cc3nc4ccc(-c5cnn(-c6ccc(F)cc6)c5)c(F)c4s3)o2)CC1] | (DMSO-d6) δ: 4.10 (s, 2H), 5.03 (s, 2H), 7.40 (t, J = 8.70 Hz, 2H), 7.91-8.04 (m, 4H), 8.30 (s, 1H), 9.02 (s, 1H). | | | |

TABLE 109

| No. | Structure | NMR(δ) | retention time | Mass | method |
|---|---|---|---|---|---|
| A-56 | 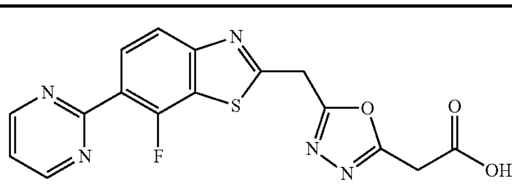 | (DMSO-d6) δ: 4.10 (s, 2H), 5.08 (s, 2H), 7.54 (t, J = 5.1 Hz, 1H), 7.99 (d, J = 9.0 Hz, 1H), 8.24 (t, J = 8.1Hz, 1H), 8.99 (d, J = 4.5 Hz, 2H). | | | |
| A-57 | 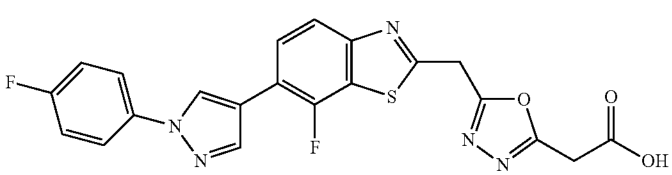 [SMILES: O=C(O)Cc1nnc(Cc2nc3ccc(-c4cnn(-c5ccc(F)cc5)c4)c(F)c3s2)o1] | (DMSO-d6) δ: 4.10 (s, 2H), 5.03 (s, 2H), 7.40 (t, J = 8.70 Hz, 2H), 7.91-8.04 (m, 4H), 8.30 (s, 1H), 9.02 (s, 1H). | | | |

TABLE 109-continued
| No. | Structure | NMR(δ) | retention time | Mass | method |
|---|---|---|---|---|---|
| A-58 | 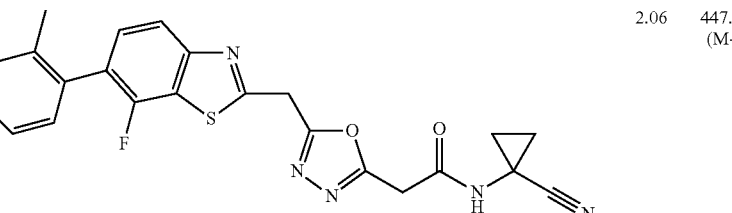 | | 1.79 | 453.00 (M+) | C |
| A-59 | 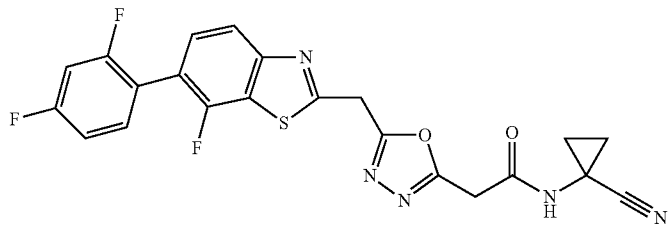 [SMILES: N#CC1(NC(=O)Cc2nnc(Cc3nc4ccc(-c5ccc(F)cc5F)c(F)c4s3)o2)CC1] | | 1.99 | 469.08 (M+) | C |
| A-60 | 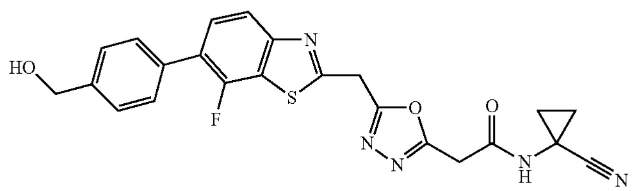 [SMILES: N#CC1(NC(=O)Cc2nnc(Cc3nc4ccc(-c5ccc(CO)cc5)c(F)c4s3)o2)CC1] | | 1.42 | 463.11 (M+) | C |
TABLE 110
| No. | Structure | retention time | Mass | method |
|---|---|---|---|---|
| A-61 | 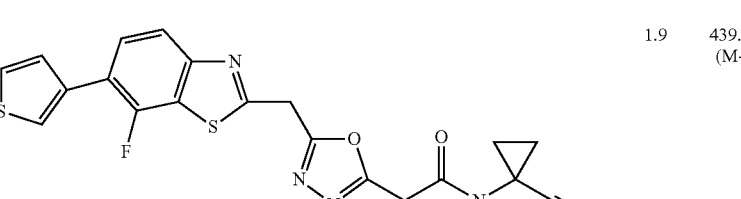 | 2.06 | 447.12 (M+) | C |
| A-62 | 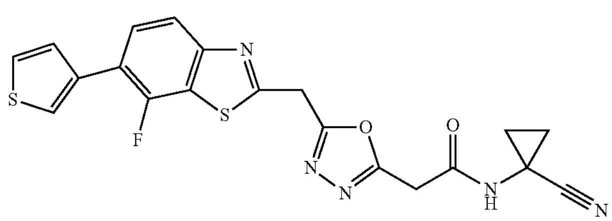 [SMILES: N#CC1(NC(=O)Cc2nnc(Cc3nc4ccc(-c5ccsc5)c(F)c4s3)o2)CC1] | 1.9 | 439.06 (M+) | C |
| A-63 | 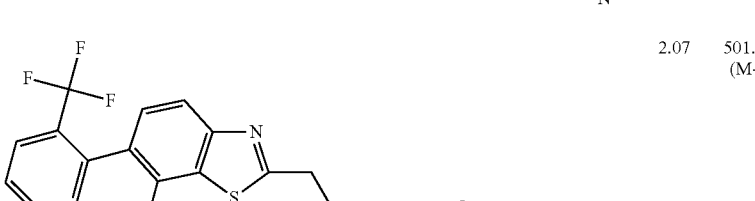 | 2.07 | 501.09 (M+) | C |

TABLE 110-continued

| No. | Structure | retention time | Mass | method |
|---|---|---|---|---|
| A-64 | 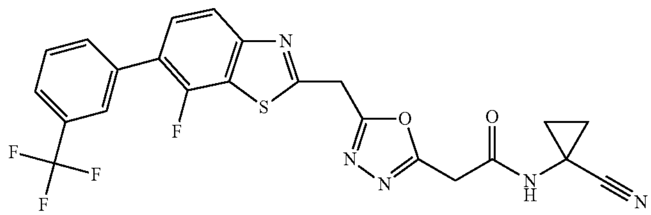 [SMILES: N#CC1(NC(=O)Cc2nnc(Cc3nc4ccc(-c5cccc(C(F)(F)F)c5)c(F)c4s3)o2)CC1] | 2.2 | 501.09 (M+) | C |
| A-65 | 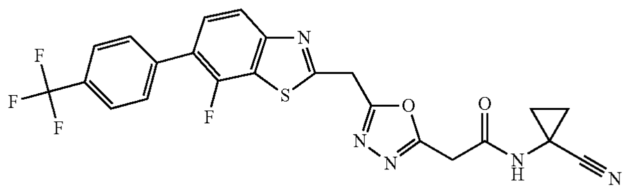 [SMILES: N#CC1(NC(=O)Cc2nnc(Cc3nc4ccc(-c5ccc(C(F)(F)F)cc5)c(F)c4s3)o2)CC1] | 2.23 | 501.09 (M+) | C |

TABLE 111

| No. | Structure | retention time | Mass | method |
|---|---|---|---|---|
| A-66 | 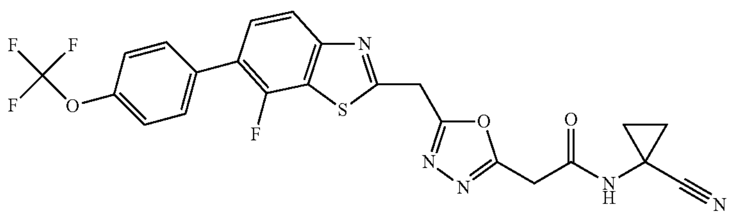 [SMILES: N#CC1(NC(=O)Cc2nnc(Cc3nc4ccc(-c5ccc(OC(F)(F)F)cc5)c(F)c4s3)o2)CC1] | 2.29 | 517.08 (M+) | C |
| A-67 | 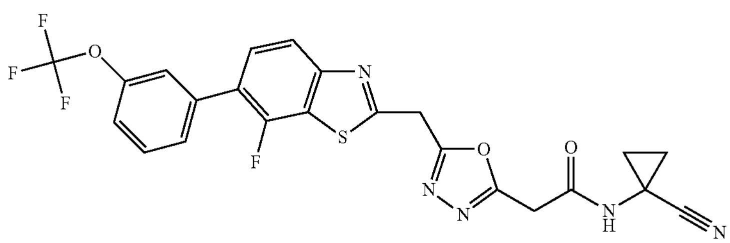 [SMILES: N#CC1(NC(=O)Cc2nnc(Cc3nc4ccc(-c5cccc(OC(F)(F)F)c5)c(F)c4s3)o2)CC1] | 2.26 | 517.08 (M+) | C |
| A-68 | 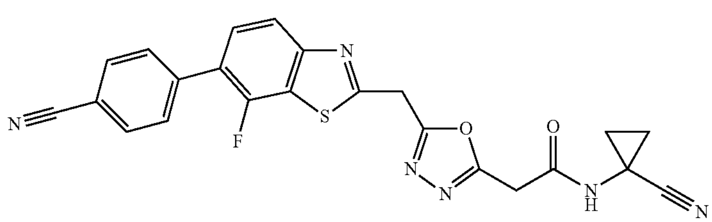 [SMILES: N#Cc1ccc(-c2ccc3nc(Cc4nnc(CC(=O)NC5(C#N)CC5)o4)sc3c2F)cc1] | 1.77 | 458.10 (M+) | C |
| A-69 | 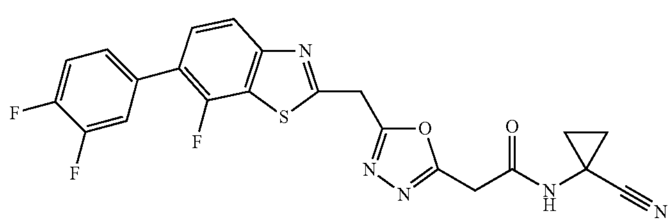 [SMILES: N#CC1(NC(=O)Cc2nnc(Cc3nc4ccc(-c5ccc(F)c(F)c5)c(F)c4s3)o2)CC1] | 2.05 | 469.08 (M+) | C |

TABLE 111-continued

| No. | Structure | retention time | Mass | method |
|---|---|---|---|---|
| A-70 | 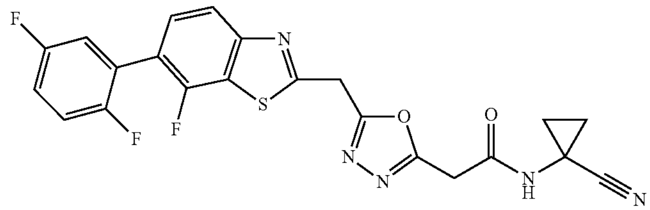 [SMILES: N#CC1(NC(=O)Cc2nnc(Cc3nc4ccc(-c5cc(F)ccc5F)c(F)c4s3)o2)CC1] | 1.96 | 469.08 (M+) | C |

TABLE 112

| No. | Structure | retention time | Mass | method |
|---|---|---|---|---|
| A-71 | 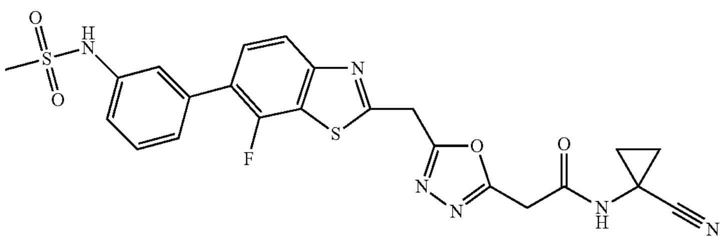 [SMILES: CS(=O)(=O)Nc1cccc(-c2ccc3nc(Cc4nnc(CC(=O)NC5(C#N)CC5)o4)sc3c2F)c1] | 1.54 | 526.09 (M+) | C |
| A-72 | 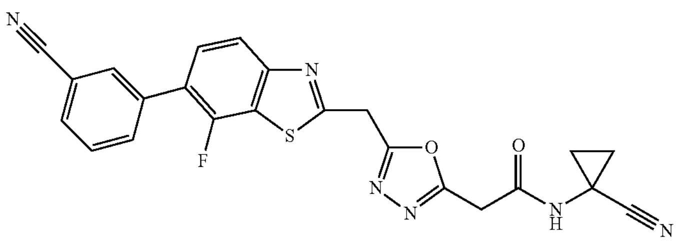 [SMILES: N#Cc1cccc(-c2ccc3nc(Cc4nnc(CC(=O)NC5(C#N)CC5)o4)sc3c2F)c1] | 1.78 | 458.10 (M+) | C |
| A-73 | 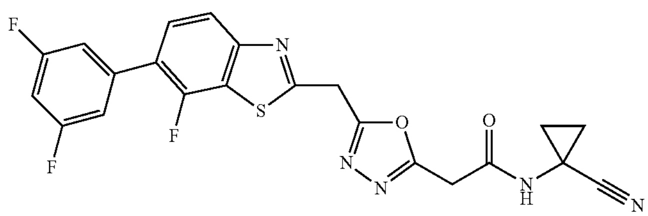 [SMILES: N#CC1(NC(=O)Cc2nnc(Cc3nc4ccc(-c5cc(F)cc(F)c5)c(F)c4s3)o2)CC1] | 2.07 | 469.08 (M+) | C |
| A-74 | 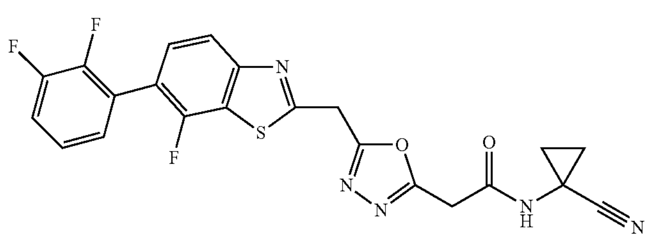 [SMILES: N#CC1(NC(=O)Cc2nnc(Cc3nc4ccc(-c5cccc(F)c5F)c(F)c4s3)o2)CC1] | 1.97 | 469.08 (M+) | C |
| A-75 | 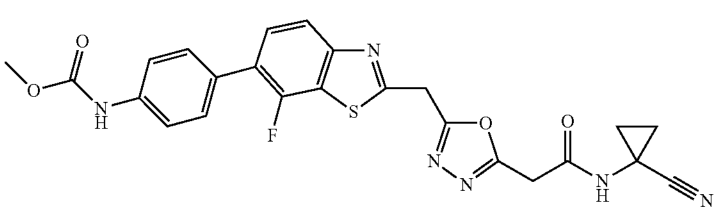 [SMILES: COC(=O)Nc1ccc(-c2ccc3nc(Cc4nnc(CC(=O)NC5(C#N)CC5)o4)sc3c2F)cc1] | 1.64 | 506.12 (M+) | C |

TABLE 113

| No. | Structure | NMR(δ) | retention time | Mass | method |
|---|---|---|---|---|---|
| A-76 | 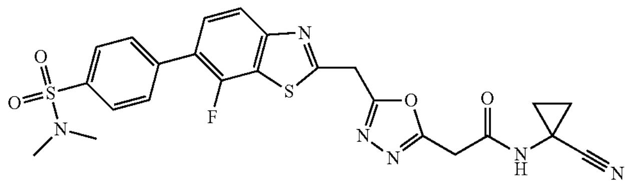 [SMILES: CN(C)S(=O)(=O)c1ccc(-c2ccc3nc(Cc4nnc(CC(=O)NC5(C#N)CC5)o4)sc3c2F)cc1] | | 1.73 | 540.11 (M+) | C |
| A-77 | 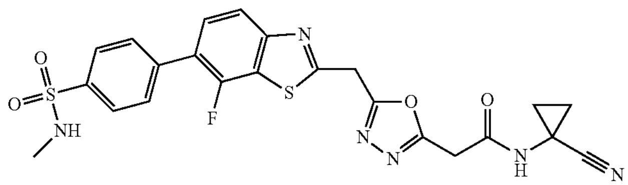 [SMILES: CNS(=O)(=O)c1ccc(-c2ccc3nc(Cc4nnc(CC(=O)NC5(C#N)CC5)o4)sc3c2F)cc1] | | 1.52 | 526.09 (M+) | C |
| A-78 | 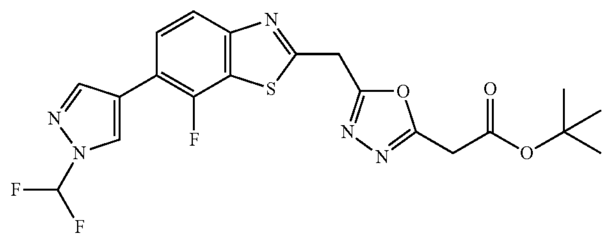 [SMILES: CC(C)(C)OC(=O)Cc1nnc(Cc2nc3ccc(-c4cnn(C(F)F)c4)c(F)c3s2)o1] | | | | |
| A-79 | 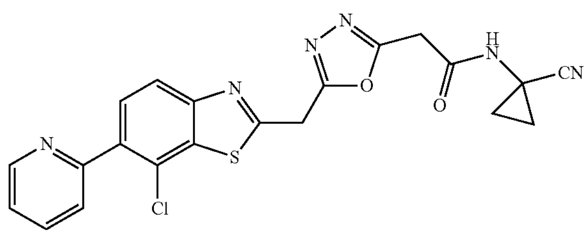 [SMILES: N#CC1(NC(=O)Cc2nnc(Cc3nc4ccc(-c5ccccn5)c(Cl)c4s3)o2)CC1] | (DMSO-d$_6$) δ: 1.14 (dd, J = 8.36, 5.32 Hz, 2H), 1.49 (dd, J = 8.11, 5.58 Hz, 2H), 3.92 (s, 2H), 5.04 (s, 2H), 7.47 (ddd, J = 7.35, 4.82, 1.01 Hz, 1H), 7.74-7.81 (m, 2H), 7.96 (td, J = 7.73, 1.69 Hz, 1H), 8.08 (d, J = 8.11 Hz, 1H), 8.74 (d, J = 5.07 Hz, 1H), 9.23 (s, 1H). | 1.43 | 450.90 (MS+) | C |
| A-80 | 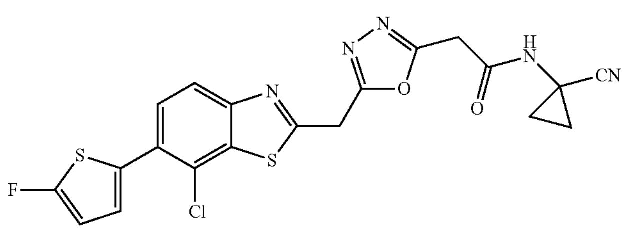 [SMILES: N#CC1(NC(=O)Cc2nnc(Cc3nc4ccc(-c5ccc(F)s5)c(Cl)c4s3)o2)CC1] | (DMSO-d$_6$) δ: 1.14 (dd, J = 8.11, 5.58 Hz, 2H), 1.49 (dd, J = 8.11, 5.58 Hz, 2H), 3.91 (s, 2H), 5.02 (s, 2H), 6.89 (dd, J = 4.31, 2.28 Hz, 1H), 7.27 (t, J = 3.80 Hz, 1H), 7.80 (d, J = 8.62 Hz, 1H), 8.03 (d, J = 8.11 Hz, 1H), 9.23 (s, 1H). | 2.16 | 473.85 (MS+) | C |

TABLE 114

| No. | Structure | NMR(δ) | retention time | Mass | method |
|---|---|---|---|---|---|
| A-81 | 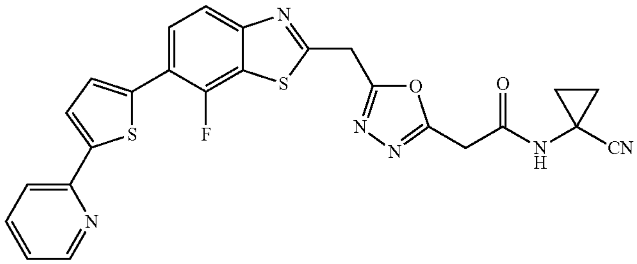 [SMILES: N#CC1(NC(=O)Cc2nnc(Cc3nc4ccc(-c5ccc(-c6ccccn6)s5)c(F)c4s3)o2)CC1] | (DMSO-d6) δ: 1.15 (dd, J = 8.1, 5.6 Hz, 2H), 1.49 (dd, J = 8.1, 5.6 Hz, 2H), 3.92 (s, 2H), 5.04 (s, 2H), 7.32 (dd, J = 6.6, 5.1 Hz, 1H), 7.74 (d, J = 3.6 Hz, 1H), 7.85-8.04 (m, 5H), 8.57 (d, J = 4.1 Hz, 1H), 9.24 (s, 1H). | 1.96 | 517.05 (MS+) | C |

TABLE 114-continued

| No. | Structure | NMR(δ) | retention time | Mass | method |
|---|---|---|---|---|---|
| A-82 | 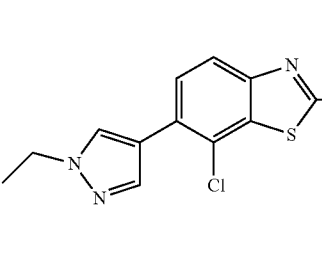 | (DMSO-d$_6$) δ: 1.14 (dd, J = 8.36, 5.32 Hz, 2H), 1.43 (t, J = 7.35 Hz, 3H), 1.49 (dd, J = 8.36, 5.32 Hz, 2H), 3.91 (s, 2H), 4.21 (q, J = 7.27 Hz, 2H), 4.98 (s, 2H), 7.79 (d, J = 8.62 Hz, 1H), 7.93-7.99 (m, 2H), 8.32 (s, 1H), 9.23 (s, 1H). | 1.59 | 467.90 (MS+) | C |
| A-83 | 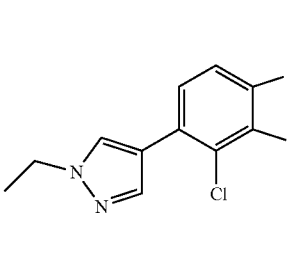 | | 1.5 | 403.85 (MS+) | C |
| A-84 | 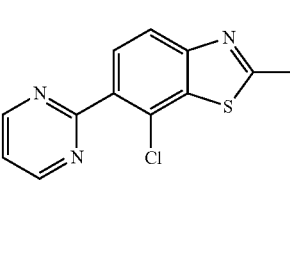 | (DMSO-d$_6$) δ: 1.15 (dd, J = 8.36, 5.83 Hz, 2H), 1.49 (dd, J = 8.11, 5.58 Hz, 2H), 3.92 (s, 2H), 5.05 (s, 2H), 7.59 (t, J = 4.82 Hz, 1H), 7.99 (d, J = 8.11 Hz, 1H), 8.10 (d, J = 8.62 Hz, 1H), 9.01 (d, J = 5.07 Hz, 2H), 9.24 (s, 1H). | 1.33 | 451.85 (MS+) | C |
| A-85 | 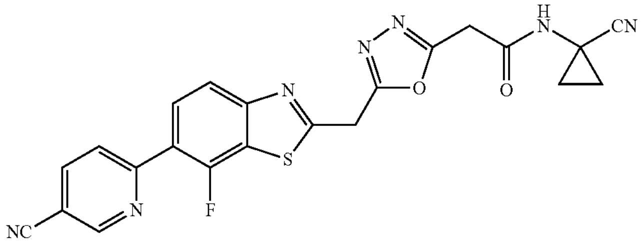 [SMILES: N#Cc1ccc(-c2ccc3nc(Cc4nnc(CC(=O)NC5(C#N)CC5)o4)sc3c2F)nc1] | (DMSO-d6) δ: 1.14 (dd, J = 8.4, 5.3 Hz, 2H), 1.49 (dd, J = 8.4, 5.2 Hz, 2H), 3.92 (s, 2H), 5.07 (s, 2H), 8.02 (d, J = 9.0 Hz, 1H), 8.10-8.19 (m, 2H), 8.46 (dd, J = 8.7, 2.1 Hz, 1H), 9.20 (d, J = 2.1 Hz, 1H), 9.24 (s, 1H). | | | |

TABLE 115

| No. | Structure | NMR(δ) | retention time | Mass | method |
|---|---|---|---|---|---|
| A-86 | 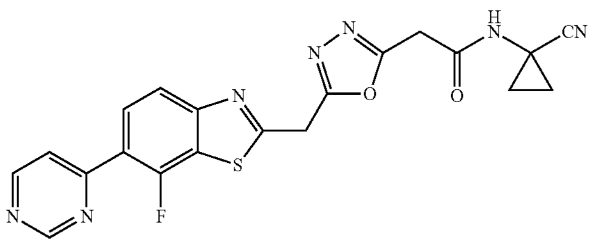 [SMILES: N#CC1(NC(=O)Cc2nnc(Cc3nc4ccc(-c5ccncn5)c(F)c4s3)o2)CC1] | (DMSO-d6) δ: 1.14 (dd, J = 8.4, 5.3 Hz, 2H), 1.49 (dd, J = 8.4, 5.3 Hz, 2H), 3.92 (s, 2H), 5.07 (s, 2H), 8.02-8.05 (m, 2H), 8.23 (t, J = 7.8 Hz, 1H), 8.95 (d, J = 5.4 Hz, 1H), 9.24 (s, 1H), 9.36 (s, 1H). | | | |

TABLE 115-continued

| No. | Structure | NMR(δ) | retention time | Mass | method |
|---|---|---|---|---|---|
| A-87 | 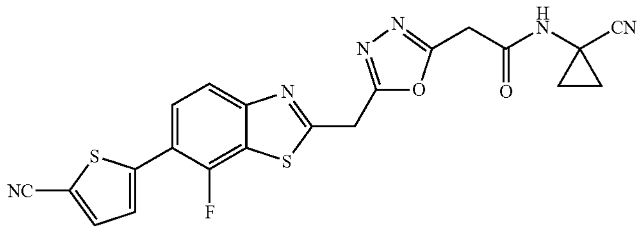 [SMILES: N#Cc1ccc(-c2ccc3nc(Cc4nnc(CC(=O)NC5(C#N)CC5)o4)sc3c2F)s1] | (DMSO-d6) δ: 1.14 (dd, J = 8.4, 5.3 Hz, 2H), 1.49 (dd, J = 8.4, 5.3 Hz, 2H), 3.92 (s, 2H), 5.06 (s, 2H), 7.87 (d, J = 3.9 Hz, 1H), 7.97 (d, J = 8.4 Hz, 1H), 8.05-8.11 (m, 2H), 9.24 (s, 1H). | | | |
| A-88 | 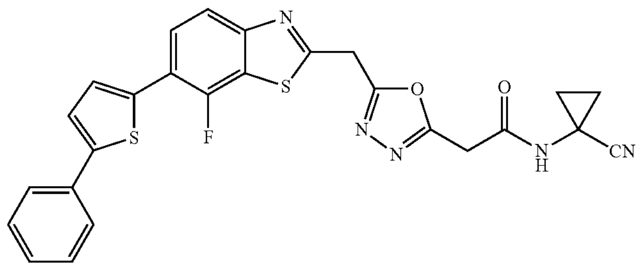 [SMILES: N#CC1(NC(=O)Cc2nnc(Cc3nc4ccc(-c5ccc(-c6ccccc6)s5)c(F)c4s3)o2)CC1] | (DMSO-d6) δ: 1.15 (dd, J = 8.4, 5.3 Hz, 2H), 1.49 (dd, J = 8.4, 5.3 Hz, 2H), 3.92 (s, 2H), 5.03 (s, 2H), 7.36 (t, J = 7.6 Hz, 1H), 7.46 (t, J = 7.6 Hz, 2H), 7.64 (dd, J = 3.8, 1.3 Hz, 1H), 7.72-7.75 (m, 3H), 7.93 (d, J = 8.6 Hz, 1H), 7.98-8.02 (m, 1H), 9.24 (s, 1H). | 2.4 | 516.25 (MS+) | C |
| A-89 | 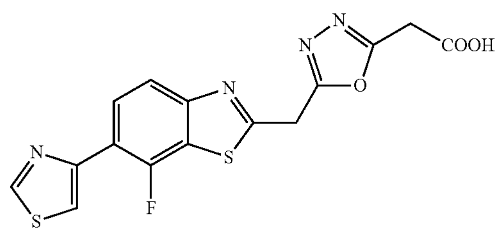 [SMILES: O=C(O)Cc1nnc(Cc2nc3ccc(-c4cscn4)c(F)c3s2)o1] | (DMSO-d$_6$) δ: 4.09 (s,2H), 5.04 (s, 2H), 7.96 (d, J = 8.62 Hz, 1H), 8.19 (t, J = 2.03 Hz, 1H), 8.31 (t, J = 8.11 Hz, 1H), 9.30 (d, J = 2.03 Hz, 1H). | 1.46 | 377.05 (MS+) | C |
| A-90 | 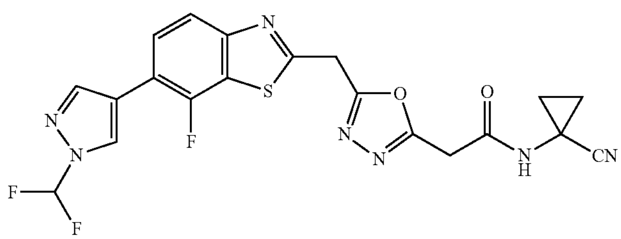 [SMILES: N#CC1(NC(=O)Cc2nnc(Cc3nc4ccc(-c5cnn(C(F)F)c5)c(F)c4s3)o2)CC1] | (DMSO-d6) δ: 1.15 (dd, J = 8.4, 5.3 Hz, 2H), 1.49 (dd, J = 8.4, 5.3 Hz, 2H), 3.92 (s, 2H), 5.02 (s, 2H), 7.71-8.11 (m, 3H), 8.38 (s, 1H), 8.77 (s, 1H), 9.24 (s, 1H). | | | |

TABLE 116

| No. | Structure | NMR(δ) | retention time | Mass | method |
|---|---|---|---|---|---|
| A-91 | 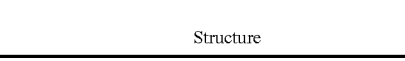 | (DMSO-d$_6$) δ: 1.14 (dd, J = 8.36, 5.83 Hz, 2H), 1.49 (dd, J = 8.36, 5.32 Hz, 2H), 3.92 (s, 2H), 5.04 (s, 2H), 7.96 (d, J = 8.62 Hz, 1H), 8.19 (t, J = 2.03 Hz, 1H), 8.31 (t, J = 8.11 Hz, 1H), 9.23 (s, 1H), 9.30 (d, J = 1.52 Hz, 1H). | 1.59 | 440.85 (MS+) | C |

The compounds shown below were prepared and inhibitory activity on endothelial lipase (EL) was examined. The compounds shown below can be synthesized by appropriately combine of the above general synthesis methods, the above examples, reference examples, known technique and the like.

TABLE 117

| No. | Structure | NMR(δ) |
|---|---|---|
| S-49 | 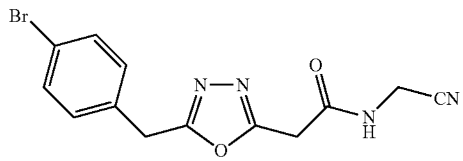 [SMILES: N#CCNC(=O)Cc1nnc(Cc2ccc(Br)cc2)o1] | $^1$H-NMR (DMSO-d$_6$) δ: 3.93 (s, 2H), 4.19 (d, J = 3.9 Hz, 2H), 4.27 (s, 2H), 7.28 (d, J = 8.4 Hz, 2H), 7.55 (d, J = 8.1 Hz, 2H), 9.00 (br-s, 1H). |
| S-50 | 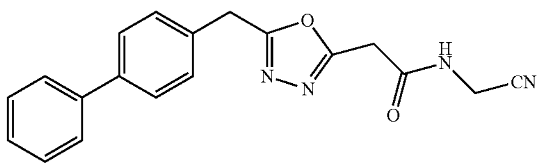 [SMILES: N#CCNC(=O)Cc1nnc(Cc2ccc(-c3ccccc3)cc2)o1] | $^1$H-NMR (DMSO-d$_6$) δ: 3.93 (s, 2H), 4.19 (s, 2H), 4.32 (s, 2H), 7.32-7.49 (m, 5H), 7.63-7.66 (m, 4H), 9.00 (br-s, 1H). |
| S-51 | 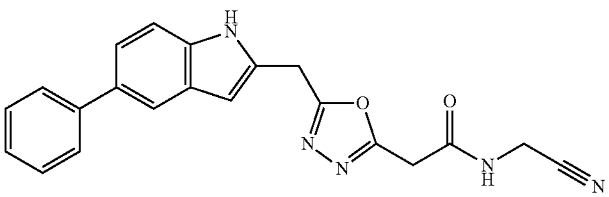 [SMILES: N#CCNC(=O)Cc1nnc(Cc2cc3cc(-c4ccccc4)ccc3[nH]2)o1] | 1H-NMR (DMSO-d6) δ: 3.95 (s, 2H), 4.19 (d, J = 5.4 Hz, 2H), 4.56 (s, 2H), 7.26 (m, 1H), 6.37 (s, 1H), 7.37-7.45 (m, 4H), 7.63 (d, J = 7.2 Hz, 2H), 7.73 (s, 1H), 9.02 (t, J = 3.0 Hz, 1H), 11.26 (s, 1H). |
| S-52 | 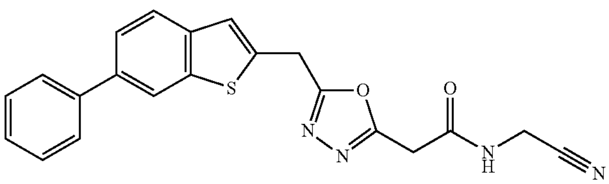 [SMILES: N#CCNC(=O)Cc1nnc(Cc2cc3ccc(-c4ccccc4)cc3s2)o1] | $^1$H-NMR (DMSO-d$_6$) δ: 3.97 (s, 2H), 4.20 (d, J = 3.0 Hz, 2H), 4.68 (s, 2H), 7.35-7.50 (m, 4H), 7.68 (dd, J = 6.0, 3.0 Hz, 1H), 7.74 (d, J = 6.0 Hz, 2H), 7.88 (d, J = 6.0 Hz, 1H), 8.25 (s, 1H), 9.02 (t, J = 3.0 Hz, 1H) |
| S-53 | 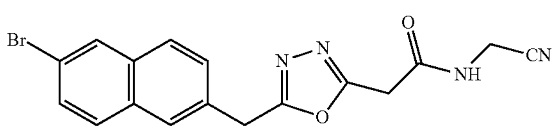 [SMILES: N#CCNC(=O)Cc1nnc(Cc2ccc3cc(Br)ccc3c2)o1] | $^1$H-NMR (DMSO-d$_6$) δ: 3.93 (s, 2H), 4.17 (d, J = 5.58 Hz, 2H), 4.44 (s, 2H), 7.51 (dd, J = 8.36, 1.77 Hz, 1H), 7.64 (dd, J = 8.36, 1.77 Hz, 1H), 7.84-7.93 (m, 3H), 8.20 (d, J = 2.03 Hz, 1H), 8.98 (t, J = 5.58 Hz, 1H). |

TABLE 118

| No. | Structure | NMR(δ) |
|---|---|---|
| S-54 | 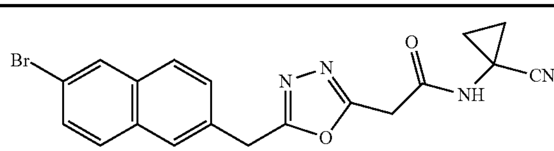 | $^1$H-NMR (DMSO-d$_6$) δ: 1.11 (dd, J = 8.36, 5.32 Hz, 2H), 1.47 (dd, J = 8.36, 5.32 Hz, 2H), 3.85 (s, 2H), 4.44 (s, 2H), 7.51 (dd, J = 8.62, 1.52 Hz, 1H), 7.64 (dd, J = 8.62, 2.03 Hz, 1H), 7.84-7.94 (m, 3H), 8.20 (d, J = 2.03 Hz, 1H), 9.18 (s, 1H). |
| S-55 | 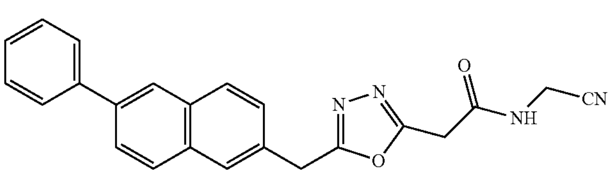 [SMILES: N#CCNC(=O)Cc1nnc(Cc2ccc3cc(-c4ccccc4)ccc3c2)o1] | $^1$H-NMR (DMSO-d$_6$) δ: 3.94 (s, 2H), 4.18 (d, J = 5.58 Hz, 2H), 4.46 (s, 2H), 7.40 (t, J = 7.35 Hz, 1H), 7.45-7.55 (m, 3H), 7.80-7.88 (m, 4H), 7.96-8.01 (m, 2H), 8.22 (br s, 1H), 8.99 (t, J = 5.32 Hz, 1H). |

TABLE 118-continued

| No. | Structure | NMR(δ) |
|---|---|---|
| S-56 | 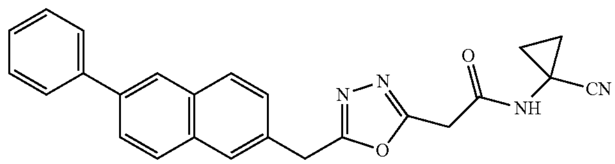 [SMILES: N#CC1(NC(=O)Cc2nnc(Cc3ccc4cc(-c5ccccc5)ccc4c3)o2)CC1] | $^1$H-NMR (DMSO-d$_6$) δ: 1.12 (dd, J = 8.11, 5.58 Hz, 2H), 1.47 (dd, J = 8.11, 5.58 Hz, 2H), 3.86 (s, 2H), 4.46 (s, 2H), 7.40 (t, J = 7.35 Hz, 1H), 7.45-7.55 (m, 3H), 7.80-7.89 (m, 4H), 7.96-8.01 (m, 2H), 8.22 (br s, 1H), 9.19 (s, 1H). |
| S-57 | 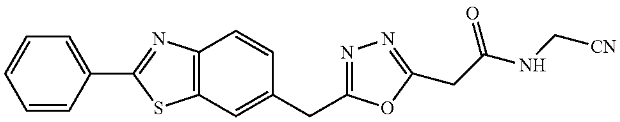 [SMILES: N#CCNC(=O)Cc1nnc(Cc2ccc3nc(-c4ccccc4)sc3c2)o1] | $^1$H-NMR (DMSO-d$_6$) δ: 3.94 (s, 2H), 4.18 (d, J = 5.58 Hz, 2H), 4.44 (s, 2H), 7.50 (dd, J = 8.36, 1.77 Hz, 1H), 7.56-7.61 (m, 3H), 8.02-8.12 (m, 4H), 8.99 (t, J = 5.58 Hz, 1H). |
| S-58 | 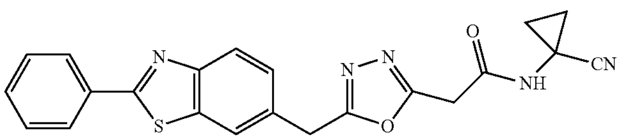 [SMILES: N#CC1(NC(=O)Cc2nnc(Cc3ccc4nc(-c5ccccc5)sc4c3)o2)CC1] | $^1$H-NMR (DMSO-d$_6$) δ: 1.13 (dd, J = 8.36, 5.32 Hz, 2H), 1.48 (dd, J = 8.36, 5.32 Hz, 2H), 3.86 (s, 2H), 4.45 (s, 2H), 7.50 (dd, J = 8.62, 1.52 Hz, 1H), 7.57-7.61 (m, 3H), 8.02-8.12 (m, 4H), 9.20 (s, 1H). |

TABLE 119

| No. | Structure | NMR(δ) |
|---|---|---|
| S-59 | 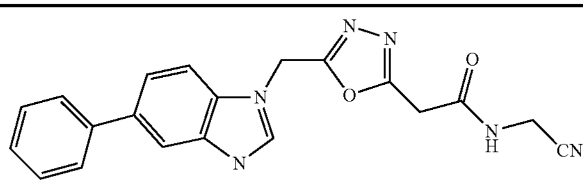 | $^1$H-NMR (DMSO-d$_6$) δ: 3.96 (s, 2H), 4.18 (d, J = 5.58 Hz, 2H), 5.95 (s, 2H), 7.34 (t, J = 7.35 Hz, 1H), 7.43-7.49 (m, 2H), 7.58-7.73 (m, 4H), 7.94 (d, J = 1.01 Hz, 1H), 8.41 (s, 1H), 9.00 (t, J = 5.58 Hz, 1H). |
| S-60 | 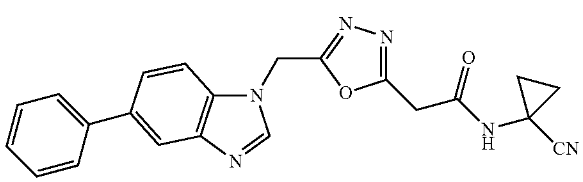 [SMILES: N#CC1(NC(=O)Cc2nnc(Cn3cnc4cc(-c5ccccc5)ccc43)o2)CC1] | $^1$H-NMR (DMSO-d$_6$) δ: 1.10 (dd, J = 8.11, 5.58 Hz, 2H), 1.47 (dd, J = 8.11, 5.58 Hz, 2H), 3.87 (s, 2H), 5.95 (s, 2H), 7.34 (t, J = 7.35 Hz, 1H), 7.43-7.49 (m, 2H), 7.58-7.72 (m, 4H), 7.94 (d, J = 1.01 Hz, 1H), 8.40 (s, 1H), 9.19 (s, 1H). |
| S-25 | 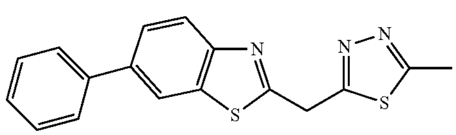 [SMILES: Cc1nnc(Cc2nc3ccc(-c4ccccc4)cc3s2)s1] | |
| S-28 | 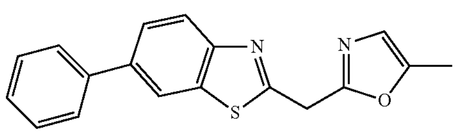 [SMILES: Cc1cnc(Cc2nc3ccc(-c4ccccc4)cc3s2)o1] | 1H-NMR (DMSO-d6) δ: 3.94 (m, 2H), 4.09 (s, 2H), 7.39 (t, J = 7.1 Hz, 1H), 7.49 (t, J = 8.4 Hz, 2H), 7.74-7.80-7.64 (m, 3H), 8.01 (d, J = 8.4 Hz, 1H), 8.38 (s, 1H), 8.82 (s, 1H). |
| S-30 | 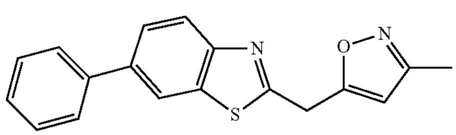 [SMILES: Cc1cc(Cc2nc3ccc(-c4ccccc4)cc3s2)on1] | 1H-NMR (CDCl3) δ: 2.30 (s, 3H), 4.58 (s, 2H), 6.10 (s, 1H), 7.38 (t, J = 8.0 Hz, 1H), 7.47 (t, J = 7.6 Hz, 2H), 7.63 (d, J = 8.4 Hz, 2H), 7.72 (d, J = 8.0 Hz, 1H), 8.06 (d, J = 8.6 Hz, 2H). |

TABLE 120

| No. | Structure | NMR(δ) |
|---|---|---|
| S-32 | 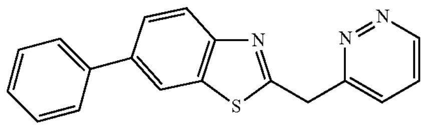 [SMILES: c1ccc(-c2ccc3nc(Cc4cccnn4)sc3c2)cc1] | 1H-NMR (CDCl3) δ: 4.87 (s, 2H), 7.38 (t, J = 7.6 Hz, 1H), 7.44-7.49 (m, 3H), 7.70 (d, J = 2.0 Hz, 3H), 7.72 (d, J = 2.0 Hz, 1H), 8.05 (d, J = 2.0 Hz, 2H), 9.15 (s, 1H) |
| S-34 | 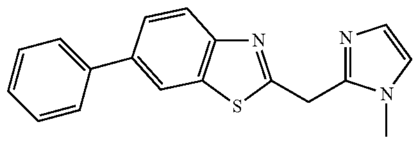 [SMILES: Cn1ccnc1Cc1nc2ccc(-c3ccccc3)cc2s1] | 1H-NMR (CDCl3) δ: 3.66 (s, 3H), 4.63 (s, 2H), 6.88 (d, J = 1.0 Hz, 1H), 7.05 (s, 1H), 7.37 (t, J = 7.4 Hz, 1H), 7.46 (t, J = 7.4 Hz, 2H), 7.62 (d, J = 7.1 Hz, 2H), 7.69 (dd, J = 8.4, 1.8 Hz, 1H), 8.00-8.03 (m, 2H). |
| S-36 | 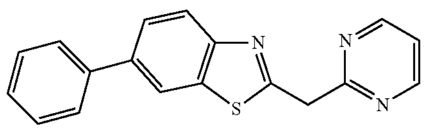 [SMILES: c1ccc(-c2ccc3nc(Cc4ncccn4)sc3c2)cc1] | 1H-NMR (DMSO-d6) δ: 4.80 (s, 2H), 7.39 (t, J = 6.8 Hz, 1H), 7.45-7.52 (m, 3H), 7.73-7.80 (m, 3H), 8.01 (d, J = 8.6 Hz, 1H), 8.37 (s, 1H), 8.83 (d, J = 5.1 Hz, 2H). |
| S-40 | 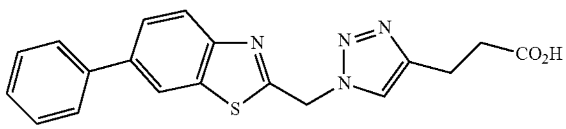 [SMILES: O=C(O)CCc1cn(Cc2nc3ccc(-c4ccccc4)cc3s2)nn1] | 1H-NMR (DMSO-d6) δ: 2.60 (t, J = 6.3 Hz, 2H), 2.89 (t, J = 7.1 Hz, 2H), 6.13 (s, 2H), 7.40 (t, J = 7.4 Hz, 1H), 7.50 (t, J = 7.6 Hz, 2H), 7.74 (d, J = 7.6 Hz, 2H), 7.84 (dd, J = 8.6, 1.5 Hz, 1H), 8.06-8.09 (m, 2H), 8.41 (d, J = 1.0 Hz, 1H) |
| S-41 | 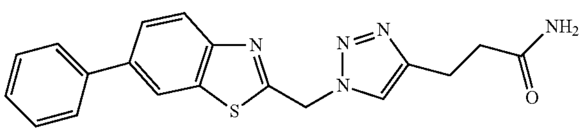 [SMILES: NC(=O)CCc1cn(Cc2nc3ccc(-c4ccccc4)cc3s2)nn1] | 1H-NMR (CDCl3) δ: 2.69 (t, J = 7.1 Hz, 2H), 3.08 (t, J = 7.1 Hz, 2H), 5.28 (br s, 1H), 5.73 (br s, 1H), 5.93 (s, 2H), 7.39 (t, J = 7.4 Hz, 1H), 7.47 (t, J = 7.6 Hz, 2H), 7.61-7.64 (m, 3H), 7.75 (dd, J = 8.6, 1.5 Hz, 1H), 8.04-8.10 (m, 2H). |

TABLE 121

| No. | Structure | NMR(δ) |
|---|---|---|
| S-42 | 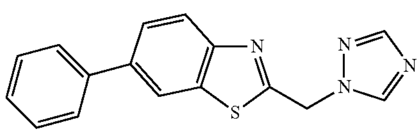 [SMILES: c1ccc(-c2ccc3nc(Cn4cncn4)sc3c2)cc1] | 1H-NMR (CDCl3) δ: 5.81 (s, 2H), 7.39 (t, J = 7.6 Hz, 1H), 7.47 (t, J = 7.6 Hz, 2H), 7.63 (d, J = 6.8 Hz, 2H), 7.74 (dd, J = 8.8, 1.6 Hz, 1H), 8.05-8.10 (m, 3H), 8.34 (s, 1H). |
| S-43 | 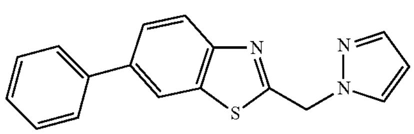 [SMILES: c1ccc(-c2ccc3nc(Cn4cccn4)sc3c2)cc1] | 1H-NMR (CDCl3) δ: 5.76 (s, 2H), 6.37 (t, J = 2.0 Hz, 1H), 7.37 (t, J = 7.4 Hz, 1H), 7.46 (t, J = 7.9 Hz, 2H), 7.63 (dd, J = 8.9, 7.9 Hz, 4H), 7.71 (dd, J = 8.4, 1.8 Hz, 1H), 8.02 (s, 1H), 8.07 (d, J = 8.1 Hz, 1H). |
| S-44 | 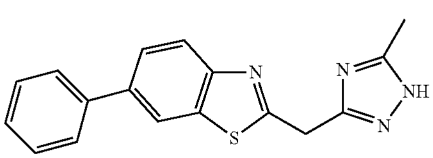 [SMILES: Cc1nc(Cc2nc3ccc(-c4ccccc4)cc3s2)n[nH]1] | 1H-NMR (CDCl3) δ: 2.47 (s, 3H), 4.63 (s, 2H), 7.38 (t, J = 7.1 Hz, 1H), 7.46 (t, J = 7.6 Hz, 2H), 7.62 (d, J = 7.6 Hz, 2H), 7.70 (dd, J = 8.4, 1.8 Hz, 1H), 8.04-8.06 (m, 2H). |

TABLE 121-continued

| No. | Structure | NMR(δ) |
|---|---|---|
| S-46 | 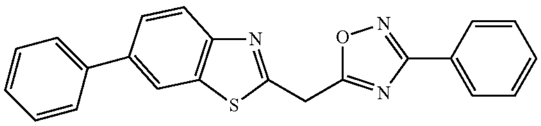 [SMILES: c1ccc(-c2ccc3nc(Cc4nc(-c5ccccc5)no4)sc3c2)cc1] | $^1$H-NMR (DMSO-d$_6$) δ: 5.15 (s, 2H), 7.35-7.68 (m, 6H), 7.76 (d, J = 7.10 Hz, 2H), 7.83 (dd, J = 8.62, 2.03 Hz, 1H), 8.00-8.08 (m, 3H), 8.46 (d, J = 2.03 Hz, 1H). |
| S-47 | 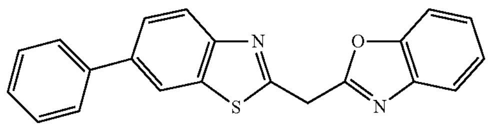 [SMILES: c1ccc(-c2ccc3nc(Cc4nc5ccccc5o4)sc3c2)cc1] | $^1$H-NMR (DMSO-d$_6$) δ: 5.01 (s, 2H), 7.37-7.44 (m, 3H), 7.50 (t, J = 7.60 Hz, 2H), 7.71-7.78 (m, 4H), 7.82 (dd, J = 8.62, 2.03 Hz, 1H), 8.05 (d, J = 8.62 Hz, 1H), 8.43 (d, J = 2.03 Hz, 1H). |

TABLE 122

| No. | Structure | NMR(δ) |
|---|---|---|
| S-48 | 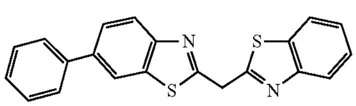 [SMILES: c1ccc(-c2ccc3nc(Cc4nc5ccccc5s4)sc3c2)cc1] | $^1$H-NMR (DMSO-d$_6$) δ: 5.12 (s, 2H), 7.38-7.55 (m, 5H), 7.71-7.77 (m, 2H), 7.82 (dd, J = 8.62, 1.52 Hz, 1H), 8.01 (d, J = 8.11 Hz, 1H), 8.04-8.13 (m, 2H), 8.41 (d, J = 1.52 Hz, 1H). |

Reference Example 1

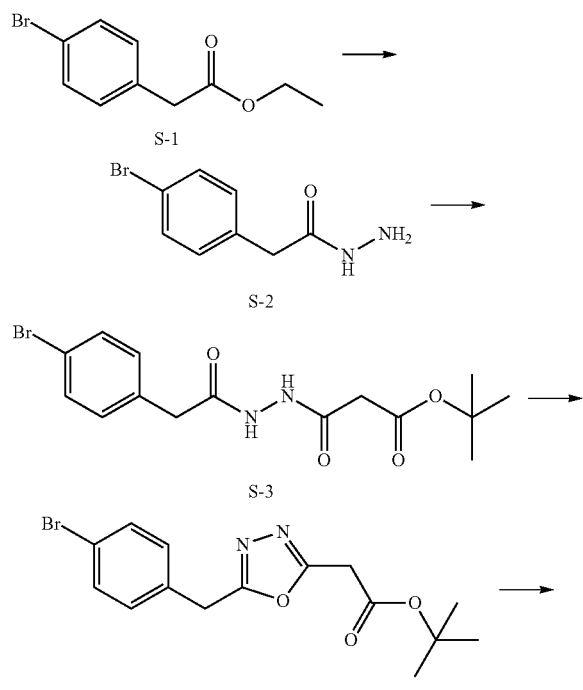

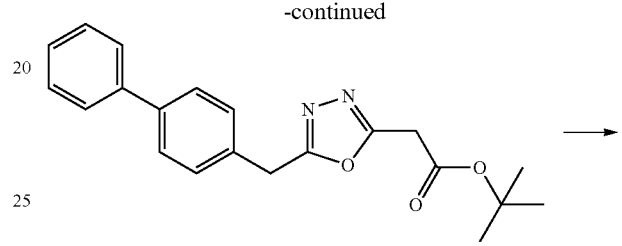

To a solution of ethyl 2-(4-bromophenyl)acetate (S-1) (2 g, 8.23 mmol) in ethanol (20 mL) was added hydrazine hydrate (0.82 g, 16.5 mmol), then the reaction mixture was refluxed for 5 hours. The reaction solution was cooled to room temperature. The obtained crystal was collected by filtration to give Compound (S-2) (1.2 g, 64%).

Compound (S-2); $^1$H-NMR (DMSO-d6) δ: 4.21 (d, J=3.9 Hz, 2H), 7.21 (d, J=8.1 Hz, 2H), 7.48 (dd, J=6.3, 1.8 Hz, 2H), 9.21 (br-s, 1H)

To a solution of Compound (S-2) (1.2 g, 5.24 mmol) in anhydrous dimethylformamide (10 ml) were successively added 3-tert-butoxy-3-oxopropanoic acid (1 g, 6.29 mmol), WSCD HCl (1.31 g, 6.81 mmol) and HOBt (0.21 g, 1.57 mmol) under nitrogen atmosphere at room temperature, then the reaction mixture was stirred for 14 hours. To the reaction solution was added 1N hydrochloric acid, then the reaction solution was extracted with ethyl acetate. The extraction was washed with brine and dried over sodium sulfate. To the residue was added ethyl acetate/hexane, then the insoluble residue was collected by filtration to give Compound (S-3) (1.68 g, 86%).

Compound (S-3); $^1$H-NMR (DMSO-d6) δ: 1.40 (s, 9H), 3.17 (s, 2H), 3.46 (s, 2H), 7.25 (d, J=8.4 Hz, 2H), 7.51 (d, J=8.4 Hz, 2H), 10.19 (br-s, 2H)

To a solution of Compound (S-3) (1 g, 2.69 mmol) in anhydrous dimethoxyethane (10 ml) was added Burgess reagent (963 mg, 4.0 mmol), then the reaction mixture was stirred at 90° C. for 2 hour. The solvent was removed under reduced pressure. To the residue was added water, then the mixture was extracted with ethyl acetate. The extraction was washed with brine and dried over sodium sulfate. The solvent was removed under reduced pressure. The obtained residue was purified by column chromatography to give Compound (S-4) (671 mg, 71%). Compound (S-4); 1H-NMR (CDCl3) δ: 1.40 (s, 9H), 3.82 (s, 2H), 4.16 (s, 2H), 7.18 (d, J=8.4 Hz, 2H), 7.47 (d, J=8.4 Hz, 2H)

To a solution of Compound (S-4) (400 mg, 1.13 mmol) in anhydrous 1,4-dioxane (200 ml) were added TETRAKIS (TRIPHENYLPHOSPHINE) PALLADIUM (0) (41.4 mg, 0.057 mmol), PHENYLBORONIC ACID (180 mg, 1.47 mmol) and 2M aqueous potassium carbonate solution (850 μl, 1.7 mmol) under nitrogen atmosphere at room temperature, then the reaction mixture was stirred at 120° C. for 15 minutes under microwave irradiation. To the reaction solution were added hydrochloric acid and ethyl acetate, then the reaction solution was extracted with ethyl acetate. The extraction was washed with brine and dried over sodium sulfate. The solvent was removed under reduced pressure. The obtained residue was purified by column chromatography to give Compound (S-5) (302 mg, 76%).

Compound (S-5); 1H-NMR (CDCl3) δ: 1.40 (s, 9H), 3.85 (s, 2H), 4.26 (s, 2H), 7.35-7.48 (m, 5H), 7.57 (d, J=7.8 Hz, 4H)

To a solution of Compound (S-5) (290 mg, 0.83 mmol) in dichloromethane (1.5 mL) was added trifluoroacetic acid (1 mL), then the reaction mixture was stirred at room temperature for 2 hours. The solvent was removed under reduced pressure. The obtained crystal was washed with hexane to give Compound (S-6) (173 mg, 71%). Compound (S-6); 1H-NMR (DMSO-d6) δ: 4.03 (s, 2H), 4.32 (s, 2H), 7.35-7.49 (m, 5H), 7.65 (d, J=8.1 Hz, 4H)

To a solution of Compound (S-6) (70 mg, 0.24 mmol) in dimethylformamide (3 ml) were successively added 2-aminoacetonitrile hydrochloride (33 mg, 0.36 mmol), WSCD HCl (59.3 mg, 0.31 mmol), HOBt (6.4 mg, 0.048 mmol) and Et$_3$N (0.1 mL, 0.71 mmol) under nitrogen atmosphere, then the reaction mixture was stirred at room temperature for 2 hours. To the reaction solution was added 1N hydrochloric acid, then the reaction solution was extracted with ethyl acetate. The extraction was washed with brine and dried over sodium sulfate. The solvent was removed under reduced pressure. The obtained residue was purified by column chromatography to give Compound (S-7) (58 mg, 73%).

Compound (S-7); 1H-NMR (DMSO-d6) δ: 3.94 (s, 2H), 4.19 (s, 2H), 4.32 (s, 2H), 7.35-7.49 (m, 5H), 7.65 (d, J=8.1 Hz, 4H), 9.00 (br-s, 1H)

Reference Example 2

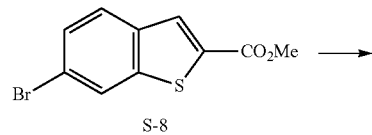

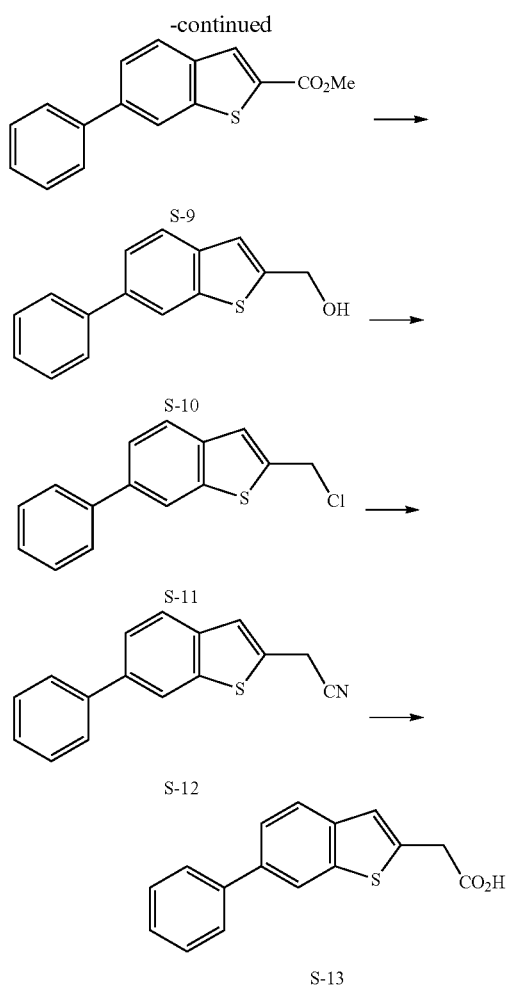

To a solution of Compound (S-8) (24 g, 88 mmol) in anhydrous 1,4-dioxane (150 mL) were added TETRAKIS (TRIPHENYLPHOSPHINE) PALLADIUM (0) (5.1 g, 4.4 mmol), PHENYLBORONIC ACID (16.1 g, 132 mmol) and potassium phosphate (37.4 g, 176 mmol) under nitrogen atmosphere, then the reaction mixture was refluxed at 80° C. for 12 hours. To the reaction solution was added water, then the reaction solution was extracted with ethyl acetate. The extraction was washed with brine and dried over sodium sulfate. The solvent was removed under reduced pressure. The obtained residue was purified by column chromatography to give Compound (S-9) (18.8 g, 79%).

Compound (S-9); $^1$H-NMR (DMSO-d6) δ: 3.91 (s, 3H), 7.42 (t, J=7.6 Hz, 1H), 7.51 (t, J=8.0 Hz, 2H), 8.11 (d, J=8.0 Hz, 1H), 8.24 (s, 1H), 8.40 (s, 1H)

To a solution of Lithium Aluminum Hydride (2.33 g, 61.5 mmol) in anhydrous tetrahydrofuran (60 mL) was added a solution of Compound (S-9) (13.8 g, 51.2 mmol) in anhydrous tetrahydrofuran (70 mL) under nitrogen atmosphere with ice-cooling, then the reaction mixture was stirred at 5° C. for 1 hour. To the reaction solution was added water, then the reaction solution was extracted with ethyl acetate. The extraction was washed with brine and dried over sodium sulfate. The solvent was removed under reduced pressure. The obtained residue was purified by column chromatography to give Compound (S-10) (14.5 g, quant).

Compound (S-10); $^1$H-NMR (DMSO-d$_6$) δ: 4.76 (dd, J=5.58, 1.01 Hz, 2H), 5.67 (t, J=5.83 Hz, 1H), 7.29 (s, 1H), 7.37 (t, J=7.35 Hz, 1H), 7.48 (dd, J=7.60, 7.35 Hz, 2H), 7.65 (dd, J=8.11, 1.52 Hz, 1H), 7.75 (d, J=7.60 Hz, 2H), 7.84 (d, J=8.11 Hz, 1H), 8.23 (d, J=1.52 Hz, 1H).

To a solution of Compound (S-10) (10.5 g, 43.7 mmol) in anhydrous toluene (100 mL) was added thionyl chloride (3.83 ml, 52.4 mmol) under nitrogen atmosphere, then the reaction mixture was stirred at 55° C. for 24 hours. The solvent was removed under reduced pressure. To the residue was added chloroform, then the obtained crystal was collected by filtration to give Compound (S-11) (14.5 g, quant). Compound (S-11); $^1$H-NMR (DMSO-$d_6$) δ: 5.17 (s, 2H), 7.38 (t, J=7.35 Hz, 1H), 7.46-7.56 (m, 3H), 7.68-7.78 (m, 3H), 7.91 (d, J=8.62 Hz, 1H), 8.29 (d, J=1.01 Hz, 1H).

To a solution of Compound (S-11) (5 g, 19.32 mmol) in anhydrous dimethylformamide (50 mL) was added potassium cyanide (1.887 g, 29.0 mmol), then the reaction mixture was stirred at 80° C. for 4 hours To the reaction solution were added 10% aqueous sodium bicarbonate solution and ethyl acetate, then the reaction solution was extracted with ethyl acetate. The organic layer was washed with brine and dried over sodium sulfate. The solvent was removed under reduced pressure. The obtained residue was purified by column chromatography to give Compound (S-12) (3.4 g, 71%).

To a solution of Compound (S-12) (2 g, 8.02 mmol) in acetic acid (15 mL) was added concentrated hydrochloric acid (15 ml, 494 mmol), then the reaction mixture was stirred at 90° C. for 6 hours. The insoluble residue was collected by filtration, then the reaction solution was extracted with diethylether. The organic layer was washed with brine and dried over sodium sulfate. The solvent was removed under reduced pressure to give Compound (S-13) (2.3 g, quant).

Reference Example 3

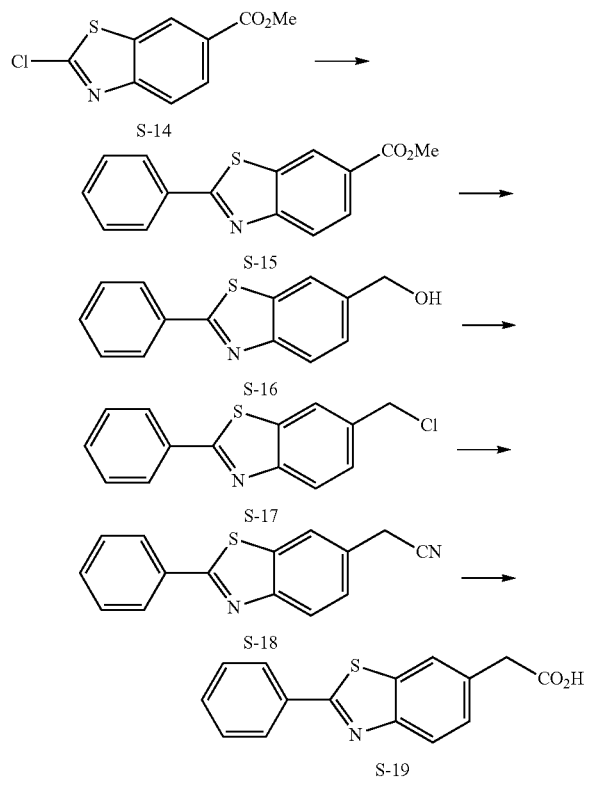

To a solution of methyl 2-chlorobenzo[d] thiazole-6-carboxylate (S-14) (1.4 g, 6.15 mmol) in anhydrous 1,4-dioxane (15 ml) were added TETRAKIS(TRIPHENYLPHOSPHINE) PALLADIUM (0) (0.497 g, 0.430 mmol), PHENYLBORONIC ACID (900 mg, 7.38 mmol) and potassium phosphate (3.92 g, 18.5 mmol) under nitrogen atmosphere at room temperature, then the reaction mixture was stirred at 120° C. for 30 minutes under microwave irradiation. The insoluble residue was collected by filtration, then the solvent was removed under reduced pressure. The obtained residue was purified by column chromatography to give Compound (S-15) (1.6 g, 48%).

Compound (S-15); $^1$H-NMR (DMSO-d6) δ: 3.92 (s, 3H), 7.59-7.64 (m, 3H), 8.09-8.16 (m, 4H), 8.83 (s, 1H)

To a solution of Lithium Aluminum Hydride (0.264 g, 6.95 mmol) in anhydrous tetrahydrofuran (10 mL) was added a solution of Compound (S-15) (1.56 g, 5.79 mmol) in anhydrous tetrahydrofuran (25 mL) under nitrogen atmosphere, then the reaction mixture was stirred at 2° C. for 2 hours. To the reaction solution was added water, then the reaction solution was extracted with ethyl acetate. The extraction was washed with brine and dried over sodium sulfate. The solvent was removed under reduced pressure. The obtained residue was purified by column chromatography to give Compound (S-16) (1.29 g, 92%).

Compound (S-16); $^1$H-NMR (CDCl3) δ: 1.89 (t, J=4 Hz, 1H), 4.84 (d, J=8 Hz, 3H), 7.46-7.50 (m, 4H), 7.93 (s, 1H), 8.03-8.11 (m, 3H)

To a solution of Compound (S-16) (10.5 g, 43.7 mmol) in anhydrous 1,4-dioxane (15 mL) were added ZINC CHLORIDE (210 mg, 0.16 mmol) and thionyl chloride (0.76 ml, 10.4 mmol) under nitrogen atmosphere, then the reaction mixture was stirred at 40° C. for 10 minutes. The part of the solvent was removed under reduced pressure. To the residue was added aqueous sodium bicarbonate solution, then the mixture was extracted with dichloromethane. The extraction was washed with brine, then dried over sodium sulfate. The solvent was removed under reduced pressure. The obtained crystal was collected by filtration to give Compound (S-17) (1.25 g, 93%). Compound (S-17); $^1$H-NMR (DMSO-d6) δ: 4.94 (s, 2H), 7.57-7.64 (m, 4H), 8.06-8.13 (m, 3H), 8.24 (d, J=4 Hz, 1H)

To a solution of Compound (S-17) (1.2 g, 4.62 mmol) in acetonitrile (20 mL) were added sodium cyanide (0.294 g, 6.01 mmol) and water (2 ml), then the reaction mixture was refluxed for 4 hours. The part of the solvent was removed under reduced pressure. To the residue was added water, then the mixture was stirred. The obtained crystal was collected by filtration to give Compound (S-18) (1.15 g, 99%).

Compound (S-18); $^1$H-NMR (DMSO-$d_6$) δ: 4.22 (s, 2H), 7.50-7.62 (m, 4H), 8.05-8.18 (m, 4H).

To a solution of Compound (S-18) (1.07 g, 4.27 mmol) in acetic acid (10 mL) was added concentrated sulfuric acid (4.75 ml, 85 mmol), then the reaction mixture was refluxed for 6 hours. After the completion of the reaction, to the reaction solution was added water (50 ml). The reaction solution was stirred for 30 minutes, then the obtained crystal was collected by filtration to give Compound (S-19) (1.03 g, 89%).

Compound (S-19); ¹H-NMR (CDCl₃) δ: 3.80 (s, 2H), 7.41 (dd, J=8.36, 1.77 Hz, 1H), 7.49-7.51 (m, 3H), 7.84 (d, J=1.01 Hz, 1H), 8.01-8.10 (m, 3H).

Reference Example 4

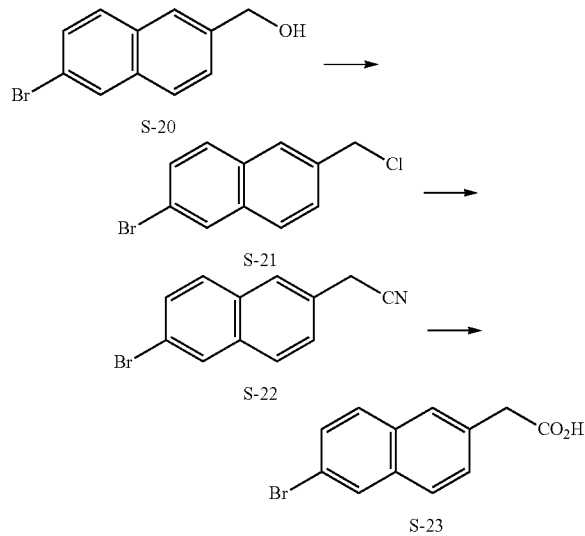

Compound (S-23); ¹H-NMR (DMSO-d₆) δ: 3.75 (s, 2H), 7.48 (dd, J=8.36, 1.77 Hz, 1H), 7.62 (dd, J=8.62, 2.03 Hz, 1H), 7.80-7.88 (m, 3H), 8.18 (d, J=2.03 Hz, 1H), 12.41 (brs, 1H).

Reference Example 5

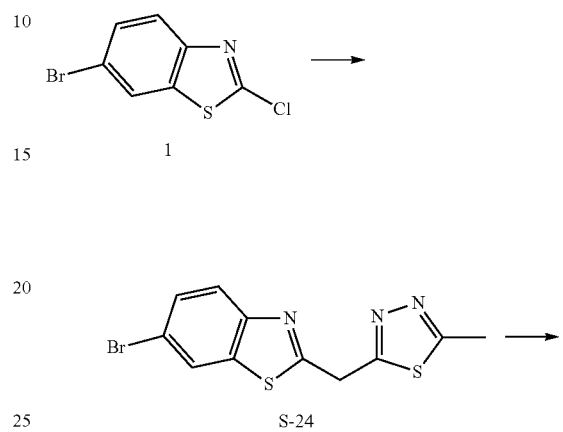

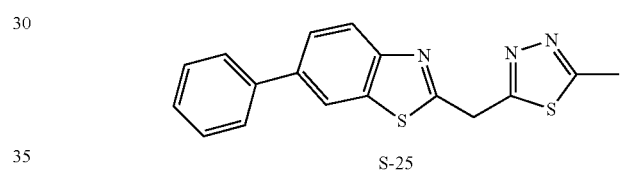

To 1,4-dioxane (30 ml) was added (6-bromonaphthalen-2-yl) methanol (S-20) (3.2 g, 13.50 mmol), then the reaction mixture was dissolved at 40° C. To the reaction mixture were added zinc chloride (0.055 g, 0.405 mmol) and thionyl chloride (1.970 ml, 27.0 mmol) at 40° C., then the reaction mixture was stirred for 10 minutes. The part of the solvent was removed under reduced pressure. To the residue was added 10% aqueous sodium bicarbonate solution, then the mixture was extracted with ethyl acetate. The extraction was washed respectively with 10% aqueous sodium bicarbonate solution and brine, then dried over sodium sulfate. The solvent was removed under reduced pressure to give Compound (S-21) (3.39 g, 98%) as a white crystal.

Compound (S-21); ¹H-NMR (CDCl₃) δ: 4.73 (s, 2H), 7.51-7.59 (m, 2H), 7.68-7.81 (m, 3H), 8.00 (d, J=2.03 Hz, 1H).

To a solution of Compound (S-21) (3.35 g, 13.11 mmol) in acetonitrile (40 mL) were added sodium cyanide (850 mg, 17.34 mmol) and water (4 ml), then the reaction mixture was refluxed for 5 hours. To the reaction solution was added 10% aqueous sodium bicarbonate solution, then the reaction solution was extracted with ethyl acetate. The extraction was washed respectively with 10% aqueous sodium bicarbonate solution and brine, then dried over magnesium sulfate. The solvent was removed under reduced pressure. The obtained residue was purified by column chromatography to give Compound (S-22) (3.1 g, 96%).

Compound (S-22); ¹H-NMR (CDCl₃) δ: 3.90 (s, 2H), 7.41 (dd, J=8.62, 1.52 Hz, 1H), 7.59 (dd, J=8.87, 1.77 Hz, 1H), 7.70 (d, J=8.62 Hz, 1H), 7.75-7.82 (m, 2H), 8.01 (d, J=1.52 Hz, 1H).

To a mixed solution of Compound (S-22) (3 g, 12.19 mmol) in acetic acid (30 ml) and water (15 ml) was added concentrated sulfuric acid (13.54 ml, 244 mmol), then the reaction mixture was refluxed for 3 hours. The reaction solution was cooled to room temperature. To the reaction solution was added water, then the reaction solution was stirred. The obtained crystal was collected by filtration to give Compound (S-23) (3.2 g, 99%).

To a solution of 2,5-dimethyl-1,3,4-thiadiazole (459 mg, 4.02 mmol) in anhydrous tetrahydrofuran (20 mL) was added sodium hexamethyldisilazide (2.17 mL, 4.12 mmol) under nitrogen atmosphere at −60° C., then the reaction mixture was stirred for 1.5 hours. To the reaction mixture was added dropwise a solution of 6-bromo-2-chlorobenzo[d] thiazole 1 (500 mg, 2.01 mmol) in anhydrous tetrahydrofuran (20 mL) at −60° C., then the reaction mixture was stirred at −60° C. for 2 hours. The reaction mixture was cooled to room temperature. To the reaction mixture were added 1N hydrochloric acid and ethyl acetate, then the reaction mixture was extracted with ethyl acetate. The organic layer was washed with brine and dried over magnesium sulfate. The solvent was removed under reduced pressure. The obtained residue was purified by column chromatography to give Compound (S-24) (656 mg, 64%).

Compound (S-24); ¹H-NMR (CDCl3) δ: 2.77 (s, 3H), 4.88 (s, 2H), 7.60 (d, J=8.0 Hz, 1H), 7.87 (d, J=8.8 Hz, 1H), 8.00 (s, 1H)

To a solution of Compound (S-24) (100 mg, 0.307 mmol) in 1,4-dioxane (1.2 ml) were added PHENYLBORONIC ACID (44.8 mg, 0.37 mmol), TETRAKIS(TRIPHENYLPHOSPHINE) PALLADIUM (0) (35.4 mg, 0.031 mmol) and NaHCO₃ (64.4 mg, 0.77 mmol), then the reaction mixture was stirred at 140° C. for 10 minutes under microwave irradiation. To the reaction solution were added water and ethyl acetate, then the reaction solution was extracted with ethyl acetate. The organic layer was washed with brine and dried over sodium sulfate. The solvent was removed under reduced pressure. The obtained residue was purified by column chromatography to give Compound (S-25) (52 mg, 53%) as a yellow solid.

Reference Example 6

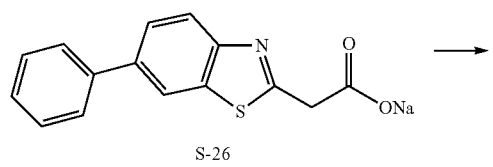

S-26

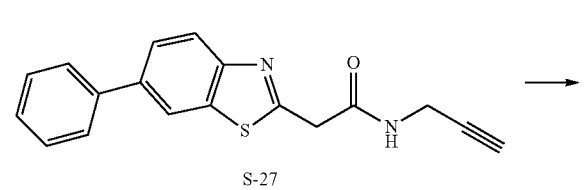

S-27

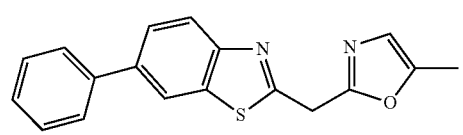

S-28

To a solution of Compound (S-26) (250 mg, 0.86 mmol) in anhydrous dimethylformamide (2.5 ml) were successively added pyridine (0.35 ml, 4.29 mmol), prop-2-yn-1-amine (95 mg, 1.72 mmol) and HATU (489 mg, 1.29 mmol) at room temperature, then the reaction mixture was stirred for 2 hours. To the reaction solution were added 0.1N hydrochloric acid and ethyl acetate, then the reaction solution was extracted with ethyl acetate. The organic layer was washed respectively with 10% aqueous sodium bicarbonate solution and brine and dried over magnesium sulfate. The solvent was removed under reduced pressure. The obtained residue was purified by column chromatography to give Compound (S-27) (189 mg, 72%) as a yellow solid.

Compound (S-27); 1H-NMR (DMSO-d6) δ: 2.31 (s, 3H), 4.60 (s, 2H), 6.73 (s, 1H), 7.37 (t, J=7.1 Hz, 1H), 7.47 (t, J=7.5 Hz, 2H), 7.63 (t, J=7.6 Hz, 2H), 7.70 (d, J=8.0 Hz, 1H), 8.04-8.08 (m, 2H).

To a solution of Compound (S-27) (50 mg, 0.163 mmol) in anhydrous acetonitrile (2 mL) was added gold(III) chloride (4.95 mg, 0.016 mmol), then the reaction mixture was stirred at 70° C. for 3 hours. The reaction solution was cooled to room temperature. To the reaction solution were added 0.1N hydrochloric acid and ethyl acetate, then the reaction solution was extracted with ethyl acetate. The organic layer was washed with brine and dried over sodium sulfate. The solvent was removed under reduced pressure. The obtained residue was purified by column chromatography to give Compound (S-28) (17 mg, 34%).

Compound (S-28); 1H-NMR (DMSO-d6) δ: 3.94 (m, 2H), 4.09 (s, 2H), 7.39 (t, J=7.1 Hz, 1H), 7.49 (t, J=8.4 Hz, 2H), 7.74-7.80-7.64 (m, 3H), 8.01 (d, J=8.4 Hz, 1H), 8.38 (s, 1H), 8.82 (s, 1H).

Reference Example 7

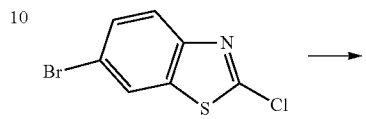

1

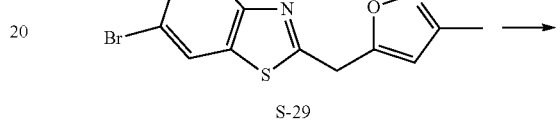

S-29

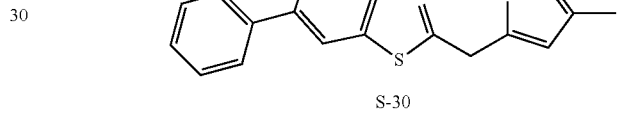

S-30

To a solution of 3,5-dimethylisoxazole (234 mg, 2.41 mmol) in anhydrous THF (10 mL) was added LHMDS (3.02 mL, 3.02 mmol) under nitrogen atmosphere at −60° C., then the reaction mixture was stirred for 30 minutes. To the reaction solution was added dropwise a solution of 6-bromo-2-chlorobenzo[d] thiazole 1 (300 mg, 1.21 mmol) in anhydrous tetrahydrofuran (10 ml) at −60° C., then the reaction solution was stirred with ice-cooling for 4 hours. To the reaction solution were added 1N hydrochloric acid and ethyl acetate, then the reaction solution was extracted with ethyl acetate. The organic layer was washed with brine and dried over magnesium sulfate. The solvent was removed under reduced pressure. The obtained residue was purified by column chromatography to give Compound (S-29) (232 mg, 62.2%) as a yellow solid.

Compound (S-29); 1H-NMR (CDCl3) δ: 2.30 (s, 3H), 4.54 (s, 2H), 6.09 (s, 1H), 7.59 (d, J=8.0 Hz, 1H), 7.86 (d, J=9.2 Hz, 1H), 7.99 (s, 1H)

To a solution of Compound (S-29) (220 mg, 0.72 mmol) in anhydrous 1,4-dioxane (2 ml) were added PHENYLBORONIC ACID (108 mg, 0.89 mmol), TETRAKIS(TRIPHENYLPHOSPHINE) PALLADIUM (0) (82 mg, 0.071 mmol) and Na₂CO₃ (189 mg, 1.78 mmol), then the reaction mixture was stirred at 120° C. for 15 minutes under microwave irradiation. To the reaction solution were added 0.1N hydrochloric acid and ethyl acetate, then the reaction solution was extracted with ethyl acetate. The organic layer was washed with brine and dried over sodium sulfate. The solvent was removed under reduced pressure. The obtained residue was purified by column chromatography to give Compound (S-30) (70 mg, 32%) as a yellow oil.

Compound (S-30); 1H-NMR (CDCl3) δ: 2.30 (s, 3H), 4.58 (s, 2H), 6.10 (s, 1H), 7.38 (t, J=8.0 Hz, 1H), 7.47 (t, J=7.6 Hz, 2H), 7.63 (d, J=8.4 Hz, 2H), 7.72 (d, J=8.0 Hz, 1H), 8.06 (d, J=8.6 Hz, 2H).

Reference Example 8

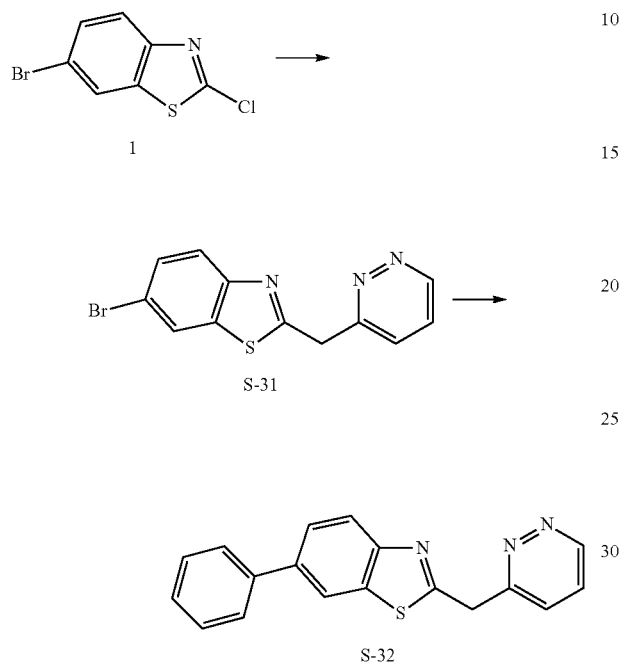

Compound (S-32); 1H-NMR (CDCl3) δ: 4.87 (s, 2H), 7.38 (t, J=7.6 Hz, 1H), 7.44-7.49 (m, 3H), 7.70 (d, J=2.0 Hz, 3H), 7.72 (d, J=2.0 Hz, 1H), 8.05 (d, J=2.0 Hz, 2H), 9.15 (s, 1H)

Reference Example 9

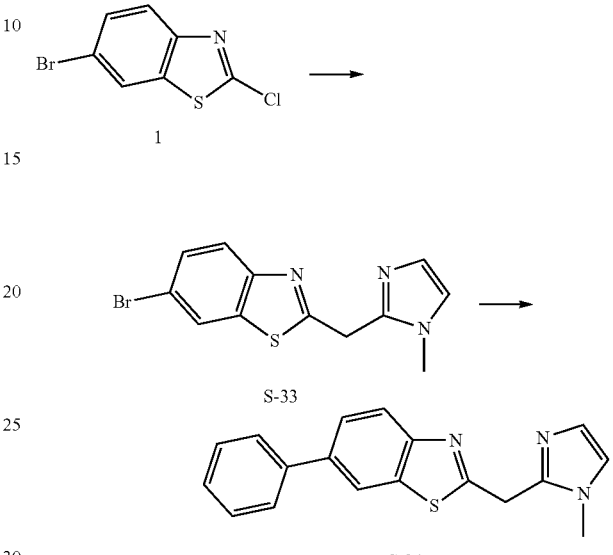

To a solution of 3-methylpyridazine (379 mg, 4.02 mmol) in anhydrous tetrahydrofuran (20 mL) was added lithium hexamethyldisilazide (4.12 mL, 4.12 mmol) under nitrogen atmosphere at −60° C., then the reaction mixture was stirred for 50 minutes. To the reaction solution was added dropwise a solution of 6-bromo-2-chlorobenzo[d]thiazole 1 (500 mg, 2.01 mmol) in anhydrous tetrahydrofuran (20 ml) with ice-cooling, then the reaction solution was stirred for 2 hours. To the reaction solution were added saturated aqueous ammonium chloride solution and ethyl acetate, then the reaction solution was extracted with ethyl acetate. The organic layer was washed with brine and dried over magnesium sulfate. The solvent was removed under reduced pressure. The obtained residue was purified by column chromatography to give Compound (S-31) (98 mg, 16%) as a yellow solid.

Compound (S-31); 1H-NMR (CDCl3) δ: 2.30 (s, 3H), 4.54 (s, 2H), 6.09 (s, 1H), 7.59 (d, J=8.0 Hz, 1H), 7.86 (d, J=9.2 Hz, 1H), 7.99 (s, 1H)

To a solution of Compound (S-31) (94 mg, 0.31 mmol) in 1,4-dioxane (1.2 ml) were added PHENYLBORONIC ACID (44.9 mg, 0.368 mmol), TETRAKIS(TRIPHENYLPHOSPHINE) PALLADIUM (0) (35.5 mg, 0.031 mmol) and NaHCO3 (64.4 mg, 0.77 mmol), then the reaction mixture was stirred at 140° C. for 10 minutes under microwave irradiation. To the reaction solution were added water and ethyl acetate, then the reaction solution was extracted with ethyl acetate. The organic layer was washed with brine and dried over sodium sulfate. The solvent was removed under reduced pressure. The obtained residue was purified by column chromatography to give Compound (S-32) (47 mg, 51%) as a yellow oil.

To a solution of 1,2-dimethyl-1H-imidazole (387 mg, 4.02 mmol) in anhydrous tetrahydrofuran (20 mL) was added n-butyllithium (2.58 mL, 4.12 mmol) under nitrogen atmosphere at −60° C., then the reaction mixture was stirred for 50 minutes. To the reaction solution was added dropwise a solution of 6-bromo-2-chlorobenzo[d]thiazole 1 (500 mg, 2.012 mmol) in anhydrous tetrahydrofuran (20 ml), then the reaction solution was stirred at −55° C. for 30 minutes. To the reaction solution were added saturated aqueous ammonium chloride solution and ethyl acetate, then the reaction solution was extracted with ethyl acetate. The organic layer was washed with brine and dried over magnesium sulfate. The solvent was removed under reduced pressure. The obtained residue was purified by column chromatography to give Compound (S-33) (469 mg, 76%) as a yellow solid.

Compound (S-33); 1H-NMR (CDCl3) δ: 3.64 (s, 3H), 4.57 (s, 2H), 6.88 (s, 1H), 7.03 (s, 1H), 7.56 (dd, J=8.6, 2.0 Hz, 1H), 7.82 (d, J=8.6 Hz, 1H), 7.95 (s, 1H).

To a solution of Compound (S-33) (100 mg, 0.32 mmol) in 1,4-dioxane (1.2 ml) were added PHENYLBORONIC ACID (47.5 mg, 0.389 mmol), TETRAKIS(TRIPHENYLPHOSPHINE) PALLADIUM (0) (37.5 mg, 0.032 mmol) and NaHCO3 (68.1 mg, 0.81 mmol), then the reaction mixture was stirred at 140° C. for 10 minutes under microwave irradiation. To the reaction solution were added water and ethyl acetate, then the reaction solution was extracted with ethyl acetate. The organic layer was washed with brine and dried over sodium sulfate. The solvent was removed under reduced pressure. The obtained residue was purified by column chromatography to give Compound (S-34) (49 mg, 49%) as a yellow solid.

Compound (S-34); 1H-NMR (CDCl3) δ: 3.66 (s, 3H), 4.63 (s, 2H), 6.88 (d, J=1.0 Hz, 1H), 7.05 (s, 1H), 7.37 (t, J=7.4 Hz, 1H), 7.46 (t, J=7.4 Hz, 2H), 7.62 (d, J=7.1 Hz, 2H), 7.69 (dd, J=8.4, 1.8 Hz, 1H), 8.00-8.03 (m, 2H).

Reference Example 10

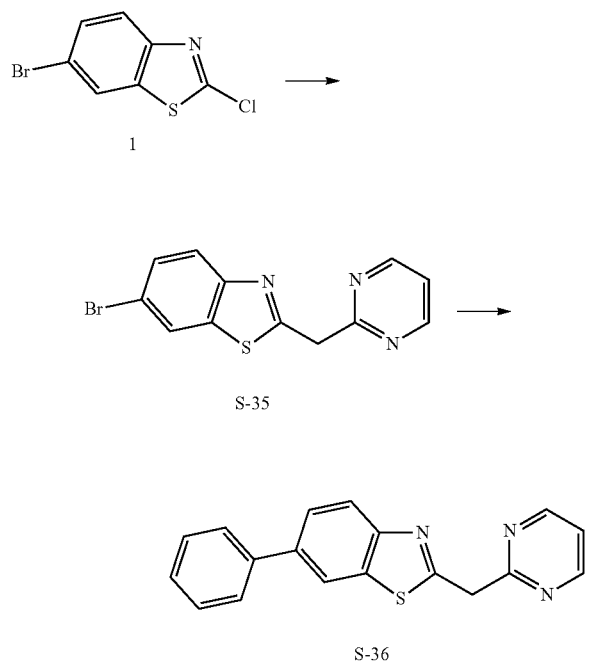

To a solution of 6-bromo-2-chlorobenzo[d]thiazole 1 (500 mg, 2.012 mmol) and 2-methylpyrimidine (379 mg, 4.02 mmol) in anhydrous tetrahydrofuran (20 mL) was added lithium hexamethyldisilazide (4.12 mL, 4.12 mmol) under nitrogen atmosphere at −60° C., then the reaction mixture was stirred for 1 hour. The reaction mixture was continuously stirred with ice-cooling for 1 hour. To the reaction solution was added dropwise a solution of 6-bromo-2-chlorobenzo[d]thiazole 1 (500 mg, 2.01 mmol) in anhydrous tetrahydrofuran (20 ml), then the reaction solution was stirred for 2 hours. To the reaction solution were added saturated aqueous ammonium chloride solution and ethyl acetate, then the reaction solution was extracted with ethyl acetate. The organic layer was washed with brine and dried over magnesium sulfate. The solvent was removed under reduced pressure. The obtained residue was purified by column chromatography to give Compound (S-35) (183 mg, 30%) as a yellow solid.

Compound (S-35); 1H-NMR (CDCl3) δ: 4.82 (s, 2H), 7.25 (m, 1H), 7.57 (dd, J=8.0, 1.6 Hz, 1H), 7.89 (d, J=8.6 Hz, 1H), 7.99 (s, 1H), 8.77 (d, J=5.2 Hz, 1H)

To a solution of Compound (S-35) (100 mg, 0.33 mmol) in 1,4-dioxane (1.2 ml) were added PHENYLBORONIC ACID (47.8 mg, 0.392 mmol), TETRAKIS(TRIPHENYLPHOSPHINE) PALLADIUM (0) (47.8 mg, 0.039 mmol) and sodium hydrogen carbonate (68.3 mg, 0.82 mmol), then the reaction mixture was stirred at 140° C. for 20 minutes under microwave irradiation. To the reaction solution were added water and ethyl acetate, then the reaction solution was extracted with ethyl acetate. The organic layer was washed with brine and dried over sodium sulfate. The solvent was removed under reduced pressure. The obtained residue was purified by column chromatography to give Compound (S-36) (45 mg, 45%) as a yellow solid.

Compound (S-36); 1H-NMR (DMSO-d6) δ: 4.80 (s, 2H), 7.39 (t, J=6.8 Hz, 1H), 7.45-7.52 (m, 3H), 7.73-7.80 (m, 3H), 8.01 (d, J=8.6 Hz, 1H), 8.37 (s, 1H), 8.83 (d, J=5.1 Hz, 2H).

Reference Example 11

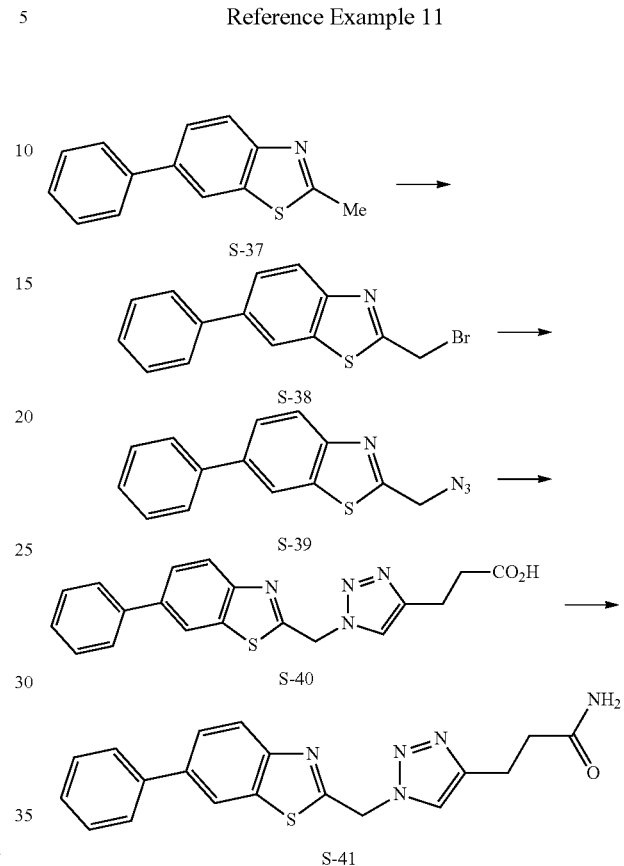

To a solution of Compound (S-37) (2.33 g, 10.34 mmol) in carbon tetrachloride (31 mL) were added NBS (2209 mg, 12.41 mmol) and AIBN (67.9 mg, 0.414 mmol) under nitrogen atmosphere, then the reaction mixture was refluxed for 7 hours. To the reaction solution were added water and dichloromethane, then the reaction solution was extracted with dichloromethane. The organic layer was washed with brine and dried over magnesium sulfate. The solvent was removed under reduced pressure. The obtained residue was purified by column chromatography to give Compound (S-38) (432 mg, 14%) as a yellow solid.

Compound (S-38); 1H-NMR (CDCl3) δ: 4.83 (s, 2H), 7.39 (t, J=7.6 Hz, 1H), 7.48 (t, J=8.0 Hz, 2H), 7.64 (d, J=7.2 Hz, 2H), 7.74 (d, J=8.0 Hz, 1.6 Hz, 1H), 8.06-8.09 (m, 2H)

To a solution of Compound (S-38) (186 mg, 0.611 mmol) in anhydrous N-methylpyrrolidone (3 mL) were added TBAB (19.71 mg, 0.061 mmol) and sodium azide (79 mg, 1.223 mmol) under nitrogen atmosphere, then the reaction mixture was stirred at room temperature for 2 hours. To the reaction solution were added water and ethyl acetate, then the reaction solution was extracted with ethyl acetate. The organic layer was washed with brine and dried over magnesium sulfate. The solvent was removed under reduced pressure. The obtained residue was purified by column chromatography to give Compound (S-39) (158 mg, 97%) as a yellow solid.

Compound (S-39); 1H-NMR (CDCl3) δ: 4.81 (s, 2H), 7.39 (t, J=8.4 Hz, 1H), 7.49 (t, J=8.0 Hz, 2H), 7.65 (d, J=4.8 Hz, 2H), 7.74 (d, J=4 Hz, 1H), 8.06-8.10 (m, 2H)

To a t-butanol (3 ml) and water (3 ml) was suspended Compound (S-39) (83 mg, 0.312 mmol). To the reaction mixture were added pent-4-ynoic acid (30.6 mg, 0.312 mmol), sodium(R)-2-((S)-1,2-dihydroxyethyl)-4-hydroxy-5-oxo-2,5-dihydrofuran-3-olate (18.52 mg, 0.093 mmol) and copper (II) sulfate pentahydrate (11.67 mg, 0.047 mmol) at room temperature, then the reaction mixture was stirred for 15 hours. To the reaction solution were added water and ethyl acetate, then the reaction solution was extracted with ethyl acetate. The extraction was washed with brine and dried over magnesium sulfate. The solvent was removed under reduced pressure. The obtained crystal was washed with a mixed solvent of ethyl acetate and n-hexane to give Compound (S-40) (84 mg, 74%).

Compound (S-40); 1H-NMR (DMSO-d6) δ: 2.60 (t, J=6.3 Hz, 2H), 2.89 (t, J=7.1 Hz, 2H), 6.13 (s, 2H), 7.40 (t, J=7.4 Hz, 1H), 7.50 (t, J=7.6 Hz, 2H), 7.74 (d, J=7.6 Hz, 2H), 7.84 (dd, J=8.6, 1.5 Hz, 1H), 8.06-8.09 (m, 2H), 8.41 (d, J=1.0 Hz, 1H)

To a solution of Compound (S-40) (53 mg, 0.145 mmol) in anhydrous tetrahydrofuran (2 mL) was added CDI (35.4 mg, 0.218 mmol) under nitrogen atmosphere, then the reaction mixture was stirred at room temperature for 2 hours. To the reaction solution was added aqueous ammonia, then the reaction solution was stirred for 1 hour. To the reaction solution was added water, then the obtained crystal was washed with ethyl acetate to give Compound (S-41) (48 mg, 91%) as a yellow solid.

Compound (S-41); 1H-NMR (CDCl3) δ: 2.69 (t, J=7.1 Hz, 2H), 3.08 (t, J=7.1 Hz, 2H), 5.28 (br s, 1H), 5.73 (br s, 1H), 5.93 (s, 2H), 7.39 (t, J=7.4 Hz, 1H), 7.47 (t, J=7.6 Hz, 2H), 7.61-7.64 (m, 3H), 7.75 (dd, J=8.6, 1.5 Hz, 1H), 8.04-8.10 (m, 2H).

Reference Example 12

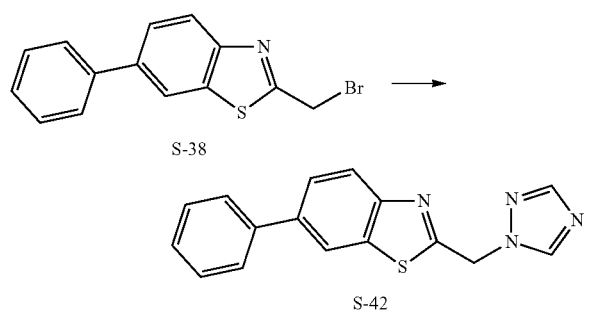

To a solution of 1H-1,2,4-triazole (17.48 mg, 0.253 mmol) in anhydrous dimethylformamide (1 mL) was added sodium hydride (8.68 mg, 0.217 mmol) under nitrogen atmosphere, then the reaction mixture was stirred at room temperature for 40 minutes. To the reaction mixture was added Compound (S-38) (55 mg, 0.181 mmol) at room temperature, then the reaction mixture was stirred at room temperature for 1 hour. To the reaction solution were added water and ethyl acetate, then the reaction solution was extracted with ethyl acetate. The extraction was washed with brine and dried over magnesium sulfate. The solvent was removed under reduced pressure. The obtained residue was purified by column chromatography to give Compound (S-42) (20 mg, 38%).

Compound (S-42); 1H-NMR (CDCl3) δ: 5.81 (s, 2H), 7.39 (t, J=7.6 Hz, 1H), 7.47 (t, J=7.6 Hz, 2H), 7.63 (d, J=6.8 Hz, 2H), 7.74 (dd, J=8.8, 1.6 Hz, 1H), 8.05-8.10 (m, 3H), 8.34 (s, 1H).

Reference Example 13

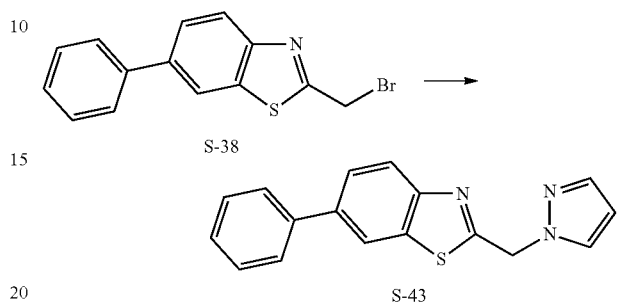

To a solution of 1H-pyrazole (17.23 mg, 0.253 mmol) in anhydrous dimethylformamide (1 mL) was added sodium hydride (8.68 mg, 0.217 mmol) under nitrogen atmosphere, then the reaction mixture was stirred at room temperature for 40 minutes. To the reaction mixture was added Compound (S-38) (55 mg, 0.181 mmol) at room temperature, then the reaction mixture was stirred at room temperature for 1 hour. To the reaction solution were added water and ethyl acetate, then the reaction solution was extracted with ethyl acetate. The extraction was washed with brine and dried over magnesium sulfate. The solvent was removed under reduced pressure. The obtained residue was purified by column chromatography to give Compound (S-43) (14 mg, 27%).

Compound (S-43); 1H-NMR (CDCl3) δ: 5.76 (s, 2H), 6.37 (t, J=2.0 Hz, 1H), 7.37 (t, J=7.4 Hz, 1H), 7.46 (t, J=7.9 Hz, 2H), 7.63 (dd, J=8.9, 7.9 Hz, 4H), 7.71 (dd, J=8.4, 1.8 Hz, 1H), 8.02 (s, 1H), 8.07 (d, J=8.1 Hz, 1H).

Reference Example 14

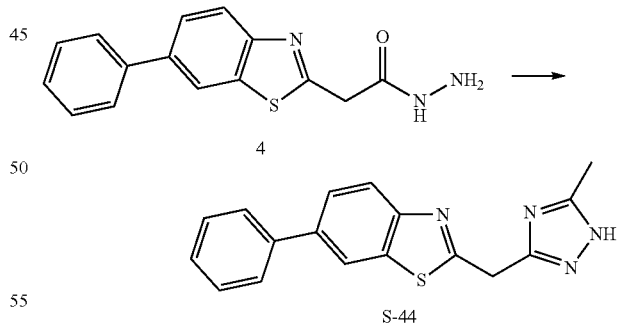

To a solution of 2-(6-phenylbenzo[d]thiazol-2-yl)acetohydrazide 4 (50 mg, 0.176 mmol) in 2-propanol (2 ml) were added ethyl acetimidate hydrochloride (32.7 mg, 0.265 mmol) and triethylamine (0.978 mL, 7.06 mmol) at room temperature, then the reaction mixture was stirred at 120° C. for 30 minutes under microwave irradiation. To the reaction solution was added 10% aqueous citric acid solution, then the reaction solution was extracted with ethyl acetate. The organic layer was washed with brine and dried over sodium sulfate. The solvent was removed under reduced pressure.

The obtained residue was purified by column chromatography to give Compound (S-44) (28 mg, 52%).

Compound (S-44); 1H-NMR (CDCl3) δ: 2.47 (s, 3H), 4.63 (s, 2H), 7.38 (t, J=7.1 Hz, 1H), 7.46 (t, J=7.6 Hz, 2H), 7.62 (d, J=7.6 Hz, 2H), 7.70 (dd, J=8.4, 1.8 Hz, 1H), 8.04-8.06 (m, 2H).

Reference Example 15

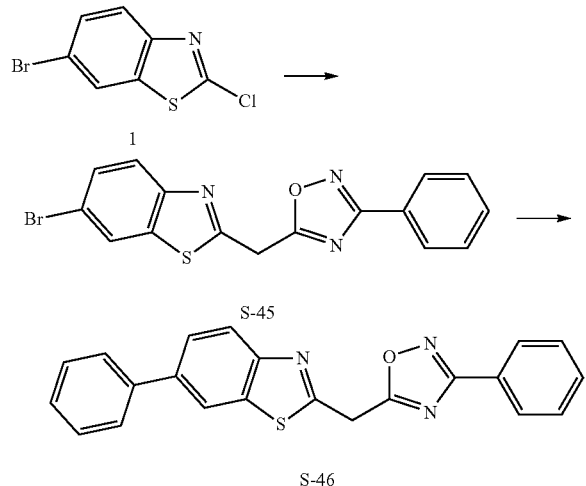

To a solution of 5-methyl-3-phenyl-1,2,4-oxadiazole (160 mg, 0.999 mmol) in anhydrous tetrahydrofuran (2 mL) was added lithium hexamethyldisilazide (1M, toluene solution) (2.2 mL, 2.2 mmol) under nitrogen atmosphere at −60° C., then the reaction mixture was stirred for 30 minutes. To the reaction solution was added dropwise a solution of 6-bromo-2-chlorobenzo[d] thiazole 1 (298 mg, 1.199 mmol) in anhydrous tetrahydrofuran (3 ml), then the reaction solution was stirred at −10° C. for 2 hours. To the reaction solution were added water and ethyl acetate, then the reaction solution was extracted with ethyl acetate. The extraction was washed with brine and dried over magnesium sulfate. The solvent was removed under reduced pressure. The obtained residue was purified by column chromatography to give Compound (S-45) (227 mg, 61%).

Compound (S-45); $^1$H-NMR (DMSO-d$_6$) δ: 5.13 (s, 2H), 7.55-7.62 (m, 3H), 7.68 (dd, J=8.62, 2.03 Hz, 1H), 7.94 (d, J=8.62 Hz, 1H), 8.01 (dd, J=7.86, 1.77 Hz, 2H), 8.44 (d, J=2.03 Hz, 1H).

To a solution of Compound (S-45) (150 mg, 0.403 mmol) in 1,4-dioxane (1.5 ml) were added PHENYLBORONIC ACID (54.0 mg, 0.443 mmol), TETRAKIS(TRIPHENYLPHOSPHINE) PALLADIUM (0) (32.6 mg, 0.028 mmol) and 3N aqueous potassium carbonate solution (0.40 mL, 1.21 mmol), then the reaction mixture was stirred at 120° C. for 25 minutes under microwave irradiation. To the reaction solution were added water and ethyl acetate, then the reaction solution was extracted with ethyl acetate. The organic layer was washed respectively with 10% aqueous sodium bicarbonate solution and brine and dried over magnesium sulfate. The solvent was removed under reduced pressure. The obtained residue was purified by column chromatography to give Compound (S-46) (31 mg, 21%) as a yellow solid.

Compound (S-46); $^1$H-NMR (DMSO-d$_6$) δ: 5.15 (s, 2H), 7.35-7.68 (m, 6H), 7.76 (d, J=7.10 Hz, 2H), 7.83 (dd, J=8.62, 2.03 Hz, 1H), 8.00-8.08 (m, 3H), 8.46 (d, J=2.03 Hz, 1H).

Reference Example 16

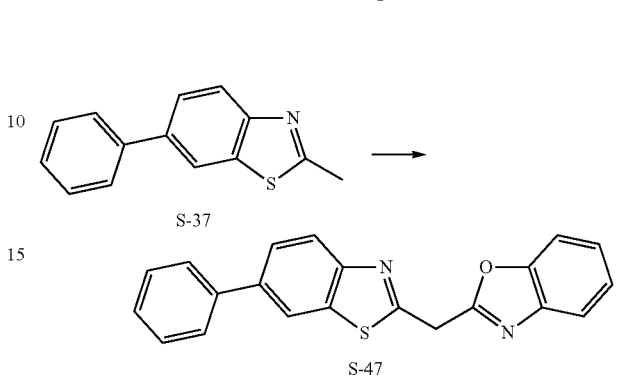

To a solution of 2-methyl-6-phenylbenzo[d]thiazole (S-37) (200 mg, 0.888 mmol) in anhydrous tetrahydrofuran (2 mL) was added lithium hexamethyldisilazide (1M, toluene solution) (1.953 ml, 1.953 mmol) under nitrogen atmosphere at −60° C., then the reaction mixture was stirred for 30 minutes. To the reaction solution was added 2-chlorobenzo[d] oxazole (0.114 ml, 0.976 mmol), then the reaction solution was stirred at −10° C. for 2 hours. To the reaction solution were added water and ethyl acetate, then the reaction solution was extracted with ethyl acetate. The extraction was washed with brine and dried over magnesium sulfate. The solvent was removed under reduced pressure. The obtained residue was purified by column chromatography to give Compound (S-47) (170 mg, 56%).

Compound (S-47); $^1$H-NMR (DMSO-d$_6$) δ: 5.01 (s, 2H), 7.37-7.44 (m, 3H), 7.50 (t, J=7.60 Hz, 2H), 7.71-7.78 (m, 4H), 7.82 (dd, J=8.62, 2.03 Hz, 1H), 8.05 (d, J=8.62 Hz, 1H), 8.43 (d, J=2.03 Hz, 1H).

Reference Example 17

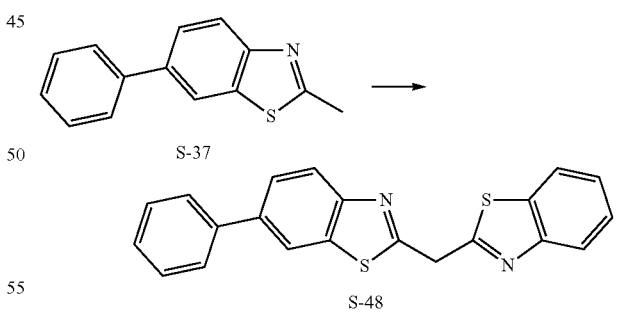

To a solution of 2-methyl-6-phenylbenzo[d]thiazole (S-37) (200 mg, 0.888 mmol) in anhydrous tetrahydrofuran (2 mL) was added lithium hexamethyldisilazide (1M, toluene solution) (1.953 ml, 1.953 mmol) under nitrogen atmosphere at −60° C., then the reaction mixture was stirred for 30 minutes. To the reaction solution was added 2-chlorobenzo[d] thiazole (0.121 ml, 0.976 mmol), then the reaction solution was stirred at −10° C. for 2 hours. To the reaction solution were added water and ethyl acetate, then the reaction solution was extracted with ethyl acetate. The extraction was washed with brine and dried over magnesium sulfate. The solvent was removed under reduced pressure. The obtained residue was purified by column chromatography to give Compound (S-48) (200 mg, 63%).

Compound (S-48); $^1$H-NMR (DMSO-$d_6$) δ: 5.12 (s, 2H), 7.38-7.55 (m, 5H), 7.71-7.77 (m, 2H), 7.82 (dd, J=8.62, 1.52 Hz, 1H), 8.01 (d, J=8.11 Hz, 1H), 8.04-8.13 (m, 2H), 8.41 (d, J=1.52 Hz, 1H).

Test Example 1

Evaluation Method of Human Endothelial Lipase (EL) Inhibitory Activity Using Human High-Density Lipoprotein (HDL)

After the present compound dissolved in DMSO was added to become 0.5% DMSO to the reaction buffer consisting of 20 mM tris hydrochloric acid (pH7.4), bovine serum albumin (0.5%), calcium chloride (4 mM), sodium chloride (150 mM) and human HDL (2 mg/ml), the EL enzyme was added (total volume was 20 μl).

After 4-hour reaction at 37° C., non-esterified fatty acid (NEFA) generated from HDL by EL was measured with a commercially available assay kit and the amount of NEFA was used as an index of enzyme activity. Considering the enzyme activity without the inhibitor as a control value, the inhibition rate of each concentration of the present compound was calculated, and 50% inhibitory concentration (IC50 value) was calculated from an inhibition curve.

The result of Test Example 1 is shown below.
Compound (I-1-3): IC50=0.026 μM
Compound (I-1-9): IC50=0.26 μM
Compound (I-1-2): IC50=0.12 μM
Compound (I-1-23): IC50=0.073 μM
Compound (I-1-27): IC50=0.085 μM
Compound (I-1-31): IC50=0.083 μM
Compound (I-1-43): IC50=0.39 μM
Compound (I-1-82): IC50=0.052 μM
Compound (I-1-7): IC50=0.019 μM
Compound (I-1-85): IC50=0.006 μM
Compound (I-1-83): IC50=0.005 μM
Compound (I-2-196): IC50=0.036 μM
Compound (I-2-197): IC50=0.012 μM
Compound (I-2-198): IC50=0.015 μM
Compound (I-2-204): IC50=0.19 μM
Compound (I-2-215): IC50=2.5 μM
Compound (I-2-216): IC50=23 μM
Compound (I-3-1): IC50=0.011 μM
Compound (I-3-4): IC50=0.004 μM
Compound (I-3-6): IC50=0.052 μM
Compound (I-3-11): IC50=0.009 μM
Compound (I-3-12): IC50=0.078 μM
Compound (I-3-21): IC50=0.25 μM
Compound (I-3-23): IC50=0.4 μM
Compound (I-3-30): IC50=0.046 μM
Compound (I-3-37): IC50=0.002 μM
Compound (I-3-41): IC50=0.014 μM
Compound (I-3-48): IC50=0.008 μM
Compound (I-3-56): IC50=0.004 μM
Compound (I-3-93): IC50=0.028 μM
Compound (I-3-112): IC50=0.044 μM
Compound (I-3-145): IC50=0.069 μM
Compound (I-3-146): IC50=0.027 μM
Compound (I-3-163): IC50=0.009 μM
Compound (A-2): IC50=0.013 μM
Compound (A-5): IC50=0.008 μM
Compound (A-9): IC50=0.011 μM
Compound (A-10): IC50=0.008 μM
Compound (A-13): IC50=0.022 μM
Compound (A-14): IC50=0.16 μM
Compound (A-17): IC50=0.041 μM
Compound (A-19): IC50=0.11 μM
Compound (A-21): IC50=0.065 μM
Compound (A-25): IC50=0.042 μM
Compound (A-29): IC50=0.014 μM The present compound selectively inhibits endothelial lipase as shown in Test Example 1, and has high selectivity for hepatic lipase (HL) and lipoprotein lipase (LPL). Selectivity was analyzed by the following tests.

Test Example 2

Evaluation Method of Human Hepatic Lipase (HL) Inhibitory Activity Using Human Very Low-Density Lipoprotein (VLDL)

After an inhibitor dissolved in DMSO was added to become 0.5% DMSO to the reaction buffer consisting of 20 mM tris hydrochloric acid (pH7.4), bovine serum albumin (0.5%), calcium chloride (4 mM), sodium chloride (150 mM) and human VLDL (0.5 mg/ml), the HL enzyme was added (total volume was 20 μl).

After 4-hour reaction at 37° C., non-esterified fatty acid (NEFA) generated from VLDL by HL was measured with a commercially available assay kit and the amount of NEFA was used as an index of enzyme activity. Considering the enzyme activity without the inhibitor as a control value, the inhibition rate of each concentration of an inhibitor was calculated, and 50% inhibitory concentration (IC50 value) was calculated from an inhibition curve.

Test Example 3

Evaluation Method of Human Lipoprotein Lipase (LPL) Inhibitory Activity Using Human Very Low-Density Lipoprotein (VLDL)

After an inhibitor dissolved in DMSO was added to become 0.5% DMSO to the reaction buffer consisting of 20 mM tris hydrochloric acid (pH7.4), bovine serum albumin (0.5%), calcium chloride (4 mM), sodium chloride (150 mM) and human VLDL (0.5 mg/ml), the LPL enzyme was added (total volume was 20 μl).

After 4-hour reaction at 37° C., non-esterified fatty acid (NEFA) generated from HDL by LPL was measured with a commercially available assay kit and the amount of NEFA was used as an index of enzyme activity. Considering the enzyme activity without the inhibitor as a control value, the inhibition rate of each concentration of an inhibitor was calculated, and 50% inhibitory concentration (IC50 value) was calculated from an inhibition curve.

The results of Test Example 2 and 3 indicated that the present compound inhibited the endothelial lipase selectively and had high selectivity for hepatic Lipase (HL) and lipoprotein lipase (LPL).

Serum HDL cholesterol elevating effect can be examined as follows.

Pharmacological Test on HDL Elevating Effect

The C57BL/6J mice at 8-25-weeks old were divided into 5-9 animals per group and administered test compound (20-200 mg/kg/day) orally. To the control group, 0.5% methyl cellulose solution (10 mL/kg) of the vehicle was administered orally. The blood was collected from tail vein before and 24-hour after the administration of compound, and serum HDL cholesterol concentration was measured with [koresutesuto] N HDL (Daiiti chemical Ltd.). The animals were separated into groups so that the mean value of weight and serum HDL cholesterol level become almost equal between each examination groups. The efficacy of the test compound was shown as the rate of changes compared to the values before administration (the HDL cholesterol elevating rate; % Initial), and significant differences against the values of control groups were evaluated.

Usefulness for medicaments was analyzed by the following examinations etc.

CYP3A4 Fluorescent MBI Test

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (HFC) emitting fluorescent light.

The reaction conditions were as follows: substrate, 5.6 μmol/L 7-BFC; pre-reaction time, 0 or 30 minutes; reaction time, 15 minutes; reaction temperature, 25° C. (room temperature); CYP3A4 content (enzyme expressed in *Escherichia coli*), at pre-reaction 62.5 pmol/mL, at reaction 6.25 pmol/mL (at 10-fold dilution); test drug concentration, 0.625, 1.25, 2.5, 5, 10, 20 μmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted with a substrate and a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane) =4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. When a difference between IC50 values is 5 μM or more, this was defined as (+) and, when the difference is 3 μM or less, this was defined as (−).

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 μmol/L ethoxyresorufin (CYP1A2), 100 μmol/L tolbutamide (CYP2C9), 50 μmol/L S-mephenitoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 μmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2C9 metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and IC50 was calculated by reverse presumption by a logistic model using a concentration and an inhibition rate.

FAT Test

Each 20 μL of freeze-stored *Salmonella typhimurium* (TA98 and TA100 strain) was inoculated in 10 mL of liquid nutrient medium (2.5% Oxoid nutrient broth No. 2), and the cultures were incubated at 37° C. under shaking for 10 hours. 9 mL of TA98 culture was centrifuged (2000×g, 10 minutes) to remove medium, and the bacteria was suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate 0.25 g/L, $MgSO_4 \cdot 7H_2O$: 0.1 g/L), and the suspension was added to 110 mL of Exposure medium (Micro F buffer containing Biotin: 8 μg/mL, histidine: 0.2 μg/mL, glucose: 8 mg/mL). 3.16 mL of TA100 culture was added to 120 mL of Exposure medium to prepare the test bacterial solution. 588 μL of the test bacterial solution (or mixed solution of 498 μl of the test bacterial solution and 90 μL of the S9 mix in the case with metabolic activation system) was mixed with each 12 μL of the following solution: DMSO solution of the test substance (eight dose levels from maximum dose 50 mg/mL at 2-fold ratio); DMSO as negative control; 50 μg/mL of 4-nitroquinoline-1-oxide DMSO solution as positive control for TA98 without metabolic activation system; 0.25 μg/mL of 2-(2-furyl)-3-(5-nitro-2-furyl)acrylamide DMSO solution as positive control for TA100 without metabolic activation system; 40 μg/mL of 2-aminoanthracene DMSO solution as positive control for TA98 with metabolic activation system; or 20 μg/mL of 2-aminoanthracene DMSO solution as positive control for TA100 with metabolic activation system. 12 μl of the solution and 588 μL of the test bacterial solution (a mixed solution of 498 μl of the test bacterial solution and 90 μL of S9 mix with metabolic activation condition) were mixed and incubated at 37° C. under shaking for 90 minutes. 460 μL of the bacterial solution exposed to the test substance was mixed with 2300 μL of Indicator medium (Micro F buffer containing biotin: 8 μg/mL, histidine 0.2 μg/mL, glucose: 8 mg/mL, Bromo Cresol Purple: 37.5 μg/mL), each 50 μL was dispensed into 48 wells per dose in the microwell plates, and was subjected to stationary cultivation at 37° C. for 3 days. A well containing the bacteria, which has obtained the ability of proliferation by mutation in the gene coding amino acid (histidine) synthetase, turns the color from purple to yellow due to pH change. The number of the yellow wells among the 48 total wells per dose was counted, and evaluate the mutagenicity by comparing with the negative control group. (−) means that mutagenicity is negative and (+) means positive.

Solubility Test

The solubility of a compound was determined under a condition in which 1% DMSO was added. 10 mM compound solution was prepared using DMSO, and then 6 μL of the compound solution was added to 594 μL of artificial intestinal juice in pH 6.8 (to 250 mL of 0.2 mol/L potassium dihydrogen phosphate reagent solution was added 118 mL of 0.2 mol/L NaOH reagent solution and water to provide a final volume of 1000 mL). After standing at 25 degrees Celsius for 16 hours, the mixed solution was filtrated with suction. The filtrate was diluted twice with methanol/water (1/1), and then a concentration in the filtration was measured with HPLC or LC/MS/MS by the absolute calibration method.

Metabolism Stability Test

Using commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was performed in the presence of 5 mM UDP-glucuronic acid in place of NADPH, followed by similar operations.

hERG Test

For the purpose of assessing risk of an electrocardiogram QT interval prolongation, effects on delayed rectifier K+ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazine ethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the % inhibition relative to the tail peak current before application of the test substance was calculated, and compared with the vehicle-applied group (0.1% dimethyl sulfoxide solution) to assess influence of the test substance on $I_{Kr}$.

Powder Solubility Test

Appropriate amounts of the test substances are put into appropriate containers. To the respective containers are added 200 μL of JP-1 fluid (sodium chloride 2.0 g, hydrochloric acid 7.0 mL and water to reach 1000 mL), 200 μL of JP-2 fluid (phosphate buffer (pH 6.8) 500 mL and water 500 mL), and 200 μL of 20 mmol/L TCA (sodium taurocholate)/JP-2 fluid (TCA 1.08 g and water to reach 100 mL). In the case that the test compound is dissolved after the addition of the test fluid, the bulk powder is added as appropriate. The containers are sealed, and shaken for 1 hour at 37° C. The mixtures are filtered, and 100 μl of methanol is added to each of the filtrate (100 μL) so that the filtrates are two-fold diluted. The dilution ratio may be changed if necessary. The dilutions are observed for bubbles and precipitates, and then the containers are sealed and shaken. Quantification is performed by HPLC with an absolute calibration method.

BA Test

Materials and methods for studies on oral absorption (1) Animals: mice or rats (2) Animal husbandry:

Mice and rats had free access to solid food and sterilized bottled tap water.

(3) Setting of Dose and group compositions:

orally or intravenously administered at a predetermined dose; Group compositions were as shown below (Dose depends on the compound)

Oral: 1 to 30 mg/kg (n=2 to 3)

Intravenous: 0.5 to 10 mg/kg (n=2 to 3)

(4) Preparation for dosing formulation:

for oral administration, in a solution or a suspension state; for intravenous administration, in a solubilized state (5) Dosing procedure:

In oral administration study, the test suspension was dosed to the stomach of rats by using a gavage tube In intravenous administration study, the test solution was dosed to rats via tail vein using a syringe with a needle.

(6) Evaluation items:

Blood was collected at each time point, and plasma concentration of the test substance was determined by a LC/MS/MS system.

(7) Data analysis:

Regarding the transition of the plasma concentration, area under the plasma concentration-time curve (AUC) was calculated by means of WinNonlin® program, respectively. Bioavailability (BA) was calculated by using AUC values in oral administration study and in intravenous administration study.

Formulation Example 1

A hard gelatin capsule is prepared by using the following ingredients:

|  | Dose (mg/capsule) |
| --- | --- |
| Active ingredient | 250 |
| Starch (dry) | 200 |
| Magnesium stearate | 10 |
| Total | 460 mg |

Formulation Example 2

A tablet is prepared by using the following ingredients:

|  | Dose (mg/tablet) |
| --- | --- |
| Active ingredient | 250 |
| Cellulose (microcrystal) | 400 |
| Silicon dioxide (fumed) | 10 |
| Stearic acid | 5 |
| Total | 665 mg |

The ingredients are mixed, and compressed to form tables each weighing 665 mg.

Formulation Example 3

An aerosol solution containing the following ingredients is prepared:

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient and ethanol are mixed, and the mixture is added to part of propellant 22, cooled to −30° C., and transferred to a packing machine. Then, a necessary amount is supplied to a stainless steel container, and diluted with the remaining propellant. A bubble unit is attached to the container.

Formulation Example 4

A tablet containing 60 mg of the active ingredient is prepared in the following manner:

| Active ingredient | 60 mg |
| --- | --- |
| Starch | 45 mg |
| Microcrystalline cellulose | 35 mg |
| Polyvinylpyrrolidone (10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. An aqueous solution containing polyvinylpyrrolidone is mixed with obtained powder and then the mixture is passed through a No. 14 mesh U.S. sieve. Granules obtained in this manner are dried at 50° C. and passed through a No. 18 mesh U.S. sieve. The sodium carboxymethyl starch, magnesium stearate and talc that are passed through a No. 60 mesh U.S. sieve in advance, are added to the granules, mixed, and then compressed by a tableting machine to obtain tablets each weighing 150 mg.

Formulation Example 5

A capsule containing 80 mg of the active ingredient is prepared in the following manner:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, starch, cellulose, and magnesium stearate are mixed, and passed through a No. 45 mesh U.S. sieve, and filled into a hard gelatin capsule in 200 mg quantities.

Formulation Example 6

Suppository containing 225 mg of the active ingredient is prepared in the following manner:

| Active ingredient | 225 mg |
| --- | --- |
| Saturated fatty acid glyceride | 2000 mg |
| Total | 2225 mg |

The active ingredient is passed through a No. 60 mesh U.S. sieve, and suspended in saturated fatty acid glyceride that is melted by heating least necessarily in advance. Then, the resultant mixture is put into an apparent 2 g mold, and cooled.

Formulation Example 7

A suspension containing 50 mg of the active ingredient is prepared in the following manner:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Pigment | q.v. |
| Purified water to total | 5 mL |

The active ingredient is passed through a No. 45 mesh U.S. sieve, and mixed with sodium carboxymethyl cellulose and syrup to form a smooth paste. The benzoic acid solution and the flavor diluted with part of water are added, and stirred. Then a sufficient amount of water is added to achieve required volume.

Formulation Example 8

An intravenous formulation is prepared in the following manner:

| Active ingredient | 100 mg |
| --- | --- |
| Saturated fatty acid glyceride | 1000 mL |

The solution of the above ingredients is intravenously administered to a patient usually at a speed of 1 mL per minute.

INDUSTRIAL APPLICABILITY

As is apparent from the above test examples, the compounds according to the present invention show inhibitory activity on endothelial lipase. Therefore, the compounds according to the present invention are very useful as therapeutic agents for lipid metabolism abnormality, hyperlipidemia or arteriosclerosis.

The invention claimed is:
1. A compound represented by the formula (I):

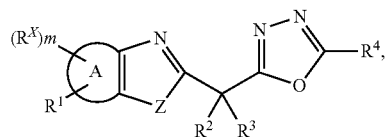

or its pharmaceutically acceptable salt,
wherein
Ring A is aromatic carbocycle or aromatic heterocycle,
Z is —O— or —S—,
$R^1$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino,
$R^2$ and $R^3$ are each independently hydrogen, halogen, hydroxy, cyano, nitro, carboxy, substituted or unsubstituted alkyl or substituted or unsubstituted alkyloxy, or $R^2$ and $R^3$ taken together may form oxo,
$R^4$ is a group represented by the formula: —$(CR^6R^7)_n$—$R^8$,
wherein $R^6$ and $R^7$ are each independently hydrogen, halogen, hydroxy, carboxy, substituted or unsubstituted alkyl or substituted or unsubstituted alkyloxy, or $R^6$ and $R^7$ taken together with the adjacent carbon atom to which they are attached may form a substituted or unsubstituted ring,
n is an integer of 0 to 3,
$R^8$ is carboxy, cyano, substituted or unsubstituted alkyl, substituted or unsubstituted acyl, with the proviso that n is not 0 when $R^8$ is substituted or unsubstituted acyl, substituted or unsubstituted alkyloxycarbonyl, substituted or unsubstituted alkylsulfonyl, substituted or unsubstituted carbamoyl, substituted or unsubstituted amino, substituted or unsubstituted carbamoyloxy or substituted or unsubstituted alkyloxy,
$R^x$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl or substituted or unsubstituted amino, and m is an integer of 0 to 3.

2. The compound according to claim 1, or its pharmaceutically acceptable salt, wherein Z is —O—.
3. The compound according to claim 1, or its pharmaceutically acceptable salt, wherein Z is —S—.
4. The compound according to claim 1, or its pharmaceutically acceptable salt, wherein Ring A is aromatic carbocycle.
5. The compound according to claim 1, or its pharmaceutically acceptable salt, wherein Ring A is benzene ring.
6. The compound according to claim 1, or its pharmaceutically acceptable salt, wherein the compound represented by the formula (I) is a compound represented by the formula (II):

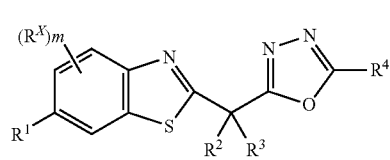

wherein $R^1$, $R^2$, $R^3$, $R^4$, $R^x$ and m are as defined in claim 1.
7. The compound according to claim 1, or its pharmaceutically acceptable salt, wherein $R^1$ is hydrogen, halogen, cyano, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl or substituted or unsubstituted amino.

8. The compound according to claim 1, or its pharmaceutically acceptable salt, wherein $R^1$ is hydrogen, halogen, cyano, substituted or unsubstituted alkyl, substituted or unsubstituted aryl, substituted or unsubstituted heteroaryl, substituted or unsubstituted aryloxy, substituted or unsubstituted heteroaryloxy, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl or substituted or unsubstituted amino.

9. The compound according to claim 1, or its pharmaceutically acceptable salt, wherein $R^1$ is substituted or unsubstituted aryl.

10. The compound according to claim 1, or its pharmaceutically acceptable salt, wherein $R^8$ is carboxy, cyano, substituted or unsubstituted alkyloxycarbonyl, substituted or unsubstituted alkylsulfonyl, substituted or unsubstituted carbamoyl, substituted or unsubstituted amino or substituted or unsubstituted carbamoyloxy.

11. The compound according to claim 10, or its pharmaceutically acceptable salt, wherein $R^8$ is carboxy, cyano, substituted or unsubstituted carbamoyl or substituted or unsubstituted amino.

12. The compound according to claim 11, or its pharmaceutically acceptable salt, wherein $R^8$ is substituted or unsubstituted carbamoyl.

13. The compound according to claim 12, or its pharmaceutically acceptable salt, wherein $R^8$ is a group represented by the formula: $-(C=O)-NR^9-(CR^{10}R^{11})-R^{12}$, wherein $R^9$ is hydrogen, substituted or unsubstituted alkyl, substituted or unsubstituted aryl, substituted or unsubstituted heteroaryl, substituted or unsubstituted cycloalkyl, substituted or unsubstituted cycloalkenyl or substituted or unsubstituted heterocyclyl, $R^{10}$ and $R^{11}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl or substituted or unsubstituted alkyloxy, $R^{10}$ and $R^{11}$ taken together with the adjacent carbon atom to which they are attached may form a substituted or unsubstituted ring, and $R^{12}$ is cyano, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl or substituted or unsubstituted alkyloxycarbonyl.

14. The compound according to claim 1, or its pharmaceutically acceptable salt, wherein n is 1.

15. The compound according to claim 1, or its pharmaceutically acceptable salt, wherein $R^2$ and $R^3$ are hydrogen.

16. A pharmaceutical composition comprising the compound according to claim 1, or its pharmaceutically acceptable salt.

17. A pharmaceutical composition comprising the compound according to claim 1, or its pharmaceutically acceptable salt, which has an inhibitory activity on endothelial lipase.

* * * * *